United States Patent
Macleod et al.

(10) Patent No.: US 9,567,588 B2
(45) Date of Patent: *Feb. 14, 2017

(54) MODULATION OF ANDROGEN RECEPTOR EXPRESSION

(71) Applicant: Ionis Pharmaceuticals, Inc., Carlsbad, CA (US)

(72) Inventors: Robert A. Macleod, Carlsbad, CA (US); Youngsoo Kim, Carlsbad, CA (US); Tianyuan Zhou, Carlsbad, CA (US); Susan M. Freier, Carlsbad, CA (US); Punit Seth, Carlsbad, CA (US); Eric Swayze, Carlsbad, CA (US); Brett Monia, Carlsbad, CA (US)

(73) Assignee: Ionis Pharmaceuticals, Inc., Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/854,281

(22) Filed: Sep. 15, 2015

(65) Prior Publication Data

US 2016/0068846 A1   Mar. 10, 2016

Related U.S. Application Data

(63) Continuation of application No. 14/050,574, filed on Oct. 10, 2013, now Pat. No. 9,175,291.

(60) Provisional application No. 61/712,756, filed on Oct. 11, 2012, provisional application No. 61/712,780, filed on Oct. 11, 2012, provisional application No. 61/723,701, filed on Nov. 7, 2012, provisional application No. 61/777,813, filed on Mar. 12, 2013, provisional application No. 61/777,851, filed on Mar. 12, 2013, provisional application No. 61/777,895, filed on Mar. 12, 2013.

(51) Int. Cl.
| | | |
|---|---|---|
| *C12N 15/11* | (2006.01) | |
| *C12N 15/113* | (2010.01) | |
| *A61K 31/7088* | (2006.01) | |
| *A61K 31/4166* | (2006.01) | |

(52) U.S. Cl.
CPC ....... *C12N 15/1138* (2013.01); *A61K 31/4166* (2013.01); *A61K 31/7088* (2013.01); *C12N 2310/11* (2013.01); *C12N 2310/315* (2013.01); *C12N 2310/321* (2013.01); *C12N 2310/3231* (2013.01); *C12N 2310/3341* (2013.01); *C12N 2310/341* (2013.01); *C12N 2310/346* (2013.01); *C12N 2320/30* (2013.01)

(58) Field of Classification Search
None
See application file for complete search history.

(56) References Cited

U.S. PATENT DOCUMENTS

2005/0246794 A1* 11/2005 Khvorova et al. ... A61K 31/713
800/286

FOREIGN PATENT DOCUMENTS

| WO | WO 2012006241 A2 * | 1/2012 | ......... C12N 15/1138 |
| WO | WO 2012/120374 | 9/2012 | |

OTHER PUBLICATIONS

Aartsma-Rus A "Overview on AON design" Methods Mol Biol. (2012) 867:117-29.
Chan et al., "Antisense oligonucleotides: from design to therapeutic application" Clin Exp Pharmacol Physiol. (2006) 33(5-6):533-40.
Hamy et al., "Specific block of androgen receptor activity by antisense oligonucleotides" Prostate Cancer Prostatic Dis. (2003) 6(1):27-33.

* cited by examiner

*Primary Examiner* — Kate Poliakova-Georgantas
(74) *Attorney, Agent, or Firm* — Ionis Pharmaceuticals, Inc.

(57) ABSTRACT

Certain embodiments are directed to compounds and compositions targeted to human androgen receptor (AR) for inhibiting androgen receptor levels in a cell, which can be useful for methods of treating cancer and inhibiting cancer cell growth or proliferation.

30 Claims, No Drawings

MODULATION OF ANDROGEN RECEPTOR EXPRESSION

CROSS-REFERENCE TO RELATED PATENT APPLICATIONS

This application is a continuation of U.S. patent application Ser. No. 14/050,574, filed Oct. 10, 2013, which claims the benefit of priority to U.S. Provisional Patent Application No. 61/712,780 filed Oct. 11, 2012; U.S. Provisional Patent Application No. 61/712,756 filed Oct. 11, 2012; U.S. Provisional Patent Application No. 61/723,701 filed Nov. 7, 2012; U.S. Provisional Patent Application No. 61/777,813 filed Mar. 12, 2103; U.S. Provisional Patent Application No. 61/777,851 filed Mar. 12, 2103 and U.S. Provisional Patent Application No. 61/777,895 filed Mar. 12, 2103. The entire text of the above-referenced patent applications is incorporated herein by reference in their entirety.

SEQUENCE LISTING

The present application is being filed along with a Sequence Listing in electronic format. The Sequence Listing is provided as a file entitled BIOL0212WOSEQ.txt created Sep. 17, 2013, which is approximately 556 KB in size. The information in the electronic format of the sequence listing is incorporated herein by reference in its entirety.

FIELD

Certain embodiments are directed to compounds and compositions targeted to human androgen receptor (AR) for inhibiting androgen receptor levels in a cell, which can be useful for methods of treating cancer and inhibiting cancer cell growth or proliferation.

BACKGROUND

Androgen receptor (AR) belongs to the superfamily of nuclear receptors and is activated by binding to its hormone ligands: androgen, testosterone, or DHT. Upon binding hormone ligand in the cytoplasm, androgen receptor translocates to the nucleus where it binds DNA and functions as a transcription factor to regulate expression of a number of target genes, such as prostate specific antigen (PSA) and TMPRSS2. Knudsen et al. (Trends Endocrinol Metab 21: 315-24, 2010) Bennett et al. (Int J Biochem Cell Biol. 42:813-827, 201).

Androgen receptor (AR) signaling is a critical survival pathway for prostate cancer cells, and androgen-deprivation therapy (ADT), also known as "chemical castration", is a first-line treatment strategy against hormone-sensitive, androgen-dependent prostate cancer that reduces circulating androgen levels and thereby inhibits AR activity. Although a majority of patients initially respond to ADT, most will eventually develop castrate resistance in which the disease progresses despite castrate levels of testosterone. This type of cancer is known as castrate-resistant prostate cancer (CRPC). There are a number of mechanisms underlying the development of castrate (castration) resistance including an increase in the expression of AR protein which can sensitize cells to low levels of androgen, AR mutations that can alter transactivation or sensitize AR to alternative ligands and the emergence of alternatively spliced forms of AR, which lack the ligand binding domain but can nevertheless act to promote tumour growth in the absence of ligand stimulation. Additionally prostate tumors may also synthesize their own androgens thereby increasing the local intra-tumoral testosterone levels available to activate the AR.

Androgen receptor (AR) signaling is a critical survival pathway for prostate cancer cells, and androgen-deprivation therapy (ADT) remains the principal treatment for patients with locally advanced and metastatic disease. Although a majority of patients initially respond to ADT, most will eventually develop castrate resistance in which the disease progresses despite castrate levels of testosterone. This type of cancer is known as castrate-resistant prostate cancer (CRPC) (Karantos et al., Oncogene advance online: 1-13, 2013). There are a number of mechanisms underlying the development of castration resistance including an increase in the expression of AR protein which can sensitize cells to low levels of androgen (Gregory et al., Cancer Res 61: 2892-2898, 2001; Linja et al., Cancer Res 61: 3550-3555, 2001), AR mutations that can alter transactivation or sensitize AR to alternative ligands (Scher et al., J Clin Oncol 23: 8253-8261, 2005) and the emergence of alternatively spliced forms of AR, which lack the ligand binding domain but can nevertheless act to promote tumour growth in the absence of ligand stimulation (Yingming et al., Cancer Res 73:483-489, 2013). Additionally prostate tumors may also synthesize their own androgens thereby increasing the local intra-tumoral testosterone levels available to activate the AR (Attard et al., Cancer Cell 16:458-462, 2009).

The fact that the androgen receptor remains active in castrate resistant prostate cancer has led to the development of new agents that inhibit the production of androgen ligands or block the actions of these ligands on the AR. These new agents include abiraterone acetate which inhibits 17-α-hydroxylase/17,20-lyase (CYP17) activity resulting in a reduction in residual androgens synthesized by the adrenals and in the prostate tumour itself deBono et al. (N Engl J Med 364: 1995-2006, 2011) and enzalutamide which prevents androgen ligand from binding to AR, translocating to the nucleus, and binding to DNA (Scher et al., N Engl J Med 367:1187-1197, 2012). A number of other androgen synthesis inhibitors or androgen receptor blockers are under development either pre-clinically or clinically and include for example, ARN509, ODM201, TOK001, VT464.

Although the activity of agents such as enzalutamide and abiraterone in CRPC is very encouraging, neither works in all patients and both are associated with the development of additional resistance through re-activation of the AR by the mechanisms described above (Yingming et al., Cancer Res 73:483-489, 2013). Thus, there is a continued need to identify alternative therapies for the treatment of CRPC, and in particular those that can either remove and/or inhibit the activity of all forms of AR including for example, wildtype, mutated and splice variant ARs.

The present invention provides antisense oligonclueotides which by virtue of their design and mode of action (base-pair with the AR RNA target and mediate its destruction by RNase H, an enzyme that destroys the RNA in a DNA/RNA duplex) are aimed at inhibiting the major forms of AR By targeting an appropriate region of the AR mRNA the antisense oligonucleotide will result in inhibition of the major forms (full length, splice variant and mutated forms) of androgen receptor proteins and therefore be suitable for the treatment of patients with CRPC.

Aside from prostate cancer, AR is also implicated as a factor in the progression of other tumours such as breast cancer. In breast cancer AR is expressed in 70-80% of tumours which are also ER positive and in 12% cases which are known as triple negative (no expression of ER, PR and HER2) (Hickey et al., Molecular Endocrinology 26: 1252-

1267, 2012). In pre-clinical studies, the androgen receptor antagonist bicalutamide induces anti-proliferative responses in vitro in breast cancer cells and this is potentiated by addition of a Pi3K/mTOR inhibitor (Ni et al., Cancer Cell 20: 119-131, 2011). The 2nd generation anti-androgen, enzalutamide inhibits dihydrotestosterone (DHT) mediated proliferation in ER+/AR+ breast cancer cells and is as effective as tamoxifen at inhibiting estrogen-stimulated breast cancer tumour growth in pre-clinical models in vivo (Cochrane et al., Cancer Res 72(24 Supplement): P2-14-02, 2012). Enzalutamide also inhibits proliferation in HER2+ and triple-negative breast cancer cells. It appears that in situations where estrogen action is reduced (eg. long-term estrogen deprivation or absence of ER) AR levels increase and can become oncogenic. This would suggest that AR antagonists may be best positioned in triple negative or hormone resistant breast cancer settings (Hickey et al., Molecular Endocrinology 26: 1252-1267, 2012). AR targeted therapies are currently under investigation in clinical trials for breast cancer (NCT00468715, NCT01597193, NCT01381874, NCT00755886).

AR is also expressed in a variety of other tumours, including, but not limited to bladder, ovarian, gastric, lung and liver. Pre-clinical data support a similar role as in breast cancer, to promote tumour cell proliferation survival; thus blocking AR in these tumours could have therapeutic clinical benefit (Chang et al., Oncogene advance online: 1-10, 2013).

SUMMARY

Several embodiments provided herein relate to the discovery of compounds and compositions for inhibiting androgen receptor levels in a cell, which can be useful for methods of treating cancer and inhibiting proliferation or growth of cancer cells, such as prostate, breast, ovarian, gastric or bladder cancer or cancer cells.

DETAILED DESCRIPTION

It is to be understood that both the foregoing general description and the following detailed description are exemplary and explanatory only and are not restrictive of the invention, as claimed. Herein, the use of the singular includes the plural unless specifically stated otherwise. As used herein, the use of "or" means "and/or" unless stated otherwise. Furthermore, the use of the term "including" as well as other forms, such as "includes" and "included", is not limiting. Also, terms such as "element" or "component" encompass both elements and components comprising one unit and elements and components that comprise more than one subunit, unless specifically stated otherwise.

The section headings used herein are for organizational purposes only and are not to be construed as limiting the subject matter described. All documents, or portions of documents, cited in this application, including, but not limited to, patents, patent applications, articles, books, and treatises, are hereby expressly incorporated by reference for the portions of the document discussed herein, as well as in their entirety.

Definitions

Unless specific definitions are provided, the nomenclature utilized in connection with, and the procedures and techniques of, analytical chemistry, synthetic organic chemistry, and medicinal and pharmaceutical chemistry described herein are those well known and commonly used in the art. Standard techniques may be used for chemical synthesis, and chemical analysis. Where permitted, all patents, applications, published applications and other publications, GENBANK Accession Numbers and associated sequence information obtainable through databases such as National Center for Biotechnology Information (NCBI) and other data referred to throughout in the disclosure herein are incorporated by reference for the portions of the document discussed herein, as well as in their entirety.

Unless otherwise indicated, the following terms have the following meanings:

"2'-O-methoxyethyl" (also 2'-MOE and 2'-O($CH_2$)$_2$—$OCH_3$) refers to an O-methoxy-ethyl modification at the 2' position of a sugar ring, e.g. a furanose ring. A 2'-O-methoxyethyl modified sugar is a modified sugar.

"2'-MOE nucleoside" (also 2'-O-methoxyethyl nucleoside) means a nucleoside comprising a 2'-MOE modified sugar moiety.

"2'-substituted nucleoside" means a nucleoside comprising a substituent at the 2'-position of the furanosyl ring other than H or OH. In certain embodiments, 2' substituted nucleosides include nucleosides with bicyclic sugar modifications.

"3' target site" refers to the nucleotide of a target nucleic acid which is complementary to the 3'-most nucleotide of a particular antisense compound.

"5' target site" refers to the nucleotide of a target nucleic acid which is complementary to the 5'-most nucleotide of a particular antisense compound.

"5-methylcytosine" means a cytosine modified with a methyl group attached to the 5' position. A 5-methylcytosine is a modified nucleobase.

"About" means within ±7% of a value. For example, if it is stated, "the compounds affected at least about 70% inhibition of Androgen Receptor", it is implied that Androgen Receptor levels are inhibited within a range of 63% and 77%.

"Administration" or "administering" refers to routes of introducing an antisense compound provided herein to a subject to perform its intended function. An example of a route of administration that can be used includes, but is not limited to parenteral administration, such as subcutaneous, intravenous, or intramuscular injection or infusion.

"Androgen-receptor positive" with respect to breast cancer or a breast cancer cell refers to a breast cancer or a breast cancer cell that expresses androgen receptor.

"Animal" refers to a human or non-human animal, including, but not limited to, mice, rats, rabbits, dogs, cats, pigs, and non-human primates, including, but not limited to, monkeys and chimpanzees.

"Anti-androgenic agent" refers to a therapeutic compound or drug which is an androgen synthesis inhibitor or an androgen receptor blocker.

"Antisense activity" means any detectable or measurable activity attributable to the hybridization of an antisense compound to its target nucleic acid. In certain embodiments, antisense activity is a decrease in the amount or expression of a target nucleic acid or protein encoded by such target nucleic acid.

"Antisense compound" means an oligomeric compound that is is capable of undergoing hybridization to a target nucleic acid through hydrogen bonding. Examples of antisense compounds include single-stranded and double-stranded compounds, such as, antisense oligonucleotides, siRNAs, shRNAs, ssRNAs, and occupancy-based compounds.

"Antisense inhibition" means reduction of target nucleic acid levels in the presence of an antisense compound complementary to a target nucleic acid compared to target nucleic acid levels in the absence of the antisense compound.

"Antisense mechanisms" are all those mechanisms involving hybridization of a compound with target nucleic acid, wherein the outcome or effect of the hybridization is either target degradation or target occupancy with concomitant stalling of the cellular machinery involving, for example, transcription or splicing.

"Antisense oligonucleotide" means a single-stranded oligonucleotide having a nucleobase sequence that permits hybridization to a corresponding region or segment of a target nucleic acid.

"Base complementarity" refers to the capacity for the precise base pairing of nucleobases of an antisense oligonucleotide with corresponding nucleobases in a target nucleic acid (i.e., hybridization), and is mediated by Watson-Crick, Hoogsteen or reversed Hoogsteen hydrogen binding between corresponding nucleobases.

"Bicyclic sugar moiety" means a modified sugar moiety comprising a 4 to 7 membered ring (including but not limited to a furanosyl) comprising a bridge connecting two atoms of the 4 to 7 membered ring to form a second ring, resulting in a bicyclic structure. In certain embodiments, the 4 to 7 membered ring is a sugar ring. In certain embodiments the 4 to 7 membered ring is a furanosyl. In certain such embodiments, the bridge connects the 2'-carbon and the 4'-carbon of the furanosyl.

Also included within the definition of LNA according to the invention are LNAs in which the 2'-hydroxyl group of the ribosyl sugar ring is connected to the 4' carbon atom of the sugar ring, thereby forming a methyleneoxy (4-$CH_2$—O-2') bridge to form the bicyclic sugar moiety. The bridge can also be a methylene (—$CH_2$—) group connecting the 2' oxygen atom and the 4' carbon atom, for which the term methyleneoxy (4-$CH_2$—O-2') LNA is used. Furthermore; in the case of the bicylic sugar moiety having an ethylene bridging group in this position, the term ethyleneoxy (4'-$CH_2CH_2$—O-2') LNA is used. α-L-methyleneoxy (4-$CH_2$—O-2'), an isomer of methyleneoxy (4-$CH_2$—O-2') LNA is also encompassed within the definition of LNA, as used herein.

"Cap structure" or "terminal cap moiety" means chemical modifications, which have been incorporated at either terminus of an antisense compound.

"Castrate-resistant prostate cancer" or "Castration-resistant prostate cancer" and prostate cancer cells refer to the reduction of sensitivity of prostate cancer and prostate cancer cells to androgen deprivation therapy or an anti-androgenic agent.

"cEt" or "constrained ethyl" means a bicyclic sugar moiety comprising a bridge connecting the 4'-carbon and the 2'-carbon, wherein the bridge has the formula: 4-CH($CH_3$)—O-2'.

"Constrained ethyl nucleoside" (also cEt nucleoside) means a nucleoside comprising a bicyclic sugar moiety comprising a 4'-CH($CH_3$)—O-2' bridge.

"Chemically distinct region" refers to a region of an antisense compound that is in some way chemically different than another region of the same antisense compound. For example, a region having 2'-O-methoxyethyl nucleotides is chemically distinct from a region having nucleotides without 2'-O-methoxyethyl modifications.

"Chimeric antisense compounds" means antisense compounds that have at least 2 chemically distinct regions, each position having a plurality of subunits.

"Complementarity" means the capacity for pairing between nucleobases of a first nucleic acid and a second nucleic acid.

"Comprise," "comprises" and "comprising" will be understood to imply the inclusion of a stated step or element or group of steps or elements but not the exclusion of any other step or element or group of steps or elements.

"Contiguous nucleobases" means nucleobases immediately adjacent to each other.

"Deoxyribonucleotide" means a nucleotide having a hydrogen at the 2' position of the sugar portion of the nucleotide. Deoxyribonucleotides may be modified with any of a variety of substituents.

"Designing" or "Designed to" refer to the process of designing an oligomeric compound that specifically hybridizes with a selected nucleic acid molecule.

"Downstream" refers to the relative direction toward the 3' end or C-terminal end of a nucleic acid.

"Efficacy" means the ability to produce a desired effect.

"Estrogen-receptor (ER) positive" with respect to breast cancer or a breast cancer cell refers to breast cancer or a breast cancer cell that expresses estrogen receptor (ER).

"Estrogen-receptor (ER) negative" with respect to breast cancer or a breast cancer cell refers to breast cancer or a breast cancer cell that does not express estrogen receptor (ER).

"Expression" includes all the functions by which a gene's coded information is converted into structures present and operating in a cell. Such structures include, but are not limited to the products of transcription and translation.

"Fully complementary" or "100% complementary" means each nucleobase of a first nucleic acid has a complementary nucleobase in a second nucleic acid. In certain embodiments, a first nucleic acid is an antisense compound and a target nucleic acid is a second nucleic acid.

"Gapmer" means a chimeric antisense compound in which an internal region having a plurality of nucleosides that support RNase H cleavage is positioned between external regions having one or more nucleosides, wherein the nucleosides comprising the internal region are chemically distinct from the nucleoside or nucleosides comprising the external regions. The internal region may be referred to as the "gap" and the external regions may be referred to as the "wings."

"Her2/neu negative" with respect to breast cancer or a breast cancer cell refers to breast cancer or a breast cancer cell that does not express Her2/neu.

"Hybridization" means the annealing of complementary nucleic acid molecules. In certain embodiments, complementary nucleic acid molecules include, but are not limited to, an antisense compound and a nucleic acid target. In certain embodiments, complementary nucleic acid molecules include, but are not limited to, an antisense oligonucleotide and a nucleic acid target.

"Immediately adjacent" means there are no intervening elements between the immediately adjacent elements.

"Individual" means a human or non-human animal selected for treatment or therapy.

"Induce", "inhibit", "potentiate", "elevate", "increase", "decrease", upregulate", "downregulate", or the like, generally denote quantitative differences between two states.

"Inhibiting the expression or activity" refers to a reduction, blockade of the expression or activity and does not necessarily indicate a total elimination of expression or activity.

"Internucleoside linkage" refers to the chemical bond between nucleosides.

"Lengthened" antisense oligonucleotides are those that have one or more additional nucleosides relative to an antisense oligonucleotide disclosed herein.

"Linked deoxynucleoside" means a nucleic acid base (A, G, C, T, U) substituted by deoxyribose linked by a phosphate ester to form a nucleotide.

"Linked nucleosides" means adjacent nucleosides linked together by an internucleoside linkage.

"Mismatch" or "non-complementary nucleobase" refers to the case when a nucleobase of a first nucleic acid is not capable of pairing with the corresponding nucleobase of a second or target nucleic acid.

"Modified internucleoside linkage" refers to a substitution or any change from a naturally occurring internucleoside bond (i.e. a phosphodiester internucleoside bond).

"Modified nucleobase" means any nucleobase other than adenine, cytosine, guanine, thymidine, or uracil. An "unmodified nucleobase" means the purine bases adenine (A) and guanine (G), and the pyrimidine bases thymine (T), cytosine (C) and uracil (U).

"Modified nucleoside" means a nucleoside having, independently, a modified sugar moiety and/or modified nucleobase.

"Modified nucleotide" means a nucleotide having, independently, a modified sugar moiety, modified internucleoside linkage, or modified nucleobase.

"Modified oligonucleotide" means an oligonucleotide comprising at least one modified internucleoside linkage, a modified sugar, and/or a modified nucleobase.

"Modified sugar" means substitution and/or any change from a natural sugar moiety.

"Monomer" refers to a single unit of an oligomer. Monomers include, but are not limited to, nucleosides and nucleotides, whether naturally occuring or modified.

"Motif" means the pattern of unmodified and modified nucleosides in an antisense compound.

"Natural sugar moiety" means a sugar moiety found in DNA (2'-H) or RNA (2'-OH).

"Naturally occurring internucleoside linkage" means a 3' to 5' phosphodiester linkage.

"Non-complementary nucleobase" refers to a pair of nucleobases that do not form hydrogen bonds with one another or otherwise support hybridization.

"Nucleic acid" refers to molecules composed of monomeric nucleotides. A nucleic acid includes, but is not limited to, ribonucleic acids (RNA), deoxyribonucleic acids (DNA), single-stranded nucleic acids, and double-stranded nucleic acids.

"Nucleobase" means a heterocyclic moiety capable of pairing with a base of another nucleic acid.

"Nucleobase complementarity" refers to a nucleobase that is capable of base pairing with another nucleobase. For example, in DNA, adenine (A) is complementary to thymine (T). For example, in RNA, adenine (A) is complementary to uracil (U). In certain embodiments, complementary nucleobase refers to a nucleobase of an antisense compound that is capable of base pairing with a nucleobase of its target nucleic acid. For example, if a nucleobase at a certain position of an antisense compound is capable of hydrogen bonding with a nucleobase at a certain position of a target nucleic acid, then the position of hydrogen bonding between the oligonucleotide and the target nucleic acid is considered to be complementary at that nucleobase pair.

"Nucleobase sequence" means the order of contiguous nucleobases independent of any sugar, linkage, and/or nucleobase modification.

"Nucleoside" means a nucleobase linked to a sugar.

"Nucleoside mimetic" includes those structures used to replace the sugar or the sugar and the base and not necessarily the linkage at one or more positions of an oligomeric compound such as for example nucleoside mimetics having morpholino, cyclohexenyl, cyclohexyl, tetrahydropyranyl, bicyclo or tricyclo sugar mimetics, e.g., non furanose sugar units. Nucleotide mimetic includes those structures used to replace the nucleoside and the linkage at one or more positions of an oligomeric compound such as for example peptide nucleic acids or morpholinos (morpholinos linked by —N(H)—C(=O)—O— or other non-phosphodiester linkage). Sugar surrogate overlaps with the slightly broader term nucleoside mimetic but is intended to indicate replacement of the sugar unit (furanose ring) only. The tetrahydropyranyl rings provided herein are illustrative of an example of a sugar surrogate wherein the furanose sugar group has been replaced with a tetrahydropyranyl ring system. "Mimetic" refers to groups that are substituted for a sugar, a nucleobase, and/or internucleoside linkage. Generally, a mimetic is used in place of the sugar or sugar-internucleoside linkage combination, and the nucleobase is maintained for hybridization to a selected target.

"Nucleotide" means a nucleoside having a phosphate group covalently linked to the sugar portion of the nucleoside.

"Oligomeric compound" means a polymer of linked monomeric subunits which is capable of hybridizing to at least a region of a nucleic acid molecule.

"Oligonucleoside" means an oligonucleotide in which the internucleoside linkages do not contain a phosphorus atom.

"Oligonucleotide" means a polymer of linked nucleosides each of which can be modified or unmodified, independent one from another.

"Phosphorothioate linkage" means a linkage between nucleosides where the phosphodiester bond is modified by replacing one of the non-bridging oxygen atoms with a sulfur atom. A phosphorothioate linkage is a modified internucleoside linkage.

"Portion" means a defined number of contiguous (i.e., linked) nucleobases of a nucleic acid. In certain embodiments, a portion is a defined number of contiguous nucleobases of a target nucleic acid. In certain embodiments, a portion is a defined number of contiguous nucleobases of an antisense compound "Progesterone receptor (PR) negative" with respect to breast cancer or a breast cancer cell refers to breast cancer or a breast cancer cell that does not express progesterone receptor (PR).

"Region" is defined as a portion of the target nucleic acid having at least one identifiable structure, function, or characteristic.

"Ribonucleotide" means a nucleotide having a hydroxy at the 2' position of the sugar portion of the nucleotide. Ribonucleotides may be modified with any of a variety of substituents.

"Segments" are defined as smaller or sub-portions of regions within a target nucleic acid.

"Sites," as used herein, are defined as unique nucleobase positions within a target nucleic acid.

"Specifically hybridizable" refers to an antisense compound having a sufficient degree of complementarity between an antisense oligonucleotide and a target nucleic acid to induce a desired effect, while exhibiting minimal or no effects on non-target nucleic acids under conditions in which specific binding is desired, i.e., under physiological conditions in the case of in vivo assays and therapeutic treatments. "Stringent hybridization conditions" or "stringent conditions" refer to conditions under which an oligomeric compound will hybridize to its target sequence, but to a minimal number of other sequences.

"Subject" means a human or non-human animal selected for treatment or therapy.

"Synergy" or "synergize" refers to an effect of a combination that is greater than additive of the effects of each component alone.

"Target" refers to a protein, the modulation of which is desired.

"Target gene" refers to a gene encoding a target.

"Targeting" means the process of design and selection of an antisense compound that will specifically hybridize to a target nucleic acid and induce a desired effect.

"Target nucleic acid," "target RNA," "target RNA transcript" and "nucleic acid target" all mean a nucleic acid capable of being targeted by antisense compounds.

"Target region" means a portion of a target nucleic acid to which one or more antisense compounds is targeted.

"Target segment" means the sequence of nucleotides of a target nucleic acid to which an antisense compound is targeted. "5' target site" refers to the 5'-most nucleotide of a target segment. "3' target site" refers to the 3'-most nucleotide of a target segment.

"Treating cancer" refers to performing actions that lead to amelioration of cancer or of the symptoms accompanied therewith. The combination of said actions is encompassed by the term "treatment." Amelioration of cancer includes, but is not limited to, reducing the number of cancer cells in a subject or reducing the number of cancer cells in the subject. Said treatment as used herein also includes an entire restoration of the health with respect to cancer. It is to be understood that treatment as used in accordance with embodiments provided herein may not be effective in all subjects to be treated. However, a population of subjects suffering from cancer referred to herein can be successfully treated. In certain embodiments, "treating cancer" can be described by a number of different parameters including, but not limited to, reduction in the size of a tumor in a subject having cancer, reduction in the growth or proliferation of a tumor in a subject having cancer, preventing metastasis or reducing the extent of metastasis, and/or extending the survival of a subject having cancer compared to control. The cancer referred to in this definition can be any cancer including one selected from prostate cancer, breast cancer, ovarian cancer, gastric cancer and bladder cancer.

"Unmodified" nucleobases mean the purine bases adenine (A) and guanine (G), and the pyrimidine bases thymine (T), cytosine (C) and uracil (U).

"Unmodified nucleotide" means a nucleotide composed of naturally occuring nucleobases, sugar moieties, and internucleoside linkages. In certain embodiments, an unmodified nucleotide is an RNA nucleotide (i.e. β-D-ribonucleosides) or a DNA nucleotide (i.e. β-D-deoxyribonucleoside).

"Upstream" refers to the relative direction toward the 5' end or N-terminal end of a nucleic acid.

Certain Embodiments

Certain embodiments provide methods, compounds, and compositions for inhibiting androgen receptor (AR) mRNA expression.

Certain embodiments provide antisense compounds or compositions targeted to an androgen receptor nucleic acid. In certain embodiments, the androgen receptor nucleic acid is the sequences set forth in GENBANK Accession No. NT_011669.17_TRUNC_5079000_5270000 (incorporated herein as SEQ ID NO: 1), GENBANK Accession No. NM_000044.3 (incorporated herein as SEQ ID NO: 2), GENBANK Accession No. NM_001011645.2 (incorporated herein as SEQ ID NO: 3), GENBANK Accession No. FJ235916.1 (incorporated herein as SEQ ID NO: 4), GENBANK Accession No. FJ235917.1 (incorporated herein as SEQ ID NO: 5), GENBANK Accession No. FJ235918.1 (incorporated herein as SEQ ID NO: 6), GENBANK Accession No. FJ235919.1 (incorporated herein as SEQ ID NO: 7), or GENBANK Accession No. FJ235920.1 (incorporated herein as SEQ ID NO: 8).

In certain embodiments, the compounds or compositions comprise a modified oligonucleotide 10 to 30 linked nucleosides in length targeted to AR. The AR target can have a sequence recited in any one of SEQ ID NOs: 1-8 or a portion thereof or a variant thereof. In certain embodiments, the AR target can have a sequence of known AR splicing variants including, but are not limited to, AR-V1, AR-V2, AR-V3, AR-V4, AR-V5, AR-V6, and AR-V7 (also referred to as AR3), which contain exons 1-3 but lack exons 4-8. AR-V1, AR-V2, AR-V3, AR-V4, AR-V5, AR-V6, AR-V7, and additional splicing variants targetable by compounds provided herein are described in Hu et al., *Cancer Res* 2009; 69:16-22 and US Patent Application Publication No. US 2010/0068802, each of which is incorporated herein by reference in its entirety.

In certain embodiments, the compounds or compositions comprise a modified oligonucleotide consisting of 10 to 30 linked nucleosides and having a nucleobase sequence comprising at least 8, 9, 10, 11, 12, 13, 14, 15, 16, 17, 18, 19, or 20 contiguous nucleobases of any of SEQ ID NOs: 12-179. In certain embodiments, one or more modified nucleosides in the wing segment have a modified sugar. In certain embodiments, the modified sugar is a bicyclic sugar. In certain embodiments, the modified nucleoside is an LNA nucleoside. In certain embodiments, the modified nucleoside is a 2'-substituted nucleoside. In certain embodiments, 2' substituted nucleosides include nucleosides with bicyclic sugar modifications. In certain embodiments, the modified nucleoside is a 2'-MOE nucleoside. In certain embodiments, the modified nucleoside is a constrained ethyl (cEt) nucleoside.

In certain embodiments, the compounds or compositions comprise a modified oligonucleotide consisting of 10 to 30 linked nucleosides and having a nucleobase sequence consisting of a nucleobase sequence of any of SEQ ID NOs: 12-179. In certain embodiments, one or more modified nucleosides in the wing segment have a modified sugar. In certain embodiments, the modified sugar is a bicyclic sugar. In certain embodiments, the modified nucleoside is an LNA nucleoside. In certain embodiments, the modified nucleoside is a 2'-substituted nucleoside. In certain embodiments, 2' substituted nucleosides include nucleosides with bicyclic sugar modifications. In certain embodiments, the modified nucleoside is a 2'-MOE nucleoside. In certain embodiments, the modified nucleoside is a constrained ethyl (cEt) nucleoside.

In certain embodiments, the compounds or compositions targeted to androgen receptor comprise a single-stranded modified oligonucleotide consisting of 16 linked nucleosides having a nucleobase sequence consisting of the sequence of SEQ ID NO: 35, 39, 43, 124, 150, 155, 169, or 175, or a pharmaceutically acceptable salt thereof. In certain embodiments, the antisense compound targeted to human AR is ISIS 560131, ISIS 569213, ISIS 569216, ISIS 569221, ISIS 569236, ISIS 579671, ISIS 586124, ISIS 583918, ISIS 584149, ISIS 584163, ISIS 584269, or ISIS 584468.

In certain embodiments, the modified oligonucleotide comprises: a) a gap segment consisting of linked deoxynucleosides; b) a 5' wing segment consisting of linked nucleosides; and c) a 3' wing segment consisting of linked nucleosides. The gap segment is positioned between the 5' wing segment and the 3' wing segment and each nucleoside of each wing segment comprises a modified sugar.

In certain embodiments, the modified oligonucleotide consists of 20 linked nucleosides, the gap segment consisting of 10 linked deoxynucleosides, the 5' wing segment consisting of five linked nucleosides, the 3' wing segment consisting of five linked nucleosides, each nucleoside of each wing segment comprises a 2'-O-methoxyethyl sugar, each internucleoside linkage is a phosphorothioate linkage and each cytosine is a 5-methylcytosine.

In certain embodiments, the modified oligonucleotide consists of 16 linked nucleosides, a gap segment consisting of 10 linked deoxynucleosides, a 5' wing segment consisting of three linked nucleosides, a 3' wing segment consisting of three linked nucleosides, each nucleoside of each wing segment comprises a constrained ethyl (cEt) sugar, each internucleoside linkage is a phosphorothioate linkage and each cytosine is a 5-methylcytosine.

In certain embodiments, the modified oligonucleotide consists of 16 linked nucleosides, a gap segment consisting of 9 linked deoxynucleosides, a 5' wing segment consisting of three linked nucleosides, a 3' wing segment consisting of four linked nucleosides; the three linked nucleosides of the 5' wing segment are each a constrained ethyl (cEt) sugar; the four linked nucleosides of the 3' wing segment are a constrained ethyl (cEt) sugar, a constrained ethyl (cEt) sugar, a constrained ethyl (cEt) sugar, and a 2'-O-methoxyethyl sugar in the 5' to 3' direction; each internucleoside linkage is a phosphorothioate linkage; and each cytosine is a 5-methylcytosine.

In certain embodiments, the modified oligonucleotide consists of 16 linked nucleosides, a gap segment consisting of 8 linked deoxynucleosides, a 5' wing segment consisting of five linked nucleosides, a 3' wing segment consisting of three linked nucleosides; the five linked nucleosides of the 5' wing segment are each a constrained ethyl (cEt) sugar; the three linked nucleosides of the 3' wing segment are each a constrained ethyl (cEt) sugar; each internucleoside linkage is a phosphorothioate linkage; and each cytosine is a 5-methylcytosine.

In certain embodiments, the modified oligonucleotide consists of 16 linked nucleosides, a gap segment consisting of 8 linked deoxynucleosides, a 5' wing segment consisting of four linked nucleosides, a 3' wing segment consisting of four linked nucleosides; the four linked nucleosides of the 5' wing segment are a 2'-O-methoxyethyl sugar, a constrained ethyl (cEt) sugar, a constrained ethyl (cEt) sugar, and a constrained ethyl (cEt) sugar in the 5' to 3' direction; the four linked nucleosides of the 3' wing segment are a constrained ethyl (cEt) sugar, a constrained ethyl (cEt) sugar, a constrained ethyl (cEt) sugar, and a 2'-O-methoxyethyl sugar in the 5' to 3' direction; each internucleoside linkage is a phosphorothioate linkage; and each cytosine is a 5-methylcytosine.

In certain embodiments, the modified oligonucleotide consists of 16 linked nucleosides, a gap segment consisting of 8 linked deoxynucleosides, a 5' wing segment consisting of five linked nucleosides, a 3' wing segment consisting of three linked nucleosides; the five linked nucleosides of the 5' wing segment are a 2'-O-methoxyethyl sugar, a 2'-O-methoxyethyl sugar, a constrained ethyl (cEt) sugar, a constrained ethyl (cEt) sugar, and a constrained ethyl (cEt) sugar in the 5' to 3' direction; the three linked nucleosides of the 3' wing segment are each a constrained ethyl (cEt) sugar; each internucleoside linkage is a phosphorothioate linkage; and each cytosine is a 5-methylcytosine.

In certain embodiments, the modified oligonucleotide consists of 16 linked nucleosides, a gap segment consisting of 7 linked deoxynucleosides, a 5' wing segment consisting of seven linked nucleosides, a 3' wing segment consisting of two linked nucleosides; the seven linked nucleosides of the 5' wing segment are a 2'-O-methoxyethyl sugar, a constrained ethyl (cEt) sugar, a constrained ethyl (cEt) sugar, a 2'-O-methoxyethyl sugar, a 2'-O-methoxyethyl sugar, a constrained ethyl (cEt) sugar, and a constrained ethyl (cEt) sugar in the 5' to 3' direction; the two linked nucleosides of the 3' wing segment are each a constrained ethyl (cEt) sugar; each internucleoside linkage is a phosphorothioate linkage; and each cytosine is a 5-methylcytosine.

In certain embodiments, the modified oligonucleotide consists of 16 linked nucleosides, a gap segment consisting of 7 linked deoxynucleosides, a 5' wing segment consisting of six linked nucleosides, a 3' wing segment consisting of three linked nucleosides; the six linked nucleosides of the 5' wing segment are a 2'-O-methoxyethyl sugar, a constrained ethyl (cEt) sugar, a constrained ethyl (cEt) sugar, a 2'-O-methoxyethyl sugar, a constrained ethyl (cEt) sugar, and a constrained ethyl (cEt) sugar in the 5' to 3' direction; the three linked nucleosides of the 3' wing segment are each a constrained ethyl (cEt) sugar; each internucleoside linkage is a phosphorothioate linkage; and each cytosine is a 5-methylcytosine.

In certain embodiments, the modified oligonucleotide consists of 16 linked nucleosides, a gap segment consisting of 7 linked deoxynucleosides, a 5' wing segment consisting of five linked nucleosides, a 3' wing segment consisting of four linked nucleosides; the five linked nucleosides of the 5' wing segment are a 2'-O-methoxyethyl sugar, a 2'-O-methoxyethyl sugar, a constrained ethyl (cEt) sugar, a constrained ethyl (cEt) sugar, and a constrained ethyl (cEt) sugar in the 5' to 3' direction; the four linked nucleosides of the 3' wing segment are a constrained ethyl (cEt) sugar, a constrained ethyl (cEt) sugar, a constrained ethyl (cEt) sugar, and a 2'-O-methoxyethyl sugar in the 5' to 3' direction; each internucleoside linkage is a phosphorothioate linkage; and each cytosine is a 5-methylcytosine.

In certain embodiments, the modified oligonucleotide consists of 16 linked nucleosides, a gap segment consisting of 7 linked deoxynucleosides, a 5' wing segment consisting of four linked nucleosides, a 3' wing segment consisting of five linked nucleosides; the four linked nucleosides of the 5' wing segment are a 2'-O-methoxyethyl sugar, a constrained ethyl (cEt) sugar, a constrained ethyl (cEt) sugar, and a constrained ethyl (cEt) sugar in the 5' to 3' direction; the five linked nucleosides of the 3' wing segment are a constrained ethyl (cEt) sugar, a constrained ethyl (cEt) sugar, a constrained ethyl (cEt) sugar, a 2'-O-methoxyethyl sugar, and a 2'-O-methoxyethyl sugar in the 5' to 3' direction; each internucleoside linkage is a phosphorothioate linkage; and each cytosine is a 5-methylcytosine.

In certain embodiments, the compounds or compositions targeted to androgen receptor comprise a single-stranded modified oligonucleotide consisting of 16 linked nucleosides having a nucleobase sequence consisting of the sequence of SEQ ID NO: 35, 39, 43, 124, 150, 155, 169, or 175, or a pharmaceutically acceptable salt thereof, wherein the modified oligonucleotide comprises a gap segment consisting of deoxynucleosides; a 5' wing segment; and a 3' wing segment, wherein the gap segment is positioned between the 5' wing segment and the 3' wing segment and each nucleoside of each wing segment comprises a modified sugar. In certain embodiments, each internucleoside linkage of the modified oligonucleotide is a phosphorothioate linkage. In certain embodiments, each cytosine of the modified oligonucleotide is a 5'-methylcytosine.

In certain embodiments, a compound targeted to androgen receptor comprises a single-stranded modified oligonucleotide consisting of 16 linked nucleosides having a nucleobase sequence consisting of the sequence of SEQ ID NO: 35, or a pharmaceutically acceptable salt thereof, wherein the modified oligonucleotide comprises:
 a gap segment consisting of 9 linked deoxynucleosides;
 a 5' wing segment consisting of three linked nucleosides; and
 a 3' wing segment consisting of four linked nucleosides;
 wherein the gap segment is positioned between the 5' wing segment and the 3' wing segment; the three linked nucleosides of the 5' wing segment are each a constrained ethyl (cEt) sugar; the four linked nucleosides of the 3' wing segment are a constrained ethyl (cEt) sugar, a constrained ethyl (cEt) sugar, a constrained ethyl (cEt) sugar, and a 2'-O-methoxyethyl sugar in the 5' to 3' direction; each internucleoside linkage is a phosphorothioate linkage; and each cytosine is a 5-methylcytosine.

In certain embodiments, a compound targeted to androgen receptor comprises a single-stranded modified oligonucleotide consisting of 16 linked nucleosides having a nucleobase sequence consisting of the sequence of SEQ ID NO: 39, or a pharmaceutically acceptable salt thereof, wherein the modified oligonucleotide comprises:
 a gap segment consisting of 9 linked deoxynucleosides;
 a 5' wing segment consisting of three linked nucleosides; and
 a 3' wing segment consisting of four linked nucleosides;
 wherein the gap segment is positioned between the 5' wing segment and the 3' wing segment; the three linked nucleosides of the 5' wing segment are each a constrained ethyl (cEt) sugar; the four linked nucleosides of the 3' wing segment are a constrained ethyl (cEt) sugar, a constrained ethyl (cEt) sugar, a constrained ethyl (cEt) sugar, and a 2'-O-methoxyethyl sugar in the 5' to 3' direction; each internucleoside linkage is a phosphorothioate linkage; and each cytosine is a 5-methylcytosine.

In certain embodiments, a compound targeted to androgen receptor comprises a single-stranded modified oligonucleotide consisting of 16 linked nucleosides having a nucleobase sequence consisting of the sequence of SEQ ID NO: 39, or a pharmaceutically acceptable salt thereof, wherein the modified oligonucleotide comprises:
 a gap segment consisting of 8 linked deoxynucleosides;
 a 5' wing segment consisting of four linked nucleosides; and
 a 3' wing segment consisting of four linked nucleosides;
 wherein the gap segment is positioned between the 5' wing segment and the 3' wing segment; the four linked nucleosides of the 5' wing segment are a 2'-O-methoxyethyl sugar, a constrained ethyl (cEt) sugar, a constrained ethyl (cEt) sugar, and a constrained ethyl (cEt) sugar in the 5' to 3' direction; the four linked nucleosides of the 3' wing segment are a constrained ethyl (cEt) sugar, a constrained ethyl (cEt) sugar, a constrained ethyl (cEt) sugar, and a 2'-O-methoxyethyl sugar in the 5' to 3' direction; each internucleoside linkage is a phosphorothioate linkage; and each cytosine is a 5-methylcytosine.

In certain embodiments, a compound targeted to androgen receptor comprises a single-stranded modified oligonucleotide consisting of 16 linked nucleosides having a nucleobase sequence consisting of the sequence of SEQ ID NO: 39, or a pharmaceutically acceptable salt thereof, wherein the modified oligonucleotide comprises:
 a gap segment consisting of 8 linked deoxynucleosides;
 a 5' wing segment consisting of five linked nucleosides; and
 a 3' wing segment consisting of three linked nucleosides;
 wherein the gap segment is positioned between the 5' wing segment and the 3' wing segment; the five linked nucleosides of the 5' wing segment are a 2'-O-methoxyethyl sugar, a 2'-O-methoxyethyl sugar, a constrained ethyl (cEt) sugar, a constrained ethyl (cEt) sugar, and a constrained ethyl (cEt) sugar in the 5' to 3' direction; the three linked nucleosides of the 3' wing segment are each a constrained ethyl (cEt) sugar; each internucleoside linkage is a phosphorothioate linkage; and each cytosine is a 5-methylcytosine.

In certain embodiments, a compound targeted to androgen receptor comprises a single-stranded modified oligonucleotide consisting of 16 linked nucleosides having a nucleobase sequence consisting of the sequence of SEQ ID NO: 39, or a pharmaceutically acceptable salt thereof, wherein the modified oligonucleotide comprises:
 a gap segment consisting of 7 linked deoxynucleosides;
 a 5' wing segment consisting of four linked nucleosides; and
 a 3' wing segment consisting of five linked nucleosides;
 wherein the gap segment is positioned between the 5' wing segment and the 3' wing segment; the four linked nucleosides of the 5' wing segment are a 2'-O-methoxyethyl sugar, a constrained ethyl (cEt) sugar, a constrained ethyl (cEt) sugar, and a constrained ethyl (cEt) sugar in the 5' to 3' direction; the five linked nucleosides of the 3' wing segment are a constrained ethyl (cEt) sugar, a constrained ethyl (cEt) sugar, a constrained ethyl (cEt) sugar, a 2'-O-methoxyethyl sugar, and a 2'-O-methoxyethyl sugar in the 5' to 3' direction; each internucleoside linkage is a phosphorothioate linkage; and each cytosine is a 5-methylcytosine.

In certain embodiments, a compound targeted to androgen receptor comprises a single-stranded modified oligonucleotide consisting of 16 linked nucleosides having a nucleobase sequence consisting of the sequence of SEQ ID NO: 35, or a pharmaceutically acceptable salt thereof, wherein the modified oligonucleotide comprises:
 a gap segment consisting of 7 linked deoxynucleosides;
 a 5' wing segment consisting of six linked nucleosides; and
 a 3' wing segment consisting of three linked nucleosides;
 wherein the gap segment is positioned between the 5' wing segment and the 3' wing segment; the six linked nucleosides of the 5' wing segment are a 2'-O-methoxyethyl sugar, a constrained ethyl (cEt) sugar, a constrained ethyl (cEt) sugar, a 2'-O-methoxyethyl sugar, a constrained ethyl (cEt) sugar, and a constrained ethyl (cEt) sugar in the 5' to 3' direction; the three linked nucleosides of the 3' wing segment are each a constrained ethyl (cEt) sugar; each internucleoside linkage is a phosphorothioate linkage; and each cytosine is a 5-methylcytosine.

In certain embodiments, a compound targeted to androgen receptor comprises a single-stranded modified oligonucleotide consisting of 16 linked nucleosides having a nucleobase sequence consisting of the sequence of SEQ ID NO: 43, or a pharmaceutically acceptable salt thereof, wherein the modified oligonucleotide comprises:

a gap segment consisting of 10 linked deoxynucleosides;
a 5' wing segment consisting of three linked nucleosides; and
a 3' wing segment consisting of three linked nucleosides;
wherein the gap segment is positioned between the 5' wing segment and the 3' wing segment; each nucleoside of each wing segment comprises a constrained ethyl (cEt) sugar; each internucleoside linkage is a phosphorothioate linkage; and each cytosine is a 5-methylcytosine.

In certain embodiments, a compound targeted to androgen receptor comprises a single-stranded modified oligonucleotide consisting of 16 linked nucleosides having a nucleobase sequence consisting of the sequence of SEQ ID NO: 124, or a pharmaceutically acceptable salt thereof, wherein the modified oligonucleotide comprises:

a gap segment consisting of 10 linked deoxynucleosides;
a 5' wing segment consisting of three linked nucleosides; and
a 3' wing segment consisting of three linked nucleosides;
wherein the gap segment is positioned between the 5' wing segment and the 3' wing segment; each nucleoside of each wing segment comprises a constrained ethyl (cEt) sugar; each internucleoside linkage is a phosphorothioate linkage; and each cytosine is a 5-methylcytosine.

In certain embodiments, a compound targeted to androgen receptor comprises a single-stranded modified oligonucleotide consisting of 16 linked nucleosides having a nucleobase sequence consisting of the sequence of SEQ ID NO: 150, or a pharmaceutically acceptable salt thereof, wherein the modified oligonucleotide comprises:

a gap segment consisting of 10 linked deoxynucleosides;
a 5' wing segment consisting of three linked nucleosides; and
a 3' wing segment consisting of three linked nucleosides;
wherein the gap segment is positioned between the 5' wing segment and the 3' wing segment; each nucleoside of each wing segment comprises a constrained ethyl (cEt) sugar; each internucleoside linkage is a phosphorothioate linkage; and each cytosine is a 5-methylcytosine.

In certain embodiments, a compound targeted to androgen receptor comprises a single-stranded modified oligonucleotide consisting of 16 linked nucleosides having a nucleobase sequence consisting of the sequence of SEQ ID NO: 155, or a pharmaceutically acceptable salt thereof, wherein the modified oligonucleotide comprises:

a gap segment consisting of 10 linked deoxynucleosides;
a 5' wing segment consisting of three linked nucleosides; and
a 3' wing segment consisting of three linked nucleosides;
wherein the gap segment is positioned between the 5' wing segment and the 3' wing segment; each nucleoside of each wing segment comprises a constrained ethyl (cEt) sugar; each internucleoside linkage is a phosphorothioate linkage; and each cytosine is a 5-methylcytosine.

In certain embodiments, a compound targeted to androgen receptor comprises a single-stranded modified oligonucleotide consisting of 16 linked nucleosides having a nucleobase sequence consisting of the sequence of SEQ ID NO: 169, or a pharmaceutically acceptable salt thereof, wherein the modified oligonucleotide comprises:

a gap segment consisting of 10 linked deoxynucleosides;
a 5' wing segment consisting of three linked nucleosides; and
a 3' wing segment consisting of three linked nucleosides;
wherein the gap segment is positioned between the 5' wing segment and the 3' wing segment; each nucleoside of each wing segment comprises a constrained ethyl (cEt) sugar; each internucleoside linkage is a phosphorothioate linkage; and each cytosine is a 5-methylcytosine.

In certain embodiments, a compound targeted to androgen receptor comprises a single-stranded modified oligonucleotide consisting of 16 linked nucleosides having a nucleobase sequence consisting of the sequence of SEQ ID NO: 175, or a pharmaceutically acceptable salt thereof, wherein the modified oligonucleotide comprises:

a gap segment consisting of 10 linked deoxynucleosides;
a 5' wing segment consisting of three linked nucleosides; and
a 3' wing segment consisting of three linked nucleosides;
wherein the gap segment is positioned between the 5' wing segment and the 3' wing segment; each nucleoside of each wing segment comprises a constrained ethyl (cEt) sugar; each internucleoside linkage is a phosphorothioate linkage; and each cytosine is a 5-methylcytosine.

In certain embodiments, an antisense compound or antisense oligonucleotide targeted to an androgen receptor nucleic acid is complementary within the following nucleotide regions of SEQ ID NO: 1: 2957-2972, 3079-3094, 3099-3114, 3109-3124, 3113-3128, 3120-3135, 3133-3148, 3224-3239, 3226-3241, 3351-3366, 3353-3368, 3361-3376, 3388-3403, 3513-3528, 3517-3532, 3519-3534, 3641-3656, 3735-3750, 3764-3779, 3768-3783, 3798-3813, 3799-3814, 3851-3866, 3870-3885, 3874-3889, 3876-3891, 3878-3893, 3884-3899, 3886-3901, 3888-3903, 3901-3916, 3956-3971, 3962-3977, 3964-3979, 3967-3982, 4019-4034, 4038-4053, 4049-4064, 4056-4071, 4059-4074, 4062-4077, 4066-4081, 4070-4085, 4101-4116, 4103-4118, 4105-4120, 4109-4124, 4305-4320, 4405-4420, 4532-4547, 4534-4549, 4537-4552, 4539-4554, 4555-4570, 4571-4586, 4573-4588, 4578-4593, 4597-4612, 4632-4647, 4655-4670, 4656-4671, 4662-4677, 4699-4714, 4747-4762, 4750-4765, 4752-4767, 4754-4769, 4755-4770, 4769-4784, 4798-4813, 4804-4819, 4807-4822, 4833-4848, 4837-4852, 4839-4854, 4865-4880, 4868-4883, 4872-4887, 4874-4889, 4876-4891, 4887-4902, 4889-4904, 4916-4931, 4918-4933, 4938-4953, 4942-4957, 4944-4959, 4951-4966, 5050-5065, 5052-5067, 5054-5069, 5056-5071, 5060-5075, 5061-5076, 5062-5077, 5133-5148, 5141-5156, 5155-5170, 5265-5280, 5293-5308, 5308-5323, 5392-5407, 5448-5463, 5469-5484, 5481-5496, 5483-5498, 5486-5501, 5488-5503, 5494-5509, 5521-5536, 5666-5681, 6222-6237, 6701-6716, 7543-7558, 8471-8486, 8638-8653, 9464-9479, 10217-10232, 10250-10265, 10865-10880, 11197-11212, 11855-11870, 13189-13204, 13321-13336, 13346-13361, 16555-16570, 16793-16808, 16968-16983, 17206-17221, 18865-18880, 29329-29344, 32290-32305, 33315-33330, 39055-39070, 40615-40630, 42017-42032, 56050-56065, 58719-58734, 58720-58739, 58720-58735, 58721-58736, 58722-58737, 58723-58738, 58724-58739, 58724-58739, 58725-58740, 58725-58740, 58725-58740, 58750-58769, 58750-58765, 58751-58766, 58752-58767, 58753-58768, 58754-58769, 58755-58770, 60902-60917, 67454-67469, 102156-102171, 114874-114889, 115272-115287, 115365-115380, 134971-134986, 139682-139697, 139762-139777, 139782-139797, 144856-144871, 144938-144953, 148406-148421, 148443-148458, 148520-148535, 181695-181710, 182958-182973, or 183049-183064.

In certain embodiments, an antisense compound or antisense oligonucleotide targeted to an androgen receptor nucleic acid target the following nucleotide regions of SEQ ID NO: 1: 2957-2972, 3079-3094, 3099-3114, 3109-3124, 3113-3128, 3120-3135, 3133-3148, 3224-3239, 3226-3241, 3351-3366, 3353-3368, 3361-3376, 3388-3403, 3513-3528, 3517-3532, 3519-3534, 3641-3656, 3735-3750, 3764-3779, 3768-3783, 3798-3813, 3799-3814, 3851-3866, 3870-3885, 3874-3889, 3876-3891, 3878-3893, 3884-3899, 3886-3901, 3888-3903, 3901-3916, 3956-3971, 3962-3977, 3964-3979, 3967-3982, 4019-4034, 4038-4053, 4049-4064, 4056-4071, 4059-4074, 4062-4077, 4066-4081, 4070-4085, 4101-4116, 4103-4118, 4105-4120, 4109-4124, 4305-4320, 4405-4420, 4532-4547, 4534-4549, 4537-4552, 4539-4554, 4555-4570, 4571-4586, 4573-4588, 4578-4593, 4597-4612, 4632-4647, 4655-4670, 4656-4671, 4662-4677, 4699-4714, 4747-4762, 4750-4765, 4752-4767, 4754-4769, 4755-4770, 4769-4784, 4798-4813, 4804-4819, 4807-4822, 4833-4848, 4837-4852, 4839-4854, 4865-4880, 4868-4883, 4872-4887, 4874-4889, 4876-4891, 4887-4902, 4889-4904, 4916-4931, 4918-4933, 4938-4953, 4942-4957, 4944-4959, 4951-4966, 5050-5065, 5052-5067, 5054-5069, 5056-5071, 5060-5075, 5061-5076, 5062-5077, 5133-5148, 5141-5156, 5155-5170, 5265-5280, 5293-5308, 5308-5323, 5392-5407, 5448-5463, 5469-5484, 5481-5496, 5483-5498, 5486-5501, 5488-5503, 5494-5509, 5521-5536, 5666-5681, 6222-6237, 6701-6716, 7543-7558, 8471-8486, 8638-8653, 9464-9479, 10217-10232, 10250-10265, 10865-10880, 11197-11212, 11855-11870, 13189-13204, 13321-13336, 13346-13361, 16555-16570, 16793-16808, 16968-16983, 17206-17221, 18865-18880, 29329-29344, 32290-32305, 33315-33330, 39055-39070, 40615-40630, 42017-42032, 56050-56065, 58719-58734, 58720-58739, 58720-58735, 58721-58736, 58722-58737, 58723-58738, 58724-58739, 58724-58739, 58725-58740, 58725-58740, 58725-58740, 58750-58769, 58750-58765, 58751-58766, 58752-58767, 58753-58768, 58754-58769, 58755-58770, 60902-60917, 67454-67469, 102156-102171, 114874-114889, 115272-115287, 115365-115380, 134971-134986, 139682-139697, 139762-139777, 139782-139797, 144856-144871, 144938-144953, 148406-148421, 148443-148458, 148520-148535, 181695-181710, 182958-182973, or 183049-183064.

In certain embodiments, antisense compounds or antisense oligonucleotides target a region of an androgen receptor nucleic acid. In certain embodiments, such compounds or oligonucleotides targeted to a region of an androgen receptor nucleic acid have a contiguous nucleobase portion that is complementary to an equal length nucleobase portion of the region. For example, the portion can be at least an 8, 9, 10, 11, 12, 13, 14, 15, or 16 contiguous nucleobases portion complementary to an equal length portion of a region recited herein. In certain embodiments, such compounds or oligonucleotide target the following nucleotide regions of SEQ ID NO: 1: 2957-2972, 3079-3094, 3099-3114, 3109-3124, 3113-3128, 3120-3135, 3133-3148, 3224-3239, 3226-3241, 3351-3366, 3353-3368, 3361-3376, 3388-3403, 3513-3528, 3517-3532, 3519-3534, 3641-3656, 3735-3750, 3764-3779, 3768-3783, 3798-3813, 3799-3814, 3851-3866, 3870-3885, 3874-3889, 3876-3891, 3878-3893, 3884-3899, 3886-3901, 3888-3903, 3901-3916, 3956-3971, 3962-3977, 3964-3979, 3967-3982, 4019-4034, 4038-4053, 4049-4064, 4056-4071, 4059-4074, 4062-4077, 4066-4081, 4070-4085, 4101-4116, 4103-4118, 4105-4120, 4109-4124, 4305-4320, 4405-4420, 4532-4547, 4534-4549, 4537-4552, 4539-4554, 4555-4570, 4571-4586, 4573-4588, 4578-4593, 4597-4612, 4632-4647, 4655-4670, 4656-4671, 4662-4677, 4699-4714, 4747-4762, 4750-4765, 4752-4767, 4754-4769, 4755-4770, 4769-4784, 4798-4813, 4804-4819, 4807-4822, 4833-4848, 4837-4852, 4839-4854, 4865-4880, 4868-4883, 4872-4887, 4874-4889, 4876-4891, 4887-4902, 4889-4904, 4916-4931, 4918-4933, 4938-4953, 4942-4957, 4944-4959, 4951-4966, 5050-5065, 5052-5067, 5054-5069, 5056-5071, 5060-5075, 5061-5076, 5062-5077, 5133-5148, 5141-5156, 5155-5170, 5265-5280, 5293-5308, 5308-5323, 5392-5407, 5448-5463, 5469-5484, 5481-5496, 5483-5498, 5486-5501, 5488-5503, 5494-5509, or 5521-5536.

In certain embodiments, an antisense compound or antisense oligonucleotide provided herein targets AR within exon 1, for example within nucleotide regions 2863-5593 (exon 1) or 27672-27853 (exon 1B) of SEQ ID NO: 1. In certain embodiments, an antisense compound provided herein targeted to exon 1 of AR is complementary within any of the following nucleotide regions of SEQ ID NO: 1: 2957-2972, 3079-3094, 3099-3114, 3109-3124, 3113-3128, 3120-3135, 3133-3148, 3224-3239, 3226-3241, 3351-3366, 3353-3368, 3361-3376, 3388-3403, 3513-3528, 3517-3532, 3519-3534, 3641-3656, 3735-3750, 3764-3779, 3768-3783, 3798-3813, 3799-3814, 3851-3866, 3870-3885, 3874-3889, 3876-3891, 3878-3893, 3884-3899, 3886-3901, 3888-3903, 3901-3916, 3956-3971, 3962-3977, 3964-3979, 3967-3982, 4019-4034, 4038-4053, 4047-4062, 4049-4064, 4056-4071, 4059-4074, 4062-4077, 4066-4081, 4070-4085, 4101-4116, 4103-4118, 4105-4120, 4109-4124, 4305-4320, 4405-4420, 4532-4547, 4534-4549, 4537-4552, 4539-4554, 4555-4570, 4571-4586, 4573-4588, 4578-4593, 4597-4612, 4632-4647, 4655-4670, 4656-4671, 4662-4677, 4699-4714, 4747-4762, 4750-4765, 4752-4767, 4754-4769, 4755-4770, 4769-4784, 4798-4813, 4804-4819, 4807-4822, 4833-4848, 4837-4852, 4839-4854, 4865-4880, 4868-4883, 4872-4887, 4874-4889, 4876-4891, 4887-4902, 4889-4904, 4916-4931, 4918-4933, 4938-4953, 4942-4957, 4944-4959, 4951-4966, 5050-5065, 5052-5067, 5054-5069, 5056-5071, 5060-5075, 5061-5076, 5062-5077, 5133-5148, 5141-5156, 5155-5170, 5265-5280, 5293-5308, 5308-5323, 5392-5407, 5448-5463, 5469-5484, 5481-5496, 5483-5498, 5486-5501, 5488-5503, 5494-5509, or 5521-5536.

In certain embodiments, an antisense compound or antisense oligonucleotide provided herein targets AR within exon 2, for example within nucleotide regions 102087-102238 (exon 2) or 139551-139834 (exon 2c) of SEQ ID NO: 1. In certain embodiments, an antisense compound provided herein targeted to exon 2 of AR is complementary within any of the following nucleotide regions of SEQ ID NO: 1: 102155-102170, 102156-102171, 139682-139697, 139762-139777, or 139782-139797.

In certain embodiments, an antisense compound or antisense oligonucleotide provided herein targets AR within exon 3, for example within nucleotide regions 144841-144957 (exon 3), 148380-148594 (exon 3b), or 153504-154908 (exon 3d) of SEQ ID NO: 1. In certain embodiments, an antisense compound provided herein targeted to exon 3 of AR is complementary within any of the following nucleotide regions of SEQ ID NO: 1: 144856-144871, 144938-144953, 148406-148421, 148443-148458, or 148520-148535.

In certain embodiments, an antisense compound or antisense oligonucleotide provided herein targets AR within exon 7, for example within nucleotide region 181658-181815 of SEQ ID NO: 1. In certain embodiments, an antisense compound provided herein targeted to exon 7 of AR is complementary within nucleotide region 181695-181710 of SEQ ID NO: 1.

In certain embodiments, an antisense compound or antisense oligonucleotide provided herein targets AR within exon 8, for example within nucleotide region 182517-189455 of SEQ ID NO: 1. In certain embodiments, an antisense compound provided herein targeted to exon 8 of AR is complementary within nucleotide regions 182958-182973 or 183049-183064 of SEQ ID NO: 1.

In certain embodiments, an antisense compound or antisense oligonucleotide provided herein targets AR within intron 1, for example within nucleotide regions 5594-27671 or 27854-102086 of SEQ ID NO: 1. In certain embodiments, an antisense compound provided herein targeted to intron 1 of AR is complementary within any of the following nucleotide regions of SEQ ID NO: 1: 5666-5681, 6222-6237, 6701-6716, 7543-7558, 8471-8486, 8638-8653, 9464-9479, 10217-10232, 10250-10265, 10865-10880, 11197-11212, 11855-11870, 13189-13204, 13321-13336, 13346-13361, 16555-16570, 16793-16808, 16968-16983, 17206-17221, 18865-18880, 29329-29344, 32290-32305, 33315-33330, 39055-39070, 40615-40630, 42017-42032, 56050-56065, 58719-58734, 58720-58739, 58720-58735, 58721-58736, 58722-58737, 58723-58738, 58724-58739, 58724-58739, 58725-58740, 58725-58740, 58725-58740, 58750-58769, 58750-58765, 58751-58766, 58752-58767, 58753-58768, 58754-58769, 58755-58770, 60902-60917, or 67454-67469.

In certain embodiments, an antisense compound or antisense oligonucleotide provided herein targets AR within intron 2, for example within nucleotide regions 102239-139550 or 139835-144840 of SEQ ID NO: 1. In certain embodiments, an antisense compound provided herein targeted to intron 2 of AR is complementary within any of the following nucleotide regions of SEQ ID NO: 1: 114874-114889, 115272-115287, 115365-115380, or 134971-134986.

In certain embodiments, the following nucleotide regions of SEQ ID NO: 1, when targeted by antisense compounds or antisense oligonucleotides, display at least 50% inhibition: 3099-3114, 3120-3135, 3351-3366, 3353-3368, 3361-3376, 3513-3528, 3519-3534, 3768-3783, 3799-3814, 3851-3866, 3888-3903, 4059-4074, 4534-4549, 4555-4570, 4571-4586, 4578-4593, 4655-4670, 4699-4714, 4750-4765, 4755-4770, 4865-4880, 5054-5069, 5060-5075, 5061-5076, 5062-5077, 5155-5170, 5265-5280, 5392-5407, 5448-5463, 5483-5498, 7543-7558, 8471-8486, 8638-8653, 9464-9479, 10217-10232, 10250-10265, 10865-10880, 11197-11212, 11855-11870, 13189-13204, 13321-13336, 13346-13361, 16555-16570, 16793-16808, 16968-16983, 17206-17221, 18865-18880, 29329-29344, 32290-32305, 33315-33330, 39055-39070, 40615-40630, 42017-42032, 56050-56065, 58719-58734, 58720-58735, 58720-58739, 58721-58736, 58722-58737, 58723-58738, 58724-58739, 58725-58740, 58750-58765, 58750-58769, 58751-58766, 58752-58767, 58753-58768, 58754-58769, 58755-58770, 60902-60917, 67454-67469, 102156-102171, 114874-114889, 114874-114889, 115272-115287, 115365-115380, 134971-134986, 144856-144871, 181695-181710, 182958-182973, and 183049-183064.

In certain embodiments, the following nucleotide regions of SEQ ID NO: 1, when targeted by antisense compounds or antisense oligonucleotides, display at least 60% inhibition: 3799-3814, 3851-3866, 3888-3903, 4059-4074, 4534-4549, 4555-4570, 4571-4586, 4578-4593, 4655-4670, 4699-4714, 4755-4770, 4865-4880, 5060-5075, 5061-5076, 5062-5077, 5155-5170, 5265-5280, 5392-5407, 5448-5463, 5483-5498, 7543-7558, 8471-8486, 8638-8653, 9464-9479, 10217-10232, 10250-10265, 10865-10880, 11197-11212, 11855-11870, 13189-13204, 13321-13336, 13346-13361, 16555-16570, 16793-16808, 16968-16983, 17206-17221, 18865-18880, 29329-29344, 32290-32305, 33315-33330, 42017-42032, 56050-56065, 58719-58734, 58720-58735, 58720-58739, 58721-58736, 58722-58737, 58723-58738, 58724-58739, 58725-58740, 58750-58765, 58750-58769, 58751-58766, 58752-58767, 58753-58768, 58754-58769, 58755-58770, 67454-67469, 102156-102171, 115272-115287, 115365-115380, 144856-144871, 181695-181710, 182958-182973, and 183049-183064.

In certain embodiments, the following nucleotide regions of SEQ ID NO: 1, when targeted by antisense compounds or antisense oligonucleotides, display at least 70% inhibition: 3799-3814, 3851-3866, 3888-3903, 4059-4074, 4534-4549, 4655-4670, 4699-4714, 4755-4770, 4865-4880, 5060-5075, 5062-5077, 5155-5170, 5265-5280, 5392-5407, 5448-5463, 5483-5498, 7543-7558, 8471-8486, 8638-8653, 9464-9479, 10865-10880, 11197-11212, 11855-11870, 13189-13204, 13321-13336, 13346-13361, 16555-16570, 16793-16808, 16968-16983, 17206-17221, 18865-18880, 33315-33330, 42017-42032, 58719-58734, 58720-58739, 58720-58735, 58721-58736, 58722-58737, 58723-58738, 58724-58739, 58725-58740, 58750-58769, 58750-58765, 58751-58766, 58752-58767, 58753-58768, 58754-58769, 58755-58770, 102156-102171, 115365-115380, 144856-144871, 181695-181710, 182958-182973, and 183049-183064.

In certain embodiments, the following nucleotide regions of SEQ ID NO: 1, when targeted by antisense compounds or antisense oligonucleotides, display at least 80% inhibition: 3799-3814, 3851-3866, 3888-3903, 4059-4074, 4534-4549, 4655-4670, 4699-4714, 4755-4770, 4865-4880, 5060-5075, 5062-5077, 5155-5170, 5265-5280, 5392-5407, 5448-5463, 5483-5498, 8471-8486, 8638-8653, 9464-9479, 10865-10880, 11197-11212, 13189-13204, 16793-16808, 58719-58734, 58720-58735, 58721-58736, 58722-58737, 58723-58738, 58724-58739, 58725-58740, 58750-58765, 58751-58766, 58752-58767, 58753-58768, 58754-58769, 58755-58770, 102156-102171, 144856-144871, 181695-181710, 182958-182973, and 183049-183064.

In certain embodiments, the following nucleotide regions of SEQ ID NO: 1, when targeted by antisense compounds or antisense oligonucleotides, display at least 90% inhibition: 4534-4549, 5060-5075, 5062-5077, 5155-5170, 5265-5280, 5448-5463, 58720-58735, 58721-58736, 58722-58737, 58723-58738, 58724-58739, 58725-58740, 58750-58765, 58751-58766, 58752-58767, 58753-58768, 58754-58769, 58755-58770, 182958-182973, and 183049-183064.

In certain embodiments, the following antisense compounds or antisense oligonucleotides target a region of an androgen receptor nucleic acid and effect at least a 50% inhibition of an androgen receptor mRNA, ISIS IDs: 549332, 549334, 549338, 549347, 549358, 549360, 549361, 549362, 549366, 549371, 549372, 549374, 549377, 549379, 549380, 549381, 549387, 549390, 549414, 549432, 549434, 549457, 549458, 549459, 560071, 560098, 560099, 560100, 560131, 560132, 560133, 560137, 569213, 569215, 569216, 569220, 569222, 569223, 569227, 569228, 569229, 569236, 569238, 583559, 583567, 583608, 583609, 583613, 583635, 583638, 583662, 583795, 583796, 583799, 583834, 583919, 584145, 584148, 584149, 584152, 584157, 584158, 584162, 584163, 584165, 584166, 584167, 584168, 584179, 584180, 584183, 584184, 584192, 584233, 584242, 584245, 584263, 584269, 584274, 584312, 584329, 584361, 584465, 584465, 584468, 584469, 584469, 584495, 584495, 585233, 585259, 585262, 585263, 585264, 585265, 585268, 585269, 585271, 585274, 586124, 586224, 586224, 586225, 586225, 586227, and 586227.

In certain embodiments, the following antisense compounds or antisense oligonucleotides target a region of an androgen receptor nucleic acid and effect at least a 50% inhibition of an androgen receptor mRNA, SEQ ID NOs: 12, 13, 14, 15, 16, 17, 18, 19, 20, 21, 22, 23, 24, 25, 26, 27, 29, 31, 32, 33, 34, 35, 36, 37, 38, 39, 40, 41, 42, 43, 46, 49, 53, 54, 55, 57, 59, 63, 92, 93, 95, 101, 125, 148, 149, 150, 151, 152, 153, 154, 155, 156, 157, 158, 159, 160, 161, 162, 163, 164, 165, 166, 167, 168, 169, 170, 171, 172, 173, 174, 175, 176, and 177.

In certain embodiments, the following antisense compounds or antisense oligonucleotides target a region of an androgen receptor nucleic acid and effect at least a 60% inhibition of an androgen receptor mRNA, ISIS IDs: 549332, 549334, 549338, 549347, 549358, 549360, 549361, 549362, 549366, 549371, 549372, 549374, 549377, 549379, 549380, 549381, 549387, 549390, 549414, 549432, 549434, 549457, 549458, 549459, 560071, 560098, 560099, 560100, 560131, 560137, 569213, 569216, 569222, 569228, 569236, 583795, 583796, 583799, 584145, 584148, 584149, 584152, 584157, 584158, 584162, 584163, 584165, 584166, 584167, 584168, 584179, 584180, 584183, 584184, 584192, 584233, 584242, 584245, 584274, 584312, 584361, 584468, 584469, 585233, 585259, 585262, 585263, 585264, 585265, 585268, 585269, 585274, 586124, 586224, 586225, and 586227.

In certain embodiments, the following antisense compounds or antisense oligonucleotides target a region of an androgen receptor nucleic acid and effect at least a 60% inhibition of an androgen receptor mRNA, SEQ ID NOs: 12, 13, 14, 15, 16, 17, 18, 19, 20, 21, 22, 23, 24, 25, 26, 27, 29, 31, 32, 33, 34, 35, 36, 37, 38, 39, 40, 41, 42, 43, 92, 93, 95, 148, 149, 150, 151, 152, 153, 154, 155, 156, 157, 158, 159, 160, 161, 162, 163, 164, 165, 166, 167, 170, 171, 173, 175, and 176.

In certain embodiments, the following antisense compounds or antisense oligonucleotides target a region of an androgen receptor nucleic acid and effect at least a 70% inhibition of an androgen receptor mRNA, ISIS IDs: 549332, 549334, 549338, 549347, 549358, 549360, 549361, 549362, 549366, 549371, 549372, 549374, 549377, 549379, 549380, 549381, 549387, 549390, 549414, 549432, 549434, 549457, 549458, 549459, 560071, 560098, 560099, 560100, 560131, 560137, 569222, 584145, 584148, 584149, 584152, 584162, 584163, 584165, 584166, 584167, 584168, 584179, 584180, 584183, 584184, 584192, 584245, 584274, 584469, 585259, 585262, 585268, 585269, 586124, 586224, 586225, and 586227.

In certain embodiments, the following antisense compounds or antisense oligonucleotides target a region of an androgen receptor nucleic acid and effect at least a 70% inhibition of an androgen receptor mRNA, SEQ ID NOs: 12, 13, 14, 15, 16, 17, 18, 19, 20, 21, 22, 23, 24, 25, 26, 27, 29, 31, 32, 33, 34, 35, 36, 37, 38, 39, 40, 41, 43, 148, 149, 150, 151, 154, 155, 156, 157, 158, 159, 160, 161, 162, 163, 164, 167, 170, and 176.

In certain embodiments, the following antisense compounds or antisense oligonucleotides target a region of an androgen receptor nucleic acid and effect at least a 80% inhibition of an androgen receptor mRNA, ISIS IDs: 549332, 549334, 549338, 549347, 549358, 549360, 549361, 549362, 549366, 549371, 549372, 549374, 549377, 549379, 549380, 549381, 549387, 549390, 549414, 549432, 549434, 549457, 549458, 549459, 560098, 560099, 560100, 560137, 584148, 584149, 584152, 584162, 584163, 584166, 584180, 586124, 586224, 586225, and 586227.

In certain embodiments, the following antisense compounds or antisense oligonucleotides target a region of an androgen receptor nucleic acid and effect at least a 80% inhibition of an androgen receptor mRNA, SEQ ID NOs: 12, 13, 14, 15, 16, 17, 18, 19, 20, 21, 22, 23, 24, 25, 26, 27, 29, 31, 32, 33, 34, 35, 36, 37, 39, 40, 41, 43, 149, 150, 151, 154, 155, 157, and 161.

In certain embodiments, the following antisense compounds or antisense oligonucleotides target a region of an androgen receptor nucleic acid and effect at least a 90% inhibition of an androgen receptor mRNA, ISIS IDs: 549358, 549371, 549372, 549374, 549377, 549380, 549432, 549434, 549457, 549458, 549459, 560098, 560099, 560100, 560137, and 586224.

In certain embodiments, the following antisense compounds or antisense oligonucleotides target a region of an androgen receptor nucleic acid and effect at least a 90% inhibition of an androgen receptor mRNA, SEQ ID NOs: 16, 21, 22, 23, 24, 26, 33, 34, 35, 36, 37, 39, 40, and 41.

Percent inhibition of androgen receptor mRNA can be determined using standard methods known to those of skill in the art, such as described in Example 1.

It is understood that the sequence set forth in each SEQ ID NO in the examples contained herein is independent of any modification to a sugar moiety, an internucleoside linkage, or a nucleobase. As such, antisense compounds defined by a SEQ ID NO may comprise, independently, one or more modifications to a sugar moiety, an internucleoside linkage, or a nucleobase. Antisense compounds described by ISIS number (ISIS #) indicate a combination of nucleobase sequence, chemical modification, and motif.

In certain embodiments, the compounds or compositions as described herein are efficacious by virtue of having at least one of an in vitro $IC_{50}$ of less than 250 nM, less than 200 nM, less than 150 nM, less than 100 nM, less than 90 nM, less than 80 nM, less than 70 nM, less than 65 nM, less than 60 nM, less than 55 nM, less than 50 nM, less than 45 nM, less than 40 nM, less than 35 nM, less than 30 nM, less than 25 nM, or less than 20 nM when delivered to HuVEC cells. In certain embodiments inhibition is measured with primer probe set RTS3559, as described herein.

In certain embodiments, the compounds or compositions as described herein are highly tolerable as demonstrated by having at least one of an increase an ALT or AST value of no more than 4 fold, 3 fold, or 2 fold over saline treated animals or an increase in liver, spleen, or kidney weight of no more than 30%, 20%, 15%, 12%, 10%, 5%, or 2%. In certain embodiments, the compounds or compositions as described herein are highly tolerable as demonstrated by having no increase of ALT or AST over saline treated animals. In certain embodiments, the compounds or compositions as described herein are highly tolerable as demonstrated by having no increase in liver, spleen, or kidney weight over saline treated animals.

In certain embodiments, an antisense compound provided herein targets an AR splicing variant that includes exon 1 encoding the N-terminal domain and exons 2 and 3 encoding the DNA binding domain, but does not include at least a portion of exon 4 encoding the short hinge region or at least a portion of exons 4-8 encoding the ligand binding domain.

An example of such an AR splicing variant includes, but is not limited to, AR-V7, which contains exons 1-3 but lacks exons 4-8. Additional examples of such AR splicing variants include, for example, AR3, AR4, AR4b, AR5, and AR6 (SEQ ID NOs: 4-8, respectively). In certain embodiments, an antisense compound targeted to AR upstream of the 3' end of exon 3 and/or upstream of the ligand binding domain is capable of inhibiting androgen receptor levels to a greater extent than an antisense compound targeted to the ligand binding domain, such as EZN-4176, which is targeted to exon 4 and corresponds to SEQ ID NO: 58 described in U.S. Pat. No. 7,737,125.

In certain embodiments, an antisense compound targets an AR splicing variant that has a functional DNA binding domain, but not a functional ligand binding domain. It will be understood that in certain embodiments an antisense compound can target an AR splicing variant that includes the entire or at least a functional portion of exon 1 encoding the N-terminal domain and the entire or at least a functional portion of exons 2 and 3 encoding the DNA binding domain, but does not include at least a functional portion of exon 4 encoding the short hinge region or at least a functional portion of exons 4-8 encoding the ligand binding domain. It is contemplated that certain AR splicing variants targeted by the antisense compounds provided herein substantially consisting of exons 1-3 may also include a non-functional portion of nucleic acid sequence from a genomic region or exons 4-8. It is contemplated that the splicing process may give rise to such AR splicing variants that retain DNA binding function but not ligand binding function. In certain embodiments, an antisense compound targeted to an AR splicing variant that has a functional DNA binding domain, but not a functional ligand binding domain, is capable of inhibiting growth or proliferation of prostate cancer cells that are castrate-resistant. In certain embodiments, an antisense compound targeted to an AR splicing variant that has a functional DNA binding domain, but not a functional ligand binding domain, is capable of inhibiting growth or proliferation of a prostate cancer cell resistant to a diarylhydantoin AR inhibitor of Formula XI to a greater extent than an antisense compound targeted to the ligand binding domain, such as EZN-4176, which is targeted to exon 4 and corresponds to SEQ ID NO: 58 described in U.S. Pat. No. 7,737,125. In certain embodiments, an antisense compound provided herein targets AR within exon 1, which is upstream of the 3' end of exon 3 and/or upstream of the ligand binding domain. In certain embodiments, an antisense compound provided herein targets AR within exon 2, which is upstream of the 3' end of exon 3 and/or upstream of the ligand binding domain. In certain embodiments, an antisense compound provided herein targets AR within intron 1, which is upstream of the 3' end of exon 3 and/or upstream of the ligand binding domain.

In certain embodiments, an antisense compound provided herein is capable of reducing expression of both full-length AR and an AR splicing variant that includes exon 1 encoding the N-terminal domain and exons 2 and 3 encoding the DNA binding domain, but does not include at least a portion of exon 4 encoding the short hinge region or at least a portion of any one of exons 4-8 encoding the ligand binding domain. In certain embodiments, such an antisense compound targets human androgen receptor upstream of the ligand binding domain. In certain embodiments, such antisense compounds target human androgen receptor upstream of the 3' end of exon 3. In certain embodiments, an antisense compound provided herein targets AR within exon 1, which is upstream of the 3' end of exon 3 and/or upstream of the ligand binding domain. In certain embodiments, an antisense compound provided herein targets AR within exon 2, which is upstream of the 3' end of exon 3 and/or upstream of the ligand binding domain. In certain embodiments, an antisense compound provided herein targets AR within intron 1, which is upstream of the 3' end of exon 3 and/or upstream of the ligand binding domain.

In certain embodiments, an antisense compound provided herein targets an AR splicing variant that includes exon 1 encoding the N-terminal domain and exons 2 and 3 encoding the DNA binding domain, but does not include at least a portion of exon 4 encoding the short hinge region or at least a portion of exons 4-8 encoding the ligand binding domain. An example of such an AR splicing variant includes, but is not limited to, AR-V7, which contains exons 1-3 but lacks exons 4-8.

Certain embodiments are drawn to an antisense compound targeted to human androgen receptor (AR) upstream of the ligand binding domain that is capable of inhibiting growth or proliferation of the resistant prostate cancer cell to a greater extent than an antisense compound targeted to the ligand binding domain, such as EZN-4176, which is targeted to exon 4 and corresponds to SEQ ID NO: 58 described in U.S. Pat. No. 7,737,125. In certain embodiments, an antisense compound targeted to human androgen receptor (AR) upstream of the ligand binding domain is targeted to a region of AR upstream of the 3' end of exon 3. In certain embodiments, an antisense compound provided herein targets AR within exon 1, which is upstream of the 3' end of exon 3 and/or upstream of the ligand binding domain. In certain embodiments, an antisense compound provided herein targets AR within exon 2, which is upstream of the 3' end of exon 3 and/or upstream of the ligand binding domain. In certain embodiments, an antisense compound provided herein targets AR within intron 1, which is upstream of the 3' end of exon 3 and/or upstream of the ligand binding domain.

In certain embodiments, the nucleobase sequence of a modified oligonucleotide provided herein is at least 70%, 75%, 80%, 85%, 90%, 95% or 100% complementary to any one of SEQ ID NOs: 1-8, as measured over the entirety of the modified oligonucleotide.

In certain embodiments, an antisense compound is a modified oligonucleotide consisting of 12 to 30 linked nucleosides and having a nucleobase sequence at least 90% complementary to any of SEQ ID NOs: 1-8 as measured over the entirety of said modified oligonucleotide.

In certain embodiments, an antisense compound is a modified oligonucleotide consisting of 12 to 30 linked nucleosides and having a nucleobase sequence 100% complementary to any of SEQ ID NOs: 1-8 as measured over the entirety of said modified oligonucleotide. In certain embodiments, a compound or modified oligonucleotide provided herein is single-stranded.

In certain embodiments, a modified oligonucleotide provided herein consists of 8, 9, 10, 11, 12, 13, 14, 15, 16, 17, 18, 19, 20, 21, 22, 23, 24, 25, 26, 27, 28, 29 or 30 linked nucleosides. In certain embodiments, the modified oligonucleotide consists of 20 linked nucleosides. In certain embodiments, the modified oligonucleotide consists of 16 linked nucleosides.

In certain embodiments, at least one internucleoside linkage of a modified oligonucleotide provided herein is a modified internucleoside linkage. In certain embodiments, each internucleoside linkage is a phosphorothioate internucleoside linkage.

In certain embodiments, at least one nucleoside of the modified oligonucleotide comprises a modified sugar. In certain embodiments, at least one modified sugar comprises a 2'-O-methoxyethyl group (2'-O(CH$_2$)$_2$—OCH$_3$). In certain embodiments, the modified sugar comprises a 2'-O—CH$_3$ group.

In certain embodiments, at least one modified sugar is a bicyclic sugar. In certain embodiments, the bicyclic sugar comprises a 4'-(CH$_2$)$_n$—O-2' bridge, wherein n is 1 or 2. In certain embodiments, the bicyclic sugar comprises a 4'-CH$_2$—O-2' bridge. In certain embodiments, the bicyclic sugar comprises a 4-CH(CH$_3$)—O-2' bridge.

In certain embodiments, at least one nucleoside of a modified oligonucleotide provided herein comprises a modified nucleobase. In certain embodiments, the modified nucleobase is a 5-methylcytosine.

In certain embodiments, a modified oligonucleotide provided herein consists of a single-stranded modified oligonucleotide.

In certain embodiments, compounds or compositions provided herein comprise a salt of the modified oligonucleotide.

Compositions and Methods for Formulating Pharmaceutical Compositions

Antisense oligonucleotides may be admixed with pharmaceutically acceptable active or inert substances for the preparation of pharmaceutical compositions or formulations. Compositions and methods for the formulation of pharmaceutical compositions are dependent upon a number of criteria, including, but not limited to, route of administration, extent of disease, or dose to be administered.

An antisense compound targeted to an androgen receptor nucleic acid can be utilized in pharmaceutical compositions by combining the antisense compound with a suitable pharmaceutically acceptable diluent or carrier. In certain embodiments, a pharmaceutically acceptable diluent is water, such as sterile water suitable for injection. Accordingly, in one embodiment, employed in the methods described herein is a pharmaceutical composition comprising an antisense compound targeted to an androgen receptor nucleic acid and a pharmaceutically acceptable diluent. In certain embodiments, the pharmaceutically acceptable diluent is water. In certain embodiments, the antisense compound is an antisense oligonucleotide provided herein.

Pharmaceutical compositions comprising antisense compounds encompass any pharmaceutically acceptable salts, esters, or salts of such esters, or any other oligonucleotide which, upon administration to an animal, including a human, is capable of providing (directly or indirectly) the biologically active metabolite or residue thereof. Accordingly, for example, the disclosure is also drawn to pharmaceutically acceptable salts of antisense compounds, prodrugs, pharmaceutically acceptable salts of such prodrugs, and other bioequivalents. Suitable pharmaceutically acceptable salts include, but are not limited to, sodium and potassium salts.

A prodrug can include the incorporation of additional nucleosides at one or both ends of an antisense compound which are cleaved by endogenous nucleases within the body, to form the active antisense compound.

In certain embodiments, the compounds or compositions further comprise a pharmaceutically acceptable carrier or diluent.

Certain Indications

Certain aspects of the invention are directed to methods of treating cancer which comprises administering an antisense compound targeted to androgen receptor as provided herein. In certain embodiments, the cancer is AR positive. In certain embodiments, the cancer is prostate cancer, breast cancer, ovarian cancer, bladder cancer or gastric cancer. In certain embodiments, the antisense compound targeted to androgen receptor comprises a modified oligonucleotide consisting of 10 to 30 linked nucleosides and having a nucleobase sequence comprising at least 8, 9, 10, 11, 12, 13, 14, 15, 16, 17, 18, 19, or 20 contiguous nucleobases of any of SEQ ID NOs: 12-179. In certain embodiments, the antisense compound targeted to androgen receptor comprises a modified oligonucleotide consisting of 10 to 30 linked nucleosides and having a nucleobase sequence comprising any of SEQ ID NOs: 12-179. In certain embodiments, the antisense compound targeted to androgen receptor comprises a modified oligonucleotide consisting of the nucleobase sequence of any of SEQ ID NOs: 12-179. In certain embodiments, the antisense compound targeted to androgen receptor comprises a modified oligonucleotide consisting of 16 linked nucleosides and having a nucleobase sequence consisting of SEQ ID NO: 35, 39, 43, 124, 150, 155, 169, or 175. In certain embodiments, the antisense compound is single-stranded. In certain embodiments, the antisense compound targeted to androgen receptor is ISIS 560131, ISIS 569213, ISIS 569216, ISIS 569221, ISIS 569236, ISIS 579671, ISIS 586124, ISIS 583918, ISIS 584149, ISIS 584163, ISIS 584269, or ISIS 584468.

Certain aspects are directed to an antisense compound targeted to androgen receptor provided herein for use in treating cancer. In certain embodiments, the cancer is AR positive. In certain embodiments, the cancer is prostate cancer, breast cancer, ovarian cancer, bladder cancer or gastric cancer. In certain embodiments, the antisense compound targeted to androgen receptor comprises a modified oligonucleotide consisting of 10 to 30 linked nucleosides and having a nucleobase sequence comprising at least 8, 9, 10, 11, 12, 13, 14, 15, 16, 17, 18, 19, or 20 contiguous nucleobases of any of SEQ ID NOs: 12-179. In certain embodiments, the antisense compound targeted to androgen receptor comprises a modified oligonucleotide consisting of 10 to 30 linked nucleosides and having a nucleobase sequence comprising any of SEQ ID NOs: 12-179. In certain embodiments, the antisense compound targeted to androgen receptor comprises a modified oligonucleotide consisting of the nucleobase sequence of any of SEQ ID NOs: 12-179. In certain embodiments, the antisense compound targeted to androgen receptor comprises a modified oligonucleotide consisting of 16 linked nucleosides and having a nucleobase sequence consisting of SEQ ID NO: 35, 39, 43, 124, 150, 155, 169, or 175. In certain embodiments, the antisense compound is single-stranded. In certain embodiments, the antisense compound targeted to androgen receptor is ISIS 560131, ISIS 569213, ISIS 569216, ISIS 569221, ISIS 569236, ISIS 579671, ISIS 586124, ISIS 583918, ISIS 584149, ISIS 584163, ISIS 584269, or ISIS 584468.

Certain aspects are directed to use of an antisense compound targeted to androgen receptor provided herein for the manufacture of a medicament for treating cancer. In certain embodiments, the cancer is AR positive. In certain embodiments, the cancer is prostate cancer, breast cancer, ovarian cancer, bladder cancer or gastric cancer. In certain embodiments, the antisense compound targeted to androgen receptor comprises a modified oligonucleotide consisting of 10 to 30 linked nucleosides and having a nucleobase sequence comprising at least 8, 9, 10, 11, 12, 13, 14, 15, 16, 17, 18, 19, or 20 contiguous nucleobases of any of SEQ ID NOs: 12-179. In certain embodiments, the antisense compound targeted to androgen receptor comprises a modified oligonucleotide consisting of 10 to 30 linked nucleosides and having a nucleobase sequence comprising any of SEQ ID NOs: 12-179. In certain embodiments, the antisense compound targeted to androgen receptor comprises a modified oligonucleotide consisting of the nucleobase sequence of any of SEQ ID NOs: 12-179. In certain embodiments, the antisense compound targeted to androgen receptor comprises a modified oligonucleotide consisting of 16 linked nucleosides and having a nucleobase sequence consisting of SEQ ID NO: 35, 39, 43, 124, 150, 155, 169, or 175. In certain embodiments, the antisense compound is single-stranded. In certain embodiments, the antisense compound targeted to androgen receptor is ISIS 560131, ISIS 569213, ISIS 569216, ISIS 569221, ISIS 569236, ISIS 579671, ISIS 586124, ISIS 583918, ISIS 584149, ISIS 584163, ISIS 584269, or ISIS 584468.

Certain aspects of the invention are directed to the use of an antisense compound targeted to human androgen receptor (AR) as described herein, for treating a cancer patient whose cancer has become resistant to treatment with an anti-androgenic agent (e.g. compound or drug). In certain embodiments, said cancer is prostate cancer. In certain embodiments, said patient is one that has, or whose cancer has, developed resistance to treatment with an agent selected from: MDV3100, ARN-059, ODM-201, abiraterone acetate, TOK001, TAK700 and VT464. In certain embodiments, the antisense compound targeted to androgen receptor comprises a modified oligonucleotide consisting of 10 to 30 linked nucleosides and having a nucleobase sequence comprising at least 8, 9, 10, 11, 12, 13, 14, 15, 16, 17, 18, 19, or 20 contiguous nucleobases of any of SEQ ID NOs: 12-179. In certain embodiments, the antisense compound targeted to androgen receptor comprises a modified oligonucleotide consisting of 10 to 30 linked nucleosides and having a nucleobase sequence comprising any of SEQ ID NOs: 12-179. In certain embodiments, the antisense compound targeted to androgen receptor comprises a modified oligonucleotide consisting of the nucleobase sequence of any of SEQ ID NOs: 12-179. In certain embodiments, the antisense compound targeted to androgen receptor comprises a modified oligonucleotide consisting of 16 linked nucleosides and having a nucleobase sequence consisting of SEQ ID NO: 35, 39, 43, 124, 150, 155, 169, or 175. In certain embodiments, the antisense compound targets AR within exon 1, for example within nucleotide regions 2863-5593 (exon 1) or 27672-27853 (exon 1B) of SEQ ID NO: 1. In certain embodiments, an antisense compound provided herein targeted to exon 1 of AR is complementary within any of the following nucleotide regions of SEQ ID NO: 1: 2957-2972, 3079-3094, 3099-3114, 3109-3124, 3113-3128, 3120-3135, 3133-3148, 3224-3239, 3226-3241, 3351-3366, 3353-3368, 3361-3376, 3388-3403, 3513-3528, 3517-3532, 3519-3534, 3641-3656, 3735-3750, 3764-3779, 3768-3783, 3798-3813, 3799-3814, 3851-3866, 3870-3885, 3874-3889, 3876-3891, 3878-3893, 3884-3899, 3886-3901, 3888-3903, 3901-3916, 3956-3971, 3962-3977, 3964-3979, 3967-3982, 4019-4034, 4038-4053, 4049-4064, 4056-4071, 4059-4074, 4062-4077, 4066-4081, 4070-4085, 4101-4116, 4103-4118, 4105-4120, 4109-4124, 4305-4320, 4405-4420, 4532-4547, 4534-4549, 4537-4552, 4539-4554, 4555-4570, 4571-4586, 4573-4588, 4578-4593, 4597-4612, 4632-4647, 4655-4670, 4656-4671, 4662-4677, 4699-4714, 4747-4762, 4750-4765, 4752-4767, 4754-4769, 4755-4770, 4769-4784, 4798-4813, 4804-4819, 4807-4822, 4833-4848, 4837-4852, 4839-4854, 4865-4880, 4868-4883, 4872-4887, 4874-4889, 4876-4891, 4887-4902, 4889-4904, 4916-4931, 4918-4933, 4938-4953, 4942-4957, 4944-4959, 4951-4966, 5050-5065, 5052-5067, 5054-5069, 5056-5071, 5060-5075, 5061-5076, 5062-5077, 5133-5148, 5141-5156, 5155-5170, 5265-5280, 5293-5308, 5308-5323, 5392-5407, 5448-5463, 5469-5484, 5481-5496, 5483-5498, 5486-5501, 5488-5503, 5494-5509, or 5521-5536. In certain embodiments, an antisense compound provided herein targets AR within exon 2, for example within nucleotide regions 102087-102238 (exon 2) or 139551-139834 (exon 2c) of SEQ ID NO: 1. In certain embodiments, an antisense compound provided herein targeted to exon 2 of AR is complementary within any of the following nucleotide regions of SEQ ID NO: 1: 102155-102170, 102156-102171, 139682-139697, 139762-139777, or 139782-139797. In certain embodiments, an antisense compound provided herein targets AR within exon 3, for example within nucleotide regions 144841-144957 (exon 3), 148380-148594 (exon 3b), or 153504-154908 (exon 3d) of SEQ ID NO: 1. In certain embodiments, an antisense compound provided herein targeted to exon 3 of AR is complementary within any of the following nucleotide regions of SEQ ID NO: 1: 144856-144871, 144938-144953, 148406-148421, 148443-148458, or 148520-148535. In certain embodiments, an antisense compound provided herein targets AR within intron 1, for example within nucleotide regions 5594-27671 or 27854-102086 of SEQ ID NO: 1. In certain embodiments, an antisense compound provided herein targeted to intron 1 of AR is complementary within any of the following nucleotide regions of SEQ ID NO: 1: 5666-5681, 6222-6237, 6701-6716, 7543-7558, 8471-8486, 8638-8653, 9464-9479, 10217-10232, 10250-10265, 10865-10880, 11197-11212, 11855-11870, 13189-13204, 13321-13336, 13346-13361, 16555-16570, 16793-16808, 16968-16983, 17206-17221, 18865-18880, 29329-29344, 32290-32305, 33315-33330, 39055-39070, 40615-40630, 42017-42032, 56050-56065, 58719-58734, 58720-58739, 58720-58735, 58721-58736, 58722-58737, 58723-58738, 58724-58739, 58724-58739, 58725-58740, 58725-58740, 58725-58740, 58750-58769, 58750-58765, 58751-58766, 58752-58767, 58753-58768, 58754-58769, 58755-58770, 60902-60917, or 67454-67469. In certain embodiments, an antisense compound provided herein targets AR within intron 2, for example within nucleotide regions 102239-139550 or 139835-144840 of SEQ ID NO: 1. In certain embodiments, an antisense compound provided herein targeted to intron 2 of AR is complementary within any of the following nucleotide regions of SEQ ID NO: 1: 114874-114889, 115272-115287, 115365-115380, or 134971-134986. In certain embodiments, the antisense compound is single-stranded. In certain embodiments, the antisense compound targeted to androgen receptor is ISIS 560131, ISIS 569213, ISIS 569216, ISIS 569221, ISIS 569236, ISIS 579671, ISIS 586124, ISIS 583918, ISIS 584149, ISIS 584163, ISIS 584269, or ISIS 584468.

By resistant to treatment with a particular agent (e.g. compound or drug) is meant that the agent is less or no longer effective in halting the growth or spread of the cancer and so the patient, or their cancer, has become less responsive or sensitive to it over time. Typically such patient would be classed as resistant to said agent and would no longer be treated with such agent. A subject having prostate cancer resistant to an agent selected from: MDV3100, ARN-059, ODM-201, abiraterone acetate, TOK001, TAK700 and VT464 can include, for example, a patient who previously received said agent but whose prostate cancer has become less sensitive or responsive to a agent. For example, prostate cancer resistant to an anti-androgenic agent selected from: MDV3100, ARN-059, ODM-201, abiraterone acetate, TOK001, TAK700 and VT464, can include prostate cancer that has increased in tumor volume, metastasis, or progression despite treatment with the agent. In certain embodiments, prostate cancer resistant to an anti-androgenic agent selected from: MDV3100, ARN-059, ODM-201, abiraterone acetate, TOK001, TAK700 and VT464, can include prostate cancer that is refractory to the agent and is not decreasing in tumor volume, metastasis, or progression despite treatment. Several embodiments relate to a method of treating prostate cancer resistant to an anti-androgenic agent selected from: MDV3100, ARN-059, ODM-201, abiraterone acetate, TOK001, TAK700 and VT464, in a subject comprising identifying the subject as having prostate cancer resistant to the agent and administering to the subject an antisense compound targeted to human androgen receptor (AR) upstream of the 3' end of exon 3 and/or upstream of the ligand binding domain, as described herein. Several embodiments relate to a method of treating prostate cancer resistant to an anti-androgenic agent selected from: MDV3100, ARN-059, ODM-201, abiraterone acetate, TOK001, TAK700 and VT464, in a subject comprising administering to a subject identified or diagnosed as having prostate cancer resistant to said anti-androgenic agent an antisense compound targeted to human androgen receptor (AR) upstream of the 3' end of exon 3 and/or upstream of the ligand binding domain, as described herein. In certain embodiments, prostate cancer cells resistant to an anti-androgenic agent selected from: MDV3100, ARN-059, ODM-201, abiraterone acetate, TOK001, TAK700 and VT464, preferentially expresses an AR splicing variant over full-length AR.

Certain aspects of the invention are directed to a method of treating a patient suffering from prostate cancer wherein the patient has, or their cancer has, developed or become resistant to treatment with an anti-androgenic agent (compound or drug) comprising administering to said patient an antisense compound targeted to human androgen receptor (AR) as described herein. In certain embodiments, said patient is one that has developed resistance to treatment with an agent selected from: MDV3100, ARN-059, ODM-201, abiraterone acetate, TOK001, TAK700 and VT464. In certain embodiments, the antisense compound targeted to androgen receptor comprises a modified oligonucleotide consisting of 10 to 30 linked nucleosides and having a nucleobase sequence comprising at least 8, 9, 10, 11, 12, 13, 14, 15, 16, 17, 18, 19, or 20 contiguous nucleobases of any of SEQ ID NOs: 12-179. In certain embodiments, the antisense compound targeted to androgen receptor comprises a modified oligonucleotide consisting of 10 to 30 linked nucleosides and having a nucleobase sequence comprising any of SEQ ID NOs: 12-179. In certain embodiments, the antisense compound targeted to androgen receptor comprises a modified oligonucleotide consisting of the nucleobase sequence of any of SEQ ID NOs: 12-179. In certain embodiments, the antisense compound targeted to androgen receptor comprises a modified oligonucleotide consisting of 16 linked nucleosides and having a nucleobase sequence consisting of SEQ ID NO: 35, 39, 43, 124, 150, 155, 169, or 175. In certain embodiments, the antisense compound is single-stranded. In certain embodiments, the antisense compound targeted to androgen receptor is ISIS 560131, ISIS 569213, ISIS 569216, ISIS 569221, ISIS 569236, ISIS 579671, ISIS 586124, ISIS 583918, ISIS 584149, ISIS 584163, ISIS 584269, or ISIS 584468.

A prostate cancer that has developed or become resistant to treatment with an anti-androgenic agent is referred to as castrate-resistant prostate cancer (CRPC). Thus, in several embodiments, a prostate cancer cell resistant to an anti-androgenic agent, such as MDV3100, was previously exposed to the inhibitor and has become less responsive or sensitive to it over time. For example, MDV3100 might initially inhibit prostate cancer cell growth or proliferation in the patient, but over time such inhibitory effect may be diminished when the cells become resistant to the inhibitor.

Certain aspects of the invention are directed to the use of an antisense compound targeted to androgen receptor provided herein for the manufacture of a medicament for treating cancer in a patient whose cancer has become become resistant to treatment with an anti-androgenic agent (compound or drug). In certain embodiments the cancer is prostate cancer. In certain embodiments, said patient is one that has, or whose cancer has, developed resistance to treatment with an agent selected from: MDV3100, ARN-059, ODM-201, abiraterone acetate, TOK001, TAK700 and VT464. In certain embodiments, the antisense compound targeted to androgen receptor comprises a modified oligonucleotide consisting of 10 to 30 linked nucleosides and having a nucleobase sequence comprising at least 8, 9, 10, 11, 12, 13, 14, 15, 16, 17, 18, 19, or 20 contiguous nucleobases of any of SEQ ID NOs: 12-179. In certain embodiments, the antisense compound targeted to androgen receptor comprises a modified oligonucleotide consisting of 10 to 30 linked nucleosides and having a nucleobase sequence comprising any of SEQ ID NOs: 12-179. In certain embodiments, the antisense compound targeted to androgen receptor comprises a modified oligonucleotide consisting of the nucleobase sequence of any of SEQ ID NOs: 12-179. In certain embodiments, the antisense compound targeted to androgen receptor comprises a modified oligonucleotide consisting of 16 linked nucleosides and having a nucleobase sequence consisting of SEQ ID NO: 35, 39, 43, 124, 150, 155, 169, or 175. In certain embodiments, the antisense compound is single-stranded. In certain embodiments, the antisense compound targeted to androgen receptor is ISIS 560131, ISIS 569213, ISIS 569216, ISIS 569221, ISIS 569236, ISIS 579671, ISIS 586124, ISIS 583918, ISIS 584149, ISIS 584163, ISIS 584269, or ISIS 584468.

Enzalutamide:

MDV3100, also known as enzalutamide (Xtandi™) and by the IUPAC name 4-(3-(4-cyano-3-(trifluoromethyl)phenyl)-5,5-dimethyl-4-oxo-2-thioxoimidazolidin-1-yl)-2-fluoro-N-methylbenzamide, is an androgen receptor ligand binding inhibitor belonging to the diarylhydantoin class of androgen receptor inhibitors represented by Formula XI. MDV3100 has the following chemical formula:

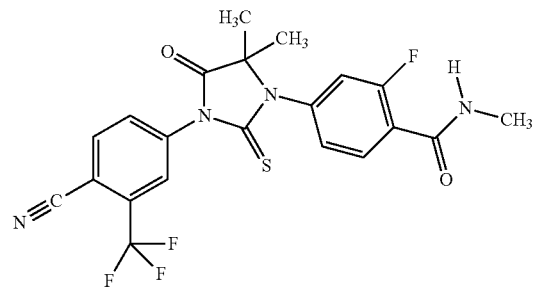 [SMILES: CNC(=O)c1ccc(N2C(=S)N(c3ccc(C#N)c(C(F)(F)F)c3)C(=O)C2(C)C)cc1F]

MDV3100 and additional diarylhydantoin androgen receptor inhibitors suitable for use in certain embodiments provided herein are described in U.S. Pat. No. 7,709,517, US Patent Application Publication No. US20100172975 and US Patent Application Publication No. US20100210665, which are incorporated herein by reference in their entireties.

ARN-509:

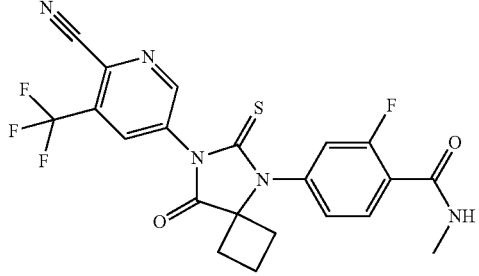

(XII)

The compound of Formula XII, also known as ARN-509 and by the IUPAC name 4-(7-(6-Cyano-5-(trifluoromethyl)pyridin-3-yl)-6,8-dioxo-5,7-diazaspiro[3.4]octan-5-yl)-2-fluoro-N-methylbenzamide, is an androgen receptor ligand binding inhibitor. ARN-509 and additional androgen receptor inhibitors suitable for use in certain embodiments provided herein are described in WO 2007126765, WO 2008119015 and US Patent Application Publication No. 2013/0116258, which are incorporated herein by reference in their entirety.

Abiraterone Acetate

The compound of Formula XIII, which is also known as Abiraterone acetate and ZYTIG-A® and by the IUPAC name [(3S,8R,9S,10R,13S,14S)-10,13-dimethyl-17-(3-pyridyl)-2,3,4,7,8,9,11,12,14,15-decahydro-1H-cyclopenta[a]phenanthren-3-yl]acetate, is an androgen biosynthesis inhibitor and has the following chemical formula:

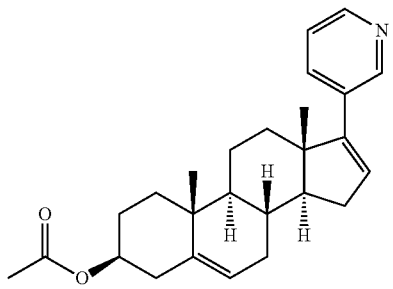

(XIII)

The structure and synthesis of Abiraterone acetate is described in Potter et al., Journal of Medicinal Chemistry (38(13), 2463-71, 1995), which is incorporated herein by reference in its entirety.

Galeterone:

The compound of Formula XIV, which is also known as TOK-001 and Galeterone, and by the IUPAC name (3S,10R,13S)-17-(1H-benzo[d]imidazol-1-yl)-10,13-dimethyl-2,3,4,7,8,9,10,11,12,13,14,15-dodecahydro-1H-cyclopenta[a]phenanthren-3-ol, has the following chemical formula:

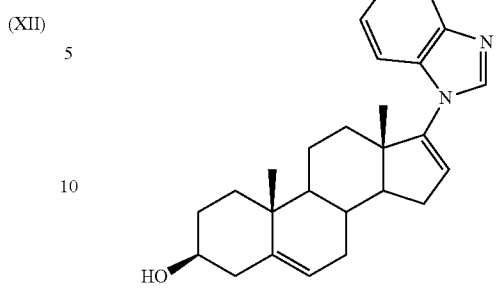

(XIV)

The structure and synthesis of TOK-001 is described in Handratta et al., (Journal of Medicinal Chemistry (2005), 48(8), 2972-84, 2005), which is incorporated herein by reference in its entirety:

Orteronel:

The compound of Formula XV, which is also known as TAK-700 and Orteronel and by the IUPAC name 6-[7(S)-hydroxy-6,7-dihydro-5H-pyrrolo[1,2-c]imidazol-7-yl]-N-methylnaphthalene-2-carboxamide, is an androgen biosynthesis inhibitor and has the following chemical formula:

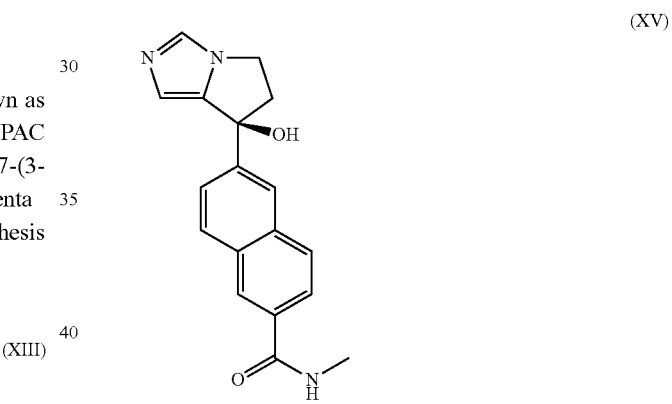

(XV)

The structure and synthesis of TAK-700 is described in Kaku et al., Bioorganic and Medicinal Chemistry (19(21), 6383-99, 2011).

Yin et al., (Int. J. Mol. Sci., 14(7):13958-13978, 2013) discusses recent progress with various pharmaceutical therapies, including ODM-21, VT464, ARN509, TAK700 and TOK-001, for castration-resistant prostate cancer.

Certain Combinations and Combination Therapies

In certain embodiments, a first agent comprising the compound described herein is co-administered with one or more secondary agents. In certain embodiments, such second agents are designed to treat the same disease, disorder, or condition as the first agent described herein. In certain embodiments, such second agents are designed to treat a different disease, disorder, or condition as the first agent described herein. In certain embodiments, a first agent is designed to treat an undesired side effect of a second agent. In certain embodiments, second agents are co-administered with the first agent to treat an undesired effect of the first agent. In certain embodiments, such second agents are designed to treat an undesired side effect of one or more pharmaceutical compositions as described herein. In certain embodiments, second agents are co-administered with the first agent to produce a combinational effect. In certain embodiments, second agents are co-administered with the first agent to produce a synergistic effect. In certain embodiments, the co-administration of the first and second agents permits use of lower dosages than would be required to achieve a therapeutic or prophylactic effect if the agents were administered as independent therapy.

In certain embodiments, one or more compounds or compositions provided herein are co-administered with one or more anti-androgenic agents. In certain embodiments, one or more compounds or compositions provided herein and one or more anti-androgenic agents, are administered at different times. In certain embodiments, one or more compounds or compositions provided herein and one or more anti-androgenic agents, are prepared together in a single formulation. In certain embodiments, one or more compounds or compositions provided herein and one or more anti-androgenic agents, are prepared separately. In certain embodiments, an anti-androgenic agent is selected from MDV3100, ARN-059, ODM-201, abiraterone, TOK001, TAK700 and VT464.

Certain aspects of the invention are directed to the use of an antisense compound targeted to human androgen receptor (AR) as described herein in combination with an anti-androgenic agent. In particular embodiments such use is in a method of treating a patient suffering from cancer or in the manufacture of a medicament for treating cancer. In certain embodiments the cancer is selected from: prostate cancer, breast cancer, ovarian cancer, bladder cancer or gastric cancer. Particular classes of anti-androgenic agents are the second generation anti-hormonal agents such as: enzalutamide (MDV3100), ARN-059, ODM-201, abiraterone acetate, Galeterone (TOK001), orteronel (TAK700) and VT464 (see Yin et al. supra).

Certain aspects are drawn to a combination of an antisense compound targeted to human androgen receptor (AR) as described herein and an anti-androgenic agent, such as a second generation anti-hormonal agent selected from: MDV3100, ARN-059, ODM-201, abiraterone, TOK001, TAK700 and VT464.

In certain embodiments, such a combination of an antisense compound targeted to androgen receptor (AR) as described herein and an anti-androgenic agent, such as a second generation anti-hormonal agent selected from: MDV3100, ARN-059, ODM-201, abiraterone, TOK001, TAK700 and VT464, is useful for inhibiting cancer cell growth or proliferation and/or treating cancer. In certain embodiments the cancer is selected from: prostate cancer, breast cancer, ovarian cancer, bladder cancer or gastric cancer. In certain embodiments the cancer is prostate cancer. In certain embodiments the cancer is breast cancer. In certain embodiments, an antisense compound targeted to AR as described herein and an anti-androgenic agent, such as a second generation anti-hormonal agent selected from: MDV3100, ARN-059, ODM-201, abiraterone, TOK001, TAK700 and VT464, synergize in combination to inhibit growth or proliferation of a cancer cell. In several embodiments, the cancer cell is a prostate cancer cell which is or has become castration-resistant. In various embodiments, the cancer cell is a prostate cancer cell which is or has become resistant to a second generation anti-hormonal agent selected from: MDV3100, ARN-059, ODM-201, abiraterone, TOK001, TAK700 and VT464. In certain embodiments, the antisense compound targeted to androgen receptor comprises a modified oligonucleotide consisting of 10 to 30 linked nucleosides and having a nucleobase sequence comprising at least 8, 9, 10, 11, 12, 13, 14, 15, 16, 17, 18, 19, or 20 contiguous nucleobases of any of SEQ ID NOs: 12-179. In certain embodiments, the antisense compound targeted to androgen receptor comprises a modified oligonucleotide consisting of 10 to 30 linked nucleosides and having a nucleobase sequence comprising any of SEQ ID NOs: 12-179. In certain embodiments, the antisense compound targeted to androgen receptor comprises a modified oligonucleotide consisting of the nucleobase sequence of any of SEQ ID NOs: 12-179. In certain embodiments, the antisense compound targeted to androgen receptor comprises a modified oligonucleotide consisting of 16 linked nucleosides and having a nucleobase sequence consisting of SEQ ID NO: 35, 39, 43, 124, 150, 155, 169, or 175. In certain embodiments, the antisense compound targeted to androgen receptor is ISIS 560131, ISIS 569213, ISIS 569216, ISIS 569221, ISIS 569236, ISIS 579671, ISIS 586124, ISIS 583918, ISIS 584149, ISIS 584163, ISIS 584269, or ISIS 584468.

Several embodiments are drawn to a combination of an antisense compound targeted to human androgen receptor (AR) and a diarylhydantoin AR inhibitor of Formula XI, such as MDV3100. In several embodiments, a diarylhydantoin Androgen Receptor (AR) inhibitor is a compound of Formula XVI:

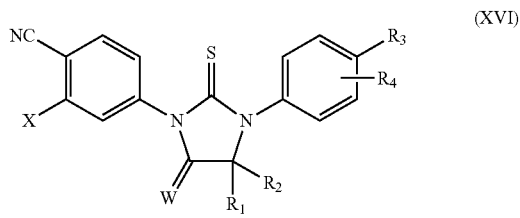

(XVI)

wherein X is selected from the group consisting of trifluoromethyl and iodo, wherein W is selected from the group consisting of O and NR5, wherein R5 is selected from the group consisting of H, methyl, and $$\begin{array}{c}\diagdown\\ \diagup\end{array}\!\!=\!\!D\\ \underset{|}{E}\\ G$$

wherein D is S or O and E is N or O and G is alkyl, aryl, substituted alkyl or substituted aryl; or D is S or a and E-G together are C1-C4 lower alkyl, wherein R1 and R2 together comprise eight or fewer carbon atoms and are selected from the group consisting of alkyl, substituted alkyl including haloalkyl, and, together with the carbon to which they are linked, a cycloalkyl or substituted cycloalkyl group, wherein R3 is selected from the group consisting of hydrogen, halogen, methyl, C1-C4 alkoxy, formyl, haloacetoxy, trifluoromethyl, cyano, nitro, hydroxyl, phenyl, amino, methylcarbamoyl, methoxycarbonyl, acetamido, methanesulfonamino, methanesulfonyl, 4-methanesulfonyl-1-piperazinyl, piperazinyl, and C1-C6 alkyl or alkenyl optionally substituted with hydroxyl, methoxycarbonyl, cyano, amino, amido, nitro, carbamoyl, or substituted carbamoyl including methylcarbamoyl, dimethylcarbamoyl, and hydroxyethylcarbamoyl, wherein R4 is selected from the group consisting of hydrogen, halogen, alkyl, and haloalkyl, and wherein R3 is not methylaminomethyl or dimethylaminomethyl.

R5 may be

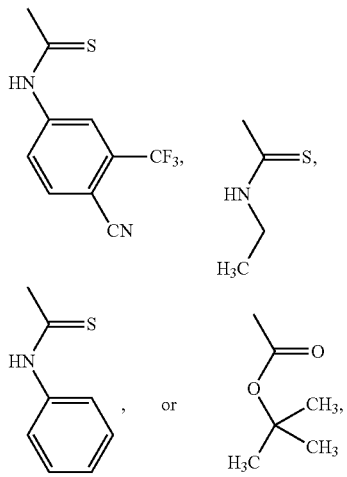

In certain embodiments, such a combination of an antisense compound targeted to androgen receptor (AR) and a diarylhydantoin AR inhibitor of Formula XVI, such as MDV3100, is useful for inhibiting prostate cancer cell growth or proliferation and/or treating prostate cancer. In certain embodiments, an antisense compound targeted to AR and a diarylhydantoin AR inhibitor of Formula XVI, such as MDV3100, synergize in combination to inhibit growth or proliferation of a prostate cancer cell. In several embodiments, the prostate cancer cell is castration-resistant. In various embodiments, the prostate cancer cell is resistant to a diarylhydantoin AR inhibitor of Formula XVI, such as MDV3100. In certain embodiments, the prostate cancer cell or castration-resistant prostate cancer cell preferentially expresses an AR splicing variant over full-length AR. In certain embodiments the antisense compound targeted to AR as described herein and the other anti-androgenic agent are used in combination treatment by administering the two agents simultaneously, separately or sequentially. In certain embodiments the two agents are formulated as a fixed dose combination product. In other embodiments the two agents are provided to the patient as separate units which can then either be taken simultaneously or serially (sequentially).

In certain embodiments, antisense compounds useful for inhibiting prostate cancer cell and/or castration-resistant prostate cancer cell growth or proliferation in combination with another anti-androgenic agent, such as a second generation anti-hormonal agent selected from: MDV3100, ARN-059, ODM-201, abiraterone, TOK001, TAK700 and VT464, target human androgen receptor upstream of the 3' end of exon 3 and/or upstream of the ligand binding domain. In certain embodiments, an antisense compound provided herein targets AR within exon 1, exon 2, exon 3, intron 1, or intron 2 as described herein.

In certain embodiments, an antisense compound provided herein targets an AR splicing variant that includes exon 1 encoding the N-terminal domain and exons 2 and 3 encoding the DNA binding domain, but does not include at least a portion of exon 4 encoding the short hinge region or at least a portion of exons 4-8 encoding the ligand binding domain. An example of such an AR splicing variant includes, but is not limited to, AR-V7, which contains exons 1-3 but lacks exons 4-8. Additional examples of such AR splicing variants include, for example, AR3, AR4, AR4b, AR5, and AR6 (SEQ ID NOs: 4-8, respectively). In certain embodiments, the prostate cancer cell, which may be castration-resistant, preferentially expresses an AR splicing variant over full-length AR. In particular embodiments the prostate cancer cell is castration-resistant to an anti-androgenic agent selected from: MDV3100, ARN-059, ODM-201, abiraterone, TOK001, TAK700 and VT464 In certain embodiments, an antisense compound targeted to AR upstream of the 3' end of exon 3 and/or upstream of the ligand binding domain is capable of inhibiting growth or proliferation of a prostate cancer cell, including a castration-resistant prostate cancer cell, in combination with an anti-androgenic agent selected from: MDV3100, ARN-059, ODM-201, abiraterone, TOK001, TAK700 and VT464, to a greater extent than an antisense compound targeted to the ligand binding domain, such as EZN-4176, which is targeted to exon 4 and corresponds to SEQ ID NO: 58 described in U.S. Pat. No. 7,737,125, in combination with the same anti-androgenic agent selected from: MDV3100, ARN-059, ODM-201, abiraterone, TOK001, TAK700 and VT464. In certain embodiments, the combination of an antisense compound as described herein and the anti-androgenic agent selected from: MDV3100, ARN-059, ODM-201, abiraterone, TOK001, TAK700 and VT464, provides a synergistic (e.g. greater-than-additive) effect in inhibiting the growth or proliferation of a prostate cancer cell, such as a castration-resistant prostate cancer cell, compared to the antisense compound alone or the anti-androgenic agent selected from: MDV3100, ARN-059, ODM-201, abiraterone, TOK001, TAK700 and VT464 alone. Accordingly, in certain embodiments the amounts of either or both of the antisense compound and/or anti-androgenic agent selected from: MDV3100, ARN-059, ODM-201, abiraterone, TOK001, TAK700 and VT464, when used in combination can be less than the corresponding amount of either the antisense compound alone or the anti-androgenic agent selected from: MDV3100, ARN-059, ODM-201, abiraterone, TOK001, TAK700 and VT464, alone necessary to achieve an equivalent level of prostate cancer cell growth or proliferation inhibition.

In certain embodiments, an antisense compound provided herein useful for inhibiting prostate cancer cell and/or castration-resistant prostate cancer cell growth or proliferation in combination with an anti-androgenic agent selected from: MDV3100, ARN-059, ODM-201, abiraterone, TOK001, TAK700 and VT464, targets an AR splicing variant that has a functional DNA binding domain, but not a functional ligand binding domain. It will be understood that in certain embodiments an antisense compound can target an AR splicing variant that includes the entire or at least a functional portion of exon 1 encoding the N-terminal domain and the entire or at least a functional portion of exons 2 and 3 encoding the DNA binding domain, but does not include at least a functional portion of exon 4 encoding the short hinge region or at least a functional portion of exons 4-8 encoding the ligand binding domain. It is contemplated that certain AR splicing variants targeted by the antisense compounds provided herein substantially consisting of exons 1-3 may also include a non-functional portion of nucleic acid sequence from a genomic region or exons 4-8. It is contemplated that the splicing process may give rise to such AR splicing variants that retain DNA binding function but not ligand binding function. In certain embodiments, the prostate cancer cell, which may be castrate-resistant, preferentially expresses an AR splicing variant over full-length AR.

In certain embodiments the prostate cancer cell is castrate-resistant to an anti-androgenic agent selected from: MDV3100, ARN-059, ODM-201, abiraterone, TOK001, TAK700 and VT464. In certain embodiments, an antisense compound provided herein targets AR within exon 1, which is upstream of the 3' end of exon 3 and/or upstream of the ligand binding domain. In certain embodiments, an antisense compound provided herein targets AR within exon 1, exon 2, exon 3, intron 1, or intron 2 as described herein.

In certain embodiments, an antisense compound targeted to an AR splicing variant that has a functional DNA binding domain, but not a functional ligand binding domain, is capable of inhibiting growth or proliferation of a prostate cancer cell, including a castration-resistant prostate cancer cell, in combination with a an anti-androgenic agent selected from: MDV3100, ARN-059, ODM-201, abiraterone, TOK001, TAK700 and VT464, to a greater extent than an antisense compound targeted to the ligand binding domain, such as EZN-4176, which is targeted to exon 4 and corresponds to SEQ ID NO: 58 described in U.S. Pat. No. 7,737,125, in combination with a the same anti-androgenic agent selected from: MDV3100, ARN-059, ODM-201, abiraterone, TOK001, TAK700 and VT464. In certain embodiments, the combination of an antisense compound and anti-androgenic agent selected from: MDV3100, ARN-059, ODM-201, abiraterone, TOK001, TAK700 and VT464, provides a synergistic (e.g. greater-than-additive) effect in inhibiting the growth or proliferation of a prostate cancer cell, such as a castration-resistant prostate cancer cell, compared to the antisense compound alone or the anti-androgenic agent alone. Accordingly, in certain embodiments the amounts of either or both of the antisense compound and/or anti-androgenic agent selected from: MDV3100, ARN-059, ODM-201, abiraterone, TOK001, TAK700 and VT464, when used in combination can be less than the corresponding amount of either the antisense compound alone or anti-androgenic agent, alone necessary to achieve an equivalent level of prostate cancer cell growth or proliferation inhibition.

In certain embodiments, an antisense compound provided herein useful for inhibiting prostate cancer cell and/or castration-resistant prostate cancer cell growth or proliferation in combination with a anti-androgenic agent selected from: MDV3100, ARN-059, ODM-201, abiraterone, TOK001, TAK700 and VT464 is capable of reducing expression of both full-length AR and an AR splicing variant that includes exon 1 encoding the N-terminal domain and exons 2 and 3 encoding the DNA binding domain, but does not include at least a portion of exon 4 encoding the short hinge region or at least a portion of any one of exons 4-8 encoding the ligand binding domain. In certain embodiments, such an antisense compound targets human androgen receptor upstream of the ligand binding domain. In certain embodiments, such antisense compounds target human androgen receptor upstream of the 3' end of exon 3. In certain embodiments, an antisense compound provided herein targets AR within exon 1, which is upstream of the 3' end of exon 3 and/or upstream of the ligand binding domain.

In certain embodiments, there is provided a combination of an antisense compound targeted to human androgen receptor (AR) as described herein and an anti-androgenic agent selected from: MDV3100, ARN-059, ODM-201, abiraterone, TOK001, TAK700 and VT464, wherein the antisense compound comprises a modified oligonucleotide consisting of 10 to 30 linked nucleosides and having a nucleobase sequence comprising at least 8, 9, 10, 11, 12, 13, 14, 15, 16, 17, 18, 19, or 20 contiguous nucleobases of any of SEQ ID NOs: 12-179. In certain embodiments, there is provided a combination of an antisense compound targeted to human androgen receptor (AR) and an anti-androgenic agent selected from: MDV3100, ARN-059, ODM-201, abiraterone, TOK001, TAK700 and VT464, wherein the antisense compound comprises a modified oligonucleotide consisting of 10 to 30 linked nucleosides and having a nucleobase sequence comprising any of SEQ ID NOs: 12-179. In certain embodiments, there is provided a combination of an antisense compound targeted to human androgen receptor (AR) and an anti-androgenic agent selected from: MDV3100, ARN-059, ODM-201, abiraterone, TOK001, TAK700 and VT464, wherein the antisense compound comprises a modified oligonucleotide consisting of the nucleobase sequence of any of SEQ ID NOs: 12-179. In certain embodiments, there is provided a combination of an antisense compound targeted to human androgen receptor (AR) and a diarylhydantoin AR inhibitor of Formula XI, such as MDV3100, wherein the antisense compound comprises a modified oligonucleotide consisting of 16 linked nucleosides and having a nucleobase sequence consisting of SEQ ID NO: 35, 39, 43, 124, 150, 155, 169, or 175. In certain embodiments, there is provided a combination of an antisense compound targeted to human androgen receptor (AR) and a diarylhydantoin AR inhibitor of Formula XI, such as MDV3100, wherein the antisense compound targeted to androgen receptor is ISIS 560131, ISIS 569213, ISIS 569216, ISIS 569221, ISIS 569236, ISIS 579671, ISIS 586124, ISIS 583918, ISIS 584149, ISIS 584163, ISIS 584269, or ISIS 584468.

Several embodiments are drawn to a method of inhibiting prostate cancer cell growth or proliferation comprising contacting the prostate cancer cell with an antisense compound targeted to human androgen receptor (AR) and an anti-androgenic agent selected from: MDV3100, ARN-059, ODM-201, abiraterone, TOK001, TAK700 and VT464. In certain embodiments, the antisense compound and an anti-androgenic agent selected from: MDV3100, ARN-059, ODM-201, abiraterone, TOK001, TAK700 and VT464, synergize in combination to inhibit the growth or proliferation of the prostate cancer cell. In several embodiments, the prostate cancer cell is castration-resistant. In various embodiments, the prostate cancer cell is castration-resistant by being resistant to an anti-androgenic agent selected from: MDV3100, ARN-059, ODM-201, abiraterone, TOK001, TAK700 and VT464. In certain embodiments, the prostate cancer cell or castration-resistant prostate cancer cell preferentially expresses an AR splicing variant over full-length AR.

In certain aspects of any of the foregoing embodiments, antisense compounds useful for inhibiting prostate cancer cell growth or proliferation in combination with a diarylhydantoin AR inhibitor of Formula XVI, such as MDV3100, can target (i) human androgen receptor upstream of the 3' end of exon 3 and/or upstream of the ligand binding domain or (ii) an AR splicing variant that has a functional DNA binding domain, but not a functional ligand binding domain; and/or is capable of (i) reducing expression of both full-length AR and an AR splicing variant that includes exon 1 encoding the N-terminal domain and exons 2 and 3 encoding the DNA binding domain, but does not include at least a portion of exon 4 encoding the short hinge region or at least a portion of any one of exons 4-8 encoding the ligand binding domain; with the proviso that the antisense compounds do not have a nucleobase sequence consisting of any of SEQ ID NOs: 194-215 identified in Table A below.

TABLE A

| SEQ ID NO: | Sequence |
|---|---|
| 194 | GAGAACCATCCTCACC |
| 195 | GGACCAGGTAGCCTGT |
| 196 | CCCCTGGACTCAGATG |
| 197 | GCACAAGGAGTGGGAC |
| 198 | GCTGTGAAGAGAGTGT |
| 199 | TTTGACACAAGTGGGA |
| 200 | GTGACACCCAGAAGCT |
| 201 | CATCCCTGCTTCATAA |
| 202 | TGGGGAGAACCATCCTCACCCTGC |
| 203 | TCCAGGACCAGGTAGCCTGTGGGG |
| 204 | TGTTCCCCTGGACTCAGATGCTCC |
| 205 | TGGGGCACAAGGAGTGGGACGCAC |
| 206 | TTCGGCTGTGAAGAGAGTGTGCCA |
| 207 | CGCTTTTGACACAAGTGGGACTGG |
| 208 | CATAGTGACACCCAGAAGCTTCAT |
| 209 | GAGTCATCCCTGCTTCATAACATT |
| 210 | CTGTGAAGAGAGT |
| 211 | TGTGAAGAGAGT |
| 212 | TTGACACAAGTGGG |
| 213 | TGACACAAGTGG |
| 214 | TGACACCCAGAAGC |
| 215 | GACACCCAGAAG |

In certain aspects of any of the foregoing embodiments, antisense compounds useful for inhibiting growth or proliferation of a prostate cancer cell resistant to anti-androgenic agent selected from: MDV3100, ARN-059, ODM-201, abiraterone, TOK001, TAK700 and VT464, can target (i) human androgen receptor upstream of the 3' end of exon 3 and/or upstream of the ligand binding domain or (ii) an AR splicing variant that has a functional DNA binding domain, but not a functional ligand binding domain; and/or is capable of (i) reducing expression of both full-length AR and an AR splicing variant that includes exon 1 encoding the N-terminal domain and exons 2 and 3 encoding the DNA binding domain, but does not include at least a portion of exon 4 encoding the short hinge region or at least a portion of any one of exons 4-8 encoding the ligand binding domain; or (ii) inhibiting growth or proliferation of the resistant prostate cancer cell to a greater extent than an antisense compound targeted to the ligand binding domain, such as EZN-4176; with the proviso that the antisense compounds do not have a nucleobase sequence consisting of any of SEQ ID NOs: 194-215 described in U.S. Pat. No. 7,737,125 as SEQ ID NOs: 2-9, 49-50, 52-53, 55-56, and 86-93 (herein incorporated by reference), and identified in Table A.

Certain aspects are directed to methods of treating breast cancer and methods of inhibiting breast cancer cell growth or proliferation with an antisense oligonucleotide targeted to human androgen receptor (AR) as described herein. In certain embodiments, the breast cancer has one or more of the following characteristics: Androgen Receptor positive, dependent on androgen for growth, Estrogen Receptor (ER) negative, independent of estrogen for growth, Progesterone Receptor (PR) negative, independent of progesterone for growth, or Her2/neu negative. In certain embodiments, the breast cancer or breast cancer cell is apocrine.

Certain embodiments are drawn to a method of treating breast cancer in a subject comprising administering to the subject an antisense compound targeted to human androgen receptor (AR). Certain embodiments are drawn to a method of treating breast cancer in a subject comprising identifying a subject having breast cancer and administering to the subject an antisense compound targeted to human androgen receptor (AR), thereby treating the subject's breast cancer. Certain embodiments are directed to a method of inhibiting growth or proliferation of a breast cancer cell comprising contacting the breast cancer cell with an antisense compound targeted to human androgen receptor (AR). Certain embodiments relate to a method of inhibiting AR expression in a subject having or at risk of having breast cancer comprising identifying a subject breast cancer, and administering to the subject an antisense compound targeted to human AR, wherein the antisense compound inhibits AR expression in the subject.

In certain embodiments, the breast cancer or breast cancer cell has one or more of the following characteristics: Androgen Receptor positive, dependent on androgen for growth, Estrogen Receptor (ER) negative, independent of estrogen for growth, Progesterone Receptor (PR) negative, independent of progesterone for growth, or Her2/neu negative. In certain embodiments, the breast cancer or breast cancer cell is ER, PR, and HER2 triple negative and AR positive (ER−, PR−, HER2−, AR+). In certain embodiments, the breast cancer or breast cancer cell is ER negative and AR positive (ER−, AR+). In certain embodiments, the breast cancer or breast cancer cell is ER positive and AR positive (ER+, AR+).

In certain embodiments, the breast cancer or breast cancer cell is apocrine. Apocrine breast cancers are often "triple negative", meaning that the cells do not express ER, PR, or HER2 receptors, and usually, but not necessarily, AR positive. In certain embodiments, an apocrine breast cancer or breast cancer cell is ER, PR, and HER2 triple negative and AR positive (ER−, PR−, HER2−, AR+). In certain embodiments, an apocrine breast cancer or breast cancer cell is ER negative and AR positive (ER−, AR+). In certain embodiments, an apocrine breast cancer or breast cancer cell originates from the sweat gland of the breast. In certain embodiments, an apocrine breast cancer or breast cancer cell is a ductal cancer or cancer cell of the breast. In certain embodiments, an apocrine breast cancer can have any one or more of the following features: a large amount of eosinophilic granular cytoplasm, well-defined margins, large vesicular nuclei, a nuclear to cytoplasmic ratio of about 1:2, and/or accumulations of secreted granules in the apical cytoplasm known as apical snouts.

In certain embodiments, the breast cancer or breast cancer cell is an ER negative and AR positive (ER−, AR+) molecular apocrine breast cancer or breast cancer cell. In certain aspects, an ER negative and AR positive (ER−, AR+) molecular apocrine breast cancer or breast cancer cell can further be PR positive, PR negative, HER2 negative, or HER2 positive.

Breast cancer can be identified as positive or negative with respect to hormone receptors, such as ER, PR, or HER2 by standard histological techniques. For example, histological breast cancer samples can be classified as "triple negative" (ER−, PR−, HER2−) when less than 1% of cells demonstrate nuclear staining for estrogen and progesterone receptors, and immunohistochemical staining for HER2 shows a 0, 1-fold, or a 2-fold positive score and a FISH ratio (HER2 gene signals to chromosome 17 signals) of less than 1.8 according to the relevant ASCO and CAP guidelines. (Meyer, P. et al., PLoS ONE 7(5): e38361 (2012)).

In certain embodiments, an antisense compound useful for treating breast cancer or inhibiting growth or proliferation of a breast cancer cell target provided herein targets AR within exon 1, which is upstream of the 3' end of exon 3 and/or upstream of the ligand binding domain. In certain embodiments, an antisense compound provided herein targets AR within exon 1, for example within nucleotide regions 2863-5593 (exon 1) or 27672-27853 (exon 1B) of SEQ ID NO: 1. In certain embodiments, an antisense compound provided herein targeted to exon 1 of AR is complementary within any of the following nucleotide regions of SEQ ID NO: 1: 3353-3368, 3361-3376, 3519-3534, 3735-3750, 3768-3783, 3798-3813, 3799-3814, 3851-3866, 3870-3885, 3874-3889, 3888-3903, 4047-4062, 4062-4077, 4109-4124, 4534-4549, 4537-4552, 4555-4570, 4571-4586, 4573-4588, 4578-4593, 4655-4670, 4750-4765, 4752-4767, 4833-4848, 4837-4852, 4839-4854, 4865-4880, 4872-4887, 4874-4889, 4876-4891, 4916-4931, 4918-4933, 5052-5067, 5054-5069, 5060-5075, 5061-5076, 5061-5076, 5062-5077, 5155-5170, 5265-5280, 5293-5308, 5392-5407, 5448-5463, 5483-5498, 5486-5501, or 5494-5509.

In certain embodiments, an antisense compound provided herein targets AR within exon 2, which is upstream of the 3' end of exon 3 and/or upstream of the ligand binding domain. In certain embodiments, an antisense compound useful for treating breast cancer or inhibiting growth or proliferation of a breast cancer cell target provided herein targets AR within exon 2, for example within nucleotide regions 102087-102238 (exon 2) or 139551-139834 (exon 2c) of SEQ ID NO: 1. In certain embodiments, an antisense compound provided herein targeted to exon 2 of AR is complementary within any of the following nucleotide regions of SEQ ID NO: 1: 102155-102170 or 102156-107171.

In certain aspects, an antisense compound useful for treating breast cancer or inhibiting growth or proliferation of a breast cancer cell provided herein targets AR within intron 1, which is upstream of the 3' end of exon 3 and/or upstream of the ligand binding domain. In certain embodiments, an antisense compound provided herein targets AR within intron 1, for example within nucleotide regions 5594-27671 or 27854-102086 of SEQ ID NO: 1. In certain aspects, an antisense compound provided herein targeted to intron 1 of AR is complementary within any of the following nucleotide regions of SEQ ID NO: 1: 5666-5681, 6701-6716, 7543-7558, 8471-8486, 8638-8653, 9464-9479, 10865-10880, 11197-11212, 11855-11870, 13189-13204, 13321-13336, 13346-13361, 16793-16808, 16968-16983, 17206-17221, 18865-18880, 32290-32305, 33315-33330, 39055-39070, 40615-40630, 42017-42032, 56050-56065, 58719-58734, 58720-58735, 58721-58736, 58722-58737, 58723-58738, 58725-58740, 58750-58765, 58751-58766, 58752-58767, 58753-58768, 58754-58769, or 58755-58770.

In certain aspects of any of the foregoing embodiments, antisense compounds useful for treating breast cancer or inhibiting growth or proliferation of a breast cancer cell target human androgen receptor upstream of the 3' end of exon 3 and/or upstream of the ligand binding domain. In certain embodiments, antisense compounds provided herein, including but not limited to those that target human androgen receptor upstream of the 3' end of exon 3 and/or upstream of the ligand binding domain, can treat breast cancer or inhibiting growth or proliferation of a breast cancer cell to a greater extent than an antisense compound targeted to the ligand binding domain, such as EZN-4176; with the proviso that the antisense compounds do not have a nucleobase sequence consisting of any of SEQ ID NOs: 194-215 described in U.S. Pat. No. 7,737,125 as SEQ ID NOs: 2-9, 49-50, 52-53, 55-56, and 86-93 (herein incorporated by reference), and identified in Table A.

Antisense Compounds

Oligomeric compounds include, but are not limited to, oligonucleotides, oligonucleosides, oligonucleotide analogs, oligonucleotide mimetics, antisense compounds, antisense oligonucleotides, and siRNAs. An oligomeric compound may be "antisense" to a target nucleic acid, meaning that is is capable of undergoing hybridization to a target nucleic acid through hydrogen bonding.

In certain embodiments, an antisense compound has a nucleobase sequence that, when written in the 5' to 3' direction, comprises the reverse complement of the target segment of a target nucleic acid to which it is targeted. In certain such embodiments, an antisense oligonucleotide has a nucleobase sequence that, when written in the 5' to 3' direction, comprises the reverse complement of the target segment of a target nucleic acid to which it is targeted.

In certain embodiments, an antisense compound is 10-30 subunits in length. In certain embodiments, an antisense compound is 12 to 30 subunits in length. In certain embodiments, an antisense compound is 12 to 22 subunits in length. In certain embodiments, an antisense compound is 14 to 30 subunits in length. In certain embodiments, an antisense compound is 14 to 20 subunits in length. In certain embodiments, an antisense compound is 15 to 30 subunits in length. In certain embodiments, an antisense compound is 15 to 20 subunits in length. In certain embodiments, an antisense compound is 16 to 30 subunits in length. In certain embodiments, an antisense compound is 16 to 20 subunits in length. In certain embodiments, an antisense compound is 17 to 30 subunits in length. In certain embodiments, an antisense compound is 17 to 20 subunits in length. In certain embodiments, an antisense compound is 18 to 30 subunits in length. In certain embodiments, an antisense compound is 18 to 21 subunits in length. In certain embodiments, an antisense compound is 18 to 20 subunits in length. In certain embodiments, an antisense compound is 20 to 30 subunits in length. In other words, such antisense compounds are from 12 to 30 linked subunits, 14 to 30 linked subunits, 14 to 20 subunits, 15 to 30 subunits, 15 to 20 subunits, 16 to 30 subunits, 16 to 20 subunits, 17 to 30 subunits, 17 to 20 subunits, 18 to 30 subunits, 18 to 20 subunits, 18 to 21 subunits, 20 to 30 subunits, or 12 to 22 linked subunits, respectively. In certain embodiments, an antisense compound is 14 subunits in length. In certain embodiments, an antisense compound is 16 subunits in length. In certain embodiments, an antisense compound is 17 subunits in length. In certain embodiments, an antisense compound is 18 subunits in length. In certain embodiments, an antisense compound is 20 subunits in length. In other embodiments, the antisense compound is 8 to 80, 12 to 50, 13 to 30, 13 to 50, 14 to 30, 14 to 50, 15 to 30, 15 to 50, 16 to 30, 16 to 50, 17 to 30, 17 to 50, 18 to 22, 18 to 24, 18 to 30, 18 to 50, 19 to 22, 19 to 30, 19 to 50, or 20 to 30 linked subunits. In certain such embodiments, the antisense compounds are 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 linked subunits in length, or a range defined by any two of the above values. In some embodiments the antisense compound is an antisense oligonucleotide, and the linked subunits are nucleotides.

In certain embodiments antisense oligonucleotides may be shortened or truncated. For example, a single subunit may be deleted from the 5' end (5' truncation), or alternatively from the 3' end (3' truncation). A shortened or truncated antisense compound targeted to an Androgen Receptor nucleic acid may have two subunits deleted from the 5' end, or alternatively may have two subunits deleted from the 3' end, of the antisense compound. Alternatively, the deleted nucleosides may be dispersed throughout the antisense compound, for example, in an antisense compound having one nucleoside deleted from the 5' end and one nucleoside deleted from the 3' end.

When a single additional subunit is present in a lengthened antisense compound, the additional subunit may be located at the 5' or 3' end of the antisense compound. When two or more additional subunits are present, the added subunits may be adjacent to each other, for example, in an antisense compound having two subunits added to the 5' end (5' addition), or alternatively to the 3' end (3' addition), of the antisense compound. Alternatively, the added subunits may be dispersed throughout the antisense compound, for example, in an antisense compound having one subunit added to the 5' end and one subunit added to the 3' end.

It is possible to increase or decrease the length of an antisense compound, such as an antisense oligonucleotide, and/or introduce mismatch bases without eliminating activity. For example, in Woolf et al. (Proc. Natl. Acad. Sci. USA 89:7305-7309, 1992), a series of antisense oligonucleotides 13-25 nucleobases in length were tested for their ability to induce cleavage of a target RNA in an oocyte injection model. Antisense oligonucleotides 25 nucleobases in length with 8 or 11 mismatch bases near the ends of the antisense oligonucleotides were able to direct specific cleavage of the target mRNA, albeit to a lesser extent than the antisense oligonucleotides that contained no mismatches. Similarly, target specific cleavage was achieved using 13 nucleobase antisense oligonucleotides, including those with 1 or 3 mismatches.

Gautschi et al. (*J. Natl. Cancer Inst.* 93:463-471, March 2001) demonstrated the ability of an oligonucleotide having 100% complementarity to the bcl-2 mRNA and having 3 mismatches to the bcl-xL mRNA to reduce the expression of both bcl-2 and bcl-xL in vitro and in vivo. Furthermore, this oligonucleotide demonstrated potent anti-tumor activity in vivo.

Maher and Dolnick (*Nuc. Acid. Res.* 16:3341-3358, 1988) tested a series of tandem 14 nucleobase antisense oligonucleotides, and a 28 and 42 nucleobase antisense oligonucleotides comprised of the sequence of two or three of the tandem antisense oligonucleotides, respectively, for their ability to arrest translation of human DHFR in a rabbit reticulocyte assay. Each of the three 14 nucleobase antisense oligonucleotides alone was able to inhibit translation, albeit at a more modest level than the 28 or 42 nucleobase antisense oligonucleotides.

Certain Antisense Compound Motifs and Mechanisms

In certain embodiments, antisense compounds have chemically modified subunits arranged in patterns, or motifs, to confer to the antisense compounds properties such as enhanced inhibitory activity, increased binding affinity for a target nucleic acid, or resistance to degradation by in vivo nucleases.

Chimeric antisense compounds typically contain at least one region modified so as to confer increased resistance to nuclease degradation, increased cellular uptake, increased binding affinity for the target nucleic acid, and/or increased inhibitory activity. A second region of a chimeric antisense compound may confer another desired property e.g., serve as a substrate for the cellular endonuclease RNase H, which cleaves the RNA strand of an RNA:DNA duplex.

Antisense activity may result from any mechanism involving the hybridization of the antisense compound (e.g., oligonucleotide) with a target nucleic acid, wherein the hybridization ultimately results in a biological effect. In certain embodiments, the amount and/or activity of the target nucleic acid is modulated. In certain embodiments, the amount and/or activity of the target nucleic acid is reduced. In certain embodiments, hybridization of the antisense compound to the target nucleic acid ultimately results in target nucleic acid degradation. In certain embodiments, hybridization of the antisense compound to the target nucleic acid does not result in target nucleic acid degradation. In certain such embodiments, the presence of the antisense compound hybridized with the target nucleic acid (occupancy) results in a modulation of antisense activity. In certain embodiments, antisense compounds having a particular chemical motif or pattern of chemical modifications are particularly suited to exploit one or more mechanisms. In certain embodiments, antisense compounds function through more than one mechanism and/or through mechanisms that have not been elucidated. Accordingly, the antisense compounds described herein are not limited by particular mechanism.

Antisense mechanisms include, without limitation, RNase H mediated antisense; RNAi mechanisms, which utilize the RISC pathway and include, without limitation, siRNA, ssRNA and microRNA mechanisms; and occupancy based mechanisms. Certain antisense compounds may act through more than one such mechanism and/or through additional mechanisms.

RNase H-Mediated Antisense

In certain embodiments, antisense activity results at least in part from degradation of target RNA by RNase H. RNase H is a cellular endonuclease that cleaves the RNA strand of an RNA:DNA duplex. It is known in the art that single-stranded antisense compounds which are "DNA-like" elicit RNase H activity in mammalian cells. Accordingly, antisense compounds comprising at least a portion of DNA or DNA-like nucleosides may activate RNase H, resulting in cleavage of the target nucleic acid. In certain embodiments, antisense compounds that utilize RNase H comprise one or more modified nucleosides. In certain embodiments, such antisense compounds comprise at least one block of 1-8 modified nucleosides. In certain such embodiments, the modified nucleosides do not support RNase H activity. In certain embodiments, such antisense compounds are gapmers, as described herein. In certain such embodiments, the gap of the gapmer comprises DNA nucleosides. In certain such embodiments, the gap of the gapmer comprises DNA-like nucleosides. In certain such embodiments, the gap of the gapmer comprises DNA nucleosides and DNA-like nucleosides.

Certain antisense compounds having a gapmer motif are considered chimeric antisense compounds. In a gapmer an internal region having a plurality of nucleotides that supports RNaseH cleavage is positioned between external regions having a plurality of nucleotides that are chemically distinct from the nucleosides of the internal region. In the case of an antisense oligonucleotide having a gapmer motif, the gap segment generally serves as the substrate for endonuclease cleavage, while the wing segments comprise modified nucleosides. In certain embodiments, the regions of a gapmer are differentiated by the types of sugar moieties comprising each distinct region. The types of sugar moieties that are used to differentiate the regions of a gapmer may in some embodiments include β-D-ribonucleosides, β-D-deoxyribonucleosides, 2'-modified nucleosides (such 2'-modified nucleosides may include 2'-MOE and 2'-O—CH$_3$, among others), and bicyclic sugar modified nucleosides (such bicyclic sugar modified nucleosides may include those having a constrained ethyl). In certain embodiments, nucleosides in the wings may include several modified sugar moieties, including, for example 2'-MOE and bicyclic sugar moieties such as constrained ethyl or LNA. In certain embodiments, wings may include several modified and unmodified sugar moieties. In certain embodiments, wings may include various combinations of 2'-MOE nucleosides, bicyclic sugar moieties such as constrained ethyl nucleosides or LNA nucleosides, and 2'-deoxynucleosides.

Each distinct region may comprise uniform sugar moieties, variant, or alternating sugar moieties. The wing-gap-wing motif is frequently described as "X-Y-Z", where "X" represents the length of the 5'-wing, "Y" represents the length of the gap, and "Z" represents the length of the 3'-wing. "X" and "Z" may comprise uniform, variant, or alternating sugar moieties. In certain embodiments, "X" and "Y" may include one or more 2'-deoxynucleosides. "Y" may comprise 2'-deoxynucleosides. As used herein, a gapmer described as "X-Y-Z" has a configuration such that the gap is positioned immediately adjacent to each of the 5'-wing and the 3' wing. Thus, no intervening nucleotides exist between the 5'-wing and gap, or the gap and the 3'-wing. Any of the antisense compounds described herein can have a gapmer motif. In certain embodiments, "X" and "Z" are the same; in other embodiments they are different. In certain embodiments, "Y" is between 8 and 15 nucleosides. X, Y, or Z can be any of 1, 2, 3, 4, 5, 6, 7, 8, 9, 10, 11, 12, 13, 14, 15, 16, 17, 18, 19, 20, 25, 30 or more nucleosides.

In certain embodiments, the antisense compound targeted to an Androgen Receptor nucleic acid has a gapmer motif in which the gap consists of 6, 7, 8, 9, 10, 11, 12, 13, 14, 15, or 16 linked nucleosides.

In certain embodiments, the antisense oligonucleotide has a sugar motif described by Formula A as follows: $(J)_m$-$(B)_n$-$(J)_p$-$(B)_r$-$(A)_t$-$(D)_g$-$(A)_v$-$(B)_w$-$(J)_x$-$(B)_y$-$(J)_z$ wherein:
each A is independently a 2'-substituted nucleoside;
each B is independently a bicyclic nucleoside;
each J is independently either a 2'-substituted nucleoside or a 2'-deoxynucleoside; each D is a 2'-deoxynucleoside;
m is 0-4; n is 0-2; p is 0-2; r is 0-2; t is 0-2; v is 0-2; w is 0-4; x is 0-2; y is 0-2; z is 0-4; g is 6-14; provided that:
at least one of m, n, and r is other than 0;
at least one of w and y is other than 0;
the sum of m, n, p, r, and t is from 2 to 5; and
the sum of v, w, x, y, and z is from 2 to 5.

RNAi Compounds

In certain embodiments, antisense compounds are interfering RNA compounds (RNAi), which include double-stranded RNA compounds (also referred to as short-interfering RNA or siRNA) and single-stranded RNAi compounds (or ssRNA). Such compounds work at least in part through the RISC pathway to degrade and/or sequester a target nucleic acid (thus, include microRNA/microRNA-mimic compounds). In certain embodiments, antisense compounds comprise modifications that make them particularly suited for such mechanisms.

i. ssRNA Compounds

In certain embodiments, antisense compounds including those particularly suited for use as single-stranded RNAi compounds (ssRNA) comprise a modified 5'-terminal end. In certain such embodiments, the 5'-terminal end comprises a modified phosphate moiety. In certain embodiments, such modified phosphate is stabilized (e.g., resistant to degradation/cleavage compared to unmodified 5'-phosphate). In certain embodiments, such 5'-terminal nucleosides stabilize the 5'-phosphorous moiety. Certain modified 5'-terminal nucleosides may be found in the art, for example in WO/2011/139702.

In certain embodiments, the 5'-nucleoside of an ssRNA compound has Formula IIc:

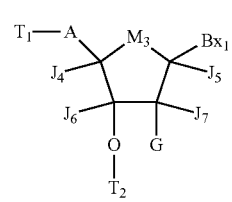

IIc wherein:
$T_1$ is an optionally protected phosphorus moiety;
$T_2$ is an internucleoside linking group linking the compound of Formula IIc to the oligomeric compound;
A has one of the formulas:

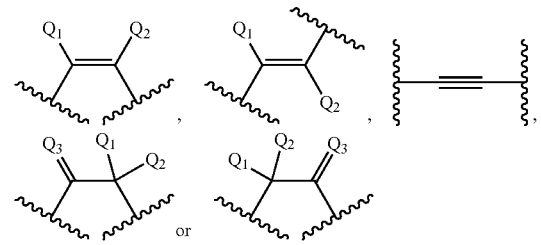

$Q_1$ and $Q_2$ are each, independently, H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl, substituted $C_2$-$C_6$ alkynyl or $N(R_3)(R_4)$;

$Q_3$ is O, S, $N(R_5)$ or $C(R_6)(R_7)$;

each $R_3$, $R_4$ $R_5$, $R_6$ and $R_7$ is, independently, H, $C_1$-$C_6$ alkyl, substituted $C_1$-$C_6$ alkyl or $C_1$-$C_6$ alkoxy;

$M_3$ is O, S, $NR_{14}$, $C(R_{15})(R_{16})$, $C(R_{15})(R_{16})C(R_{17})(R_{18})$, $C(R_{15})$=$C(R_{17})$, $OC(R_{15})(R_{16})$ or $OC(R_{15})(Bx_2)$;

$R_{14}$ is H, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;

$R_{15}$, $R_{16}$, $R_{17}$ and $R_{18}$ are each, independently, H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;

$Bx_1$ is a heterocyclic base moiety;

or if $Bx_2$ is present then $Bx_2$ is a heterocyclic base moiety and $Bx_1$ is H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;

$J_4$, $J_5$, $J_6$ and $J_7$ are each, independently, H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;

or $J_4$ forms a bridge with one of $J_5$ or $J_7$ wherein said bridge comprises from 1 to 3 linked biradical groups selected from O, S, $NR_{19}$, $C(R_{20})(R_{21})$, $C(R_{20})$=$C(R_{21})$, $C[=C(R_{20})(R_{21})]$ and $C(=O)$ and the other two of $J_5$, $J_6$ and $J_7$ are each, independently, H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;

each $R_{19}$, $R_{20}$ and $R_{21}$ is, independently, H, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;

G is H, OH, halogen or O—$[C(R_8)(R_6)]_n$—$[(C=O)_m$—$X_1]_j$—Z;

each $R_8$ and $R_9$ is, independently, H, halogen, $C_1$-$C_6$ alkyl or substituted $C_1$-$C_6$ alkyl;

$X_1$ is O, S or $N(E_1)$;

Z is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to about 6;

m is 0 or 1;

j is 0 or 1;

each substituted group comprises one or more optionally protected substituent groups independently selected from halogen, $OJ_1$, $N(J_1)(J_2)$, =$NJ_1$, $SJ_1$, $N_3$, CN, $OC(=X_2)J_1$, $OC(=X_2)N(J_1)(J_2)$ and $C(=X_2)N(J_1)(J_2)$;

$X_2$ is O, S or $NJ_3$;

each $J_1$, $J_2$ and $J_3$ is, independently, H or $C_1$-$C_6$ alkyl;

when j is 1 then Z is other than halogen or $N(E_2)(E_3)$; and wherein said oligomeric compound comprises from 8 to 40 monomeric subunits and is hybridizable to at least a portion of a target nucleic acid.

In certain embodiments, $M_3$ is O, CH=CH, $OCH_2$ or $OC(H)(Bx_2)$. In certain embodiments, $M_3$ is O.

In certain embodiments, $J_4$, $J_5$, $J_6$ and $J_7$ are each H. In certain embodiments, $J_4$ forms a bridge with one of $J_5$ or $J_7$.

In certain embodiments, A has one of the formulas:

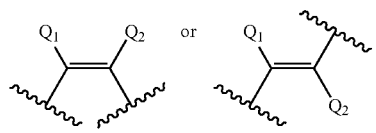

wherein:

$Q_1$ and $Q_2$ are each, independently, H, halogen, $C_1$-$C_6$ alkyl, substituted $C_1$-$C_6$ alkyl, $C_1$-$C_6$ alkoxy or substituted $C_1$-$C_6$ alkoxy. In certain embodiments, $Q_1$ and $Q_2$ are each H. In certain embodiments, $Q_1$ and $Q_2$ are each, independently, H or halogen. In certain embodiments, $Q_1$ and $Q_2$ is H and the other of $Q_1$ and $Q_2$ is F, $CH_3$ or $OCH_3$.

In certain embodiments, $T_1$ has the formula:

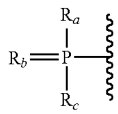

wherein:

$R_a$ and $R_c$ are each, independently, protected hydroxyl, protected thiol, $C_1$-$C_6$ alkyl, substituted $C_1$-$C_6$ alkyl, $C_1$-$C_6$ alkoxy, substituted $C_1$-$C_6$ alkoxy, protected amino or substituted amino; and $R_b$ is O or S. In certain embodiments, $R_b$ is O and $R_a$ and $R_c$ are each, independently, $OCH_3$, $OCH_2CH_3$ or $CH(CH_3)_2$.

In certain embodiments, G is halogen, $OCH_3$, $OCH_2F$, $OCHF_2$, $OCF_3$, $OCH_2CH_3$, $O(CH_2)_2F$, $OCH_2CHF_2$, $OCH_2CF_3$, $OCH_2$—CH=$CH_2$, $O(CH_2)_2$—$OCH_3$, $O(CH_2)_2$—$SCH_3$, $O(CH_2)_2$—$OCF_3$, $O(CH_2)_3$—$N(R_{10})(R_{11})$, $O(CH_2)_2$—$ON(R_{10})(R_{11})$, $O(CH_2)_2$—$O(CH_2)_2$—$N(R_{10})(R_{11})$, $OCH_2C(=O)$—$N(R_{10})(R_{11})$, $OCH_2C(=O)$—$N(R_{12})$—$(CH_2)_2$—$N(R_{10})(R_{11})$ or $O(CH_2)_2$—$N(R_{12})$—$C(=NR_{13})[N(R_{10})(R_{11})]$ wherein $R_{10}$, $R_{11}$, $R_{12}$ and $R_{13}$ are each, independently, H or $C_1$-$C_6$ alkyl. In certain embodiments, G is halogen, $OCH_3$, $OCF_3$, $OCH_2CH_3$, $OCH_2CF_3$, $OCH_2$—CH=$CH_2$, $O(CH_2)_2$—$OCH_3$, $O(CH_2)_2$—$O(CH_2)_2$—$N(CH_3)_2$, $OCH_2C(=O)$—$N(H)CH_3$, $OCH_2C(=O)$—$N(H)$—$(CH_2)_2$—$N(CH_3)_2$ or $OCH_2$—$N(H)$—$C(=NH)NH_2$. In certain embodiments, G is F, $OCH_3$ or $O(CH_2)_2$—$OCH_3$. In certain embodiments, G is $O(CH_2)_2$—$OCH_3$.

In certain embodiments, the 5'-terminal nucleoside has Formula IIe:

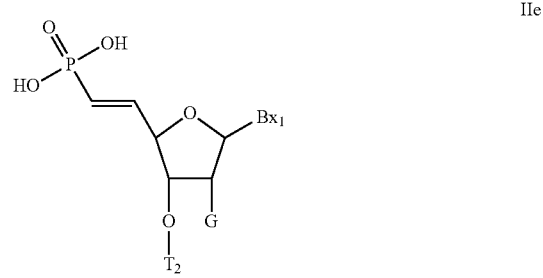

In certain embodiments, antisense compounds, including those particularly suitable for ssRNA comprise one or more type of modified sugar moieties and/or naturally occurring sugar moieties arranged along an oligonucleotide or region thereof in a defined pattern or sugar modification motif Such motifs may include any of the sugar modifications discussed herein and/or other known sugar modifications.

In certain embodiments, the oligonucleotides comprise or consist of a region having uniform sugar modifications. In certain such embodiments, each nucleoside of the region comprises the same RNA-like sugar modification. In certain embodiments, each nucleoside of the region is a 2'-F nucleoside. In certain embodiments, each nucleoside of the region is a 2'-OMe nucleoside. In certain embodiments, each nucleoside of the region is a 2'-MOE nucleoside. In certain embodiments, each nucleoside of the region is a cEt nucleoside. In certain embodiments, each nucleoside of the region is an LNA nucleoside. In certain embodiments, the uniform region constitutes all or essentially all of the oligonucleotide. In certain embodiments, the region constitutes the entire oligonucleotide except for 1-4 terminal nucleosides.

In certain embodiments, oligonucleotides comprise one or more regions of alternating sugar modifications, wherein the nucleosides alternate between nucleotides having a sugar modification of a first type and nucleotides having a sugar modification of a second type. In certain embodiments, nucleosides of both types are RNA-like nucleosides. In certain embodiments the alternating nucleosides are selected from: 2'-OMe, 2'-F, 2'-MOE, LNA, and cEt. In certain embodiments, the alternating modificatios are 2'-F and 2'-OMe. Such regions may be contiguous or may be interupted by differently modified nucleosides or conjugated nucleosides.

In certain embodiments, the alternating region of alternating modifications each consist of a single nucleoside (i.e., the patern is $(AB)_xA_y$, wheren A is a nucleoside having a sugar modification of a first type and B is a nucleoside having a sugar modification of a second type; x is 1-20 and y is 0 or 1). In certain embodiments, one or more alternating regions in an alternating motif includes more than a single nucleoside of a type. For example, oligonucleotides may include one or more regions of any of the following nucleoside motifs:

```
AABBAA;

ABBABB;

AABAAB;

ABBABAABB;

ABABAA;

AABABAB;

ABABAA;

ABBAABBABABAA;

BABBAABBABABAA;
or

ABABBAABBABABAA;
``` wherein A is a nucleoside of a first type and B is a nucleoside of a second type. In certain embodiments, A and B are each selected from 2'-F, 2'-OMe, BNA, and MOE.

In certain embodiments, oligonucleotides having such an alternating motif also comprise a modified 5' terminal nucleoside, such as those of formula IIc or IIe.

In certain embodiments, oligonucleotides comprise a region having a 2-2-3 motif Such regions comprises the following motif:

$-(A)_2-(B)_x-(A)_2-(C)_y-(A)_3-$ wherein: A is a first type of modifed nucleosde;

B and C, are nucleosides that are differently modified than A, however, B and C may have the same or different modifications as one another;

x and y are from 1 to 15.

In certain embodiments, A is a 2'-OMe modified nucleoside. In certain embodiments, B and C are both 2'-F modified nucleosides. In certain embodiments, A is a 2'-OMe modified nucleoside and B and C are both 2'-F modified nucleosides.

In certain embodiments, oligonucleosides have the following sugar motif:

$5'-(Q)-(AB)_xA_y-(D)_z$ wherein:

Q is a nucleoside comprising a stabilized phosphate moiety. In certain embodiments, Q is a nucleoside having Formula IIc or IIe;

A is a first type of modifed nucleoside;

B is a second type of modified nucleoside;

D is a modified nucleoside comprising a modification different from the nucleoside adjacent to it. Thus, if y is 0, then D must be differently modified than B and if y is 1, then D must be differently modified than A. In certain embodiments, D differs from both A and B.

X is 5-15;

Y is 0 or 1;

Z is 0-4.

In certain embodiments, oligonucleosides have the following sugar motif:

$5'-(Q)-(A)_x-(D)_z$ wherein:

Q is a nucleoside comprising a stabilized phosphate moiety. In certain embodiments, Q is a nucleoside having Formula IIc or IIe;

A is a first type of modifed nucleoside;

D is a modified nucleoside comprising a modification different from A.

X is 11-30;

Z is 0-4.

In certain embodiments A, B, C, and D in the above motifs are selected from: 2'-OMe, 2'-F, 2'-MOE, LNA, and cEt. In certain embodiments, D represents terminal nucleosides. In certain embodiments, such terminal nucleosides are not designed to hybridize to the target nucleic acid (though one or more might hybridize by chance). In certain embodiments, the nucleobase of each D nucleoside is adenine, regardless of the identity of the nucleobase at the corresponding position of the target nucleic acid. In certain embodiments the nucleobase of each D nucleoside is thymine.

In certain embodiments, antisense compounds, including those particularly suited for use as ssRNA comprise modified internucleoside linkages arranged along the oligonucleotide or region thereof in a defined pattern or modified internucleoside linkage motif. In certain embodiments, oligonucleotides comprise a region having an alternating internucleoside linkage motif. In certain embodiments, oligonucleotides comprise a region of uniformly modified internucleoside linkages. In certain such embodiments, the oligonucleotide comprises a region that is uniformly linked by phosphorothioate internucleoside linkages. In certain embodiments, the oligonucleotide is uniformly linked by phosphoro-thioate internucleoside linkages. In certain embodiments, each internucleoside linkage of the oligonucleotide is selected from phosphodiester and phosphorothioate. In certain embodiments, each internucleoside linkage of the oligonucleotide is selected from phosphodiester and phosphorothioate and at least one internucleoside linkage is phosphorothioate.

In certain embodiments, the oligonucleotide comprises at least 6 phosphorothioate internucleoside linkages. In certain embodiments, the oligonucleotide comprises at least 8 phosphorothioate internucleoside linkages. In certain embodiments, the oligonucleotide comprises at least 10 phosphorothioate internucleoside linkages. In certain embodiments, the oligonucleotide comprises at least one block of at least 6 consecutive phosphorothioate internucleoside linkages. In certain embodiments, the oligonucleotide comprises at least one block of at least 8 consecutive phosphorothioate internucleoside linkages. In certain embodiments, the oligonucleotide comprises at least one block of at least 10 consecutive phosphorothioate internucleoside linkages. In certain embodiments, the oligonucleotide comprises at least one block of at least 12 consecutive phosphoro-thioate internucleoside linkages. In certain such embodiments, at least one such block is located at the 3' end of the oligonucleotide. In certain such embodiments, at least one such block is located within 3 nucleosides of the 3' end of the oligonucleotide.

Oligonucleotides having any of the various sugar motifs described herein, may have any linkage motif. For example, the oligonucleotides, including but not limited to those described above, may have a linkage motif selected from non-limiting the table below:

| 5' most linkage | Central region | 3'-region |
|---|---|---|
| PS | Alternating PO/PS | 6 PS |
| PS | Alternating PO/PS | 7 PS |
| PS | Alternating PO/PS | 8 PS | ii. siRNA Compounds

In certain embodiments, antisense compounds are double-stranded RNAi compounds (siRNA). In such embodiments, one or both strands may comprise any modification motif described above for ssRNA. In certain embodiments, ssRNA compounds may be unmodified RNA. In certain embodiments, siRNA compounds may comprise unmodified RNA nucleosides, but modified internucleoside linkages.

Several embodiments relate to double-stranded compositions wherein each strand comprises a motif defined by the location of one or more modified or unmodified nucleosides. In certain embodiments, compositions are provided comprising a first and a second oligomeric compound that are fully or at least partially hybridized to form a duplex region and further comprising a region that is complementary to and hybridizes to a nucleic acid target. It is suitable that such a composition comprise a first oligomeric compound that is an antisense strand having full or partial complementarity to a nucleic acid target and a second oligomeric compound that is a sense strand having one or more regions of complementarity to and forming at least one duplex region with the first oligomeric compound.

The compositions of several embodiments modulate gene expression by hybridizing to a nucleic acid target resulting in loss of its normal function. In some embodiments, the target nucleic acid is Androgen Receptor. In certain embodiment, the degradation of the targeted Androgen Receptor is facilitated by an activated RISC complex that is formed with compositions of the invention.

Several embodiments are directed to double-stranded compositions wherein one of the strands is useful in, for example, influencing the preferential loading of the opposite strand into the RISC (or cleavage) complex. The compositions are useful for targeting selected nucleic acid molecules and modulating the expression of one or more genes. In some embodiments, the compositions of the present invention hybridize to a portion of a target RNA resulting in loss of normal function of the target RNA.

Certain embodiments are drawn to double-stranded compositions wherein both the strands comprises a hemimer motif, a fully modified motif, a positionally modified motif or an alternating motif Each strand of the compositions of the present invention can be modified to fulfil a particular role in for example the siRNA pathway. Using a different motif in each strand or the same motif with different chemical modifications in each strand permits targeting the antisense strand for the RISC complex while inhibiting the incorporation of the sense strand. Within this model, each strand can be independently modified such that it is enhanced for its particular role. The antisense strand can be modified at the 5'-end to enhance its role in one region of the RISC while the 3'-end can be modified differentially to enhance its role in a different region of the RISC.

The double-stranded oligonucleotide molecules can be a double-stranded polynucleotide molecule comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof. The double-stranded oligonucleotide molecules can be assembled from two separate oligonucleotides, where one strand is the sense strand and the other is the antisense strand, wherein the antisense and sense strands are self-complementary (i.e. each strand comprises nucleotide sequence that is complementary to nucleotide sequence in the other strand; such as where the antisense strand and sense strand form a duplex or double-stranded structure, for example wherein the double-stranded region is about 15 to about 30, e.g., about 15, 16, 17, 18, 19, 20, 21, 22, 23, 24, 25, 26, 27, 28, 29 or 30 base pairs; the antisense strand comprises nucleotide sequence that is complementary to nucleotide sequence in a target nucleic acid molecule or a portion thereof and the sense strand comprises nucleotide sequence corresponding to the target nucleic acid sequence or a portion thereof (e.g., about 15 to about 25 or more nucleotides of the double-stranded oligonucleotide molecule are complementary to the target nucleic acid or a portion thereof). Alternatively, the double-stranded oligonucleotide is assembled from a single oligonucleotide, where the self-complementary sense and antisense regions of the siRNA are linked by means of a nucleic acid based or non-nucleic acid-based linker(s).

The double-stranded oligonucleotide can be a polynucleotide with a duplex, asymmetric duplex, hairpin or asymmetric hairpin secondary structure, having self-complementary sense and antisense regions, wherein the antisense region comprises nucleotide sequence that is complementary to nucleotide sequence in a separate target nucleic acid molecule or a portion thereof and the sense region having nucleotide sequence corresponding to the target nucleic acid sequence or a portion thereof. The double-stranded oligonucleotide can be a circular single-stranded polynucleotide having two or more loop structures and a stem comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof, and wherein the circular polynucleotide can be processed either in vivo or in vitro to generate an active siRNA molecule capable of mediating RNAi.

In certain embodiments, the double-stranded oligonucleotide comprises separate sense and antisense sequences or regions, wherein the sense and antisense regions are covalently linked by nucleotide or non-nucleotide linkers molecules as is known in the art, or are alternately non-covalently linked by ionic interactions, hydrogen bonding, van der waals interactions, hydrophobic interactions, and/or stacking interactions. In certain embodiments, the double-stranded oligonucleotide comprises nucleotide sequence that is complementary to nucleotide sequence of a target gene. In another embodiment, the double-stranded oligonucleotide interacts with nucleotide sequence of a target gene in a manner that causes inhibition of expression of the target gene.

As used herein, double-stranded oligonucleotides need not be limited to those molecules containing only RNA, but further encompasses chemically modified nucleotides and non-nucleotides. In certain embodiments, the short interfering nucleic acid molecules lack 2'-hydroxy (2'-OH) containing nucleotides. In certain embodiments short interfering nucleic acids optionally do not include any ribonucleotides (e.g., nucleotides having a 2'-OH group). Such double-stranded oligonucleotides that do not require the presence of ribonucleotides within the molecule to support RNAi can however have an attached linker or linkers or other attached or associated groups, moieties, or chains containing one or more nucleotides with 2'-OH groups. Optionally, double-stranded oligonucleotides can comprise ribonucleotides at about 5, 10, 20, 30, 40, or 50% of the nucleotide positions. As used herein, the term siRNA is meant to be equivalent to other terms used to describe nucleic acid molecules that are capable of mediating sequence specific RNAi, for example short interfering RNA (siRNA), double-stranded RNA (dsRNA), micro-RNA (miRNA), short hairpin RNA (shRNA), short interfering oligonucleotide, short interfering nucleic acid, short interfering modified oligonucleotide, chemically modified siRNA, post-transcriptional gene silencing RNA (ptgsRNA), and others. In addition, as used herein, the term RNAi is meant to be equivalent to other terms used to describe sequence specific RNA interference, such as post transcriptional gene silencing, translational inhibition, or epigenetics. For example, double-stranded oligonucleotides can be used to epigenetically silence genes at both the post-transcriptional level and the pre-transcriptional level. In a non-limiting example, epigenetic regulation of gene expression by siRNA molecules of the invention can result from siRNA mediated modification of chromatin structure or methylation pattern to alter gene expression (see, for example, Verdel et al., 2004, Science, 303, 672-676; Pal-Bhadra et al., 2004, Science, 303, 669-672; Allshire, 2002, Science, 297, 1818-1819; Volpe et al., 2002, Science, 297, 1833-1837; Jenuwein, 2002, Science, 297, 2215-2218; and Hall et al., 2002, Science, 297, 2232-2237).

It is contemplated that compounds and compositions of several embodiments provided herein can target Androgen Receptor by a dsRNA-mediated gene silencing or RNAi mechanism, including, e.g., "hairpin" or stem-loop double-stranded RNA effector molecules in which a single RNA strand with self-complementary sequences is capable of assuming a double-stranded conformation, or duplex dsRNA effector molecules comprising two separate strands of RNA. In various embodiments, the dsRNA consists entirely of ribonucleotides or consists of a mixture of ribonucleotides and deoxynucleotides, such as the RNA/DNA hybrids disclosed, for example, by WO 00/63364, filed Apr. 19, 2000, or U.S. Ser. No. 60/130,377, filed Apr. 21, 1999. The dsRNA or dsRNA effector molecule may be a single molecule with a region of self-complementarity such that nucleotides in one segment of the molecule base pair with nucleotides in another segment of the molecule. In various embodiments, a dsRNA that consists of a single molecule consists entirely of ribonucleotides or includes a region of ribonucleotides that is complementary to a region of deoxyribonucleotides. Alternatively, the dsRNA may include two different strands that have a region of complementarity to each other.

In various embodiments, both strands consist entirely of ribonucleotides, one strand consists entirely of ribonucleotides and one strand consists entirely of deoxyribonucleotides, or one or both strands contain a mixture of ribonucleotides and deoxyribonucleotides. In certain embodiments, the regions of complementarity are at least 70, 80, 90, 95, 98, or 100% complementary to each other and to a target nucleic acid sequence. In certain embodiments, the region of the dsRNA that is present in a double-stranded conformation includes at least 19, 20, 21, 22, 23, 24, 25, 26, 27, 28, 29, 30, 50, 75, 100, 200, 500, 1000, 2000 or 5000 nucleotides or includes all of the nucleotides in a cDNA or other target nucleic acid sequence being represented in the dsRNA. In some embodiments, the dsRNA does not contain any single stranded regions, such as single stranded ends, or the dsRNA is a hairpin. In other embodiments, the dsRNA has one or more single stranded regions or overhangs. In certain embodiments, RNA/DNA hybrids include a DNA strand or region that is an antisense strand or region (e.g., has at least 70, 80, 90, 95, 98, or 100% complementarity to a target nucleic acid) and an RNA strand or region that is a sense strand or region (e.g., has at least 70, 80, 90, 95, 98, or 100% identity to a target nucleic acid), and vice versa.

In various embodiments, the RNA/DNA hybrid is made in vitro using enzymatic or chemical synthetic methods such as those described herein or those described in WO 00/63364, filed Apr. 19, 2000, or U.S. Ser. No. 60/130,377, filed Apr. 21, 1999. In other embodiments, a DNA strand synthesized in vitro is complexed with an RNA strand made in vivo or in vitro before, after, or concurrent with the transformation of the DNA strand into the cell. In yet other embodiments, the dsRNA is a single circular nucleic acid containing a sense and an antisense region, or the dsRNA includes a circular nucleic acid and either a second circular nucleic acid or a linear nucleic acid (see, for example, WO 00/63364, filed Apr. 19, 2000, or U.S. Ser. No. 60/130,377, filed Apr. 21, 1999.) Exemplary circular nucleic acids include lariat structures in which the free 5' phosphoryl group of a nucleotide becomes linked to the 2' hydroxyl group of another nucleotide in a loop back fashion.

In other embodiments, the dsRNA includes one or more modified nucleotides in which the 2' position in the sugar contains a halogen (such as fluorine group) or contains an alkoxy group (such as a methoxy group) which increases the half-life of the dsRNA in vitro or in vivo compared to the corresponding dsRNA in which the corresponding 2' position contains a hydrogen or an hydroxyl group. In yet other embodiments, the dsRNA includes one or more linkages between adjacent nucleotides other than a naturally-occurring phosphodiester linkage. Examples of such linkages include phosphoramide, phosphorothioate, and phosphorodithioate linkages. The dsRNAs may also be chemically modified nucleic acid molecules as taught in U.S. Pat. No. 6,673,661. In other embodiments, the dsRNA contains one or two capped strands, as disclosed, for example, by WO 00/63364, filed Apr. 19, 2000, or U.S. Ser. No. 60/130,377, filed Apr. 21, 1999.

In other embodiments, the dsRNA can be any of the at least partially dsRNA molecules disclosed in WO 00/63364, as well as any of the dsRNA molecules described in U.S. Provisional Application 60/399,998; and U.S. Provisional Application 60/419,532, and PCT/US2003/033466, the teaching of which is hereby incorporated by reference. Any of the dsRNAs may be expressed in vitro or in vivo using the methods described herein or standard methods, such as those described in WO 00/63364.

Occupancy

In certain embodiments, antisense compounds are not expected to result in cleavage or the target nucleic acid via RNase H or to result in cleavage or sequestration through the RISC pathway. In certain such embodiments, antisense activity may result from occupancy, wherein the presence of the hybridized antisense compound disrupts the activity of the target nucleic acid. In certain such embodiments, the antisense compound may be uniformly modified or may comprise a mix of modifications and/or modified and unmodified nucleosides.

Target Nucleic Acids, Target Regions and Nucleotide Sequences

Nucleotide sequences that encode human Androgen Receptor include, without limitation, the following: GEN-BANK Accession No. NT_011669.17_TRUNC_5079000_5270000 (incorporated herein as SEQ ID NO: 1), GENBANK Accession No. NM_000044.3 (incorporated herein as SEQ ID NO: 2), GENBANK Accession No. NM_001011645.2 (incorporated herein as SEQ ID NO: 3), GENBANK Accession No. FJ235916.1 (incorporated herein as SEQ ID NO: 4), GENBANK Accession No. FJ235917.1 (incorporated herein as SEQ ID NO: 5), GENBANK Accession No. FJ235918.1 (incorporated herein as SEQ ID NO: 6), GENBANK Accession No. FJ235919.1 (incorporated herein as SEQ ID NO: 7), and GENBANK Accession No. FJ235920.1 (incorporated herein as SEQ ID NO: 8).

Androgen Receptor mRNA encodes several functional domains. In certain embodiments, full-length Androgen Receptor mRNA includes exon 1 encoding the N-terminal domain, exons 2 and 3 encoding the DNA binding domain, exon 4 encoding the short hinge region, and exons 4-8 encoding the ligand binding domain.

In certain embodiments, Androgen Receptor splicing variants targetable by the antisense compounds provided herein include exon 1 encoding the N-terminal domain and exons 2 and 3 encoding the DNA binding domain, or functional portions thereof, but does not include at least a portion of exon 4 encoding the short hinge region or at least a portion of exons 4-8 encoding the ligand binding domain. Examples of such AR splicing variants include, but are not limited to, AR-V1, AR-V2, AR-V3, AR-V4, AR-V5, AR-V6, and AR-V7 (also referred to as AR3), which contain exons 1-3 but lack exons 4-8. AR-V1, AR-V2, AR-V3, AR-V4, AR-V5, AR-V6, AR-V7, and additional splicing variants targetable by the antisense compounds provided herein are described in Hu et al., *Cancer Res* 2009; 69:16-22 and US Patent Application Publication No. US 2010/0068802, each of which is incorporated herein by reference in its entirety. Further examples of such AR splicing variants targetable by the antisense compounds provided herein include, but are not limited to, AR3, AR4, AR4b, AR5, and AR6 (SEQ ID NOs: 4-8, respectively) as described in Guo et al., *Cancer Res.* 2009; 69: 2305-13, which is incorporated herein by reference in its entirety.

Hybridization

In some embodiments, hybridization occurs between an antisense compound disclosed herein and an Androgen Receptor. The most common mechanism of hybridization involves hydrogen bonding (e.g., Watson-Crick, Hoogsteen or reversed Hoogsteen hydrogen bonding) between complementary nucleobases of the nucleic acid molecules.

Hybridization can occur under varying conditions. Stringent conditions are sequence-dependent and are determined by the nature and composition of the nucleic acid molecules to be hybridized.

Methods of determining whether a sequence is specifically hybridizable to a target nucleic acid are well known in the art. In certain embodiments, the antisense compounds provided herein are specifically hybridizable with Androgen Receptor.

Complementarity

An antisense compound and a target nucleic acid are complementary to each other when a sufficient number of nucleobases of the antisense compound can hydrogen bond with the corresponding nucleobases of the target nucleic acid, such that a desired effect will occur (e.g., antisense inhibition of a target nucleic acid, such as an Androgen Receptor nucleic acid).

Non-complementary nucleobases between an antisense compound and an Androgen Receptor nucleic acid may be tolerated provided that the antisense compound remains able to specifically hybridize to a target nucleic acid. Moreover, an antisense compound may hybridize over one or more segments of an Androgen Receptor nucleic acid such that intervening or adjacent segments are not involved in the hybridization event (e.g., a loop structure, mismatch or hairpin structure).

In certain embodiments, the antisense compounds provided herein, or a specified portion thereof, are, or are at least, 70%, 80%, 85%, 86%, 87%, 88%, 89%, 90%, 91%, 92%, 93%, 94%, 95%, 96%, 97%, 98%, 99%, or 100% complementary to an Androgen Receptor nucleic acid, a target region, target segment, or specified portion thereof. Percent complementarity of an antisense compound with a target nucleic acid can be determined using routine methods.

For example, an antisense compound in which 18 of 20 nucleobases of the antisense compound are complementary to a target region, and would therefore specifically hybridize, would represent 90 percent complementarity. In this example, the remaining noncomplementary nucleobases may be clustered or interspersed with complementary nucleobases and need not be contiguous to each other or to complementary nucleobases. As such, an antisense compound which is 18 nucleobases in length having four non-complementary nucleobases which are flanked by two regions of complete complementarity with the target nucleic acid would have 77.8% overall complementarity with the target nucleic acid and would thus fall within the scope of the present invention. Percent complementarity of an antisense compound with a region of a target nucleic acid can be determined routinely using BLAST programs (basic local alignment search tools) and PowerBLAST programs known in the art (Altschul et al., *J. Mol. Biol.*, 1990, 215, 403 410; Zhang and Madden, Genome Res., 1997, 7, 649 656). Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482 489).

In certain embodiments, the antisense compounds provided herein, or specified portions thereof, are fully complementary (i.e. 100% complementary) to a target nucleic acid, or specified portion thereof. For example, an antisense compound may be fully complementary to an Androgen Receptor nucleic acid, or a target region, or a target segment or target sequence thereof. As used herein, "fully complementary" means each nucleobase of an antisense compound is capable of precise base pairing with the corresponding nucleobases of a target nucleic acid. For example, a 20 nucleobase antisense compound is fully complementary to a target sequence that is 400 nucleobases long, so long as there is a corresponding 20 nucleobase portion of the target nucleic acid that is fully complementary to the antisense compound. Fully complementary can also be used in reference to a specified portion of the first and/or the second nucleic acid. For example, a 20 nucleobase portion of a 30 nucleobase antisense compound can be "fully complementary" to a target sequence that is 400 nucleobases long. The 20 nucleobase portion of the 30 nucleobase oligonucleotide is fully complementary to the target sequence if the target sequence has a corresponding 20 nucleobase portion wherein each nucleobase is complementary to the 20 nucleobase portion of the antisense compound. At the same time, the entire 30 nucleobase antisense compound may or may not be fully complementary to the target sequence, depending on whether the remaining 10 nucleobases of the antisense compound are also complementary to the target sequence.

The location of a non-complementary nucleobase may be at the 5' end or 3' end of the antisense compound. Alternatively, the non-complementary nucleobase or nucleobases may be at an internal position of the antisense compound. When two or more non-complementary nucleobases are present, they may be contiguous (i.e. linked) or non-contiguous. In one embodiment, a non-complementary nucleobase is located in the wing segment of a gapmer antisense oligonucleotide.

In certain embodiments, antisense compounds that are, or are up to 11, 12, 13, 14, 15, 16, 17, 18, 19, or 20 nucleobases in length comprise no more than 4, no more than 3, no more than 2, or no more than 1 non-complementary nucleobase(s) relative to a target nucleic acid, such as an Androgen Receptor nucleic acid, or specified portion thereof.

In certain embodiments, antisense compounds that are, or are up to 11, 12, 13, 14, 15, 16, 17, 18, 19, 20, 21, 22, 23, 24, 25, 26, 27, 28, 29, or 30 nucleobases in length comprise no more than 6, no more than 5, no more than 4, no more than 3, no more than 2, or no more than 1 non-complementary nucleobase(s) relative to a target nucleic acid, such as an Androgen Receptor nucleic acid, or specified portion thereof.

The antisense compounds provided also include those which are complementary to a portion of a target nucleic acid. As used herein, "portion" refers to a defined number of contiguous (i.e. linked) nucleobases within a region or segment of a target nucleic acid. A "portion" can also refer to a defined number of contiguous nucleobases of an antisense compound. In certain embodiments, the antisense compounds, are complementary to at least an 8 nucleobase portion of a target segment. In certain embodiments, the antisense compounds are complementary to at least a 9 nucleobase portion of a target segment. In certain embodiments, the antisense compounds are complementary to at least a 10 nucleobase portion of a target segment. In certain embodiments, the antisense compounds are complementary to at least an 11 nucleobase portion of a target segment. In certain embodiments, the antisense compounds are complementary to at least a 12 nucleobase portion of a target segment. In certain embodiments, the antisense compounds are complementary to at least a 13 nucleobase portion of a target segment. In certain embodiments, the antisense compounds are complementary to at least a 14 nucleobase portion of a target segment. In certain embodiments, the antisense compounds are complementary to at least a 15 nucleobase portion of a target segment. Also contemplated are antisense compounds that are complementary to at least a 9, 10, 11, 12, 13, 14, 15, 16, 17, 18, 19, 20, or more nucleobase portion of a target segment, or a range defined by any two of these values.

Identity

The antisense compounds provided herein may also have a defined percent identity to a particular nucleotide sequence, SEQ ID NO, or compound represented by a specific Isis number, or portion thereof. As used herein, an antisense compound is identical to the sequence disclosed herein if it has the same nucleobase pairing ability. For example, a RNA which contains uracil in place of thymidine in a disclosed DNA sequence would be considered identical to the DNA sequence since both uracil and thymidine pair with adenine. Shortened and lengthened versions of the antisense compounds described herein as well as compounds having non-identical bases relative to the antisense compounds provided herein also are contemplated. The non-identical bases may be adjacent to each other or dispersed throughout the antisense compound. Percent identity of an antisense compound is calculated according to the number of bases that have identical base pairing relative to the sequence to which it is being compared.

In certain embodiments, the antisense compounds, or portions thereof, are at least 70%, 75%, 80%, 85%, 90%, 95%, 96%, 97%, 98%, 99% or 100% identical to one or more of the antisense compounds or SEQ ID NOs, or a portion thereof, disclosed herein.

In certain embodiments, a portion of the antisense compound is compared to an equal length portion of the target nucleic acid. In certain embodiments, an 8, 9, 10, 11, 12, 13, 14, 15, 16, 17, 18, 19, 20, 21, 22, 23, 24, or 25 nucleobase portion is compared to an equal length portion of the target nucleic acid.

In certain embodiments, a portion of the antisense oligonucleotide is compared to an equal length portion of the target nucleic acid. In certain embodiments, an 8, 9, 10, 11, 12, 13, 14, 15, 16, 17, 18, 19, 20, 21, 22, 23, 24, or 25 nucleobase portion is compared to an equal length portion of the target nucleic acid.

Modifications

A nucleoside is a base-sugar combination. The nucleobase (also known as base) portion of the nucleoside is normally a heterocyclic base moiety. Nucleotides are nucleosides that further include a phosphate group covalently linked to the sugar portion of the nucleoside. For those nucleosides that include a pentofuranosyl sugar, the phosphate group can be linked to the 2', 3' or 5' hydroxyl moiety of the sugar. Oligonucleotides are formed through the covalent linkage of adjacent nucleosides to one another, to form a linear polymeric oligonucleotide. Within the oligonucleotide structure, the phosphate groups are commonly referred to as forming the internucleoside linkages of the oligonucleotide.

Modifications to antisense compounds encompass substitutions or changes to internucleoside linkages, sugar moieties, or nucleobases. Modified antisense compounds are often preferred over native forms because of desirable properties such as, for example, enhanced cellular uptake, enhanced affinity for nucleic acid target, increased stability in the presence of nucleases, or increased inhibitory activity.

Chemically modified nucleosides may also be employed to increase the binding affinity of a shortened or truncated antisense oligonucleotide for its target nucleic acid. Consequently, comparable results can often be obtained with shorter antisense compounds that have such chemically modified nucleosides.

Modified Internucleoside Linkages

The naturally occuring internucleoside linkage of RNA and DNA is a 3' to 5' phosphodiester linkage. Antisense compounds having one or more modified, i.e. non-naturally occurring, internucleoside linkages are often selected over antisense compounds having naturally occurring internucleoside linkages because of desirable properties such as, for example, enhanced cellular uptake, enhanced affinity for target nucleic acids, and increased stability in the presence of nucleases.

Oligonucleotides having modified internucleoside linkages include internucleoside linkages that retain a phosphorus atom as well as internucleoside linkages that do not have a phosphorus atom. Representative phosphorus containing internucleoside linkages include, but are not limited to, phosphodiesters, phosphotriesters, methylphosphonates, phosphoramidate, and phosphorothioates. Methods of preparation of phosphorous-containing and non-phosphorous-containing linkages are well known.

In certain embodiments, antisense compounds targeted to an Androgen Receptor nucleic acid comprise one or more modified internucleoside linkages. In certain embodiments, the modified internucleoside linkages are phosphorothioate linkages. In certain embodiments, each internucleoside linkage of an antisense compound is a phosphorothioate internucleoside linkage.

Modified Sugar Moieties

Antisense compounds can optionally contain one or more nucleosides wherein the sugar group has been modified. Such sugar modified nucleosides may impart enhanced nuclease stability, increased binding affinity, or some other beneficial biological property to the antisense compounds. In certain embodiments, nucleosides comprise chemically modified ribofuranose ring moieties. Examples of chemically modified ribofuranose rings include without limitation, addition of substitutent groups (including 5' and 2' substituent groups), bridging of non-geminal ring atoms to form bicyclic nucleic acids (BNA), replacement of the ribosyl ring oxygen atom with S, N(R), or $C(R_1)(R_2)$ (R, $R_1$ and $R_2$ are each independently H, $C_1$-$C_{12}$ alkyl or a protecting group) and combinations thereof. Examples of chemically modified sugars include 2'-F-5'-methyl substituted nucleoside (see PCT International Application WO 2008/101157 Published on Aug. 21, 2008 for other disclosed 5',2'-bis substituted nucleosides) or replacement of the ribosyl ring oxygen atom with S with further substitution at the 2'-position (see published U.S. Patent Application US2005-0130923, published on Jun. 16, 2005) or alternatively 5'-substitution of a BNA (see PCT International Application WO 2007/134181 Published on Nov. 22, 2007 wherein 4'-($CH_2$)—O-2' (LNA) is substituted with for example a 5'-methyl or a 5'-vinyl group).

Examples of nucleosides having modified sugar moieties include without limitation nucleosides comprising 5'-vinyl, 5'-methyl (R or S), 4'-S, 2'-F, 2'-$OCH_3$, 2'-$OCH_2CH_3$, 2'-$OCH_2CH_2F$ and 2'-$O(CH_2)_2OCH_3$ substituent groups. The substituent at the 2' position can also be selected from allyl, amino, azido, thio, O-allyl, O—$C_1$-$C_{10}$ alkyl, $OCF_3$, $OCH_2F$, $O(CH_2)_2SCH_3$, $O(CH_2)_2$—O—$N(R_m)(R_n)$, O—$CH_2$—C(=O)—$N(R_m)(R_n)$, and O—$CH_2$—C(=O)—$N(R_1)$—$(CH_2)_2$—$N(R_m)(R_n)$, where each $R_1$, $R_m$ and $R_n$ is, independently, H or substituted or unsubstituted $C_1$-$C_{10}$ alkyl.

As used herein, "bicyclic nucleosides" refer to modified nucleosides comprising a bicyclic sugar moiety. Examples of bicyclic nucleosides include without limitation nucleosides comprising a bridge between the 4' and the 2' ribosyl ring atoms. In certain embodiments, antisense compounds provided herein include one or more bicyclic nucleosides comprising a 4' to 2' bridge. Examples of such 4' to 2' bridged bicyclic nucleosides, include but are not limited to one of the formulae: 4'-($CH_2$)—O-2' (LNA); 4'-($CH_2$)—S-2; 4'-($CH_2$)$_2$—O-2' (ENA); 4-CH($CH_3$)—O-2' (also referred to as constrained ethyl or cEt) and 4'-CH($CH_2OCH_3$)—O-2' (and analogs thereof see U.S. Pat. No. 7,399,845, issued on Jul. 15, 2008); 4'-C($CH_3$)($CH_3$)—O-2' (and analogs thereof see published International Application WO/2009/006478, published Jan. 8, 2009); 4-$CH_2$—N($OCH_3$)-2' (and analogs thereof see published International Application WO/2008/ 150729, published Dec. 11, 2008); 4-$CH_2$—O—N($CH_3$)-2' (see published U.S. Patent Application US2004-0171570, published Sep. 2, 2004); 4-$CH_2$—N(R)—O-2', wherein R is H, $C_1$-$C_{12}$ alkyl, or a protecting group (see U.S. Pat. No. 7,427,672, issued on Sep. 23, 2008); 4-$CH_2$—C—(H)($CH_3$)-2' (see Chattopadhyaya et al., *J. Org. Chem.*, 2009, 74, 118-134); and 4-$CH_2$—C(=$CH_2$)-2' (and analogs thereof see published International Application WO 2008/154401, published on Dec. 8, 2008).

Further reports related to bicyclic nucleosides can also be found in published literature (see for example: Singh et al., *Chem. Commun.*, 1998, 4, 455-456; Koshkin et al., *Tetrahedron*, 1998, 54, 3607-3630; Wahlestedt et al., *Proc. Natl. Acad. Sci. U.S.A*, 2000, 97, 5633-5638; Kumar et al., *Bioorg. Med. Chem. Lett.*, 1998, 8, 2219-2222; Singh et al., *J. Org. Chem.*, 1998, 63, 10035-10039; Srivastava et al., *J. Am. Chem. Soc.*, 2007, 129(26) 8362-8379; Elayadi et al., *Curr. Opinion Invest. Drugs*, 2001, 2, 558-561; Braasch et al., *Chem. Biol.*, 2001, 8, 1-7; and Orum et al., *Curr. Opinion Mol. Ther.*, 2001, 3, 239-243; U.S. Pat. Nos. 6,268,490; 6,525,191; 6,670,461; 6,770,748; 6,794,499; 7,034,133; 7,053,207; 7,399,845; 7,547,684; and 7,696,345; U.S. Patent Publication No. US2008-0039618; US2009-0012281; U.S. Patent Ser. Nos. 60/989,574; 61/026,995; 61/026,998; 61/056,564; 61/086,231; 61/097,787; and 61/099,844; Published PCT International applications WO 1994/014226; WO 2004/106356; WO 2005/021570; WO 2007/134181; WO 2008/150729; WO 2008/154401; and WO 2009/006478. Each of the foregoing bicyclic nucleosides can be prepared having one or more stereochemical sugar configurations including for example α-L-ribofuranose and β-D-ribofuranose (see PCT international application PCT/DK98/00393, published on Mar. 25, 1999 as WO 99/14226).

In certain embodiments, bicyclic sugar moieties of BNA nucleosides include, but are not limited to, compounds having at least one bridge between the 4' and the 2' position of the pentofuranosyl sugar moiety wherein such bridges independently comprises 1 or from 2 to 4 linked groups independently selected from —[C($R_a$)($R_b$)]$_n$—, —C($R_a$)=C($R_b$)—, —C($R_a$)=N—, —C(=O)—, —C(=$NR_a$)—, —C(=S)—, —O—, —Si($R_a$)$_2$—, —S(=O)$_x$—, and —N($R_a$)—;

wherein:

x is 0, 1, or 2;

n is 1, 2, 3, or 4;

each $R_a$ and $R_b$ is, independently, H, a protecting group, hydroxyl, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, heterocycle radical, substituted heterocycle radical, heteroaryl, substituted heteroaryl, $C_5$-$C_7$ alicyclic radical, substituted $C_5$-$C_7$ alicyclic radical, halogen, $OJ_1$, $NJ_1J_2$, $SJ_1$, $N_3$, $COOJ_1$, acyl (C(=O)—H), substituted acyl, CN, sulfonyl (S(=O)$_2$-$J_1$), or sulfoxyl (S(=O)-$J_1$); and each $J_1$ and $J_2$ is, independently, H, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, acyl (C(=O)—H), substituted acyl, a heterocycle radical, a substituted heterocycle radical, $C_1$-$C_{12}$ aminoalkyl, substituted $C_1$-$C_{12}$ aminoalkyl or a protecting group.

In certain embodiments, the bridge of a bicyclic sugar moiety is —[C($R_a$)($R_b$)]$_n$—, —[C($R_a$)($R_b$)]$_n$—O—, —C($R_aR_b$)—N(R)—O— or —C($R_aR_b$)—O—N(R)—. In certain embodiments, the bridge is 4-$CH_2$-2', 4'-($CH_2$)$_2$-2', 4'-($CH_2$)$_3$-2', 4-$CH_2$—O-2', 4'-($CH_2$)$_2$—O-2', 4-$CH_2$—O—

N(R)-2' and 4-CH$_2$—N(R)—O-2'- wherein each R is, independently, H, a protecting group or C$_1$-C$_{12}$ alkyl.

In certain embodiments, bicyclic nucleosides are further defined by isomeric configuration. For example, a nucleoside comprising a 4'-2' methylene-oxy bridge, may be in the α-L configuration or in the β-D configuration. Previously, α-L-methyleneoxy (4-CH$_2$—O-2') BNA's have been incorporated into antisense oligonucleotides that showed antisense activity (Frieden et al., *Nucleic Acids Research*, 2003, 21, 6365-6372).

In certain embodiments, bicyclic nucleosides include, but are not limited to, (A) α-L-methyleneoxy (4'-CH$_2$—O-2') BNA, (B) β-D-methyleneoxy (4'-CH$_2$—O-2') BNA, (C) ethyleneoxy (4'-(CH$_2$)$_2$—O-2') BNA, (D) aminooxy (4'-CH$_2$—O—N(R)-2') BNA, (E) oxyamino (4'-CH$_2$—N(R)—O-2') BNA, and (F) methyl(methyleneoxy) (4'-CH(CH$_3$)—O-2') BNA, (G) methylene-thio (4'-CH$_2$—S-2') BNA, (H) methylene-amino (4'-CH$_2$—N(R)-2') BNA, (I) methyl carbocyclic (4'-CH$_2$—CH(CH$_3$)-2') BNA, (J) propylene carbocyclic (4'-(CH$_2$)$_3$-2') BNA and (K) vinyl BNA as depicted below:

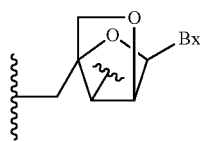
(A)

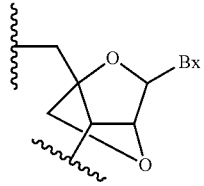
(B)

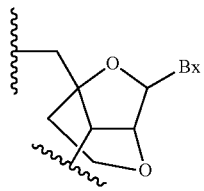
(C)

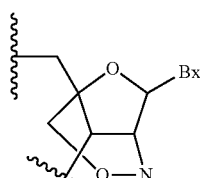
(D)

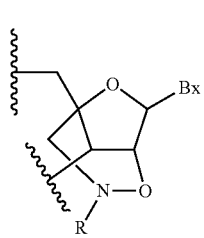
(E)

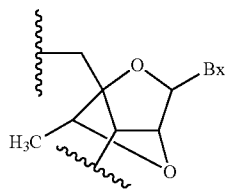
(F)

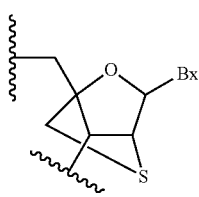
(G)

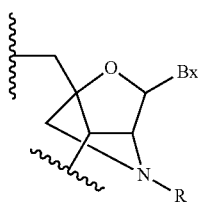
(H)

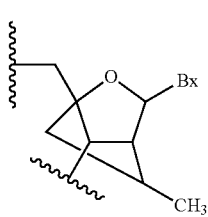
(I)

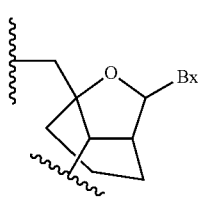
(J)

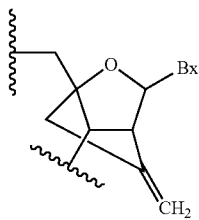
(K)

wherein Bx is the base moiety and R is independently H, a protecting group, C$_1$-C$_{12}$ alkyl or C$_1$-C$_{12}$ alkoxy.

In certain embodiments, bicyclic nucleosides are provided having Formula I:

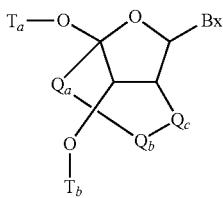

wherein:

Bx is a heterocyclic base moiety;
-$Q_a$-$Q_b$-$Q_c$- is —$CH_2$—N($R_c$)—$CH_2$—, —C(=O)—N($R_c$)—$CH_2$—, —$CH_2$—O—N($R_c$)—, —$CH_2$—N($R_c$)—O— or —N($R_c$)—O—$CH_2$;

$R_c$ is $C_1$-$C_{12}$ alkyl or an amino protecting group; and $T_a$ and $T_b$ are each, independently H, a hydroxyl protecting group, a conjugate group, a reactive phosphorus group, a phosphorus moiety or a covalent attachment to a support medium.

In certain embodiments, bicyclic nucleosides are provided having Formula II:

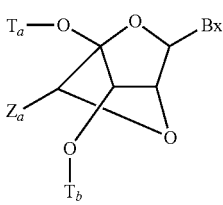

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$Z_a$ is $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl, substituted $C_2$-$C_6$ alkynyl, acyl, substituted acyl, substituted amide, thiol or substituted thio.

In one embodiment, each of the substituted groups is, independently, mono or poly substituted with substituent groups independently selected from halogen, oxo, hydroxyl, $OJ_c$, $NJ_cJ_d$, $SJ_c$, $N_3$, OC(=X)$J_c$, and $NJ_cC$(=X)$NJ_cJ_d$, wherein each $J_c$, $J_d$ and $J_e$ is, independently, H, $C_1$-$C_6$ alkyl, or substituted $C_1$-$C_6$ alkyl and X is O or $NJ_c$.

In certain embodiments, bicyclic nucleosides are provided having Formula III:

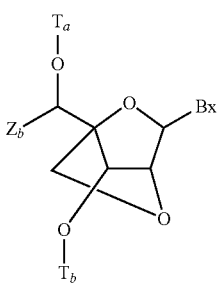

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$Z_b$ is $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl, substituted $C_2$-$C_6$ alkynyl or substituted acyl (C(=O)—).

In certain embodiments, bicyclic nucleosides are provided having Formula IV:

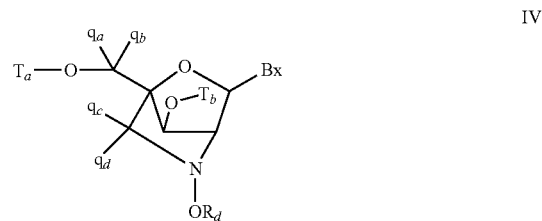

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$R_d$ is $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;

each $q_a$, $q_b$, $q_c$ and $q_d$ is, independently, H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl, $C_1$-$C_6$ alkoxyl, substituted $C_1$-$C_6$ alkoxyl, acyl, substituted acyl, $C_1$-$C_6$ aminoalkyl or substituted $C_1$-$C_6$ aminoalkyl;

In certain embodiments, bicyclic nucleosides are provided having Formula V:

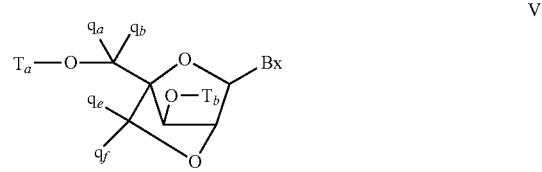

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$q_a$, $q_b$, $q_e$ and $q_f$ are each, independently, hydrogen, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxy, substituted $C_1$-$C_{12}$ alkoxy, $OJ_j$, $SJ_j$, $SOJ_j$, $SO_2J_j$, $NJ_jJ_k$, $N_3$, CN, C(=O)$OJ_j$, C(=O)$NJ_jJ_k$, C(=O)$J_j$, O—C(=O)—$NJ_jJ_k$, N(H)C(=NH)$NJ_jJ_k$, N(H)C(=O)$NJ_jJ_k$ or N(H)C(=S)$NJ_jJ_k$;

or $q_e$ and $q_f$ together are =C($q_g$)($q_h$);

$q_g$ and $q_h$ are each, independently, H, halogen, $C_1$-$C_{12}$ alkyl or substituted $C_1$-$C_{12}$ alkyl.

The synthesis and preparation of the methyleneoxy (4-$CH_2$—O-2') BNA monomers adenine, cytosine, guanine, 5-methyl-cytosine, thymine and uracil, along with their oligomerization, and nucleic acid recognition properties have been described (Koshkin et al., *Tetrahedron*, 1998, 54, 3607-3630). Bicyclic nucleic acids (BNAs) and preparation thereof are also described in WO 98/39352 and WO 99/14226.

Analogs of methyleneoxy (4-CH$_2$—O-2') BNA and 2'-thio-BNAs, have also been prepared (Kumar et al., *Bioorg. Med. Chem. Lett.*, 1998, 8, 2219-2222). Preparation of locked nucleoside analogs comprising oligodeoxyribonucleotide duplexes as substrates for nucleic acid polymerases has also been described (Wengel et al., WO 99/14226). Furthermore, synthesis of 2'-amino-BNA, a novel comformationally restricted high-affinity oligonucleotide analog has been described in the art (Singh et al., *J. Org. Chem.*, 1998, 63, 10035-10039). In addition, 2'-amino- and 2'-methylamino-BNA's have been prepared and the thermal stability of their duplexes with complementary RNA and DNA strands has been previously reported.

In certain embodiments, bicyclic nucleosides are provided having Formula VI:

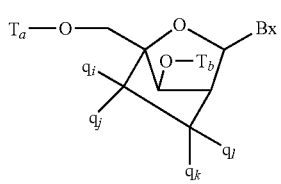

wherein:
Bx is a heterocyclic base moiety;
T$_a$ and T$_b$ are each, independently, H, a hydroxyl protecting group, a conjugate group, a reactive phosphorus group, a phosphorus moiety or a covalent attachment to a support medium;
each q$_i$, q$_j$, q$_k$ and q$_l$ is, independently, H, halogen, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_1$-C$_{12}$ alkoxyl, substituted C$_1$-C$_{12}$ alkoxyl, OJ$_j$, SJ$_j$, SOJ$_j$, N$_3$, CN, C(=O)OJ$_j$, C(=O)NJ$_j$J$_k$, C(=O)J$_j$, O—C(=O)NJ$_j$J$_k$, N(H)C(=NH)NJ$_j$J$_k$, N(H)C(=O)NJ$_j$J$_k$ or N(H)C(=S)NJ$_j$J$_k$; and
q$_i$ and q$_j$ or q$_l$ and q$_k$ together are =C(q$_g$)(q$_h$), wherein q$_g$ and q$_h$ are each, independently, H, halogen, C$_1$-C$_{12}$ alkyl or substituted C$_1$-C$_{12}$ alkyl.

One carbocyclic bicyclic nucleoside having a 4'-(CH$_2$)$_3$-2' bridge and the alkenyl analog bridge 4'-CH=CH—CH$_2$-2' have been described (Freier et al., *Nucleic Acids Research*, 1997, 25(22), 4429-4443 and Albaek et al., *J. Org. Chem.*, 2006, 71, 7731-7740). The synthesis and preparation of carbocyclic bicyclic nucleosides along with their oligomerization and biochemical studies have also been described (Srivastava et al., *J. Am. Chem. Soc.*, 2007, 129(26), 8362-8379).

As used herein, "4'-2' bicyclic nucleoside" or "4 to 2' bicyclic nucleoside" refers to a bicyclic nucleoside comprising a furanose ring comprising a bridge connecting two carbon atoms of the furanose ring connects the 2' carbon atom and the 4' carbon atom of the sugar ring.

As used herein, "monocylic nucleosides" refer to nucleosides comprising modified sugar moieties that are not bicyclic sugar moieties. In certain embodiments, the sugar moiety, or sugar moiety analogue, of a nucleoside may be modified or substituted at any position.

As used herein, "2'-modified sugar" means a furanosyl sugar modified at the 2' position. In certain embodiments, such modifications include substituents selected from: a halide, including, but not limited to substituted and unsubstituted alkoxy, substituted and unsubstituted thioalkyl, substituted and unsubstituted amino alkyl, substituted and unsubstituted alkyl, substituted and unsubstituted allyl, and substituted and unsubstituted alkynyl. In certain embodiments, 2' modifications are selected from substituents including, but not limited to: O[(CH$_2$)$_n$O]$_m$CH$_3$, O(CH$_2$)$_n$NH$_2$, O(CH$_2$)$_n$CH$_3$, O(CH$_2$)$_n$F, O(CH$_2$)$_n$ONH$_2$, OCH$_2$C(=O)N(H)CH$_3$, and O(CH$_2$)$_n$ON[(CH$_2$)$_n$CH$_3$]$_2$, where n and m are from 1 to about 10. Other 2'- substituent groups can also be selected from: C$_1$-C$_{12}$ alkyl, substituted alkyl, alkenyl, alkynyl, alkaryl, aralkyl, O-alkaryl or O-aralkyl, SH, SCH$_3$, OCN, Cl, Br, CN, F, CF$_3$, OCF$_3$, SOCH$_3$, SO$_2$CH$_3$, ONO$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving pharmacokinetic properties, or a group for improving the pharmacodynamic properties of an antisense compound, and other substituents having similar properties. In certain embodiments, modifed nucleosides comprise a 2'-MOE side chain (Baker et al., *J. Biol. Chem.*, 1997, 272, 11944-12000). Such 2'-MOE substitution have been described as having improved binding affinity compared to unmodified nucleosides and to other modified nucleosides, such as 2'-O-methyl, O-propyl, and O-aminopropyl. Oligonucleotides having the 2'-MOE substituent also have been shown to be antisense inhibitors of gene expression with promising features for in vivo use (Martin, *Helv. Chim. Acta*, 1995, 78, 486-504; Altmann et al., *Chimia*, 1996, 50, 168-176; Altmann et al., *Biochem. Soc. Trans.*, 1996, 24, 630-637; and Altmann et al., *Nucleosides Nucleotides*, 1997, 16, 917-926).

As used herein, a "modified tetrahydropyran nucleoside" or "modified THP nucleoside" means a nucleoside having a six-membered tetrahydropyran "sugar" substituted in for the pentofuranosyl residue in normal nucleosides (a sugar surrogate). Modified THP nucleosides include, but are not limited to, what is referred to in the art as hexitol nucleic acid (HNA), anitol nucleic acid (ANA), manitol nucleic acid (MNA) (see Leumann, *Bioorg. Med. Chem.*, 2002, 10, 841-854) or fluoro HNA (F-HNA) having a tetrahydropyran ring system as illustrated below:

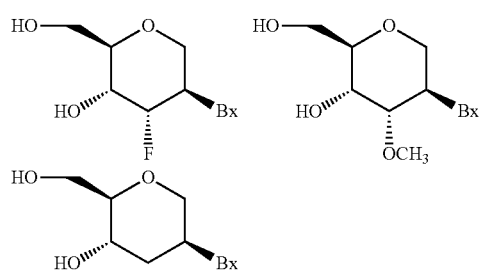

In certain embodiments, sugar surrogates are selected having Formula VII:

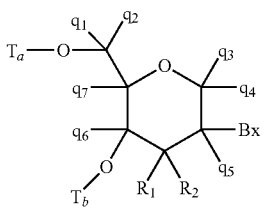

wherein independently for each of said at least one tetrahydropyran nucleoside analog of Formula VII:

Bx is a heterocyclic base moiety;

$T_a$ and $T_b$ are each, independently, an internucleoside linking group linking the tetrahydropyran nucleoside analog to the antisense compound or one of $T_a$ and $T_b$ is an internucleoside linking group linking the tetrahydropyran nucleoside analog to the antisense compound and the other of $T_a$ and $T_b$ is H, a hydroxyl protecting group, a linked conjugate group or a 5' or 3'-terminal group;

$q_1$, $q_2$, $q_3$, $q_4$, $q_5$, $q_6$ and $q_7$ are each independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl; and each of $R_1$ and $R_2$ is selected from hydrogen, hydroxyl, halogen, substituted or unsubstituted alkoxy, $NJ_1J_2$, $SJ_1$, $N_3$, $OC(=X)J_1$, $OC(=X)NJ_1J_2$, $NJ_3C(=X)NJ_1J_2$ and CN, wherein X is O, S or $NJ_1$ and each $J_1$, $J_2$ and $J_3$ is, independently, H or $C_1$-$C_6$ alkyl.

In certain embodiments, the modified THP nucleosides of Formula VII are provided wherein $q_1$, $q_2$, $q_3$, $q_4$, $q_5$, $q_6$ and $q_7$ are each H. In certain embodiments, at least one of $q_1$, $q_2$, $q_3$, $q_4$, $q_5$, $q_6$ and $q_7$ is other than H. In certain embodiments, at least one of $q_1$, $q_2$, $q_3$, $q_4$, $q_5$, $q_6$ and $q_7$ is methyl. In certain embodiments, THP nucleosides of Formula VII are provided wherein one of $R_1$ and $R_2$ is fluoro. In certain embodiments, $R_1$ is fluoro and $R_2$ is H; $R_1$ is methoxy and $R_2$ is H, and $R_1$ is methoxyethoxy and $R_2$ is H.

In certain embodiments, sugar surrogates comprise rings having more than 5 atoms and more than one heteroatom. For example nucleosides comprising morpholino sugar moieties and their use in oligomeric compounds has been reported (see for example: Braasch et al., *Biochemistry*, 2002, 41, 4503-4510; and U.S. Pat. Nos. 5,698,685; 5,166,315; 5,185,444; and 5,034,506). As used here, the term "morpholino" means a sugar surrogate having the following formula:

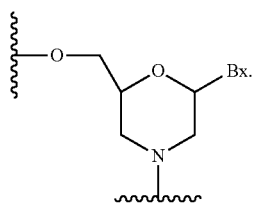

In certain embodiments, morpholinos may be modified, for example by adding or altering various substituent groups from the above morpholino structure. Such sugar surrogates are referred to herein as "modifed morpholinos."

Combinations of modifications are also provided without limitation, such as 2'-F-5'-methyl substituted nucleosides (see PCT International Application WO 2008/101157 published on Aug. 21, 2008 for other disclosed 5',2'-bis substituted nucleosides) and replacement of the ribosyl ring oxygen atom with S and further substitution at the 2'-position (see published U.S. Patent Application US2005-0130923, published on Jun. 16, 2005) or alternatively 5'-substitution of a bicyclic nucleic acid (see PCT International Application WO 2007/134181, published on Nov. 22, 2007 wherein a 4-$CH_2$—O-2' bicyclic nucleoside is further substituted at the 5' position with a 5'-methyl or a 5'-vinyl group). The synthesis and preparation of carbocyclic bicyclic nucleosides along with their oligomerization and biochemical studies have also been described (see, e.g., Srivastava et al., *J. Am. Chem. Soc.* 2007, 129(26), 8362-8379).

In certain embodiments, antisense compounds comprise one or more modified cyclohexenyl nucleosides, which is a nucleoside having a six-membered cyclohexenyl in place of the pentofuranosyl residue in naturally occurring nucleosides. Modified cyclohexenyl nucleosides include, but are not limited to those described in the art (see for example commonly owned, published PCT Application WO 2010/036696, published on Apr. 10, 2010, Robeyns et al., *J. Am. Chem. Soc.*, 2008, 130(6), 1979-1984; Horváth et al., *Tetrahedron Letters*, 2007, 48, 3621-3623; Nauwelaerts et al., *J. Am. Chem. Soc.*, 2007, 129(30), 9340-9348; Gu et al., *Nucleosides, Nucleotides & Nucleic Acids*, 2005, 24(5-7), 993-998; Nauwelaerts et al., *Nucleic Acids Research*, 2005, 33(8), 2452-2463; Robeyns et al., *Acta Crystallographica, Section F: Structural Biology and Crystallization Communications*, 2005, F61(6), 585-586; Gu et al., *Tetrahedron*, 2004, 60(9), 2111-2123; Gu et al., *Oligonucleotides*, 2003, 13(6), 479-489; Wang et al., *J. Org. Chem.*, 2003, 68, 4499-4505; Verbeure et al., *Nucleic Acids Research*, 2001, 29(24), 4941-4947; Wang et al., *J. Org. Chem.*, 2001, 66, 8478-82; Wang et al., *Nucleosides, Nucleotides & Nucleic Acids*, 2001, 20(4-7), 785-788; Wang et al., *J. Am. Chem.*, 2000, 122, 8595-8602; Published PCT application, WO 06/047842; and Published PCT Application WO 01/049687; the text of each is incorporated by reference herein, in their entirety). Certain modified cyclohexenyl nucleosides have Formula X.

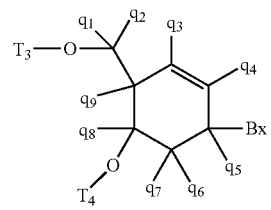

wherein independently for each of said at least one cyclohexenyl nucleoside analog of Formula X:

Bx is a heterocyclic base moiety;

$T_3$ and $T_4$ are each, independently, an internucleoside linking group linking the cyclohexenyl nucleoside analog to an antisense compound or one of $T_3$ and $T_4$ is an internucleoside linking group linking the tetrahydropyran nucleoside analog to an antisense compound and the other of $T_3$ and $T_4$ is H, a hydroxyl protecting group, a linked conjugate group, or a 5'- or 3'-terminal group; and $q_1$, $q_2$, $q_3$, $q_4$, $q_5$, $q_6$, $q_7$, $q_8$ and $q_9$ are each, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or other sugar substituent group.

As used herein, "2'-modified" or "2'-substituted" refers to a nucleoside comprising a sugar comprising a substituent at the 2' position other than H or OH. 2'-modified nucleosides, include, but are not limited to, bicyclic nucleosides wherein the bridge connecting two carbon atoms of the sugar ring connects the 2' carbon and another carbon of the sugar ring; and nucleosides with non-bridging 2'substituents, such as allyl, amino, azido, thio, O-allyl, O—$C_1$-$C_{10}$ alkyl, —$OCF_3$, O—$(CH_2)_2$—O—$CH_3$, 2'-O$(CH_2)_2SCH_3$, O—$(CH_2)_2$—O—N$(R_m)(R_n)$ or O—$CH_2$—C(=O)—N$(R_m)(R_n)$, where each $R_m$ and $R_n$ is, independently, H or substituted or unsubstituted $C_1$-$C_{10}$ alkyl. 2'-modifed nucleosides may further comprise other modifications, for example at other positions of the sugar and/or at the nucleobase.

As used herein, "2'-F" refers to a nucleoside comprising a sugar comprising a fluoro group at the 2' position of the sugar ring.

As used herein, "2'-OMe" or "2'-$OCH_3$" or "2'-O-methyl" each refers to a nucleoside comprising a sugar comprising an —$OCH_3$ group at the 2' position of the sugar ring.

As used herein, "oligonucleotide" refers to a compound comprising a plurality of linked nucleosides. In certain embodiments, one or more of the plurality of nucleosides is modified. In certain embodiments, an oligonucleotide comprises one or more ribonucleosides (RNA) and/or deoxyribonucleosides (DNA).

Many other bicyclo and tricyclo sugar surrogate ring systems are also known in the art that can be used to modify nucleosides for incorporation into antisense compounds (see for example review article: Leumann, *Bioorg. Med. Chem.*, 2002, 10, 841-854). Such ring systems can undergo various additional substitutions to enhance activity.

Methods for the preparations of modified sugars are well known to those skilled in the art. Some representative U.S. patents that teach the preparation of such modified sugars include without limitation, U.S.: 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,670,633; 5,700,920; 5,792,847 and 6,600,032 and International Application PCT/US2005/019219, filed Jun. 2, 2005 and published as WO 2005/121371 on Dec. 22, 2005, and each of which is herein incorporated by reference in its entirety.

In nucleotides having modified sugar moieties, the nucleobase moieties (natural, modified or a combination thereof) are maintained for hybridization with an appropriate nucleic acid target.

In certain embodiments, antisense compounds comprise one or more nucleosides having modified sugar moieties. In certain embodiments, the modified sugar moiety is 2'-MOE. In certain embodiments, the 2'-MOE modified nucleosides are arranged in a gapmer motif. In certain embodiments, the modified sugar moiety is a bicyclic nucleoside having a (4'-CH($CH_3$)—O-2') bridging group. In certain embodiments, the (4-CH($CH_3$)—O-2') modified nucleosides are arranged throughout the wings of a gapmer motif.

Modified Nucleobases

Nucleobase (or base) modifications or substitutions are structurally distinguishable from, yet functionally interchangeable with, naturally occurring or synthetic unmodified nucleobases. Both natural and modified nucleobases are capable of participating in hydrogen bonding. Such nucleobase modifications can impart nuclease stability, binding affinity or some other beneficial biological property to antisense compounds. Modified nucleobases include synthetic and natural nucleobases such as, for example, 5-methylcytosine (5-me-C). Certain nucleobase substitutions, including 5-methylcytosine substitutions, are particularly useful for increasing the binding affinity of an antisense compound for a target nucleic acid. For example, 5-methylcytosine substitutions have been shown to increase nucleic acid duplex stability by 0.6-1.2° C. (Sanghvi, Y. S., Crooke, S. T. and Lebleu, B., eds., Antisense Research and Applications, CRC Press, Boca Raton, 1993, pp. 276-278).

Additional modified nucleobases include 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH3) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine.

Heterocyclic base moieties can also include those in which the purine or pyrimidine base is replaced with other heterocycles, for example 7-deaza-adenine, 7-deazaguanosine, 2-aminopyridine and 2-pyridone. Nucleobases that are particularly useful for increasing the binding affinity of antisense compounds include 5-substituted pyrimidines, 6-azapyrimidines and N-2, N-6 and 0-6 substituted purines, including 2 aminopropyladenine, 5-propynyluracil and 5-propynylcytosine.

In certain embodiments, antisense compounds targeted to an androgen receptor nucleic acid comprise one or more modified nucleobases. In certain embodiments, shortened or gap-widened antisense oligonucleotides targeted to an androgen receptor nucleic acid comprise one or more modified nucleobases. In certain embodiments, the modified nucleobase is 5-methylcytosine. In certain embodiments, each cytosine is a 5-methylcytosine.

Conjugated Antisense Compounds

Antisense compounds may be covalently linked to one or more moieties or conjugates which enhance the activity, cellular distribution or cellular uptake of the resulting antisense oligonucleotides. Typical conjugate groups include cholesterol moieties and lipid moieties. Additional conjugate groups include carbohydrates, phospholipids, biotin, phenazine, folate, phenanthridine, anthraquinone, acridine, fluoresceins, rhodamines, coumarins, and dyes.

Antisense compounds can also be modified to have one or more stabilizing groups that are generally attached to one or both termini of antisense compounds to enhance properties such as, for example, nuclease stability. Included in stabilizing groups are cap structures. These terminal modifications protect the antisense compound having terminal nucleic acid from exonuclease degradation, and can help in delivery and/or localization within a cell. The cap can be present at the 5'-terminus (5'-cap), or at the 3'-terminus (3'-cap), or can be present on both termini. Cap structures are well known in the art and include, for example, inverted deoxy abasic caps. Further 3' and 5'-stabilizing groups that can be used to cap one or both ends of an antisense compound to impart nuclease stability include those disclosed in WO 03/004602 published on Jan. 16, 2003.

In certain embodiments, antisense compounds, including, but not limited to those particularly suited for use as ssRNA, are modified by attachment of one or more conjugate groups. In general, conjugate groups modify one or more properties of the attached oligonucleotide, including but not limited to pharmacodynamics, pharmacokinetics, stability, binding, absorption, cellular distribution, cellular uptake, charge and clearance. Conjugate groups are routinely used in the chemical arts and are linked directly or via an optional conjugate linking moiety or conjugate linking group to a parent compound such as an oligonucleotide. Conjugate groups includes without limitation, intercalators, reporter molecules, polyamines, polyamides, polyethylene glycols, thioethers, polyethers, cholesterols, thiocholesterols, cholic acid moieties, folate, lipids, phospholipids, biotin, phenazine, phenanthridine, anthraquinone, adamantane, acridine, fluoresceins, rhodamines, coumarins and dyes. Certain conjugate groups have been described previously, for example: cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-S-tritylthiol (Manoharan et al., Ann. N.Y. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., do-decan-diol or undecyl residues (Saison-Behmoaras et al., EMBO J., 1991, 10, 1111-1118; Kabanov et al., FEBS Lett., 1990, 259, 327-330; Svinarchuk et al., Biochimie, 1993, 75, 49-54), a phospholipid, e.g., di-hexadecyl-rac-glycerol or triethyl-ammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Manoharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim Biophys. Acta, 1995, 1264, 229-237), or an octadecylamine or hexylaminocarbonyl-oxycholesterol moiety (Crooke et al., J. Pharmacol. Exp. Ther., 1996, 277, 923-937).

For additional conjugates including those useful for ssRNA and their placement within antisense compounds, see e.g., PCT Publication No.; WO2013/033230.

Compositions and Methods for Formulating Pharmaceutical Compositions

Antisense oligonucleotides may be admixed with pharmaceutically acceptable active or inert substances for the preparation of pharmaceutical compositions or formulations. Compositions and methods for the formulation of pharmaceutical compositions are dependent upon a number of criteria, including, but not limited to, route of administration, extent of disease, or dose to be administered.

An antisense compound targeted to an androgen receptor nucleic acid can be utilized in pharmaceutical compositions by combining the antisense compound with a suitable pharmaceutically acceptable diluent or carrier. In certain embodiments, a pharmaceutically acceptable diluent is water, such as sterile water suitable for injection. Accordingly, in one embodiment, employed in the methods described herein is a pharmaceutical composition comprising an antisense compound targeted to an androgen receptor nucleic acid and a pharmaceutically acceptable diluent. In certain embodiments, the pharmaceutically acceptable diluent is water. In certain embodiments, the antisense compound is an antisense oligonucleotide provided herein.

Pharmaceutical compositions comprising antisense compounds encompass any pharmaceutically acceptable salts, esters, or salts of such esters, or any other oligonucleotide which, upon administration to an animal, including a human, is capable of providing (directly or indirectly) the biologically active metabolite or residue thereof. Accordingly, for example, the disclosure is also drawn to pharmaceutically acceptable salts of antisense compounds, prodrugs, pharmaceutically acceptable salts of such prodrugs, and other bioequivalents. Suitable pharmaceutically acceptable salts include, but are not limited to, sodium and potassium salts.

A prodrug can include the incorporation of additional nucleosides at one or both ends of an antisense compound which are cleaved by endogenous nucleases within the body, to form the active antisense compound.

In Vitro Testing of Antisense Oligonucleotides

Described herein are methods for treatment of cells with antisense oligonucleotides, which can be modified appropriately for treatment with other antisense compounds.

Cells may be treated with antisense oligonucleotides when the cells reach approximately 60-80% confluency in culture.

One reagent commonly used to introduce antisense oligonucleotides into cultured cells includes the cationic lipid transfection reagent LIPOFECTIN (Invitrogen, Carlsbad, Calif.). Antisense oligonucleotides may be mixed with LIPOFECTIN in OPTI-MEM 1 (Invitrogen, Carlsbad, Calif.) to achieve the desired final concentration of antisense oligonucleotide and a LIPOFECTIN concentration that may range from 2 to 12 ug/mL per 100 nM antisense oligonucleotide.

Another reagent used to introduce antisense oligonucleotides into cultured cells includes LIPOFECTAMINE (Invitrogen, Carlsbad, Calif.). Antisense oligonucleotide is mixed with LIPOFECTAMINE in OPTI-MEM 1 reduced serum medium (Invitrogen, Carlsbad, Calif.) to achieve the desired concentration of antisense oligonucleotide and a LIPOFECTAMINE concentration that may range from 2 to 12 ug/mL per 100 nM antisense oligonucleotide.

Another technique used to introduce antisense oligonucleotides into cultured cells includes electroporation.

Yet another technique used to introduce antisense oligonucleotides into cultured cells includes free uptake of the oligonucleotides by the cells.

Cells are treated with antisense oligonucleotides by routine methods. Cells may be harvested 16-24 hours after antisense oligonucleotide treatment, at which time RNA or protein levels of target nucleic acids are measured by methods known in the art and described herein. In general, when treatments are performed in multiple replicates, the data are presented as the average of the replicate treatments.

The concentration of antisense oligonucleotide used varies from cell line to cell line. Methods to determine the optimal antisense oligonucleotide concentration for a particular cell line are well known in the art. Antisense oligonucleotides are typically used at concentrations ranging from 1 nM to 300 nM when transfected with LIPOFECTAMINE. Antisense oligonucleotides are used at higher concentrations ranging from 625 to 20,000 nM when transfected using electroporation.

RNA Isolation

RNA analysis can be performed on total cellular RNA or poly(A)+mRNA. Methods of RNA isolation are well known in the art. RNA is prepared using methods well known in the art, for example, using the TRIZOL Reagent (Invitrogen, Carlsbad, Calif.) according to the manufacturer's recommended protocols.

EMBODIMENTS

E1. A compound comprising a modified oligonucleotide consisting of 10 to 30 linked nucleosides and having a nucleobase sequence comprising at least 8 contiguous nucleobases of any of the nucleobase sequences of SEQ ID NOs: 12-179.

E2. A compound comprising a modified oligonucleotide consisting of 16 to 30 linked nucleosides and having a nucleobase sequence comprising the nucleobase sequence of any one of SEQ ID NOs: 12-179.

E 3. A compound comprising a modified oligonucleotide consisting of the nucleobase sequence of any one of SEQ ID NOs: 12-179.

E 4. A compound comprising a modified oligonucleotide consisting of 10 to 30 linked nucleosides and having a nucleobase sequence comprising at least 8 contiguous nucleobases of any of the nucleobase sequences of SEQ ID NO: 35, 39, 43, 124, 150, 155, 169, or 175.

E 5. A compound comprising a modified oligonucleotide consisting of 16 to 30 linked nucleosides and having a nucleobase sequence comprising the nucleobase sequence of SEQ ID NO: 35, 39, 43, 124, 150, 155, 169, or 175.

E6. A compound comprising a modified oligonucleotide consisting of 16 linked nucleosides and having a nucleobase sequence consisting of the nucleobase sequence of SEQ ID NO: 35, 39, 43, 124, 150, 155, 169, or 175.

E7. A compound comprising a modified oligonucleotide consisting of 10 to 30 linked nucleosides complementary within nucleotides 2957-2972, 3079-3094, 3099-3114, 3109-3124, 3113-3128, 3120-3135, 3133-3148, 3224-3239, 3226-3241, 3351-3366, 3353-3368, 3361-3376, 3388-3403, 3513-3528, 3517-3532, 3519-3534, 3641-3656, 3735-3750, 3764-3779, 3768-3783, 3798-3813, 3799-3814, 3851-3866, 3870-3885, 3874-3889, 3876-3891, 3878-3893, 3884-3899, 3886-3901, 3888-3903, 3901-3916, 3956-3971, 3962-3977, 3964-3979, 3967-3982, 4019-4034, 4038-4053, 4049-4064, 4056-4071, 4059-4074, 4062-4077, 4066-4081, 4070-4085, 4101-4116, 4103-4118, 4105-4120, 4109-4124, 4305-4320, 4405-4420, 4532-4547, 4534-4549, 4537-4552, 4539-4554, 4555-4570, 4571-4586, 4573-4588, 4578-4593, 4597-4612, 4632-4647, 4655-4670, 4656-4671, 4662-4677, 4699-4714, 4747-4762, 4750-4765, 4752-4767, 4754-4769, 4755-4770, 4769-4784, 4798-4813, 4804-4819, 4807-4822, 4833-4848, 4837-4852, 4839-4854, 4865-4880, 4868-4883, 4872-4887, 4874-4889, 4876-4891, 4887-4902, 4889-4904, 4916-4931, 4918-4933, 4938-4953, 4942-4957, 4944-4959, 4951-4966, 5050-5065, 5052-5067, 5054-5069, 5056-5071, 5060-5075, 5061-5076, 5062-5077, 5133-5148, 5141-5156, 5155-5170, 5265-5280, 5293-5308, 5308-5323, 5392-5407, 5448-5463, 5469-5484, 5481-5496, 5483-5498, 5486-5501, 5488-5503, 5494-5509, 5521-5536, 5666-5681, 6222-6237, 6701-6716, 7543-7558, 8471-8486, 8638-8653, 9464-9479, 10217-10232, 10250-10265, 10865-10880, 11197-11212, 11855-11870, 13189-13204, 13321-13336, 13346-13361, 16555-16570, 16793-16808, 16968-16983, 17206-17221, 18865-18880, 29329-29344, 32290-32305, 33315-33330, 39055-39070, 40615-40630, 42017-42032, 56050-56065, 58719-58734, 58720-58739, 58721-58736, 58722-58737, 58723-58738, 58724-58739, 58725-58740, 58750-58769, 58751-58766, 58752-58767, 58753-58768, 58754-58769, 58755-58770, 60902-60917, 67454-67469, 114874-114889, 115272-115287, 115365-115380, 134971-134986, 102156-102171, 139682-139697, 139762-139777, 139782-139797, 144856-144871, 144938-144953, 148406-148421, 148443-148458, 148520-148535, 181695-181710, 182958-182973, or 183049-183064 of SEQ ID NO: 1, wherein said modified oligonucleotide is at least 90% complementary to SEQ ID NO: 1.

E8. A compound comprising a modified oligonucleotide consisting of 10 to 30 linked nucleosides having a nucleobase sequence comprising a portion of at least 8 contiguous nucleobases 100% complementary to an equal length portion of nucleobases 2957-2972, 3079-3094, 3099-3114, 3109-3124, 3113-3128, 3120-3135, 3133-3148, 3224-3239, 3226-3241, 3351-3366, 3353-3368, 3361-3376, 3388-3403, 3513-3528, 3517-3532, 3519-3534, 3641-3656, 3735-3750, 3764-3779, 3768-3783, 3798-3813, 3799-3814, 3851-3866, 3870-3885, 3874-3889, 3876-3891, 3878-3893, 3884-3899, 3886-3901, 3888-3903, 3901-3916, 3956-3971, 3962-3977, 3964-3979, 3967-3982, 4019-4034, 4038-4053, 4049-4064, 4056-4071, 4059-4074, 4062-4077, 4066-4081, 4070-4085, 4101-4116, 4103-4118, 4105-4120, 4109-4124, 4305-4320, 4405-4420, 4532-4547, 4534-4549, 4537-4552, 4539-4554, 4555-4570, 4571-4586, 4573-4588, 4578-4593, 4597-4612, 4632-4647, 4655-4670, 4656-4671, 4662-4677, 4699-4714, 4747-4762, 4750-4765, 4752-4767, 4754-4769, 4755-4770, 4769-4784, 4798-4813, 4804-4819, 4807-4822, 4833-4848, 4837-4852, 4839-4854, 4865-4880, 4868-4883, 4872-4887, 4874-4889, 4876-4891, 4887-4902, 4889-4904, 4916-4931, 4918-4933, 4938-4953, 4942-4957, 4944-4959, 4951-4966, 5050-5065, 5052-5067, 5054-5069, 5056-5071, 5060-5075, 5061-5076, 5062-5077, 5133-5148, 5141-5156, 5155-5170, 5265-5280, 5293-5308, 5308-5323, 5392-5407, 5448-5463, 5469-5484, 5481-5496, 5483-5498, 5486-5501, 5488-5503, 5494-5509, 5521-5536, 5666-5681, 6222-6237, 6701-6716, 7543-7558, 8471-8486, 8638-8653, 9464-9479, 10217-10232, 10250-10265, 10865-10880, 11197-11212, 11855-11870, 13189-13204, 13321-13336, 13346-13361, 16555-16570, 16793-16808, 16968-16983, 17206-17221, 18865-18880, 29329-29344, 32290-32305, 33315-33330, 39055-39070, 40615-40630, 42017-42032, 56050-56065, 58719-58734, 58720-58739, 58721-58736, 58722-58737, 58723-58738, 58724-58739, 58725-58740, 58750-58769, 58751-58766, 58752-58767, 58753-58768, 58754-58769, 58755-58770, 60902-60917, 67454-67469, 114874-114889, 115272-115287, 115365-115380, 134971-134986, 102156-102171, 139682-139697, 139762-139777, 139782-139797, 144856-144871, 144938-144953, 148406-148421, 148443-148458, 148520-148535, 181695-181710, 182958-182973, or 183049-183064 of SEQ ID NO: 1, wherein the nucleobase sequence of the modified oligonucleotide is complementary to SEQ ID NO: 1.

E9. The compound of any one of E1, E7, or E8, wherein the compound comprises a modified oligonucleotide consisting of 10 to 30 linked nucleosides complementary within exon 1 nucleotides 2957-2972, 3079-3094, 3099-3114, 3109-3124, 3113-3128, 3120-3135, 3133-3148, 3224-3239, 3226-3241, 3351-3366, 3353-3368, 3361-3376, 3388-3403, 3513-3528, 3517-3532, 3519-3534, 3641-3656, 3735-3750, 3764-3779, 3768-3783, 3798-3813, 3799-3814, 3851-3866, 3870-3885, 3874-3889, 3876-3891, 3878-3893, 3884-3899, 3886-3901, 3888-3903, 3901-3916, 3956-3971, 3962-3977, 3964-3979, 3967-3982, 4019-4034, 4038-4053, 4049-4064, 4056-4071, 4059-4074, 4062-4077, 4066-4081, 4070-4085, 4101-4116, 4103-4118, 4105-4120, 4109-4124, 4305-4320, 4405-4420, 4532-4547, 4534-4549, 4537-4552, 4539-4554, 4555-4570, 4571-4586, 4573-4588, 4578-4593, 4597-4612, 4632-4647, 4655-4670, 4656-4671, 4662-4677, 4699-4714, 4747-4762, 4750-4765, 4752-4767, 4754-4769, 4755-4770, 4769-4784, 4798-4813, 4804-4819, 4807-4822, 4833-4848, 4837-4852, 4839-4854, 4865-4880, 4868-4883, 4872-4887, 4874-4889, 4876-4891, 4887-4902, 4889-4904, 4916-4931, 4918-4933, 4938-4953, 4942-4957, 4944-4959, 4951-4966, 5050-5065, 5052-5067, 5054-5069, 5056-5071, 5060-5075, 5061-5076, 5062-5077, 5133-5148, 5141-5156, 5155-5170, 5265-5280, 5293-5308, 5308-5323, 5392-5407, 5448-5463, 5469-5484, 5481-5496, 5483-5498, 5486-5501, 5488-5503, 5494-5509, or 5521-5536 of SEQ ID NO:1.

E10. The compound of E9, wherein the compound comprises a modified oligonucleotide consisting of 10 to 30 linked nucleosides complementary within exon 1 nucleotides 5052-5067 of SEQ ID NO:1.

E11. The compound of any one of E1, E7, or E8, wherein the compound comprises a modified oligonucleotide consisting of 10 to 30 linked nucleosides complementary within intron 1 nucleotides 5666-5681, 6222-6237, 6701-6716, 7543-7558, 8471-8486, 8638-8653, 9464-9479, 10217-10232, 10250-10265, 10865-10880, 11197-11212, 11855-11870, 13189-13204, 13321-13336, 13346-13361, 16555-16570, 16793-16808, 16968-16983, 17206-17221, 18865-18880, 29329-29344, 32290-32305, 33315-33330, 39055-39070, 40615-40630, 42017-42032, 56050-56065, 58719-58734, 58720-58739, 58721-58736, 58722-58737, 58723-58738, 58724-58739, 58725-58740, 58750-58769, 58751-58766, 58752-58767, 58753-58768, 58754-58769, 58755-58770, 60902-60917, 67454-67469, 114874-114889, 115272-115287, 115365-115380, or 134971-134986 of SEQ ID NO:1.

E12. The compound of E11, wherein the compound comprises a modified oligonucleotide consisting of 10 to 30 linked nucleosides complementary within intron 1 nucleotides 8638-8653, 11197-11212, 40615-40630, 58719-58734, 58720-58735, or 58721-58736 of SEQ ID NO:1.

E13. The compound of any one of E1-12, wherein the modified oligonucleotide comprises at least one modified sugar.

E14. The compound of E13, wherein at least one modified sugar comprises a 2'-O-methoxyethyl group.

E15. The compound of E13, wherein the at least one modified sugar is a bicyclic sugar.

E16. The compound of E15, wherein the bicyclic sugar comprises a 4'-CH(CH$_3$)—O-2' group.

E17. The compound of E15, wherein the bicyclic sugar comprises a 4'-CH$_2$—O-2' or 4'-(CH$_2$)$_2$—O-2'group.

E18. The compound of any one of E1-17, wherein the modified oligonucleotide comprises at least one modified internucleoside linkage.

E19. The compound of E18, wherein each internucleoside linkage of the antisense oligonucleotide is a phosphorothioate internucleoside linkage.

E20. The compound of any one of E1-19, wherein the modified oligonucleotide comprises at least one modified nucleobase.

E21. The compound of E20, wherein the modified nucleobase is a 5-methylcytosine.

E22. The compound of any one of E1-21, wherein the modified oligonucleotide comprises:
 a gap segment consisting of linked deoxynucleosides;
 a 5' wing segment consisting of linked nucleosides; and
 a 3' wing segment consisting of linked nucleosides;
 wherein the gap segment is positioned between the 5' wing segment and the 3' wing segment and wherein each nucleoside of each wing segment comprises a modified sugar.

E23. The compound of E22, wherein the modified oligonucleotide comprises:
 a gap segment consisting of ten linked deoxynucleosides;
 a 5' wing segment consisting of 3 linked nucleosides; and
 a 3' wing segment consisting of 3 linked nucleosides;
 wherein the gap segment is positioned between the 5' wing segment and the 3' wing segment, wherein each nucleoside of each wing segment comprises a 2'-O-methoxyethyl sugar or a constrained ethyl sugar; and wherein each internucleoside linkage is a phosphorothioate linkage.

E24. A compound comprising a single-stranded modified oligonucleotide consisting of 16 linked nucleosides having a nucleobase sequence consisting of the sequence of SEQ ID NO: 35, or a pharmaceutically acceptable salt thereof, wherein the modified oligonucleotide comprises:
 a gap segment consisting of 9 linked deoxynucleosides;
 a 5' wing segment consisting of three linked nucleosides; and
 a 3' wing segment consisting of four linked nucleosides;
 wherein the gap segment is positioned between the 5' wing segment and the 3' wing segment; the three linked nucleosides of the 5' wing segment are each a constrained ethyl (cEt) sugar; the four linked nucleosides of the 3' wing segment are a constrained ethyl (cEt) sugar, a constrained ethyl (cEt) sugar, a constrained ethyl (cEt) sugar, and a 2'-O-methoxyethyl sugar in the 5' to 3' direction; each internucleoside linkage is a phosphorothioate linkage; and each cytosine is a 5-methylcytosine.

E25. A compound comprising a single-stranded modified oligonucleotide consisting of 16 linked nucleosides having a nucleobase sequence consisting of the sequence of SEQ ID NO: 39, or a pharmaceutically acceptable salt thereof, wherein the modified oligonucleotide comprises:
 a gap segment consisting of 9 linked deoxynucleosides;
 a 5' wing segment consisting of three linked nucleosides; and
 a 3' wing segment consisting of four linked nucleosides;
 wherein the gap segment is positioned between the 5' wing segment and the 3' wing segment; the three linked nucleosides of the 5' wing segment are each a constrained ethyl (cEt) sugar; the four linked nucleosides of the 3' wing segment are a constrained ethyl (cEt) sugar, a constrained ethyl (cEt) sugar, a constrained ethyl (cEt) sugar, and a 2'-O-methoxyethyl sugar in the 5' to 3' direction; each internucleoside linkage is a phosphorothioate linkage; and each cytosine is a 5-methylcytosine.

E26. A compound comprising a single-stranded modified oligonucleotide consisting of 16 linked nucleosides having a nucleobase sequence consisting of the sequence of SEQ ID NO: 39, or a pharmaceutically acceptable salt thereof, wherein the modified oligonucleotide comprises:
 a gap segment consisting of 8 linked deoxynucleosides;
 a 5' wing segment consisting of four linked nucleosides; and
 a 3' wing segment consisting of four linked nucleosides;
 wherein the gap segment is positioned between the 5' wing segment and the 3' wing segment; the four linked nucleosides of the 5' wing segment are a 2'-O-methoxyethyl sugar, a constrained ethyl (cEt) sugar, a constrained ethyl (cEt) sugar, and a constrained ethyl (cEt) sugar in the 5' to 3' direction; the four linked nucleosides of the 3' wing segment are a constrained ethyl (cEt) sugar, a constrained ethyl (cEt) sugar, a constrained ethyl (cEt) sugar, and a 2'-O-methoxyethyl sugar in the 5' to 3' direction; each internucleoside linkage is a phosphorothioate linkage; and each cytosine is a 5-methylcytosine.

E27. A compound comprising a single-stranded modified oligonucleotide consisting of 16 linked nucleosides having a nucleobase sequence consisting of the sequence of SEQ ID NO: 39, or a pharmaceutically acceptable salt thereof, wherein the modified oligonucleotide comprises:
 a gap segment consisting of 8 linked deoxynucleosides;
 a 5' wing segment consisting of five linked nucleosides; and
 a 3' wing segment consisting of three linked nucleosides;
 wherein the gap segment is positioned between the 5' wing segment and the 3' wing segment; the five linked nucleosides of the 5' wing segment are a 2'-O-methoxyethyl sugar, a 2'-O-methoxyethyl sugar, a constrained ethyl (cEt)

sugar, a constrained ethyl (cEt) sugar, and a constrained ethyl (cEt) sugar in the 5' to 3' direction; the three linked nucleosides of the 3' wing segment are each a constrained ethyl (cEt) sugar; each internucleoside linkage is a phosphorothioate linkage; and each cytosine is a 5-methylcytosine.

E28. A compound comprising a single-stranded modified oligonucleotide consisting of 16 linked nucleosides having a nucleobase sequence consisting of the sequence of SEQ ID NO: 39, or a pharmaceutically acceptable salt thereof, wherein the modified oligonucleotide comprises:
a gap segment consisting of 7 linked deoxynucleosides;
a 5' wing segment consisting of four linked nucleosides; and
a 3' wing segment consisting of five linked nucleosides;
wherein the gap segment is positioned between the 5' wing segment and the 3' wing segment; the four linked nucleosides of the 5' wing segment are a 2'-O-methoxyethyl sugar, a constrained ethyl (cEt) sugar, a constrained ethyl (cEt) sugar, and a constrained ethyl (cEt) sugar in the 5' to 3' direction; the five linked nucleosides of the 3' wing segment are a constrained ethyl (cEt) sugar, a constrained ethyl (cEt) sugar, a constrained ethyl (cEt) sugar, a 2'-O-methoxyethyl sugar, and a 2'-O-methoxyethyl sugar in the 5' to 3' direction; each internucleoside linkage is a phosphorothioate linkage; and each cytosine is a 5-methylcytosine.

E29. A compound comprising a single-stranded modified oligonucleotide consisting of 16 linked nucleosides having a nucleobase sequence consisting of the sequence of SEQ ID NO: 35, or a pharmaceutically acceptable salt thereof, wherein the modified oligonucleotide comprises:
a gap segment consisting of 7 linked deoxynucleosides;
a 5' wing segment consisting of six linked nucleosides; and
a 3' wing segment consisting of three linked nucleosides;
wherein the gap segment is positioned between the 5' wing segment and the 3' wing segment; the six linked nucleosides of the 5' wing segment are a 2'-O-methoxyethyl sugar, a constrained ethyl (cEt) sugar, a constrained ethyl (cEt) sugar, a 2'-O-methoxyethyl sugar, a constrained ethyl (cEt) sugar, and a constrained ethyl (cEt) sugar in the 5' to 3' direction; the three linked nucleosides of the 3' wing segment are each a constrained ethyl (cEt) sugar; each internucleoside linkage is a phosphorothioate linkage; and each cytosine is a 5-methylcytosine.

E30. A compound comprising a single-stranded modified oligonucleotide consisting of 16 linked nucleosides having a nucleobase sequence consisting of the sequence of SEQ ID NO: 43, or a pharmaceutically acceptable salt thereof, wherein the modified oligonucleotide comprises:
a gap segment consisting of 10 linked deoxynucleosides;
a 5' wing segment consisting of three linked nucleosides; and
a 3' wing segment consisting of three linked nucleosides;
wherein the gap segment is positioned between the 5' wing segment and the 3' wing segment; each nucleoside of each wing segment comprises a constrained ethyl (cEt) sugar; each internucleoside linkage is a phosphorothioate linkage; and each cytosine is a 5-methylcytosine.

E31. A compound comprising a single-stranded modified oligonucleotide consisting of 16 linked nucleosides having a nucleobase sequence consisting of the sequence of SEQ ID NO: 124, or a pharmaceutically acceptable salt thereof, wherein the modified oligonucleotide comprises:
a gap segment consisting of 10 linked deoxynucleosides;
a 5' wing segment consisting of three linked nucleosides; and
a 3' wing segment consisting of three linked nucleosides;
wherein the gap segment is positioned between the 5' wing segment and the 3' wing segment; each nucleoside of each wing segment comprises a constrained ethyl (cEt) sugar; each internucleoside linkage is a phosphorothioate linkage; and each cytosine is a 5-methylcytosine.

E32. A compound comprising a single-stranded modified oligonucleotide consisting of 16 linked nucleosides having a nucleobase sequence consisting of the sequence of SEQ ID NO: 150, or a pharmaceutically acceptable salt thereof, wherein the modified oligonucleotide comprises:
a gap segment consisting of 10 linked deoxynucleosides;
a 5' wing segment consisting of three linked nucleosides; and
a 3' wing segment consisting of three linked nucleosides;
wherein the gap segment is positioned between the 5' wing segment and the 3' wing segment; each nucleoside of each wing segment comprises a constrained ethyl (cEt) sugar; each internucleoside linkage is a phosphorothioate linkage; and each cytosine is a 5-methylcytosine.

E33. A compound comprising a single-stranded modified oligonucleotide consisting of 16 linked nucleosides having a nucleobase sequence consisting of the sequence of SEQ ID NO: 155, or a pharmaceutically acceptable salt thereof, wherein the modified oligonucleotide comprises:
a gap segment consisting of 10 linked deoxynucleosides;
a 5' wing segment consisting of three linked nucleosides; and
a 3' wing segment consisting of three linked nucleosides;
wherein the gap segment is positioned between the 5' wing segment and the 3' wing segment; each nucleoside of each wing segment comprises a constrained ethyl (cEt) sugar; each internucleoside linkage is a phosphorothioate linkage; and each cytosine is a 5-methylcytosine.

E34. A compound comprising a single-stranded modified oligonucleotide consisting of 16 linked nucleosides having a nucleobase sequence consisting of the sequence of SEQ ID NO: 169, or a pharmaceutically acceptable salt thereof, wherein the modified oligonucleotide comprises:
a gap segment consisting of 10 linked deoxynucleosides;
a 5' wing segment consisting of three linked nucleosides; and
a 3' wing segment consisting of three linked nucleosides;
wherein the gap segment is positioned between the 5' wing segment and the 3' wing segment; each nucleoside of each wing segment comprises a constrained ethyl (cEt) sugar; each internucleoside linkage is a phosphorothioate linkage; and each cytosine is a 5-methylcytosine.

E35. A compound comprising a single-stranded modified oligonucleotide consisting of 16 linked nucleosides having a nucleobase sequence consisting of the sequence of SEQ ID NO: 175, or a pharmaceutically acceptable salt thereof, wherein the modified oligonucleotide comprises:
a gap segment consisting of 10 linked deoxynucleosides;
a 5' wing segment consisting of three linked nucleosides; and
a 3' wing segment consisting of three linked nucleosides;
wherein the gap segment is positioned between the 5' wing segment and the 3' wing segment; each nucleoside of each wing segment comprises a constrained ethyl (cEt) sugar; each internucleoside linkage is a phosphorothioate linkage; and each cytosine is a 5-methylcytosine.

E36. The compound of any one of E1-35, wherein the modified oligonucleotide is at least 90% complementary to a nucleic acid encoding androgen receptor.

E37. The compound of any one of E1-36, wherein the antisense oligonucleotide is 100% complementary to a nucleic acid encoding androgen receptor.

E38. The compound of E37, wherein the nucleic acid encoding androgen receptor comprises the nucleotide sequence of any one of SEQ ID NOs: 1-8.

E39. A composition comprising the compound of any one of E1-38, or pharmaceutically acceptable salt thereof, and a pharmaceutically acceptable diluent or carrier.

E40. A composition comprising the compound of any one of E1-38 and a diarylhydantoin Androgen Receptor (AR) inhibitor of Formula XVI:

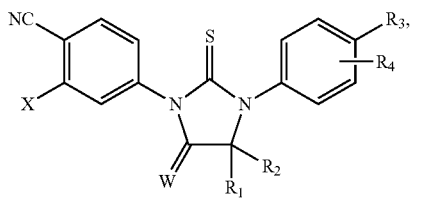

wherein X is selected from the group consisting of trifluoromethyl and iodo, wherein W is selected from the group consisting of O and NR5, wherein R5 is selected from the group consisting of H, methyl, and

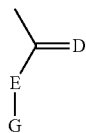

wherein D is S or O and E is N or O and G is alkyl, aryl, substituted alkyl or substituted aryl; or D is S or O and E-G together are C1-C4 lower alkyl, wherein R1 and R2 together comprise eight or fewer carbon atoms and are selected from the group consisting of alkyl, substituted alkyl including haloalkyl, and, together with the carbon to which they are linked, a cycloalkyl or substituted cycloalkyl group, wherein R3 is selected from the group consisting of hydrogen, halogen, methyl, C1-C4 alkoxy, formyl, haloacetoxy, trifluoromethyl, cyano, nitro, hydroxyl, phenyl, amino, methylcarbamoyl, methoxycarbonyl, acetamido, methanesulfonamino, methanesulfonyl, 4-methanesulfonyl-1-piperazinyl, piperazinyl, and C1-C6 alkyl or alkenyl optionally substituted with hydroxyl, methoxycarbonyl, cyano, amino, amido, nitro, carbamoyl, or substituted carbamoyl including methylcarbamoyl, dimethylcarbamoyl, and hydroxyethylcarbamoyl, wherein R4 is selected from the group consisting of hydrogen, halogen, alkyl, and haloalkyl, and wherein R3 is not methylaminomethyl or dimethylaminomethyl.

R5 may be

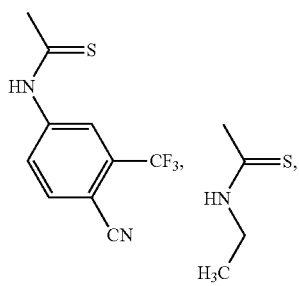

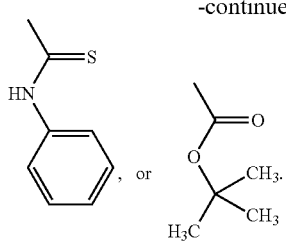

E41. The composition of E40, wherein the diarylhydantoin Androgen Receptor (AR) inhibitor is MDV3100.

E42. A composition comprising the compound of any one of E1-38 and an anti-androgenic agent selected from: MDV3100, ARN-059, ODM-201, abiraterone, TOK001, TAK700 and VT464.

E43. A method of treating cancer comprising administering to a subject having cancer the compound of any one of E1-38 or composition of any one of E39-42, thereby treating cancer in the subject.

E44. An antisense compound of any one of E1-38 or composition of any one of E39-42 for use in treating cancer E45. The compound or composition of E44, wherein the cancer is prostate cancer, breast cancer, ovarian cancer, gastric cancer or bladder cancer.

E46. The compound or composition of E45, wherein the cancer is castrate-resistant prostate cancer.

E47. The compound or composition of E46, wherein the castrate-resistant prostate cancer is resistant to an anti-androgenic agent selected from: MDV3100, ARN-059, ODM-201, abiraterone, TOK001, TAK700 and VT464.

E48. The method of E43, wherein the cancer is prostate cancer, breast cancer, ovarian cancer, gastric cancer or bladder cancer.

E49. The method of E48, wherein the cancer is castrate-resistant prostate cancer.

E50. The method of E49, wherein the castrate-resistant prostate cancer is resistant to an anti-androgenic agent selected from: MDV3100, ARN-059, ODM-201, abiraterone, TOK001, TAK700 and VT464.

E51. The compound of E44-47 or the method of E49 or E50, wherein the antisense compound targets an AR splicing variant.

E52. The compound or method of E51, wherein the AR splicing variant lacks a functional ligand binding domain.

E53. The compound of E44-47 or the method of any one of E49-52, wherein the antisense compound is capable of reducing expression of full-length AR and an AR splicing variant lacking any one of exons 4-8.

E54. The compound or method of E51, wherein the AR splicing variant consists of exons 1-3.

E55. The compound of E44-47 or the method of any one of E49-52, wherein the antisense compound is targeted to AR upstream of the 3' end of exon 3 and is capable of inhibiting growth or proliferation of the prostate cancer cell to a greater extent than an antisense compound targeted to a region of AR downstream of the 3' end of exon 3.

E56. The compound or method of E55, wherein the antisense compound targeted to a region of AR downstream of the 3' end of exon 3 is capable of reducing levels of full-length AR but not an AR splicing variant consisting of exons 1-3.

E57. The compound or method of E56, wherein the region downstream of the 3' end of exon 3 comprises exon 4.

E58. The compound of E44-47 or the method of any one of E49-52, wherein the prostate cancer cell preferentially expresses an AR splicing variant over full-length AR.

E59. The compound or method of E58, wherein the AR splicing variant lacks a functional ligand binding domain.

E60. A method of treating prostate cancer resistant to a anti-androgenic agent selected from: MDV3100, ARN-059, ODM-201, abiraterone, TOK001, TAK700 and VT464 in a subject comprising administering to the subject an antisense compound targeted to human androgen receptor (AR) upstream of the 3' end of exon 3, thereby treating the prostate cancer.

E61. The method of E60, wherein the subject is diagnosed as having prostate cancer resistant to the anti-androgenic agent selected from: MDV3100, ARN-059, ODM-201, abiraterone, TOK001, TAK700 and VT464.

E62. The method of E60 or E61, wherein the antisense compound targets an AR splicing variant.

E63. The method of E62, wherein the AR splicing variant lacks a functional ligand binding domain.

E64. The method of any one of E60-63, wherein the antisense compound is capable of reducing expression of full-length AR and an AR splicing variant lacking any one of exons 4-8.

E65. The method of E64, wherein the AR splicing variant consists of exons 1-3.

E66. The method of any one of E60-65, wherein the antisense compound is targeted to AR upstream of the 3' end of exon 3 and is capable of inhibiting growth or proliferation of a prostate cancer cell resistant to the diarylhydantoin Androgen Receptor (AR) inhibitor to a greater extent than an antisense compound targeted to a region of AR downstream of the 3' end exon 3.

E67. The method of E66, wherein the antisense compound targeted to a region of AR downstream of the 3' end of exon 3 is capable of reducing levels of full-length AR but not an AR splicing variant lacking any one of exons 4-8.

E68. The method of E67, wherein the AR splicing variant consists of exons 1-3.

E69. The method of E68, wherein the region downstream of the 3' end of exon 3 comprises exon 4.

E70. The method of any one of E60-69, wherein the prostate cancer is castration-resistant.

E71. The method of any one of E60-70, wherein the prostate cancer comprises cells that preferentially express an AR splicing variant over full-length AR.

E72. The method of E71, wherein the AR splicing variant lacks any one of exons 4-8.

E73. The method of E72, wherein the AR splicing variant consists of exons 1-3.

E74. The method of E72, wherein the AR splicing variant lacks a functional ligand binding domain.

E75. A method of inhibiting prostate cancer cell growth or proliferation comprising contacting the prostate cancer cell with an antisense compound targeted to human androgen receptor (AR) and anti-androgenic agent selected from: MDV3100, ARN-059, ODM-201, abiraterone, TOK001, TAK700 and VT464, wherein the antisense compound and the anti-androgenic agent synergize in combination to inhibit the growth or proliferation of the prostate cancer cell.

E76. The method of E75, wherein the antisense compound is targeted to AR upstream of the 3' end of exon 3.

E77. The method of E75 or E76, wherein the prostate cancer cell is contacted with an amount of the antisense compound and an amount of anti-androgenic agent that are each or both less in combination than the amount of either the antisense compound or anti-androgenic agent alone effective in inhibiting the growth or proliferation of said prostate cancer cell.

E78. The method of any one of E75-77, wherein the antisense compound and anti-androgenic agent provide a greater-than-additive effect compared to the antisense compound alone or anti-androgenic agent alone in inhibiting the growth or proliferation of said prostate cancer cell.

E79. The method of any one of E75-78, wherein the antisense compound targets an AR splicing variant.

E80. The method of E79, wherein the AR splicing variant lacks a functional ligand binding domain.

E81. The method of any one of E75-80, wherein the antisense compound is capable of reducing expression of full-length AR and an AR splicing variant consisting of exons 1-3.

E82. A method of inhibiting growth or proliferation of an androgen receptor (AR)-positive breast cancer cell comprising contacting the breast cancer cell with an antisense compound targeted to human androgen receptor (AR) wherein the growth or proliferation of the breast cancer cell is inhibited.

E83. A method of inhibiting AR expression in a subject having or at risk of having an androgen receptor (AR)-positive breast cancer comprising:
  identifying a subject having or at risk of having AR-positive breast cancer, and
  administering to the subject an antisense compound targeted to human AR,
wherein the antisense compound inhibits AR expression in the subject.

E84. A method of treating AR-positive breast cancer in a subject comprising administering to the subject an antisense compound targeted to human androgen receptor (AR), thereby treating the breast cancer in the subject.

E85. The method of any one of E82-84, wherein the AR-positive breast cancer or breast cancer cell is dependent on androgen expression for growth.

E86. The method of any one of E82-85, wherein the breast cancer or breast cancer cell is estrogen receptor (ER)-negative, progesterone receptor (PR)-negative, or Her2/neu-negative.

E87. The method of any one of E82-85, wherein the breast cancer or breast cancer cell is ER-positive and AR-positive.

E88. The method of any one of E82-85, wherein the breast cancer or breast cancer cell is ER-negative and AR-positive.

E89. The method of any one of E82-88, wherein the breast cancer or breast cancer cell is an apocrine breast cancer or breast cancer cell.

E90. The method of any one of E60-88, wherein the antisense compound is the compound of any one of E1-38, or pharmaceutically acceptable salt thereof.

E91. The method of any one of E60-88, wherein the antisense compound is the compound of any one of E24-35, or pharmaceutically acceptable salt thereof.

EXAMPLES

Non-Limiting Disclosure and Incorporation by Reference

While certain compounds, compositions and methods described herein have been described with specificity in accordance with certain embodiments, the following examples serve only to illustrate the compounds described herein and are not intended to limit the same. Each of the

Example 1

Antisense Inhibition of Human AR in HuVEC Cells

Antisense oligonucleotides were designed targeting an AR nucleic acid and were tested for their effects on AR mRNA in vitro. The antisense oligonucleotides were tested in a series of experiments that had similar culture conditions. The results for each experiment are presented in separate tables shown below. Cultured HuVEC cells at a density of 20,000 cells per well were transfected using electroporation with 500 nM antisense oligonucleotide. After a treatment period of approximately 24 hours, RNA was isolated from the cells and AR mRNA levels were measured by quantitative real-time PCR. Human primer probe set RTS3559 (forward sequence TCCTTCACCAATGTCAACTCC, designated herein as SEQ ID NO: 9; reverse sequence GAGCCATCCAAACTCTTGAGA, designated herein as SEQ ID NO: 10; probe sequence AGTACCGCATGCACAAGTCCCG, designated herein as SEQ ID NO: 11) was used to measure mRNA levels. AR mRNA levels were adjusted according to total RNA content, as measured by RIBOGREEN®. Results are presented as percent inhibition of AR, relative to untreated control cells. A total of 155 oligonucleotides were tested. Only those oligonucleotides which were selected for further study are shown in Tables 1 and 2.

The newly designed chimeric antisense oligonucleotides in Tables 1 and 2 were designed as 3-10-3 (S)-cET gapmers. The gapmers are 16 nucleosides in length, wherein the central gap segment comprises of ten 2'-deoxynucleosides and is flanked by wing segments on both the 5' direction and on the 3' direction comprising three nucleosides. Each nucleoside in the 5' wing segment and each nucleoside in the 3' wing segment has an (S)-cEt modification. The internucleoside linkages throughout each gapmer are phosphorothioate linkages. All cytosine residues throughout each gapmer are 5-methylcytosines. "Start site" indicates the 5'-most nucleoside to which the gapmer is targeted in the human gene sequence. "Stop site" indicates the 3'-most nucleoside to which the gapmer is targeted human gene sequence. Each gapmer listed in Tables 1 and 2 is targeted to either the human AR genomic sequence, designated herein as SEQ ID NO: 1 (GENBANK Accession No. NT_011669.17 truncated from nucleotides 5079000 to 5270000) or the human AR mRNA sequence, designated herein as SEQ ID NO: 2 (GENBANK Accession No. NM_000044.3), or both. 'n/a.' indicates that the oligonucleotide does not target that particular gene sequence.

TABLE 1

| Target Start Site for SEQ ID NO: 1 | Target Start Site for SEQ ID NO: 2 | ISIS No | Sequence | % inhibition | SEQ ID NO |
|---|---|---|---|---|---|
| 3799 | 937 | 549332 | GCGCTCTGACAGCCTC | 84 | 12 |
| 3851 | 989 | 549334 | CACCTGCGGGAAGCTC | 83 | 13 |
| 3888 | 1026 | 549338 | GGCTGTGATGATGCGG | 83 | 14 |
| 4047 | 1185 | 549345 | TCTGGAACAGATTCTG | 82 | 191 |
| 4059 | 1197 | 549347 | CTTCGCGCACGCTCTG | 84 | 15 |
| 4534 | 1672 | 549358 | ATGGTGCTGGCCTCGC | 91 | 16 |
| 4655 | 1793 | 549360 | GGTCGAAGTGCCCCCT | 89 | 17 |
| 4699 | 1837 | 549361 | GACACCGACACTGCCT | 84 | 18 |
| 4755 | 1893 | 549362 | CCCGAAGCTGTTCCCC | 85 | 19 |
| 4865 | 2003 | 549366 | CTTGCCTGCGCTGTCG | 84 | 20 |
| 5060 | 2198 | 549371 | GTTGTAGTAGTCGCGA | 93 | 21 |
| 5062 | 2200 | 549372 | AAGTTGTAGTAGTCGC | 92 | 22 |
| 5155 | 2293 | 549374 | GCGCTGCCGTAGTCCA | 93 | 23 |
| 5265 | 2403 | 549377 | AGGATGAGGAAGCGGC | 90 | 24 |
| 5392 | 2530 | 549379 | GCTCCCGCCTCGCCGC | 86 | 25 |
| 5448 | 2586 | 549380 | CGCTTTCCTGGCCCGC | 94 | 26 |
| 5483 | 2621 | 549381 | GCCGCCAGGGTACCAC | 89 | 27 |
| n/a | 2721 | 549383 | CCAAACGCATGTCCCC | 88 | 28 |
| 102155 | 2800 | 549386 | GCTTCATCTCCACAGA | 77 | 192 |
| 102156 | 2801 | 549387 | AGCTTCATCTCCACAG | 84 | 29 |

TABLE 1-continued

| Target Start Site for SEQ ID NO: 1 | Target Start Site for SEQ ID NO: 2 | ISIS No | Sequence | % inhibition | SEQ ID NO |
|---|---|---|---|---|---|
| n/a | 2871 | 549388 | TCCCTTCAGCGGCTCT | 88 | 30 |
| 144856 | 2801 | 549390 | TTTCTGCTGGCGCACA | 89 | 31 |

TABLE 2

| Target Start Site for SEQ ID NO: 1 | Target Start Site for SEQ ID NO: 2 | ISIS No | Sequence | % inhibition | SEQ ID NO |
|---|---|---|---|---|---|
| 181695 | 3602 | 549414 | GTTCATTCGAAGTTCA | 81 | 32 |
| 182958 | 4164 | 549432 | GAGGATCATCACAGAT | 90 | 33 |
| 183049 | 4255 | 549434 | CTAAACTTCCCGTGGC | 96 | 34 |
| 58721 58751 | n/a | 549457 | TTGATTTAATGGTTGC | 98 | 35 |
| 58722 58752 | n/a | 549458 | GTTGATTTAATGGTTG | 95 | 36 |
| 58725 58755 | n/a | 549459 | ATGGTTGATTTAATGG | 96 | 37 |

Example 2

Dose-Dependent Antisense Inhibition of Human AR in HuVEC Cells

Gapmers from the study described above exhibiting significant in vitro inhibition of AR mRNA were selected and tested at various doses in HuVEC cells. Cells were plated at a density of 20,000 cells per well and transfected using electroporation with 18.5 nM, 55.6 nM, 166.7 nM, 500.0 nM and 1500.0 nM concentrations of antisense oligonucleotide, as specified in Tables 3 and 4. After a treatment period of approximately 16 hours, RNA was isolated from the cells and AR mRNA levels were measured by quantitative real-time PCR. Human AR primer probe set RTS3559 was used to measure mRNA levels. AR mRNA levels were adjusted according to total RNA content, as measured by RIBOGREEN®. Results are presented as percent inhibition of AR, relative to untreated control cells. The antisense oligonucleotides were tested in a series of experiments that had similar culture conditions. The results for each experiment are presented in separate tables shown below.

The half maximal inhibitory concentration (IC$_{50}$) of each oligonucleotide is also presented in Tables 3 and 4. As illustrated, AR mRNA levels were reduced in a dose-dependent manner in the antisense oligonucleotide treated cells.

TABLE 3

| ISIS No | 18.5 nM | 55.6 nM | 166.7 nM | 500.0 nM | 1500.0 nM | IC$_{50}$ (nM) |
|---|---|---|---|---|---|---|
| 549358 | 0 | 29 | 63 | 85 | 95 | 141 |
| 549360 | 2 | 44 | 58 | 79 | 83 | 116 |
| 549361 | 0 | 12 | 30 | 52 | 66 | 525 |
| 549362 | 0 | 10 | 23 | 57 | 74 | 447 |
| 549371 | 0 | 30 | 52 | 83 | 88 | 148 |
| 549372 | 0 | 22 | 51 | 85 | 89 | 150 |
| 549374 | 15 | 40 | 59 | 83 | 92 | 108 |
| 549377 | 0 | 13 | 52 | 72 | 93 | 216 |
| 549379 | 9 | 11 | 51 | 68 | 88 | 237 |
| 549380 | 14 | 50 | 87 | 94 | 98 | 62 |
| 549381 | 4 | 14 | 33 | 71 | 91 | 261 |
| 549383 | 2 | 10 | 34 | 75 | 88 | 270 |
| 549388 | 0 | 15 | 42 | 36 | 86 | 428 |
| 549390 | 12 | 0 | 35 | 55 | 91 | 369 |

TABLE 4

| ISIS No | 18.5 nM | 55.6 nM | 166.7 nM | 500.0 nM | 1500.0 nM | IC$_{50}$ (nM) |
|---|---|---|---|---|---|---|
| 549332 | 24 | 35 | 57 | 79 | 79 | 104 |
| 549334 | 9 | 29 | 46 | 63 | 72 | 253 |
| 549338 | 30 | 32 | 47 | 67 | 78 | 154 |
| 549347 | 5 | 15 | 37 | 62 | 71 | 357 |
| 549366 | 8 | 44 | 58 | 72 | 91 | 129 |
| 549387 | 2 | 9 | 41 | 68 | 92 | 261 |
| 549414 | 0 | 21 | 35 | 53 | 76 | 366 |
| 549432 | 10 | 15 | 46 | 80 | 92 | 179 |
| 549434 | 27 | 38 | 60 | 86 | 96 | 85 |
| 549457 | 50 | 70 | 95 | 99 | 99 | 18 |

TABLE 4-continued

| ISIS No | 18.5 nM | 55.6 nM | 166.7 nM | 500.0 nM | 1500.0 nM | IC$_{50}$ (nM) |
|---|---|---|---|---|---|---|
| 549458 | 22 | 48 | 84 | 97 | 98 | 57 |
| 549459 | 51 | 61 | 90 | 94 | 97 | 18 |

Example 3

Antisense Inhibition of Human AR in HuVEC Cells

Additional antisense oligonucleotides were designed targeting an AR nucleic acid and were tested for their effects on AR mRNA in vitro. Cultured HuVEC cells at a density of 20,000 cells per well were transfected using electroporation with 500 nM antisense oligonucleotide. After a treatment period of approximately 24 hours, RNA was isolated from the cells and AR mRNA levels were measured by quantitative real-time PCR. Human primer probe set RTS3559 was used to measure mRNA levels. AR mRNA levels were adjusted according to total RNA content, as measured by RIBOGREEN®. Results are presented as percent inhibition of AR, relative to untreated control cells. A total of 82 oligonucleotides were tested. Only those oligonucleotides which were selected for further study are shown in Table 5.

The newly designed chimeric antisense oligonucleotides in Table 5 were designed as 3-10-3 (S)-cET gapmers or 5-10-5 MOE gapmers. The 3-10-3 (S)-cEt gapmers are 16 nucleosides in length, wherein the central gap segment comprises of ten 2'-deoxynucleosides and is flanked by wing segments on both the 5' direction and on the 3' direction comprising three nucleosides. Each nucleoside in the 5' wing segment and each nucleoside in the 3' wing segment has an (S)-cEt modification. The 5-10-5 MOE gapmer is 20 nucleosides in length, wherein the central gap segment comprises of ten 2'-deoxynucleosides and is flanked by wing segments on the 5' direction and the 3' direction comprising five nucleosides each. Each nucleoside in the 5' wing segment and each nucleoside in the 3' wing segment has a 2'-MOE modification. The internucleoside linkages throughout each gapmer are phosphorothioate linkages. All cytosine residues throughout each gapmer are 5-methylcytosines. "Start site" indicates the 5'-most nucleoside to which the gapmer is targeted in the human gene sequence. "Stop site" indicates the 3'-most nucleoside to which the gapmer is targeted human gene sequence. Each gapmer listed in Table 5 is targeted to the human AR genomic sequence, designated herein as SEQ ID NO: 1 (GENBANK Accession No. NT_011669.17 truncated from nucleotides 5079000 to 5270000)

TABLE 5

| Target Start Site | Target Stop Site | ISIS No | ISIS No | Motif | % inhibition | SEQ ID NO |
|---|---|---|---|---|---|---|
| 58721 58751 | 58736 58766 | 549457 | TTGATTTAATGGTTGC | 3-10-3 | 98 | 35 |
| 58722 58752 | 58737 58767 | 549458 | GTTGATTTAATGGTTG | 3-10-3 | 94 | 36 |
| 58725 58755 | 58740 58770 | 549459 | ATGGTTGATTTAATGG | 3-10-3 | 92 | 37 |
| 58720 58750 | 58739 58769 | 560071 | TGGTTGATTTAATGGTTGCA | 5-10-5 | 73 | 38 |
| 58720 58750 | 58735 58765 | 560098 | TGATTTAATGGTTGCA | 3-10-3 | 99 | 39 |
| 58723 58753 | 58738 58768 | 560099 | GGTTGATTTAATGGTT | 3-10-3 | 95 | 40 |
| 58724 58754 | 58739 58769 | 560100 | TGGTTGATTTAATGGT | 3-10-3 | 91 | 41 |
| 58721 58751 | 58736 58766 | 560137 | TTGATTTAATGGTTGC | 3-10-3 | 95 | 35 |

Example 4

Dose-Dependent Antisense Inhibition of Human AR in HuVEC Cells

Gapmers from the studies described above exhibiting significant in vitro inhibition of AR mRNA were selected and tested at various doses in HuVEC cells. Cells were plated at a density of 20,000 cells per well and transfected using electroporation with 31.3 nM, 62.5 nM, 125.0 nM, 250.0 nM, 500.0 nM, and 1000.0 nM concentrations of antisense oligonucleotide, as specified in Table 6. After a treatment period of approximately 16 hours, RNA was isolated from the cells and AR mRNA levels were measured by quantitative real-time PCR. Human AR primer probe set RTS3559 was used to measure mRNA levels. AR mRNA levels were adjusted according to total RNA content, as measured by RIBOGREEN®. Results are presented as percent inhibition of AR, relative to untreated control cells. The antisense oligonucleotides were tested in a series of experiments that had similar culture conditions. The results for each experiment are presented in separate tables shown below.

The half maximal inhibitory concentration (IC$_{50}$) of each oligonucleotide is also presented in Table 6. As illustrated, AR mRNA levels were reduced in a dose-dependent manner in the antisense oligonucleotide treated cells.

TABLE 6

| ISIS No | 31.25 nM | 62.5 nM | 125.0 nM | 250.0 nM | 500.0 nM | 1000.0 nM | IC$_{50}$ (μM) |
|---|---|---|---|---|---|---|---|
| 549457 | 40 | 57 | 78 | 89 | 96 | 96 | 0.03 |
| 549458 | 15 | 25 | 47 | 70 | 88 | 93 | 0.1 |
| 549459 | 16 | 23 | 50 | 71 | 85 | 92 | 0.1 |
| 560071 | 7 | 0 | 19 | 40 | 57 | 76 | 0.4 |
| 560098 | 20 | 41 | 64 | 83 | 94 | 94 | 0.1 |
| 560099 | 13 | 29 | 58 | 72 | 89 | 94 | 0.1 |
| 560100 | 16 | 24 | 53 | 69 | 81 | 93 | 0.1 |
| 560137 | 27 | 49 | 61 | 82 | 91 | 96 | 0.1 |

Example 5

Antisense Inhibition of Human AR in HuVEC Cells

Additional antisense oligonucleotides were designed targeting an AR nucleic acid and were tested for their effects on AR mRNA in vitro. Cultured HuVEC cells at a density of 20,000 cells per well were transfected using electroporation with 250 nM antisense oligonucleotide. After a treatment period of approximately 24 hours, RNA was isolated from the cells and AR mRNA levels were measured by quantitative real-time PCR. Human primer probe set RTS3559 was used to measure mRNA levels. AR mRNA levels were adjusted according to total RNA content, as measured by RIBOGREEN®. Results are presented as percent inhibition of AR, relative to untreated control cells. A total of 40 oligonucleotides were tested. Only those oligonucleotides which were selected for further study are shown in Table 7.

The newly designed chimeric antisense oligonucleotides in Table 7 were designed as 3-10-3 (S)-cET gapmers or deoxy, MOE and (S)-cEt oligonucleotides. The 3-10-3 (S)-cEt gapmers are 16 nucleosides in length, wherein the central gap segment comprises of ten 2'-deoxynucleosides and is flanked by wing segments on both the 5' direction and on the 3' direction comprising three nucleosides. Each nucleoside in the 5' wing segment and each nucleoside in the 3' wing segment has an (S)-cEt modification. The deoxy, MOE and (S)-cEt oligonucleotides are 16 nucleosides in length wherein the nucleoside have either a MOE sugar modification, an (S)-cEt sugar modification, or a deoxy modification. The 'Chemistry' column describes the sugar modifications of each oligonucleotide. 'k' indicates an (S)-cEt sugar modification; the number indicates the number of deoxynucleosides; and 'e' indicates a MOE modification. The internucleoside linkages throughout each gapmer are phosphorothioate linkages. All cytosine residues throughout each gapmer are 5-methylcytosines. The SEQ ID NO listed in the table refers to the oligonucleotide sequence. "Start site" indicates the 5'-most nucleoside to which the gapmer is targeted in the human gene sequence. "Stop site" indicates the 3'-most nucleoside to which the gapmer is targeted human gene sequence. Each gapmer listed in Table 7 is targeted to the human AR genomic sequence, designated herein as SEQ ID NO: 1 (GENBANK Accession No. NT_011669.17 truncated from nucleotides 5079000 to 5270000).

TABLE 7

| Target Start Site | Target Stop Site | Sequence | ISIS No | Chemistry | % inhibition | SEQ ID NO |
|---|---|---|---|---|---|---|
| 58721 58751 | 58736 58766 | TTGATTTAATGGTTGC | 549457 | kkk-10-kkk | 67 | 35 |
| 58722 58752 | 58737 58767 | GTTGATTTAATGGTTG | 549458 | kkk-10-kkk | 71 | 36 |
| 58720 58750 | 58735 58765 | TGATTTAATGGTTGCA | 560098 | kkk-10-kkk | 69 | 39 |
| 58721 58751 | 58736 58766 | TTGATTTAATGGTTGC | 560131 | kkk-9-kkke | 74 | 35 |
| 58721 58751 | 58736 58766 | TTGATTTAATGGTTGC | 560137 | ekkk-8-kkke | 66 | 35 |
| 58720 58750 | 58735 58765 | TGATTTAATGGTTGCA | 569213 | kkk-9-kkke | 69 | 39 |
| 58720 58750 | 58735 58765 | TGATTTAATGGTTGCA | 569216 | ekkk-8-kkke | 68 | 39 |
| 58721 58751 | 58736 58766 | TTGATTTAATGGTTGC | 569222 | eekkk-8-kkk | 74 | 35 |
| 58721 58751 | 58736 58766 | TTGATTTAATGGTTGC | 569228 | eekkk-7-kkke | 67 | 35 |
| 58720 58750 | 58735 58765 | TGATTTAATGGTTGCA | 569236 | ekkk-7-kkkee | 66 | 39 |

Example 6

Dose-Dependent Antisense Inhibition of Human AR in HuVEC Cells

Gapmers from the studies described above exhibiting significant in vitro inhibition of AR mRNA were selected and tested at various doses in HuVEC cells. Cells were plated at a density of 20,000 cells per well and transfected using electroporation with 31.3 nM, 62.5 nM, 125.0 nM, 250.0 nM, 500.0 nM, and 1000.0 nM concentrations of antisense oligonucleotide, as specified in Table 8. After a treatment period of approximately 16 hours, RNA was isolated from the cells and AR mRNA levels were measured by quantitative real-time PCR. Human AR primer probe set RTS3559 was used to measure mRNA levels. AR mRNA levels were adjusted according to total RNA content, as measured by RIBOGREEN®. Results are presented as percent inhibition of AR, relative to untreated control cells. The antisense oligonucleotides were tested in a series of experiments that had similar culture conditions. The results for each experiment are presented in separate tables shown below.

The half maximal inhibitory concentration ($IC_{50}$) of each oligonucleotide is also presented in Table 8. As illustrated, AR mRNA levels were reduced in a dose-dependent manner in the antisense oligonucleotide treated cells.

TABLE 8

| ISIS No | 31.25 nM | 62.5 nM | 125.0 nM | 250.0 nM | 500.0 nM | 1000.0 nM | $IC_{50}$ (μM) |
|---|---|---|---|---|---|---|---|
| 549457 | 34 | 44 | 75 | 82 | 93 | 96 | 0.06 |
| 549458 | 30 | 36 | 54 | 70 | 85 | 90 | 0.10 |
| 560098 | 30 | 54 | 65 | 78 | 89 | 97 | 0.07 |
| 560131 | 16 | 48 | 65 | 82 | 89 | 97 | 0.09 |
| 560137 | 35 | 39 | 64 | 73 | 89 | 94 | 0.08 |
| 569213 | 35 | 53 | 65 | 83 | 94 | 96 | 0.06 |
| 569216 | 38 | 51 | 68 | 83 | 91 | 96 | 0.05 |
| 569222 | 36 | 48 | 67 | 83 | 91 | 98 | 0.06 |
| 569228 | 26 | 43 | 62 | 78 | 88 | 92 | 0.09 |
| 569236 | 17 | 39 | 54 | 79 | 84 | 92 | 0.11 |

Example 7

Dose-Dependent Antisense Inhibition of Human AR in HuVEC Cells

Additional antisense oligonucleotides were designed as deoxy, MOE and (S)-cEt oligonucleotides targeting AR gene sequences and were tested at various doses in HuVEC cells. The oligonucleotides are 16 nucleosides in length wherein the nucleoside have either a MOE sugar modification, an (S)-cEt sugar modification, or a deoxy modification. The 'Chemistry' column describes the sugar modifications of each oligonucleotide. 'k' indicates an (S)-cEt sugar modification; the number indicates the number of deoxynucleosides; otherwise 'd' indicates deoxyribose; and 'e' indicates a MOE modification. The internucleoside linkages throughout each gapmer are phosphorothioate linkages. All cytosine residues throughout each gapmer are 5-methylcytosines. The SEQ ID NO listed in the table refers to the oligonucleotide sequence. "Start site" indicates the 5'-most nucleoside to which the gapmer is targeted in the human gene sequence. "Stop site" indicates the 3'-most nucleoside to which the gapmer is targeted human gene sequence. Each gapmer listed in Table 9 is targeted to the human AR genomic sequence, designated herein as SEQ ID NO: 1 (GENBANK Accession No. NT_011669.17 truncated from nucleotides 5079000 to 5270000)

TABLE 9

| Target Start Site | Target Stop Site | Sequence | ISIS No | Chemistry | SEQ ID NO |
|---|---|---|---|---|---|
| 58720 58750 | 58735 58765 | TGATTTAATGGTTGCA | 569221 | eekkk-8-kkk | 39 |
| 58720 58750 | 58735 58765 | TGATTTAATGGTTGCA | 569227 | eekkk-7-kkke | 39 |
| 58720 58750 | 58735 58765 | TGATTTAATGGTTGCA | 569236 | ekkk-7-kkkee | 39 |
| 58720 58750 | 58735 58765 | TGATTTAATGGTTGCA | 579666 | ekkeekk-7-kk | 39 |
| 58721 58751 | 58736 58766 | TTGATTTAATGGTTGC | 579667 | ekkeekk-7-kk | 35 |
| 58720 58750 | 58735 58765 | TGATTTAATGGTTGCA | 579670 | ekkekk-7-kkk | 39 |
| 58721 58751 | 58736 58766 | TTGATTTAATGGTTGC | 579671 | ekkekk-7-kkk | 35 |
| 58721 58751 | 58736 58766 | TTGATTTAATGGTTGC | 569228 | eekkk-7-kkke | 35 |
| 58723 58753 | 58738 58768 | GGTTGATTTAATGGTT | 579669 | ekkeekk-7-kk | 40 |
| 58722 58752 | 58737 58767 | GTTGATTTAATGGTTG | 579672 | ekkekk-7-kkk | 36 |

TABLE 9-continued

| Target Start Site | Target Stop Site | Sequence | ISIS No | Chemistry | SEQ ID NO |
|---|---|---|---|---|---|
| 58722 58752 | 58737 58767 | GTTGATTTAATGGTTG | 569217 | ekkk-8-kkke | 36 |
| 58723 58753 | 58738 58768 | GGTTGATTTAATGGTT | 569214 | kkk-9-kkke | 40 |
| 58723 58753 | 58738 58768 | GGTTGATTTAATGGTT | 560099 | kkk-10-kkk | 40 |

Cells were plated at a density of 20,000 cells per well and transfected using electroporation with 62.5 nM, 125.0 nM, 250.0 nM, 500.0 nM, and 1000.0 nM concentrations of antisense oligonucleotide, as specified in Tables 10-12. After a treatment period of approximately 16 hours, RNA was isolated from the cells and AR mRNA levels were measured by quantitative real-time PCR. Human AR primer probe set RTS3559 was used to measure mRNA levels. AR mRNA levels were adjusted according to total RNA content, as measured by RIBOGREEN®. Results are presented as percent inhibition of AR, relative to untreated control cells. The antisense oligonucleotides were tested in a series of experiments that had similar culture conditions. The results for each experiment are presented in separate tables shown below.

The half maximal inhibitory concentration ($IC_{50}$) of each oligonucleotide is also presented in Tables 10-12. As illustrated, AR mRNA levels were reduced in a dose-dependent manner in some of the antisense oligonucleotide treated cells.

TABLE 10

| ISIS No | 62.5 nM | 125.0 nM | 250.0 nM | 500.0 nM | 1000.0 nM | $IC_{50}$ (nM) |
|---|---|---|---|---|---|---|
| 549458 | 25 | 46 | 55 | 64 | 78 | 203 |
| 569227 | 8 | 40 | 33 | 51 | 73 | 388 |
| 569228 | 29 | 44 | 63 | 77 | 87 | 158 |
| 569236 | 4 | 35 | 54 | 68 | 88 | 252 |
| 579666 | 33 | 34 | 47 | 64 | 80 | 229 |
| 579667 | 30 | 29 | 44 | 36 | 76 | 411 |

TABLE 11

| ISIS No | 62.5 nM | 125.0 nM | 250.0 nM | 500.0 nM | 1000.0 nM | $IC_{50}$ (nM) |
|---|---|---|---|---|---|---|
| 549458 | 16 | 22 | 44 | 64 | 74 | 324 |
| 579669 | 24 | 39 | 45 | 74 | 91 | 207 |
| 579670 | 27 | 28 | 55 | 75 | 70 | 236 |
| 579671 | 6 | 40 | 54 | 57 | 77 | 288 |
| 579672 | 9 | 30 | 50 | 72 | 86 | 258 |

TABLE 12

| ISIS No | 62.5 nM | 125.0 nM | 250.0 nM | 500.0 nM | 1000.0 nM | $IC_{50}$ (nM) |
|---|---|---|---|---|---|---|
| 549458 | 19 | 22 | 45 | 38 | 71 | 470 |
| 569214 | 20 | 26 | 61 | 62 | 76 | 265 |
| 569217 | 34 | 39 | 49 | 64 | 64 | 247 |
| 569221 | 12 | 32 | 59 | 57 | 73 | 294 |

Example 8

Antisense Inhibition of Human AR in HuVEC Cells

Additional antisense oligonucleotides were designed targeting an AR nucleic acid and were tested for their effects on AR mRNA in vitro. Cultured HuVEC cells at a density of 20,000 cells per well were transfected using electroporation with 1,000 nM antisense oligonucleotide. After a treatment period of approximately 24 hours, RNA was isolated from the cells and AR mRNA levels were measured by quantitative real-time PCR. Human primer probe set RTS3559 was used to measure mRNA levels. AR mRNA levels were adjusted according to total RNA content, as measured by RIBOGREEN®. Results are presented as percent inhibition of AR, relative to untreated control cells. A total of 75 oligonucleotides were tested. Only those oligonucleotides which were selected for further study are shown in Table 13.

The newly designed chimeric antisense oligonucleotides in Table 13 were designed as 3-10-3 (S)-cET gapmers, 3-9-4 (S)-cEt gapmers, 4-8-4 (S)-cEt gapmers, 4-9-3 (S)-cEt gapmers, 5-7-4 (S)-cEt gapmers, 5-8-3 (S)-cEt gapmers, 6-7-3 (S)-cEt gapmers, or deoxy, MOE and (S)-cEt oligonucleotides. The 3-10-3 (S)-cEt gapmers are 16 nucleosides in length, wherein the central gap segment comprises of ten 2'-deoxynucleosides and is flanked by wing segments on both the 5' direction and on the 3' direction comprising three nucleosides. The 3-9-4 (S)-cEt gapmers are 16 nucleosides in length, wherein the central gap segment comprises of nine 2'-deoxynucleosides and is flanked by a wing segment on the 5' direction comprising three nucleotides and on the 3' direction comprising four nucleosides. The 4-8-4 (S)-cEt gapmers are 16 nucleosides in length, wherein the central gap segment comprises of eight 2'-deoxynucleosides and is flanked by wing segments on both the 5' direction and on the 3' direction comprising four nucleotides. The 4-9-3 (S)-cEt gapmers are 16 nucleosides in length, wherein the central gap segment comprises of nine 2'-deoxynucleosides and is flanked by a wing segment on the 5' direction comprising four nucleotides and on the 3' direction comprising three nucleosides. The 5-7-4 (S)-cEt gapmers are 16 nucleosides in length, wherein the central gap segment comprises of seven 2'-deoxynucleosides and is flanked by a wing segment on the 5' direction comprising five nucleotides and on the 3' direction comprising four nucleotides. The 5-8-3 (S)-cEt gapmers are 16 nucleosides in length, wherein the central gap segment comprises of eight 2'-deoxynucleosides and is flanked by a wing segment on the 5' direction comprising five nucleotides and on the 3' direction comprising three nucleosides. The 6-7-3 (S)-cEt gapmers are 16 nucleosides in length, wherein the central gap segment comprises of seven 2'-deoxynucleosides and is flanked by a wing segment on the 5' direction comprising six nucleotides and on the 3' direction comprising three nucleosides. Each nucleoside in the 5' wing segment and each nucleoside in the 3' wing segment has an (S)-cEt modification. The deoxy, MOE and (S)-cEt oligonucleotides are 16 nucleosides in length wherein the nucleoside have either a MOE sugar modification, an (S)-cEt sugar modification, or a deoxy modification. The 'Chemistry' column describes the sugar modifications of each oligonucleotide. 'k' indicates an (S)-cEt sugar modification; the number indicates the number of deoxynucleosides; otherwise 'd' indicates deoxyribose; and 'e' indicates a MOE modification. The internucleoside linkages throughout each gapmer are phosphorothioate linkages. All cytosine residues throughout each gapmer are 5-methylcytosines.

The SEQ ID NO listed in the table refers to the oligonucleotide sequence. "Start site" indicates the 5'-most nucleoside to which the gapmer is targeted in the human gene sequence. "Stop site" indicates the 3'-most nucleoside to which the gapmer is targeted human gene sequence. Each gapmer listed in Table 13 is targeted to the human AR genomic sequence, designated herein as SEQ ID NO: 1 (GENBANK Accession No. NT_011669.17 truncated from nucleotides 5079000 to 5270000).

TABLE 13

| Target Start Site | Target Stop Site | Sequence | ISIS No | Chemistry | % inhibition | SEQ ID NO |
|---|---|---|---|---|---|---|
| 5062 | 5077 | AAGTTGTAGTAGTCGC | 549372 | kkk-10-kkk | 64 | 22 |
| 5061 | 5076 | AGTTGTAGTAGTCGCG | 585233 | kkk-8-keeee | 69 | 42 |
| 5062 | 5077 | AAGTTGTAGTAGTCGC | 585259 | ekkk-9-kkk | 71 | 22 |
| 5062 | 5077 | AAGTTGTAGTAGTCGC | 585262 | kkk-9-kkke | 77 | 22 |
| 5062 | 5077 | AAGTTGTAGTAGTCGC | 585263 | kkk-8-kkkee | 69 | 22 |
| 5062 | 5077 | AAGTTGTAGTAGTCGC | 585264 | kkk-7-kkkeee | 62 | 22 |
| 5062 | 5077 | AAGTTGTAGTAGTCGC | 585265 | eekk-8-kkee | 69 | 22 |
| 5062 | 5077 | AAGTTGTAGTAGTCGC | 585268 | keke-8-ekek | 72 | 22 |
| 5062 | 5077 | AAGTTGTAGTAGTCGC | 585269 | ekek-8-ekek | 73 | 22 |
| 5062 | 5077 | AAGTTGTAGTAGTCGC | 585271 | ekk-10-kke | 57 | 22 |
| 5062 | 5077 | AAGTTGTAGTAGTCGC | 585274 | kkk-10-kke | 65 | 22 |
| 58719 | 58734 | GATTTAATGGTTGCAA | 586124 | kkk-10-kkk | 82 | 43 |
| 58720 58750 | 58735 58765 | TGATTTAATGGTTGCA | 569227 | eekkk-7-kkke | 51 | 39 |
| 58722 58752 | 58737 58767 | GTTGATTTAATGGTTG | 560132 | kkk-9-kkke | 58 | 36 |
| 58722 58752 | 58737 58767 | GTTGATTTAATGGTTG | 569229 | eekkk-7-kkke | 57 | 36 |
| 58722 58752 | 58737 58767 | GTTGATTTAATGGTTG | 569238 | ekkk-7-kkkee | 51 | 36 |
| 58722 58752 | 58737 58767 | GTTGATTTAATGGTTG | 549458 | kkk-10-kkk | 87 | 36 |
| 58722 58752 | 58737 58767 | GTTGATTTAATGGTTG | 569223 | eekkk-8-kkk | 59 | 36 |
| 58724 58754 | 58739 58769 | TGGTTGATTTAATGGT | 569215 | kkk-9-kkke | 59 | 41 |
| 58725 58755 | 58740 58770 | ATGGTTGATTTAATGG | 560133 | kkk-9-kkke | 53 | 37 |
| 58725 58755 | 58740 58770 | ATGGTTGATTTAATGG | 569220 | ekkk-8-kkke | 58 | 37 |
| 58721 58751 | 58736 58766 | TTGATTTAATGGTTGC | 586224 | kkkkk-8-kkk | 90 | 35 |
| 58722 58752 | 58737 58767 | GTTGATTTAATGGTTG | 586225 | kkkkk-8-kkk | 88 | 36 |
| 58720 58750 | 58735 58765 | TGATTTAATGGTTGCA | 586227 | kkkkk-8-kkk | 87 | 39 |

Example 9

Dose-Dependent Antisense Inhibition of Human AR in HuVEC Cells

Antisense oligonucleotides from the studies described above exhibiting significant in vitro inhibition of AR mRNA were selected and tested at various doses in HuVEC cells. Cells were plated at a density of 20,000 cells per well and transfected using electroporation with 31.25 nM, 62.5 nM, 125.0 nM, 250.0 nM, 500.0 nM, and 1000.0 nM concentrations of antisense oligonucleotide, as specified in Table 14. After a treatment period of approximately 16 hours, RNA was isolated from the cells and AR mRNA levels were measured by quantitative real-time PCR. Human AR primer probe set RTS3559 was used to measure mRNA levels. AR mRNA levels were adjusted according to total RNA content, as measured by RIBOGREEN®. Results are presented as percent inhibition of AR, relative to untreated control cells. The antisense oligonucleotides were tested in a series of experiments that had similar culture conditions. The results for each experiment are presented in separate tables shown below.

The half maximal inhibitory concentration ($IC_{50}$) of each oligonucleotide is also presented in Table 14. As illustrated, AR mRNA levels were reduced in a dose-dependent manner in the antisense oligonucleotide treated cells.

TABLE 14

| ISIS No | 31.25 nM | 62.5 nM | 125.0 nM | 250.0 nM | 500.0 nM | 1000.0 nM | $IC_{50}$ nM |
|---|---|---|---|---|---|---|---|
| 549372 | 2  | 17 | 31 | 51 | 61 | 80 | 271 |
| 549458 | 0  | 19 | 40 | 63 | 74 | 90 | 196 |
| 560132 | 8  | 19 | 21 | 53 | 65 | 85 | 252 |
| 560133 | 17 | 15 | 24 | 35 | 58 | 79 | 336 |
| 569215 | 12 | 2  | 26 | 55 | 71 | 90 | 234 |
| 569220 | 11 | 29 | 34 | 43 | 59 | 78 | 275 |
| 569223 | 21 | 20 | 30 | 59 | 73 | 87 | 191 |
| 569227 | 13 | 22 | 45 | 46 | 61 | 74 | 255 |
| 569229 | 16 | 14 | 36 | 47 | 74 | 84 | 220 |
| 569238 | 4  | 32 | 33 | 54 | 71 | 88 | 202 |

Example 10

Dose-Dependent Antisense Inhibition of Human AR in HuVEC Cells

Gapmers from Example 8 exhibiting significant in vitro inhibition of AR mRNA were selected and tested at various doses in HuVEC cells. Cells were plated at a density of 20,000 cells per well and transfected using electroporation with 46.9 nM, 187.5 nM, 750.0 nM, and 3000.0 nM concentrations of antisense oligonucleotide, as specified in Table 15. After a treatment period of approximately 16 hours, RNA was isolated from the cells and AR mRNA levels were measured by quantitative real-time PCR. Human AR primer probe set RTS3559 was used to measure mRNA levels. AR mRNA levels were adjusted according to total RNA content, as measured by RIBOGREEN®. Results are presented as percent inhibition of AR, relative to untreated control cells.

The half maximal inhibitory concentration ($IC_{50}$) of each oligonucleotide is also presented in Table 15. As illustrated, AR mRNA levels were reduced in a dose-dependent manner in antisense oligonucleotide treated cells.

TABLE 15

| ISIS No | 46.9 nM | 187.5 nM | 750.0 nM | 3000.0 nM | $IC_{50}$ (µM) |
|---|---|---|---|---|---|
| 549372 | 9  | 41 | 66 | 87 | 0.29 |
| 549458 | 15 | 50 | 85 | 96 | 0.19 |
| 586124 | 28 | 47 | 84 | 94 | 0.13 |
| 586224 | 39 | 75 | 93 | 98 | 0.05 |
| 586225 | 17 | 61 | 89 | 97 | 0.13 |
| 586227 | 20 | 60 | 88 | 96 | 0.13 |

Example 11

Antisense Inhibition of Human AR in HuVEC Cells

Additional antisense oligonucleotides were designed targeting an AR nucleic acid and were tested for their effects on AR mRNA in vitro. Cultured HuVEC cells at a density of 20,000 cells per well were transfected using electroporation with 500 nM antisense oligonucleotide. After a treatment period of approximately 24 hours, RNA was isolated from the cells and AR mRNA levels were measured by quantitative real-time PCR. Human primer probe set RTS3559 was used to measure mRNA levels. AR mRNA levels were adjusted according to total RNA content, as measured by RIBOGREEN®. Results are presented as percent inhibition of AR, relative to untreated control cells. A total of 616 oligonucleotides were tested. Only those oligonucleotides which were selected for further study are shown in Tables 16-23.

The newly designed chimeric antisense oligonucleotides in Tables 16-23 were designed as 3-10-3 (S)-cET gapmers. The gapmers are 16 nucleosides in length, wherein the central gap segment comprises of ten 2'-deoxynucleosides and is flanked by wing segments on both the 5' direction and on the 3' direction comprising three nucleosides. Each nucleoside in the 5' wing segment and each nucleoside in the 3' wing segment has an (S)-cEt modification. The internucleoside linkages throughout each gapmer are phosphorothioate linkages. All cytosine residues throughout each gapmer are 5-methylcytosines.

The SEQ ID NO listed in the table refers to the oligonucleotide sequence. "Start site" indicates the 5'-most nucleoside to which the gapmer is targeted in the human gene sequence. "Stop site" indicates the 3'-most nucleoside to which the gapmer is targeted human gene sequence. Each gapmer listed in Tables 16-23 is targeted to either the human AR genomic sequence, designated herein as SEQ ID NO: 1 (GENBANK Accession No. NT_011669.17 truncated from nucleotides 5079000 to 5270000) or the human AR mRNA sequence, designated herein as SEQ ID NO: 2 (GENBANK Accession No. NM_000044.3), or both. 'n/a.' indicates that the oligonucleotide does not target that particular gene sequence.

TABLE 16

| Target Start Site | Target Stop Site | Sequence | ISIS No | % inhibition | SEQ ID NO |
|---|---|---|---|---|---|
| 5062 | 5077 | AAGTTGTAGTAGTCGC | 549372 | 47 | 22 |
| 58722 58752 | 58737 58767 | GTTGATTTAATGGTTG | 549458 | 60 | 36 |
| 2957 | 2972 | ACAGCACTGGAGCGGC | 583542 | 45 | 44 |
| 3079 | 3094 | AACTTCACCGAAGAGG | 583556 | 43 | 45 |
| 3099 | 3114 | AGTCTTTAGCAGCTTT | 583559 | 52 | 46 |
| 3109 | 3124 | GCTTCCTCCGAGTCTT | 583564 | 45 | 47 |
| 3113 | 3128 | CCTTGCTTCCTCCGAG | 583566 | 47 | 48 |
| 3120 | 3135 | GCACTTTCCTTGCTTC | 583567 | 52 | 49 |
| 3133 | 3148 | TCAGTCCTACCAGGCA | 583571 | 43 | 50 |
| 3224 | 3239 | GACTGAGGCAGCTGCG | 583583 | 45 | 51 |
| 3226 | 3241 | CCGACTGAGGCAGCTG | 583584 | 44 | 52 |

TABLE 17

| Target Start Site | Target Stop Site | Sequence | ISIS No | % inhibition | SEQ ID NO |
|---|---|---|---|---|---|
| 5062 | 5077 | AAGTTGTAGTAGTCGC | 549372 | 40 | 22 |
| 58722 58752 | 58737 58767 | GTTGATTTAATGGTTG | 549458 | 46 | 36 |
| 3351 | 3366 | GCTAGCTCGCCCGCTC | 583608 | 51 | 53 |
| 3353 | 3368 | CAGCTAGCTCGCCCGC | 583609 | 51 | 54 |
| 3361 | 3376 | GCAATGTGCAGCTAGC | 583613 | 51 | 55 |
| 3388 | 3403 | GTCGCCTGGCTCCTAA | 583620 | 41 | 56 |
| 3513 | 3528 | CTGGCTCCGCACTCGG | 583635 | 50 | 57 |
| 3517 | 3532 | ATCTCTGGCTCCGCAC | 583637 | 43 | 58 |
| 3519 | 3534 | TGATCTCTGGCTCCGC | 583638 | 51 | 59 |
| 3641 | 3656 | AGTGTCCACTGAAGTA | 583642 | 42 | 60 |
| 3735 | 3750 | AGGCTCACAGTCTGTC | 583649 | 46 | 61 |
| 3764 | 3779 | GACACACGGTGGACAA | 583660 | 44 | 62 |
| 3768 | 3783 | AGAAGACACACGGTGG | 583662 | 51 | 63 |
| 3798 | 3813 | CGCTCTGACAGCCTCA | 583667 | 42 | 64 |

TABLE 18

| Target Start Site | Target Stop Site | Sequence | ISIS No | % inhibition | SEQ ID NO |
|---|---|---|---|---|---|
| 5062 | 5077 | AAGTTGTAGTAGTCGC | 549372 | 26 | 22 |
| 58722 58752 | 58737 58767 | GTTGATTTAATGGTTG | 549458 | 48 | 36 |

TABLE 18-continued

| Target Start Site | Target Stop Site | Sequence | ISIS No | % inhibition | SEQ ID NO |
|---|---|---|---|---|---|
| 3870 | 3885 | GTCGCTGCAGCTAGCT | 583685 | 47 | 65 |
| 3874 | 3889 | GGTAGTCGCTGCAGCT | 583687 | 41 | 66 |
| 3876 | 3891 | GCGGTAGTCGCTGCAG | 583688 | 38 | 67 |
| 3878 | 3893 | ATGCGGTAGTCGCTGC | 583689 | 39 | 68 |
| 3884 | 3899 | GTGATGATGCGGTAGT | 583692 | 41 | 69 |
| 3886 | 3901 | CTGTGATGATGCGGTA | 583693 | 36 | 70 |
| 3901 | 3916 | GAAGAGTTCAACAGGC | 583700 | 36 | 71 |
| 3956 | 3971 | GCTTGGCTGAATCTTC | 583709 | 39 | 72 |
| 3962 | 3977 | CCTTGAGCTTGGCTGA | 583712 | 37 | 73 |
| 3964 | 3979 | ATCCTTGAGCTTGGCT | 583713 | 36 | 74 |
| 3967 | 3982 | TCCATCCTTGAGCTTG | 583714 | 36 | 75 |
| 4019 | 4034 | GTAGGTCTTGGACGGC | 583719 | 36 | 76 |
| 4038 | 4053 | GATTCTGGAAAGCTCC | 583727 | 40 | 77 |
| 4049 | 4064 | GCTCTGGAACAGATTC | 583728 | 45 | 78 |
| 4056 | 4071 | CGCGCACGCTCTGGAA | 583731 | 34 | 79 |
| 4062 | 4077 | TCACTTCGCGCACGCT | 583734 | 46 | 80 |
| 4066 | 4081 | TGGATCACTTCGCGCA | 583736 | 47 | 81 |
| 4070 | 4085 | GTTCTGGATCACTTCG | 583738 | 36 | 82 |
| 4101 | 4116 | CGCTCGCGGCCTCTGG | 583745 | 40 | 83 |
| 4103 | 4118 | TGCGCTCGCGGCCTCT | 583746 | 32 | 84 |
| 4105 | 4120 | GCTGCGCTCGCGGCCT | 583747 | 35 | 85 |

TABLE 19

| Target Start Site | Target Stop Site | Sequence | ISIS No | % inhibition | SEQ ID NO |
|---|---|---|---|---|---|
| 5062 | 5077 | AAGTTGTAGTAGTCGC | 549372 | 39 | 22 |
| 58722 58752 | 58737 58767 | GTTGATTTAATGGTTG | 549458 | 50 | 36 |
| 4109 | 4124 | AGGTGCTGCGCTCGCG | 583749 | 36 | 86 |
| 4305 | 4320 | GCTGTTCCTCATCCAG | 583759 | 38 | 87 |
| 4405 | 4420 | TGCTGCGGCAGCCCCT | 583771 | 40 | 88 |
| 4532 | 4547 | GGTGCTGGCCTCGCTC | 583787 | 37 | 89 |
| 4537 | 4552 | TGCATGGTGCTGGCCT | 583789 | 39 | 90 |
| 4539 | 4554 | GTTGCATGGTGCTGGC | 583790 | 39 | 91 |
| 4555 | 4570 | TGCTGTTGCTGAAGGA | 583795 | 63 | 92 |
| 4571 | 4586 | GGATACTGCTTCCTGC | 583796 | 65 | 93 |
| 4573 | 4588 | TCGGATACTGCTTCCT | 583797 | 35 | 94 |
| 4578 | 4593 | TGCCTTCGGATACTGC | 583799 | 65 | 95 |

TABLE 19-continued

| Target Start Site | Target Stop Site | Sequence | ISIS No | % inhibition | SEQ ID NO |
|---|---|---|---|---|---|
| 4597 | 4612 | CTCGCTCTCCCGCTGC | 583802 | 37 | 96 |
| 4632 | 4647 | TGTCCTTGGAGGAAGT | 583809 | 45 | 97 |
| 4656 | 4671 | TGGTCGAAGTGCCCCC | 583818 | 42 | 98 |
| 4662 | 4677 | CAGAAATGGTCGAAGT | 583821 | 42 | 99 |

TABLE 20

| Target Start Site | Target Stop Site | Sequence | ISIS No | % inhibition | SEQ ID NO |
|---|---|---|---|---|---|
| 5062 | 5077 | AAGTTGTAGTAGTCGC | 549372 | 23 | 22 |
| 58722 58752 | 58737 58767 | GTTGATTTAATGGTTG | 549458 | 54 | 36 |
| 4747 | 4762 | TGTTCCCCTGGACTCA | 583833 | 37 | 100 |
| 4750 | 4765 | AGCTGTTCCCCTGGAC | 583834 | 52 | 101 |
| 4752 | 4767 | GAAGCTGTTCCCCTGG | 583835 | 44 | 102 |
| 4754 | 4769 | CCGAAGCTGTTCCCCT | 583836 | 37 | 103 |
| 4769 | 4784 | GTACATGCAATCCCCC | 583843 | 35 | 104 |
| 4798 | 4813 | ACAGCGGGTGGAACTC | 583847 | 34 | 105 |
| 4804 | 4819 | GGACGCACAGCGGGTG | 583850 | 38 | 106 |
| 4807 | 4822 | GTGGGACGCACAGCGG | 583851 | 33 | 107 |
| 4833 | 4848 | TGCATTCGGCCAATGG | 583853 | 33 | 108 |
| 4837 | 4852 | CCTTTGCATTCGGCCA | 583855 | 44 | 109 |
| 4839 | 4854 | AACCTTTGCATTCGGC | 583856 | 45 | 110 |
| 4868 | 4883 | GCTCTTGCCTGCGCTG | 583862 | 32 | 111 |
| 4872 | 4887 | CAGTGCTCTTGCCTGC | 583864 | 46 | 112 |
| 4874 | 4889 | TTCAGTGCTCTTGCCT | 583865 | 45 | 113 |
| 4876 | 4891 | TCTTCAGTGCTCTTGC | 583866 | 32 | 114 |
| 4887 | 4902 | ACTCAGCAGTATCTTC | 583868 | 34 | 115 |
| 4889 | 4904 | ATACTCAGCAGTATCT | 583871 | 47 | 116 |
| 4916 | 4931 | TTTGGTGTAACCTCCC | 583880 | 39 | 117 |
| 4918 | 4933 | CCTTTGGTGTAACCTC | 583881 | 47 | 118 |
| 4938 | 4953 | CTAGGCTCTCGCCTTC | 583890 | 32 | 119 |
| 4942 | 4957 | CAGCCTAGGCTCTCGC | 583892 | 35 | 120 |
| 4944 | 4959 | AGCAGCCTAGGCTCTC | 583893 | 34 | 121 |
| 4951 | 4966 | CTGCCAGAGCAGCCTA | 583896 | 37 | 122 |

TABLE 21

| Target Start Site | Target Stop Site | Sequence | ISIS No | % inhibition | SEQ ID NO |
|---|---|---|---|---|---|
| 5062 | 5077 | AAGTTGTAGTAGTCGC | 549372 | 37 | 22 |
| 58722 58752 | 58737 58767 | GTTGATTTAATGGTTG | 549458 | 47 | 36 |
| 5050 | 5065 | TCGCGACTCTGGTACG | 583917 | 37 | 123 |
| 5052 | 5067 | AGTCGCGACTCTGGTA | 583918 | 47 | 124 |
| 5054 | 5069 | GTAGTCGCGACTCTGG | 583919 | 55 | 125 |
| 5056 | 5071 | TAGTAGTCGCGACTCT | 583920 | 42 | 126 |
| 5061 | 5076 | AGTTGTAGTAGTCGCG | 583922 | 37 | 42 |
| 5133 | 5148 | TCTCCAGCTTGATGCG | 583932 | 39 | 127 |
| 5141 | 5156 | CAGCGGGTTCTCCAGC | 583933 | 38 | 128 |
| 5293 | 5308 | CCTTCTTCGGCTGTGA | 583969 | 44 | 129 |
| 5308 | 5323 | GGTCCATACAACTGGC | 583975 | 42 | 130 |

TABLE 22

| Target Start Site on SEQ ID NO: 1 | Target Start Site on SEQ ID NO: 2 | Sequence | ISIS No | % inhibition | SEQ ID NO |
|---|---|---|---|---|---|
| 5062 | 2200 | AAGTTGTAGTAGTCGC | 549372 | 46 | 22 |
| 58722 58752 | n/a n/a | GTTGATTTAATGGTTG | 549458 | 39 | 36 |
| 5469 | 2607 | ACACATCAGGTGCGGT | 583990 | 30 | 131 |
| 5481 | 2619 | CGCCAGGGTACCACAC | 583996 | 33 | 132 |
| 5486 | 2624 | CATGCCGCCAGGGTAC | 583998 | 45 | 133 |
| 5488 | 2626 | ACCATGCCGCCAGGGT | 583999 | 29 | 134 |
| 5494 | 2632 | CTGCTCACCATGCCGC | 584002 | 30 | 135 |
| 5521 | 2659 | ACACAAGTGGGACTGG | 584006 | 33 | 136 |
| n/a | 2870 | CCCTTCAGCGGCTCTT | 584044 | 29 | 137 |

TABLE 23

| Target Start Site | Target Stop Site | Sequence | ISIS No | % inhibition | SEQ ID NO |
|---|---|---|---|---|---|
| 5062 | 5077 | AAGTTGTAGTAGTCGC | 549372 | 25 | 22 |
| 58722 58752 | 58737 58767 | GTTGATTTAATGGTTG | 549458 | 51 | 36 |
| 144938 | 144953 | CAGAGTCATCCCTGCT | 584069 | 36 | 138 |
| 148406 | 148421 | CACCCTCAAGATTCTT | 584100 | 36 | 139 |
| 148443 | 148458 | AAGGTAGTCTTTAAGG | 584106 | 30 | 140 |

TABLE 23-continued

| Target Start Site | Target Stop Site | Sequence | ISIS No | % inhibition | SEQ ID NO |
|---|---|---|---|---|---|
| 148520 | 148535 | GTTTTCAAATGCAGCC | 584111 | 33 | 141 |
| 139682 | 139697 | GCCATGAGACAGCTTT | 584125 | 35 | 142 |
| 139762 | 139777 | ATTCTTGACTGTCTGA | 584128 | 38 | 143 |
| 139782 | 139797 | GCATGCCAGCTGGCTC | 584130 | 29 | 144 |
| 5666 | 5681 | CGCGCAGGTAGGAGCC | 584138 | 35 | 145 |
| 6222 | 6237 | TCTAAACATGACGGTT | 584139 | 37 | 146 |
| 6701 | 6716 | ATGCAATTGCCTGCCA | 584141 | 39 | 147 |

Example 12

Antisense Inhibition of Human AR in HuVEC Cells

Additional antisense oligonucleotides were designed targeting an AR nucleic acid and were tested for their effects on AR mRNA in vitro. Cultured HuVEC cells at a density of 20,000 cells per well were transfected using electroporation with 1,000 nM antisense oligonucleotide. After a treatment period of approximately 24 hours, RNA was isolated from the cells and AR mRNA levels were measured by quantitative real-time PCR. Human primer probe set RTS3559 was used to measure mRNA levels. AR mRNA levels were adjusted according to total RNA content, as measured by RIBOGREEN®. Results are presented as percent inhibition of AR, relative to untreated control cells. A total of 385 oligonucleotides were tested. Only those oligonucleotides which were selected for further study are shown in Tables 24-28.

The newly designed chimeric antisense oligonucleotides in Tables 24-28 were designed as 3-10-3 (S)-cET gapmers. The gapmers are 16 nucleosides in length, wherein the central gap segment comprises of ten 2'-deoxynucleosides and is flanked by wing segments on both the 5' direction and on the 3' direction comprising three nucleosides. Each nucleoside in the 5' wing segment and each nucleoside in the 3' wing segment has an (S)-cEt modification. The internucleoside linkages throughout each gapmer are phosphorothioate linkages. All cytosine residues throughout each gapmer are 5-methylcytosines.

The SEQ ID NO listed in the table refers to the oligonucleotide sequence. "Start site" indicates the 5'-most nucleoside to which the gapmer is targeted in the human gene sequence. "Stop site" indicates the 3'-most nucleoside to which the gapmer is targeted human gene sequence. Each gapmer listed in Tables 24-28 is targeted to the human AR genomic sequence, designated herein as SEQ ID NO: 1 (GENBANK Accession No. NT_011669.17 truncated from nucleotides 5079000 to 5270000)

TABLE 24

| Target Start Site | Target Stop Site | Sequence | ISIS No | % inhibition | SEQ ID NO |
|---|---|---|---|---|---|
| 5062 | 5077 | AAGTTGTAGTAGTCGC | 549372 | 63 | 22 |
| 58722 | 58737 | GTTGATTTAATGGTTG | 549458 | 88 | 36 |
| 58752 | 58767 | | | | |
| 7543 | 7558 | ATGGGAGTAACTTTTG | 584145 | 76 | 148 |
| 8471 | 8486 | CATATTATTGTGCTGC | 584148 | 85 | 149 |
| 8638 | 8653 | GTCAATATCAAAGCAC | 584149 | 85 | 150 |
| 9464 | 9479 | GAGTTGTGATTTCAGG | 584152 | 88 | 151 |
| 10217 | 10232 | TTGATGGAATGCTGAT | 584157 | 69 | 152 |
| 10250 | 10265 | GGTTAACTTTCTCTGA | 584158 | 69 | 153 |
| 10865 | 10880 | TGGATTGTAAATTACG | 584162 | 82 | 154 |
| 11197 | 11212 | GAACATTATTAGGCTA | 584163 | 81 | 155 |
| 11855 | 11870 | TCAATCTAGATACCAT | 584165 | 70 | 156 |
| 13189 | 13204 | CACATCAGAAGGAGTA | 584166 | 89 | 157 |
| 13321 | 13336 | GAGTGTTAATGAAGAC | 584167 | 78 | 158 |
| 13346 | 13361 | CTGATTAGCTATGACC | 584168 | 70 | 159 |

TABLE 24-continued

| Target Start Site | Target Stop Site | Sequence | ISIS No | % inhibition | SEQ ID NO |
|---|---|---|---|---|---|
| 16555 | 16570 | ATGAGTCCTCAGAATC | 584179 | 74 | 160 |
| 16793 | 16808 | GTAGATTCTAGCTTTG | 584180 | 81 | 161 |
| 16968 | 16983 | ACAGGCTCTGACTAGG | 584183 | 76 | 162 |
| 17206 | 17221 | TGTGTGACCCTTGGAC | 584184 | 78 | 163 |
| 18865 | 18880 | AAGTATGAGCATGGTT | 584192 | 73 | 164 |

TABLE 25

| Target Start Site | Target Stop Site | Sequence | ISIS No | % inhibition | SEQ ID NO |
|---|---|---|---|---|---|
| 5062 | 5077 | AAGTTGTAGTAGTCGC | 549372 | 59 | 22 |
| 58722 58752 | 58737 58767 | GTTGATTTAATGGTTG | 549458 | 76 | 36 |
| 29329 | 29344 | GGATTCTCTACACACA | 584233 | 62 | 165 |
| 32290 | 32305 | CCATTTGTGCCAAACC | 584242 | 62 | 166 |
| 33315 | 33330 | AGGTTAGGGAGTAGGC | 584245 | 70 | 167 |
| 39055 | 39070 | TAGGGTTTGGTCAGAA | 584263 | 56 | 168 |
| 40615 | 40630 | CCTTATGGATGCTGCT | 584269 | 57 | 169 |
| 42017 | 42032 | GTTATCTTACTCTCCC | 584274 | 70 | 170 |

TABLE 26

| Target Start Site | Target Stop Site | Sequence | ISIS No | % inhibition | SEQ ID NO |
|---|---|---|---|---|---|
| 5062 | 5077 | AAGTTGTAGTAGTCGC | 549372 | 58 | 22 |
| 58722 58752 | 58737 58767 | GTTGATTTAATGGTTG | 549458 | 79 | 36 |
| 56050 | 56065 | GATTGTGTATAGCTGC | 584312 | 65 | 171 |
| 60902 | 60917 | GGTTATGGTTCTGTCT | 584329 | 58 | 172 |
| 67454 | 67469 | CTTCATTGCAGGTCTG | 584361 | 61 | 173 |

TABLE 27

| Target Start Site | Target Stop Site | Sequence | ISIS No | % inhibition | SEQ ID NO |
|---|---|---|---|---|---|
| 5062 | 5077 | AAGTTGTAGTAGTCGC | 549372 | 70 | 22 |
| 58722 58752 | 58737 58767 | GTTGATTTAATGGTTG | 549458 | 76 | 36 |
| 114874 | 114889 | TAGCCAACTTTCTTTA | 584465 | 58 | 174 |

TABLE 27-continued

| Target Start Site | Target Stop Site | Sequence | ISIS No | % inhibition | SEQ ID NO |
|---|---|---|---|---|---|
| 115272 | 115287 | CATTGTACTATGCCAG | 584468 | 64 | 175 |
| 115365 | 115380 | TTTGGTAACATTAGGC | 584469 | 74 | 176 |
| 134971 | 134986 | ATGGTTGTCCTGTACA | 584495 | 58 | 177 |

TABLE 28

| Target Start Site | Target Stop Site | Sequence | ISIS No | % inhibition | SEQ ID NO |
|---|---|---|---|---|---|
| 5062 | 5077 | AAGTTGTAGTAGTCGC | 549372 | 54 | 22 |
| 58722 58752 | 58737 58767 | GTTGATTTAATGGTTG | 549458 | 65 | 36 |
| 114874 | 114889 | TAGCCAACTTTCTTTA | 584465 | 54 | 174 |
| 115365 | 115380 | TTTGGTAACATTAGGC | 584469 | 63 | 176 |
| 134971 | 134986 | ATGGTTGTCCTGTACA | 584495 | 53 | 177 |

Example 13

Dose-Dependent Antisense Inhibition of Human AR in HuVEC Cells

Gapmers from the studies described above exhibiting significant in vitro inhibition of AR mRNA were selected and tested at various doses in HuVEC cells. Cells were plated at a density of 20,000 cells per well and transfected using electroporation with 46.9 nM, 187.5 nM, 750.0 nM, and 3000.0 nM concentrations of antisense oligonucleotide, as specified in Tables 29-37. After a treatment period of approximately 16 hours, RNA was isolated from the cells and AR mRNA levels were measured by quantitative real-time PCR. Human AR primer probe set RTS3559 was used to measure mRNA levels. AR mRNA levels were adjusted according to total RNA content, as measured by RIBOGREEN®. Results are presented as percent inhibition of AR, relative to untreated control cells.

The half maximal inhibitory concentration (IC$_{50}$) of each oligonucleotide is also presented in Tables 29-37. As illustrated, AR mRNA levels were reduced in a dose-dependent manner in some of the antisense oligonucleotide treated cells.

TABLE 29

| ISIS No | 46.9 nM | 187.5 nM | 750.0 nM | 3000.0 nM | IC$_{50}$ (µM) |
|---|---|---|---|---|---|
| 549372 | 7 | 41 | 70 | 91 | 0.32 |
| 549458 | 21 | 72 | 91 | 97 | 0.11 |
| 583542 | 9 | 28 | 47 | 66 | 0.90 |
| 583556 | 19 | 47 | 68 | 66 | 0.34 |
| 583559 | 30 | 49 | 63 | 80 | 0.22 |
| 583564 | 16 | 33 | 55 | 74 | 0.52 |
| 583566 | 0 | 28 | 50 | 74 | 0.73 |
| 583567 | 17 | 34 | 60 | 79 | 0.43 |
| 583571 | 18 | 36 | 53 | 59 | 0.80 |

TABLE 29-continued

| ISIS No | 46.9 nM | 187.5 nM | 750.0 nM | 3000.0 nM | IC$_{50}$ (µM) |
|---|---|---|---|---|---|
| 583583 | 21 | 31 | 49 | 64 | 0.79 |
| 583584 | 24 | 44 | 52 | 73 | 0.41 |
| 583608 | 12 | 46 | 67 | 76 | 0.35 |
| 583609 | 16 | 48 | 63 | 73 | 0.36 |
| 583613 | 24 | 60 | 70 | 75 | 0.19 |
| 583635 | 35 | 56 | 69 | 78 | 0.13 |
| 583638 | 33 | 64 | 79 | 85 | 0.11 |
| 583649 | 28 | 50 | 68 | 84 | 0.20 |
| 583660 | 21 | 39 | 61 | 72 | 0.42 |
| 583662 | 27 | 59 | 75 | 75 | 0.15 |

TABLE 30

| ISIS No | 46.9 nM | 187.5 nM | 750.0 nM | 3000.0 nM | IC$_{50}$ (µM) |
|---|---|---|---|---|---|
| 549372 | 13 | 29 | 69 | 90 | 0.37 |
| 549458 | 22 | 62 | 92 | 97 | 0.13 |
| 583620 | 0 | 17 | 44 | 54 | 1.85 |
| 583637 | 22 | 32 | 59 | 75 | 0.45 |
| 583642 | 18 | 35 | 67 | 74 | 0.46 |
| 583667 | 35 | 55 | 73 | 82 | 0.14 |
| 583685 | 32 | 53 | 73 | 81 | 0.16 |
| 583687 | 34 | 67 | 83 | 81 | 0.08 |
| 583688 | 3 | 26 | 50 | 60 | 1.05 |
| 583689 | 20 | 34 | 62 | 74 | 0.44 |
| 583692 | 8 | 47 | 61 | 71 | 0.44 |
| 583709 | 8 | 50 | 70 | 84 | 0.29 |
| 583712 | 15 | 47 | 72 | 78 | 0.29 |
| 583727 | 18 | 49 | 70 | 76 | 0.29 |
| 583728 | 9 | 48 | 67 | 70 | 0.40 |
| 583734 | 29 | 60 | 74 | 75 | 0.12 |
| 583736 | 21 | 38 | 60 | 63 | 0.51 |
| 583738 | 16 | 40 | 56 | 71 | 0.51 |
| 583745 | 19 | 51 | 68 | 77 | 0.27 |

TABLE 31

| ISIS No | 46.9 nM | 187.5 nM | 750.0 nM | 3000.0 nM | IC$_{50}$ (µM) |
|---|---|---|---|---|---|
| 549372 | 5 | 36 | 69 | 88 | 0.36 |
| 549458 | 24 | 59 | 92 | 98 | 0.13 |
| 583693 | 12 | 39 | 64 | 80 | 0.38 |
| 583700 | 14 | 34 | 57 | 71 | 0.55 |
| 583713 | 29 | 51 | 67 | 74 | 0.22 |
| 583714 | 22 | 34 | 59 | 79 | 0.40 |
| 583719 | 22 | 46 | 65 | 72 | 0.32 |
| 583731 | 18 | 24 | 47 | 58 | 1.31 |
| 583746 | 24 | 44 | 65 | 67 | 0.35 |
| 583747 | 13 | 38 | 50 | 69 | 0.64 |
| 583771 | 17 | 27 | 47 | 69 | 0.77 |
| 583789 | 30 | 49 | 71 | 85 | 0.19 |
| 583790 | 17 | 42 | 65 | 81 | 0.32 |
| 583795 | 37 | 61 | 83 | 90 | 0.09 |
| 583796 | 38 | 69 | 83 | 90 | 0.07 |
| 583799 | 29 | 60 | 76 | 85 | 0.14 |
| 583809 | 13 | 37 | 68 | 81 | 0.36 |
| 583818 | 9 | 46 | 71 | 84 | 0.31 |
| 583821 | 11 | 35 | 61 | 77 | 0.46 |

TABLE 32

| ISIS No | 46.9 nM | 187.5 nM | 750.0 nM | 3000.0 nM | IC$_{50}$ (µM) |
|---|---|---|---|---|---|
| 549372 | 15 | 39 | 70 | 86 | 0.30 |
| 549458 | 19 | 58 | 89 | 96 | 0.15 |
| 583749 | 34 | 40 | 75 | 87 | 0.17 |
| 583759 | 5 | 28 | 61 | 67 | 0.63 |
| 583787 | 15 | 31 | 66 | 74 | 0.43 |
| 583797 | 21 | 50 | 74 | 82 | 0.22 |
| 583802 | 17 | 25 | 47 | 60 | 1.07 |
| 583834 | 34 | 54 | 73 | 84 | 0.13 |
| 583835 | 20 | 55 | 74 | 88 | 0.19 |
| 583836 | 11 | 27 | 67 | 86 | 0.39 |
| 583850 | 9 | 21 | 54 | 78 | 0.60 |
| 583855 | 22 | 50 | 81 | 91 | 0.18 |
| 583856 | 31 | 55 | 74 | 89 | 0.14 |
| 583864 | 30 | 49 | 72 | 85 | 0.17 |
| 583864 | 0 | 47 | 62 | 85 | 0.37 |
| 583865 | 33 | 42 | 68 | 85 | 0.19 |
| 583871 | 28 | 30 | 68 | 87 | 0.28 |
| 583880 | 13 | 52 | 78 | 92 | 0.22 |
| 583881 | 28 | 50 | 85 | 91 | 0.15 |

TABLE 33

| ISIS No | 46.9 nM | 187.5 nM | 750.0 nM | 3000.0 nM | IC$_{50}$ (µM) |
|---|---|---|---|---|---|
| 549372 | 14 | 33 | 64 | 90 | 0.34 |
| 549458 | 21 | 61 | 90 | 96 | 0.13 |
| 583833 | 26 | 43 | 70 | 74 | 0.26 |
| 583843 | 22 | 40 | 67 | 85 | 0.30 |
| 583847 | 8 | 30 | 60 | 84 | 0.46 |
| 583851 | 8 | 24 | 54 | 76 | 0.61 |
| 583853 | 24 | 51 | 70 | 80 | 0.21 |
| 583862 | 15 | 37 | 64 | 79 | 0.41 |
| 583866 | 17 | 48 | 71 | 91 | 0.24 |
| 583868 | 19 | 31 | 59 | 81 | 0.41 |
| 583890 | 0 | 0 | 17 | 33 | >30 |
| 583892 | 22 | 38 | 68 | 83 | 0.27 |
| 583893 | 15 | 35 | 62 | 79 | 0.42 |
| 583896 | 13 | 17 | 49 | 69 | 0.86 |
| 583918 | 16 | 47 | 68 | 86 | 0.30 |
| 583919 | 27 | 60 | 85 | 91 | 0.14 |
| 583920 | 11 | 16 | 50 | 72 | 0.76 |
| 583969 | 12 | 26 | 66 | 86 | 0.44 |
| 583975 | 19 | 49 | 55 | 88 | 0.36 |

TABLE 34

| ISIS No | 46.9 nM | 187.5 nM | 750.0 nM | 3000.0 nM | IC$_{50}$ (µM) |
|---|---|---|---|---|---|
| 549372 | 14 | 36 | 64 | 88 | 0.32 |
| 549458 | 14 | 53 | 84 | 95 | 0.18 |
| 583917 | 6 | 30 | 50 | 70 | 0.64 |
| 583922 | 16 | 43 | 76 | 92 | 0.23 |
| 583932 | 9 | 35 | 64 | 81 | 0.38 |
| 583933 | 22 | 25 | 56 | 81 | 0.41 |
| 583990 | 0 | 9 | 33 | 56 | 1.92 |
| 583996 | 26 | 12 | 50 | 70 | 0.71 |
| 583998 | 4 | 25 | 38 | 70 | 0.89 |
| 583999 | 13 | 12 | 30 | 64 | 1.53 |
| 584002 | 12 | 46 | 70 | 92 | 0.25 |
| 584006 | 21 | 26 | 59 | 88 | 0.35 |
| 584044 | 23 | 30 | 51 | 78 | 0.44 |
| 584069 | 18 | 40 | 63 | 82 | 0.30 |
| 584100 | 6 | 5 | 20 | 44 | 7.79 |
| 584125 | 12 | 12 | 47 | 76 | 0.72 |
| 584128 | 20 | 22 | 41 | 72 | 0.74 |
| 584139 | 13 | 33 | 56 | 85 | 0.4 |
| 584141 | 22 | 37 | 61 | 85 | 0.29 |

TABLE 35

| ISIS No | 46.9 nM | 187.5 nM | 750.0 nM | 3000.0 nM | IC$_{50}$ (µM) |
|---|---|---|---|---|---|
| 549372 | 0 | 28 | 64 | 88 | 0.42 |
| 549458 | 13 | 49 | 84 | 91 | 0.19 |
| 584106 | 3 | 13 | 12 | 32 | >30 |
| 584111 | 22 | 30 | 59 | 84 | 0.33 |
| 584130 | 0 | 10 | 11 | 37 | >30 |
| 584138 | 2 | 40 | 62 | 89 | 0.37 |
| 584145 | 6 | 32 | 63 | 88 | 0.36 |
| 584148 | 16 | 48 | 79 | 95 | 0.20 |
| 584149 | 11 | 37 | 68 | 89 | 0.31 |
| 584152 | 28 | 59 | 87 | 95 | 0.11 |
| 584162 | 24 | 45 | 80 | 92 | 0.18 |
| 584163 | 19 | 37 | 74 | 90 | 0.25 |
| 584166 | 34 | 52 | 84 | 92 | 0.10 |
| 584167 | 13 | 45 | 76 | 93 | 0.21 |
| 584179 | 1 | 25 | 62 | 87 | 0.44 |
| 584180 | 26 | 56 | 84 | 96 | 0.12 |
| 584183 | 3 | 41 | 64 | 87 | 0.31 |
| 584184 | 9 | 42 | 76 | 93 | 0.23 |
| 584192 | 1 | 34 | 73 | 95 | 0.30 |

TABLE 36

| ISIS No | 46.9 nM | 187.5 nM | 750.0 nM | 3000.0 nM | IC$_{50}$ (µM) |
|---|---|---|---|---|---|
| 549372 | 2 | 26 | 61 | 85 | 0.42 |
| 549458 | 1 | 51 | 83 | 96 | 0.23 |
| 584157 | 6 | 6 | 52 | 82 | 0.59 |
| 584158 | 14 | 37 | 70 | 89 | 0.26 |
| 584165 | 12 | 34 | 66 | 89 | 0.30 |
| 584168 | 5 | 32 | 70 | 91 | 0.32 |
| 584233 | 0 | 30 | 66 | 86 | 0.39 |
| 584242 | 12 | 38 | 66 | 93 | 0.27 |
| 584245 | 4 | 33 | 69 | 90 | 0.32 |
| 584263 | 9 | 24 | 67 | 90 | 0.34 |
| 584269 | 6 | 26 | 69 | 92 | 0.34 |
| 584274 | 17 | 36 | 74 | 93 | 0.23 |
| 584312 | 17 | 37 | 65 | 93 | 0.26 |
| 584329 | 0 | 17 | 67 | 86 | 0.46 |
| 584361 | 0 | 18 | 71 | 87 | 0.41 |
| 584465 | 0 | 0 | 32 | 51 | 2.5 |
| 584468 | 9 | 26 | 60 | 90 | 0.37 |
| 584469 | 13 | 46 | 73 | 89 | 0.22 |
| 584495 | 0 | 14 | 55 | 74 | 0.65 |

TABLE 37

| ISIS No | 46.9 nM | 187.5 nM | 750.0 nM | 3000.0 nM | IC$_{50}$ (µM) |
|---|---|---|---|---|---|
| 549372 | 9 | 41 | 66 | 87 | 0.29 |
| 549458 | 15 | 50 | 85 | 96 | 0.19 |
| 586124 | 28 | 47 | 84 | 94 | 0.13 |
| 586195 | 41 | 62 | 90 | 95 | 0.07 |
| 586197 | 27 | 47 | 77 | 94 | 0.14 |
| 586198 | 39 | 62 | 89 | 96 | 0.07 |
| 586199 | 25 | 56 | 89 | 97 | 0.13 |
| 586200 | 23 | 44 | 85 | 95 | 0.15 |
| 586205 | 34 | 67 | 89 | 95 | 0.07 |
| 586207 | 0 | 39 | 79 | 93 | 0.3 |
| 586208 | 32 | 70 | 88 | 93 | 0.08 |
| 586212 | 20 | 60 | 86 | 94 | 0.13 |
| 586221 | 39 | 72 | 94 | 98 | 0.04 |
| 586224 | 39 | 75 | 93 | 98 | 0.05 |
| 586225 | 17 | 61 | 89 | 97 | 0.13 |
| 586227 | 20 | 60 | 88 | 96 | 0.13 |
| 586232 | 24 | 45 | 82 | 91 | 0.17 |
| 586240 | 14 | 49 | 83 | 93 | 0.18 |
| 586570 | 16 | 44 | 81 | 91 | 0.21 |

Example 14

Selection of Antisense Oligonucleotides Targeting Human Androgen Receptor (AR) mRNA for Assays with Prostate Cancer Cell Lines Antisense oligonucleotides from those presented in the studies above, targeting different regions of the human AR genomic sequence, were selected for further studies in prostate cancer cell lines. AR-V7 and AR-V567es are major AR splice variants detected in cancer patients as described in Hornberg, E. et al., PLoS One 2011. Vol. 6.

The following ISIS oligonucleotides were selected for further studies: ISIS 549372, which targets the human AR genomic sequence at exon 1; ISIS 549434, which targets the human AR genomic sequence at the 3'-end of exon 8 beyond the stop codon of AR; ISIS 560131, which targets the human AR genomic sequence at intron 1; and ISIS 569236, which targets the human AR genomic sequence at intron 1. Another antisense oligonucleotide, ISIS 554221 (ACCAAGTTTCTTCAGC, designated herein as SEQ ID NO: 178), was designed as a 3-10-3 LNA gapmer with phosphorothioate backbone targeted to exon 4, (i.e. the ligand binding domain) of AR identical to an antisense oligonucleotide designated as SEQ ID NO: 58 of U.S. Pat. No. 7,737,125 for use as a benchmark.

Example 15

Effect of Antisense Inhibition of Human Androgen Receptor (AR) mRNA on Androgen Receptor Protein Levels in MDV3100-Resistant C4-2B Cells C4-2B cells are androgen-independent human prostate adenocarcinoma cells commonly used in the field of oncology and have been established as clinically relevant cultured cells (Thalmann, G. N. et al., Cancer Res. 1994. 54: 2577). MDV3100 or Enzalutamide is an experimental androgen receptor antagonist drug developed by Medivation for the treatment of castration-resistant prostate cancer. ISIS 549372, ISIS 554221, and ISIS 549434 were tested in MDV3100-resistant (MR) C4-2B cells.

The cells were cultured in the presence of 5 µM concentration of MDV3100 over the course of 2 months to induce MDV3100 resistance. ISIS 549372, ISIS 549434, and ISIS 554221 at 1 µM concentration of antisense oligonucleotide were each added to the culture media at 1 µM concentration for free uptake by the cells. After a treatment period of 2 days, cells were harvested in RIPA buffer containing protease inhibitors. The presence of bands for full-length AR, as well as the variant form, AR-V7, was detected by western blot using AR antibody (N-20, Santa Cruz). Treatment of the cells with ISIS 549372 reduced full-length AR and AR-V7 more extensively than treatment with either ISIS 554221 or ISIS 549434.

Example 16

Effect of Antisense Inhibition of Human Androgen Receptor (AR) mRNA on AR-Target Genes in MDV3100-Resistant C4-2B Cells The effect of antisense inhibition of AR on AR target genes was analyzed. ISIS 549372, ISIS 549458, ISIS 554221, and ISIS 549434 were tested in C4-2B MR cells.

Cells were plated at a density of 40,000 cells per well in 96-well plates and cultured in RPMI1640 medium with 10% fetal bovine serum. The cells were cultured in the presence of 5 µM concentration of MDV3100 over the course of 2 months to induce MDV3100 resistance. ISIS 549372, ISIS 549458, ISIS 549434, and ISIS 554221 were each added at 0.04 µM, 0.20 µM, 1.00 µM, and 5.00 µM concentrations of antisense oligonucleotide to culture media for free uptake by the cells. A control oligonucleotide, ISIS 347526 (sequence TCTTATGTTTCCGAACCGTT (SEQ ID NO: 179) 5-10-5 MOE gapmer) with no known target region in human gene sequences, was included as a negative control. After a treatment period of 24 hrs, total AR mRNA levels were measured by quantitative real-time PCR using primer probe set RTS3559. Human AR primer probe set hAR_LTS00943 (forward sequence GCCCCTGGATGGATAGCTACT, designated herein as SEQ ID NO: 180; reverse sequence CCACAGATCAGGCAGGTCTTC, designated herein as SEQ ID NO: 181; probe sequence ACTGCCAGGGACCAT-GTTTTGCCC, designated herein as SEQ ID NO: 182) was used to measure AR-V7 mRNA levels. AR mRNA levels were adjusted to human actin mRNA levels. Results are presented in Table 38 as percent inhibition of total AR, relative to untreated control cells. Treatment of the cells with ISIS 549372, ISIS 549458, and ISIS 549434 reduced total AR transcript levels in a dose dependent manner more extensively than treatment with ISIS 554221.

Western analysis of full-length AR, as well as the AR-V7 variant, was also conducted in a manner similar to the assay described above. The assay demonstrated that treatment with ISIS 549372 and ISSI 549458 reduced levels of full-length AR and AR-V7. Treatment with ISIS 549434 reduced levels of full-length AR but not that of AR-V7. Treatment with ISIS 554221 reduced levels of full-length AR less extensively compared to ISIS 549372, and did not reduce levels of AR-V7. The control oligonucleotide ISIS 347526 did not reduce protein levels, as expected.

The mRNA level of the AR target gene, KLK2 was measured using the primer probe set hKLK2_LTS00963 (forward sequence CTTGCGCCCCAGGAGTCT, designated herein as SEQ ID NO: 183; reverse sequence CTCA-GAGTAAGCTCTAGCACACATGTC, designated herein as SEQ ID NO: 184; probe sequence AGTGTGTGAGCCTC-CATCTCCTGTCCAA, designated herein as SEQ ID NO: 185). The mRNA level of the AR target gene, KLK3 was measured using the primer probe set RTS1072 (forward sequence GCCAAGGAGGGAGGGTCTT, designated herein as SEQ ID NO: 186; reverse sequence CCCCCCATAGTGAATCAGCTT, designated herein as SEQ ID NO: 187; probe sequence ATGAAGTAAGGA-GAGGGACTGGACCCCC, designated herein as SEQ ID NO: 188). As presented in Tables 39 and 40, treatment with I ISIS 549372, ISIS 549458, and ISIS 549434 reduced target gene levels in a dose dependent manner more extensively than treatment with ISIS 554221.

TABLE 38

Percent inhibition of full-length AR mRNA in C4-2B MR cells

| ISIS No | 0.04 µM | 0.20 µM | 1.00 µM | 5.00 µM |
|---|---|---|---|---|
| 549372 | 35 | 47 | 88 | 91 |
| 549434 | 9 | 36 | 66 | 88 |
| 549458 | 41 | 78 | 94 | 97 |
| 554221 | 0 | 0 | 0 | 23 |
| 347526 | 28 | 35 | 31 | 17 |

TABLE 39

Percent inhibition of KLK3 mRNA in C4-2B MR cells

| ISIS No | 0.04 µM | 0.20 µM | 1.00 µM | 5.00 µM |
|---|---|---|---|---|
| 549372 | 17 | 35 | 68 | 80 |
| 549434 | 10 | 47 | 42 | 64 |
| 549458 | 0 | 42 | 81 | 92 |
| 554221 | 0 | 0 | 47 | 56 |
| 347526 | 5 | 38 | 42 | 16 |

TABLE 40

Percent inhibition of KLK2 mRNA in C4-2B MR cells

| ISIS No | 0.04 µM | 0.20 µM | 1.00 µM | 5.00 µM |
|---|---|---|---|---|
| 549372 | 14 | 16 | 57 | 87 |
| 549434 | 5 | 27 | 49 | 68 |
| 549458 | 35 | 47 | 87 | 93 |
| 554221 | 24 | 25 | 56 | 66 |
| 347526 | 28 | 29 | 23 | 22 |

Example 17

Effect of Antisense Inhibition of Human Androgen Receptor (AR) mRNA on the Proliferative Ability of MDV3100-Resistant C4-2B Cells The effect of antisense inhibition of AR on the proliferative ability of cancer cells was analyzed. ISIS 549372, ISIS 549458, ISIS 554221, and ISIS 549434 were tested in C4-2B MR cells.

ISIS 549372, ISIS 549434, ISIS 549458, and ISIS 554221 were each added to the culture media at 0.04 µM, 0.20 µM, 1.00 µM, and 5.00 µM concentration of antisense oligonucleotide. ISIS 347526 was included as a negative control. After a treatment period of 6 days, the proliferative capacity of the cancer cells was measured with using CellTiter 96® AQueous One Solution Cell Proliferation kit (Promega), following the manufacturer's instructions. Results are presented in Table 41 as percent inhibition of proliferation, relative to non-treated cells. Treatment of the cells with ISIS 549372, ISIS 549434, and ISIS 549458 reduced proliferation of the cells in a dose dependent manner more extensively than treatment with ISIS 554221.

TABLE 41

Percent inhibition of C4-2B MR cell proliferation

| ISIS No | 0.04 µM | 0.20 µM | 1.00 µM | 5.00 µM |
|---|---|---|---|---|
| 549372 | 0 | 4 | 25 | 43 |
| 549434 | 0 | 0 | 21 | 22 |
| 549458 | 8 | 16 | 41 | 56 |
| 554221 | 11 | 12 | 0 | 24 |
| 347526 | 11 | 22 | 7 | 16 |

Example 18

Effect of Antisense Inhibition of Human Androgen Receptor (AR) mRNA on MDV3100-Resistant LMR20 Cells An MDV3100-resistant cell line, designated as LMR20, was created. The effect of antisense inhibition of AR on the proliferative ability and AR mRNA levels of LMR20 cells was analyzed. ISIS 560131, ISIS 549458, and ISIS 569236 were tested along with the LNA gapmer, ISIS 554221.

LnCaP cells were incubated with increasing concentrations of MDV3100 for approximately 6 months. A single clone was selected after extensive culturing in the presence of 20 µM MDV3100. The clone, LMR20, maintained the ability to allow free uptake of antisense oligonucleotides without lipid-mediated transfection, while demonstrating an approximately ten-fold increase in $IC_{50}$ when treated with MDV3100, compared to parental LnCaP cells.

Study 1

LMR20 cells were plated at 1,500 cells per well in phenol red-free medium with charcoal-stripped fetal bovine serum (CSS), to remove any androgens from the medium (Life Technologies). ISIS 560131, ISIS 549458, ISIS 569236, and ISIS 554221 were individually added to the culture media at 0.04 µM, 0.2 µM, 1.0 µM, or 5.0 µM concentration. ISIS 549148, which has no known human target sequence, was included as a control. The synthetic androgen agonist, R1881, (Takeda, A. N. et al., Mol. Pharmacol. 2007. 71: 473-82) was added on day 1 at 1 nM dose to a set of cells also treated with each of the antisense oligonucleotides. DHT was added on day 1 at a dose of 10 nM to another set of cells also treated with each of the antisense oligonucleotides. MDV3100 was added on day 1 at a dose of 10 nM to another set of cells untreated with antisense oligonucleotide, which served as a control. After a treatment period of 5 days, the proliferative ability of the cancer cells was measured by the standard MTT assay. Results are presented in Table 42 as percent inhibition of proliferation, relative to non-treated cells.

As presented in Table 42, in the presence of androgen agonists R1881 or DHT, ISIS 560131, ISIS 549458, and ISIS 569236 significantly inhibited MDV3100-resistant prostate cancer cell proliferation in a dose dependent manner more extensively than ISIS 554221 Inhibition of proliferation by the antisense oligonucleotides was also either comparable or more potent than with treatment with MDV3100.

TABLE 42

Percent inhibition of LMR20 cell proliferation

| Treatment | ASO (µM) | ISIS 560131 | ISIS 569236 | ISIS 549458 | ISIS 554221 | MDV3100 |
|---|---|---|---|---|---|---|
| CSS | 0.04 | 0 | 0 | 0 | 0 | 0 |
|  | 0.20 | 0 | 10 | 0 | 1 | 5 |

TABLE 42-continued

Percent inhibition of LMR20 cell proliferation

| Treatment | ASO (µM) | ISIS 560131 | ISIS 569236 | ISIS 549458 | ISIS 554221 | MDV3100 |
|---|---|---|---|---|---|---|
| | 1.0 | 9 | 0 | 0 | 2 | 0 |
| | 5.0 | 16 | 12 | 5 | 16 | 11 |
| CSS + R1881 | 0.04 | 0 | 0 | 0 | 1 | 0 |
| | 0.20 | 13 | 2 | 22 | 10 | 5 |
| | 1.0 | 55 | 34 | 59 | 19 | 31 |
| | 5.0 | 70 | 61 | 74 | 54 | 67 |
| CSS + DHT | 0.04 | 0 | 0 | 0 | 0 | 0 |
| | 0.20 | 13 | 10 | 25 | 0 | 1 |
| | 1.0 | 57 | 32 | 60 | 10 | 13 |
| | 5.0 | 71 | 57 | 70 | 36 | 41 |

Study 2

LMR20 cells were plated at 1,500 cells per well in phenol red-free medium with CSS. ISIS 560131, ISIS 549458, ISIS 569236, and the LNA gapmer ISIS 554221 were individually added to the culture media at 0.04 µM, 0.2 µM, 1.0 µM, or 5.0 µM concentration. ISIS 549148, which has no known human target sequence, was included as a control. MDV3100 was added on day 1 at a dose of 10 nM to a set of cells, and served as a control. DHT was added on day 1 at a dose of 10 nM for 72 hrs to one set of cells also treated with each of the antisense oligonucleotides or MDV3100. R1881 was added on day 1 at a dose of 10 nM for 72 hrs to another set of cells also treated with each of the antisense oligonucleotides or MDV3100. mRNA levels of AR, prostate-specific antigen (PSA) and TMPRSS2, an androgen-regulated gene (Lin, B., et al., Cancer Res. 1999. 59: 4180), were measured. Results are presented in Tables 43-45 as mRNA levels expressed as a percentage of the baseline values. mRNA levels may be lowered or increased after treatment.

As presented in Tables 43-45, ISIS 560131, ISIS 549458, and ISIS 569236 reduced AR mRNA levels in LMR20 cells, treated with or without either AR agonist, in a dose dependent manner relative to the baseline. Treatment with the LNA gapmer ISIS 554221 did not alter AR mRNA levels. ISIS 560131, ISIS 549458, and ISIS 569236 reduced PSA levels and TMPRSS2 more extensively than the LNA gapmer ISIS 554221 or MDV3100. Treatment with MDV3100 increased the levels of AR mRNA in cells treated with AR agonist, and did not reduce either PSA or TMPRSS2 mRNA levels.

TABLE 43 mRNA levels (% baseline value) of cells without AR agonist treatment

| Gene | ASO (µM) | 560131 | 569236 | 549458 | 554221 | MDV3100 |
|---|---|---|---|---|---|---|
| AR | 0.04 | 107 | 104 | 101 | 124 | 106 |
| | 0.20 | 74 | 87 | 75 | 140 | 101 |
| | 1.0 | 29 | 42 | 30 | 132 | 99 |
| | 5.0 | 17 | 27 | 25 | 98 | 92 |
| PSA | 0.04 | 113 | 122 | 135 | 106 | 98 |
| | 0.20 | 83 | 90 | 85 | 118 | 93 |
| | 1.0 | 75 | 78 | 50 | 58 | 90 |
| | 5.0 | 71 | 73 | 72 | 87 | 113 |
| TMPRSS2 | 0.04 | 94 | 92 | 96 | 110 | 95 | 101 |
| | 0.20 | 67 | 81 | 85 | 117 | 119 |
| | 1.0 | 52 | 59 | 54 | 77 | 119 |
| | 5.0 | 45 | 48 | 62 | 73 | 141 |

TABLE 44 mRNA levels (% baseline value) after treatment with DHT

| Gene | ASO (µM) | 560131 | 569236 | 549458 | 554221 | MDV3100 |
|---|---|---|---|---|---|---|
| AR | 0.04 | 89 | 94 | 91 | 137 | 105 |
| | 0.20 | 55 | 77 | 66 | 135 | 124 |
| | 1.0 | 25 | 44 | 34 | 136 | 110 |
| | 5.0 | 20 | 34 | 31 | 100 | 143 |
| PSA | 0.04 | 74 | 108 | 93 | 97 | 124 |
| | 0.20 | 61 | 79 | 71 | 86 | 108 |
| | 1.0 | 35 | 46 | 47 | 64 | 95 |
| | 5.0 | 35 | 46 | 47 | 64 | 95 |
| TMPRSS2 | 0.04 | 112 | 113 | 127 | 121 | 134 |
| | 0.20 | 108 | 123 | 119 | 118 | 144 |
| | 1.0 | 93 | 111 | 106 | 122 | 132 |
| | 5.0 | 71 | 110 | 91 | 114 | 124 |

TABLE 45 mRNA levels (% baseline value) after treatment with R1881

| Gene | ASO (µM) | 560131 | 569236 | 549458 | 554221 | MDV3100 |
|---|---|---|---|---|---|---|
| AR | 0.04 | 87 | 89 | 88 | 131 | 94 |
| | 0.20 | 65 | 80 | 56 | 133 | 107 |
| | 1.0 | 30 | 44 | 25 | 124 | 115 |
| | 5.0 | 26 | 37 | 32 | 99 | 136 |
| PSA | 0.04 | 92 | 90 | 93 | 100 | 84 |
| | 0.20 | 77 | 90 | 67 | 93 | 101 |
| | 1.0 | 44 | 57 | 50 | 80 | 92 |
| | 5.0 | 35 | 41 | 44 | 57 | 87 |
| TMPRSS2 | 0.04 | 132 | 126 | 137 | 136 | 114 |
| | 0.20 | 117 | 131 | 119 | 134 | 125 |
| | 1.0 | 88 | 98 | 96 | 125 | 133 |
| | 5.0 | 76 | 95 | 96 | 122 | 139 |

Example 19

Effect of Antisense Inhibition of Human Androgen Receptor (AR) mRNA in Combination with MDV3100 on the Proliferative Ability of C4-2B Cells The effect of antisense inhibition of AR in combination with different doses of MDV3100 on the proliferative ability of cancer cells was analyzed. ISIS 549372, ISIS 549434, ISIS 549458, and ISIS 554221 were tested in C4-2B cells.

C4-2B cells were plated at 1,500 cells per well. ISIS 549372, ISIS 549434, ISIS 549458, or ISIS 554221 were individually added to the culture media at 0.1 µM concentration. ISIS 347526 was included as a negative control. MDV3100 was also added on day 1 at doses of 0.25 µM or 1.00 µM. After a treatment period of 6 days, the proliferative capacity of the cancer cells was measured with CellTiter 96® AQueous One Solution Cell Proliferation kit (Promega), following the manufacturer's instructions. Results are presented in Table 46 as percent inhibition of proliferation, relative to non-treated cells. Treatment of the cells with ISIS 549372 or ISIS 549458 reduced proliferation of the cells more extensively than treatment with ISIS 554221. For instance, as presented in Table 46, treatment with ISIS 549372 alone reduced cell proliferation by 59% and treatment with ISIS 549458 reduced cell proliferation by 74% compared to ISIS 554221 alone, which reduced cell proliferation by 23%.

As presented in Tables 46 and 47, ISIS 549372 or ISIS 549458 in combination with MDV3100 inhibited prostate cancer cell proliferation to a greater extent than an equal molar concentration of ISIS 554221 in combination of MDV3100.

To find out whether treatment of the cells with ISIS 549372 or ISIS 549458 was synergistic with MDV3100, the assay was repeated at 0.1 µM ASO. As presented in Table 46, treatment with ISIS 549372 or ISIS 549458 was synergistic with MDV3100. For instance, MDV3100 alone at 0.25 µM inhibited proliferation by 4%; ISIS 549372 alone at 0.1 µM inhibited cell proliferation by 23%; in combination, cell proliferation was inhibited by 66%. Similarly, ISIS 549458 alone at 0.1 µM inhibited cell proliferation by 39%; in combination, cell proliferation was inhibited by 75%. Hence, the combination of ISIS 549372 or ISIS 549458 and MDV3100 was synergistic (i.e. greater than additive) in terms of inhibition of prostate cancer cell proliferation.

TABLE 46

Percent inhibition of C4-2B cell proliferation with 0.1 µM ASO

| | MDV3100 | | |
| --- | --- | --- | --- |
| | 0 µM | 0.25 µM | 1 µM |
| PBS | 0 | 9 | 38 |
| ISIS 549372 | 23 | 44 | 66 |
| ISIS 549458 | 39 | 59 | 75 |
| ISIS 554221 | 9 | 29 | 59 |
| ISIS 141923 | 0 | 4 | 38 |

TABLE 47

Percent inhibition of C4-2B cell proliferation with 0.2 µM ASO

| | MDV3100 | | |
| --- | --- | --- | --- |
| | 0 µM | 0.25 µM | 1 µM |
| PBS | 0 | 20 | 46 |
| ISIS 549372 | 59 | 69 | 77 |
| ISIS 549458 | 74 | 75 | 79 |
| ISIS 554221 | 23 | 45 | 67 |
| ISIS 141923 | 0 | 5 | 50 |

Example 20

Effect of Antisense Inhibition of Human Androgen Receptor (AR) mRNA in Combination with MDV3100 on the Proliferative Ability of LNCaP Cells The effect of antisense inhibition of AR in combination with different doses of MDV3100 on the proliferative ability of cancer cells was analyzed. ISIS 560131 and ISIS 569236 were tested in LNCaP cells.

LNCaP cells were plated at 1,000 cells per well. ISIS 560131 or ISIS 569236 was individually added to the culture media at 0.08 µM, 0.04 µM, 0.2 µM, or 1.0 µM concentration. ISIS 549148 was included as a negative control. MDV3100 was added to the ISIS oligonucleotide-treated cells on day 2 at doses of 0.016 µM, 0.08 µM, 0.4 µM, or 2.0 µM. After a treatment period of 5 days, the proliferative capacity of the cancer cells was measured with CellTiter 96® AQueous One or CellTiter-Glo® Solution Cell Proliferation kit (Promega), following the manufacturer's instructions. Results are presented in Tables 48-52 as percent inhibition of proliferation, relative to non-treated cells.

As presented in the Tables, treatment with ISIS 560131 or ISIS 569236 was synergistic with MDV3100. For instance, MDV3100 with control oligonucleotide, ISIS 549148, at 0.08 µM inhibited proliferation by an average of 7%; ISIS 560131 alone at 0.04 µM inhibited cell proliferation by 24%; in combination, cell proliferation was inhibited by 41%. Similarly, ISIS 569236 alone at 0.04 µM inhibited cell proliferation by 9%; in combination, cell proliferation was inhibited by 26%. Hence, the combination of ISIS 560131 or ISIS 569236 and MDV3100 was synergistic (i.e. greater than additive) in terms of inhibition of prostate cancer cell proliferation.

TABLE 48

Proliferation (% untreated control) in LNCaP without MDV-3100

| | ASO Dose | | | |
| --- | --- | --- | --- | --- |
| | 0.08 µM | 0.04 µM | 0.2 µM | 1.0 µM |
| ISIS 560131 | 106 | 76 | 50 | 26 |
| ISIS 569236 | 106 | 91 | 60 | 35 |
| ISIS 549148 | 104 | 101 | 91 | 82 |

TABLE 49

Proliferation (% untreated control) in LNCaP with 0.016 µM MDV-3100

| | ASO Dose | | | |
| --- | --- | --- | --- | --- |
| | 0.08 µM | 0.04 µM | 0.2 µM | 1.0 µM |
| ISIS 560131 | 103 | 71 | 49 | 25 |
| ISIS 569236 | 104 | 92 | 58 | 29 |
| ISIS 549148 | 106 | 86 | 83 | 59 |

TABLE 50

Proliferation (% untreated control) in LNCaP with 0.08 µM MDV-3100

| | ASO Dose | | | |
| --- | --- | --- | --- | --- |
| | 0.08 µM | 0.04 µM | 0.2 µM | 1.0 µM |
| ISIS 560131 | 99 | 59 | 48 | 27 |
| ISIS 569236 | 98 | 74 | 51 | 31 |
| ISIS 549148 | 93 | 101 | 89 | 90 |

TABLE 51

Proliferation (% untreated control) in LNCaP with 0.4 µM MDV-3100

| | ASO Dose | | | |
| --- | --- | --- | --- | --- |
| | 0.08 µM | 0.04 µM | 0.2 µM | 1.0 µM |
| ISIS 560131 | 68 | 50 | 40 | 26 |
| ISIS 569236 | 61 | 48 | 41 | 27 |
| ISIS 549148 | 65 | 57 | 50 | 48 |

TABLE 52

Proliferation (% untreated control) in LNCaP with 2.0 µM MDV-3100

| | ASO Dose | | | |
|---|---|---|---|---|
| | 0.08 µM | 0.04 µM | 0.2 µM | 1.0 µM |
| ISIS 560131 | 45 | 42 | 38 | 23 |
| ISIS 569236 | 44 | 41 | 35 | 23 |
| ISIS 549148 | 39 | 42 | 41 | 32 |

Example 21

Effect of Antisense Inhibition of Human Androgen Receptor (AR) mRNA in Combination with MDV3100 on the Proliferative Ability of C4-2B Cells The effect of antisense inhibition of AR in combination with different doses of MDV3100 on the proliferative ability of cancer cells was analyzed. ISIS 560131 and ISIS 569236 were tested in C4-2B cells.

C4-2B cells were plated at 1,000 cells per well. ISIS 560131 or ISIS 569236 was individually added to the culture media at 0.08 µM, 0.04 µM, 0.2 µM, or 1.0 µM concentration. ISIS 549148 was included as a negative control. MDV3100 was added to the ISIS oligonucleotide-treated cells on day 2 at doses of 0.016 µM, 0.08 µM, 0.4 µM, or 2.0 µM. After a treatment period of 5 days, the proliferative capacity of the cancer cells was measured with CellTiter 96® AQueous One Solution Cell Proliferation kit (Promega), following the manufacturer's instructions. Results are presented in Tables 53-57 as percent inhibition of proliferation, relative to non-treated cells.

As presented in the Tables, treatment with ISIS 560131 or ISIS 569236 was synergistic with MDV3100. For instance, MDV3100 with control oligonucleotide, ISIS 549148, at 0.4 µM inhibited proliferation by an average of 6%; ISIS 560131 alone at 0.08 µM inhibited cell proliferation by 16%; in combination, cell proliferation was inhibited by 31%. Similarly, MDV3100 with control oligonucleotide, ISIS 549148, at 0.08 µM did not inhibit proliferation (0%); ISIS 569236 alone at 0.2 µM inhibited cell proliferation by 37%; in combination, cell proliferation was inhibited by 52%. Hence, the combination of ISIS 560131 or ISIS 569236 and MDV3100 was synergistic (i.e. greater than additive) in terms of inhibition of prostate cancer cell proliferation.

TABLE 53

Proliferation (% untreated control) in C4-2B without MDV-3100

| | ASO Dose | | | |
|---|---|---|---|---|
| | 0.08 µM | 0.04 µM | 0.2 µM | 1.0 µM |
| ISIS 560131 | 84 | 59 | 47 | 41 |
| ISIS 569236 | 100 | 72 | 63 | 51 |
| ISIS 549148 | 111 | 117 | 118 | 126 |

TABLE 54

Proliferation (% untreated control) in C4-2B with 0.016 µM MDV-3100

| | ASO Dose | | | |
|---|---|---|---|---|
| | 0.08 µM | 0.04 µM | 0.2 µM | 1.0 µM |
| ISIS 560131 | 104 | 71 | 53 | 39 |
| ISIS 569236 | 107 | 74 | 65 | 55 |
| ISIS 549148 | 110 | 107 | 124 | 103 |

TABLE 55

Proliferation (% untreated control) in C4-2B with 0.08 µM MDV-3100

| | ASO Dose | | | |
|---|---|---|---|---|
| | 0.08 µM | 0.04 µM | 0.2 µM | 1.0 µM |
| ISIS 560131 | 66 | 73 | 56 | 42 |
| ISIS 569236 | 89 | 79 | 51 | 43 |
| ISIS 549148 | 84 | 125 | 123 | 114 |

TABLE 56

Proliferation (% untreated control) in C4-2B with 0.4 µM MDV-3100

| | ASO Dose | | | |
|---|---|---|---|---|
| | 0.08 µM | 0.04 µM | 0.2 µM | 1.0 µM |
| ISIS 560131 | 69 | 69 | 48 | 48 |
| ISIS 569236 | 90 | 63 | 48 | 39 |
| ISIS 549148 | 89 | 110 | 88 | 88 |

TABLE 57

Proliferation (% untreated control) in C4-2B with 2.0 µM MDV-3100

| | ASO Dose | | | |
|---|---|---|---|---|
| | 0.08 µM | 0.04 µM | 0.2 µM | 1.0 µM |
| ISIS 560131 | 37 | 42 | 49 | 43 |
| ISIS 569236 | 44 | 45 | 48 | 46 |
| ISIS 549148 | 47 | 40 | 52 | 59 |

Example 22

Effect of Antisense Inhibition of Human Androgen Receptor (AR) mRNA in Combination with MDV3100 on the Proliferative Ability of 22RV1 Cells The effect of antisense inhibition of AR in combination with different doses of MDV3100 on the proliferative ability of cancer cells was analyzed. ISIS 560131 and ISIS 569236 were tested in 22RV1 cells.

22RV1 cells were plated at 2,000 cells per well in 5% CSS medium for 48 hours. Cells were transfected using RNAiMAX reagent with ISIS 560131 or ISIS 569236 at 0.4 nM, 1.34 nM, 4 nM, or 13.4 nM concentrations. ISIS 549148 was included as a negative control. DHT at 1 nM and/or MDV3100 at doses of 0.04 µM, 0.2 µM, 1.0 µM, or 5.0 µM were added after 4 hours. After a treatment period of 3 days, the proliferative capacity of the cancer cells was measured with CellTiter 96® AQueous One Solution Cell Proliferation kit (Promega), following the manufacturer's instructions. Results are presented in Tables 58-62 as percent inhibition of proliferation, relative to non-treated cells.

As presented in the Tables, treatment with ISIS 560131 or ISIS 569236 was synergistic with MDV3100. For instance, MDV3100 with control oligonucleotide, ISIS 549148, at 1.0 µM inhibited proliferation by an average of 5%; ISIS 560131 alone at 1.34 nM inhibited cell proliferation by 3%; in combination, cell proliferation was inhibited by 23%. Similarly, MDV3100 with control oligonucleotide, ISIS 549148, at 1.0 µM inhibited proliferation by 5%; ISIS 569236 alone at 1.0 µM inhibited cell proliferation by 17%; in combination, cell proliferation was inhibited by 30%. Hence, the combination of ISIS 560131 or ISIS 569236 and MDV3100 was synergistic (i.e. greater than additive) in terms of inhibition of prostate cancer cell proliferation.

TABLE 58

Proliferation (% untreated control) in 22RV1 without MDV-3100

| | ASO Dose | | | |
|---|---|---|---|---|
| | 0.4 nM | 1.34 nM | 4.0 nM | 13.4 nM |
| ISIS 560131 | 103 | 97 | 77 | 57 |
| ISIS 569236 | 97 | 83 | 69 | 37 |
| ISIS 549148 | 109 | 109 | 109 | 99 |

TABLE 59

Proliferation (% untreated control) in 22RV1 cells with 0.04 µM MDV-3100

| | ASO Dose | | | |
|---|---|---|---|---|
| | 0.4 nM | 1.34 nM | 4.0 nM | 13.4 nM |
| ISIS 560131 | 96 | 80 | 65 | 39 |
| ISIS 569236 | 83 | 70 | 61 | 24 |
| ISIS 549148 | 106 | 106 | 100 | 85 |

TABLE 60

Proliferation (% untreated control) in 22RV1 cells with 0.2 µM MDV-3100

| | ASO Dose | | | |
|---|---|---|---|---|
| | 0.4 nM | 1.34 nM | 4.0 nM | 13.4 nM |
| ISIS 560131 | 95 | 90 | 76 | 51 |
| ISIS 569236 | 93 | 77 | 60 | 20 |
| ISIS 549148 | 101 | 115 | 110 | 96 |

TABLE 61

Proliferation (% untreated control) in 22RV1 cells with 1.0 µM MDV-3100

| | ASO Dose | | | |
|---|---|---|---|---|
| | 0.4 nM | 1.34 nM | 4.0 nM | 13.4 nM |
| ISIS 560131 | 96 | 77 | 63 | 40 |
| ISIS 569236 | 79 | 70 | 52 | 18 |
| ISIS 549148 | 106 | 95 | 98 | 82 |

TABLE 62

Proliferation (% untreated control) in 22RV1 cells with 5.0 µM MDV-3100

| | ASO Dose | | | |
|---|---|---|---|---|
| | 0.4 nM | 1.34 nM | 4.0 nM | 13.4 nM |
| ISIS 560131 | 91 | 76 | 63 | 41 |
| ISIS 569236 | 82 | 72 | 52 | 24 |
| ISIS 549148 | 96 | 102 | 98 | 85 |

Example 23

Effect of Antisense Inhibition of Human Androgen Receptor (AR) mRNA on CWR22-RV1 Cells The effect of antisense inhibition of AR on the proliferative ability of cancer cells was analyzed. ISIS 549372, ISIS 549434, ISIS 549458, and ISIS 554221 were tested in CWR22-RV1 cells.

CWR22-RV1 cells were plated and transfected using RNAiMax reagent (Life Technologies) with ISIS oligonucleotides at 1.7 nM, 5.0 nM, 16.7 nM, or 50 nM concentrations. ISIS 347526 was included as a negative control. After a treatment period of 6 days, the target reduction and proliferative capacity of the cancer cells was measured.

Antisense inhibition of AR full-length mRNA was measured with the RTS3559 primer probe set. The results are presented in Table 63 as percent inhibition relative to non-treated cells. The reduction in V7 splice variant of the AR mRNA was also measured by RT-PCR using SYBR Green staining (Hu, R. et al., Cancer Res. 2009. 69: 16-22). The results are presented in Table 64, as percent reduction, relative to non-treated cells. Cell proliferation was measured with CellTiter 96® AQueous One Solution Cell Proliferation kit (Promega), following the manufacturer's instructions. Results are presented in Table 65 as percent inhibition of proliferation, relative to non-treated cells.

TABLE 63

Percent inhibition of AR full-length mRNA

| Dose (nM) | ISIS 549372 | ISIS 549434 | ISIS 549458 | ISIS 554221 | ISIS 347526 |
|---|---|---|---|---|---|
| 1.7 | 24 | 27 | 28 | 24 | 0 |
| 5.0 | 53 | 46 | 41 | 41 | 3 |
| 16.7 | 64 | 69 | 61 | 67 | 4 |
| 50.0 | 78 | 86 | 78 | 72 | 0 |

TABLE 64

Percent inhibition of AR splice variant, V7

| Dose (nM) | ISIS 549372 | ISIS 549434 | ISIS 549458 | ISIS 554221 | ISIS 347526 |
|---|---|---|---|---|---|
| 1.7 | 23 | 0 | 18 | 25 | 17 |
| 5.0 | 35 | 20 | 34 | 1 | 0 |
| 16.7 | 56 | 4 | 58 | 7 | 0 |
| 50.0 | 82 | 23 | 82 | 35 | 10 |

TABLE 65

Percent inhibition of cell proliferation

| Dose (nM) | ISIS 549372 | ISIS 549434 | ISIS 549458 | ISIS 554221 | ISIS 347526 |
|---|---|---|---|---|---|
| 1.7 | 0 | 8 | 0 | 17 | 0 |
| 5.0 | 0 | 15 | 0 | 11 | 0 |
| 16.7 | 25 | 13 | 17 | 27 | 0 |
| 50.0 | 53 | 38 | 40 | 47 | 0 |

Example 24

Effect of Antisense Inhibition of Human Androgen Receptor (AR) mRNA by Free Uptake of Antisense Oligonucleotide by C4-2B Cells The effect of free uptake of antisense oligonucleotides on AR mRNA levels was investigated. ISIS 549372, ISIS 549434, ISIS 549458, and ISIS 554221 were tested.

Cells were plated at a concentration of 1,000 cells/well in 96-well plates to measure cell proliferation, and at 4,000 cells/well to measure target reduction. ISIS 549458, ISIS 549372, ISIS 549434, and ISIS 554221 were added individually at 0.04 µM, 0.20 µM, 1.00 µM, or 5.00 µM. After an incubation period of 24 hrs, mRNA levels were measured using hAR_LTS00943. The data is presented in Table 66. The results indicate that ISIS 549458, ISIS 549372, and ISIS 549434 inhibited AR mRNA expression more potently than ISIS 554221.

On day 6, cells plated for measuring proliferation were incubated with MTT reagent until the development of color. Color intensity was measured using a spectrophotometer at 490 nm. The data is presented in Table 67.

TABLE 66

Percent inhibition of AR full-length mRNA

| Dose (µM) | ISIS 549372 | ISIS 549434 | ISIS 549458 | ISIS 554221 |
|---|---|---|---|---|
| 0.04 | 10 | 10 | 16 | 0 |
| 0.20 | 36 | 35 | 48 | 0 |
| 1.00 | 73 | 52 | 80 | 0 |
| 5.00 | 80 | 55 | 86 | 0 |

TABLE 67

Percent inhibition of cell proliferation

| Dose (µM) | ISIS 549372 | ISIS 549434 | ISIS 549458 | ISIS 554221 |
|---|---|---|---|---|
| 0.04 | 8 | 0 | 7 | 0 |
| 0.20 | 34 | 14 | 31 | 10 |
| 1.00 | 44 | 35 | 45 | 21 |
| 5.00 | 45 | 37 | 41 | 30 |

Example 25

Effect of Antisense Inhibition of Human Androgen Receptor (AR) mRNA by Free Uptake of Antisense Oligonucleotide by LnCaP Cells The effect of free uptake of antisense oligonucleotides on AR mRNA levels was investigated.

Cells were plated at a concentration of 4,000 cells/well in 96-well plates. ISIS oligonucleotides, specified in Table 68, were added individually at 0.02 µM, 0.10 µM, 0.50 µM, 2.50 µM, or 10.00 µM. After an incubation period of 24 hrs, mRNA levels were measured using primer probe set hAR_LTS00943. The data is presented in Table 68. The results indicate that most of the ISIS oligonucleotides inhibited AR mRNA expression more potently than ISIS 554221 at each concentration.

TABLE 68

Percent inhibition of AR mRNA

| ISIS No | 0.02 µM | 0.1 µM | 0.5 µM | 2.5 µM | 10 µM |
|---|---|---|---|---|---|
| 554221 | 0 | 0 | 0 | 0 | 17 |
| 549372 | 0 | 0 | 21 | 63 | 78 |
| 549458 | 4 | 14 | 67 | 86 | 89 |
| 560131 | 0 | 0 | 13 | 31 | 57 |
| 569213 | 3 | 0 | 31 | 59 | 78 |
| 569216 | 15 | 17 | 49 | 66 | 82 |
| 569221 | 18 | 31 | 49 | 78 | 91 |
| 569227 | 0 | 0 | 4 | 33 | 55 |
| 569236 | 3 | 2 | 21 | 43 | 70 |
| 579666 | 0 | 8 | 30 | 49 | 68 |
| 579667 | 0 | 0 | 8 | 12 | 40 |
| 579671 | 15 | 0 | 19 | 54 | 71 |
| 583918 | 8 | 0 | 0 | 0 | 13 |
| 584149 | 0 | 0 | 0 | 14 | 39 |
| 584163 | 0 | 0 | 19 | 41 | 70 |
| 584269 | 0 | 0 | 0 | 12 | 23 |
| 584468 | 0 | 0 | 10 | 44 | 73 |
| 586124 | 0 | 0 | 19 | 64 | 82 |
| 586227 | 0 | 0 | 14 | 44 | 59 |

Example 26

Effect of Antisense Inhibition of Human Androgen Receptor (AR) mRNA in the Presence of DHT on the Proliferative Ability of 22RV1 Cells Dihydrotestosterone (DHT) is an androgen hormone and AR activator. The effect of antisense inhibition of AR on the proliferative ability of cancer cells treated with DHT was analyzed. ISIS 560131 and ISIS 569236 were tested in the human prostate carcinoma cell line, 22RV1.

22RV1cells were plated at 1,500 cells per well. ISIS 560131 and ISIS 569236 were individually transfected into the cells using RNAiMAX™ reagent (Life Technologies) at 1.34 nM, 4.00 nM, 13.4 nM, or 40.0 nM concentration. ISIS 549148, which has no known human target sequence, was included as a control. Separate sets of cells, also treated with each of the antisense oligonucleotides, were treated with DHT added on day 1 at a final concentration of 1 nM. After a treatment period of 5 days, the proliferative ability of the cancer cells was measured using the standard MTT assay. Results are presented in Table 69 as percent inhibition of proliferation, relative to non-treated cells.

As presented in Table 69, both ISIS 560131 and ISIS 569236 significantly inhibited prostate cancer cell proliferation even in the presence of AR activator, DHT, compared to the control. The control oligonucleotide did not show any effect on proliferation, as expected.

TABLE 69

Percent inhibition of 22RV1 cell proliferation

|  | ASO (nM) | ISIS 560131 | ISIS 569236 | ISIS 549148 |
|---|---|---|---|---|
| −DHT | 1.34 | 0 | 0 | 0 |
|  | 4.0 | 2 | 18 | 0 |
|  | 13.4 | 29 | 47 | 4 |
|  | 40.0 | 54 | 64 | 0 |
| +DHT | 1.34 | 0 | 0 | 0 |
|  | 4.0 | 1 | 6 | 0 |
|  | 13.4 | 13 | 32 | 3 |
|  | 40.0 | 34 | 56 | 0 |

Example 27

Time-Course Study of Treatment C4-2B Cells with ISIS Oligonucleotides Targeting AR The effect of antisense inhibition of on C4-2B cancer cells on gene expression was analyzed. ISIS 560131 and ISIS 569236 were tested.

AR mRNA Analysis

C4-2B cells were plated at 1,000 cells per well in complete medium. ISIS 560131 or ISIS 569236 was individually added to the culture media to the final concentrations of 0.04 µM, 0.2 µM, 1.0 µM, or 5.0 µM concentrations without using transfection reagent. ISIS 549148 was included as a negative control. MDV3100 was added at dose of 0.04 µM, 0.2 µM, 1.0 µM, or 5.0 µM in a separate set of cells. After a treatment period of 8 hours, 24 hours, and 48 hours, AR expression was measured with primer probe set hAR-LTS00943. Results are presented in Tables 70-72 as percent expression of AR, relative to non-treated cells. Treatment of the cells with ISIS 560131 or ISIS 569236 reduced AR expression in the cells relative to the control set. Treatment with MDV-3100 increased AR expression at the 48 hour time-point.

TABLE 70

Percent expression of AR compared to the control group in 8 hours

|  | 0.04 µM | 0.2 µM | 1 µM | 5.0 µM |
|---|---|---|---|---|
| ISIS 560131 | 110 | 85 | 68 | 45 |
| ISIS 569236 | 100 | 87 | 84 | 58 |
| ISIS 549148 | 116 | 105 | 111 | 110 |
| MDV-3100 | 99 | 100 | 92 | 103 |

TABLE 71

Percent expression of AR compared to the control group in 24 hours

|  | 0.04 µM | 0.2 µM | 1 µM | 5.0 µM |
|---|---|---|---|---|
| ISIS 560131 | 47 | 18 | 5 | 4 |
| ISIS 569236 | 103 | 35 | 15 | 5 |
| ISIS 549148 | 87 | 85 | 87 | 107 |
| MDV-3100 | 88 | 99 | 96 | 84 |

TABLE 72

Percent expression of AR compared to the control group in 48 hours

|  | 0.04 µM | 0.2 µM | 1 µM | 5.0 µM |
|---|---|---|---|---|
| ISIS 560131 | 33 | 5 | 6 | 4 |
| ISIS 569236 | 80 | 19 | 7 | 2 |
| ISIS 549148 | 98 | 90 | 87 | 99 |
| MDV-3100 | 94 | 94 | 113 | 126 |

AR Protein Analysis

Protein levels in the cells were also analyzed. The cells were harvested in RIPA buffer containing protease inhibitors. The presence of bands for full-length AR was detected by western blot using AR antibody (N-20, SC-816, Santa Cruz Biotechnology). Full-length AR was significantly reduced in cells treated with ISIS 560131 or ISIS 569236 for 24 hours and 48 hours, normalized to the levels of the house-keeping gene, GAPDH.

mRNA Expression Analysis of Downstream Genes

Expression analysis of prostate-specific antigen (PSA) and TMPRSS2 were also analyzed. Results are presented in Tables 73-75 as percent inhibition of PSA expression and Tables 76-78 as percent inhibition of TMPRSS2 expression, relative to non-treated cells. Treatment of the cells with ISIS 560131 or ISIS 569236 reduced PSA and TMPRSS2 expression in the cells relative to the control set at the 24 hr and 48 hr time points. Treatment with MDV-3100 also reduced downstream gene expressions but not as potently as that with the ISIS oligonucleotides.

TABLE 73

Percent inhibition of PSA expression compared to the control group in 8 hours

|  | 0.04 µM | 0.2 µM | 1 µM | 5.0 µM |
|---|---|---|---|---|
| ISIS 560131 | 12 | 0 | 3 | 1 |
| ISIS 569236 | 18 | 3 | 0 | 0 |
| ISIS 549148 | 1 | 8 | 8 | 0 |
| MDV-3100 | 0 | 3 | 23 | 33 |

TABLE 74

Percent inhibition of PSA expression compared to the control group in 24 hours

|  | 0.04 µM | 0.2 µM | 1 µM | 5.0 µM |
|---|---|---|---|---|
| ISIS 560131 | 27 | 46 | 56 | 60 |
| ISIS 569236 | 10 | 34 | 44 | 54 |
| ISIS 549148 | 22 | 13 | 16 | 6 |
| MDV-3100 | 24 | 24 | 53 | 65 |

TABLE 75

Percent inhibition of PSA expression compared to the control group in 48 hours

|  | 0.04 µM | 0.2 µM | 1 µM | 5.0 µM |
|---|---|---|---|---|
| ISIS 560131 | 20 | 61 | 71 | 80 |
| ISIS 569236 | 4 | 45 | 68 | 76 |
| ISIS 549148 | 2 | 0 | 18 | 10 |
| MDV-3100 | 5 | 5 | 32 | 63 |

TABLE 76

Percent inhibition of TMPRSS2 expression compared to the control group in 8 hours

|  | 0.04 μM | 0.2 μM | 1 μM | 5.0 μM |
|---|---|---|---|---|
| ISIS 560131 | 0 | 0 | 6 | 0 |
| ISIS 569236 | 0 | 0 | 0 | 0 |
| ISIS 549148 | 5 | 0 | 0 | 0 |
| MDV-3100 | 0 | 6 | 45 | 52 |

TABLE 77

Percent inhibition of TMPRSS2 expression compared to the control group in 24 hours

|  | 0.04 μM | 0.2 μM | 1 μM | 5.0 μM |
|---|---|---|---|---|
| ISIS 560131 | 35 | 57 | 66 | 67 |
| ISIS 569236 | 10 | 32 | 57 | 66 |
| ISIS 549148 | 29 | 10 | 29 | 10 |
| MDV-3100 | 23 | 31 | 63 | 72 |

TABLE 78

Percent inhibition of TMPRSS2 expression compared to the control group in 48 hours

|  | 0.04 μM | 0.2 μM | 1 μM | 5.0 μM |
|---|---|---|---|---|
| ISIS 560131 | 46 | 71 | 77 | 76 |
| ISIS 569236 | 22 | 57 | 70 | 75 |
| ISIS 549148 | 0 | 4 | 0 | 0 |
| MDV-3100 | 5 | 16 | 46 | 59 |

Example 28

Antisense Inhibition of AR mRNA in LNCaP Cells Cultured in Complete Media and CSS Media The effect of antisense inhibition of AR in LNCaP cells cultured in complete medium, as well as CSS medium with DHT, was investigated.

Gene Expression in Complete Medium

Cells were plated at 1,000 cells per well. ISIS 560131 or ISIS 569236 was added individually at 0.04 μM, 0.2 μM, 1.0 μM, or 5.0 μM. ISIS 549148 was included as a negative control. MDV3100 was added a dose of 0.04 μM, 0.2 μM, 1.0 μM, or 5.0 μM. μM in a separate set of cells. After an incubation period of 48 hours, RNA levels of AR, PSA and TMPRSS2 were measured. The data is presented in Tables 79-81.

Protein analysis of full-length AR also demonstrated a dose-dependent decrease of expression, normalized to levels of the house-keeping gene, GAPDH.

TABLE 79

Percent expression of AR in LNCaP cells cultured in complete medium

|  | 0.04 μM | 0.2 μM | 1 μM | 5.0 μM |
|---|---|---|---|---|
| ISIS 560131 | 101 | 53 | 17 | 7 |
| ISIS 569236 | 98 | 90 | 47 | 20 |
| ISIS 549148 | 102 | 111 | 109 | 109 |
| MDV-3100 | 111 | 133 | 121 | 139 |

TABLE 80

Percent inhibition of PSA expression in LNCaP cells cultured in complete medium

|  | 0.04 μM | 0.2 μM | 1 μM | 5.0 μM |
|---|---|---|---|---|
| ISIS 560131 | 0 | 60 | 87 | 90 |
| ISIS 569236 | 0 | 19 | 63 | 81 |
| ISIS 549148 | 0 | 0 | 0 | 0 |
| MDV-3100 | 0 | 35 | 84 | 87 |

TABLE 81

Percent inhibition of TMPRSS2 expression in LNCaP cells cultured in complete medium

|  | 0.04 μM | 0.2 μM | 1 μM | 5.0 μM |
|---|---|---|---|---|
| ISIS 560131 | 0 | 25 | 50 | 51 |
| ISIS 569236 | 0 | 5 | 40 | 48 |
| ISIS 549148 | 0 | 0 | 0 | 0 |
| MDV-3100 | 0 | 0 | 34 | 39 |

Gene Expression in CSS Medium and CSS+DHT Media

Cells were plated at 2,000 cells per well and cultured in phenol red-free RPMI supplemented with 5% charcoal stripped serum (Gibco) media for 16 hours. ISIS 560131 or ISIS 569236 was added individually at 0.04 μM, 0.2 μM, 1.0 μM, or 5.0 μM to each cell set. ISIS 549148 was included as a negative control. MDV3100 was added at 0.04 μM, 0.2 μM, 1.0 μM, or 5.0 μM in a separate set of cells. After an incubation period of 4 hrs, DHT was added to the medium to a final concentration of 1 nM as indicated. RNAs were collected 48 hrs later and levels of AR, PSA and TMPRSS2 were measured. The data is presented in Table 82-85. In the absence of DHT, AR expression in LNCaP cells was 95%, PSA expression was 7% and TMPRSS2 expression was 24% compared to the untreated control.

TABLE 82

Percent expression of AR in LNCaP cells cultured in CSS medium

|  | 0.04 μM | 0.2 μM | 1 μM | 5.0 μM |
|---|---|---|---|---|
| ISIS 560131 | 81 | 46 | 16 | 5 |
| ISIS 569236 | 94 | 66 | 35 | 13 |
| ISIS 549148 | 106 | 97 | 96 | 104 |
| MDV-3100 | 91 | 67 | 64 | 77 |

TABLE 83

Percent expression of AR in LNCaP cells cultured in CSS + DHT medium

|  | 0.04 μM | 0.2 μM | 1 μM | 5.0 μM |
|---|---|---|---|---|
| ISIS 560131 | 101 | 71 | 27 | 10 |
| ISIS 569236 | 104 | 86 | 55 | 21 |
| ISIS 549148 | 98 | 102 | 96 | 111 |
| MDV-3100 | 107 | 121 | 110 | 113 |

TABLE 84

Percent inhibition of PSA expression in LNCaP cells cultured in CSS + DHT medium

|  | 0.04 µM | 0.2 µM | 1 µM | 5.0 µM |
|---|---|---|---|---|
| ISIS 560131 | 10 | 21 | 21 | 72 |
| ISIS 569236 | 4 | 11 | 45 | 59 |
| ISIS 549148 | 0 | 8 | 0 | 9 |
| MDV-3100 | 15 | 38 | 81 | 82 |

TABLE 85

Percent inhibition of TMPRSS2 expression in LNCaP cells cultured in CSS + DHT medium

|  | 0.04 µM | 0.2 µM | 1 µM | 5.0 µM |
|---|---|---|---|---|
| ISIS 560131 | 6 | 11 | 26 | 64 |
| ISIS 569236 | 6 | 8 | 40 | 50 |
| ISIS 549148 | 0 | 0 | 1 | 10 |
| MDV-3100 | 8 | 24 | 60 | 69 |

Effect on Proliferation in CSS Medium and CSS+DHT Media

After a treatment period of 5 days in complete medium or CSS+1 nM DHT medium, the proliferative capacity of the cancer cells was measured with using CellTiter 96® AQueous One Solution or CellTiter-Glo® solution Cell Proliferation kit (Promega), following the manufacturer's instructions. Results are presented in Tables 86 and 87 as percent inhibition of proliferation, relative to non-treated cells. Treatment of the cells with ISIS 560131, ISIS 569236, and MDV-3100 reduced proliferation of the cells in a dose dependent compared to the control. Treatment with ISIS oligonucleotides in CSS+DHT medium reduced the proliferative capacity to a greater extent than treatment with MVD-3100. The proliferative capacity of cells cultured in CSS medium without DHT is 17% of untreated control levels.

TABLE 86

Proliferation (% untreated control) in LNCaP cells cultured in complete medium

|  | 0.04 µM | 0.2 µM | 1 µM | 5.0 µM |
|---|---|---|---|---|
| ISIS 560131 | 96 | 70 | 48 | 45 |
| ISIS 569236 | 100 | 85 | 68 | 54 |
| ISIS 549148 | 101 | 95 | 94 | 110 |
| MDV-3100 | 107 | 88 | 65 | 45 |

TABLE 87

Proliferation (% untreated control) in LNCaP cells cultured in CSS + DHT medium

|  | 0.04 µM | 0.2 µM | 1 µM | 5.0 µM |
|---|---|---|---|---|
| ISIS 560131 | 97 | 81 | 46 | 8 |
| ISIS 569236 | 95 | 99 | 54 | 17 |
| ISIS 549148 | 112 | 96 | 95 | 89 |
| MDV-3100 | 112 | 95 | 74 | 33 |

Example 29

Antisense Inhibition of AR mRNA in C4-2 Cells Cultured in Complete Media and CSS Media The effect of antisense inhibition of AR mRNA levels in C4-2 cells cultured in complete medium, as well as CSS medium with DHT, was investigated.

Gene Expression in Complete Medium

Cells were plated at 1,000 cells per well. ISIS 560131 or ISIS 569236 was added individually at 0.04 µM, 0.2 µM, 1.0 µM, or 5.0 µM. ISIS 549148 was included as a negative control. MDV3100 was added at 0.04 µM, 0.2 µM, 1.0 µM, or 5.0 µM in a separate set of cells. After an incubation period of 48 hrs, RNA levels of AR, PSA and TMPRSS2 were measured. The data is presented in Tables 88-90. Treatment with ISIS oligonucleotide inhibited AR expression, whereas treatment with MDV-3100 increased AR expression in the cells.

Protein analysis of full-length AR and PSA also demonstrated a dose-dependent decrease of expression, normalized to levels of the house-keeping gene, GAPDH.

TABLE 88

Percent expression of AR in C4-2 cells cultured in complete medium

|  | 0.04 µM | 0.2 µM | 1 µM | 5.0 µM |
|---|---|---|---|---|
| ISIS 560131 | 48 | 13 | 8 | 8 |
| ISIS 569236 | 72 | 27 | 11 | 9 |
| ISIS 549148 | 89 | 90 | 84 | 86 |
| MDV-3100 | 95 | 99 | 132 | 137 |

TABLE 89

Percent inhibition of PSA expression in C4-2 cells cultured in complete medium

|  | 0.04 µM | 0.2 µM | 1 µM | 5.0 µM |
|---|---|---|---|---|
| ISIS 560131 | 48 | 78 | 88 | 89 |
| ISIS 569236 | 35 | 62 | 83 | 88 |
| ISIS 549148 | 15 | 24 | 24 | 23 |
| MDV-3100 | 28 | 40 | 72 | 89 |

TABLE 90

Percent inhibition of TMPRSS2 expression in C4-2 cells cultured in complete medium

|  | 0.04 µM | 0.2 µM | 1 µM | 5.0 µM |
|---|---|---|---|---|
| ISIS 560131 | 29 | 62 | 76 | 71 |
| ISIS 569236 | 17 | 54 | 67 | 67 |
| ISIS 549148 | 2 | 7 | 10 | 0 |
| MDV-3100 | 10 | 20 | 44 | 67 |

Gene Expression in CSS+DHT Media

Cells were plated at 2,000 cells per well and cultured in CSS media with 1 nM DHT. ISIS 560131 or ISIS 569236 was added individually at 0.04 µM, 0.2 µM, 1.0 µM, or 5.0 µM to each cell set. ISIS 549148 was included as a negative control. MDV3100 was added at 0.04 µM, 0.2 µM, 1.0 µM, or 5.0 µM in a separate set of cells. After an incubation period of 48 hrs, RNA levels of AR, PSA and TMPRSS2 were measured. The data is presented in Table 91-93. In the absence of DHT, AR expression in C4-2 cells was 153%, PSA expression was 42% and TMPRSS2 expression was 23% compared to the untreated control. Treatment with ISIS oligonucleotide inhibited AR expression, whereas treatment with MDV-3100 increased AR expression in the cells.

TABLE 91

Percent expression of AR in C4-2 cells cultured in CSS + DHT medium

|  | 0.04 µM | 0.2 µM | 1 µM | 5.0 µM |
| --- | --- | --- | --- | --- |
| ISIS 560131 | 88 | 57 | 20 | 15 |
| ISIS 569236 | 89 | 82 | 52 | 23 |
| ISIS 549148 | 101 | 101 | 118 | 111 |
| MDV-3100 | 101 | 109 | 156 | 148 |

TABLE 92

Percent inhibition of PSA expression in C4-2 cells cultured in CSS + DHT medium

|  | 0.04 µM | 0.2 µM | 1 µM | 5.0 µM |
| --- | --- | --- | --- | --- |
| ISIS 560131 | 10 | 24 | 49 | 74 |
| ISIS 569236 | 0 | 4 | 57 | 64 |
| ISIS 549148 | 0 | 8 | 21 | 22 |
| MDV-3100 | 9 | 8 | 51 | 73 |

TABLE 93

Percent inhibition of TMPRSS2 expression in C4-2 cells cultured in CSS + DHT medium

|  | 0.04 µM | 0.2 µM | 1 µM | 5.0 µM |
| --- | --- | --- | --- | --- |
| ISIS 560131 | 10 | 17 | 51 | 78 |
| ISIS 569236 | 0 | 11 | 61 | 67 |
| ISIS 549148 | 3 | 0 | 22 | 28 |
| MDV-3100 | 9 | 0 | 44 | 78 |

Effect on Proliferation in CSS Medium and CSS+DHT Media

After a treatment period of 5 days in complete medium or CSS+1 nM DHT medium, the proliferative capacity of the cancer cells was measured with using CellTiter 96® AQueous One Solution or CellTiter-Glo® Cell Proliferation kit (Promega), following the manufacturer's instructions. Results are presented in Tables 94 and 95 as percent inhibition of proliferation, relative to non-treated cells. Treatment of the cells with ISIS 560131, ISIS 569236, and MDV-3100 reduced proliferation of the cells in a dose dependent manner compared to the control. The proliferative capacity of cells cultured in CSS medium without DHT is 17% of untreated control levels.

TABLE 94

Proliferation (% untreated control) in C4-2 cells cultured in complete medium

|  | 0.04 µM | 0.2 µM | 1 µM | 5.0 µM |
| --- | --- | --- | --- | --- |
| ISIS 560131 | 104 | 82 | 70 | 51 |
| ISIS 569236 | 103 | 81 | 57 | 58 |
| ISIS 549148 | 106 | 112 | 91 | 94 |
| MDV-3100 | 105 | 108 | 71 | 67 |

TABLE 95

Proliferation (% untreated control) in C4-2 cells cultured in CSS + DHT medium

|  | 0.04 µM | 0.2 µM | 1 µM | 5.0 µM |
| --- | --- | --- | --- | --- |
| ISIS 560131 | 106 | 94 | 47 | 31 |
| ISIS 569236 | 99 | 99 | 88 | 51 |
| ISIS 549148 | 102 | 82 | 82 | 91 |
| MDV-3100 | 122 | 124 | 87 | 22 |

Example 30

Antisense Inhibition of AR mRNA in C4-2B Cells Cultured in Complete Media and CSS Media The effect of antisense inhibition of AR mRNA levels in C4-2B cells cultured in complete medium, as well as CSS medium with DHT, was investigated.

Gene Expression in Complete Medium

Cells were plated at 1,000 cells per well. ISIS 560131 or ISIS 569236 was added individually at 0.04 µM, 0.2 µM, 1.0 µM, or 5.0 µM. ISIS 549148 was included as a negative control. MDV3100 was added at 0.04 µM, 0.2 µM, 1.0 µM, or 5.0 µM in a separate set of cells. After an incubation period of 48 hrs, RNA levels of AR, PSA and TMPRSS2 were measured. The data is presented in Tables 96-98. Treatment with ISIS oligonucleotide inhibited AR expression, whereas treatment with MDV-3100 increased AR expression in the cells.

Protein analysis of full-length AR also demonstrated a dose-dependent decrease of expression, normalized to levels of the house-keeping gene, GAPDH.

TABLE 96

Percent expression of AR in C4-2B cells cultured in complete medium

|  | 0.04 µM | 0.2 µM | 1 µM | 5.0 µM |
| --- | --- | --- | --- | --- |
| ISIS 560131 | 34 | 15 | 14 | 14 |
| ISIS 569236 | 61 | 23 | 20 | 16 |
| ISIS 549148 | 101 | 91 | 88 | 87 |
| MDV-3100 | 108 | 121 | 157 | 182 |

TABLE 97

Percent inhibition of PSA expression in C4-2B cells cultured in complete medium

|  | 0.04 µM | 0.2 µM | 1 µM | 5.0 µM |
| --- | --- | --- | --- | --- |
| ISIS 560131 | 56 | 84 | 89 | 92 |
| ISIS 569236 | 30 | 72 | 81 | 89 |
| ISIS 549148 | 3 | 11 | 18 | 14 |
| MDV-3100 | 8 | 27 | 73 | 88 |

TABLE 98

Percent inhibition of TMPRSS2 expression in C4-2B cells cultured in complete medium

|  | 0.04 µM | 0.2 µM | 1 µM | 5.0 µM |
| --- | --- | --- | --- | --- |
| ISIS 560131 | 46 | 71 | 72 | 75 |
| ISIS 569236 | 33 | 59 | 69 | 73 |

TABLE 98-continued

Percent inhibition of TMPRSS2 expression in C4-2B cells cultured in complete medium

|  | 0.04 μM | 0.2 μM | 1 μM | 5.0 μM |
|---|---|---|---|---|
| ISIS 549148 | 0 | 2 | 4 | 0 |
| MDV-3100 | 3 | 24 | 55 | 71 |

Gene Expression in CSS+DHT Media

Cells were plated at 2,000 cells per well and cultured in CSS media with 1 nM DHT. ISIS 560131 or ISIS 569236 was added individually at 0.04 μM, 0.2 μM, 1.0 μM, or 5.0 μM to each cell set. ISIS 549148 was included as a negative control. MDV3100 was added at 0.04 μM, 0.2 μM, 1.0 μM, or 5.0 μM in a separate set of cells. After an incubation period of 48 hrs, RNA levels of AR, PSA and TMPRSS2 were measured. The data is presented in Tables 99-101. In the absence of DHT, AR expression in C4-2 cells was 188%, PSA expression was 43% and TMPRSS2 expression was 27% compared to the untreated control. Treatment with ISIS oligonucleotide inhibited AR expression, whereas treatment with MDV-3100 increased AR expression in the cells.

TABLE 99

Percent expression of AR in C4-2B cells cultured in CSS + DHT medium

|  | 0.04 μM | 0.2 μM | 1 μM | 5.0 μM |
|---|---|---|---|---|
| ISIS 560131 | 55 | 31 | 15 | 13 |
| ISIS 569236 | 67 | 49 | 24 | 19 |
| ISIS 549148 | 91 | 104 | 101 | 95 |
| MDV-3100 | 112 | 144 | 165 | 173 |

TABLE 100

Percent inhibition of PSA expression in C4-2B cells cultured in CSS + DHT medium

|  | 0.04 μM | 0.2 μM | 1 μM | 5.0 μM |
|---|---|---|---|---|
| ISIS 560131 | 0 | 17 | 50 | 61 |
| ISIS 569236 | 0 | 5 | 33 | 46 |
| ISIS 549148 | 0 | 0 | 0 | 0 |
| MDV-3100 | 0 | 0 | 37 | 45 |

TABLE 101

Percent inhibition of TMPRSS2 expression in C4-2B cells cultured in CSS + DHT medium

|  | 0.04 μM | 0.2 μM | 1 μM | 5.0 μM |
|---|---|---|---|---|
| ISIS 560131 | 0 | 34 | 60 | 76 |
| ISIS 569236 | 0 | 6 | 43 | 59 |
| ISIS 549148 | 0 | 0 | 0 | 3 |
| MDV-3100 | 0 | 11 | 48 | 66 |

Effect on Proliferation in CSS Medium and CSS+DHT Media

After a treatment period of 5 days in complete medium or CSS+1 nM DHT medium, the proliferative capacity of the cancer cells was measured with using CellTiter 96® AQueous One or CellTiter-Glo® Solution Cell Proliferation kit (Promega), following the manufacturer's instructions. Results are presented in Tables 102 and 103 as percent inhibition of proliferation, relative to non-treated cells. Treatment of the cells with ISIS 560131, ISIS 569236, and MDV-3100 reduced proliferation of the cells in a dose dependent compared to the control. Treatment with ISIS oligonucleotides in CSS+DHT medium reduced the proliferative capacity to a greater extent than treatment with MVD-3100. The proliferative capacity of cells cultured in CSS medium without DHT is 12% of untreated control levels.

TABLE 102

Proliferation (% untreated control) in C4-2B cells cultured in complete medium

|  | 0.04 μM | 0.2 μM | 1 μM | 5.0 μM |
|---|---|---|---|---|
| ISIS 560131 | 93 | 50 | 50 | 41 |
| ISIS 569236 | 98 | 64 | 55 | 48 |
| ISIS 549148 | 119 | 97 | 103 | 98 |
| MDV-3100 | 131 | 105 | 72 | 60 |

TABLE 103

Proliferation (% untreated control) in C4-2B cells cultured in CSS + DHT medium

|  | 0.04 μM | 0.2 μM | 1 μM | 5.0 μM |
|---|---|---|---|---|
| ISIS 560131 | 111 | 75 | 49 | 40 |
| ISIS 569236 | 109 | 109 | 67 | 39 |
| ISIS 549148 | 109 | 131 | 119 | 114 |
| MDV-3100 | 125 | 100 | 83 | 17 |

Example 31

Antisense Inhibition of AR mRNA in VCaP Cells Cultured in Complete Media and CSS Media The effect of antisense inhibition of AR in VCaP prostate cancer cells (Korenchuk, S. et al., In Vivo. 2001. 15: 163-168) cultured in complete medium, as well as CSS medium with DHT, was investigated. VCaP cells express both full length AR, as well as the V7 variant.

Gene Expression in Complete Medium

Cells were plated at 10,000 cells per well. ISIS 560131 or ISIS 569236 was added individually at 1.34 nM, 4 nM, 13.4 nM, or 40 nM using RNAiMax transfection reagent. ISIS 549148 was included as a negative control. After an incubation period of 48 hrs, RNA levels of full length AR, the V7 variant, PSA and TMPRSS2 were measured. The data is presented in Tables 104-107.

Protein analysis of full-length AR and the V7 variant also demonstrated a dose-dependent decrease of expression of both compared to levels of the house-keeping gene, GAPDH.

TABLE 104

Percent inhibition of full-length AR in VCaP cells cultured in complete medium

|  | 1.34 nM | 4.0 nM | 13.4 nM | 40 nM |
|---|---|---|---|---|
| ISIS 560131 | 0 | 59 | 77 | 84 |
| ISIS 569236 | 0 | 41 | 49 | 74 |
| ISIS 549148 | 0 | 8 | 5 | 17 |

TABLE 105

Percent inhibition of AR V7 variant in VCaP cells cultured in complete medium

|  | 1.34 nM | 4.0 nM | 13.4 nM | 40 nM |
| --- | --- | --- | --- | --- |
| ISIS 560131 | 0 | 57 | 78 | 84 |
| ISIS 569236 | 0 | 40 | 53 | 80 |
| ISIS 549148 | 0 | 8 | 0 | 14 |

TABLE 106

Percent inhibition of PSA expression in VCaP cells cultured in complete medium

|  | 1.34 nM | 4.0 nM | 13.4 nM | 40 nM |
| --- | --- | --- | --- | --- |
| ISIS 560131 | 2 | 24 | 35 | 46 |
| ISIS 569236 | 7 | 19 | 40 | 52 |
| ISIS 549148 | 2 | 0 | 0 | 20 |

TABLE 107

Percent inhibition of TMPRSS2 expression in VCaP cells cultured in complete medium

|  | 1.34 nM | 4.0 nM | 13.4 nM | 40 nM |
| --- | --- | --- | --- | --- |
| ISIS 560131 | 0 | 0 | 0 | 4 |
| ISIS 569236 | 0 | 0 | 0 | 36 |
| ISIS 549148 | 0 | 0 | 0 | 0 |

A separate set of cells was treated with MDV-3100 at 0.04 µM, 0.2 µM, 1.0 µM, or 5.0 µM. After an incubation period of 48 hrs, RNA levels of full length AR, the V7 variant, PSA and TMPRSS2 were measured. The data is presented in Tables 108 expressed as percent expression of gene levels compared to the untreated control.

TABLE 108

Percent of gene expression in VCaP cells treated with MDV-3100 and cultured in complete medium

|  | 0.04 µM | 0.2 µM | 1.0 µM | 5.0 µM |
| --- | --- | --- | --- | --- |
| Full length AR | 136 | 135 | 160 | 178 |
| AR V7 variant | 172 | 179 | 244 | 237 |
| PSA | 105 | 76 | 75 | 61 |
| TMPRSS2 | 131 | 121 | 135 | 141 |

Gene Expression in CSS+DHT Media

Cells were plated at 15,000 cells per well and cultured in CSS media for 16 hours. Cells were then transfected using RNAiMax reagent with ISIS 560131 or ISIS 569236 at 1.34 nM, 4 nM, 13.4 nM, or 40 nM to each cell set. ISIS 549148 was included as a negative control. After 4 hrs, 1 nM DHT was added. MDV3100 was added in a separate set of cells at doses of 0.04 µM, 0.2 µM, 1.0 µM, or 5.0 µM. After an incubation period of 48 hrs, RNA levels of AR, PSA and TMPRSS2 were measured. The data is presented in Tables 109-113. In the absence of DHT, AR expression in VCaP cells was 555%, V7 variant expression was 656%, PSA expression was 11%, and TMPRSS2 expression was 22% compared to the untreated control.

TABLE 109

Percent inhibition of full-length AR in VCaP cells cultured in CSS medium

|  | 1.34 nM | 4.0 nM | 13.4 nM | 40 nM |
| --- | --- | --- | --- | --- |
| ISIS 560131 | 12 | 16 | 37 | 38 |
| ISIS 569236 | 23 | 21 | 38 | 35 |
| ISIS 549148 | 0 | 0 | 0 | 0 |

TABLE 110

Percent inhibition of AR V7 variant in VCaP cells cultured in CSS + DHT medium

|  | 1.34 nM | 4.0 nM | 13.4 nM | 40 nM |
| --- | --- | --- | --- | --- |
| ISIS 560131 | 27 | 31 | 39 | 41 |
| ISIS 569236 | 37 | 33 | 48 | 39 |
| ISIS 549148 | 12 | 0 | 0 | 5 |

TABLE 111

Percent inhibition of PSA expression in VCaP cells cultured in CSS + DHT medium

|  | 1.34 nM | 4.0 nM | 13.4 nM | 40 nM |
| --- | --- | --- | --- | --- |
| ISIS 560131 | 0 | 35 | 69 | 73 |
| ISIS 569236 | 8 | 25 | 62 | 74 |
| ISIS 549148 | 0 | 3 | 9 | 0 |

TABLE 112

Percent inhibition of TMPRSS2 expression in VCaP cells cultured in CSS + DHT medium

|  | 1.34 nM | 4.0 nM | 13.4 nM | 40 nM |
| --- | --- | --- | --- | --- |
| ISIS 560131 | 0 | 21 | 49 | 57 |
| ISIS 569236 | 6 | 19 | 40 | 54 |
| ISIS 549148 | 0 | 0 | 0 | 0 |

TABLE 113

Percent of gene expression in VCaP cells treated with MDV-3100 and cultured in CSS + DHT medium

|  | 0.04 µM | 0.2 µM | 1.0 µM | 5.0 µM |
| --- | --- | --- | --- | --- |
| Full length AR | 114 | 94 | 142 | 233 |
| AR V7 variant | 82 | 65 | 101 | 181 |
| PSA | 90 | 72 | 57 | 30 |
| TMPRSS2 | 115 | 96 | 70 | 42 |

Effect on Proliferation

After a treatment period of 5 days in complete medium or CSS+1 nM DHT medium, the proliferative capacity of the cancer cells was measured with using CellTiter 96® AQueous One or CellTiter-Glo® Solution Cell Proliferation kit (Promega), following the manufacturer's instructions. Results are presented in Tables 114-116 as percent inhibition of proliferation, relative to non-treated cells. Treatment of the cells with ISIS 560131, ISIS 569236, and MDV-3100 reduced proliferation of the cells in a dose dependent compared to the control. Treatment with ISIS oligonucleotides in CSS+DHT medium reduced the proliferative capacity to a greater extent than treatment with MVD-3100.

The proliferative capacity of cells cultured in CSS medium without DHT is 12% of untreated control levels.

TABLE 114

Proliferation (% untreated control) in VCaP cells cultured in complete medium

|  | 1.34 nM | 4.0 nM | 13.4 nM | 40 nM |
|---|---|---|---|---|
| ISIS 560131 | 98 | 66 | 53 | 48 |
| ISIS 569236 | 98 | 76 | 68 | 59 |
| ISIS 549148 | 98 | 98 | 113 | 106 |

TABLE 115

Proliferation (% untreated control) in VCaP cells cultured in CSS + DHT medium

|  | 1.34 nM | 4.0 nM | 13.4 nM | 40 nM |
|---|---|---|---|---|
| ISIS 560131 | 95 | 65 | 42 | 37 |
| ISIS 569236 | 83 | 68 | 61 | 45 |
| ISIS 549148 | 114 | 123 | 104 | 92 |

TABLE 116

Proliferation (% untreated control) in VCaP cells treated with MDV-3100

|  | Complete medium | CSS + DHT medium |
|---|---|---|
| 0.04 μM | 49 | 117 |
| 0.2 μM | 44 | 119 |
| 1.0 μM | 27 | 71 |
| 5.0 μM | 17 | 65 |

Effect on Apoptosis

After a treatment period of 72 hours in complete medium, apoptosis of the cancer cells was measured with Caspase-Glo 3/7 assay (Promega). Results are presented in Tables 117 and 118 as percent apoptosis of the cells, relative to non-treated cells. Treatment of the cells with ISIS 560131, ISIS 569236, and MDV-3100 increased apoptosis of the cells in a dose dependent compared to the control.

Apoptosis was also measured by protein western blot analysis of cleaved PARP levels, which were shown to be increased in a dose-dependent manner in cells treated with ISIS 560131, ISIS 569236, and MDV-3100.

TABLE 117

Apoptosis (% untreated control) in VCaP cells cultured in complete medium

|  | 1.34 nM | 4.0 nM | 13.4 nM | 40 nM |
|---|---|---|---|---|
| ISIS 560131 | 189 | 253 | 356 | 262 |
| ISIS 569236 | 176 | 293 | 402 | 581 |
| ISIS 549148 | 131 | 108 | 103 | 146 |

TABLE 118

Apoptosis (% untreated control) in VCaP cells treated with MDV-3100

| | % |
|---|---|
| 0.04 μM | 186 |
| 0.2 μM | 210 |
| 1.0 μM | 612 |
| 5.0 nM | 528 |

Example 32

Antisense Inhibition of AR mRNA in 22RV1 Cells Cultured in Complete Media and CSS Media The effect of antisense inhibition of AR in 22RV1 cells cultured in complete medium, as well as CSS medium with DHT, was investigated.

Gene Expression in Complete Medium

Cells were plated at 1,000 cells per well. ISIS 560131 or ISIS 569236 was added individually at 1.34 nM, 4 nM, 13.4 nM, or 40 nM using RNAiMax transfection reagent. ISIS 549148 was included as a negative control. After an incubation period of 48 hrs, RNA levels of full length AR, the V7 variant, PSA and TMPRSS2 were measured. The data is presented in Tables 119-122.

Protein analysis of full-length AR and the V7 variant also demonstrated a dose-dependent decrease of expression compared to levels of the house-keeping gene, GAPDH.

TABLE 119

Percent inhibition of full-length AR in 22RV1 cells cultured in complete medium

|  | 1.34 nM | 4.0 nM | 13.4 nM | 40 nM |
|---|---|---|---|---|
| ISIS 560131 | 7 | 19 | 49 | 76 |
| ISIS 569236 | 17 | 15 | 37 | 71 |
| ISIS 549148 | 6 | 0 | 11 | 17 |

TABLE 120

Percent inhibition of AR V7 variant in 22RV1 cells cultured in complete medium

|  | 1.34 nM | 4.0 nM | 13.4 nM | 40 nM |
|---|---|---|---|---|
| ISIS 560131 | 12 | 29 | 57 | 81 |
| ISIS 569236 | 30 | 2 | 46 | 81 |
| ISIS 549148 | 0 | 0 | 22 | 26 |

TABLE 121

Percent inhibition of PSA expression in 22RV1 cells cultured in complete medium

|  | 1.34 nM | 4.0 nM | 13.4 nM | 40 nM |
|---|---|---|---|---|
| ISIS 560131 | 10 | 20 | 27 | 36 |
| ISIS 569236 | 0 | 17 | 25 | 7 |
| ISIS 549148 | 9 | 11 | 17 | 27 |

TABLE 122

Percent inhibition of TMPRSS2 expression in 22RV1 cells cultured in complete medium

|  | 1.34 nM | 4.0 nM | 13.4 nM | 40 nM |
|---|---|---|---|---|
| ISIS 560131 | 7 | 3 | 19 | 32 |
| ISIS 569236 | 0 | 13 | 21 | 36 |
| ISIS 549148 | 15 | 9 | 14 | 4 |

A separate set of cells was treated with MDV-3100 at 0.04 µM, 0.2 µM, 1.0 µM, or 5.0 µM. After an incubation period of 48 hrs, RNA levels of full length AR, the V7 variant, PSA and TMPRSS2 were measured. The data is presented in Tables 123 expressed as percent expression of gene levels compared to the untreated control.

TABLE 123

Percent of gene expression in 22RV1 cells treated with MDV-3100 and cultured in complete medium

|  | 0.04 µM | 0.2 µM | 1.0 µM | 5.0 µM |
|---|---|---|---|---|
| Full length AR | 103 | 93 | 81 | 83 |
| AR V7 variant | 106 | 98 | 87 | 77 |
| PSA | 83 | 70 | 71 | 86 |
| TMPRSS2 | 101 | 80 | 82 | 93 |

Gene Expression in CSS+DHT Media

Cells were plated at 2,000 cells per well and cultured in CSS media for 16 hours. Cells were then transfected using RNAiMax reagent with ISIS 560131 or ISIS 569236 at 1.34 nM, 4 nM, or 13.4 nM to each cell set. ISIS 549148 was included as a negative control. After 4 hrs, 1 nM DHT was added. MDV3100 was added in a separate set of cells at doses of 0.04 µM, 0.2 µM, 1.0 µM, or 5.0 µM. After an incubation period of 48 hrs, RNA levels of AR, AR V7 variant, PSA and TMPRSS2 were measured. The data is presented in Tables 124-128. In the absence of DHT, AR expression in VCaP cells was 555%, V7 variant expression was 656%, PSA expression was 11%, and TMPRSS2 expression was 22% compared to the untreated control.

Treatment with ISIS oligonucleotides resulted in significant inhibition of full length AR and the V7 variant, as well as downstream gene expression. Treatment with ISIS oligonucleotides resulted in inhibition of gene expression to a greater extent than treatment with MVD-3100.

TABLE 124

Percent inhibition of full-length AR in 22RV1 cells cultured in CSS + DHT medium

|  | 1.34 nM | 4.0 nM | 13.4 nM |
|---|---|---|---|
| ISIS 560131 | 65 | 85 | 93 |
| ISIS 569236 | 59 | 89 | 97 |
| ISIS 549148 | 2 | 13 | 22 |

TABLE 125

Percent inhibition of AR V7 variant in 22RV1 cells cultured in CSS + DHT medium

|  | 1.34 nM | 4.0 nM | 13.4 nM |
|---|---|---|---|
| ISIS 560131 | 63 | 83 | 93 |
| ISIS 569236 | 54 | 88 | 97 |
| ISIS 549148 | 19 | 19 | 32 |

TABLE 126

Percent inhibition of PSA expression in 22RV1 cells cultured in CSS + DHT medium

|  | 1.34 nM | 4.0 nM | 13.4 nM |
|---|---|---|---|
| ISIS 560131 | 3 | 50 | 66 |
| ISIS 569236 | 28 | 49 | 70 |
| ISIS 549148 | 8 | 23 | 29 |

TABLE 127

Percent inhibition of TMPRSS2 expression in 22RV1 cells cultured in CSS + DHT medium

|  | 1.34 nM | 4.0 nM | 13.4 nM |
|---|---|---|---|
| ISIS 560131 | 39 | 50 | 59 |
| ISIS 569236 | 27 | 50 | 75 |
| ISIS 549148 | 0 | 3 | 1 |

TABLE 128

Percent of gene expression in 22RV1 cells treated with MDV-3100 and cultured in CSS + DHT medium

|  | 0.04 µM | 0.2 µM | 1.0 µM | 5.0 µM |
|---|---|---|---|---|
| Full length AR | 5 | 11 | 6 | 18 |
| AR V7 variant | 16 | 17 | 19 | 12 |
| PSA | 15 | 19 | 18 | 16 |
| TMPRSS2 | 17 | 9 | 26 | 18 |

Effect on Proliferation

After a treatment period of 5 days in complete medium, the proliferative capacity of the cancer cells was measured with using CellTiter 96® AQueous One or CellTiter-Glo® Solution Cell Proliferation kit (Promega), following the manufacturer's instructions. Results are presented in Tables 129 and 130 as percent inhibition of proliferation, relative to non-treated cells. Treatment of the cells with ISIS 560131, ISIS 569236, and MDV-3100 reduced proliferation of the cells in a dose dependent compared to the control. Treatment with ISIS oligonucleotides in CSS+DHT medium reduced the proliferative capacity to a greater extent than treatment with MVD-3100. The proliferative capacity of cells cultured in CSS medium without DHT is 12% of untreated control levels.

TABLE 129

Proliferation (% untreated control) in 22RV1 cells cultured in complete medium

|  | 1.34 nM | 4.0 nM | 13.4 nM | 40 nM |
|---|---|---|---|---|
| ISIS 560131 | 94 | 72 | 50 | 17 |
| ISIS 569236 | 92 | 53 | 20 | 7 |
| ISIS 549148 | 97 | 97 | 101 | 83 |

TABLE 130

Proliferation (% untreated control) in
22RV1 cells treated with MDV-3100

| | % |
|---|---|
| 0.04 μM | 87 |
| 0.2 μM | 83 |
| 1.0 μM | 81 |
| 5.0 μM | 74 |

Effect on Apoptosis

After a treatment period of 72 hours in complete medium or CSS+DHT medium, apoptosis of the cancer cells was measured with Caspase-glo 3/7 assay kit (Promega). Results are presented in Tables 131 and 132 as percent apoptosis of the cells, relative to non-treated cells. Treatment of the cells with ISIS 560131 and ISIS 569236 increased apoptosis of the cells in a dose dependent compared to the control.

TABLE 131

Apoptosis (% untreated control) in 22RV1
cells cultured in complete medium

| | 1.34 nM | 4.0 nM | 13.4 nM | 40 nM |
|---|---|---|---|---|
| ISIS 560131 | 99 | 127 | 131 | 566 |
| ISIS 569236 | 91 | 141 | 333 | 1452 |
| ISIS 549148 | 81 | 76 | 72 | 123 |

TABLE 132

Apoptosis (% untreated control) in 22RV1
cells cultured in CSS + DHT medium

| | 1.34 nM | 4.0 nM | 13.4 nM | 40 nM |
|---|---|---|---|---|
| ISIS 560131 | 121 | 113 | 172 | 518 |
| ISIS 569236 | 127 | 106 | 257 | 1136 |
| ISIS 549148 | 113 | 94 | 102 | 108 |

Example 33

Effect of ISIS Antisense Oligonucleotides Targeting Human Androgen Receptor in Cynomolgus Monkeys Cynomolgus monkeys were treated with ISIS antisense oligonucleotides selected from studies described above. Antisense oligonucleotide efficacy and tolerability were evaluated. The human antisense oligonucleotides tested are cross-reactive with the rhesus genomic sequence (GENBANK Accession No. NW_001218131.1 truncated from nucleotides 134001 to 308000 and designated herein as SEQ ID NO: 189). The target start site and target region of each oligonucleotide to SEQ ID NO: 189, as well as the details of their chemistry and sequence, is presented in Table 133.

TABLE 133

Antisense oligonucleotides complementary to SEQ ID NO: 189

| ISIS No | Target Start Site | Target Region | Sequence | Chemistry | SEQ ID NO |
|---|---|---|---|---|---|
| 560131 | 59450 | Intron | TTGATTTAATGGTTGC | Deoxy, MOE, and (S)-cEt | 35 |
| 569213 | 59449 | Intron | TGATTTAATGGTTGCA | Deoxy, MOE, and (S)-cEt | 39 |
| | 59479 | | TGATTTAATGGTTGCA | | 39 |
| 569216 | 59449 | Intron | TGATTTAATGGTTGCA | Deoxy, MOE, and (S)-cEt | 39 |
| | 59479 | | TGATTTAATGGTTGCA | | 39 |
| 569221 | 59449 | Intron | TGATTTAATGGTTGCA | Deoxy, MOE, and (S)-cEt | 39 |
| | 59479 | | TGATTTAATGGTTGCA | | 39 |
| 569236 | 59449 | Intron | TGATTTAATGGTTGCA | Deoxy, MOE, and (S)-cEt | 39 |
| | 59479 | | TGATTTAATGGTTGCA | | 39 |
| 579671 | 59450 | Intron | TTGATTTAATGGTTGC | Deoxy, MOE, and (S)-cEt | 35 |
| 586124 | 59448 | Intron | GATTTAATGGTTGCAA | 3-10-3 (S)-cEt | 43 |
| 583918 | 3754 | Exon | AGTCGCGACTCTGGTA | 3-10-3 (S)-cEt | 124 |
| 584149 | 7260 | Intron | GTCAATATCAAAGCAC | 3-10-3 (S)-cEt | 150 |
| 584163 | 9811 | Intron | GAACATTATTAGGCTA | 3-10-3 (S)-cEt | 155 |
| 584269 | 41322 | Intron | CCTTATGGATGCTGCT | 3-10-3 (S)-cEt | 169 |
| 584468 | 109552 | Intron | CATTGTACTATGCCAG | 3-10-3 (S)-cEt | 175 |

Treatment

Prior to the study, the monkeys were kept in quarantine for a 30-day period, during which the animals were observed daily for general health. The monkeys were 2-4 years old and weighed between 2 and 4 kg. Thirteen groups of four randomly assigned male cynomolgus monkeys each were injected subcutaneously with ISIS oligonucleotide or PBS. PBS solution or ISIS oligonucleotides, at a dose of 40 mg/kg, were administered with a loading regimen consisting of four doses on the first week of the study (days 1, 3, 5, and 7), followed by a maintenance regimen consisting of once weekly administration starting on Day 14 (weeks 2 to 6). Subcutaneous injections were performed in clock-wise rotations at 4 sites on the back; one site per dose. The injection sites were delineated by tattoo, while sedated using ketamine, and were separated by a minimum of 3 cm.

During the study period, the monkeys were observed a minimum of once daily for signs of illness or distress. The protocols described in the Example were approved by the Institutional Animal Care and Use Committee (IACUC).

Target Reduction
RNA Analysis

RNA was extracted from liver, heart, skeletal muscle, kidney, and prostate tissues for real-time PCR analysis of AR using primer probe set RTS3559. The results were normalized to RIBOGREEN®. Results are presented as percent inhibition of AR mRNA, relative to PBS control. As shown in Table 134, treatment with ISIS antisense oligonucleotides resulted in significant reduction of AR mRNA, relative to the PBS control. 'n/a' indicates that mRNA levels were not measured in that organ.

TABLE 134

Percent Inhibition of AR mRNA in the cynomolgus monkey relative to the PBS control

| ISIS No | Heart | Skeletal Muscle | Kidney | Liver | Prostate |
|---|---|---|---|---|---|
| 560131 | 32 | 30 | 19 | 65 | 27 |
| 569221 | 52 | 35 | 31 | 60 | n/a |
| 569236 | 42 | 47 | 42 | 33 | 32 |
| 579671 | 24 | 31 | 53 | 33 | n/a |
| 583918 | 76 | 74 | 73 | 88 | 58 |
| 584149 | 33 | 63 | 77 | 93 | 45 |
| 584163 | 53 | 73 | 90 | 98 | 58 |
| 584269 | 72 | 76 | 92 | 96 | 41 |
| 584468 | 33 | 53 | 88 | 97 | 50 |

Protein Analysis

Serum testosterone protein levels were measured in the plasma with an ELISA kit (Enzo Life Sciences), following the manufacturer's instructions. The results are presented in Table 135, expressed in ng/mL. The results indicate that some of the ISIS oligonucleotides reduced testosterone protein levels.

TABLE 135

Testosterone protein levels in the cynomolgus monkey

| | ng/mL |
|---|---|
| PBS | 12.6 |
| ISIS 560131 | 14.7 |
| ISIS 569221 | 8.8 |
| ISIS 569236 | 12.7 |
| ISIS 579671 | 7.3 |

TABLE 135-continued

Testosterone protein levels in the cynomolgus monkey

| | ng/mL |
|---|---|
| ISIS 584269 | 14.1 |
| ISIS 584468 | 13.6 |

Tolerability Studies
Body and Organ Weight Measurements

To evaluate the effect of ISIS oligonucleotides on the overall health of the animals, body and organ weights were measured. Body weights were measured on day 42 and are presented in Table 136. Organ weights were measured at the time of euthanasia and the data is also presented in Table 136. Specifically, treatment with ISIS 560131 was well tolerated in terms of the body and organ weights of the monkeys.

TABLE 136

Final body and organ weights in cynomolgus monkeys

| Treatment | Body Wt (kg) | Spleen (g) | Heart (g) | Kidney (g) | Mesenteric lymph nodes (g) | Liver (g) |
|---|---|---|---|---|---|---|
| PBS | 2.5 | 2.6 | 8.5 | 13 | 1.4 | 58 |
| ISIS 560131 | 2.4 | 2.5 | 9.8 | 12 | 2.0 | 58 |
| ISIS 569213 | 2.4 | 5.3 | 8.3 | 16 | 2.4 | 69 |
| ISIS 569216 | 2.6 | 4.9 | 9.3 | 15 | 2.7 | 71 |
| ISIS 569221 | 2.5 | 3.3 | 8.5 | 14 | 3.5 | 68 |
| ISIS 569236 | 2.4 | 3.2 | 8.4 | 12 | 2.4 | 56 |
| ISIS 579671 | 2.4 | 3.2 | 8.8 | 14 | 2.5 | 62 |
| ISIS 586124 | 2.5 | 3.3 | 9.4 | 14 | 2.8 | 58 |
| ISIS 583918 | 2.5 | 4.6 | 8.9 | 12 | 3.5 | 60 |
| ISIS 584149 | 2.5 | 2.2 | 9.3 | 13 | 2.1 | 60 |
| ISIS 584163 | 2.5 | 3.2 | 8.4 | 15 | 3.3 | 54 |
| ISIS 584269 | 2.5 | 4.7 | 8.7 | 13 | 3.6 | 60 |
| ISIS 584468 | 2.5 | 4.1 | 8.3 | 13 | 3.8 | 60 |

Liver Function

To evaluate the effect of ISIS oligonucleotides on hepatic function, the monkeys were fasted overnight. Approximately, 1.5 mL of blood samples were collected on day 44 from all the study groups. Blood was collected in tubes without anticoagulant for serum separation. The tubes were kept at room temperature for a minimum of 90 min and then centrifuged at 3,000 rpm for 10 min. Levels of various liver function markers were measured using a Toshiba 120FR NEO chemistry analyzer (Toshiba Co., Japan). The results are presented in Table 137. Specifically, treatment with ISIS 560131 was well tolerated in terms of the liver function markers.

TABLE 137

Liver function markers in cynomolgus monkey plasma

| Treatment | Albumin (g/dL) | AST (IU/L) | ALT (IU/L) |
|---|---|---|---|
| PBS | 4.2 | 37 | 39 |
| ISIS 560131 | 4.0 | 87 | 68 |
| ISIS 569213 | 3.7 | 80 | 47 |
| ISIS 569216 | 3.7 | 93 | 75 |
| ISIS 569221 | 4.0 | 73 | 48 |
| ISIS 569236 | 4.1 | 45 | 35 |
| ISIS 579671 | 4.0 | 53 | 56 |
| ISIS 586124 | 3.9 | 94 | 56 |
| ISIS 583918 | 4.1 | 73 | 75 |
| ISIS 584149 | 4.5 | 58 | 57 |

TABLE 137-continued

Liver function markers in cynomolgus monkey plasma

| Treatment | Albumin (g/dL) | AST (IU/L) | ALT (IU/L) |
|---|---|---|---|
| ISIS 584163 | 4.2 | 68 | 50 |
| ISIS 584269 | 4.0 | 81 | 75 |
| ISIS 584468 | 4.0 | 52 | 46 |

Hematology

To evaluate any effect of ISIS oligonucleotides in cynomolgus monkeys on hematologic parameters, blood samples of approximately 0.5 mL of blood was collected day 44 from each of the available study animals in tubes containing $K_2$-EDTA. Samples were analyzed for red blood cell (RBC) count, white blood cells (WBC) count, platelet count, hemoglobin content and hematocrit, using an ADVIA2120i hematology analyzer (SIEMENS, USA). The data is presented in Table 138.

The data indicate treatment with most of the oligonucleotides did not cause any changes in hematologic parameters outside the expected range for antisense oligonucleotides at this dose. Specifically, treatment with ISIS 560131 was well tolerated in terms of the hematology of the monkeys.

TABLE 138

Hematological parameters in cynomolgus monkeys

| Treatment | RBC (×10$^6$ μL) | Platelets (×10$^3$ μL) | WBC (×10$^3$ μL) | Hemoglobin (g/dL) | HCT (%) |
|---|---|---|---|---|---|
| PBS | 5.3 | 426 | 13.6 | 13.2 | 43 |
| ISIS 560131 | 5.8 | 392 | 11.3 | 13.1 | 44 |
| ISIS 569213 | 5.6 | 426 | 12.9 | 12.5 | 42 |
| ISIS 569216 | 5.6 | 504 | 12.2 | 12.8 | 43 |
| ISIS 569221 | 5.6 | 406 | 11.1 | 12.9 | 45 |
| ISIS 569236 | 5.7 | 358 | 14.4 | 13.1 | 44 |
| ISIS 579671 | 5.4 | 438 | 10.0 | 12.5 | 42 |
| ISIS 586124 | 5.8 | 391 | 10.4 | 13.6 | 45 |
| ISIS 583918 | 5.8 | 435 | 12.7 | 13.3 | 46 |
| ISIS 584149 | 5.7 | 478 | 11.3 | 13.7 | 45 |
| ISIS 584163 | 5.5 | 461 | 9.1 | 12.8 | 44 |
| ISIS 584269 | 5.2 | 522 | 9.8 | 12.4 | 41 |
| ISIS 584468 | 5.9 | 408 | 11.1 | 13.5 | 45 |

Kidney Function

To evaluate the effect of ISIS oligonucleotides on kidney function, the monkeys were fasted overnight. Approximately, 1.5 mL of blood samples were collected from all the study groups on day 44. Blood was collected in tubes without anticoagulant for serum separation. The tubes were kept at room temperature for a minimum of 90 min and then centrifuged at 3,000 rpm for 10 min. Levels of BUN and creatinine were measured using a Toshiba 120FR NEO chemistry analyzer (Toshiba Co., Japan). Results are presented in Table 139, expressed in mg/dL. The plasma chemistry data indicate that most of the ISIS oligonucleotides did not have any effect on the kidney function outside the expected range for antisense oligonucleotides. Specifically, treatment with ISIS 560131 was well tolerated in terms of the kidney function of the monkeys.

Kidney function was also assessed by urinalysis. Fresh urine from all animals was collected on day 44 using a clean cage pan on wet ice. Food was removed overnight the day before fresh urine collection was done but water was supplied. The total protein and creatinine levels were measured using a Toshiba 120FR NEO automated chemistry analyzer (Toshiba Co., Japan) and the protein to creatinine ratio was calculated. The results are presented in Table 140.

TABLE 139

Plasma BUN and creatinine levels (mg/dL) in cynomolgus monkeys

| Treatment | BUN | Creatinine |
|---|---|---|
| PBS | 30.5 | 0.78 |
| ISIS 560131 | 23.7 | 0.84 |
| ISIS 569213 | 29.4 | 0.91 |
| ISIS 569216 | 28.4 | 0.81 |
| ISIS 569221 | 20.2 | 0.86 |
| ISIS 569236 | 24.9 | 0.87 |
| ISIS 579671 | 22.7 | 0.74 |
| ISIS 586124 | 23.8 | 0.87 |
| ISIS 583918 | 24.5 | 0.87 |
| ISIS 584149 | 26.4 | 0.85 |
| ISIS 584163 | 22.4 | 0.82 |
| ISIS 584269 | 21.8 | 0.89 |
| ISIS 584468 | 22.2 | 0.78 |

TABLE 140

Urine protein/creatinine ratio in cynomolgus monkeys

| Treatment | Ratio |
|---|---|
| PBS | 0.00 |
| ISIS 560131 | 0.02 |
| ISIS 569213 | 0.02 |
| ISIS 569216 | 0.08 |
| ISIS 569221 | 0.00 |
| ISIS 569236 | 0.02 |
| ISIS 579671 | 0.00 |
| ISIS 586124 | 0.01 |
| ISIS 583918 | 0.01 |
| ISIS 584149 | 0.01 |
| ISIS 584163 | 0.01 |
| ISIS 584269 | 0.00 |
| ISIS 584468 | 0.00 |

C-Reactive Protein Level Analysis

To evaluate any inflammatory effect of ISIS oligonucleotides in cynomolgus monkeys, the monkeys were fasted overnight. Approximately, 1.5 mL of blood samples were collected from all the study groups on day 44. Blood was collected in tubes without anticoagulant for serum separation. The tubes were kept at room temperature for a minimum of 90 min and then centrifuged at 3,000 rpm for 10 min. C-reactive protein (CRP), which is synthesized in the liver and which serves as a marker of inflammation, was measured on day 43 using a Toshiba 120FR NEO chemistry analyzer (Toshiba Co., Japan). Complement C3 was also measured similarly, and the data is presented as a percentage of baseline values. The results are presented in Table 141 and indicate that treatment with most of the ISIS oligonucleotides did not cause any inflammation in monkeys.

TABLE 141

C-reactive protein and C3 levels in cynomolgus monkey plasma

| Treatment | CRP (mg/dL) | C3 (% of baseline) |
|---|---|---|
| PBS | 2.5 | 118 |
| ISIS 560131 | 1.7 | 100 |
| ISIS 569213 | 2.8 | 60 |
| ISIS 569216 | 3.6 | 94 |

TABLE 141-continued

C-reactive protein and C3 levels
in cynomolgus monkey plasma

| Treatment | CRP (mg/dL) | C3 (% of baseline) |
|---|---|---|
| ISIS 569221 | 4.9 | 91 |
| ISIS 569236 | 2.6 | 103 |
| ISIS 579671 | 4.5 | 101 |
| ISIS 586124 | 4.0 | 93 |
| ISIS 583918 | 3.5 | 89 |
| ISIS 584149 | 1.7 | 110 |
| ISIS 584163 | 1.0 | 102 |
| ISIS 584269 | 4.9 | 102 |
| ISIS 584468 | 1.3 | 111 |

Pharmacokinetics Studies

The concentrations of the full-length oligonucleotide in the kidney and the liver of select treatment groups were measured. The method used is a modification of previously published methods (Leeds et al., 1996; Geary et al., 1999) which consist of a phenol-chloroform (liquid-liquid) extraction followed by a solid phase extraction. An internal standard (ISIS 355868, a 27-mer 2'-O-methoxyethyl modified phosphorothioate oligonucleotide, GCGTTTGCTCT-TCTTCTTGCGTTTTT, designated herein as SEQ ID NO: 190) was added prior to extraction. Tissue sample concentrations were calculated using calibration curves, with a lower limit of quantitation (LLOQ) of approximately 1.14 µg/g.

The results are presented in Table 142, expressed as µg/g tissue. The kidney to liver ratio was also calculated and is presented in Table 142.

TABLE 142

Oligonucleotide concentration of in cynomolgous monkeys

| Treatment | Liver | Kidney | K/L ratio |
|---|---|---|---|
| ISIS 560131 | 793 | 2029 | 2.6 |
| ISIS 569221 | 966 | 1372 | 1.4 |
| ISIS 569236 | 898 | 1282 | 1.4 |
| ISIS 579671 | 871 | 2576 | 3.0 |
| ISIS 584269 | 698 | 2823 | 4.0 |
| ISIS 584468 | 474 | 2441 | 5.2 |

Example 34

Effect of Antisense Inhibition of Androgen Receptor (AR) on an Androgen Receptor-Dependent Breast Cancer Orthotopic Model MDA-MB-453 cells express AR in the absence of estrogen receptors and progesterone receptor (Hall, R. E. et al., Eur. J. Cancer 1994. 30: 484-490). The effect of inhibition of AR mRNA expression with antisense oligonucleotides was examined in MDA-MB-453 tumor-bearing mice.

Study 1

ISIS 569216 (TGATTTAATGGTTGCA; SEQ ID NO: 39), which is the antisense oligonucleotide tested in the assay, was designed as a deoxy, MOE and (S)cEt oligonucleotide, and is 16 nucleosides in length. The chemistry of the oligonucleotide is 5'-Te Gk Ak Tk Td Td Ad Ad Td Gd Gd Td Tk Gk Ck A, where 'e' denotes a 2'-O-methoxyethyl ribose; 'k' denotes an (S)-cEt; 'd' denotes a 2'-deoxyribose. The internucleoside linkages throughout the oligonucleotide are phosphorothioate (P=S) linkages. All cytosine residues throughout the oligonucleotide are 5-methylcytosines. ISIS 569216 has two target start sites, 58720 and 58750, on the human AR genomic sequence (GENBANK Accession No. NT_011669.17 truncated from nucleosides 5079000 to 5270000, SEQ ID NO: 1).

Treatment

MDA-MB-453 breast carcinoma cells ($5\times10^6$), mixed with 50% Matrigel, were injected into the mammary fat pad of 10 female NSG mice. Dihydrotestosterone (DHT) pellets, the active form of the major circulating androgen, testosterone, were implanted subcutaneously at the same time. Once the tumor reached a size of 100 $mm^3$, the mice were randomly divided into two treatment groups. The first treatment group was injected with ISIS 569216 administered by subcutaneous injection at a dose of 50 mg/kg five times a week for 4 weeks. The second treatment group was injected with vehicle only, administered by subcutaneous injection five times a week for 4 weeks, and served as the control group. Tumor growth was monitored once a week and mice were sacrificed on day 32 after treatment. Tumor tissue and TB-interface samples were collected and processed for further analysis.

RNA Analysis

Tumors were excised and the tissue was processed for RNA extraction and qPCR analyses. AR mRNA expression was assessed at the TB-interface and normalized to actin mRNA expression. AR mRNA expression in mice treated with ISIS 569216 was inhibited by 48% compared to the control group.

Measurement of Tumor Volume

Tumor volumes were measured on a regular basis throughout the study period, using Vernier calipers. As shown in Table 143, tumor volumes were significantly decreased in mice treated with ISIS 569216 compared to the control group.

TABLE 143

Tumor volume on different days in the
MDA_MB-453 cancer orthotopic model

| | Day 16 | Day 23 | Day 30 | Day 37 | Day 44 | Day 51 |
|---|---|---|---|---|---|---|
| ISIS 569216 | 134 | 142 | 173 | 125 | 92 | 73 |
| Control | 111 | 141 | 155 | 195 | 287 | 347 |

Study 2.

Treatment

MDA-MB-453 cells obtained from ATCC were maintained in Leibovitz's L-15 media with 10% FBS. Female NSG mice (Jackson Laboratories) were implanted in the mammary fat pad with $5\times10^6$ tumor cells in growth-factor-reduced matrigel (1:1). DHT pellets were also implanted at the same time in the mice between the shoulder blades.

After 20 days, the mice were then randomly divided into treatment groups. Groups of mice were injected with 50 mg/kg of ISIS 569236 or ISIS 560131 administered subcutaneously 5 days per week for 2 weeks. A group of mice were similarly treated with control oligonucleotide, ISIS 549148 (a 3-10-3 (S)-cEt gapmer with sequence GGCTAC- TACGCCGTCA, designated herein as SEQ ID NO: 193, with no known human sequence). Another control group of mice was similarly treated with PBS.

Measurement of Tumor Growth

Tumor volumes were measured on a regular basis throughout the study period, using Vernier calipers. As shown in Table 144, tumor volumes were decreased in mice treated with antisense oligonucleotides targeting AR compared to the control group.

TABLE 144

Tumor volumes in the MDA-MB-453 model

| | Day 0 | Day 8 | Day 13 | Day 20 | Day 23 | Day 27 | Day 29 |
|---|---|---|---|---|---|---|---|
| PBS | 136 | 336 | 331 | 358 | 338 | 417 | 481 |
| ISIS 549148 | 148 | 303 | 312 | 365 | 413 | 490 | 550 |

TABLE 144-continued

Tumor volumes in the MDA-MB-453 model

| | Day 0 | Day 8 | Day 13 | Day 20 | Day 23 | Day 27 | Day 29 |
|---|---|---|---|---|---|---|---|
| ISIS 560131 | 144 | 261 | 243 | 204 | 232 | 233 | 258 |
| ISIS 569236 | 134 | 283 | 260 | 230 | 264 | 329 | 323 |

RNA Analysis

RNA extraction was performed using an RNA extraction kit from Qiagen. AR RNA expression was measured using primer probe set LTS00943 and normalized to human actin mRNA expression.

Human AR RNA expression was assessed in tumor tissue. AR RNA expression in mice treated with ISIS 560131 was inhibited by 35% and AR expression in mice treated with ISIS 569236 was inhibited by 19% compared to the control group.

What is claimed:

1. A single-stranded modified oligonucleotide consisting of 12 to 30 linked nucleosides having a nucleobase sequence comprising an at least 12 contiguous nucleobase portion of SEQ ID NO: 12 or 175, wherein the modified oligonucleotide is at least 90% complementary to SEQ ID NO: 1 and comprises:
 a gap segment consisting of linked deoxynucleosides;
 a 5' wing segment consisting of linked nucleosides;
 a 3' wing segment consisting of linked nucleosides;
 wherein the gap segment is positioned between the 5' wing segment and the 3' wing segment and wherein each nucleoside of each wing segment comprises a modified sugar.

2. The single-stranded modified oligonucleotide of claim 1, wherein each internucleoside linkage is a phosphorothioate linkage.

3. The single-stranded modified oligonucleotide of claim 1, wherein the modified sugar comprises a 2'-O-methoxyethyl sugar.

4. The single-stranded modified oligonucleotide of claim 1, wherein the modified sugar comprises a bicyclic sugar.

5. The single-stranded modified oligonucleotide of claim 4, wherein the bicyclic sugar comprises a group selected from: 4'-CH(CH3)-O-2', 4'-CH2-O-2', and 4'-(CH2)2-O-2'.

6. The single-stranded modified oligonucleotide of claim 1, wherein each cytosine is a 5-methylcytosine.

7. The single-stranded modified oligonucleotide of claim 1, wherein the modified oligonucleotide is 100% complementary to SEQ ID NO: 1.

8. The single-stranded modified oligonucleotide of claim 1, wherein the modified oligonucleotide comprises:
 a gap segment consisting of linked deoxynucleosides;
 a 5' wing segment consisting of linked nucleosides;
 a 3' wing segment consisting of linked nucleosides;
 wherein the gap segment is positioned between the 5' wing segment and the 3' wing segment, each nucleoside of each wing segment comprises a modified sugar, wherein each internucleoside linkage is a phosphorothioate linkage, and wherein each cytosine is a 5-methylcytosine.

9. The single-stranded modified oligonucleotide of claim 8, wherein the modified sugar comprises a 2'-O-methoxyethyl sugar.

10. The single-stranded modified oligonucleotide of claim 8, wherein the modified sugar comprises a bicyclic sugar.

11. The single-stranded modified oligonucleotide of claim 10, wherein the bicyclic sugar comprises a group selected from: 4'-CH(CH3)-O-2', 4'-CH2-O-2', and 4'-(CH2)2-O-2'.

12. A single-stranded modified oligonucleotide consisting of 16 to 30 linked nucleosides having a nucleobase sequence comprising the nucleobase sequence of any one of SEQ ID NOs: 12, 13, 35, 39, 43, 124, 150, 155, 169, or 175, wherein the modified oligonucleotide comprises:
 a gap segment consisting of linked deoxynucleosides;
 a 5' wing segment consisting of linked nucleosides;
 a 3' wing segment consisting of linked nucleosides;
 wherein the gap segment is positioned between the 5' wing segment and the 3' wing segment and wherein each nucleoside of each wing segment comprises a modified sugar.

13. The single-stranded modified oligonucleotide of claim 12, wherein each internucleoside linkage is a phosphorothioate linkage.

14. The single-stranded modified oligonucleotide of claim 12, wherein the modified sugar comprises a 2'-O-methoxyethyl sugar.

15. The single-stranded modified oligonucleotide of claim 12, wherein the modified sugar comprises a bicyclic sugar.

16. The single-stranded modified oligonucleotide of claim 15, wherein the bicyclic sugar comprises a group selected from: 4'-CH(CH3)-O-2', 4'-CH2-O-2', and 4'-(CH2)2-O-2'.

17. The single-stranded modified oligonucleotide of claim 12, wherein each cytosine is a 5-methylcytosine.

18. The single-stranded modified oligonucleotide of claim 12, wherein the modified oligonucleotide is 100% complementary to SEQ ID NO: 1.

19. The single-stranded modified oligonucleotide of claim 12, wherein the modified oligonucleotide comprises:
 a gap segment consisting of linked deoxynucleosides;
 a 5' wing segment consisting of linked nucleosides;
 a 3' wing segment consisting of linked nucleosides;
 wherein the gap segment is positioned between the 5' wing segment and the 3' wing segment, each nucleoside of each wing segment comprises a modified sugar, wherein each internucleoside linkage is a phosphorothioate linkage, and wherein each cytosine is a 5-methylcytosine.

20. The single-stranded modified oligonucleotide of claim 12, wherein the modified oligonucleotide consists of 16 linked nucleosides having a nucleobase sequence consisting of the nucleobase sequence of any one of SEQ ID NOs: 12, 13, 35, 39, 43, 124, 150, 155, 169, or 175.

21. The single-stranded modified oligonucleotide of claim 20, wherein each internucleoside linkage is a phosphorothioate linkage.

22. The single-stranded modified oligonucleotide of claim 20, wherein the modified sugar comprises a 2'-O-methoxyethyl sugar.

23. The single-stranded modified oligonucleotide of claim 20, wherein the modified sugar comprises a bicyclic sugar.

24. The single-stranded modified oligonucleotide of claim 23, wherein the bicyclic sugar comprises a group selected from: 4'-CH(CH3)-O-2', 4'-CH2-O-2', and 4'-(CH2)2-O-2'.

25. The single-stranded modified oligonucleotide of claim 20, wherein each cytosine is a 5-methylcytosine.

26. The single-stranded modified oligonucleotide of claim 20, wherein the modified oligonucleotide has a nucleobase sequence consisting of the nucleobase sequence of any one of SEQ ID NOs: 43, 124, 150, 155, 169, or 175, and wherein the modified oligonucleotide comprises:
 a gap segment consisting of ten linked deoxynucleosides;
 a 5' wing segment consisting of 3 linked nucleosides; and
 a 3' wing segment consisting of 3 linked nucleosides;
wherein the gap segment is positioned between the 5' wing segment and the 3' wing segment; wherein each nucleoside of each wing segment comprises a constrained ethyl nucleoside; wherein each internucleoside linkage of the modified oligonucleotide is a phosphorothioate linkage; and wherein each cytosine of the modified oligonucleotide is a 5-methylcytosine.

27. A method of treating cancer in a subject comprising administering to the subject the compound of claim 26, thereby treating cancer in the subject.

28. The method of claim 27, wherein the cancer is prostate cancer, breast cancer, ovarian cancer, gastric cancer, or bladder cancer.

29. The method of claim 27, wherein the cancer is castrate-resistant prostate cancer.

30. The method of claim 29, wherein the castrate-resistant prostate cancer is resistant to an anti-androgenic agent selected from: MDV3100, ARN-059, ODM-201, abiraterone, TOK001, TAK700, and VT464.

* * * * *

SEQUENCE LISTING

```
<160> NUMBER OF SEQ ID NOS: 215

<210> SEQ ID NO 1
<211> LENGTH: 191001
<212> TYPE: DNA
<213> ORGANISM: Homo sapiens

<400> SEQUENCE: 1
ctgacagaaa gcagatcatt ggttgcctga ggaggaggag tataggagag gtggagggaa      60
aatgtacaaa gtggcacaat aaaaacttt ggaatcatag atatattcac tatcttgatt     120
gagtgatgat ttcatgagtg cacgcgtgtg tcaaaaatga tcaatttatg caactttaaa    180
tatgtgcagt ttattgtata tatcaattat acctcagtac ggctattaaa aagaaaccct    240
ctggctgcac aatgcagaac tgattctagg aaagagtgga gggaggatga ccatttacag    300
tgctccaggt ggaagagaac ggtgccttct ggaagtgaac taggttggca acaacagaga    360
tgaaataaat gggcagatgt gtgagatact taggaaataa aacccgatgg tcaccatttt    420
ccaaaggtca gctcatcctg gctttccaga gcaaagagct agggaagact ttattaataa    480
atccctcttg aagttgcaga ggaagcttat agcagaaact tactctcaac ctgactaatc    540
tgagagaaca cctctggttc catttgatta ctaaaaaact gcaaagaaca ggaggagaaa    600
gaagaagaaa gctggtacaa acagtgaact tatataatat taatcaataa ttgtctcttg    660
ttcttaaaag caatgggaag aaaatgagat ttgagctgga agatcagagt tcaaaatcca    720
aataaagtat atggccctaa tatgcttata gtagttaacc tttcctgata atgatataat    780
tgttgacagc accatcttta aaaataaaaa taacatagta atccttcaga tttgtagaat    840
gctttcctgt ttacaagttt gttctataca cattatgtct tttaaatgac acactagcct    900
tctgagggta acttatattg gcaacagttt tcagatgtgg aaactgtgaa gacaatgttg    960
gtgatgtgga agcaacataa actttggagt ctttcagacc caggtttgaa tgtcagactg   1020 cttttattc agagtaactt cagagcatta tttctcacct taattttttt tcaggcctct    1080
ttgtgtctat gtgtcctctt cactcctgtc cattgttcat tcagtgattt ttgcaccttc   1140
cttcactgtt agtgtgtaga cacatagttc tcctggctct gagacctatg ttaattccat   1200
tctaccatcc tgccagccca ctcaattcct attgagcaat gctagttgaa agttgtggtg   1260
ggattaaatg ttgcaatgag tattcaaatg aggttgaagt atctacgcat tctacttaca   1320
tatggtgagg tatattcaag gaaggctgta gccattaaaa tctcaggaaa taattttca    1380
```

```
cctcctcagg tgaaagggtc ttcaggcctt tgtgttctgg aaggttcatt tatagccatt    1440
tcccaaatga caatgcgatt gatgagtcta gagtctagct caaatagcaa tggactggaa    1500
gactagttta ggttttacta atgtggaaca tagaacaaat tatgtccttg tttcagcctg    1560
ttcatctgtg aaatagagcc tatcatatcc agtcttcctt gcctttaggt ttgagttacc    1620
ttctttggtc aaggtaagta aatgcctatg atgtttggct gtgcacaaga taaagctaca    1680
acaaagctac aacccatctt ttctctgtag aagactgcaa aaagcaaaag agacccaggc    1740
aaaaatctcg gaatgacttt tggaacagag agcctcccca gaatcagaag tcaaaggaat    1800
ttaaaacata gggaggccca gggtctctac tgacataaag gaaagatgtt ttccttatag    1860
gtttacgttt acattttctc tctctttcca ttcccacttg catctccacc tttacacagg    1920
gcttatggga cctcctccac aaaagagcag ttgcagtaac ccacatcatc ctctacgcct    1980
ggctgtccat caagaggcga aaagcagccc tatataggtt ctatccttgg atagttccag    2040
ttgtaaagtt taaaatatgc gaaggcaact tggaaaagca agcggctgca tacaaagcaa    2100
acgtttacag agctctggac aaaattgagc gcctatgtgt acatggcaag tgtttttagt    2160
gtttgtgtgt ttacctgctt gtctgggtga ttttgccttt gagagtctgg atgagaaatg    2220
catggttaaa ggcaattcca gacaggaaga aaggcagaga agagggtaga aatgacctct    2280
gattcttggg gctgagggtt cctagagcaa atggcacaat gccacgaggc ccgatctatc    2340
cctatgacgg aatctaaggt ttcagcaagt atctgctggc ttggtcatgg cttgctcctc    2400
agtttgtagg agactctccc actctcccat ctgcgcgctc ttatcagtcc tgaaaagaac    2460
ccctggcagc caggagcagg tattcctatc gtccttttcc tccctccctc gcctccaccc    2520
tgttggtttt ttagattggg ctttggaacc aaatttggtg agtgctggcc tccaggaaat    2580
ctggagccct ggcgcctaaa ccttggttta ggaaagcagg agctattcag gaagcagggg    2640
tcctccaggg ctagagctag cctctcctgc cctcgcccac gctgcgccag cacttgtttc    2700
tccaaagcca ctaggcaggc gttagcgcgc ggtgagggga ggggagaaaa ggaaagggga    2760
ggggagggaa aaggaggtgg gaaggcaagg aggccggccc ggtgggggcg ggacccgact    2820
cgcaaactgt tgcatttgct ctccacctcc cagcgccccc tccagatccc ggggagccca    2880
gcttgctggg agagcgggac ggtccggagc aagcccagag gcagaggagg cgacagaggg    2940
aaaaagggcc gagctagccg ctccagtgct gtacaggagc cgaagggacg caccacgcca    3000
gccccagccc ggctccagcg acagccaacg cctcttgcag cgcggcggct tcgaagccgc    3060
cgcccggagc tgcccttcc tcttcggtga agttttaaa agctgctaaa gactcggagg    3120
aagcaaggaa agtgcctggt aggactgacg gctgcctttg tcctcctcct ctccaccccg    3180 cctccccca cctgccttc cccccctccc ccgtcttctc tcccgcagct gcctcagtcg    3240
gctactctca gccaaccccc ctcaccaccc ttctccccac ccgcccccc gccccgtcg     3300 gcccagcgct gccagcccga gtttgcagag aggtaactcc ctttggctgc gagcgggcga    3360
gctagctgca cattgcaaag aaggctctta ggagccaggc gactggggag cggcttcagc    3420
actgcagcca cgaccgcct ggttaggctg cacgcggaga gaaccctctg ttttccccca     3480
ctctctctcc acctcctcct gccttcccca ccccgagtgc ggagccagag atcaaaagat    3540
gaaaaggcag tcaggtcttc agtagccaaa aacaaaaca aacaaaaaca aaaagccga     3600 aataaaagaa aaagataata actcagttct tatttgcacc tacttcagtg gacactgaat    3660
ttggaaggtg gaggattttg ttttttttctt ttaagatctg ggcatctttt gaatctaccc   3720
```

| | |
|---|---|
| ttcaagtatt aagagacaga ctgtgagcct agcagggcag atcttgtcca ccgtgtgtct | 3780 |
| tcttctgcac gagactttga ggctgtcaga gcgcttttg cgtggttgct cccgcaagtt | 3840 |
| tccttctctg gagcttcccg caggtgggca gctagctgca gcgactaccg catcatcaca | 3900 |
| gcctgttgaa ctcttctgag caagagaagg ggaggcgggg taagggaagt aggtggaaga | 3960 |
| ttcagccaag ctcaaggatg gaagtgcagt tagggctggg aagggtctac cctcggccgc | 4020 |
| cgtccaagac ctaccgagga gctttccaga atctgttcca gagcgtgcgc gaagtgatcc | 4080 |
| agaacccggg ccccaggcac ccagaggccg cgagcgcagc acctcccggc gccagtttgc | 4140 |
| tgctgctgca gcagcagcag cagcagcagc agcagcagca gcagcagcag cagcagcagc | 4200 |
| agcagcagca gcagcaagag actagcccca ggcagcagca gcagcagcag ggtgaggatg | 4260 |
| gttctcccca agcccatcgt agaggcccca caggctacct ggtcctggat gaggaacagc | 4320 |
| aaccttcaca gccgcagtcg gccctggagt gccaccccga gagaggttgc gtcccagagc | 4380 |
| ctggagccgc cgtggccgcc agcaaggggc tgccgcagca gctgccagca cctccggacg | 4440 |
| aggatgactc agctgcccca tccacgttgt ccctgctggg ccccactttc cccggcttaa | 4500 |
| gcagctgctc cgctgacctt aaagacatcc tgagcgaggc cagcaccatg caactccttc | 4560 |
| agcaacagca gcaggaagca gtatccgaag gcagcagcag cgggagagcg agggaggcct | 4620 |
| cgggggctcc cacttcctcc aaggacaatt acttaggggg cacttcgacc atttctgaca | 4680 |
| acgccaagga gttgtgtaag gcagtgtcgg tgtccatggg cctgggtgtg gaggcgttgg | 4740 |
| agcatctgag tccaggggaa cagcttcggg gggattgcat gtacgcccca cttttgggag | 4800 |
| ttccacccgc tgtgcgtccc actccttgtg ccccattggc cgaatgcaaa ggttctctgc | 4860 |
| tagacgacag cgcaggcaag agcactgaag atactgctga gtattcccct ttcaagggag | 4920 |
| gttacaccaa agggctagaa ggcgagagcc taggctgctc tggcagcgct gcagcaggga | 4980 |
| gctccgggac acttgaactg ccgtctaccc tgtctctcta caagtccgga gcactggacg | 5040 |
| aggcagctgc gtaccagagt cgcgactact acaactttcc actggctctg gccgaccgc | 5100 |
| cgcccccctcc gccgcctccc catccccacg ctcgcatcaa gctggagaac ccgctggact | 5160 |
| acggcagcgc ctgggcggct gcggcggcgc agtgccgcta ggggacctg gcgagcctgc | 5220 |
| atggcgcggg tgcagcggga cccggttctg ggtcaccctc agccgccgct tcctcatcct | 5280 |
| ggcacactct cttcacagcc gaagaaggcc agttgtatgg accgtgtggt ggtgggtggg | 5340 |
| gtggtggcgg cggcggcggc ggcggcggcg gcggcggcgg cggcggcggc ggcggcgagg | 5400 |
| cgggagctgt agccccctac ggctacactc ggcccctca ggggctggcg gccaggaaa | 5460 |
| gcgacttcac cgcacctgat gtgtggtacc ctggcggcat ggtgagcaga gtgccctatc | 5520 |
| ccagtcccac ttgtgtcaaa agcgaaatgg gccctggat ggatagctac tccgaccttt | 5580 |
| acgggaacat gcggtaagtt tttccttcca gaaatgtcgc ctttcggccc agggcagagt | 5640 |
| cactctgtgt tctggggtat ctagcggctc ctacctgcgc gaacactcag attgcccctg | 5700 |
| ggagagctca gcagggtaaa cctagagctc tcccgtggac tcccggcctg ccagaggttt | 5760 |
| aacctgagct ctcctaattt ctgctgcgtg ccctgggtgc tgattcctgc cctcccagat | 5820 |
| tcttcaactc ccccaaccgc cccaaattct cactacctcc tggtactcga ggtcccaaac | 5880 |
| agaaatccta ttgcacgggc caccttcaga gataaagctc ccaagccctc cactcttcct | 5940 |
| ttcctcctgt cctcaaagtc tgagaacctc aacaggaatt tgggcaattt ctcctcttca | 6000 |
| ggtctgttag gatttcactt tcagcctgcg cagattagag tcaaaaagac cggcccaata | 6060 |
| gcttctcagc gggtatcctc cagagaggta aagtgaaatt ctcggttagg gaaagaaagt | 6120 |

```
ggtctctggg tgctgaggtc tgctgtgtga aagggtgaac ttctttctcc tgaagcaact    6180
ggggacttgc tccagggctg gaggtcagta gagataatcc aaaccgtcat gtttagagta    6240
ggcagagggg caactttctt ggtaaagact tcacaggatt tgcactcaca gtttctcaac    6300
gttggttgac tatgttgaaa gtagttgctt ggtcggttt tctcttgtaa agtgtttatt    6360
ttctctgtgg attataacag atccacagcc ccctacttca ggtttgcatc agatctataa    6420
agaggagaat attcttttaa tgtacaattt aattaggctt gactctgact tacaaaactg    6480
ttggaaaaca tttttttgta aagcatttcc tgctatttca gtgtgctcca aaatctccac    6540
tggggagggt ggagtgaggt tttttattat attcctttat ttttaggaca tgtttgcatt    6600
ttagaatatg tgcagttagc tctaacaaat tgagtaagaa ctcttaatga cctatgagcc    6660
gtaatcttac cccaaagttt taattagcat atgagaaaag tggcaggcaa ttgcatcgtg    6720
cttattaaaa attattcctc accgcagttg ttgagcttct tggagaccat gctgaagatt    6780
ttctccccca gcaaattaag atattagttt atctgctgag ggaggacaga ctgaattggg    6840
gaattaactc ctcaggtagg ccaggtgctg atgtccctgt ggacttttgt cttattcttt    6900
gtttctatgg ctgttttctt ttacctgtga cttctccgaa atttctttgt tagccttaac    6960
atctttgttt ggggacttaa atccagcaat ttgccttctt tcactgatgc tttccttctt    7020
acaaggtaga tagcacagtg ttagtaaaga aagaaagagg agggtaggat ttcatattat    7080
ttcgtgggct gttgaagaaa cagcttctta ccaggcttta cattccatta ggttttaat     7140 gtttgactta caagattttc agagggttca tttgatattg tcaaagtctt ttccagttaa    7200
tttagactct tcattttgt aatgggttta tgctatggga caaaaaagt attcttcatt      7260 ttataagaac aaatttactt ggtagggtta attttttttc tagggctgtc actagacggt    7320
ggagcccctc ttctactgta aacttttctt gggggaaaat gtctaaggtg catttgacc     7380 tgccatgata ctaaacccag acactggaac cttccatctt ctgcatgcct cccccacaac    7440
ttacttactt aacagggaaa aaactgatgg ttccacatat ttgctaaaaa atgtgtgcct    7500
tcaaagacaa aaccaaaatt tttagggaat aactatagag agcaaaagtt actcccatca    7560
agtagacaac gagcttggtg attttatttc aggtcttaat gaaaaaagct tctttatgag    7620
gaaggttatc atatcttggt gcctccttga cagtccgctt aaattaatga cataaactaa    7680
tgagaattta gcagttcctg cagaaagtac aagtttattt ttttttttctg gtttgtgatt   7740 gctgcactga atatgaggag tctagttaaa gggacaactg gtgttcctgt cttgtgagtt    7800
gacgaagact ttccatttct aggatataga aaatccttaa gccggtttat tgaaaattaa    7860
tcaatttaat cagaatgcaa tcaattccaa tacaaaagtt agtatttct ttctttttat     7920 tgaaaattaa tttaatcaga atacaatcaa ttccaatcca aaagttgata ttttcttact    7980
ttctcttttt ttccctcatt ttgtagggat acaatttggt gaaaggcaag agatttctta    8040
agccaaagca agagtgtctt ccctctctgt gttgcatgca ttatgtgcca tgtttgagct    8100
aaaaatctca aaattgggca ggcttccaat gacctgttgg gtccctccct ttaccattca    8160
tgtgtgtgtt tatgtacata attttgtgga ggggttttt taaaccttag taacatctgc     8220
actcactctg tgttcttata catttacagt gtttctgctg agaggaggga agatgcaaag    8280
gtggtctctt ttacttaatt tagcatgtgg tttgaacaga aggaaaaata aaaagtgatg    8340
gggcttgtgt gcaaccctga tgatatttta tggagctgtc tgtcttctct ctgagatcaa    8400
acaggactac aactttgtta attgaccact ggctcccttg gcaaaagtag ggcttcttat    8460
```

| | | | | | |
|---|---|---|---|---|---|
| attccagcaa | gcagcacaat | aatatgacaa | aaatttattc | ttgggagttg | ggttctaaga | 8520 |
| gagtgcatgc | cagaattaga | gtttggggtt | tagagaaatt | atccagatgc | caaaagaaca | 8580 |
| ttttaatttt | tctcttggta | atttgttctg | gtctccatag | taggtagtat | tttagtagtg | 8640 |
| ctttgatatt | gacaagtctt | gctcccttc | tctattagat | ttttcaaaat | aaggcatttt | 8700 |
| attaattcct | ctttccttct | cctctctcct | ctcagttatc | aagcattttt | atgactatct | 8760 |
| tacaagcaac | agtttgtctt | gtaaagcaga | attttccttt | gaaaccaaga | cagattattt | 8820 |
| ctgcccatag | gcttcaggaa | ccaatatttt | ggcaagaagc | atcttttctt | tgtggtcagc | 8880 |
| aaataggtgg | tgagttctgt | ctggatccca | acaatcaaca | cctgaggacc | aaatagccac | 8940 |
| actgggtggc | accccattcg | gaagtataca | caggaagtag | ccctcttgct | tgttcacagc | 9000 |
| tcaagtcagc | caaagattaa | cactggtgag | agatattttc | aaagaagttt | gcaggcttcc | 9060 |
| aattgcaggg | tcattttggg | gtgctttctt | gcctgtacta | attttatctc | atcaagcttc | 9120 |
| cattctttga | gctgtaaact | ttgaaataat | atactggatt | tgctggtacg | tttaattttc | 9180 |
| tttgttaagt | gttttcattc | ccatagtaat | ttttcatcta | gtgtacatat | atgcatttaa | 9240 |
| aacaaaaatt | ctttggtctc | cttatgcgta | tatgcactgc | ggcttgtaca | cgtacaagct | 9300 |
| acttggtggg | attatgtgaa | ctggagttag | aaatgtggac | aattttatta | tgattatttt | 9360 |
| taatggtgat | atcaagatca | ccagtttcat | tcggaacctt | gcataagcag | ggagcagaat | 9420 |
| gcggactggg | tgtggcaaag | caagggctta | ttttatagcc | aaacctgaaa | tcacaactct | 9480 |
| gaaaaataaa | aaaaaaaaaa | accaaacaaa | aaaatcaagt | tttgtgagct | tggtcagaga | 9540 |
| aggaaaagga | aatctctccc | tacccccac | ctccaccatt | ttctctttgt | ctgcagcttc | 9600 |
| ctcaagtgct | gcctgtcccc | gatttctctt | tattccactc | ctttcatgtt | tttgacattg | 9660 |
| aaatacagac | tcttctttcc | acttctcagg | gtatttttct | tattcacct | gtggcatgct | 9720 |
| cctaaagaat | ttctttttta | aaaaaaatct | gtagagtagt | agattagatt | aaccccagta | 9780 |
| tctctccctt | aagactagat | gacatgaggg | gattgcaaaa | tgaatagctg | ggttttttt | 9840 |
| tttttttttt | ttttacctt | gaggttaaag | cctggttcaa | cagttgctga | gagagttaac | 9900 |
| tagattgctt | gaggacttgg | caatttcata | aagtattttg | tcttatgctg | tctctgtctc | 9960 |
| tgtcttgatc | tctgtctctc | tctgtctact | gtaatgttgg | ctactttctc | tcagagcctg | 10020 |
| agagacagct | ctgagacact | tcccaggtct | gttcggttca | gacctcagta | gctggatcac | 10080 |
| aagcagtacc | caatatgcat | atgagggtgc | gtgctgcaag | tgtccggctg | gctaatctg | 10140 |
| cttaagcttc | ataaaaatta | atcatttgaa | aacaaagaaa | gatattaaag | aaattattct | 10200 |
| atctccgact | tccctatca | gcattccatc | aagttctggg | atgttaaatt | cagagaaagt | 10260 |
| taaccttatc | ttaaacacaa | agttgacttt | taaacaaaat | tgcttataaa | gttctgtaca | 10320 |
| gttaccagca | ttggttgccc | tttgtcgtac | ggaagagaat | tatgaaatct | catatttaca | 10380 |
| tagcattctt | ccaaaaaaag | agacggtgtt | ttccagttta | ttcactgcat | tcgtgtaagt | 10440 |
| gtgagtaggc | caggagggt | gcttagtgat | tacccttttg | ctaggtaaca | aagtagaaag | 10500 |
| ttagattttc | tatgatattt | gtttaccacg | taggggaacc | tctctagagc | aatactccca | 10560 |
| agctttttct | tcttgaaatt | tcccacctga | cagataatac | tttagattgt | tgctcttaag | 10620 |
| gacttctctc | agtagctgct | acatagagat | gattgtccgt | gaattattgc | ttgcacactc | 10680 |
| atgggtgatg | ctactccctc | tctctcatgg | caattcttgc | tgccaacctg | caggccacac | 10740 |
| caggattgag | ggcagctcat | ctcgataaat | ttatagcatt | aaagtgctgg | gtcatttgag | 10800 |
| aatgttgtca | atttaggtta | cttagtacct | aagttttatt | cttaaataa | cagctttatt | 10860 |

-continued

| | |
|---|---|
| gagacgtaat ttacaatcca tacaattcac tcatctaaag tgtacagttt catgcttttt | 10920 |
| agaatattca gagttgtgca accattattg caatcaattt tagaacattt taatcacccc | 10980 |
| caaaggaaac cctatgcacc tttgtgttca tcccctata ttccctcagt ccttagcaac | 11040 |
| caataatcta cttctatcta tggatgtgct tattctaaca ttttgtatga atgaaatcat | 11100 |
| gtaatatgtg gtcttttgtg actagcttct ttcacataaa atatgttttc aaggtcatcc | 11160 |
| atgttgaagc acatatcagt acttcactat tttttatagc ctaataatgt tccactatat | 11220 |
| ggatatacca cattctatct atccatttat caggtgatga gcattacggt tgtttccacc | 11280 |
| ttttggctat tatgaataat actgctgtga acattcacgt gcaagtttat tgtggacata | 11340 |
| ttcagtccac atattttgga cattttcagt tcttttggat acatacatag gattgaaatc | 11400 |
| tctgagtcat atgatacctc tgtgtttatc cttttgaaga actgtcaaac tgttttctaa | 11460 |
| agtgtctgca ctgttttaca atcccatcag caacctatgg gggtccattt cttccacatc | 11520 |
| cttgccaaca cttgttattc tctgtctttt tcattatagc tatattagtg ggtgtgaagt | 11580 |
| ggtacctcat tgtggctttt atttccattt ccctaataac aaataatgtt cagtatccat | 11640 |
| gttcttattg gccatttgta tatcttcttt tttgagaaat atctatttgg atcctttgct | 11700 |
| cagtttttag ttgggttttt tattattgag ttttaagatt tttaaaaaat atattctgga | 11760 |
| tacatgtcct ttaatagatt gtgatttgta gatattttt cacattctgt gagttgtctt | 11820 |
| ttttactttc ctttttttc ttttttacgtt cttaatggta tctagattga agcacaaaaa | 11880 |
| tgttttttaag tttgatgaag tccaattcat ctatttattt tctgttttgg cttatgattt | 11940 |
| tggcgtcgta tctaagaagt ctttgcctaa tccaagatca caaagattta catatgtttc | 12000 |
| cttctaagag ttttatagtt ttcgctattt acatttaggt cttttcatcag ttttgatgta | 12060 |
| atgtttatat atgactgagg taggggtcca acttcattct tttgcatgta gatattcagt | 12120 |
| tctcacaata ttgttgttga atctttcctc acttaactgt cttggcaccc tttgtgtaaa | 12180 |
| atcagttgac cgtaaatgtg agggtttaat tgtggactct caactatatt cagttgatct | 12240 |
| atatgtttat tcctatgccg gtaccacgtt atcttgatta ttgtaggttt ttagtgagtt | 12300 |
| ttgaaattag gaattttgaa ctcttcaact ttggtcttct ttttcaagat tgctttggct | 12360 |
| cttgtgggtc ccttgaattt tcaaatgaat tgggataagc ttgtcaattt ctacgaagaa | 12420 |
| gtcagctagg attctcacag gaactatatt aaatctgtaa accaatttgg ggagcattgt | 12480 |
| catctcaaca acgttaagtt atttcatcc ataaatatgc gatgtcttcc catttattta | 12540 |
| ggtcttcctt ttgtcaacaa ttttattgt tttcagatta taagttttgc agttctttt | 12600 |
| aaaatttatt cctaagtgat ttatttttg atactataaa ttgaactgtc ttattgattt | 12660 |
| tattttcaga ttattcgctg ccaatgtatg gaaatataat tgttttgtat attgatcttg | 12720 |
| tatcctgcaa ccttgctgaa aatacctgag ttttgaatgc ttctgggact tatggggaag | 12780 |
| agggcttctg ctgctgcact gaaagttaaa gcttacttca tttcatcctg tatgaaggct | 12840 |
| gcatggggac attcttctca gttttactca gctataaatt cgaactggta atcccatccc | 12900 |
| ctttcgggat gaataggaga gtgttttaa atgttcatct ctttagagaa cagcaggaaa | 12960 |
| gaagccagt aaggtttggg tagtttataa tccctttttt agaatttgga tttgggaact | 13020 |
| attagcaagg cagtgagtaa taataataat ttctatatag aaaactaaca tgtagaggtg | 13080 |
| acaaatgaaa tcactagcta tattaggctt atgtttaggt tatcgtaagc agctaaaatc | 13140 |
| ataatttat gttttatat gttgtccttt ggacaaagta aattccagta ctccttctga | 13200 |

```
tgtgcatttc tagatgggga aaggattcat ttactctcat ataatttaag cttctttttta   13260
gggatgtact ccatagccat gaagcaaaga taaaattcat ctatacacag actgaacttt    13320
gtcttcatta acactctagg ctaagggtca tagctaatca gctacaactg taatgtcctg    13380
ataattgtga attaactgca gggcacccag caaaaggttt agttataatc taatagctgt    13440
ctgtagagat tagcctaata aagggatttt ttaaaaaaga atctggccgg gcatggtggc    13500
tcaatcctgt aatcccagca ctttgggagg ccgaggtggg tggatcacct gagatcggga    13560
gtccaagacc agcctggcca acatggtgaa accccatgtc tactaaaaat acaaaaatta    13620
tccaggcgtt ttggtgagca cccacaatcc cagctacttg tgaggctgag gcaggaggat    13680
cacttaagcc taagaggcag aggttgcagt gagccgagat catgccactg cactccaggc    13740
tccgtcaaaa aaaaaaaaaa aaaagaatct atcaatcaac cacttttcat taagcacctg    13800
ctatgtgccc agcatgtgct aggaagagat aaggtgaaag gggacacaat tcagacagaa    13860
tcttcttgag gtaactgctt acgaggagct tatagccact aaaaacaaaa acaaacaaaa    13920
accaaacaac caaaaaccaa acagaaatgc agtatcatca tgccatgatg cctgtatgag    13980
atcctggatt gtacggtatg gatttcttaa aatgtagata ttttaaaaaa aaagaggaat    14040
gaatcaatag aggctgaagt ggtcagcaat gttacctgtg gctgctttta atccttcgtg    14100
gaagtaagta ggagcatgtc taaactcaag caatagatta aagatcttga tgtatatttt    14160
aaataacaga agttagtacc actggaaaga atgaactgga ggaatgggtt gaaatctatt    14220
tctgcttatt caatagtgca ccccagtcaa gttagttgcc aatttcttct tcagtttctt    14280
tggctatatc attgcacttg gtgggtacat gtttatgatg tctttatctg aacaagtcag    14340
caataatatg agtaataaat taaaattgaa ggtgattaat ggctctgaat ttgacataag    14400
agttgttttc ctgccttcta agtttccatt gatcctgatg aattgcacaa accaaacaat    14460
tcggggagta aggggcaca tgatgatctt ataagagctt tgctgtatta gacaacgtaa      14520
cattctgaaa tggcctacca cctaacatgg gctctgttct ctgcaggttg agtaggttcc    14580
ttgcttgtgg aactgtagtc ccgctatttg gccgctaggg ggactgcaag tgccccgtgg    14640
caggatttcc ctgggaatgg tgagcctcca ttgatggttt caacacacag ccaaggccct    14700
atcgcaggat aacttgaacc agaactgcct agcaccagac aataaataag ctactatggt    14760
acttactgtt tcatttggga tgttgtttct cgaagtggca agcatttttt agtaatattt    14820
tgactttta ataccttct ttgcatatgg agcagaaaac agtgacactg gatatattca      14880
agtagcactg tccagtttat agagaagttt catattccat tattgcattt cattcttgtt    14940
tctacctttt acaagtaact agagtttgga gtattataat agtattcata ctattacagt    15000
actattattc ccattataaa aattgtgcaa agagtggtta agttacatgt ttacaatcaa    15060
acagcttcaa agtgactgat ctggaatttc agtcccattc tttcttctcc agatcatgtg    15120
ttccctgctt ttatctcaca gctctttta ccttatagat gggaaacatg agagtcagag      15180
aggcaaaaga accacaagtg gtatcaatac tagaaattta tgaatttctt aaggcttcta    15240
ggtttgttac ccatccacca gactgatgga tttggttgtg tgagagttct gggtgccaat    15300
aaccttgcca ttctacttta cagactgcat atattcaata aatgcttatt aagcatctac    15360
tatatgccaa attctgtact aggcaccaat gatgtagtgg tgaacagaac agacaaaaat    15420
ctcttcgtgg agcagacagt ttaatgagag gagacatgta gtgtacatct gagcatgaaa    15480
agtgccatgc agaataactt cacagagtgt agggtataga gattgatggt gagagggaat    15540
attttatatt tgctggccag ggaaaacctt actggaaaag taaattttga gtagtgacct    15600
```

```
gaaggaaatt aggaaatgag ctgctatttg gacatctgga gttagaatat tccaggccca    15660
gggaaccaca ggcgcaaagg gcctgaggca ggagcacact tgctgtgatg gaggacaaag    15720
aggcccatat ggctggttta aataagtgaa ggatggtaga caatgagatc agagttaatg    15780
aggttgcatg gtaggtcttc cttaggactt tgaattttac tcctaagcag gttgtattgg    15840
acggttttga gcagggtaac atgacctgac ttacatttta acaggctccc tcctcttcat    15900
aacatctgtc actctgatat attatacgtt tgtttgttta cttactgtat gtgggggaa    15960 gagactgtgg gagcaagggg ggaagcaggg aaacaagtac actgcagtga tctgggtgag    16020
aggtgaccgt gtctcagact aaggtggtat tggtggagaa ggtaggaagt ggctgaattc    16080
tggatgagtt ttgatggtat agccaacagc atttactgac agattggata ttcactgtga    16140
aaaaaataga gatgaggatg attgccaagt ttttggtctg agtaactgga aaatgagat    16200 tgccatttac tgaaatggtg aagactgtat gtagagcagg tgcatgggca gggtagaaat    16260
caagagtttg attttttgact tataaagttt gaattatctg atgaacatcc tgatggcttc    16320
ttctcagtta gttctcatgc agtgccttca gctttgctgt tcttcaagaa aattaaaaag    16380
gaacttagag atcgcctagg ctgtaggtac cctctcccct cttttccttt actttataga    16440
ggtctataga agggtaggga cttatccaag gtgaaacagt gagctggcga cagaactagg    16500
gcacaaaccc agttctcttg aattctgaat cagtagattt tcttttttta gtgtgattct    16560
gaggactcat ttgggcaaga gtgagttttt tgttattgtt ttttgtttgt ttctttgccc    16620
aaacctaaaa ccaggtaatt aaactaaata gtgaataaaa ctgggaaact atacaaattg    16680
gttgctctcc ccaatcacac tgaaatatta ttattttttac tgaaccacat accaaaatat    16740
ttttcctgta aaaacacagt aagtgaactt ttaaaggcaa ttgagctttt aacaaagcta    16800
gaatctacag aggacctgga cagaaatggc cttaaatcct aggaaattag agttcatgga    16860
acctgggaga ccatcttgtc cagctagctc attttatggg tgaggtgcct gaggcaccaa    16920
gatggaaagg gacctggcta agctcataca gcaagctagt gcctgagcct agtcagagcc    16980
tgttttaagg gttagtcgta tgttgttttc ttgaaaaaag ttacattgga aaagtgaaaa    17040
ttctttggtc catactgaga acaaagaatt atacataatc atatataata ataatgatag    17100
cacttcctga atgtttgctg tgtaaacttt ggcaccttgc atgaattgat tcatttaatt    17160
ctcatgtcaa ctttaggaag caggcctaga gaggttaagg aacatgtcca agggtcacac    17220
agctaggaag tagcagaact tgtgtgcact cccaggaagt ctggcttcta accacaaggt    17280
tctaactact gtgcaatacc aggagcttct cagattaccc ttcacccttta ccaacccaaa    17340 tgactggtga cgtaggtgac ttcattatgc tctgccccta ttatagtcca ctgatcctca    17400
ccaaataggt gggtggccta gaggttaaag tagaggcaga gtgatggaaa ggggtggtta    17460
gaagaagttg atgactcatg atagggattg gaaaacagga ctacaggaat tattgaaaag    17520
ggcctagaga tcccaaggag gttgatctcc gactgctaca aacctgggca attcaatgcc    17580
tgcttaaata ggagagttaa gataagaaaa ataaaattgc caattttttac agtcagacat    17640 tgttttattt attttacatg tattaattca tttaatcctc aaaatactcc atgaggtagc    17700
tacaattatc atttctatgt tgtagatgaa gaaacaggca cagagcaatt aaataacatg    17760
cacaagatta gagaacaagt aagtggaagt gccaatatta gaatctaggt agttcagctc    17820
cacaacttat gttattttcc actatatttta tggaatgagg taattttctt ataacagaaa    17880
gttttttaaa tgcaaaaaca ttgtgcctga acttcaaaca ctgaacaact catatcctta    17940
```

```
atatgcacca gtttctttta agcactctta gaaggaagga tacttaacct aatgtcacat    18000
ggtgagtaag tagcagaacc ggaacttgaa tttgagactc cggactgcca gacctctttc    18060
cactctatca cttgggctcc cttctaacat tgacttgtct ccctccattc ctcctccgta    18120
ttgttctgcc cttcaccttt taattacctg tctccatcaa caagattgga cagagaattg    18180
ggagagtgag cagagtccat ttccttccag agactggaca aaaggaacaa aatgttagga    18240
aaaaatgtca gcatgtggga tttgtgggat ttacactaaa taagaaggga cacttcccag    18300
gactgacaag atgctacctc cgtccctcta ggccccaatg tgttgtgcag gatcccatag    18360
gaagtcatga atgtggttgt cagataacct ttttgttact gtggaaatgg aagcaggcta    18420
ctgcaaaaat ctgtctctcc aggttttctt ttaaagaagg tagtcttgct aaatgataac    18480
tatttcagca tttatttgaa aatgggcagt gcaggagaga aagaatttt ccaagcttgt    18540 cacattgggc cacctctctg aagcattgtc caacttctaa ttagatgagg agactgcata    18600
aaccaagagt tgagagtaaa gatggaaaca cttgatgttt ggtgtttggg tgcagaaagg    18660
attccagaac atgttttggg tctctttact ctgtccatcc ctccttccct ttcatctttg    18720
tttaaaaacc acagttagca aatgtgtagt ctgtttgcaa ttgttcatct gaaaaatttg    18780
tttgatcagc cttttgaata aaaaagacca aattagactg agatatttca gtcaccaact    18840
atctaataat agaccaaaaa ttttaaccat gctcatactt tcatatggta tgtagtttgc    18900
tttagacatt ttctgggctt cagtgaggtg ctagattgac tcaaaatatg gcaggtcaga    18960
tgtgggattg agcagggtgg actcttctct acccttccca attcagagtt ccccatcaaa    19020
gatgatctca tagtgtttga aaaccaagc tgaaggcttt gggaattagg gtgctgaagg    19080
gatatgctgt ttcccaaagc cttctcagtc attccttctc ccccagttc agattcttaa    19140 cacctctttc caggattagt gcagtgatcc cacgtccttt ctctctagct ctctctgcta    19200
ctctctaatt cctattgtat ttgtgccacc agatctttcc aaagtttagc tccaatcttg    19260
tctgtatact gctttaaatg tctattagtc tttaagctcc ttaagggtgg gagtcctgtc    19320 ttatttttc cctattcttc gtgcttaatg caaaggaagc cttgctgtat agttgtgtaa    19380
tgcatgatta caatttcagc ttctccccat tggcttatgg gttaaagtcc aaattattta    19440
aatctggtgt tcaagtcctt ttatgatctg cttattttc cagcctgaat tcctggagtt    19500
cccttacaaa actcttaaaa cccagccaaa aggatctagt cactgtcact ttaaaccatc    19560
ctcactctct tgttttttga acatgttatt tttcttataa tcccttttgac cttgaaggct    19620 atcccaattt caatactatc cattcttcta tgacagcccc ctacaaaatg aatattctca    19680
acctcccaac ccaaggagaa gtgatctata tgacacaata tggttgaaag aatgttggct    19740
tcacttcttt atctgtaaac caggggctag aaatctctag tttataagat tttgtggaga    19800
ggggatcata tgtgattatg gatgttaggc acaagtcaag agtgcataag accttttgga    19860
tttatccctt ttttctttct ccatcaatat ggtacttagt cccttaaatc agaagtactt    19920
gtgttaatgt ctgataacgt ccttctaaat ataccctaa acatctgtct ctctttaggg    19980
caaaggttgg atatatctgc aaagattctc tttggatata agatatccac agcacataac    20040
ttaacagtgg tgtacacagt aggtattcca taagtatttc tttatgaaat gattcagagt    20100
caatagtagt aagtaactgc caaaaacaac tgatggattg taagttccat taacataaat    20160
acagtcagcc ctccatatcc atggattcca tatccacaga tttaagcaac tgcagatgga    20220
aaatatattt tagagacaca gtaaaaataa caattcgaca gtaaaaaaat acaaataaaa    20280
ttatgtaaaa caactatttta cataacattg tattagctat tacaagtaat ctagatataa    20340
```

```
atgaaatata tgggggatgt ataiaggtta aatacaaata tgacaccatt ttatatgttt    20400
tagttaagga acatgaatat ttttggattt tggtattcat gggagtgggg gaatggaacc    20460
atgccccttc aaataccaag ggactattat atgggacaca gaataaagga gttgattgtc    20520
ttgctctgtt aaattctggt cagacacatt tgcaatgtat tgttcagccc cagtattcat    20580
ggagcatctc cttttgtaaa gcatggagga gctgtgagag agacatggag cagtgaacat    20640
aactattgtt tcaacgtacc tgaaggatta tcatggaata aagaagttag atgttttctt    20700
gtagtacccc aaagggcaaa agcaatgagg acagattaca gttcagtaaa cgaaagaggt    20760 ttttttttt tttttttttt tttttgaga tgggagtctt cactcttgtc gcccaggctg     20820
gagtgcaatg gcgcaatctt ggctcactgc aacctcgcct cccgggttca agtgattctc    20880
ctgccttagc ctctgagta gctgggatta caggtgtata ccaccactcc tgggtaattt     20940
tatttattat ttatttattt ctttatttat tttagtagag acggagattt catcatgttg    21000
gccaagctgg tctcaaactc ctgactgcag gtgatccgcc tgcctcggcc tcccaaattg    21060
ttgagattac aggcgtgaat caatgtgccc agcctgaaag atattttctt agaatagctt    21120 cttcaccct tcatcagaag ttgtcaacat ggaccatatg agttttgttt ggtctatatg     21180
gtgtatatgt gtgtgtgtgt gtgtgtgtgt gtgtgtgtgt gtgtatgt gtgtgtgttt      21240 attgaattac ttgctaacat tttacttcaa aattcagatt ccaccatag ggaatgaaga     21300 tctggcaata caggactttc attcctacat ggtaatgacc agctgtaggt gaaaagcagc    21360
tgatcctctg gatgggccat gcactttgca gtttgcccag gcagcactga tccgctttat    21420
tcatttaagt tacctgcttg actcttctag tcattcgagt atgtcatccc catcagatca    21480
gagacctaag caaatcttgg gtcccttgct tactccaagg gctttcactc ctcgtatagg    21540
aggagctaaa gaaatgtaca agcagcacca caataggatc agacctggct ttcaattcta    21600
gcacggccac ataacatagt tggatgacct caggacagta acataacccc tctgagcctc    21660
tagatcttca ttatctgtag agcactcttc ttatagagtt attataagaa tgaaataaaa    21720
caactaggat aaagggcatg gcacttagta ggtgctgaaa tattagttcc cttcttctaa    21780
ttcaccacac catatctgtc tatctattgg ctgaatcaca taaatagtaa attcacattc    21840
actgaagaca ttcaagaaga gtctggaccc tttgggaacc atgtataggg caaaggtttg    21900
aactcatagt agatgatttt tacagtcact ttttaacaat ttaaaagcct atagatgact    21960
ccaaaatgcc catttggatg atatgaggca tactttgtgt agttaaggat tttaaataca    22020
taacagagag gctgaagggc cttcgggaaa gaagctgggg taagagtcaa agtgtagtat    22080
gttgaccgat gttcaggaat aggctttggc atctgacaga ttttgtttta aatactggct    22140
ctgggtctta ctagcttcca gttctgggct gcttcacctc tcttgagttt cagtttcttc    22200
atttctaaaa tgaagatact aatgcttcct ttgttgggtt tttgtgaata taagtgagat    22260
aataaatgta aatatctagc ccagggcctg gtgcatagta caagcttcat aaaattgtacc   22320 tattattatt agtagtagta gtagtccaga caaacagagc ttgggaaaac gctagactct    22380
ggctgacata catgggcttt tccccaggcc actgctgcct ggcttcccct tccacaaagc    22440
tttgagtctc caaaatgctt tggctggaat gtaagcgtga ggtcattgca gataacaggg    22500
gagcatgatt tgcttcggta atgcaagtta ttaagttact tccctcagcc cagctgaaat    22560
ctcttattgg ttgatgtgtg cttcaaagtg tgagacagag ctagtctgag gagagaggga   22620
gagtgagaag attcctcttc ttggccagag gtcatggtct tccacaagga acagaatgac    22680
```

```
tcaatgcaaa ttatgggacc tctttgagtt tggggcccct acatttaaac tagtaactcc   22740
gttgcacata ttggcaccct tcccccaaca aaattactgg gcaggaattt tcttgaatcc   22800
ttccgtggcc tggaatgatc tcccttctca tccttgtgat ccacacagct ggcaaatggc   22860
aggcagcaga acaaaaacaa gcctcttagc atatagggag agaaagagtc acagcagtac   22920
tgaatttgct tgggaaccta atgttaacaa aggaccttcc tctcaacacc ccaaacagat   22980
taaaacattt ttttaacagc aagttgtgtc tcggagcagc tctttgcttg ggtatattta   23040
aagatctgct gagtcatttta agagcaggct ggcatatcct aagaggcaag gactataccc   23100
cagtctatgg gggagtaagt tgagaggtga aatctgtttg gctttctccc atggaaacaa   23160
acaaggtgat ccacttccat ctcccacgac tctggagagc atctactaag ccttcttatt   23220
ctatcaactt tgaactcctc agtgtataat agagtaaggg tgagagggaa ggagcagtcg   23280
taccagtgtc attattggta tgttcaggag ttcaatttct tcctgattca gtcttggcgg   23340
gatgtatttg tttgggaatt tatccatttt ttctagattt ttctagtttg tgtgcataga   23400
ggtgttcata ataccttctg atagttattt ttatttctgt ggtgtcagtg gtaataaccc   23460
ctgctgtctg aaattgtaat ggccctgcta ttggtagctg agagtagcat ggaagtgtca   23520
ggttgatggg ttcatttaat tcttttcttt tcagtttcag tcacatgcat tgttaccatg   23580
gcatatgaca gttgctagaa agtgaaataa tttttttct actttattct ccactgcact   23640
tctaaattta ttagtggaga aattagcagt taccaactgt tcattatagg tacacattgg   23700
ggtttcctta gagccaattt tccccctggt tttcatcttg taaatctgta atcctaaaaa   23760
ttagcaaaac ctagagcttc tctttggtcc tggcctgttt gaaccctgtt ccacagaccc   23820
caatcttctt tcttgtttga ggcaactatc cttctctttg cccaccgcca ttttccttca   23880
tctacttttc ccttctctag cacctcagac tgtcttccca cagtggcaca gcctcccact   23940
ccactttcac tgtgccatct ccttgccatc aaaaccatcc tcacagaccc ttctgaaacc   24000
acttctagga agggaaatca caatggatcc atgaaggatg ctttctggat gactttaaaa   24060
gattggtatt aagatatttt atcagtggta gcaacactga cttattcagg cagccatgcc   24120
ccggatctat aagaaatcag gtaagctaaa agttgcttga gctggcagga gacctagttc   24180
tctttttttcc tttccctctt gcattttgtt tatcgatggt tttcaaagga cttagaggct   24240
ggctttgtta tagttagttg gtaagagaaa tggtggagga ccggaaaatg ggagtggaac   24300
gaatgagcat gtttgagact aagttattac aattcctagg atgtataaat tgcttgaaat   24360
ctaccaagta ctttcagaca cattatcttt tttactcttc aaaatcaact tggaggtagg   24420
cacaacaggg atcaaatcct tagttcacag atgagtaaac tgagactgga ggaaattaaa   24480
ggagattcca aggtaactca gacaataagc aacagaacca ggatttggtg aattttttgg   24540
ggggtgggag gtacagagtc tcactcaggc tggagtgcag tggcaaggtc tcgtctcact   24600
gcaacctctg cctcctgagt tcaagtgatt ctcgtgcctc aacctcctga gtagctggga   24660
ttacagacat gtgctacaat gcctggctaa tttttgtatt tttagtagag atgaggtttt   24720
gtcatgttgc ccaggccggt cctgaattct tggtctcaag tgatccacct ccattggcct   24780
tccaaagtgc agggattata agcatgagcc actgctccca gccccagacc attaattttt   24840
gacagtaagt ccaactttt tcaagttcac agctcagatt tgctattgaa tgaatgagta   24900
tatatgtcat ttgggaacat tctttccaac ttttggttga agatttgttt tatcacttgt   24960
gaaaattttt tttcattctt agcaatgtca gtttagttaa atgagcattt catttgcgaa   25020
ttcactaatt aattatttta ttcatcaata catttcctga gtaccaactt tctatcaaac   25080
```

```
cctgtgctgg attctgaggc tacaaagaga aataagatac catctcaggc ctctaaaatc    25140
tcacagactg gggactgaca tctcagtagt aaacatatga acagcaactt gtgaaacgcc    25200
attagcaaaa tctcaagtta tattcttcag tgactatggc catcctaaaa atggggtgtc    25260
ttttatttgg ggtaaatgaa gatgaagcct tatgagaaat tgcattttaa tctaatcttg    25320
tcttgctaag aacagaagtg gaatgtttca gcctctgtgt gtgtatttgt gtgtgtgaag    25380
gttgagtgtg tgatgatgga tggggctgcg agattgttaa gtaggatcta tgggggggcct   25440 taaatggtcc tggtgagtcc caactttctg gttatgtatt tgagtagagt atgggggtga   25500
caaagattgt tgtttaagag ttgattttag attttttcca agtaaatggt cagctgactt    25560
ggagcatcat cattccactt gctttgaaaa cctgccactt aaggctcctt ccagtcatag    25620
gttaactctt tctggtcaag tattactctt tttgagcatt tacctgtcag tgacaggtac    25680
aatgttagat gttgtctctc tgttttcttg tttaatcttt actttgatcc taggtagctc    25740
ttattagttc cactttatag gtaagaaact gaatttcaga gacttgaatg acttgttcaa    25800
gatcacatag tatagtaact tggtagtttg ggacttgaat tttgattgtt cagtttttg    25860 tttgtttgtt tcctggcctc cctgctgttt tcactattcc acaccacttc agctttattt    25920
ttcatagagg ccattaaatg taccctccat cagccaaagc ctcttgcctc ccttcaacgt    25980
aactcttctc tagcgtcctc ttaataatct tctgaaaagg ttttacagcc tttctgggta    26040
ctgggaccca gagtcttaat ccaggctctt aagtgcctta tttaactgta atatggaaaa    26100
tcaaagtcac agctaattca ggaaaaatga gtttgggatg tgaatttcct aggcaacttg    26160
tcatctcttt tttacttcct tagcttcata aacttaccca caatgttccc tgaggactaa    26220
gagtaatgga gggtgatgag gaaaggcttt cctcccttcc tttccgagag tccttttagcc   26280 aaatgccaca cctcctcctg tttccctagt ctccgtgcag agatggaagt gggagataga    26340
catgggttcc tttcagccct gagttcatgc cagggttttc tttccctcta gctggactga    26400
ggtaggagga gaggttgaag tccaccaata agaccatgag tgaagaagac taaagtactt    26460
gaaagagcag cagacctacg cttaaaatac tagggtttgt gtccagactt tgtgggttac    26520
tatctgtata attttgggca agtcaacagt tctgagtcag agttccctta tcagcagatt    26580
ggaagataaa ttctaattat atagatgaaa cattaagtct agaagtaatt tgtaaattca    26640
gaaagggctt atagatttaa agtgtagccg ttttgattac cacaaactaa atcctatact    26700
tcagggataa aatcttctcc tgtttttct aaaagcctgt gcatgtgtgg tgtaagggt     26760 gggttttccc ttgtaccagc aacttagcaa ttgtagtaac ggggctgagg gcagtggcat    26820
gcttcttcat tgagcaagtg tgaaaagagg gttatgcatt caggggtcag cagatggcag    26880
gcagagtagc ccctccaaat ctccctccca taccacaaag ccctcttatt tattcaaact    26940
taacattaga agctcatttc aagtaggcac gtctgtgtct gggcgtctat tttccttctt    27000
tgtatatagc aggcatttgt caacttggtg aaaagcatta ctcttctttc catttctgag    27060
gactaattgt gcttcttcgc tagacacgag ttcaaaacag tgggttgaaa gagggcaagt    27120
ttatgccaaa gaatcagaaa tagtcataat ttagagagaa ttctagaggt cagttccctt    27180
tcgtatggac tgggcaactg aaacccagac agggaaggga attagaccaa gttcacaagc    27240
acaaacactt tactggcaca ttcagattgg aaatcgaggg cttctgctcc caggtcagaa    27300
ctaaatgccc tttctagcta gggtgttctt tgatctcagt gattttgact cttctactg     27360 cactctgggg acagtgggtt ctgcggtacc aactccaatt aaagtgggaa tatgtaccag    27420
```

| | | | | | |
|---|---|---|---|---|---|
| cccctcccct | tggttttat | ttttcagagg | cctggcagtc | agagggattc | tgatctctat | 27480 |
| atgcaatatt | ttcacactac | tgtacttatt | gaaatcacat | ttgaatcttg | gcaattaaca | 27540 |
| aggcagtaat | tggcatcagg | agggtatgtt | agtttgctta | tctgcgccgt | ccctcctctt | 27600 |
| cccaacccac | tgtgtattgc | agaatgtttt | atcagctctg | atttgccaag | ttgctctctt | 27660 |
| ctccagtagg | tgctgcgagc | agagagggat | tcctcggagg | tcatctgttc | catcttcttg | 27720 |
| cctatgcaaa | tgcctgcctg | aagctgctgg | aggctggctt | tgtaccggac | tttgtacagg | 27780 |
| gaaccaggga | aacgaatgca | gagtgctcct | gacattgcct | gtcacttttt | cccatgatac | 27840 |
| tctggcttca | caggtgggag | gttcttcaat | tgaaaactta | gaactcagtt | tctagggtag | 27900 |
| tgagtgttgt | aaggtttgga | ctgtgaccta | atattacgca | gccatgacat | tatctattag | 27960 |
| gcatctagac | tagcttgctt | gaatatctta | gcatgttgac | taatttgggg | cagaatatag | 28020 |
| tgtgggtggg | ggattttgtg | tgtggggggg | ggttgggggt | tgagcaattc | attattatta | 28080 |
| aaatgcaaaa | agcacttaat | tcgctatgat | aagattgcct | ttttcatgca | tactggccta | 28140 |
| cctgcaagac | ccctagagac | agtaagcagc | atacatggtg | tcttccagtt | ttcagccttt | 28200 |
| gtgcaaggaa | caactgtggg | tttctgcaca | tgtgttgtgg | tttgatgttt | gtatgtgatt | 28260 |
| gtgtaccagg | gtatgtgtgt | ctgttattgt | gagttcattt | ctgagcagtt | gtgacacaca | 28320 |
| gagatccaga | aacagtgtct | taccctgtgt | gctttgctag | tgggaacgtg | tcttttcttt | 28380 |
| tgtgctcgta | tctctgtgta | atcgagtgtc | ttgctaagtc | aatgtgcctc | tgtctctttt | 28440 |
| taccagttct | gtctttgtgt | ctctgtgcct | tcatgtattt | tttcccctga | gtttgcacgt | 28500 |
| ctctgtctat | gtggatatct | ctcactccag | gccactgtat | cactgtgtct | gtattacagc | 28560 |
| tgttatttc | tgtcggtgtg | tggatttcta | tgtctgtttt | catcttaatt | tgtgtgtcta | 28620 |
| agcaagactg | ttttggggtg | actatttcag | tttatgtcat | agccattctt | tgtgtgactg | 28680 |
| cttctaggta | tgtctttttc | tatgcccta | ttgtccccat | ctccatgtgt | ctctgtgtgt | 28740 |
| atatgttcta | atgtatctgc | ctacttatct | tagtttgtat | ttctctgggt | gtatatccct | 28800 |
| ctcttgcagt | tctgggcctt | tgcagttttt | ggcttatgtt | tttgtatata | tccactagaa | 28860 |
| ttggcttctt | atcttttttg | tgcatgtttt | agtttgtatg | agtgagcata | tccaactctg | 28920 |
| tctttgagaa | gcagaactgt | ctgtgtttgc | agtcagttgt | gttggctgtc | cctgtgtttg | 28980 |
| tccctgtgtg | tgcatttcat | tgtatgtgta | cgcatccatg | tatctttctg | cttctctgtg | 29040 |
| accagatatt | tctgtgtagc | tgtctatgta | tattggcttc | tgtctgtgtc | tgtgttgttg | 29100 |
| gctctacgtc | tgtgcatatg | cacccaccgg | gttcataaaa | agctcacctg | ctctccaagg | 29160 |
| aatctaccag | attattttgt | gaaataactc | acgtttcgtt | ttttacttg | ccagctgcta | 29220 |
| tggtacttaa | aagtgtgttg | gtacgtaggt | gtgcataatt | tattcatgta | ggatgtcaaa | 29280 |
| agagtcagtt | aaaaattatg | cacagtgtgt | ctttattaac | aggacacttg | tgtgtagaga | 29340 |
| atccttgaga | aatgagtggt | tagatgataa | atcttttcat | attaatttca | tgatgtcagt | 29400 |
| gaagtaaatt | tgcaagatat | gggctgcata | agaactatgt | tcttttaaa | actcagcata | 29460 |
| ttgatggtgg | agaaagcatt | tatttgtact | gcaaagtctt | atttctgata | agacatcaca | 29520 |
| aataagaatt | attgtgatga | gacttatcac | aaataagaat | tattgtgata | attcttattt | 29580 |
| gtgataagaa | ttactgggtt | agaaggtgtt | acttttctgg | ttttgtttgg | gttttttgttt | 29640 |
| tgaagtgtta | ctacagatgg | tgtcttaggg | acaaagagct | ctgaggttga | cttagaacac | 29700 |
| atggagtaca | gataaaaagg | agaatgaaaa | gtaacagaga | gatgggcata | ttccttgttt | 29760 |
| gaatggagtc | atccagggc | tcaggatgga | gtgcacagga | aatggagagg | tgaaggtcat | 29820 |

```
agagagaagt ttagcaggac cagatctttc cttgtcctgg gctgctgtga ccatataagg    29880
aaggcagtaa ggggaggggt agggatgagg aagagaccag ctctcctctt tctttctgat    29940
ggaaggttac cacctctatt taaaacttct gttcttttgg tttctctttc tttctttgat    30000
tatattattt tctggacttg ttctgccaaa gcaagaagga aattccacat gtggctcact    30060
catttattat acttgtttct ttgcacgata ttaaagacag cttgttaagt gtcactgcaa    30120
acatcataca cactgatcca ctgatatggg caggggttc tttatgccag ttctgctctc     30180
ttcccagtgt atctgtggtg cttaatgggc gcaaccatga ttttctgat gtcagtctgt     30240 gatgtcagtt gtccagtgtg tatgcaggct gcttaagagt acatacagtt ccttcacaat    30300
tatggtagtc cctgagaagg aagtggtcat taataaaaga ctaggttcag tagaaacatg    30360
taagttgtct aggtgttgga aattaataca gtactgtgct aagggaacat atatctagaa    30420
gttaactgaa ttatgctcaa taaaagagt acaaatgttt cataaatatt ttgacctaat     30480
cctcctgtaa gattaggaga gggatatttc cgatattcaa ataatttttt taattggcaa    30540
acaccttaga catactattt acataaaatt gacatgacaa aattaagtca ttgtgtctgt    30600
tttatgataa aacaggctct tttgatttag ttagaattat tgaatgtaaa ataatgaaaa    30660
ttaaaaaaaa aacaaggagg aggaatctat cctattttat aattcagacc gttgaattga    30720 gttttttcttt tgttgtattg atttaaatgc agagaagtct atgatgctgg attccagtca    30780
gaagataaac atttgtatgt gggctctaca ttgcagccaa ccttgataat ttcaaacctc    30840
gattttctca tctgtataat ggtaataata aagcctgtct cagtagctac caaatgattg    30900
catatgacaa acttctcact tatttaaggg aaaaaataag aaaaagaagg acaatagggt    30960 ggattttttca tatagtaaaa tttattcagt tagggtaata ttctgagatt gtcttctgaa    31020
gcaaaccctg caaaccctgg ccattctgtt ttgtttagga aagaattcat cagttctgat    31080
tctgcctttt ctggggaggg aggctgagta ttggattgaa gaggagtcac tacttttctg    31140
agatgatata tccgtggtaa aaattattaa tgctttgcac atgcaacata gagtgttcaa    31200
ttttgttagt caacaaatat ttaagtggca gctgttatga cctcagggggt gtagtgactt    31260 ccttattgtc ctttaattat taaaaaagaa atctatatca gaatatcagg taaactctta    31320
ttacatcaaa tattataata aagatacttt ttatattctc taaacaaagt agagatctca    31380
gatgttggtt catttatcaa tataatatta gatttgaaaa ttccagtata caaaggaaa    31440 aggacagctt cttaaagttt atagtgattt tctatgaact atcaattccg ttttttttctg   31500 ttttactggt atgatggaaa ctaaatttcg agttgtaagt agtagataat tagactgcag    31560
ggtaagcctt gagattactt cttttcaggt aggaaactct actgtgtatt tggctagttc    31620
aacctatcat gggtagtcaa aaatagttac atatacaagt cagcattttt taaattgttc    31680
agttgtgctt aagattggtc ctttccagga acaatccagc tttatcaaaa aattattgcg    31740
tacatgtaaa gtgttctgac attttaatgc tcacaatagc cgaatgacgt gggtaagaat    31800
cttcgtcttc attttataga tgaagaaatg aagacacaga gacataaatt aactgggcca    31860
gggtcctacc actagaatgt gatagatgat aatttgagct cagcacatag ttatttccct    31920
ataatatttg ttttatgatt gtatagatgt ctgctgacca accttaatct ctgctcccta    31980
agattaacca ttctacaaag cagaaactgg aggtcattca aatgaaagct ctacactttt    32040
agagggccat taacaatgct caagttaaag aaaagcaatc aaagcaaact aaaatactgg    32100
taccttcaaa cagtacttat gaattattta accttagata atttggcttt gagttagaaa    32160
```

```
gatagagtaa gatggaggaa ccaattcttc cctgggttga tatttattta tcttgctctt    32220
ttgaagtcta ggccaatcat cctatttatt ctgaatggcc cgttaacgtt tatccattta    32280
gggacagcag gtttggcaca aatggattgg ttttctgagg tcttatgtag agggctgcac    32340
tgactgactt ctgaaagtcc cccctaaccc ttcaaatctc agggtcatct ggtctcaagc    32400
cttcaattat gaatacattt ctattgcctt tttgagtaac agcacaacac tgcaagctga    32460
cccactgggt ggatggaatg gggctcttgc cctaccaccc tttggcaaac aatttgaggg    32520
tggcattgtc actacctcat tgtatatagg gtctcttgag gcccagaatg caaaataat    32580 tttcccagtg tcacacagcg agttattgtc agagtaaata tcaattttga atttgtagac    32640
cacgtggttt tacctcatca tttctgtttg ttatgaaagt tttacaaata attagaagta    32700
gaaataatga ttaaaataaa gcataactac taaaaaatag tttattgcag caccacctaa    32760
attcatctca ccactctacc agtagcatac atttcacaat tgggttaaca ttgctctgga    32820
tcttatagct gttgaagaag acaaaattct ttccattctc cagcttatat tttccccatt    32880
tgtaaaacat aatggaagtg tacggaaaat aggagttgat aattttttaag gcccttgcca    32940 gcacattagt acataggatt cttgcaagtg gtggtttact tcacttcaac tatagaaggc    33000
ctatgcgaca ccacccatag agggtagttt gaaagaaaat gctagtgact acgtgtgttt    33060
ccttcctgac atattttata gaaggtgatg agttccagca ttttttcaga cttggatctg    33120
gctttcattc cccttctcct cccaccctct aaaacaacag aggcagcaac catttacaca    33180
ctttccagaa gtaagtaagt aagactgtat tccagaaaca ccctatatca aaatggaaat    33240
atactcaagt gccccaatga cccattgggc tagtttgaac gtgtgcagtc tctgtgctcc    33300
ccgttttagc ttaagcctac tccctaacct gtcatatgtc acccagccat ggagcctagg    33360
gcaatgactg ccatcatatc tgactttatg gcctctcagc tttcaatgac tagctttgta    33420
gcagaagttt agcctctcat ccccataact ttggaagtag tgttgagata agaaacgtt    33480 gaattgaagg ttgtgttttc tagatttctt tcaattgctc cttaggcttt agaagataaa    33540
ttctcctaaa agagaggtgc tacaattaat ccaagcaaag ggaaagatgt cagtaaaact    33600
gccccttttc atagaggtgt ggcaactgct gggaaggaag aaattagcct gaggccatgt    33660
gattactaat aaaactcaaag cggcattttt ttacttctca atatgaggtt gaaactataa    33720
gcttaaattg ctgactttct ggcagcacca aacagtaagg aaaccacaaa gataaaccca    33780
aataatagag ccaattttct tttttttccgg gggggatgac ttctaactag tgatatgagg    33840
aaggataaga aaatgtttct ttgtaggaca tatgatcttt gctaagtgca ctgaatgtat    33900
gtagaggaga caagtctgct gagggtatga gaattgggcc aagatttaac acattttcaa    33960
agctccatga agaagcctac tgagcagtgg gagtggagca ggttggggat agtgaagtat    34020
ttgtaattca ttttttaaaaa gggagaggag agagaaaagg aaaaactggg ccacccatcc    34080
tttgaaaaga aaccttgaaa gaggtccaaa tatccttaga aatccttgac ttcttaaaag    34140 tgatgttttgt tttttccccc tgacaattat agaggtcaga gagttttttct tttctattac    34200 aaaacattga gagtgtgtag aaataattgt aggtagctta gccttggctg tagtcagaac    34260
ttttgtactg tgactttagg atctgtatgg aatcgtatga tatgcggata caccaaaaac    34320 tctatggtt atcaaaatgg gatagcatta aaagaaatag tgcttttgtt tagaagaaga    34380
aatgaaatgc ttgtgtccag atgcttaaag gaaggcagtg cagactttca gaaactagac    34440
tttaagagct gtactcagat actgagaagg gctgatggct gaaggaggaa caatttaaaa    34500
gaataaccgt ctctcctctc cctgtatatt ggacataaaa gaatatccca ttcttttcag    34560
```

```
aaatgtaata caacagttta gcttgctagt aacttcacat gctatttcct ttacctctta    34620
tatttgaggt gtctatttgg agtgggctgt gtttctagct attctgttta tctggtttgt    34680
ttttgttggt gtaggaaact ggtataaatt ttatttgggt aaatatcacc tcaattttca    34740
actaaagctt tatttaagtt tcacatgaaa aagacaaatg aggcaaagga agagaaaaat    34800
gcattgtcag aatcagaatt atgagaaaaa aagtcaaaca aacatatttg aaatgtccag    34860
aaaacctgtg agtttttatg tatactatac aggaaagata ttctgtcatc tggttgccaa    34920
actatggagg gtgggagact tcgaattttt gtcaaaaagt attctttcat tagaaagata    34980
catgggtgtg cttccatgtc agcaacatga ctgcagacca ggaagtcctc acggagagct    35040
ggaatatggg tattttggac tctctggtta gatgcagctt ttacttcaca tcctcagtgg    35100
tactactgta aattttcatt ttcctgtgga ataccctatt tggttccatt gtatatagtt    35160
gacaactaga attcgttcgc tgttgcttga gcccaactat aacttcttgg cactatacct    35220
atcttctgat gtgcctgtgg aagagctacc ataatgaatg tgtacatgga caaaaaaaaa    35280
gagagagaga gagagaatta aatcatgagt ttgtgccttg ggagctacag tttaaacatt    35340
tgctgttttt ctcacttaat gaaaaattta tttgaaaata acagcacaga aaggaagaaa    35400
gacaggctgg caagcatcct cctcctaata cacttatcca cgtttggata ccttggtctc    35460
agcctcagag gtcatatttt tagtaaaatg gccaccagaa ataaaggatt ttattttcca    35520
gactttggtg tttggagctg gtgtgctgag agctagcaga gaaagcccta ctcaggtaga    35580
tgtaccagag caggatggtt gctggtggat atggtggaat acctttttatg tggttatctc    35640 ctccttgtaa ctcttggctg cataacccctt attttctttt ctatttttat tctctctctt    35700
ggaaaaaaaa ttggtggtaa atttcatgt gagccatatt gtcttttaa atagtttat    35760 taatataaaa tgtacgtacc ataaagcata cccatttaaa ctgtaaatgt caatgggttt    35820
ctctctctct ctctcttttt tttttttttt ttggatgctc agagttgtgc aacaattatc    35880
aaaatcaatt ttgaacaat ttcattgccc caaaaggaaa ccctctgccc attagcagtt    35940
actccccatt tccccacccc cctgacccctt caacctagg caagcacaaa tgtactttct    36000
gtctctatag atttagccat tctggacatt tcatgtaaac agaatcatgc aatatgtcac    36060
cctttgtatc tggcttcttt cacttagcat gatgtttcca aggttcatct gcattgtagc    36120
atctgccaat acttcattcc ttatttatgg ctgaataata ttccattgta ttaatgtatc    36180
atatttgttt tttccaatca tcagttgatg gacatttggg ttgttttcat ccttttttta    36240 gctatttttaa ataatgctgc tatgaacgtt cgtgtacaag ttttttgtatg aacatctgtt    36300 tttatttctc cttggtatac acctaggagt ggaattgctg ggtaatatgg tagcttaaca    36360
tttaatcttt tgaggaactg ccagatttt ccaaagcagc agaatcattt tacatttgta    36420
ccagaagtat atgagagttt tagtttctcc acatcctcaa caacactcat tattgtcatt    36480
gtccttttca gctttttga taatagtaat ctcaatgggt gtgaattggg acccccatcat    36540 gcttttgatt tgcatttcct tgaagagtaa ggatattgat catcttttca tgtgcttatt    36600
ggccgtttgt atattttttg atcctttgct catttccaaa ttgggttatt tgtctttgca    36660
ttattgagtt gtaagatctt acaatatatt ttggatgttt gtcatttta ggatgatact    36720 tcacagttat atgatgtttt ctagcaagca tttgcgttgt tctactggtg ttacatatct    36780
tagctgcatt agccactttg ctgggtatga atgccagcag aatctaagtg accttggctt    36840
cactactgag aatgcaaccc aagaacagaa atttgtcaga aatttagcac tgaagccccc    36900
```

```
cacttcccaa acttatctgg gacaaggaga atctacattt aaagctctat actttgtgtt    36960
gtgttttttt tactttagct tggttggatt taggatcttt tcttttttgtt ttgccttatg   37020 catacctaag cagaggcaag ggaggaaagg gatatgaacc tggtagaaaa gtaagtaagc    37080
tttattcaga ttggcatatc catcttaata tggttcaatt ggctgaagaa gtatctcaac    37140
taaaactctg gaatactttg aagtaccagc aatatgtacc aaatgtactt tttatttatg    37200
tttggtctct atgtacttgt gtgtgaaaca atgagcacaa ataataccct ccttgttttt    37260 aagcaatttta tattggtgat ttaaaaataa aataaactca agtgggaaat catgaaaccc   37320
catgtaaaaa caataagagc atgttttaaa atcccacaga ctttagtttc aaatagtggt    37380 tttgctatttt cttagctgtg tgtcactgtg caagttactt tgtttctctg agtctttatt   37440
ggtgatatat gtaaaaaccc accttctcaa attattgtga ggacaaaatg aagtaattaa    37500
cataaagttc ctggtgtata ataagtgttc atattttgta tttgagcaca gggcaactgg    37560 gttttttgaaa ctgcacatta ctgttgcagt caaatctggc atgaaattag tgcatagaca   37620
gaatgggctg ggaaaatgaa aggactttga acatttatat tctgctttat ttaggcataa    37680
gtgcttaata attattgata gtttcttctg gttatctgac attttgaaga tactattacc    37740
tagcagaaat ttcttgtaat aataatctct tacacttata tactgttttg tgcctttaga    37800
agtacttaat gctctttatt tcactatctg ttcataaaca ttctctgaag caagcataca    37860
gtcagtatga attccatttt tcagatgaga cagctgaggc tgaaagacat agagttactt    37920
gtctcaattc acaaagtaaa gtgccagagt ttgaaccaga gcccaggtct tctctctcaa    37980
cgtagctctt tttctccttc attatatcag gcatagtagc aacgtattct tttactagct    38040
ttttatcttg aatatccttt tagcgacttg cctttggtgt tagtgtgcct ataacattgt    38100 cgttaatat cttaatacat ttagtggtct tggcaagcag ttttgtcttc agaaggacac    38160
tgaaatctgt ggaaaggact gcagaagatt gggtgggcag acacctatca ctttcgggc     38220 tggtagactt tctattgaag caatttgcaa ggctactttg tattgtctaa aagcactact    38280
tcagaaaagg gttgtgatgt caaaataggc actttgagtg aagaaagggc tgtaagcatg    38340 ggtgaaaat gtggtagatg attgtcttga gttattttct ttaatgtcaa acaggcagtc     38400
cttggaatgc tacttcaaaa agtgttgtat aatgttgaag atacagttac agatttccaa    38460
cacgaaactc ataaatatgc aattccctgt cctcctaggc acatgaagga aaatttatga    38520
gcttcaggtt tctatgcagc tattaaagca tatttaatct gctttgagct caagctcact    38580
ctcgttggct ctcttcgttt cttcctctta catgagcaaa ctgccttttct ttttgtttaa   38640 aaatagtaag taggtttgtt ttcctccagg tgtcatgaat gcaaacattg taatttctca    38700
tctgttcagc ctttttgcac aacaaaatgg cagcacccag gaggttgaaa gggttaaatt    38760
gttccttctc tgagtagtac cataagttgt tagtctgcta ctctttctcc cagttggcac    38820
atgaccctaa catccaatcg ctagtggtgt ggccatttt tggtcttatt ttggcctttc     38880
ctcagccacc actcatcagt tctcatgcgt atttgtcaga tcctgctccc caactccaca   38940
gttcttagtt catcttaagc atatggctgt ctgtcttttc tctaaagatc ctcaagggaa    39000 aaaaaaaaa gcatctccag ggggaattta ctgcctcata gccctgacag agatttctga    39060
ccaaacccta acgaaaaaat ttcttccctc catttgtctt ttattgtttt tacaggggag    39120
atatgtaaca taataacaat tatattgcac ataataatta cttctacaaa taataatctg    39180
ttgtcaaaaa tatacacagc tttggatttc cttattatgg cccttcatta agttgtggtt    39240
taagaatagc tatgattatt acttttgtga taattataat ccataatatg gaaacttata   39300
```

```
aaattacctt taaagtgtta ctattattct ggccacagga tggaaagttg ttcgctagtt    39360
actcatttat aacctgaatg tactttttac tgaatctaaa ggtatcatct ttgcttggca    39420
attcccatga cttgtctttc tgactcttca gatctcagct taaaagctct cccttcaaag    39480
aagccttccc tgaccactct ggttttttct tcttttttta cctctactcc ttttcccatt    39540
acttgctgtc atagcattct gtttgtttcc tttgaagtgc ctattccaat ttgtcattat    39600
gaatgagttt ttttgttctg ttgcttatta tccattttcc ccactagatt gtcaactctg    39660
tgagggcaga gaccatgata ctctgttcac tcctatatac attcccagca ctatcagact    39720
ttttggcaca tagaagatac tcagtaaata tttgttgaat gaataagtca taagaagag    39780
tttatatttt aactcttagt tgaataatct aagccaagaa ttatcaacct gggttggacg    39840
tgagaatcat taatgaatct ttaaaacaat gacaaggcaa tctatttatt aattatctcc    39900
aggtctaaac tttagcacgt atatacattt taaaagccca taagtgattc ttacgtatag    39960
ccagtgctat ctgtctcttc tcctgtcctt tcccctcctc tccttactcc tctctcatag    40020
ttttaggatt agcatggccc cacaacaaat ctttaattca catggcaatt tctaggattt    40080
atcatggaaa atgagccaaa ttgccttcaa gaagttttta cgtacctctt atatagaatg    40140
tgatgtttta tatgtacctc ttatagaatg tgagctttta agaggcatat cttattgcaa    40200
gaaatttcaa tgttgaaaaa aatattgaat atttataaag tcaaaaatgc aaactttat    40260
atgattttca aacctatgaa gttatatcat gttcaggcct tctttccagc atgtggctct    40320
cagccctggt actgtcctta accataaacc tcatctttgc cctctatagg gagaggttta    40380
tggttataat tactcatttt aaatagtgta tattagtaat gtacactatt tgtatatttg    40440
ttgactgcct cctatatgcc aaccactatg ctagaaattt tgtaatattc ttcacgatat    40500
tcaagatatt aacatatccg catttttataa atgaggaaac tgctctcaaa gaggttagtt    40560
tacacagcca gtaagccgct aagcctagat tggatggaag gtatgtgaga aaaaagcagc    40620
atccataagg ttttcattct cctaccctgt acgacagagg taatagaaat tattagttaa    40680
agaaataata gaattttaca agactctagg aagggagaat gtgaaggata cagttctcag    40740
ttactggaat gagtgccaga gtaccagtac atggcttgcc ttggggtttg gactacctat    40800
cttaactcct ttgctcctcc caatcttgat ctcatttgtt tgaaagatca tctgcccaac    40860
ataaaaatgc atttctaatt ctgtaattta agtcagtggc aagatcagat tcagttaaag    40920
tttactttcc tgacagcttt ttagtatcat atctattttg caaaactcta gtgataaatg    40980
tatgcacatt tacacataca gcatctcttc tgattctgac taagatatta ctgggttgtg    41040
tagaagtgat gggctcttta gaagaaaggt ttgatatact actaatctaa ggactgaatt    41100
ttctcatctt tgtcttttgcc ccttttgact gatgaccaga gcaggagcac ataacattct    41160
tttgtgctaa cagtatctct gcatcacatt gatcaggaga attggcatct ccagagccct    41220
gggatggtaa cttctctgtt gattttcagg aaagattagg tgatattttc tccatgggaa    41280
gaggatgttt gatgtgtgtt ggctttagca aaaggaagct tgtggagtca actgtaagta    41340
gacagaattg cctttgactt aatctgtttc agtcgttgtt catactcagg tcctccagag    41400
gacctttaag catttttatt gactttgtgg tctattacac gaaactaaag atactgattc    41460
tcagtcatga gtctgctcca aaattgccta gggaatcaaa aataattgta ccagttccta    41520
ttcctggaca ttatgattca tttggtctgg tatgaaggcc aggaatctgt attttttaaaa   41580
ttcactcaag caattttcat atatagctat aattgaaaat ctgtggctga acttctccac    41640
```

```
tcccgtatcc atcgcaatac ttccccaagg tggcatttaa gatgggccta gagggttata    41700
taagatttca atattaaaac atggattaaa agtgaagact tttcacatgg agataatttg    41760
gaagaaaaac ttgcaaaaat gtgagagcat tgagaacttt tctttcccaa ggaaagaagt    41820
ggcagcttca ttttttggtca ttgcaaacag cagtgccata catgaaagga aagtggtggt    41880
gctcatcaac tttgaataac tttgtacaga acccttgaga ctcctctctg cttataaaga    41940
aaaagtgtca actgtaaagt tgatttattt atgaaccata ggctactatg aaatctctgt    42000
tcccagctag aggcctggga gagtaagata actacttgtt tattccacgg agccactttat   42060 tagcttttc  tatagcacat acctcaaatg aagcatttca ataaaagaac cacattctat    42120
tcacatgctt cattttattc tgatttatgt aaaaattccc aaactcctca agcagtgttt    42180
ctttgtaagg caataatctt cagttctgtt gcaaaggtca ggagtgatag aatgaaaatg    42240
gtactagata caacagctct ttggtatttg catggccatt acattgccat ggggctgcaa    42300
gacttgtgag tgcttgatat tttgcttgtt gatgaatgag tctgtgtttg tgctaatgga    42360
gtgatttgag aggtagttct ccactgtcag tcaagaggtt ggttttgaaa gctgattgcc    42420
aatggtcatt ctgctaacca ctctggttct ccttagata  gagacttatt cagattcaag     42480
tcttcatgta ctttgtggca taaacattgt acacaccaga tgtattcaac aaccataaaa    42540 aaaacaatt aggactcaag tagtatgtca gagtgtagtc actgatgata tataattctc     42600
cactaccaag aagatggaag cacactgttg agtagctaca tcctacatat gttggccaga    42660 attaggaat acacatgtga tctatacatt ttgaggtatt gtctgacccc tagaaaatcc      42720
tggtgaagtt tttctggtgt cagtttggtc ttaatgttta ggaaatgccc acagactact    42780
cctgctttct gcttattcac atagtaaacg caaagcacag gactagtttg tcatctggat    42840
caaggagaaa tgagttagca gatataaaat aaatcagaaa ggaggtagtt ctcaaatatt    42900
tactccatga atagttgctg gatgttcatt aactctatag catttgttac tacttattgg    42960
ggatcctgga aagaaaatat attgtctata tccactgttc actgaggccc tctccctacc    43020
cagaaactcc ctgtctccat cactcactct ccacattcat tgacccaggg gaacagttca   43080
tggatgagtg aacttgagct ctatcttaaa ggatggagtt cgatttcaag gcaagaggta    43140
taagagaaag ttcagagaca acactggcta tggtctttgt gaagaaaagt gaattgaata   43200
ggctcctgtg gagatcttaa gtaagtactt ctggagataa ggttgaggaa aagtaggttt    43260
gaatcttcat ccagaggtag cccctaaatg tgttgagttt attgaaagag tacttgactt    43320
ggattcagac agatctgcat ttgactcctg ttttgccatt tataagaatt tgagtaatta    43380
ttgtttctaa ataagagttt attgagccaa gcactcagta aatgtttgaa tgggaaaatt    43440
aactgccctg ttttctatt  gtcagatggt cctcttcgtt ggataacttg gtaactgttg     43500
ataacctttt ctcaggaatc agaaggtaga aaggttggga aaatataaga aacaaaaagg    43560
catattccta ttttattt  catattgtct tccaactctc ccaggcttct ttgtttgcaa     43620
ggctgacttt tataatactt tttgggtaga gcaggtcctt ctttggtttg ggttaaacc     43680 gtgagtaacc ttattttcta ggtctcagcc aactttgaag ggcatgaact cacagtagcc    43740
tcactaggat cacttcagca gtgagaattt atctttcttg tataaaagtg taagagttga    43800
tggcggccag gcgcagtggc tcacgactgt aatcccagca ctttaggagg ttgagatggg    43860
tggatcacct gaggtcagga gttcaagacc agcctgacca acatggtgaa accccatgtc    43920
tactaaaaat acaaaaatta gttgggtgtg gtggcacatg cctgtaatcc cagctactca    43980
ggaggctgag acagaagaat tgcttgaacc tggaaagcag aggttggaga ttgcagtgag    44040
```

```
ccgagattgc accactgcac tccagcctgg gtgacagagt gagactgtca aaaaaaaaaa    44100
aaaaaaagag ttgatagcaa ataaactatc tgtagcataa acctcagtat tctttatcat    44160
tcagtatcaa cattattact gaaaacaata agcaatatgg actgagtttc tgtggggtgg    44220
aaatgtgaag tggatcatag catgatataa cttgtcattt ggcttccttt ataaacatta    44280
tcaactacct cagctctatc aatcacttgg cagtccgtag tgaacattat aactcaaatg    44340
actagtcagg tctgttcatt gcccatgtaa aggcatatac ctgaagtgag aagtctgagg    44400
taacttagca ataagcttgc agtacagtgt ttagtgaagc cgaggaattc aaggatttga    44460
gtcatgccag attgctccat aaccatagcc tatctttgtc acaagtaaga aggttttaaaa   44520 atcaccatac cattattggt cacaacgttt ggagatagggg aagagtttgt ggatggatca   44580
tggcagtgca tggacagtga ttagcccata acacaaccag tgaacactgt tgtacccaaa    44640
gcacataaat caccacatat actattaata tatttatgga tgacaacaga cactataatt    44700
ttatgtcagt gctttctgct gtgaaaaaca aagaaagtta agggtacctt ttttatattt    44760
gcatcatatc tccagacctt tcctttatc tccttcttgc aagttcttct ttctttcagc     44820
tgactatctg ctgttcctgc tatggctccc agtggctttt caagagggta cttgtttttt    44880
aagagaagac ccttgaagga cagagagagc ctgaatcatt caaaataatg aattactcag    44940
gatgaaattt caataatttg caagtgtgtg gagatagata ttttgaggaa gcataatttt    45000
ctatgtaccc ctcaaatcgt ggctggagat gacagcctct tccacctcca tataagacca    45060 tttcattcc ttctactttt ttctccctcc ttccccaaa cacacaaaca tacacatatc      45120
ctgtgcttca gtcacacaga acttcttact atttcatttc aattctctat ggctttgcat    45180
gttctgctcc ttctgcctag aatgctcctt tccttttttc acctggaaac atcccaattc    45240
aaatgtcacc tcccttattt ataccaactt tgtctgtaac tcctttatca cacttcttcc    45300
tgtgattagt caattcactt gtctgctgtt acacctctat gagagatgaa aattccttct    45360
ccatctctgg aactcatgcc cttcgcatat agtaggcaat ctgtaaatgt ttgaaggttg    45420
agtgaattaa tgaatgacct tcaacctttc aggcttccaa ttttctctct gaaaaggaca    45480
gccaaatgaa aactcataat tttagaagat gaggttagac ggttggtagg tgcatgcaga    45540
gaccagttat tatttaggta ttatggaagt ttatagttct tgtatgttga gttcagtgta    45600
agagtggccc caaacatagt taatgaccac tccagaccca gttgttatag agttggcccc    45660
agctgtattg cttctattta agactaggat aagaaatgac actttcctac tttttacctt    45720
attgaaaggg tagaggctca ctgttatcaa tctcagttca cttgttgatt gcactggctt    45780
gccaagtgag aatattagca cctctgcaca tttctatagc tctgccactt atgagatctt    45840
tccttcccat tgtcatattt aataatcagg atagccctat aaaatatgca ttctcatttc    45900
ccagatgagg atactaaggc tcaagtagga gaacttactt gtttagtaag atcatacagc    45960
taggaagtgg gagaggcaag agttgaaccc agatcttcct agctcctagt ccattgttct    46020
gtctactggg tcacactgga ccagccagga ggcaggaaaa tcagctgggg aatgtggtgc    46080
caacgtgtga tgtttgccta aatgtgtgca tccttgctgg aagccagcca tgattcatgc    46140
tgcataagta ttcattaatg ttcatttcat ttatttggct atccatatgc tttccagggc    46200
gaaggcaagc taggacaagg gcagacaagc agccttaaag tttgggtgct ttccttcgaa    46260
gttgagctgc ctgtttgaaa atcacacttt ttggtgatag aagatggttc cagtacagat    46320
tttatttatt actgcatcta catggataga cattttccaa agcatagctg aaaatatgtg    46380
```

```
taagtcccag aatattttct gatttagaca cagactttga gcatgataac cacatttagc  46440
atgttaggaa attctgtcag aatgcttctg gaaaggctac cttccagaa tgaaatgaaa   46500 aaagaaaagg atggactttg aaactggcta gatttgggtt atacttactc atagtgtgac  46560
cctggcaaat gatttaactt ctccgaattt cacttttctt attctttgaa gtgaaatttt  46620
aaaatgccat cttgcctgat ttttgtgaga atgaaaatga gatcccacac caggaattta  46680
gaagctactc agtaaatatt gcttctctcc tttcccttc cccagtcctg tcccccgaga   46740
cattcagtag ttattcacag gcatgcattc tgaagtctgc ctactgctcc atgttgaaat  46800
gcactgctct tgcaaggact gattatctat ttttctgtct tccaaggccc cctgtgttcc  46860
actccaccct cccaattctg ggggcttcca aagtgggcag gtacagaatg ttctgtggag  46920
catcggaggc tgttactcaa tatcttggcc agcactctca actgctcttt gcacacactc  46980
catatgaagg caaactccag atcttggagc ccatgtgtgt gtcatgcatt gtactgcttc  47040
ttgtacccaa atccatctca agggtgagta gaccaggctc agacttgtcc tgggagcaga  47100
tttctcaagc tgcccatgtc cccacactgt ttgattaaaa ggaggtgctt caaactcttt  47160
ggctttatat agactagaat cagaatgatt ggtggtgcct ctgttctcaa ggtatcccaa  47220
agcactttgt aaggaaatat gacaagcgct gaggccatgc aggccagtac aacagccgcc  47280
acccagcact tcacaattag tcatgcccag cctgggatca tcaagcctgt ttttattgga  47340
agagcaagag agagagggaa tgctagctgg caatttcccc aggtacccct tatgaaagtg  47400
cccttggctc ttccaatttc atctgaataa ccagctcagg caaattttcc tctatcaaaa  47460
agcagaatgt gatagtgaca agctgatgcc cggctgatgc cccaggacat tgactaaata  47520
gacttggcct cacaattggt ttttattctc tatctccttt cttcccttt gttcttttc    47580 tgtgtttctt tccccattgc catctgcaga gtgttctcag tcagaagtca gctgtggggt  47640
ggacagtttg tcattttaag atcatcccta ttctgtctac cttcttatc cctcatatca   47700 ttgcttttag agcaaggaca attctggaag tgaaactaca ataacactct gggctccttt  47760
ccctctagta gtactcaaca cacttgtaat tacatgttca aatttgtctt tcttatttct  47820
acttaggttc atgaaggcaa gggacatgcc tgtgttgctt actttctctt ggcaggcaca  47880
tacagcaagt cttcaaaaaa tgcttgttaa ctacaaatta agtgtttaag aagtccactg  47940
ttaattagcc gggcgcggtg gcgggcgcct gtagtcccag ctactcggga ggctgaggca  48000
ggagaatggc gtgaacccgg gaagcggagc ttgcagtgag ccgagattgc gccactgcag  48060
tccgcagtcc ggcctgggcg acagagcgag actccgtctc aaaaaaaaa aaaaaaaga   48120 agtccactgt tagtatcttt tcccctgcct agtttgtaag caactggcct cttctatttg  48180
taagttacct gttttcattt ccatatgccc caaagcaaac tttagctcac ggccttacag  48240
agtgtgtatg ttagtatgtt aaaatgaaat caactttcct ctcccaggcc ttctaattga  48300
catgaatttg ggagtagact tgcattggcc tttgtcctga cagccaacag agtcctcttc  48360
tgttgtattc actgttgcct tccatgagga tcccatggaa aaagtttgtc attgatatac  48420
attttgaggg cagactcaac ttgagtaaac ctgattgagc tttccccatc tgcctcccag  48480
agatcactgc ctgtgctttg ttaaaaagag aattatagga gtcctctcaa ggcagagagg  48540
cctaaaatta gacatggcag ccatgccttt ggtgtgcatg gaggttggat acaggcagcc  48600
agtttcccct ctgttttctc ccttgcttac acagccaagg agtggagcca agcctcaagg  48660
ggaggagctg tatactcgag catgcccgt ggttcctggc cctgactgag ggactatttt   48720
atatatccca atagagaagc gtggaagaca tctaggttgc cactgtcatt tgaaattgga  48780
```

```
attttttaaaa gagaaacctg aagacttgaa gaaagctttc ttttgcctcc ccttacagtt   48840 gattttttgag cttcttaaag ctacctagtc caaagtaccc acactcttat tcttttgtct   48900
ttcctactgg ttttattttt ttttcatctt cccaggtgtt tgatgatcac taagagcttc   48960
aacattgctc accctgacca ggtatgaagc caagagtttg gtttagggca taaaagaatg   49020
tcggaactca aggactaggt tgaggtgggg aaggggatg aaggcttctt tttttcttgg    49080
gttaagcaga aataacttag atctcagagt gaaagccttg aattatcaca tatatcactg   49140
gaaaagacta gttctttgct atgataacaa ttgttcatca tctctcccct gaggatttgg   49200
ggtcaaggcc tggctacacc ttttaatgat ttcagtcatg tgacttaacc tctttaaact   49260
tggattttct tcatctttac aatggaaatg atgacaataa tcactacctc acagatattg   49320
ataataatga tatctcacta ggaagagaat taagtaatat gagggataaa aaggcatttg   49380
taaatggtaa aatgagatta tgattttgaa agctattatt attttccttt cactgtctat   49440
tatctcaact cttctatttt cttgccttt gtacagcatg gataatttag atgtgactct    49500
ggacagaggg atggatcaga tgacttctta agttatcttc cagtttagga gttcgtaaac   49560
tatactttct cctttccaga ctatcctagt aagaaaattc tcttttaaga cagagtagaa   49620
ctctggaatt catcagtttt gatgtttctt aaagtgtaat ctaagatagt gctcctgtat   49680
taagttctga tgtctgacca ttgttcaaat aaagagtaaa atgcaaatga caggaaattg   49740
gctgcgttct gaatcctatt tttatttggg ataacaataa gcctgtatgg tcactgtgac   49800
ctttgatttg ctgtttctgc aacctcacac ttgtctcagg attcttcttc cacttctgca   49860
ctttatattg ggtttcttcc aggcatcata ttaaacttta agccaggtat gtgtatatgc   49920
atgggctgtg ggcctgaaaa aaattagccc gagagagaaa aaaatttaag tagtgggcta   49980
gaagtaagca tgctactaga aacagaattt gggaacacag ctctgggcct agaaaagcga   50040
cctgtcaact tgttacagtt aacatcaata actataggat gggtttggtg gaaaattatg   50100
ctgaccaaca gggtgggaga aatagggtc agaatatata tcgctgtaag gttgagaaaa    50160
aaagaagtga aaaaaaaaga aatgcataga gagaaaaagg agtttagagg taacatgtta   50220
aagtgtgaga aataaactgg agagcttgac ttctcttgaa tatattttta aataaagtac   50280 tccttcaac tccaaatgca gcaggcttgg ttcccttctc ctacctccat tgcggatgaa    50340
agcttaatct ttaagatggg cttggtggg tagagtacgc cccttggtga gcactgtgct    50400
ctctgcaacc ccaataaggc ccaacagggc tctccaagga ggcaaaattc tgatgataca   50460
tttctgttta gtggaaaatg ggtagggaaa attatgtctt agaatcaatt aaccaaacat   50520
aaaatcctcc aaggggcttg gtaggatgcc tagggaagag ccacgagata aaaactccag   50580
gctggaaggg cattgttgca gcactgtcat tctccagttt ctcttggagt tgtcaccacc   50640
ctctcctttg ttctcactgc tgacatcatt tgtaaaataa tttcttccct taaataaaca   50700
agacatacaa tcctctaaat gactaaagaa cagttaccta aagaaacct tagtggaaag    50760 tattttcttc atctaacgga tgattgtctt tacagaggtg gagtaaagga tgtgcgaggg   50820
agcataatca agctaagaga tgcatgctga cttaaaaggc atgatatatg tgaaactaag   50880
ataatgtgtt caagagtgat gctttgttga tgcagaacca ctgaattcct tactattatg   50940
tttgcctgac tatcggcctc ttaataaaga acttgtggtt tgagtgttca ttgaaattag   51000
ccatattagg tttatgtggg gatgtgagga tctatgtcta ccaattgcag cctctgctgc   51060
aaattggagg cagaaatctg ggctgaacaa taggtaagag tgtcaactct acagatctct   51120
```

| | |
|---|---|
| cacatgctaa gcaagcacaa tatagggcaa tccaggttta cacaaaggat taatttggga | 51180 |
| acaattatcc tcattttcac ttcctaaaaa gattttgaat aagatgtctt ttaagtaaga | 51240 |
| agctccctga atgcatttaa aatatgattt gattatgtac atttcagatt tttctacctt | 51300 |
| tctaggagta tctctgttgt ataaaaacac aaaattctgg aacttttgaa aggaagatgt | 51360 |
| gcctctcttc atacatttgt cattcttgaa cgattgtaaa atgaagtgac tgcatatcac | 51420 |
| gtcatgtgcc ctattgattt cttttcttgt tttaggaata ttcccagaaa aaaaaaaaac | 51480 |
| tttttttttt ttaaaatcta ctaagcatgc taggtaagac tgaagatgaa tctatttaag | 51540 |
| ttatgtcaat atctatttat aaagatttt gtgatattct tttcactgta gaacttcaag | 51600 |
| catatcctaa aaggaacggt tagataccct tacaaactgt ggcaatgact tactgagtaa | 51660 |
| ttgctggcaa ctgattttg gtgcttcttg ttttgatagt atagcagtgc gagtaggttt | 51720 |
| cagaagagca aaactaagac aatccaggga aatgccattt gagaatttct aactttaaaa | 51780 |
| aaacaagtaa aatagtgcca agaatattat ctaactaacc ccaaagtcta caatgtaact | 51840 |
| cttttatttt gataatgctg ttctaaccct atctacttca gtcctttccc acccagctgg | 51900 |
| tttaggaatc aaattcccaa tgtttcatca ctgttaacat tactgttta ctcttcactt | 51960 |
| tagttcttaa atggcatagt gtcttaaatt ccctcagcct ctttcacatt tgatttcttt | 52020 |
| ggaaactttt tacctttca ttgaagccca tatgatcttt tccgaaacag acccttatct | 52080 |
| ttacctcctt ctttggagtc tttctcctac ttgaatttct gaacttctta aaatggccgc | 52140 |
| tttgggttgg tgtcagtaat tcagtaataa gttttctttt cttttttttt ttttcttttt | 52200 |
| ttttgagaca gagtcttgct ctgtcaccag gctgcaggct gtagtgcagt ggagtgatct | 52260 |
| tggctcactg caacctccac ctcccgggtt caagcgattc ccttgcctca gactcccaag | 52320 |
| tagcaagtag cagcaccatg cccagctaat gtttgtattt ttagtagagt cggggtttcg | 52380 |
| ccatgttggc caggatggtc tcgatctctt gacctcatga tctgcccgcc ttgccctccc | 52440 |
| aaagtgctgg gattacaggc gtgtgccagt atgcccagcc agtaataagt tttcttaagt | 52500 |
| gctttcttaa tattctgata ttttaaaaa agatctggac tattttgtca tacaggcaac | 52560 |
| agaatgttaa accatttcat aaaacaatga caaatataca tgaattttc atcagttata | 52620 |
| aatgcatttc ctttataaca ttgaacatgt ttttgcaact gaaataagta cggttttcat | 52680 |
| ttttagaagg cacatgataa agttaaggca gtggttaatt aatttttca gattaatttt | 52740 |
| tcagaaaagt gactgtttct gtctattgtc ttaaccccag gcatcaaagg attttaatca | 52800 |
| gaaagaaccg aggaataatt tggttatttt agtgcctttt tttgagacaa agtcttattc | 52860 |
| tgtctcccag gctggagtac agtagtgcgc tcatggctta ctacagcctc gatctcctgg | 52920 |
| ttcaagtgat cctccaactt cactttccca gctaactggg accacaagtg gcaccacac | 52980 |
| tctctgcaat ttatttaat ttttcataga aatggggtct cactatgttg ccctggctgg | 53040 |
| tctcagaatc ctaggttcaa gcaatccttc cacctcagcc tcctaaagtg ctgtgatttc | 53100 |
| aggcataagc cactacactc accctattt agagctttgt caagctttgg aaagaaaacc | 53160 |
| atttataata taatagataa attatggata tttgaggcag ttttatcat agtatacatg | 53220 |
| gtaaaccaca gccccccttt ataatatttg tatttaataa aaatgaaaat attacttta | 53280 |
| tcttaaacat gttttaacaa agcaagcata tgtagattag cactaattaa aacaaaaacc | 53340 |
| tttgtaatga tagctgtttt ttatatgatt acaaaaaatt tactatacaa atttttatcc | 53400 |
| taatcagtgt gaaaaactgc aaatattagc ttataggggc agtcttcaga gtcctcttcc | 53460 |
| tacctactac tgctaataag ccaatgaaaa actctctgat gtgtgtggtg gctcaggcct | 53520 |

```
gtaatcccag cactttggga ggccaaggtg ggtggatcac ttgcactcag gagtttaaga   53580
ccagcctggg caacatggtg aaaccctgtc tctactaaaa atacaaaaaa ttagctaggc   53640
gttgtggtac gcacctgtag tcccagctac tcaggaggct gaggtgggag gatcacttga   53700
gcccaggagg ttgaggttgc agtgagccaa gatcacagga ctgcactcca gcctgagcta   53760
caaagtgaaa ccttgtcaaa aagaaagaaa gaagagagag agagagagac aggctcctcc   53820
gcttttcag ttcctaaata attttccaat ctagaatgca aaagattctg aaggaagaca    53880
gttaccattt cagatcggca gaagttgtgg ctttaatcta gactcgaata tgttttacat   53940
caaagggttg cctcaacagt gctcaaacct gcctctctga aaacatgctg agcacgaagg   54000
ttacttgaag tcttagcttg agtacttaag agagtgctat ggagggattg ttgatgagag   54060
ctgtgtcaca gctaattttt ctttagtaat taaaggttta taaaaatctt acactgtata   54120
ttgacaaatt tagcaacaaa atgagcttga gaaaaaaatc aaggcctgcc atggcatctt   54180
tgcttttttt tcttaaaaaa aaaactttt agaaagatta tgcgactgta ttatctgtaa    54240
ctactgcaat ggtgtaaatc ctgatggtat aatttgcttt ttaaagctat ctttacttca   54300
gtataactta gattaaattt attttaaatt taaatgatat ttttctcttt gtttattatt   54360
ttataatgtt tcccatagaa ttcacaaaat tcattagaaa gattttttt tacttcctta    54420
ggtcattaag attctgattt gtcaatggat ttcacataaa ccctgtcttt ccaaaaatat   54480
acaaaaaaaa aaaaaatagc caggcgtgat ggtgcgtgcc tatagtccca gctactcaga   54540
aggccgagtt ggggaggattg cttgaaccca ggaagttatg gctgcagtga gctatggtca  54600
caccactgca ctccagcctg ggcaacaaag tgagacccca tctccaataa ataaataaac   54660
aaataagtaa ataatttca ccttgaaaag cttataaatg tatgaaatca caatgagggt    54720
cgctgatata gtttggatgt gtgtccctgc ccaaatttgg ttttgaattg taatcccag    54780
tgttggagat ggggcctgga gggaggtgat tggatcatga gggcagtttt ttcatgaatg   54840
gctcagcacc atcccttgg tgctgttgtg gtgatagtaa gttctcatga gatctggttg    54900
tatagcacct cccccccttgc tctcttgttc ctgctttcac catgtgacat gcctgctccc   54960
ccttcacctt ctgccataat tttaagttgc ctgaggcctc accagaagcc gaacagatgc   55020
cggcaccatg ctttctgcac agcttgcaaa gccatgagcc aattaaacct cttttttttt   55080
tttttataaa ttacccagtc tcaagtattc tttatagcaa ggcaagaatg gacttacaca   55140
gtctcttttg tatcagggag agggtcttct tggtgactcc acttcttttc tttgtttatg   55200
tatccttcca gatgatgtat ttatttcctt tgttttcaa ttgatattta ctcttaaatt    55260
aaactaatta tttaaaaaag cattttaaag tctcatttta gattattttg actatctgat   55320
ttttaaaatg gtttaaaaaa tctatcttgg cctccatatg caatcaaata agaaacacat   55380
tttaagcata ttatttacct tgtggattct gccttcctca gtgtgttcag tctgtgtata   55440
ttcatttctc ccacactgta agaagctagt cagatgtata attggattat catgctacat   55500
aatcttagca cactcatttt aagcatacat agactagtga gcaccactca ttacatgtca   55560
tttctctaga gaaactagtt gggccatggc tgcaggactc tcacttgaaa agacatgtgt   55620
ggtgatgttt tctcaggcag ttaagcaata aagtgtaccc tgatttgcac tgaaaataaa   55680
gattccttta aagggagcag ttctagttat ctctctcttt aggtaccata tgctgaacgt   55740
ttttctatgc actaaaacag caactaggtt ttatactctg ccttacagcc tacttcacac   55800
ccatttcaca gggagaggaa cagagaggta agtgatttgc cccaaattac ataactagga   55860
```

```
agttatttgc tcagtgtgga aacttgttca gaaggtcatt tcattgaaat gtaggaagag    55920
tttctggcac ttctcttgag caggagtcaa aaacctttt ttgcactagc ccagatagta    55980
aacattttag ctttgtggg ccatatgatc tctgtcaaaa ctcctctact tcgttgttgt    56040
agtgcaaaag cagctataca caatcctgaa atgaatgggt gtggccgtgt tccagtacaa    56100
ccttacagaa aaggcaatag ctggatttg gctctgagac tgtagtttgc tgacctcagc    56160
tcttgaactg agctctttaa ctgacctcag ctcttgaact atggtacaag atcccatggt    56220
cctgtttggt acctccattt gccctccttt tcactctctg ggagcatagc taagttcaaa    56280
attgaattag gtacttgtag taagagcata cttataatcc tgggatcttc atgttgccag    56340
atattaacct cttgaagttt ttcaccacaa cctgggcact tttctgattt gctcacttct    56400
agccccacct ttgggcccct tcataagcaa acatgcaggt tttccagaga gctgtatgct    56460
actgaatgca gaaaatttgg ctcatactgg cctatgact atctgctcac tgccctgata    56520
actattttcc aagggagtgg gtgccctacc tttcctacat gaagttttt gctagtcttg    56580
ccctaaaaat tctaggtatc ccttgctttt aggataaata tgtttcactg ggaccagctg    56640
gaaaacgaaa aatagaatta tccaactacc actttaaaat tggacaaaga cttttgttgt    56700
tgttgttgga gggggtggta aacatcattt tagcagacca aatatacttt tggtgaaagg    56760
cagcctgttg caaagacaca acacttggac aagattttga agccctggtt gcctttacta    56820
ctgacttaac tacagtattt gcggacttga gcaagttgct tcccttctgt gagcctcagg    56880
ttattcatct ttgaaatgag tataataacct gtgattataa ttacttatct ggattctgca    56940
gagaattgaa ggagataatg ggtgtaaaag tactttagcg cccagcactg ctccttatga    57000
aaatgaggaa ataattgaga tgagtgagcc attgaggcaa cagtacaaaa agtgctgaaa    57060
actcactgct taaataagca cctcttactg cttttgtggc actttgtagc aatgtttttt    57120
tttttttttt tgagacggag tcttgctgtc ttgcccaggc tggagttcag tggcacgatc    57180
tcggctcact gcaacctccg cctcacaggt tcaagcattc tctgacttca gcctcctgaa    57240
tagctggatt agaggtgcgt gccaccacgc ccagctaatt tttgtatttt tagtagagac    57300
ggggtttcac catgttgatc aggttggtct cgaactcctg acctcatgat ctgcccgcct    57360
tggcctccca aaatgctagg attacagatg tgagccaccg caccccacct cagcaatgtg    57420
ttttattct gactagaaaa gtaatgtttg gttttgtttg gctctttgct taatataccc    57480
ataataaggg tacctatttg cctttggacc attagttcaa atattattt attaatatgg    57540
aattactggg ctccagaagc catagtcttc ttagctgctc cctatcccca ctctcacctc    57600
aattttttt tttcactttt gttttcttc tcagggaaag gtttgaggca aagaatgtct    57660
tcttatgatc caaaccaag catggtggtg atttattcac caagagattc ctaagtacct    57720
gtgtgatgga catggtagaa tctttgtcct gagggagcta tctagatcca ttccttctga    57780
tatgcagcca gtagccactt gtggtaatgg agcaatagaa acaacactag ttcaagtgga    57840
aacgtgagat gagaagtagg aggtggagag aactaaccag aagagggtac ccaaataaac    57900
cagaaatatg tatgtgttag agaaggggcc tattgagcgg gtggcagtgg catgtgtggc    57960
attacttgct cctgtattct ctgcttttta cttagttgtg gctttggtgg tatagtctca    58020
aatctaagtt acgtaggtaa tattgttatg tatcatgttt tggcaatgta gactaaatac    58080
ttgctcataa gagtacagga caatgaggat agtttggttt tgtttactgc atggaaaatg    58140
caggatgttt agtaaataga ttcatggcgt agtgagttca ctactaaaat cagactctga    58200
gaatgggttt gatttaaatg gctagtttag aagactgaat ttaggccact tgattgagaa    58260
```

```
aggccatttt gggtaattat aaaccaccaa cattgtgttt tgaatgttaa agcttatatt   58320
tgtcttccag ttaccagaat gtaagcttct tgaggaggga gagaggagtt ttcttaatct   58380
ctgaacctgc acctttcttc tgtgcctagc ccagtgcctg gcaccaaaca ggtgctcaat   58440
caatgttgat tctatgctac caacaaaaat gagtccatga tgtttactat tcaacaaatg   58500
aatacaattt tagagtaaat ttttactgct tacactacat gtagattttc tttttagaga   58560
tttcgcaatg ctgatttatt tcaaataag cttgaagcta agcgacaaag ctgaatgatg    58620
atttgttttt tatttatttt taaatccaaa cttacaattt tacatgtcat tgccagaaaa   58680
atcattaaat aaattatgat atgcgcatat ggaatacttt gcaaccatta aatcaaccat   58740
taaatactat gcaaccatta aatcaaccat taaatatgtt ggtatatgca aatgtgcata   58800
taccaacata ttatatagtt gagtaagaaa agctagtttc aaatgagtat gttaatatca   58860
tctgactctt gcaaaaggaa aaccatacat ttgaatgtac atatatgcat atgtttatat   58920
gtgcatagaa aaagctatga ggggatatac ctcaagttgc taaaagtggc tccacctgga   58980
gagggacatg gaaaggagtt ggctaaaaac tgaggtttgt tatggtatac acccctgcac   59040
agtttgattt tttaaaaaca atgattataa attacttttta ttatttataa aaatattatt   59100
taaaattttg gtactaaaaa cagagctcca tcaacaggtc aatggataaa gaaaatgtgg   59160
tacatatata caaccgagta ctattcgtca taaaaaaatg agaccctgtc atttttgcaa   59220
caaaatggat ggaactggaa attattatat taagtgaaat aaggcaggca cagaaaggca   59280
aacattgcat gttctcattt aatctgtgga atctaaaaat caaaacaatt gaactaatgg   59340
atatagaaag tagaaggatg gtaaccaaag gctagaaagg atagttggtg gggcagggga   59400
gggtgaggtg agcatgttta atgggcacaa aaaatagaa acaatgaata agacctatta    59460
tgtgatagca caataaggtg actatagtta ataataattt aattgtacat tttaaaataa   59520
ctaaagaggt ataataggat tgattgtaac acaaagaata aatgcttgag ggatgtatac   59580
ctcattctct ataatgtgat tagtacacat tgcatgcttc tatcaaaaat tttcatatac   59640
cccataaata tatacatcca ttgtgtactc acaaaattaa aaaaaactgt gcattaaaga   59700
aaaacaaaaa taaaaccat agttcaagtt ataacaaaa taaggtaat ttggaggaaa      59760 actgtcttca gttatattgg atatttgggg gacatttttg tatgttagtt agcaaagatc   59820
acttgaaaaa gaagattctt ccttctatga ttcaagggag cctagcaaaa aataaatgaa   59880
atgaaataaa ataatacaaa gagaaaagat tattccataa attctgctta cttatttctg   59940
gcaaacttgt tgacagcaca tgtgaccttt tggtaaaaag acattttat attttttagtt   60000 aagtttcaaa tataaattgt ttgtgttttt aaaataaatt aaatggatga tttcagccag   60060
atcattatga aaacacatga gatattgggt tatgcaatga ctaacagtgt gtacctttttc   60120 ttgatattta ttcataaact ggggaataaa agtacatttt ggcccattta ctccttaaat   60180 aatttttatgt ctcccaagga gagttgtaag ttgcttgata gtaaatgcta tgtattttgt   60240
accttagtgt atatattatg ggatttcagc gttagaagag ctcttaaatg ccgtgttcat   60300
agtccaacct gtcttctgat gcttgaaatc cccttgcagt aggaaatgca aagtagagag   60360
cagacactca ataatgtagt tagtgaatta tttagaaaga ggcattttga gcccataatg   60420
tatgataggt acttctacat ttattatttt attctttgca gacctgcaga aaactgtaag   60480
aaaaaagttt atttcagatt catgtgttta tttgattaat ctcttcatag gtttcatttt   60540
tcagctcctg tcagaaaata cagattctta taaggttcac cttttaccca taagaataat   60600
```

```
agtataaagg ggataatgtg aaatacaatc acttcacaga ctgtttcaat taaataagag   60660
ctcgtagata attcagtcca ccacacccca ttttacagat gttgaaattg aagccccccac   60720 caaaaggaaa agacttgttc aaagtcacac agcaagtcag tggtgaacct aattaggccc   60780
cctgccttcc attttagtga gattcctgtg ctgatagtca tacccatatc aaatcctctt   60840
tggcagttat agcttgccca cagtaatgtg tcctgaaaaa tatgacaatt aattaagttg   60900
gagacagaac cataacctct ttataaaaat tttctggaaa gtttacatga cagtaagtaa   60960
tatataatta gaaaggataa ttcttatttc atatttatct ttttgtttca gaataataaa   61020
ctaagctatc tctactcagt ccattttaat acaaaaatat ttttacccgg actgagtttt   61080
tatgcttttt aggaactttg tatctgcctc acttagttaa aatcctagct gcactaatca   61140
cttactgtgg tgggcagaat tctagaatga ccctgaatac cttgtccttg tatgattcct   61200
tcctctttaa gtaaggataa aaactgtgaa tatgatatca ctcccttgat taggctttgt   61260
tatatggcac agttaacttt aagaaaggac caatcacaca agccatttga aagcagaggg   61320
tttgggtatt ttttaactgg tggcagaaag ccacgcagag atttgaacat tgaggggaat   61380
ttgaatttga tgtgccagta ctaacttgaa gatagaggag gctgcatgga aagtggcctt   61440
taggagtgat ccctggctga cagccagtaa gaaaatgagg gcctcagacc tacagccata   61500
aagaattctg tcagtgaact tgaacttgga agtggattct tcctctagaa cttccatata   61560
agagtccagc ctgattgaca ccttgatttt ggacttgtga gaccctgagc agagaatcca   61620
gttgacttct gacctaaaaa aaaagtcaga taataaatga gtattgtttt aaactgctaa   61680
ttttgtgata atttgttatg cagcaataaa aaactaatat atttaccatg caaggcaagg   61740
catttatcct ctcatgattc agtttctttt tacctgacat aatggaatta atttatactg   61800
ctgtgaagtt gtagttgaga acatgactct ctaaagtaat agaggacatg tattattaat   61860
tttagtagta ttaatagtaa tgatactgat tctcccaggc ctatacaaat cctttgatac   61920
acaaatgaat agtaaaggaa cataaaattgt ctctaggtag actttcccac aatgcaattt   61980
taggatacag aggtcatatg cctgttattc tactgtggca gagaaaatat ggagcctgga   62040
aaactgttca tttgcatcac atacatcttg ggagctcact ctgaacctgg taccataata   62100
agctctgtag acagtataaa gaggaaagga atcagacatg gtgtctgacc tcaagtgtct   62160
cataacgtag tagaagaggt aaaatatggg tcacactaac tctactgcaa agtaggaagt   62220
gcttgtcgcc ttgagattga caaaatttgg taagagttca gaggagattg tctgtgaact   62280
gggccttgaa gaatagttag gatttgaata ggagaaggtg aagaaggaag gcattccagc   62340
tagggagaag agcacaaaca aaagcataga taaccttgaa catcatcata tgggataatt   62400
caatagttca gtataatgga agtataagat gcataaaaat aagtgtagta ggaaacaagt   62460
ttaaaagtat agattggggt tagtcataca aggccttgaa tttcaggcta aggagtttag   62520
acattaacat ttgttttttga acaaaggggt gaactgatca catctgtgat ttagaaagaa   62580
aattctagca atagtgtaga taagggttga tggtaaagtt tggaaggtgg tgaggcagag   62640
gctggagaca gggagcacat ttaggataga aagatgataa agagatgatt tagaagagtt   62700
gttttggaaa aggagaagac agaaaatgtt ttagaggtgt catagagata aaattggcat   62760
ggcatggtgc aaggaggtaa agcccaatag ctttgtaagg tgctgagata gattgaaatc   62820
acagagttag gaagttttag agtcaggatt agtaccaaga cagcttggct ctagatctca   62880
tacttaacac ttcagtgtata attctgagag ggtgggtaac agcaatagtc agaggaaaga   62940 accctttttat acatgatggt acaggaacaa cactggcttc caaccccaca gctgctcttt   63000
```

```
aacagaaggt cagaagctgg ggagaaatat gtgtgtgtgt gtgtgtgtgt gtgtgtgtgt    63060
gtgtgtgtgt gtgtgtatgt gccatttctg ggactaagga tgggaagtag attagttgag    63120
gccactgcag tggggtctgc aagttgctag cactcacccg ttccaagagg ccttaaaggt    63180
gttgatctgt tccctgggca tcaccacatt ccacaaatta atgttcctct gagagaatag    63240
ggtgattcaa tttcactgtg cccgaaggtt acttttgggg ttcatgtttg ttctaagtct    63300
atgctaatga tctgccaact gtctgttgt cactttctct aacccttagc atgtataaac     63360
tgatctgttg ggaaatgtgt agcatttata ggatggtagg attgtaaca tgcgatcaca     63420 ggactgttta tatagagtcc ctgggaaggg gagagaagag tatttctgtt acaaatgtgg    63480
attctttggc ccctcctcaa acttactgag gttcaagaat tgacatttat aataagcaca    63540
tatccatttt caataaacat gaaagtttca taccctcttt taatgtttga aatcctcaaa    63600
taaattagtc attggtgcca gagtatcaaa taattatggt acagaatgta tttctctgaa    63660
tgacaccttc tcccagagat tctgatatat attcctctgc actcaccctg tttgataatt    63720
accagtatat ggaccattta cctgaagaat aagagtaggg tttcctactg ttgttgaaaa    63780
tttgcttgac tcttaacaac ttgtgtgtga ctgtaacaag atcacacagg gtaaacaata   63840
ttagcttatt caaccactgg ctgaagaaat ttaggaaagt gaacacattt ttctttacat    63900
ttctctttgt tctgtgagcc ttttatgctg gaatagtttt cactgcaggc tgttattgtc    63960
tgcctccaga ggagggagtt gacctagcag tggtaactgg agagtgtttt ttgaaacctc    64020
tttccaaggt tagttgccaa tggcatcttt ggaacagtgt ccttcacttt tgtccctcag    64080
ggaccagtgt gagaatggga actttatgat ctggagctgg ttaagtgaag tccaaaaata    64140
attaagaaag tgtttccttc cctgggaatg agttcagtag gaatctcaat gtattgtaga    64200
gcactaagga ctcagcctca ggcatttgca aaggattctt ccagttgcct gtgttacaga    64260
ggacacagtt ggcatttcct tttggtgttg aggggagatg tgtacatggt tgtgagatga    64320
ctcacccttt ttgcttagat agttccactt tcattgtgga cagactcttt ggagggccag    64380
tttggcatgc acgtgtgtgt tcattccatc ctggagcatt ctttatgaga aagccatttg    64440
ttgagtggtt tgccattttg ttttacagcc actctgtggg ctatgaaatg gtcatccggc    64500
cgctttattt gtccctaaaa aaagcagttt ttcccttttct tatcttcatg gctgccaagc    64560
agcagaaaga gtaactcagg gaagccatgt gatagccttt tatctgtctg ttcagaaact    64620
gatgatgtat tggatttgat aattcatcaa atctgaggtt tactggtttg tatttgcctc    64680
aaaatgggca tataatattt tgtcaggtaa cataatagac agatcattgg cattgcttta    64740
ttgaagtgaa ttaattcaat aagcctgtaa gtgcctgaca tgtgccaggc actgtgctag    64800
gcattctgtt aacagatgag acaaatctct gtcttttagg tgttttcagt cgaacagggg    64860
agacaaatat atgagcaaat tgctattttt tttaaatttc atagtgtaca tgagtataag    64920
gtgctgaata tgtgattgat tctgagggaa aagagagata agggaaagtt ctcagagaaa    64980
gtcaagctga gggaagaaaa gcaccccaga cagagggact agcatagagc tatgctagta    65040
cattgagttt aagggaatgg cacatacttc actgttgctt cagcagacag caggcctgtt    65100
aggttacaaa gggccttgga tgacatgctg aggggtttta aaattttatt taaattttaa    65160
ttgacaaaat ataattgtat atttctgtga ggtacaatgt gacgttatga tatatgtatg    65220
caatgtagaa tgattaaatc aagctaattt gtatatctac cacctcacat acttattttt    65280
tggttagaac atttaaaatt tattctctta acaactttga aatagacaac acattattat    65340
```

```
caactgtagt caccatgttg tgcagatctc aaaaacttct aacaaaaact tttaccctt     65400
tgaagatatt gaactgtttt atgaacacaa tcttagaagg atttaaaaaa taatttgcta   65460
ttcaccaagt acttcttacg tacactgtgc atgaaatgat tattactttt tctaatatta   65520
gttttcttga ttgaggcttg gcaattatta gtttgtatgc ctttagaagg atcataagca   65580
gaggtttatc ccagtaggat ttgcatttta gaatgatgac tttgggagta aaatacagag   65640
aagtgaaacc agagatagtg ggatcattct ggagtctgtt gcctacactg aacagtagtt   65700
gagcgaaaaa ggatgggcag aatgtgttgg ttctgggtat tgcaaattca tggcacttga   65760
gtgaaaaagt ttaagccttc tattggctct tgtgaatat cttcaacatg catgactaca    65820
aatagaacac atggttttgt tgttattgtt gttgtgtttt tgttttttt tttatttgag    65880
atggagtttt gctcttcttg cccagactgg agtgcaatgg cacgaatttg ctcaccaca    65940
acctccgcct cccaggttca agcgattctc ctgcctcagc ctcctgagta gctgggatta   66000
gaatcatgcg ccaccacacc cggctaattt tgtatttta gtagaaacag gtttctccca    66060
tgttggtcag gctgtcttga actcccgacc tcagatgatc ctcccacctc ggcctcccaa   66120
agtactgaga ttacgggcat gagccaccgc gcccggccca cacggtattt ttgaaagaac   66180
agtgagcttg gattagaaca ctagtgtcca ggccctgctg ctactacata agtaattatg   66240
aatccatagc catcttgttg ctcttcttct ctgagccttg gtttctttag ctataaaatg   66300
ggaagttgaa actttctagc tacttctttg agttatgagt aacaagttag gtaatacact   66360
taaaagagaa tgtgctatac aaatactggt tcttaagaca gctgttgtta atgtactgag   66420
tattatgctt acctcacagg ttattgtga gcatcaaatg ggataatgga tttgtaagca    66480
ttttgtttaa agtgtgattc aaatgttaag aattagtaaa aatagtaaaa gaacaattca   66540
ttctccatcc agatgttctg tccccactgt gacttatgtg ctcattcaga gttgtacaga   66600
aaaacctcca cttaattttc acaagctgga gttccacatg taacagaatc atatgggacc   66660
aaaaaattct ctgtattggc ttcttccctg ccgtatttg gctctgggac caacaagaca    66720
cccatttgc atgagctgcc tgccaccaac tttgcgctca catctagttc tgttgcccat    66780
gtgcaagctg aatttgggcc cgggccccca gatctaacat gaaactcaag tttccttctg   66840
ttcaaactgt ccaggcataa tagtcttaaa gtccgatgcc cagcagagcc gtagatttt    66900
cactggccaa aaatcaacat gaaaccagat gtatctgtaa atctagtttc ataacacttt   66960
gtagtcaatg gaaatacagt agcaggcaga ccagaccaga gtttactatt tgcagtggaa   67020
ttaataacca catggaaact ttgcctttgg tatctgcgag atggaagata aggtgcgaa    67080
ttcaaagcag ttcccacctt accctctaaa ttccaacata aagaggcctt gaatgtcctt   67140
ctatcttatt gtatatttca ttaacagaag tatgttccta gctacttagt cattctatct   67200
ctattctcct ttgttttaac ttcagtggtg ccagcttaag atgctctggc tttcagcttt   67260
catggagcac gtcatgtttt taacttatc tttagggaca gaaatgttag gaagatccta    67320
gttcctcatc tctttgctcc tgacaaggaa atttagaatt gcctaaagaa aggatgtatt   67380
ggccaaccta ataataaatc agtattagtg aatctaaagc atatttgaaa aatttgtaac   67440
atgagttgaa attcagacct gcaatgaagt gttttttaaaa gatttaaaat cgaaataata   67500
taaagaatg ttaaaaacaa gtaaaacata tcactagtta atcactctac caaaattcat    67560
ttttatgttt gcatatttaa ccatttttat tttctatatt tgtccatgaa catgtgtttt   67620
tatatattgt ttatattaaa catggtttta atcatggctt atttctttta tgttttactt   67680
cttttccttt gacataaaat attgtatttt ttaaatttta attgcttctt ggcatacct    67740
```

```
tccaatattg gtggctatat agattgaagt taaaactaat tacaatcaga gaaaattaac    67800
aattcatccc ttcaatctca ttagtcacaa gttaaatact caatagccac atctatctag    67860
ttgctactgt tttgaatagt acagatataa gacattttca tcaacacaga aaattcactt    67920
ggaaagcatt gccctggagt aaatgtgcca gactgtacta tatcattttt ctcttgttgg    67980
acatctaagt tatttcttat tttttaaata ttttatataa cttgacggtg aatataccta    68040
tgtacatagc tatttgcttt ggctgaatta tttcttagaa tcaatttcaa aagtggagtt    68100
attaggtcaa agagcatgag aagatttttt ggaacctgca gtgtattgcc atagtcctct    68160
caaaaaagtt tatgtcaact taaagtactt ctagcagcat atgattgtac taatttcgct    68220
gcaatctcaa caacactgga cattataagt ttttattcta ccctattttc cattaaaaga    68280
tagcttatgc ttgattgact ttgcatttta ttttattatt aataatgatg tggtttcctt    68340
ttttctagat tttattttta tttaaggcat cctttgattt taacctgatt tttttctct    68400 aaaaattatt ctaagaaaag acaaggtgaa tacgaaatat atcctgagtt tttattttt    68460 tcttgcatgg gatttgtata tttgcacctt tgcccattta tactatgatt tcttagtgtc    68520
ttccctggca atttaatga agacttcatg tatatcaatt tttccacaaa tataatcttt    68580
ctaaaaatat gtttttttcca caatataatt cagacgtatt ctccgaaatg ttggaaaaac    68640
ttaagtaggc atcaaagcat ttgaagattt gtttaaaggt tgtttttata ccagttttaa    68700
attgtaattt aagggtcata aaataggtga aaattaaatc atttttcagt aagggggcaa    68760
gaccacttaa ctcttggaaa atacaggaaa cgtagatttc tagaggccaa gaaggaggta    68820
gggattattt tgtaactgcc cccaaccttc taacctgtaa tgaaacaaac actgaaggcc    68880
cttaaacatt tttaggctta attggctgtc cttgtactta gggcacatct aaaaatcctg    68940
aggcaaccac tcaagagaac atgcttttgt taattcaaag ggagctgtcc tacgagtgtc    69000
cagaatcctc tgtagtcttg ggcctggtgc ttgagagacc caaggaaag gtcaatggaa    69060 ttacagctta gtgttagagc tttcatgcat cacactaatt aattaatgtc ataaaggtct    69120
ctctcctgtt atgggaaaaa gcagcaaata ggaacttctg gtagggtgct taaagttggt    69180
ttgatatttt ttattagcat ttttaactaa tacaagtaat acatgcttat ggtagaatga    69240
taaaactgaa aaaaaaggta tgaaaattta gaagttctcc tactcatgac ctcacccctt    69300
ctttcactcc cagtttcact cctcagaggg taaccacagt gactagcttc ttgtgtttgg    69360
ttcctgagat tttctatgta tatatattgt tagatatatg catggtatgt tttcaaaatt    69420
cctgttacac tataattact gttctacaac ttaattttt cacttaatta atagacctta    69480
tatatgcttt tccatatcgg tatatataga tctatataag tttctcttaaa ggttgcacaa    69540 ctttcaattg tatggctgtc ttgtaattta cttttttgttt cccttactaa tggatatttc    69600
atgtttccct aactcttttg atattaagag tagtgctgca attaacatcc ttgagaggca    69660
gtatatgtgg tgtttaagat gaatggttct ggagccagac tactttggat tgaatattgg    69720
tgccaccaat tccttgctgt atgaccttag gcaagttgct taatttcttt gcctcagtgt    69780
ccttgtgtga aaaatggag gcaataatgg tcactatcca gtagggcttt tatgaggatt    69840
tagtaagtta ataatgcact ttaagaactt agttattttt agattaagta gtgaaggact    69900
atataattgt tagtataatt gtatacccttt attatcatac ttttgcatgt atagcaataa    69960
gacaaattct tagatgttta accattggac ataaggaatg tacgcatttt aagtactggt    70020
agatattacc ttttccctgc caaaaattgc aaatattgga tattaacttt ttaaatctta    70080
```

| | |
|---|---|
| gtaaatctga taagtataaa taacagttta tcatcatttt aagttgccta tcttaatttt | 70140 |
| gtgtgaaaat gattatcttt tcacatgttt ttttggccat ttatgtttct ttccatgtga | 70200 |
| actaactgtt cctggccatt gcctatttgt tgttgctgtt actatatggc ttttcatctg | 70260 |
| tttcttattg gttatggag ctctttgtat atacaggaat ttagcctcta tttatatgtg | 70320 |
| tgacaaatac ttttccaat ttatctttaa aatttgttta tgttttccta ttcatcagtc | 70380 |
| taaaattatg tagttaaatt catcattgtt ttttcttatg actttagagt ttggagatca | 70440 |
| tgcttcaaag gtctttctag gtggggatga tttaaatcat gtactggaag tattttttgcc | 70500 |
| aaaaagactc acgaattatg gatgttagag ctaaaaggga ccttagagat ttcctagttc | 70560 |
| aaccaccttt tcttcatacc ttttaatttt ttctctgcag atgaaaagaa gtttagtcct | 70620 |
| aaagaaagaa aagagtctaa aggttctcca gtaagctaat ggcaaaaatg tagactggaa | 70680 |
| cttctagctc ctgatgtgta tttcagtgat cattcaattt aaccagatgg tttcacaaaa | 70740 |
| agagctttct actaaaaaat aaaatacata cttaagcaac tcagagaatt ttttttttat | 70800 |
| ttttcagatt aattttcact tagagattca tcagcatatg tactatacat gtacaaatca | 70860 |
| cctgtgtgtt ttggatattt agttaaacaa atgtgcaaat attttaaccaa aaggagcata | 70920 |
| ttcatttgtg ttttattttc ttaatggttt tcgttatgaa tgtgaaatgt gtatttacct | 70980 |
| taacagaaat taagtatatt tttggtctga catatatgag aactgaaaag cattggcttg | 71040 |
| gctgctaact gcattctcat ctttctttct ctgctttggc aaagtctggg attaaatcta | 71100 |
| atacctttta aactgtttgg gacttcagcc agagtgacct gtcttgaatt cagaactgcg | 71160 |
| cagatcattc cccattctaa ggccctctca tgcctcctca ttgcctgtag gatgagatcc | 71220 |
| aagtacctta gcatagctta tgcactgtag tcacttgacc tctagcacct atgcagtctt | 71280 |
| ccagtcttat ttacacattc cttttgcacat gctgtttccc cgtgtggggc aactttttc | 71340 |
| ttgcctgtct gcctgcctaa gccaacttaa ataaacatca tttctgtaac ttctgtgaag | 71400 |
| ccttttccaa tctctccact ccaagacgaa ggtgtttcta taggcatgac ttctggaatg | 71460 |
| gcagatcaag gatctggtgg accctctact cagtgaaaca accgtttaac tagtaaaaat | 71520 |
| gatcaatcaa ccatttaaaa tcttcagaaa atatcctaag ggcacatagc aaaaagagaa | 71580 |
| acatttattc aagaaaagct attaagcctc agtaaaaaca gcaagagtct atggcatttg | 71640 |
| agtcatgacc tgttcctaat ccttcccta tctccattct tcaggcaagt gcaaccaaga | 71700 |
| agatggaggc ttcctctctc tcaaaatctt actccatagt tataatttca cccacaatgg | 71760 |
| ggcagaccac aagcatctct ttttttttccc ccagccctat attacagaat cactgttcta | 71820 |
| ggaaggcata gcttagagga ttggagattc cttccacacc cactttctac gtatgagggc | 71880 |
| tttgccccag ggatggtaag tcaagaatac agggatcctg cttgtgcctg cctcagctca | 71940 |
| tatataaggt aaagcttcca cactaggaaa ggcaaattaa gaggactagg gaatataccg | 72000 |
| ttatccccag ggtccacttg tagaacaggg gtgtcattct gggagaagca ggtcactgcc | 72060 |
| ccacttgtgg aacaggggag tcactcgtca ctgtccctgg ttcaaattct attgcagtga | 72120 |
| cagaggttct gtcccaggga aaggcaggtt gttaggatgg agaactccac agttctccct | 72180 |
| gaggtgactg actttatttg gaacagagca tgaagaagtt catgcctaag ggcactgtca | 72240 |
| aaaataatgg agatcttggt ggtgagcaat taagagtgga ttggtagctc catgatacta | 72300 |
| gtaacaacaa gcaaacagc agaccagcat ggaggatacc agagaaccag acaaaggaat | 72360 |
| cactaagaag agcccttgtg gaattgcact cactgctggg tgtgtggaaa gttatgcatg | 72420 |
| tgtgctttac tgtaccctct caaaagcaac ctaaacagga tgtggggtag gctctaaagc | 72480 |

```
attcctcaag ccacacatgg atccatcagt aaaatgtgga gggcttaagg ataaaaaggc   72540
ttaagtacaa tctctggccc tacattttct aaatgttatg ccaccctgac caaggggcaa   72600
ctcctacaaa gccaggcaaa ataataaaat catatttgtc tctagtggaa tggataacta   72660
tgcctaaaac tgtgcccttt gaaaagcaac tagagagata atttctgaag tgtttgtccc   72720
tacctgaatg tgtggcaaaa ttctaaactc cctgaagtgt gaaagtggtt tccaagccac   72780
atgcacatcc agtagtggta aagggtgaaa atctaactgg ctaagagggc ttcatagcaa   72840
cattaaccaa aaagtggttt atgtagtctt tgcctgcttc ataattccct aggcattcta   72900
tgctattctg tactcagaag gcttaaagtc aggttaggga aaggaggcct atgaggttac   72960
tgtgcagagg cagtgctggg aaataaatga agttaaataa atttaggcca tcgtggttta   73020
aagaatggat tgtggagata agaaggataa aggaaaccca gagtcaagaa aaataaaact   73080
tttcattggt gccatgccaa cccatatccg agcctgaggc aaaaggaaaa atgtgctccc   73140
tgatatacac ttatacaaaa tatcaactaa ttttatttgt tggactgaat agaaaaagtc   73200
aacaaaaatt aaaaataaaa aaatcatgac tatatttta ataagtggtt tatgtaaacc   73260
cagagttgac caatgggatg ccagtctcaa ccataaaaac aaacaaaaca ttgtgagtaa   73320
caacaccaga agtctcaaag tgtcagggaa accaatttca cagaagcagt tcagccaagt   73380
cactaaacaa acaaacgact aagcaaaaaa caagaatgag tctcagaaag ggtcaagtca   73440
gtatccagag ttgttacaat atagtatcta aaatattgtt ttgaactaaa aattttgagg   73500
catgcaaaga atgaggaaag tatgactcat acatggtatt atatgaaaaa atcaacaaaa   73560
aactatccat gaggaaacaa agatgttgaa attcactagg gaaagacttt aaaaaccagc   73620
tatttaaata tattcaaaga actgaaggaa ctatgtctaa aatactaaaa taagtataa    73680 taacaatttc ttgtcaagta gagaatgcca ataaagagat agaagttata aaaaagaaa    73740 aaaatggaaa atctggagtt gaaaattata ataactgaaa tgaaaaattc actagaaaag   73800
gtcacaagaa gatataactt ggcagaagaa acaatcagca aattagaaca tagatcaata   73860
tagattattc attttgaagg gtagaaagaa aaaagaatg aagaaaactg aagattccca    73920
aagaaatgta ggacatctta aagacacatc attaggagaa gaaagaagg gaaagaaaag    73980 agcagaaaga atatttttta aaaaatggat aaaatcttcc aaaatttaat gaaaaacatc   74040
aacctacaca tcaagaaaaa ttttttttaaa acttcaagca ggaaaatgta acgatattga   74100
tacttagata catcatagtc aaaatattgg agtcaaatat aaagagaaaa ttttgaaatt   74160
agcaagagaa aaatgaaatg gaaccacaat aagattaaca gctgattctc atcagaaata   74220
acagagagca gaaggcagtg caatcccata ttctaaacgt tgaaagaata aaaaaactgt   74280
cagtcaagaa tcatatattc aacaaaacta tctttaaagg taaaaatgaa atgaagacat   74340
tcctaggtaa acaaaggctg agagaatttt tcattagctg acatgccttg caagaaatac   74400
taaaagcttc ctagacagta gctttaatct gcatgaaaaa aaattccaat aaagggaaat   74460
ttgtaaataa taaaaataca tcattatata ttcttttcca cttaacttat ttaaaatcaa   74520
tttcttaaag cactatctgt aaaattgtat tgttatttga caataaaatg taaaagaggg   74580
gagtgggaat taagctaaat tggagtaagg aaatggtatc acatggtaaa ttgaatttac   74640
agaaagaaat gaaaaaatta agtggcaaat atgaagagta acattaaaaa cttctataaa   74700
ttaattgtgg cctcctttct tcccttagct tctgtaaaag acataagact attaaaaatg   74760
acaataatta taaacacatt gttttattag taataaacat agacaaatta tctacaacaa   74820
```

```
ttattattat acaaggagag ggaatggagc tgtagaggag taaagttttt ataacctact    74880
ggaactaagt cagtataaat atgatgtcga ttctgttaat ttgagatata tgttagaagc    74940
cccaaagtaa tcactgagaa aatgatgcaa aaatacagtt ttaaaaagtt aaaaacatag    75000
tttagcttat gtgtgcctag tactccatta ttattttttt attatatttt aagttctggg    75060
gtacatgtgc agaatgtgca ggtttgttac ataggcatac atgtgccatg gtggtttgct    75120
gcacccatca atccgtcata tacattaggt atttctccta atactatccc tcccctgtc     75180 ccctaacccc ctcaacaggc cctggtgtgt gatgttcccc tccctgtgtc catgtgttct    75240
cattgttcaa ctcccactta tgagtgagaa catgcggtgt ttcgttttct gttcttgtgt    75300
tagtttgctg agaatgatgg tttccagctt catccatgtc cttgcagagg acatgaactc    75360
atccttttta tggctgcata gtagtccatc gtgtatatgt gccacatttt ctttctgctt    75420
gttcccagga gaaagtggct gaagattcca gagagaagct gaatgcagtt taattctttt    75480
tgccataaac acgacaaccc attttcctgc aagctgtgtt agtttgctct cttcttggtt    75540
cattcattca tttattcata gcttccataa atatttaaca aacactaatt aggggccaag    75600
ccatgtgcta ggcacagggg ataaaactgt gaacaaaaca agcccagct actcttaagg     75660 aactgataga caaatggacc agcaaacacg ctggtcctgt tttgaaggca aagcgcctgg    75720
tgctcctgat ctcatgagca cagagcattt agcctaagtc tcatcctcct aaggcctcag    75780
aaataaggcc ttattttaat aagtgcaagt cagtcatttg aagactaaat catagaatcc    75840
tagaaaacta gtaccgggag caaggcaaaa gaatgggatg agcatgaaac atatattcag    75900
aagttgtggt gtgtaggtat ataagccaag ctcttttctt cacttgcttg ctaagtcact    75960
tagcttttct gccttttgt ttgctctgtc tggaaatgga gttaatgaaa tatatctaca     76020
tgatagggat attgagacga ttaaataaga tgctgctgtc acccagtatg cccttaccct    76080
gctgtactta gaagtatatg aaattcattt tctaaatttt tgtatgagtg tttcatgcat    76140
gcccaccacc atggaagcta ccttaagaca gtgagggact ttgtttaact tgtttgtact    76200
acatcctcag tctaatggtg tctggcttat ggtaggcacc aaatataatt ttattgacag    76260
aaaggatgat aatgaatgtg aaggcatttt taagtttatg aagtgttgtg catattgttg    76320
ttaattttaa gctgttacgt taaagaaccc ctaatccaac tctcttgagt tttatagata    76380
tcatagaaga tatatcttcc cttgacatag aagcttccct tgaaggttcc cttgactcat    76440
gtatttgcct cacagtgatt gtgcagatcc cacaagataa atttatgtga atgtgcttta    76500
tgtgcttgaa gtgctccaca aatatgggtt ttataagatg agaaaataga gtcagggaga    76560
aaggtgactg atccaaggtc atgcaaagag ttagtgtcag aatttataat ggaatttcag    76620
gctcccaact cccactccag tatactaagg cagattccag agaagaaaca gtggagagca    76680
ggcactgatg agggacaaag aaaagcaggc tccgtctggc tgcaacttgt ctcttcatgg    76740
caaaaagaaa ctaggaaagt gctatgccag agacgacatg ataactttgc agaatggaaa    76800
gagcttgttt accacattga atactttatc tgtgtttatc taacgacagt tccaccagct    76860
ctttaccact tgacttttgc ctaattcaaa aatataccaa ctatgaaaca ttttccttct    76920
cagtttttat tctagattac atttttgttca actttatctt aatgtgtagt gtagaaagag    76980
taaggtaaga gtatagcaag tggttatttt ccatttctac tgaggacaga gaaataatct    77040
aagggatttg tattagagat gaagaagtgc atggccagga catgagagat actgtgatag    77100
aatggatatt gtgaagtctt tggtagtttt tgagggaaa aaagagaagg ttttctttgt     77160
ctgatatagt ttagcaacgt cttaatttag gattcaaaag ttgttcaggg tccatcttgg    77220
```

```
ccttcaaatt aagatgccct ttgagagata acattgttgt tttcaaactc tgttctgtga  77280
cttaagaatg agaggagaag gaagaaaaga ggagaaaatt tgagggaaaa gtgcccaagc  77340
agcgtcaagg ctagacactg gaaatttatc aatgaaagcc acatggtgga tgggaatcag  77400
atatgtgcat caattatttg tgttccaatc catatagaag taccgtataa tgcaccaagc  77460
taataggtgc tttgaaagaa gaccatacaa gtggagatgt gttcctattc tatctaggga  77520
tagagtcagg aagggcttca ttgaataagt ggtagcctct tgggctgaga cctgagttat  77580
gagatgatgt ggcaaaggag acagatggct gggggcaagg tggggtcatt gaaattggag  77640
gcagtagcaa tataagcaaa gctacagggg catgaaaaag caaggttaga ttagtgaatt  77700
gcaacagggt ggtactgctg gaaggtcaca tggaaaagat tgtgaaggta ttgagataag  77760
aagctagaaa taagctttga atgccatcct agtactttga atttgcatgc tgtaagccaa  77820
gtggttttca cttggtcatt taataaaatt acagattctc aggtctcacc tgtaacttca  77880
gattcagaag agtctgctaa ctgaaggtgg aatcagtgtt ccatattgct aattagctcc  77940
tcagaggatt ctaatatatc agtgagttat gaccactgct gtaagccata ggtagttatt  78000
gaaagctgct atggagagga gccacagaag cagatgtttt agataggatt cctctggggt  78060
cctgtgtaat ttatggactg gagaggatca gacaggaagc agaaagactt gaataagaca  78120
gttgcagtta ttttggaggc aaagattctc tctctctctc tctgtgtgtg tgtgtgtgtg  78180
tgtaattgta ggaactattt aggcagtaaa attaacagat attagtcact gattgactga  78240
gtggatggca gtgataggtg gggtgcgttg agggaagtgt attacattaa gtccaggatg  78300
actcatggtt ttctaagttg agtcattggg gattgccatc caatgtgaga aactatatag  78360
tcttatcata gttgatcttg gaggtagact tgaattaaaa tcttgaagcc atcaattgct  78420
gtatgtgggt cttgggcaga acacttaagg tttctggacc tcagttattt cttctgtaaa  78480
atgaggaaaa taatgcatac ctcatgcatt tgttgtaaag actaaatgag gttaaagtat  78540
gtagagtgta gtttagtaac tgggacgtat agtggtccag taaacatcag ctgttattat  78600
tgtgctatat gttgtgatgt gtactggagt gagatggggt aggggatttt ttagtctctg  78660
ccaatgactc ctctccccat gatcaaaatc agaaaatcag tctcttatgt gttgaggagt  78720
gagacacttc tcccaagtgt ttaaggctaa taccttgcct tgttttgcct tgggccagac  78780
ctcactacac atctgtttaa gagatcaggg taagctctgt tcttggtgag tatctcaatg  78840
gggctgtttt tctagttctt gtagtttctt tgggccaaca tgaaatgtct aaccttggct  78900
tcttggttgt ggattctcgt caacatttca ctgctaccca agtgtgtct gcttacatga  78960 tgctatcttc cttcttttgg gtttctgaag ccctcagaca cttggctgaa cattttttcac  79020 atttcttaag ctatatcatc tgtgtttttcc ctgccacaga caaagtcaca aaaggacttt  79080
aagataggtt ttggttttt ttttccccag gttttttata cattttgggt aagggcaagt  79140
ggtaaatgct gcttttctgc cttaaccagt agtgtctgac agaggaggta gcatgatgat  79200
tgcagagctc actggactga aagtcagatg ctttacccgc ctagactcta gtaccaaggg  79260
gaagatggag tgatgtgggg taaatgggga gaaattacca tttattttga gtgtgccagg  79320 cctttttctca tgtattgtct aatgcatttg tcacaattct ctttgggttt gaaatgtgat  79380
tttcttcatt ttatagataa ggaaacttat gggaagggag gttaggttca tcttgtgccc  79440
aactttacat ggctagtgat caataatagt gagattcaaa ctcagatttc tctgccccaa  79500
agcctttgct ttttcctctt ttgacactgt aactaatgag aagatgtatt taactctgag  79560
```

```
tctcatttgc ctcaactgta aaatggagct ctgtaactct tgctctgtat gacagtaaat    79620
ctcctcagac cagacttatg ataggggata aggatatttg tatctttggg cccctaatgt    79680
attgaaagtg cttctaagtg cctggcacat agaagggcac tcaataaata tttaccacat    79740
tttccagaaa gagggtagct ccataatggg tgagatacat tttggtggct actgtagtgt    79800
ttaatgcttt taccatctgt taaaatgatt ttggagtata gctagataac tgatgatggt    79860
tgttatatag atttttttcat aggttgcctg ttccaaattc tatgccgtgg aagaagttaa   79920
atatccagaa tttgacagga aatattattc tacaacagat ccctggcgta agaatgataa    79980
cacctgtgtt ctagtctcag acttgcctct gaataactgt ttctcctggt caattctctg    80040
tctctatcta ggcttgaaat tccccccaaa tgatgaagga gttggactag tttagtgggg    80100
ttcagcctcg agtggccatt aaaattattt ggggatcttt gaaaaaaatt agatgcccag    80160 attttttgtcg ttgttgttgt tgttttgttt tgtttgtttt ttaattatac tttaagttct   80220
gggatacatg tgcagaacat gcaggtttgt tataggta tacacgtgcc atggtggttt      80280
gctgcaccca tcaacccgtc atctacatta ggtatttctc ctaatgctat ccctccctag    80340
tcccctaacc ccagacaggc cctggtgtgt gatgttcccc tccctgtgtc tatgtgctct    80400
cattgttcag ctcccccctta tgagtgagaa cgtgcagtgt ttggttttct gttcctgtgt   80460
tagtttgctg agaatgatgg tttccagttt catccatgtt cttcaaagg acatgaaccc     80520 atccttttt atggtggcct gatattccat ggtgtattga actgctcact ccagttcaat     80580
taaatcagaa tacagaatgt tgagaggagc atcagtattt taagaaggcc ccctagtgaa    80640
gttcaatgtg cagccaaggg tgagaaacac tggactagat gattgataag ggccatccaa    80700
ctttgatagt caacaagaga caatgctata gagtatggtg gacagagcat gggctttaga    80760
gttagccagg tatgcattca gaccctggct ctgttactta ctagttgtgt gatcttgaag    80820
aaatcaaaat ggagatacac tatgtacctg gcagtaatag ttgtggggat taagcacctt    80880
caccagagct taggacataa taagccccca gtaaatagct tctttaatat cagaagttca    80940
gatggaagat gtgagaaaaa tattggttca gtaagattta acaggtaaat taaaatcaag    81000
tatttgaaaa cattttcctg tttctttagc aatggattcc agaaacataa tgtgaaaata    81060
gctctcagtc cttagatttg atgacattgc agaagaaat ctggctagtc gtcccatggc     81120
tgattggcta tgatgctag aaagccattg gaaaaaaaaa attggctcac agaagacagc     81180
agatgtggct tgggaaatgc aaggacatga ctgtaataag gatttgtcta tccagcccca    81240
tttatgagag tgattccagg agaaaaggac agatttgtat tgtcagtggg atacgctgtt    81300
aaaaaacact tttgctacta ccactccagc tgtcttggca tgtttgttgg tgatgtaagc    81360
tacagaaaat ggaaatcacc aatagggcta tagcaacctg atgcatagtg acaagtaatt    81420
gttctattca tggttatgtg ttgtacagag cacttgctgc atgtcaggtt tgagacttga    81480
gtatgcatta gggccatgga cacccccatc ttatctttaa gtagatttca aagtaaatat    81540
ttgatgaata tgtaaaatat ttagtttggt cagtcatagg gctgagaaca tggtggcagt    81600
tacctcctag tatctgcaag caaaaaaagt ttttttcttcc tatagcaatt gccatctcag   81660 ccactttgc agcatttctt tttgctacac tttgcattaa ccattgtgc acttgtctta      81720 gcctcaaaca ggccatgaaa gctccttgag gatagggggct atgtctttttt catctttata  81780 tatgcatcat ttagcagagc tgtcccttta taatgtacta attactgaat gaagggatgc    81840
atagatgaat aaatgaatga aaagtaggag tgacctgtct tctctctttc ttcacgatgg    81900
ggactagtgt gtgtatataa ggggataatt tttgtgtcac ataaaatata accttactta    81960
```

-continued

```
gaaggcaaga cttccagaat ggtggaatga gaaccacccc cccgccccca taaatccgcc    82020
ctttcatgaa agcagtgaaa acgctagcaa acgttgtgaa aattaacttt tccagaactc    82080
tggaaaggaa acagaggctt ccaacaatct gagaagaatg tattcaagaa aaacttcggt    82140
aagctctctg atcacagtgg aaataataaa caattagtaa tagaaggata gttgggaaat    82200
tcaccatttg tgggatataa acagtggatc aaagaagaaa tcataaggga aatgagaaaa    82260
tactttgaga ttaatgaaaa tgaaaataca ttgttccaaa acttacagga tacagccaag    82320
ctaaagcagt acttaaaggg aaatttgtaa ctgcgaaggc ctatatcaac aaagacaaat    82380
gatctcaaat caagaaccta accttccacc ttagactagg aaaggaacag caaactacaa    82440
agaaagcagg aagaaagact aataaagact aaaagggaaa taaatgaaat aatagagtag    82500
aaaaacacta gaatcaatga aattaaacat tgattctttg aagagatcaa caaaactgaa    82560
aaaaacttta gtcagattga ataagaaaaa aagagagaaa attcaaatta tcaaaatgag    82620
caatgaaaat ggggccatca ctacctacct taaaaagaat tttcaaagga ttaaaagaaa    82680
atgccattgc attagttcat tctcacacaa ctataaaaaa gctacctgag atggggtagt    82740
ttatgaagaa aagcgctttta attgactcac agttccacag tctgtacagc aggcatggat    82800
catgaggcct taggaaattt acatcaggtg aaaggctaag gggcatggaa gacatgtctt    82860
cacacggcag caggagagag agcaaagagg gaagtgccac acacttttaa accatcagct    82920
ctcatgacaa ctcactcact atcatgagaa cagcaagggg aaaatctgcc ctcatgatcc    82980
aattacttcc taccaggtcc cttccccaac actggaaatt acaattcaac gtgcgatttg    83040
gatggtgtga cacagagcaa aaccatatca accatactgt atgccaaaaa attagatgac    83100
ctagatgaaa tggacaaata ctcagaaaaa cacaaactat ctaaagtgac cagtgaagaa    83160
acagaaaatc tgagtagtcc tgtaacaagt cctgtaacaa aactggatta gtaattaaga    83220
aacttcccac aaagaaaagc ccaggttcag tcttcactgg tgaatactat caaatattta    83280
aggaagattt aatccttcac aaattatttc aaaacttgga agaggctgga acccttttcca   83340 actaattctg caaagtcagc attaccctga tgccaaaacc aaagatatga cacaaaaata    83400
aaactgcagg ctaatatcac atttgaatat agataacttt ctaaaaatct caacaaaatg    83460
ctagcaaaca gaattcagca acaaataaaa agggttataa agggtgacca agtaggattt    83520
atctctggaa tgtaaattaa cattcaaaaa cctaagaata ggaggaaact ttcttaactt    83580
tgtaatggac atctctgaaa acacacagc taacatcata ctaaataggg aaagattgaa    83640 attttttcctt gtaagatcag gaacaagaca aggatgactg ttctcaccat ttcaatttac    83700
cattgtattg tagattcaag tcaaggcaat taggcaaaaa aaaaaaaaaa aaaaaaaaa    83760 aaaaagaaag aggtaaaagg cacccatatt ggaaaggaag aggtgaaaat atctatattc    83820
acagatgaca tgatcttata caagaaaac cttaaggaat ccatgataaa ctattaaaac    83880
gagtaaacga gttcagcaag gtttcagaat acaagattaa tgtgcaaaaa tcaattgtat    83940
ttctgtacac tagcaatgag caatctgaaa atgagattaa gaaaacagtt cactcacaat    84000
ataatcaaaa taccagaata cttaaaaata aatttaacaa agaagcgta agacttgtat    84060 gctgcaaacc acaaaacact gtggaaagta attaaaaatc taaataaata gaaaacatc    84120 ccttgttcat gtactagagg actcaatatt gtcaagatgg aaatactccc caaagattga    84180
aggaaatccc tatcaaaata ctggctgttt tcttagcaga aatgaaaat ctgaccctaa    84240 aattaatatt taaatacatg gaacctagga taaccaaaat aatattgaga aagaaaaaca    84300
```

```
aagtcggcgt acccatgctt cctgattcca aaccttatta caaagcagtg gtaatcaaga   84360
gtgtatggta ttggcataag gacaaacaga tcaataaatg gaatactatt gagaatccaa   84420
aagttaactc ttacatttaa gaccaattga cttttcaaaag tgttgctaag acatttcaat   84480
gaggaaagaa tagtcttttc aataaattgt actggaaaaa ttggatatcc acatgaaaat   84540
aaaagatttt ggaccacttc aaacctgcaa aaaaaataaa atgatctcat ggtgtatcat   84600
ggatctaaat gctatagagc taagatgata aatctcagaa gaaaatatca aagtaaatct   84660
ttatgacctt gaagtaggca atggttttt ggctataaca ccaaaagcac aagcaataag   84720
agaaaaaaaa ttttttaaa aaaccccttg attattttat taaaatttg ttgtgggtac   84780 aaagtaggtg tgtatattta tggggtatat gagatatttt gatacaggca tacaatgttc   84840
aatgatcata ttaggataaa tgaagtatcc agtacctcaa gcatttatca tttgtgttac   84900
aaacaatcca attatactct tttagttatt tttaaatgta cagtacatta ttattgtagt   84960
cattcccttg tgctatcaaa tactatatgt tattcattct atctaactat attattgtac   85020
ccattaacca tccccactcc cctgcctccc agctacactt cgtagcatct ggtaaccatg   85080 attcctctt atctccatga gttcagtagt ttcagctcat ggagatagac agaactaatt   85140
ttattagctc ccacaaatta gctcccatgt cagaacatgt aaagtttgtc tttctgtgcc   85200
aggtttattt cacataacat aacgaactct agttccaacc atgttggtgc aaatgacagg   85260
ctctctcttt tttttttttt tttttttttt tgagatggag tctggctgtc tcccaggctg   85320
gactgcagtg gtgcaatctc agctcactgc aagctccgcc tcccaggttc atgccattct   85380
cctgcctcag cctcctgagt agctgggact acaggcaccc gccaccatgc ccgactaatt   85440
ttatatatat atatatatat atatatttat tattattata ctttaagttt tagggtacat   85500
gtgcacaatg tgcaggttag ttacatatgt atacatgtgc catgcaggtg cgctgcaccc   85560
actaactcat catctagcat taggtatatc tcccaatgct atccctcccc cctcccccac   85620
cccacaacat tccccagagt gtgatgttcc ccttcctctg tccatgtgtt ctcattgttc   85680
aattcccacc tatgagtgag aacatgcggt gtttggtttt ttgttcttgc gatagtttac   85740
tgagaatgat gatttccaat ttcatccatg tccctacaaa ggacatgaac tcatcctttt   85800
ttatggctgc atagtattcc atggtgtata tgtgccacat tttcttaatc cagtctatca   85860
ttgttggaca tttgggttgg ttccaagtct ttgctattgt gaataatgcc gcaatgaaca   85920
tacgtgtgca tgtgtcttta tagcagcatg atttatagtc ctttgggtat atacccagta   85980
atgggatggc tggttcaaat ggtatttcta gttctagatc cctgaggaat caccacactg   86040
acttccacaa gggttgaact agtttacagt cccaccaaca gtgtcaaagt gttcctattt   86100
ctccacatcc tctccagcac ctgttgtttc ctgactttt aatgattgcc attctaactg   86160
gcgtgagatg atatctcatt gtggttttga tttgcatttc tctgatggcc agtgatggtg   86220 agcattttt catgtgtttt ttgggtgcat aaatgtcttc tttttagaag tgtctgttca   86280
tatccttcgc ccactttttg atggggtcgt ttgttttttt cttgtaaatt tgtttgagtt   86340
cattgtagat tctggatatt agcccttttgt cagatgagta cgttgcgaaa atttctctc   86400 attttgtagg ttgcctgttc aatctgatgg tagtttcttt tgctgtgcag aagctcttta   86460
gttgaattag atcccatttg tcaattttga cttttggtgt tttagacatg cttttggtgt   86520
tttagacatg aagtccttgc ccatgcctat gtcctgaatg gtaatgccta ggttttcttc   86580
tagggttttt atggttttag gtctaacgtt taagtcttta atccatctcg aattgatttt   86640
tgtataaggt gtaaggaagg gatccagttt cagctttcta catatggcta gccagttttt   86700
```

```
ccagcaccat ttattaaata gggaatcctt gccccattgc ttattttgt caggtttgtc   86760 aaagatcaga tagttgtaga tatgcggcat tatttctgag ggctctgttc tgtttcattg   86820
atctatatct ctcttttggt accagtacca tgctgttttg attactgtag ccttgtagta   86880
tagttagaag tcagggagtg tgatgcctcc agctttgttc ttttggctta ggattgactt   86940
ggggatgtgg gctcttttt ggttccatat gaactttaaa gtagtttttt ccaattctgt   87000
gaagaaagtc atcagtagct tgatggggat ggcattgaat ctataaatta ccttgggcag   87060
tatggccatt tcacgatat tgattcttcc tacccatgag catggaatgt tcttccattt   87120
gtttgtatcc tcttttattt ccttgagcag tggtttgtag ttctccttga agaggtcctt   87180
cacatccctt gaaagttgga ttcctaggta ttttattctc tttgaagcaa ttgtgaatgg   87240
gagttcactc atgatttggc tctctgtttg tctgttattg gtgtataaga atgctgtgat   87300
ttttgtacat tgattttgta tcctgagact ttgctgaagt tgcttatcag cttaaggaga   87360
ttttgggctg agacaacggg gttttctaga tatacaatca tgtcatctgc aaacagggac   87420
aatttgactt cctctttttcc taattgaata ccctttattt ccttcttctg cctaattgcc   87480
ctggccagaa cttccaacac tatgttgaat aggagtggtg agagagggca tccctgtctt   87540
gtgccagttt tcaaagagaa tgcttccagt ttttgaccat tcagtatgtt attggctgtg   87600 ggttgtcat agatagctct tattatttta aaatacggcc catcaatacc taatttattg   87660
agagttttta gcatgaagcg ttattgaatt ttgtcaaagg ccttttctgc atctattgag   87720
ataatcatgt ggttttttgtc tttggttctg tttatatgct ggattacatt tattgatttg   87780
cgtatattga accagccttg catcccaagg atgaagccca cttgatcatg gtggataagc   87840
tttttgatgt gctgctggat tccgtttgcc agtattttat tgaggatttt tgcatcaatg   87900
ttcatcaagc atattggtct aaaattctct ttttggttg tgtctctgcc cgtctttggt   87960
atcaggatga tgctggcctc ataaaatgag ttagggagga ttccctcttt ttctattgat   88020
tggaatagtt tcagaaggaa tggtaccagt tcctccttgt acctctgata gaattcggct   88080
gtgaatccat ctggtcctgg actcttttg gttggtaagc tattgattat tgccacaatt   88140
tcagatcctg ttattggtct attcagagat tcaacttctt cctggtttag tcttgggagg   88200
gtgtatgtgt caaggaattt atccatttct tctagatttt ctagtttatt tgcgtagagg   88260
tgtttgtagt attctctgat ggtagtttgt atttctgtgg gatcggtggt gatatcccct   88320
ttatcatttt ttattgtgtc tatttgattc ttctctcttt ttttcttat tagtcttgct   88380 agcagtctat caatttttgtt gatcctttca aaaaaccacc tcctggattc attaattttt   88440
tgaagggttt tttgtgtctc tatttccttt agttctgctc tgattttagt tatttcttgc   88500
cttctgctag cttttgaatg tgtttgctct tgcttttcta gttcttttaa ttgtgatgtt   88560
agggtgtcaa ttttggatct ttcctgcttt ctcttgcggg catttagtgc tataaatttc   88620
cctctacaca ctgctttgaa tgtgtcccag agattctggt atgttgtgtc tttgttctct   88680
ttggtttcaa agaacatctt tatttctgcc ttcatttcgt tatgtaccca gtagtcattc   88740
aggagcaggt tgttcagttt ccatgtagtt gagcggtttt gagtgagatt cttaatactg   88800
agttctagtt tgattgcacg gtggtctgag agatagtttg ttataatttc tgttcttta   88860 catttgctga ggagagcttt acttccaact atgtggtcaa ttttggaata ggtgtggtgt   88920
ggtgctgaaa aaaatgtata ttctgttgat ttggggtaga gagttctgta gatgtctatt   88980
aggtctgctt ggtgcagagc tgagttcaat tcctgggtat ccttgttaac tttctgtctc   89040
```

-continued

```
gttgatctgt ctaatgttga cagtggggtg ttaaagtctc ccattattaa tgtgtgagag    89100
tctaagtctc tttgtaggtc actaaggact tgctttatga atctgggtgc tcctgtattg    89160
ggtgcatata tatttaggat acttagctct tcttgttgaa ttgatccctt taccattatg    89220
taatggcctt ctttgtctct tttgatcttt gttggtttaa agtctgtttt atcagagact    89280
agaattgtaa ccctgccttt ttttttgttt tccatttgct tggtagatct tcctccatcc    89340
ttttattttg agcctatgtg tgtctctgca tatgagatgg gtttcctgaa tacagcacac    89400
tgatgggtct tgactcttta tccaatttgc cagtctgtgt cttttaattg gagcatttag    89460
tccatttaca tttaaagtta atattgttat gtgtgaattt tatcctgtca ttatgatttt    89520
agctggttat tttgctcgtt agttgatgca gtttcttcct agtctcgatg gtctttacat    89580
tttggcatga ttttgcagcg gctggtaccg gtcgttcctt tccatgttta gtgcttcctt    89640
caggacctct tttagggcag gcctggtggt gacaaaatct ctcggcattt gcttgtctgt    89700
aaaggatttt atttctcctt cacttatgaa gcttagtttg gctggatatg aaattctggg    89760
ttgaaaattc ttttctttat gaatgttgaa tattggcccc tactctcttc tggcttgtaa    89820
agtttctgcc gagagatctg ctgttagtct gatgggcttc cctttgaggg taacctgacc    89880
tttctctctg gctgccctta acattttttc cttcatttca acttttttga atctgacaat    89940
tatgtgtctt ggagttgctc ttctcaagga gtatctttgt ggcattctct gtatttcctg    90000
aatctgaatg ttggcctgcc ttgctagact ggggaggttc tcctggataa tatcctgcag    90060
agtgttttcc aacttggttc cattctcccc gtcactttca ggtacaccaa tcagacatag    90120
atttggtctt ttcccatagt cccatatttc ttggaggctt tgctcgtttc tttttattct    90180
tttttctcta aagttccctt ctcacttcat ttcattcatt tcatcttcca tcgctgatac    90240
cctttcttcc agttgatcgc attggctcct gaggtttctg cattcttcac gtagttctcg    90300
agccttagtt ttcagctcca tcagctcctt taagcacttc tctgtattgg ttattctagt    90360
tatacattct tctaaatttt tttcaaagtt ttcaacttct ttgcctttgg tttgaatgtc    90420
ctcccatagc ttggagtaat ttgattgtct gaagccttct tctctcatct catcaaagtc    90480
attctctgtc cagcttttgtt ccgttgctgg tgaggaactg cgttcctttg gaggaggaga    90540
ggcgctctgc ttttagtgt ttccagtttt tctgctctgt ttttccccat ctttgtggtt    90600
ttatctactt ttggtgtttg atgatggtga tgtacagatg ggttttttggt gtggatgtcc    90660
tttctgtttt ttagttttcc ttctaagaga caggaccctc agctgcaggt ctgttggagt    90720
acccggccgt gtgaggtgtc agtctgcccc tgctgggggg tgcctcccag ttaggctgct    90780
caggggtcag gggtcaggga cccacttgag gaggcagtct gcccattctc agatctccag    90840
ctgcgtgctg ggagaaccac tgctctcttc aaagctgtcc aacagggaca tttaagtctg    90900
cagaggttac tgctgtcttt ttgtttgtct atgccctgcc cccagaggtg aagcctatag    90960
aggcaggcag gcctccttga gctgtggtgg gctccaccca gttcgagctt cccagctgct    91020
ttgtttacct aagcaagcct gggcaatggc aggtgcccct ccccagcctc gctgccacc    91080
ttgcagtttg atctcagact gctgtgctag caataagcaa gactccatgg gcgtaggacc    91140
ctctgagcca tgtgcgggat ataatctcct ggtgcgccgt tttttaagcc cgtcagaaaa    91200
acgcagtatt tgggtgggag tgacccaatt ttccaggtgc cgtctgtcac ccctttcttt    91260
gactaggaat gggaactccc tgaccccttg cgcttcccga gtgaggcaat gcctcgccct    91320
gcttcggctc acacacggtg cgctgcaccc actgacctgc gcccactgtc tggcactccc    91380
tagtgagatg agcccgctac ctcagatgga aatgcagaaa tcacccgtct tctgcttcgc    91440
```

```
tcatgctggg agctgtagac ctgagctgtt cctattcggc catcttggct ccagaaaaaa   91500
aaattgttaa attggacttc atcaaatttg aaattttttgt gctgcaaatg ataccatcaa   91560
gaaagtgaaa atctcaccca cagaatgaga gaaagtattt gcaaatcata tatctgataa   91620
gggtattgaa tttagaatat ataaagaact cttgcaactc aatataaaaa gacaacccaa   91680
ttttaaaatg ggcaaagtat ttgaatagaa atttcttgat agaagatata caaatttaaa   91740
aatgctcaac atcattagtc attagggaaa tgcagatcaa aaccaaattg agataccggt   91800
ttacacctat taagatggct atagaataaa agaacaaata acaagtattg gctttaatgt   91860
ggaggagcca gaacccttat atattgctgg taaaatgtaa agtcatgcag ccctttgaaa   91920
tacagtctgc aagtctttaa aaaattacta tttgttattt ggttttttctt cacttttaat   91980 ttaggttcag aggtacatat gcaggtttgc tatatagcta aattgtgtgt cacaggagtt   92040
tagtgtacac attatttcat cacccaggta ataagcatgg tacccaatag gtagtttttc   92100
tatcctcacc ctcctcctac cctccaccat caagtaggcc ctggtgcctc ttgttctttt   92160
ctttgtgttc atatgtactc aatatttagc ttccacttat cagtgagaac atgtggtatt   92220
tggttttctg ttcctgcttt agtttgctta ggatactggc ctccagattc atccacgttg   92280
ctgcaaagga catgatctca ttcttttttgc atagtatact atggtgtaca tgtatcaaaa   92340
atgttactgt ttgacctagt aattctattc caaggtaaat actcaagaga atgaaaaca   92400 tgtccacaca aatacttgta cacaaatgtt cattgcagca ttatttataa tagccaaaga   92460
gtggacgaca aatgtcttcc aaatgtgggc tccaaatgtc caccaactga taatgaaaa   92520 aacaaaatgt ggtatatcca tgccatggtt tatctgtcaa taataagaaa tgaagtactc   92580
atacatgctc caacatggat gaaccttgaa aacattatgc taggtgaaaa aagcaactca   92640
caaaagacta cactgtatga ttttatttgt attaaatgtc cataaaagaa aaatattttag   92700 agatagaaag gaaattagtt tttccagggt ctgggaggag acagtatgag gagtggctgc   92760
taatgggtac aggatttctt tttggagtga tataattgct ctaaaattag tttgcagtaa   92820
tagatgtgag tatgctaaaa tgggtgaatt ttatagtatg tgaaatataa ctcagtaagc   92880
ccattaaaaa caacctaatt aaattaaaac caagctataa cagaaatatt atatggcttt   92940
ggcagtttag aatagtggga aaatatggag taagggtggg gaaatagtcc caagtataat   93000
tctggttttg tcactactag tgtatggact tggacaagtc atttgctttc tctaagtatc   93060
agtttgcata tatgcaaaat agaggtaatg atacctacct cagtggtacc ttttcaaaac   93120
cttgttcttc ctcatctctc ctctaccact ttctcataat attattacag taataaccat   93180
ttattaagca ctgtgtccgc agtggtgtgg ggctgctttta cctccacaac ttcactgaat   93240
cctcactgca gtcttgtggg atctttattt ctttgcccat tttacatgta aataaattga   93300
agtcaaatga gttgttcaag gtccttctgt tagcaagtgg cagagatgga catgaaaact   93360
agatcttcta cctatgtgtc tttccacttc aactaaagaa tttattaaag agaattgaaa   93420
agctatgaac taaatttcgg taatactttt aatagtaaac attgctgccc tcgtgaatga   93480
acacacacta aatttcaaat ctcacggtgg cagggaataa agatgctacc tatcttaagc   93540
cattacttca ccaacttctc caccaaaata ttccttgtaa ccacaaataa gtaagcacaa   93600
tagatctata aggagagaat aattgtgaac tctgatttta tcttaaaaag tcatgtaggg   93660
atgtcatgtt ccacaatgtg attaataaaa tatattttgt tactaaacac aaggaaaat   93720 attatgttcc ataaagatgt ttggtggttg cctcgacctc ttttagtttg aaaagtaggt   93780
```

```
atgtatgaga aagatatgtg tttacatgtt tacccttgcc ttctctctgt ctcttccoct   93840
ctctctccct ccctccccaa ccoctatgcc ctacacoccc gcaaccocca catgtattta   93900
cctttctcta aaagctctgc atagccaaga aaagtgctct ttttattt  taggatatta    93960
gatatttcat tttcttatgg taagacaaaa gattaaggca accaagactt acaatgtgcc   94020
taccatgtgg caggcacaga ggcaagggct tttacatgtt atttaatgta attgtaattc   94080
tcacaaaagc cgtctagagt tgaaaatatt tccaactcta aatgaggcaa atggagcaca   94140
gagagcctta attatttcac ccaaagttca gtggtagagg caggattcca acccaggtct   94200
ggtgggctcc aaatccttgt tgggttgcca ttcctcttgc taacaaataa aactggtctg   94260
tgacttttgc atttcacccc gcttccacag tcactggtgg gacttactta agttaatcag   94320
attcttcaaa gtatcoccaa gtcctccttt gaaaagaaag ttgggggaca ggaggaggag   94380
cagaggagag gagataaaaa ggaaaggagt cagggagaga gagagagaga gagaaacctg   94440
gtgatctcag ctgggtgcca aggtttccta agcccaagtt ccccatggtt gagcctgtat   94500
tgtcaggcca acagcttcta gtaatccact tttatttaat taatagtgaa actgttgaag   94560
aattgcaagt ggtgttctgg ttcagaaacc ttccgttcta tggggcactg cttttgcttc   94620
agattcataa aaccaaatgc tctgcctcaa gataataagt gaacgtgtaa ccctcggag    94680
gtaagaaaaa acacaatgtc acgtgcaaat tctgcacttg ttctcaaagc aaacctctcc   94740
tgtgtttgca attaggatgt tatctaggag catattcaaa acttttgagg ttttattt     94800
agttttctt  tcattatgtg ctgttttagt aatatcaaag aatacatgta atatataatt   94860
tatatgtcat aacaataaaa ttaatgttga tgagcccaga ttaaagaatc aacaacatta   94920
acatcatgat tgcatcaacc ctattagaat ggaagctctg tgaaggcatg gattttgtc    94980
cattttgttc actgctatat cccccaggacc tagaggagtg tcagccacat aataggagct  95040
tagtcaatat tttaaaaata agagcataaa tctacttata tcctcttttcc tcttaccatc  95100
actcccagcc tccoctcaga ggtaaccact atcctatatt tgggctttat tattcccttg   95160
cattttgata agttttcaca tgtatattcc caaataatat attgcttgct tttgcttctt   95220
tttaaacttt atataatgga atcatattgt atgtatccta ttgtgaatta tgtcttttac   95280
acaacattag tatttgagat tcaactatgt gtagctcgat tccattcctt ttcattgctg   95340
attgtagttt attggatatg tgtgccataa attatttttc tcctgtcagt taatgtttat   95400
catttatgct ttaataaaca aaactgctat gactgttcct gcatgtgcct cctagtacat   95460
atgtgaccaa ctttctctag gatataagcc tgagagaggg actgcagttg gaatttcat    95520
ttccaaagcc caaagtttag ctcatgagtc agagctgcaa tgtgcccttt gtccacacta   95580
ggtcaggatc agtgggagtg ctacccaaaa tattttgcta gctggggagt cagggagaag   95640
cagagactga cctagtgagg ccaggaggca ctatctcagg tctctagtca aatgggttg    95700
caattagtaa aagtccagat tctgaatccc cttcactatt tatcttcctc ttcctccttt   95760
acagttattt ttgttcaagg tgcactttat taaactcatg cctaacaaac aaaactctaa   95820
tgaatatttt gtctttcatt gattgtaaat tcaattaatt agattgcttg aaaaaatttt   95880
aactgtattt tcactttagt atggatgaaa atttcgattt ctttaaaaaa catttttaa    95940
taataacaca acataaagtc taccctcata acaaaattta agggcacaac accatattgt   96000
ttttttttta ttttattatt attatacttt aagttttagg gtacatgtgc acaacgtgca   96060
ggtttgttgc atatgtatac atgtgccatg ttggtgtgct gcacccatta actcgtcatt   96120
tagcattagg tatatctcct aatgctatcc ctcccccctc ccccacccc  acaacagtcc   96180
```

| | |
|---|---|
| ccagtgtgtg atgttcccct tcctgtgtcc atgtgttctc aatgttcagt tcccacctat | 96240 |
| gagtgagaac atgtggtgtt tggttttttg tccttgccat agtttgctga ggatgatggt | 96300 |
| ttccagcttc atccatgtcc ctacaaagga catgaactca tccttttta tggctgcata | 96360 |
| gtattccacg gtgtatatgt gccacatttt cttaatccag tctatcattg ttggacattt | 96420 |
| gggttggttc caagtctttg ctattgtgaa tagtgccgca ataaacatac gtgtgcatga | 96480 |
| caacaccata ttgttaactg taggcacaat gttgtacagc agacgtctag aactttttct | 96540 |
| tcaggcttaa ctgaaacttt atagccattg aacagcaaca ctccatttcc gtttcttaaa | 96600 |
| ggtcctttac aaaatgagct ttctgcgtgt ttccattttg tttatctgat aactttttt | 96660 |
| tcttttttta ttatacttta agttctgggg tacatgtgca gaatgtacag gtttgttaca | 96720 |
| taggtacaca catgccaggg tgtttggctg cacctatcaa cctgtcatct acattagata | 96780 |
| tttctcctaa tgctattccc tcccttgccc ctcaccccctc actggcccca gtgtgtgatg | 96840 |
| ttccctagcc tgtgtccaag tgttctcatt gttcaactcc cactttgag tgagaacatg | 96900 |
| cagtgtttga ttttctttc ttgtgttagt ttgctgagaa tgatggtttc cagcttcatc | 96960 |
| catgtccctg caaggacat gaactcttcc ttttatatgg ctgcacaata ttccatggtg | 97020 |
| tatatgtgcc acaatttctt tatccaatct atcattgatg ggcatttcag ttgttccaag | 97080 |
| tctttgctat tgtgaatagt gccacagtag acataagtgt gcatgtgtct ttatggtaga | 97140 |
| atgatttata atcctttgtt tataataccca gtaatagaaa tgcttggtca aatggtattt | 97200 |
| ctagttctag atccttgagg aattgccaca ctgtcttcca caatggttga actaattttac | 97260 |
| actcccacca acaatgtaaa agcgttccta tttcttcaca tcctctccag cacctgttgt | 97320 |
| ttcctgactt tttaatgatc acgattctaa ctggcgtgag atggtatttc attgtggttt | 97380 |
| tgatttgcat ttctctaatg accagtgatg atgagctttt tttcatgttt gttgaccgca | 97440 |
| taaatgtctt cttttgagaa gtgcctgttc atttccttca cccacttttt gatggggttg | 97500 |
| tttgtctttt tcttgtaaat ttgtttaagt tcattgcaca ttctggatat taattaacct | 97560 |
| ttcgtcagat ggatagactg cagaaatttt ctcccattct gtaggttgct tgttcactct | 97620 |
| gatgatcgtt tcttttgctg tgcagaagct cttgagttta attagatcac atttgtcaat | 97680 |
| cttggctctt gttgccattg cttttggtgt tttagtcatg tagtctttgc ccatgcctat | 97740 |
| gtcctgaatg gtattgccta ggttttcttc tagggttttc atggttttag gtcttacgtg | 97800 |
| actcatcttg atttaatttt tgtgtaaggt gtaaggaagg ggtccagttt cagttttctg | 97860 |
| catatggcta gctagttttc ccaacaccat ttattaaata gggaatcctt tccccattgc | 97920 |
| ttgtctttgt caggtttgtc aaagattaga tggttgtaga tgtgtggtat tatttctgag | 97980 |
| acctctgttc tgttccattg gtctatatat ctgttttggt accagtaccg tgctattttg | 98040 |
| gttactgtag ccttgtagta tagtttgaag tcaggtagca tgatgcctcc agctttgtgc | 98100 |
| ttttggctta gaattgcctt ggctatgcag gctctttatt ggttccatat gaaatttaaa | 98160 |
| gtagtttttt tataattctg cgaagaaagt cattggcagc ttgatggggt tagtattgaa | 98220 |
| tctgtaaaac actttgggca gtttggccat tttcatgata atgattcttc ctatccatga | 98280 |
| gcatggaatg gttttccatt tatttttgtc ttctcttatt tccttgagca gtggtttgta | 98340 |
| attctccttg aagaggtcct tcacatccct tgtaagttgg attcctacat attttattct | 98400 |
| gtttgtagca attgtgaatg ggagttcact catgatttgg ctctctgttt gtctgttatt | 98460 |
| ggtgtatagg aatgcttgtg atttcgcac actgattttg tatcctgaga ctttgctgaa | 98520 |

```
gttgcttgtc agcttaaggt gattttgggc tgagagaatg gggttttctg aatatacatt   98580
catgtcatct gcaaacagag acaatttgac ttcctgtttt cctatttgaa tatcctttat   98640
tgctttctct ttcctgattg ccctggccag aacttccaat actatgttga ataggggtgg   98700
tgagagacgg catccttgtc ttgttctggt tttcaaaggg agtgcttcca gtttttgacc   98760
attcagtatg atattgggtg tgggtttgtc ataaatagct cttattattt tgagatatat   98820
tccatcaata cctagtttat tgagagtttg agcatgaagc agtgttgtat tttgtcgaag   98880
gccttttctg catctattga gataatcata tggttttgtc attggttctg ttgatgtgat   98940
ggattatgtt tattgatttg tgtatgttga accagccttg catcccaggg gtgaagcgga   99000
cttgatcgtg gtggataagc ttttttgatgt gctgctggat tgggtttgcc agtatttttt   99060
tattgaggat ttttgcactg atgttcatca gggttattgg cctgacgttt tcttttttg    99120 ttgtgtctct gccaggtttt ggtatcagga tgatgctggc ccataaaatg agttagggag   99180
gattccttct ttttctgttg tttggaatag tttcggaagg aatggtacca gctcctcttt   99240
gtacatctgg tagaattcat ctgtgaatcc ttctggttct ggactttttt tggttggtag   99300
gctattaatt acttcctcaa tttcagaact tgttatagtt ctattcaggt atttgacttc   99360
ctgctttagg cttgggaggg tatatgcgtt caggaattta tctatttctt ctagattttc   99420
tattttattt gccccagagg tgtttatagt attctctgat ggtaatttgt atttctgtgg   99480
gatccgtggt gatatcccct ttatcatttt ttattgcatc tgtgattctt ctctcttttc   99540
ttctttagta gtctggctag tggtctatct acaaaataga ctgtttatct gatatttatt   99600
ttgtaattat ctaataataa ccatcattat catcatcagc attatcatta tcatctcctt   99660
tacccataca tacatttgtg tctttcaaat aataatccca tctttgaagt gcatcctcat   99720
ctttagcagt ctgcactctg ctttcttata tcatttatta tcttatttta taattattta   99780
tttccagtcc ttcttctcta acagatagta gtttcttagg gccaaggaaa tatctcgatc   99840
accactatat ccccagcacc taaccctgtg cctggtccat agggccagat gctaagagtt   99900
gagttgaacc attgtaccta atcttaacct tcattagcac aacatggttt gtcagtggtt   99960
aagaatctac actttggagt cagactcacc caggatggaa tcctggcatt gccacttatt  100020
attaatagat gcgtgatctt gaacaagttt acttaattgt tctgagcatc agtttcctct  100080
tctgcaatat agggatgata cacagctacc tggtaggttg ttgggaaaat taaatggat   100140 gatatgtatg aaatggcctg gcatatagag tgcctaaata catgttcttc tgattctatt  100200
tggacagttt gtgttagtaa cagaagtcaa aaaggtggag aaaggagaaa ggtacttgtg  100260
aaaattttct atttcttctc catgtttcat tcaggactga ggaaggggc acagttttta   100320 cccaaggaaa tgcatttttt agccaaaaga aatgatctta gcatttagct gaattatata  100380
ttggaagtaa gctccttcca tgtggaactt atggccttgc tagccttggt tgttggaag   100440 tgctcttgct ggctttctag ttagggtagg gaaaggaagg cttgtgggga atgaagatag  100500
gccatgatat caagccactg ggtttgcaaa tcagtagaat ttttattgc tttctgttgt   100560 acttgggact tgaataaagg ctgatatttg tgtcttgctg gtaaagtgct tgtaaagtga  100620
gtgaaagttt tctttgctct tgtcctgaca tagctgttca cttggggttg agggaggat   100680 aacctttcat gttttttttt tttcttcatt ctgatgactg tgctgaacat tcaaaccaaa  100740
aggccattgg tggaaagtaa aggtgagtgg tgagaagaca ataggtaat ggaaactgtg   100800 ttggacttgt aatcaaattg tcctgcactt cccctctcca gtcttaacg ttttttcatct  100860 gtacagtgga tattaaaatg agaaaataag cttgtcttca cagagttttc gttaggtgtt  100920
```

```
gacacaacaa acaggctccc attagggctc attttccttc attccttagt aaggaagaag  100980
tgcttataaa atatagcagt tgtgctcttg tgaatgatag catgggcagt tgtcatctcc  101040
ctgaagcaga tgtaacccag aatgtcactt gagttttgtt taatgcttag cataagaca   101100 taggaatgac aaaagctgac ctttgggtag tgagaacaat gttccatttt gttcaaactt  101160
gaatttttta ctataggaga ctgagaatta accttccatg aaggttttag gattggcttt  101220
ctggcccttc tccttcatat ccacctgaaa gagcttgggc gcagaagttc ttgcagaaag  101280
gcagttagac aaggtgactt ctgaagctcc agtggccaag tattttgatg gtagcctaaa  101340
agatgtccag aatcattgta catcattttt tcaacagaag cttcaggcat agggattatg  101400
cttggtactt tatgttgtgg aatggaatct ggcggatgtc catgtgatct atagaaacac  101460
ctaaggaaag tgaagaaatg agggaaaaaa agaacaaga cttttatgat aatactaatc    101520
acgatccttg tgtatttatt ccaatggcat tttatccatt atctgattta tattaccact   101580
cacagcagca gctcaatagg atgggagata ttatctctat tttatagatg agatttgagg   101640
ctcacgaagc taaagcaagg aacatcaaat cactttgata tttggtctgg ttttgttata   101700
ggtctcccct tggatgaggt aaagttacaa acctgggttc atatcattta attagtctga   101760
aaatgttgcc tggacaccac cttcagttag atatcttaac ctcaggcttc ctgccttcat   101820
tgctcccgca tatagacata gactatgaga ttggctaatc ccagagaact tccctaatcc   101880
cttggcaaga tccaaaaagg ctcagtcaca ccctacaacc atcatcttta ggagaagtct   101940
cagaaaattc agcttcacac taactaactt gagcaatgaa taatagtcat ttatgcctgc   102000
aggttaatgc tgaagacctg agacttcact tgcctatttc tgccattcag tgacatgtgt   102060
tgcattggtt ttttgtgtct ttccagtttg gagactgcca gggaccatgt tttgcccatt   102120
gactattact ttccaccca gaagacctgc ctgatctgtg gagatgaagc ttctgggtgt    102180
cactatggag ctctcacatg tggaagctgc aaggtcttct tcaaaagagc cgctgaaggt   102240
aaagggtctt gcacatgcac ttctcttttcc ctttctcctt taccttccag agagagacac   102300
taaccttcca gggcccagga ttttatcatc tcagaaatag agtcattggc aaggccctat   102360
caaataactt aggagcctaa ggaagcaaat ttttgtactt gctagttccc tggtttcagc    102420
agccttgttt gtacaggcaa tttaggcagt gaaggtggtc ccagctgggg cttgggctc    102480 agtgggtcct agaaatgaaa gaaaaattaa tgatttgaaa agatttaatt tcctcccttc    102540 ttgtttttcta ctctgctggc tagtaaagga aaaatttgtc cttattagag aggttagaag   102600
tggagaaacc ccaactgagt ccccagcctg ttccttggga tgaatatgag actgttcctt   102660
agcaaaggct tcctggcctc ggccccagaa agggagtgtt ctcactcttc agcagactat   102720
cagtctctgc acctgctccc tcctgttgtg gcctccttgg gacctgtctt tgcattaata   102780
gttcctaggt aggtaagaac tcagagtgaa gaaacacatt tattctcctc tccagagacc   102840
tgatctcaaa gcctgtccat tagtccctaa ccttaatcta aggtagcatc ttatatctgg   102900
ctaaattggc tcaagcccta gctccttagt tttatttagc ttagaacaac tcatgtctgc   102960
tcaacctcta gaggcgctca gcccacattc tgcagtagaa actcccatttc tcaggcctct   103020 tatatacggt aatgtctcct tcctctaacc acccagggct taagcttcct gcttatccac    103080
ttcaccctgt attgagggct ttcttctcaa agagacattg atgaggagcc cctagagaga   103140
gatgctgtgc tctgggacca gaccccttgt taaacaccag tattcacctc tgccccaact   103200
ttccccaaag aggtacttcc tgccaaggcc tttctctttc ctctcactgg ctggaagtgt    103260
```

```
tgagttccac ttcagaacca gaacagagaa cctttccttc tataagagct ataaaccttg 103320
agaacagtct taaaacatag gtatgtaggc cacaccattc accacgaatg tactgatact 103380
catcagaata tggaagaagc accagagagt ttgaagcatc tagagaaaag gtagaaagag 103440
aatgcccttt aactgacctc ctcagtgata gccaatcaca atgatgagtg ttgattcatc 103500
attttggcta ggtggcagaa atatctataa aacagaagct gccatgttgt tttcttccag 103560
tcctcagggc ctacaagaag gcagctatca tttggtatta ctgaaaacat gccccatgtt 103620
cagctcatac ccccaaatta cccattgcta ctgtttatgc tgggctaata tgaagcccag 103680
ggccctaatg tctaggtcta ggcagtaagg cctagagcag tgcctaaaga gcctgagagc 103740
agtgccttcc tttcttcaga gtactcatga aaggatggct gtcagaaaag gaaatgagga 103800
tgggttccag agacttcaga ccaccccaac ttccccagtg agaccctggc acctccccat 103860
accctctcac ctagcgggcc ctgtctatag agcagagaat gaaacagagc actcatctag 103920
aggtagtgtg tcagcaagcc caggcactgc accacagtaa tagcagccat atcagatggg 103980
aaaggagttc aagtgaacaa acaagcaaat tcaatagtca gatagattag attatacttg 104040
atgcttcctc tgagttttac aaatatgggt cactaaattg ttattttcag aaaacagggg 104100
aaatgctcaa tcacattgtg aaagggaaga ttttgctgtc atatcataca tcccacatgg 104160
gagctttctg cagaagttag agctgaagga gggaggcagg cagaagggca actggcaggg 104220
ctgcctggga ggagctctgc aatgaggtgg atcctgtgcc atttgagaac agggaagaaa 104280
agaaatgagg ttttggggag ggaatcaccc aactcacaga acacacagaa atccagcaag 104340
gtttcaaaac gctctacacc ttagagtctg ttaagttagg gaaactctgt gagctcatag 104400
ggccaaatgc acttgcctgc ttgaaatatg aaaaatcagc aatggattcc ttgaaaaaca 104460
atgaaaaggg aaccttctga gccccttggt tattttgaca tatggaccat agatttcagt 104520
cctgagccct ttgaaggtag gagaaggtgg tttagaaaac acacacacac acgcacacaa 104580
acacacacca gaatgaagca aaaaaaaaat tactggtgtt ttctttctcc tcccatctgt 104640
gaagctgttg gattgatttt actgccatca ttatccctgt ttgaaggcag ggggctgtct 104700
tattacccaa agaggacatt tattgatttg gtttctcttt tccatttttta caatgcatct 104760 ttatcgccca tatggccttt ctggaggtgg ttttcagtct ggcttgttga aacatcaaat 104820
tatacctgtc ttagagaaaa tagaaacaaa aatctttctc ttccttactt gcttgttgta 104880
gtcagttaac tcggactgag tattcagagt cttgattatc acttaattca tagtttcata 104940
aatctctgga atgggcatag gtacaggact taaaagcctg gcatctcaga cagaaatatg 105000
tttttagctt tggtggttta taacagatgg gacttttagg ctgtcattgg tgcagggctc 105060
agcacagagt cagttgtaat ctggacaggt tttgttgttg aggaagagtg ggaagaggga 105120
gtcctacatt ttctccttgt cagtaatgtt ggagaattgg ggtgagggtg aggctgggca 105180
gggagggtct gcatagaaaa aagggtgcgg tgagaaaaaa taatgctact aagccatgag 105240
ggtaaaatga ccaaattctg gttgagagaa acttggtcaa agtgtgtatg gggagagaaa 105300
gttggtcaaa gtctgtgtct gagtgcttgg tgggatgaac tctgggttag aaacaggcat 105360
ggagggaaat agttggttta tggagtgggt aggatgagtg gggtggtgaa agggaaggca 105420
ttttggatgc taagagacca ggaagtcaaa gcaaggcaat acacataaac agaggtaagg 105480
gctcagagag gttttagttg tgtagacttg gataagaaat tttcccttt ggacctcagt 105540 tttccttgtt tgtaaaacaa cggacttgaa ctagatattt taaaatgtgc ttccagctta 105600
gacattttgt gaccgttcta caaattacaa acataatcat catcatttca gcaaactcac 105660
```

```
atgtatttat acctgcataa gttttttggtc ttgctttcct agaaggtgac taatcccaga  105720
tcctaatcaa ttaaagaagc aatcttcaga tggggataga gccagctgag agagtgtact  105780
atggatggag tgagttaaaa ctcaggactc agattttctc cttgtgatca ttgctgggta  105840
acttcctttc ttttctattt tctcatctgg aaaatcagga tatgaatccc catctctacc  105900
tcattatgtt tcaaagaggg ttaattaatc catcatgtgc attatgtgct caagaattta  105960
ctattttttca gacattttct agtaaaacat tgaagattat atgtccattt gttttgtaca  106020
catggagtgc tgtttggtac acatcataaa attgaaactg tagtttacat tctgaactca  106080
aagaattaca ccatcctcac tgatgtttac aataggtccc aatttagttt ctttagcaaa  106140
ttttatgtaa gtatggcttt gattctctct ctcactccag gtttttgtta gggaagaaat  106200
gcaagtgaac cctcattgaa ctctttctgt cctttaaatc cattctttcc cacctcaact  106260
catgtggaat tgaatgttgc ctctagtttg gagtctagca gagagttttt ggtgcatatc  106320
agtgtcccct tcactccctg acttttcaag taacatttcc cagaggcaaa ttaactctgc  106380
taagaggatc tgcttgcagc ttcaacagag ccttcatcag gtatctttgg ccaaggagtt  106440
gactgatcct gactttgcga gtcctagaga tcttttcaca aagctcctct catgtttctg  106500
cctctgattt tcttaaatgt cacagacaga ctttagattt aggggttggt taacttttttt  106560
tgtaaagggc catgtagtaa atattttagg ctttgtagat catatggtct ctgtgtcaac  106620
tactcaactc tgcctttgta ggatgaaagc agccatagac aatactggaa ctaatgggag  106680
tagctgtgtt ccaataaaac tttatgggca ctgaaatttg aatttcactt aattttcaca  106740
tgtcgtttaa tattatttt cttttttacc atttaaaaat ttagaaatca ttcttagctc  106800
tttgggcctc acaaaaacag atggtagagt ggatttggtt tatgggctgc agtttgttga  106860
cctgtgcttt agctaatcac ttctgtactt ataaatctgc ataggttta tgttttttcca  106920
tctcttggta tcttagtagg ccagtcaaag tttgaacaac ttgttagcac agaatacctg  106980
gcctagtggc ttcttggtcc tgagcttatt tactaaacaa gagaaaaaat aaataagtct  107040
agaaatgcta gaagaggata cttttttgtt ttaatgatct agtagatcac tcctccttgc  107100
aatacccaga ggagaaactg aaaatatttc aaacattttc tagacttctg tgttgtaaat  107160
ttgtggataa ctatgaacta tatatgaatg aacttttctg gatgacacat atattccaga  107220
tggtaaaaag gaagggcttt ggggactctc tggtaccaag tgtcatggaa aaactgtgtg  107280
tctcatagaa agtagatccc aggaggccag cagagttgtg gatctgccat atattacctc  107340
atgattctgt cttcgcacac tcaccggctt aattctgggc ctccccataa cacgactaga  107400
ccacaggctt gcagaagaaa taatttagct ctgtaactca ttgaagttgg tgcccaccca  107460
agtctctgtc agtgcccaat tcgggagcca tgccaagaat ttgccattgc tgcttcatgg  107520
tggccttgtg cctgcttatt tatagcctgt gcattttatg aaacagggat taataagaag  107580
ttgccatagc acttgcacca ttatgtaaat atctgtaatg cttacataac ttttgtcact  107640
tgcaagacct tttgagtcca ttgccttctg ctaccatgcc ttaccaattt cctagtccct  107700
tattattatt tttcaattca ttatatttaa cttctgtgat acacgttcag aatatgcagg  107760
tttcttatat aggtatacac gtgccgtggt ggtgtgctgc aaccaacaac ccgtcatcta  107820
cattaggtat ttctcctaat gctatccctc cactagccca ccaccccta ataagcccca  107880
gtgtgtgatg ttcccctccc tgtgtccatg tgttctcatt gttcaactcc cacttatgag  107940
tgagaacatg cagtgtttgg ttttctgttc ctgtgtttgt tttctgagaa tgatggtttc  108000
```

```
cagcttcatc cgtgtccctg caaaggacat gaactcatcc ttttttatga ctgcatagta   108060
ttccatggtg tatatgtgcc acattttctt tatccagtat atcattgatg ggcatttcgg   108120
ttggttccaa gtctgtgcta ttgtgaatag tgctgcaata acatacgta tgcatgcgtc    108180 tttatagaag aatgacttat aatcctttgg gtatataccc agtaatggga tggctgggtc   108240
aaatggcatt tcaggttcta gatccttgag gaatctccac actgtcttcc acaatggttg   108300
aactgattta caccccacc aacaatgtaa aagtgttcct atttctccat attctctcca    108360
gcatctgttg tttcctgact ttttaatgat cgccattcta actggcattg acatggtatc   108420
tcactgtggt tttgatttgc atttccctaa tgaccagtga tgataagctt ttttcatat    108480 gtttgttggc cgcataaatg tcttcttttg agaagtgtct gttcatatcc ttcacccact   108540
ttctggtgtg gttggttatt tttttcttgt aaatttgttt aagttccttg tagattctgg   108600
atattagccc tttgtcagat ggatagattg cgaaaatttt ctctcattct gtaggttggt   108660
tgttcactct gatgatagtt tcttttgctg tgcagaagct ctttagttta attagatttc   108720
atttgtcaat tttggctttt gttgccattg cttttggtgt tttagccatg aagacttgc    108780 ccattcacaa ttgctacaaa gagaatacaa tacctaggaa tacaactcac aagggatgtg   108840
aaggacctct tcaaggagaa ctacaaacca ctgctcaagg caataagaga ggacacaaac   108900
aaaaggagaa acattccatg ctcatggata ggaacaatca atatcgtgaa aattgccata   108960
ctgcccaaag taaattatag attcaatgct atccccatta agctaccatt gactttcttc   109020
acagaattag aaaatactac tttaaatttc atatggaacc aaaaagagcc catatcccca   109080
agacaattct aagcaaaaag aataaagctg gaggtatcaa gctacctgac ttcaaactat   109140
actacaaggc tacagtaacc cttatcaatt ttttatgtgc ctctccatat tctgcagtca   109200
gaagcttctt cagtcctttc agggaattgc tgggtgacta tcaaactctg gtagttcatt   109260
tttgcagttg gctgctgttg tgaggataag agttagactc actttctctt cagagataga   109320
aattatgtat taattctctg ggttctagac ccacagcaag gagcatactg ctcctcaaaa   109380
taactgaatt ctgcgagaag ccatcattgt aaaacaacaa tatcttcagt tatagtagcc   109440
atgtgtgcaa cttctggaaa ctgttattca gattttcatg ttccttccct gtctcttcat   109500
agctaggcag ctgctttcag ccttgtacag atgctagtga gctttctacc tacaaacctg   109560
cagaaaattg aactgagatt tggaggtgaa agactcttga taaagggaac aaggtttaga   109620
attctcagtc cctttgctcc caggctgtgt tgtgactact gaggcactcc agtgaaatca   109680
ctattcctcc tatctagact aatgcctgtc tctgcagagc acctcataag aacaggcctg   109740
gtagtaatat cctcatgcat tcagtcagta aatatttaca gagtgcttac tacatatagg   109800
gtattgggct gacatatgca agatacaggg cctgcttcca ggaggttata gcttattgat   109860
cataaatgtg gcattttttt tttttgagac ggagtcttgc tctgtctgtc acccaggctg   109920
gagtgcagtg gcacgatctc ggctcactgc aacctccacc tcccaggttc atgtgatttt   109980
cctgcctcac cctcctgagc agctgagact acagggctc atcaccacac ccagcttttt    110040
tttttttttc tgtatttta gtagagacag ggtttcacca tattggccag gctggtctcg    110100
aactcctgac ctcgtgatcc acccacctca gcctcccaaa gtgctgggat tacaggcgtg   110160
aaaatgtggc aatctttaaa gctcttcagt ggatgaaagg ccaccctatc tgctgtcctt   110220
ttgaacttcg caacttcctt ggtacagagt gagaggttat tctcttggtt ttccatataa   110280
gtaaactgag gctttgccag ttcatcaaca ggtagtaaat aatatatttg gaatttgaac   110340
ccaagtcttc tggggtcaaa ggcagcattc actctgctct gtcacagcag ctcctcaaat   110400
```

```
aagccaacat agaaaccaag tactatgcct aggcaacaag aaaggcagca atgaagagca   110460
acagcagagt caaatatgag agaaggaagt taagaaagat gttaagtact gtggggagta   110520
actgagaaac caccaagtat cgctaacatc acagggaact tgtcttccta agaaaattcc   110580
aagcacttaa aaccgctggt agttcatcag caactctctt cattagatgt gcagggaca    110640 tgtgggccat agtccttcta ctaacttata ttcttcaggg gaaagttctg attctgatga   110700
gacccagcat ggtagctctt aattcactgt tgtcacacga ctatagaaca ggaagcacaa   110760
cttaacacct gtgctcatga gaattttgct ccttatgacc aagctaaaga aagagcttag   110820
acaggatgtg tggctataaa tgtagattaa tggttccttg gctctttggt ttgagccttc   110880
tcagcagagc atcccacgga gtgttttcca tggggccacg agcaagagaa atccacttcc   110940
ctcctcctca atgtcagaaa atagagaata ttgtctttca ggatagaatt aaaaagtcat   111000
agaggcagca acttgttttc ctatattagg gttttaaaat tctgttttc  cttcctctcc   111060 tgggtcagat cattgtgtgg atggaccttg atttcattgt ggtatctgta tgtggaccct   111120
gaagaccatg gacttctaac aattccttaa gttacataag cacattccta caggtcacaa   111180
gctcatttac ttacaggatg gttgatttgg tcacaggtta tttcatgaaa atacttaaaa   111240
gatttgcagt gttcaaaact gcagtatctt taaacactaa aacttgaagg aagggaattt   111300
agaaatcaaa aaatctggtc aaaccatttc atggaaaagg aaagtgaggc tcagagagag   111360
gaaattactt tcctgggttt gtatagccta taaatggcag aaatgagagc ctccctgcca   111420
tttctagttt tctgtctgag agactctcct gcctaatagc taattagcag agtcacagag   111480
gtcattacct tgcaattctc aagaattatg tgaggcagca tagtaagcat ttatggccct   111540
tggttcctag aaggagctta gtccctgata gtcatctctg cctttgccat tgtgtgagac   111600
tgtcttctgt aactgtatgt cttcctccct agtaagttaa tgagtaataa aggtattcta   111660
tagtgagagg actctgtaag acatttcttg gtgtgaggat tgttccaagg ttgttttgtg   111720
tgtatgtgca tgtataaact tttttaggga gcatattcat agcttttaca tggatctcag   111780
aggctctata acccagagaa gattacagaa taccagtctt gtctttggta aggattttat   111840
agacccatcc tgactacagt gatatccaac atggctatgt aatgactggc actttcccca   111900
cataacatat atttattcca cactcagtgc ctactgtgta catgagacct ataccgggca   111960
ctgggataag agacatgaaa taacagctaa aattgtttat tgagcagtca gtatgcatta   112020
gatgctttgt agtcattttc ttattcaatc tgtatacct  caatttacaa atgaggaaac   112080
tgaggcacag aagagttgag tgatttgccc aaagtcatac aaatagtcag tggctatgtg   112140
atgaatagtt accaacataa aagagtgaga ttactgctgt actaaaagta ggtacataat   112200
cccctgagca gacagtatga gagaatgatt tattttacct ggaaagttta ggaaggcttc   112260
acagaggagt taagggttga tctgggtctt gagggatgga taagagtttg ccagatacaa   112320
aaaggtagga agagaacttc aggaggaggg aacaggctga gcaaagacac ggcgatgtga   112380
aagtgggagg cttgtttggg gaacattatg gaatctggag gttattgtgg ggaatctcat   112440
cagatgcagc aagctgtttg acaggccttc agttggctct ttgtaccttg ctccctccgc   112500
atgctgagct gtccatagct gccctaggct ggtgtctggg attttcggaa gaaggttact   112560
atccaggtag tgtaacaaga tgcagtgcaa aagcaccaga ttggggctct ggctctgctg   112620
ctgacttacc acctggcctt aagcatgtct agttccctct ttgtacatta aaatctccat   112680
tggaacagta acatggttgt attaaatgat cttgaagatt ttacctgcac gttttgcaca   112740
```

```
tgtaccctaa aacttaaagt ataataaaaa aattaaaata aaaaataaaa atataacaat    112800 ataaatctttt aacaataatt ttagtagtaa atctctacaa ttttacagat aatccagatg    112860
catccattgg ccaatggttc actttgtatg cataatattt gggaaacagg cagacccaat    112920
ttcaatcctt agttgtaaga cttaatacat atgtgatctc gagcaaatca cttttgtatg    112980
cctctataag gataataata gctcacagaa ttattttaag aactaaatga tgtgtaataa    113040
agctactggt actcagtaag ttttgtatcc ttttcctaga gtgagtcttg gtcataggca    113100
tgcgtatact tgcagcgtcc ctgggtaggc cgaaagagca aataagagat ggtatctatg    113160
gtattcccca ggtaaaggag gccttgggtt ggcataagat ttcacttctc tttagagtta    113220
cttaattagg gaccagaaag gccatcagca tttgtatgag aatataacaa aggtcaatct    113280
cttcctcttt actttttacc tcccagtaca ctgtgagtaa cattcccag ccagcccagc    113340 cagcacgtgt tcattgcctc tcttgacttc cagactttgg acttgaaggt gtcagagctc    113400
tctgtgtatc tttgtcccca acaagataag tctgacctcc ccagcaaatt caagtcctaa    113460
gccactgtcc aggagaaaag ctagcaaggt cataaattat tctccatatt ttccagccat    113520
tggtttccct tgtccagcca gaggtgtgtc tcaaagtatg ctgaggccag attcaataga    113580
aacctgagcc agcacctgtg taaataattt ttaaagctcc ttttcctgaa gctggatgaa    113640 tattttaaa aactaagctg gattgtcttt tatctagcat gccgtctcct acattcctag    113700
tgctatggac ctcttggagg aatgtggttt ggttatagtg gtattgtctt gtctgttgtg    113760
ggggagggag acatttcttt cagaagcaag gtaatacttt ggtctggtct atgactctat    113820 tttgttaaa atgaaactat ggcagtatag tggtattcat tctgcttccc ataggttaac    113880
tttacatccc tctgtcttca cccactcttc agttctgatt cttttaaaag cagccaacca    113940
aaaccagcaa gtacatactg cttatctctg acttccacca gaatcaactt cagatcttgt    114000
ccaaagctcc atctgaagag aggggaataa cacccagcca agagccctca gggcccatca    114060
gtaagtagac atcctgtcct tgaggttcct taactctgct cagcttcaga atacagaagg    114120
ggttggttct tcatttgtgt tgtttataac taaaagcctc ctactcccca cttttttgca    114180
tagcttcttc tgccatccca cctgtgtagc ctcttcaact ccccccaaaac tcctctgtag    114240 cccatgtcac ttggaaagag ttttctttgt ctcttttgca acttgacaat gactagccag    114300
caagtttaag ttcaaattat tgttccatgg gagcagagat agatatagga aacaaaaaaa    114360
agggatatgg aggtatagag tgatttccca cctacctagt gagcactact gagatattca    114420
agtactctct acccaagaat tctattgata taaaggtaaa aaacttgatc ttaggtctaa    114480
tatccgttag tagtgtgacc ttgggaaaat gataccaccc ccaaaggctt agttttctta    114540
actgtaaaat aggcatacag atgaccaccc ccagaggatt cataaggata acatgagata    114600
aggcaacttg aaatttccta gcatagtgat agactttcga aaataaaatg aatcaaacac    114660
tgataacagt acttcctagt acacaaatga gaaatcagtc cctcatcaaa ttacagcaca    114720
ttttcaatgc tccaattatg tcactgtaga aatgctaatg tggattaaat aatttgtctg    114780
ttgctattta tacggataat ttgatagtag ttattttggg acatggatag ctttgaagcc    114840
ttacagatga gtccatcccc aagtacccaa aactaaagaa agttggctag agtgatgaca    114900
aggtggcagc acagagctcc ctgcgttctg ggccctgtcc cctagctaga gagaactcca    114960
ggctataagc atttgtattc tcatagtcca atggcaggga agaagggctg gaggtgagta    115020
gttttcactc atttattttt tcaacaagca tgtatggtat caggccttgt atgcatccag    115080
agacaaatgt gaactagccg tgtcctcaag gagattccag tctggtgggc ctgccttcca    115140
```

```
aggtcagttg cagctttagc actataaaga gcacctacct gcggcagata caatgtgatg   115200
ggacatgaca gagaaaaaat ctataagcag agcctcccca ttcccaggca ttgaaacaat   115260
cctaaccaag actggcatag tacaatgagc ctgtccctat cagcaggttt ggaagcctta   115320
acaacaacaa caaaaacaat aataatggtg atgataatca tagagcctaa tgttaccaaa   115380
cattttccat gtgttaagta ctatactaag tgcatactta atcctcacaa caatgctata   115440
agatagtaga tactcttact actaccctga ttttacaaat gtggaaactg aggcacagaa   115500
gactaagaga acaggaatac acctaattca cctcagttca acaaacatca agcatctgtt   115560
ttatgtcagg cctcgtgctg gatggcaggg agagagagat gagtaaagca tagtttcagt   115620
ccagtgggag caaatgacag cacacagtgg ggcaggtata ttgcagccct tctgcttgat   115680
gctaagaact cagtgtcagt gatgaatgaa acacagtcat tctctcaaag atcttaaagc   115740
ttagtaggag atatctgtgt ggaaacaaaa attaaatact gctgtgataa gtgtcataag   115800
agataagtgg aaaatgagag agagagatca ctgtagcaat tgattggttt aaatcaaagc   115860
ccccaaaaaa atgttattga gaattataaa acaactaatt gatttaaatc aaagcccaaa   115920
cagaagtgtt tgctaatttt atttcaattt ggttgataat ttggttgaaa tgaatttatt   115980
tcatttttta ttccatcctt acaatggaag attagtgctt gtttcccacc caaggatacc   116040
aggatatttc aggggctgta ttacaatata gttaaattat tcctttatct caaagcacat   116100
ccacactttc ccctatcctt acctttactc agggtatctc ttctgcctca ggtgcttttt   116160
ctccacattt ccatattctt aagtcctacc ttccttcagg gcctcactca aatgcctcct   116220
cctccatgaa gcattcaccc gactgaaagg taccccgccc tctcctgtac tccacatcac   116280
ttcatgggtg tctccacttc ctgctttatc tttcagtaat acacttacag ttctctttcc   116340
tccactagac tgagctcttc agaggaagac tcacttggct gaaaccatga ttttacttta   116400
aacacattga aaacctctac tggagtgcat tgtgtctggt gggcttcaac cttaattctt   116460
aagtatgtga aaacacatca cctatctgga ggtttacact ttctgctaat gactttattt   116520
ttaagcccac caccctaaca caacaaatac ttaaaacttg tcttcatttc ctttaggtct   116580
ggccctcatg catgcatata atttatagag tcactgtttt gctcggttgt cctcatgcct   116640
ctatattatt ggaggtttag attgtttcca tatactcagg ttgtattcat gtccttttt    116700
tcttttaaa tttccttagc atccatttcc accattggaa attcagggtc aaaacagggg   116760
tttgggattg gagcatgtct atcacagata accaatcatg tgttatgact taagaattta   116820
tgaaagggcc ctctacctga agatatcttg ctactgatgc tgtctcacag tgtctgaaac   116880
tcccatcata tgtggaattg ttttggaagg ctttgcctcc tgggacacat tcagccataa   116940
tcaagaaata gtattgagca ttagactgtc agtatgtcca ttagcaagac tgtggaggaa   117000
tggaatcacc aatattatat tttataggggg atacagaata caagagaagt tctgaagaga   117060
aaattcttat gtagaatagg aaggcttaga tacagcatga aagctgcagg ctttgaggag   117120
ccagaggtca aatgaaagca ttgagtattt gtttagatga aagaacagaa agggaaaaag   117180
aagcagagga agggatagta gagagaaatg tataagtttt atccatttaa cttgtaattg   117240
tgtttggcta tgggcacaat agaagcagtg agatcacttt attttatttt attctttata   117300
gacagggtct tgctatgttg cccaggctgc agtgtgcagc tcttcacaag tgtgatcata   117360
gcgtactaca ccctcaaact cctggactca agcaatcctc ccatctcagc ctcctgagta   117420
gctgggacta caagtgcaca ccaccacgcc cagtgagatc acttgaaact agggagagat   117480
```

```
gtgtgagttc tgggcaacca gtagttggct ttacatagaa ctgtaggggt caaggccaaa   117540
ggggacgtcc tgttccaagt caccttcttt ggacattaga aaaccacgag gggtttggaa   117600
atcagaaaac cagcagaggc aggaaaactc agggcagcat gggagattca gtatatacaa   117660
aaaggttcac accagtaatc aaacagaatt ttaactgctg atgtggagta gaggcagctt   117720
tgtctgctgt gtgataacca aacctttacg aatagtaggt gtatatgggg aattggaggg   117780
agataggtgg ctgtgtttag taattggttg acttcactga gatggtttgg ggattgtggc   117840
ttccagatga tcagattttc ttttttaggt agagactcca acatcattac agaactataa   117900
attacatgtg gaaagaaag gcctcctatg ttagaataga aaataaaatg ctgtggggtt   117960
gagggacaga ggtgctgtct aggaagtcag atagcgtttt ccagttctgt ccctcagagt   118020
tccttgtcct cattgagact caatttctct tactttttt tttatacttt aagttttagg   118080
gtacatgtgc acaacatgca ggtttgttac atatgtatac atgtgccatg ttggtgtgct   118140
gcacccatta actcatcatt taacattagg tatatctcct aatgctatcc ttcccctctc   118200
ccctctcccc accacaggcc ctagtgtgtg atgttcccct tcctgtgtcc atgtgttctc   118260
attgttcaat tctcacctgt gagtgagaac atgcggtgtt tggtttttg tccttgtgat   118320 agtttgctga gaatgatggt ttccagcttc atccatgtcc ctacaaagga catgaactct   118380
tcatttttta tggctgcgta gtattccatg gtatatatgt gccacatttt cttaatccag   118440
tttatcattg atggacattt gggttggttc caaggctttg ctattgtgaa tagtgccatg   118500
ataaacatac gtgtgcatgt gtctttatag cagcatgatt tataatcctt agggtatata   118560
cccagtaatg ggatggctgg gtcaaatggt atttctagtt ctagatccct gaggaatcgc   118620
cacactgact tccacaatgg ttcaactagt ttacagtccc accaacagtg taaagggtt   118680 cctatttctc cacgtcctct ccagcacctg ttgtttcctg acttttaat gatcaccatt   118740 ctaattggtg tgagatggta tctcgtggtt ttgatttgca tttctctgat ggccagtgat   118800
gatgagcatt ttttcatgtg tctgttggct gtgtaaatgt cttctttgag acgtgtctgt   118860
tcatatcctt tgcccacttt ttgatagggt tgtttgtttt tttcttgtaa atttgtttga   118920
gttctttgta gattctggat attacccttt gtcagatgag tagattgcaa aagttttctc   118980
ccattctgta ggttgcctgt tcactctgat ggtagtttct tttgctatgc agaagttctt   119040
tagttgaatt agatcccatt tgtcaatttt ggcttttgtt gccattgctt ttggtgtttt   119100
agacatgaag tccttgccca tgcctatgtc ctgaatggta ttgcgtaggt tttcttctag   119160 ggttttatg gttttaggtc taacatgtaa gtctttaatc catcttgaat taattttagt   119220
ataaggtgta aggaagggat ccagtttcag ctgtctacat atggctagcc agttttccca   119280
acaccattta ttaaataggg aatcctttcc ccatttcttg tttttgtcag gtttgtcaaa   119340
gatcagatgg ttgtatatat gcggcattat ttctcagggc tctgttctgt tccattggtc   119400
tatatctctg ttttggtacc agtaccatgc tgttttggct actgtagcct tgtagtatag   119460
tttgaagtca gatagcgtga tgcctccagc tctgttcttt tggcttaggg ttgacttggc   119520
gattcaggct cttttttggt tccatatgaa ctttaaagta gttttttcca tttctgtgaa   119580
gaaagtcatg ggtagcttga tgaggatggc attgaatcta taaattacct tgggcagtat   119640
ggccattttc acaatattga ttcttcctac ccatgagcat ggaatgttct tccatttgtt   119700
tgtatcttct tttatttcat tgagcagtgg tttgtagttc ccttgaaga ggtccttcaa   119760 gtcccttgta agttggattc ctaggtattt tattctctta gaagcaattg caaatgggag   119820
ttcactcatg atttggctct ctgttttctg ttattggtgc ataagaatgc ttgtgatttt   119880
```

```
tgcacattga ttttgtatcc tgagactttg ctgaagttgc ttatcagctt aaggagattt   119940
tgggttgaga cgatggggtt ttctaggtat acaatcatgt catctgcaaa cagagacaat   120000
ttgacttcct cttttcctaa ttgaatgccc tttatttcct tctcctgcct gattgccctg   120060
gccagaactt ccaacagtat gttgaatagg agtggtgaga gagggcatcc ctgtcttgtg   120120
ccagttttca aagggaatgc ttccagtttt tgcccattca gtatgatatt ggctgtgggt   120180
ttgtcataga tagctcttat tattttgaga tacgtcccat caataactaa tttattgaga   120240 gttttttagca tgaagcgctg ttgaattttg ttaaaggcct tttctgcatc tattgagata   120300
atcatgtggt ttttgtcgtt ggttctgttt atatgctgga ttatgtttat tgatttgcgt   120360
atattgaacc agccttgcat cccagggatg aagcccactt gatcatagtg gatacgcttt   120420
ttgctggtat tttattgagg atttttgcat caatgtttat cagggatatc ggtctaaaat   120480
tctctttttt gttgtgtctc tgcctggctt tggtatcagg atgatgttgg cctcctaaaa   120540
tgagttaggg aggattccct ctttttctat ttattggaat agtttcagaa ggaagggtac   120600
cagctcctcc ttgtacctct ggtaggattc agctgtgaat ccatctggtt ctggactttt   120660
tttgattggt aagctattag ttatatcctc aatttcagag cctgttattg gtctattcag   120720
agattcaact tcttcctggt ttagtcttgg gatggtgtat gtgtcgagga atttatccat   120780
ttcttctaga ttttctagtt tatttgcata caggtgttta tagtatgctc tgatggtagt   120840
ttgtacttct gtgggatcgg tgattatatc ccctttatca ttttttattg cgtctatttg   120900
attcttctcc cttttcttct ttattagtct tgctagtggt ctatcaattt tgttgatctt   120960
ttcaaaaaac cagttcctgg attcattgat tttttgaagg gttttttaca tctctatttc   121020
cttcagttct gctctgatct tagttatttc ttgccttctg ctagcttttg aatgtgtttg   121080
cccttgcttc tctagttctt ttaattgtga tgttagggtt tcaattttgg atctttcctg   121140 cttttctcttg tgggcattta gtgctataaa tttccctctc cacactgctt tgaatgtgtc   121200
ccagagattc tggtatgttg tgtctttgtt ctcattggtt tcaaagaaca tctttatttc   121260
tgccttcatt tcattatgta cctagtagtc attaaggagt aggttgttca gtttccatgt   121320
agttgagcgg ttttgagtga gtttcttaat cctgagttct agtttgattg cactgtagtc   121380
tgagagacag tttgttataa tttctgttct tttacatttg ctgaggagtg ctttacttcc   121440
aactatgtgt tcaattttgg aataggtgtg gtgtggtgct gaaaagaatg tatattctgt   121500
tgatttgggg tggagagttc tgtagatgtc tgttaggtct gcttgacagt ggagtgttaa   121560
agtctcccat tattattgtg tgggagtcta agtctctttg taggtctcta aggacttgct   121620
ttatgaatct gggtgctcct gtattggttg catatatatt taggatagtt agctcttctt   121680
gttgaattga tccctttacc attatgtaat ggccttcttt gtctcttttg atctttgttg   121740
gtttaaagtc tgttttatct gagactagga ttgcaatccc tgccttttg tgttttccgt   121800 ttgcttgata aatcttcttc catcccttta ttttgagcct atgtgtgtct ctgcatgtta   121860
gacgggtttc ctgaatacag cacactgatg ggtcttgtct ctttatccaa tttgccagtc   121920
tgtgtctttt aattggagca tttagcccat ttacatttaa ggttaatatt gttatgtgtg   121980
aatttgatcc tgtcattatg atgttagctg gttattttgc tcgttagttg atgcagtttc   122040
ttcctagcct cgacggtctt tacaatttgg tatgttttg cagtggctgg taccggttgt   122100
tcctttccat gtttagtgct tccttcagga gctcctgcag tgcaggcctg gtggtgacaa   122160
aatttctcag catttgcttg tctgtaaagg attttatttc tccttcacct atgaaggtta   122220
```

```
gtttggctgg atatgaaatt ctggttttaa aattcttttc tttaagaatg ttgaatattg 122280
gcccccactc tcttctggct tgtagagttt ctgctgagag atcagctctt aatctgatgg 122340
gcttcccttt gtggggaacc tgacctgttt ctctggctgc ctttaacatt ttttccttca 122400
tttcaacttt ggtgaatctg acaattatgt gtcttggagt tgctcttctc aaggagtatc 122460
tttgtggtgt tctctgtatt tcctgaattt gaatattggc ctgccttgct agattgggga 122520
agttgtcctg gataatatcc tacagagtgt tttccaactt ggttccattc tccccatcac 122580
tttcaggtac accaatcaga catagatttg gtcttttcac atagtcccat atttcttgga 122640
ggctttgttc atttcttttt attcttttc ctctgaactt ctcgcttcat ttcattcatt 122700
tgatcttcaa tcactgatac cctttcttcc agttgatcta atcggctact gaggcttgtg 122760
catttgtcac gtagttctcg tgctgtgttt ttcagctcca tcaggtcctt taaggacttc 122820
tctgcattgg ttattctagt tagccatttg tctaattttt tttcaaggtt tttaacttct 122880
ttgccatgcg ttcgaacttc ctcctttagc tcagagtagt ttgattgtct gaagccttct 122940
tctctcaact cgtcaaagtc attctccatc cagctttgtt ccattgctgg tgaggagctg 123000
cattcctttg gaggaagaaa ggcactctga tttttagagt ttccggtttt tctgctctgt 123060
tttttcccca tctttgtggt tttatctccc tttggtcttt gaagatggtg atgtacagat 123120
gagcgtttgg tgtggatgtc ctttctgttt gttagttttc cttctgtcag gaccctcagc 123180
tgcaggtctg ttggagtttg ctgcaggtcc actccagacc ctgtttgcct ggttatcagc 123240
agcagaggct gcagaacagt ggatattggt gaacagaaaa tgttgctggt tgatcattcc 123300
tctggaagtt ttgtctcaga ggaatacccg gatgtgtgag gtgtcagtct gccccctactt 123360
gggggtgcct cccagttagg ctactcgggg ttcagggaac cacttgagga ggcagtctgt 123420
ccgttctcag atctccagct gcatactggg agaaccacta ctctcttcaa agctgtcaga 123480
cagggacatt taagtctgca gaggtttctg ctgccttttg ttcggctatg ccctgccccc 123540
agaggtggag tctacagagg caggcaggcc tccttgagct gtggtgggct ccacccagtt 123600
cgagcttccc agctgctttg tttacctact caagcttcag caatggcggg caccctccc 123660
ccagcctcgc tgctgccttg cagtttggtc tcagactgct atactagcaa tgagcgaggc 123720
tctgtgggcg taggaccctc tgagccaggc acaggatata atctcctggt gtgccgtttg 123780
tgaagaccat tgaaaagtg cagtattatg gtgggagtga cccgattttc caggtgccat 123840
ctgtcacccc tttctttgac taggaaaggg aattctctga tcccttgtgc ttcctgggtg 123900
aggcgatgtc tcgccctgct ttggctcatg ctcggtgcgc tgcacccact gtcctgcacc 123960
caccatttga cactcccctg tgagatgaac ccggtacctc agttggaaat gcagaaatca 124020
cccatcttct gtgttgctca cgctgggagc tgtagactgg agctgttcct attcggccat 124080
cttcacaaaa atcttacttt ggtttctagt gttaccaccc actgttcttt ctcatctcaa 124140
ccctgagtat aagtacagat cacattcctt gggttcttag aaaataatag aaatgaactc 124200
tcattcatca aaatgcccat tagtaaatac tgagggagaa caaactagaa atccagtata 124260
gaaaataaaa ataggattat attccttgga atctcagaaa aaaacaatga agagctttct 124320
ttgggcatta gacactttcc cataaggtgg ctgactctct tttagtcatg tcagcttggc 124380
ccaatcttca cttggtagcc cttctttctt cttcattaat ccatctccta tgctcctatg 124440
gggtcctaga gaaatgccca tcatgtacac acacatctaa taacacaaag atcactctcg 124500
actagcaagc ccttttatga tggtgtgagc atttgacacc cttgttgcta gtaacatcag 124560
tgagtgacct gacccatttt tggaacagaa tatgatcagt atgttgcctc aaggaggccc 124620
```

```
tcactgttct aggaaatata attccagagt ttgctgactc acaccatgga atatatgcat 124680
aaaatggatc ctgcagataa gcctttctct gactagtttc agacattttt ttctgggtaa 124740
ttttaaagtt attttttatt tttgtgggta caaagtaggt gtatatatgt atgaggtacc 124800
tgaggcattt tgatacaagc atacagtgta taataatcac cagagttaat ggggtatccc 124860
tcaccacaag catttatcct ttctttgtga tacaaacaat ccaattatat tcttttagtt 124920
attttaagat gtaaataaa ttattgttga ctgcagtcac cctgttgagc tatcaaatac 124980
tagatcttat tcattctaac tatacttttg tacccagtag ccatcccact tcctcccctc 125040
ccactaccct tcccagcctc tgataaccat cattccactc tctatctcta tgagctcaat 125100
tgttttaagt tttagctccc acaaatatgt gagaaaatgc caagtttgtc tttctgtgcc 125160
tggcttattt cacataatat aatgtcctct agttccatcc atgttattgc aaatgacagg 125220
atctctttct tttttatggc ttaatagtac tttattgtat gtatgtacca catttcttc 125280 atccatttgt ctgttgatag acaagagttg cttccaaata ttgactattg tgaatagtgc 125340
tgcaataaac gtgggaatgc agatctcttt gatatactga ttttctttct ttagggtgta 125400
tacccagcag tgggattgct gggtcatatg atagctctat ttttagtatt ttgtggaacc 125460
tcaaatctat tctacataat ggttttactg acttacatat ccaccaacag tgtatgagga 125520
tactcttttc tccacatcct caccagcatt cattactgcc tgttctttgg atgaaagcca 125580
ttttaactgt ggtgaaatga gatctcattg ttgttttgat gtgcacttct ctgatgatca 125640
gtgaggttga ggaccttgtc atatatctgt ttgtcatttg tatgtttat tttgagagat 125700 gtctacccag atcttttgcc cattttttaa tcagattgtt agattttttt tttcctacag 125760
agtgcttgag ctcttatat gccctagtta ctagtccctg gtcagatggg tagtttgcaa 125820
atagttgctc tcattctgtg ggttgtctct tcactttgtt gatcgaatca cttgctgtgc 125880
agaaggtttt taacttgatg tgacctcatt tgtccatttt tagttgcctg tgctggtgcg 125940
gtattactca agaaattttt gcccagatta atgttctgga gagtttcccc aatgttttct 126000
tgaagtagtt tcatggattg atgtcttaga tttaagtctt taatatgttt tgattttatt 126060
tttgtatttg ctgagagata gggctctagt ttccttctgc atatggatat ccagttttc 126120 tagcaccttt tgttaaagag actattcatt ctctaatata cgttcttggc acctttgttg 126180
aaaataagtt cactgtagat gtatggactt gtttctgggt tctctgttct gttccattgg 126240
tctatgtgtc tgctttatg tgaataccat gttgttttgg ttgcaaaagc tctgtagtat 126300
aatttgaaat caggtaatgt gattcttcca gttttgctct gttcttttc ctcaagatag 126360 ctttgcctat cctgggtctc ttgtggttct atataaattt taggattatt ttttctattt 126420
atgtcaagaa tgtcattgat attttgatat aaattgcgtt gaatctgtag atagcttcag 126480
gtagtgtgga cattttaaca atatcaattc ttgaaatcca cgaacatgga atatccttct 126540
attatttgga tgtcttcttc aatttcttat attaattttt ttttagtttt cattgtagag 126600
atatttcatt tatttgacta agtttattgc taggtatttt atttttatttt tacctattga 126660 caatgggatt gctttcttga tttcttttttt agattgttca ctgttggcat acagaaatgc 126720
tactgatttt tatgtgatga ttttgtatcc cgcaacttta ctgaatttgt ttatcagttc 126780
taataggctt ttggtgcaga ctttaggctt ttccaaatat aagatcatat tatctgcaaa 126840
caagaataat ttgacttctt tcttttcaat ttggatgcct ttcatttctt tctcttgtct 126900
gattgctcta actaggactt ccagtactct gttgaataac agtggggaaa gttaacatcc 126960
```

```
ttgttttgtt tcagatctta tagccaaggc cttcagtttt tctgaattta gtatgatact    127020
agctatgggt ctgtcatata tggcttttat tatgttgaag tatgttccct agttttttga    127080
aggttttat attttaagga agataaaaat tgaactttat caaatgcttt tcatgcaaca     127140
attgaaatga tcaagtgctt tttgtctttc attctgttga tacgatgtat cacactgatt    127200
gacttgtgta tttagaacca tccttgcatc ccgtggtaaa tcccacttag tcatggtgaa    127260
tgaacttttt aatgtgttgt tgaattcagt ttgctagtat tttgttgggg attttttgcat   127320
cagtgtttat cagggatatt ggcctatagt tttcctttt tttatgtgtc ttttgggttt     127380
tgttatcagg gtaatactgg ccttgtagaa tgagtttgga atgattctct cctctatttt    127440
ttgaaatact ttgaatagga ttgatgttac ttctttaaat gtttggtaaa attctgcact    127500
gaagccattg ggtcctgggc tttttactgc tggggagact tttcattaca gcttcaatct    127560
tattacttgt tattggtctg ttcaggcttt agattttttt catgaatcaa tcttcacaag    127620
ttgtctgttt ctcaaaattt atcaatttct tctaggtttt ccaatgtatt gtcatccagt    127680
tgctcataat gccctctaat gatgccttga attttgcag taaccactgt aatgtttcct     127740
tttaatct ctgattttat ttgagctttc tcttttttc ttagtctagc taaatatttg       127800
tcaatgttgt ttgttcatcc acaaaaccaa ctttcattt cactgatctt ttgtattatt     127860
ttttccttt aattttattt atttctattc tgatatttat catttcattt cttccagtta    127920
tttgagtttg gtttgctctt gcttttccag ttctttaaga tgcattgtta ggttatttat    127980
ttgaactttt ttgatatagg tgcatattgc tataaacttt caccataata ttgcttttgc    128040
tgtatcccat aggttttagt atgttgttta gtatgtttcc aatttggtac atttcaataa    128100
attttaaat tttcttcttt atttattgac atagtcattc cagagtatac tgtttaattt     128160
ccatgtggtt tgtatagttt ccaaaattcc tcttgttatt gatttctagt tttattccat    128220
tgtggtcaga gaagaagctt gatatgaatg caattgttaa taattttttt aaaacttgtt    128280
ttgtgaccta agatatgatc tgtcattgag aatgatccat atgctgagga aagaatgtat    128340
attctgcagc cattggataa aattgtcttt aaatatctat taggtccatt taagacataa    128400
tgcagattaa agccgatgtt tcattgttca tttttctgtc tggatgatct cttcagtgct    128460
gaaagtggtg tgttaaaatc tctaaatatt attgttttgg gatctttctc ttctttcaac    128520
tctgataata tttgctttag atacctgggt gctccagtgt tgggtgcata tatacttaaa    128580
attgttgtat cctcctgatg aattgacccc tttatcatta tataatgacc ttctttttct    128640
ctttgtgtag tgtttgtctt gaaatctatt ttgtcggata ttagtattgc tgctaatttt    128700
tttggttcc atttgcatga aatatctttt tcattccttt attttcaggc agcgtgtttc     128760
tttatattta ataggtgaaa tatgtttctt gtaaataaaa attattattt taaaatattt    128820
ttaaaataat actatttttt aataagaaca attattattt tttaaaaaat ttcattagtt    128880
ttggggggcac aagtggattt tggttaaatg ggtgagttct ttagtagtgg attttgagat   128940
tttagtgcag cagccacctg agaagtgtac attacccata tattatatat atactatata    129000
tgctttatat atatagtgtg tatatataat atatatacaa ctacatattg ggtaatgtac    129060
acttctcagg tgactgctgc actaaaatct caaaatccac tactaaagaa ctcacccatt    129120
taaccaaaat ccacttgtgc ccccaaaact aatgaaattt tttaaaaaat aataattgtt    129180
cttattaaaa aatagtatta ttttaaaaat attttaaaat aataattttt atttacaaga    129240
aacataattc acctattaaa tataaagaaa cacgctgcct gaaagtaaag gaatgaaaaa    129300
gatatttcat gcaaatggaa accaaaaaaa ttagcagcta tactaatata ttatatatat    129360
```

```
actacataaa gcatatatat agtatagtat atatataata catttataaa gcatatatat  129420
agtatgtaga taatatatgt ttatatactt taagttctgg gatacatgtg cagaacgtgc  129480
aggtttctta cataggtata ctcgtgccat ggtggtttgc tgcacccatc aacctgccat  129540
atacattaag tatttctcct aatgctatct ttccctagc cctacccac tccctgacag  129600 gccctggtgt atgatgttcc cctccctgtg tccatgtgtt ctcattgttc aactgccact  129660
tatgagtgag aacatgtggt gtttggtttt ctgttcttgt gttttagttt gctgaggatg  129720
atggtttcca gcttcatcca tgtccctgca aaggacatga actcatcctt tttgatggct  129780
gcatagtatt ccatggtgta tatgtgccac gttttcttta tccagtatat cattgatggg  129840
cattttggtt ggttccaagt ctttgctatt gtgaatagtg ctgcaataaa catacgtgtg  129900
catttgtctt tatagaagaa tgattttataa tctttgggt atatacccag taatgggatt  129960
gctgagtcaa atgatatttc tggttctaga tccttaatga attgccacac tgtcttccac  130020
aatggttgaa ctaatttatg ctcccaccaa cagtgtaaaa gcgttcctat ttcttcaaat  130080
cctcaccagc atctgttgtt tcctgacttt ttaatcgcca ttctaactgg catgagatgg  130140
tatctcattg tggttttgat ttgcatttct ctaatgacca gtgatgatga gctttttttc  130200
atgtttgttg gcagcataaa tgtcttcttt tgagaagtgt ctgttcatat tcttcaccca  130260 cttttttgatg gagttatttg ttttcttctt gtaaatttgt ttaagttcct tgtcgattct  130320
ggatattagc tctttgtcag atgaatagat tgcaaaaatt ttctcccatt ctgtaagttg  130380
cctgttccct ctgctgatag tttcttctgc tgtgcagaag ctctttagtt taattagatc  130440
ccatttgtca attttggctt tgttgccat tgcttctggt gttttagtca tgaagtctct  130500
acccatgcct atgtcctgga tggtattgcc ttggttttct tctacagttt ttatggtttt  130560
aggtcttgca tttaagtctt taatccatct tgagttaatt ttgtataacg tgtaaggaag  130620
aggtccactt tcagttttct gcatgaggct aacgagtttt cccaacacca tttattaaat  130680
agggaatcct ttccccattg tttgttttg tcaagtttgt caaagatcag gtggttgtag  130740
atgtgtggtg ttatttctga ggcctctgct ctgttccacg tgtctatatc tctgttttgg  130800
taccagtacc atgctgtttt gggtactgta ccacttgatt ggtgagagag ggaatccttg  130860
tcttgcactg gttttcaaag ggaatgcttc agcttttgcc tattcagtat gaccaatatg  130920
tagtctttta ttcctcaccc tctctcaaca ccccacccc acggagtcct caaagtccat  130980
tatatcactc tgtatgtttt tgcgttctca tagcttagct cccacttata aatgagaaaa  131040
tacagtattt ggttttccat tctttggtta cttaattagt ataatggcct ccagctccat  131100
ccaggtgtct tgttttttcat ccattcagcc agtctataac ttttgcttgg agagtttcgt  131160
ccatttagat tcagcgttat gattgataac taagggctta ctcctgccat ttggttgttt  131220
tctggttatt ctgtggtctt ctcttccttt tttccttctt tcctgtctcc cttttagtga  131280
aagtggtttt ctctggtggt gtattttatt ttcttccttt ttattttttt ttgtgtgtat  131340
ttgttgcatg ttattgattt gaggttacca tgaggcttgt acataatatt ttctaactca  131400
ttatttcaaa ctgatgacaa cactctatcg cataaaaaaa catggaaaga gaaaactaat  131460
aaaaactcta cattttaact tcatctctct gcttgttgtc actttgtcgt ttctatttac  131520
atcttattgt actgtttatg tcttgaaaag tagtttcagt tattactttt gattggttca  131580
tctcatagtc tttctactca agatatgagt agttcacaca ccacaattac agtgttacaa  131640
tattctgtgt ttttctgtgt actttcaatt acccatgagt tttgtatttt cagataattt  131700
```

```
gttattgctc actaacatcc tattctttca gattaaagag ctcccttag catttcttgt   131760
aggaaaagtc tggtgttaat gaattcctc agctcttgtt gatctgtgaa agtctttatt   131820
tttccttcat gtttcaagga tattttcact ggatagtcta ttctagggta aaagttttt    131880
ttttttttt cttcagccct tcaggtaagt catgccactc tctcctggcc tataaggcta   131940
ccactgaaaa gtctgctgcc agacatatat gagttccatt ctatgttact tgtttatttt   132000
ctcttgttac ttttaggatc ctttctttat ctttgacctt tgggagtttg attattaaat   132060
gccttgaggt ggtcttttt ggattaaatc ttcttcgtgt tcttgtactt ggatattaat    132120
atctttctct aggtttggga agttctctgt tattatccct ttgaataaac tttctaccaa   132180
gatctctctt tctctctctg tctctctctc tctctctctc tccttcttaa ggccaataac   132240
ttttagattt gcccttttga ggctgttttc tagatctcgt aggtgtgctt cattgtttgc   132300
tatttttttt ttttttttgt ctcttctgac tacatttca aatagcctgt tttaaaactc   132360
actaattctt tcttttgcct ggtcaattat gctgttaaga gactctgagg cattcttcag   132420
tgtgtcagtt gcattttca gcaccagaat gtctgcttat tttttttag attatttcca    132480
tctctttgtt aaatatatct gatagaattc tgaattcttt cttagtgtta tctttaattt   132540
ccttgaattt cctcaacaca actatttga attatctgtc tgaaaggtca catatctcta    132600
ttttccagg attgctatct ggtgctttat ttagttcatt ttgtgaggtc atgtttcct     132660
ggatggtgtt aatgctagta gatgttttc agtgtctgag cattgaaaag ttagatgttt    132720
attgtagtct tcacagtctg ggcttgttca tacctgccct ccttgggaga cttccaagt    132780
attcgaaggg atttggatgc tgtgatctta gtctttggtc actgcagcca tatctgcttt   132840
atggagcatc ccatgctcag taatgctgtg gctctttcag actcatagag ttactgcctg   132900
catgctcttg ggtaagagcc aggaaaattc cctggattac caagcagaga ctcttgttct   132960
cttctctcac tttccccaa acaaatagag tctctctctc tctctctctt tctctctctc    133020
tctccctc tcattctctg ccgacctgcc tgaatctggg gtagggatga cacaatcaca    133080
tttgtagtca acaccattgg gactgtgcta ggtcagaccc aaagctggca cagcactgag   133140
tctcgcccaa cgcccacaga gaccactccc tgggtaatgt ctgtgtttgc tcaaagccta   133200
agggctatac aatcagtcag tggtgaagcc agcctgtctt atgtccttcc cttcagggtg   133260
atgagttcct caagcaggtc cagggatggt gtccaggagc caaggcctcg agctgtgact   133320
gagctggcac ccaatccata agacaaagat ttttccaca cttccttcc ttgtcctcaa     133380
gcaaaggagt ctctccctgt ggccaccacc acccccatgt tcatggcaag tattgtctgg   133440
ctaccaccaa tcttcactca aggcccaggg gttctttagt tagcttatgg tgaatgctac   133500
caaggctgag tctctccctt caaggaagtg ggctcctctc tggcccaggg caggtccgga   133560
aatactatcc aagagccaag gcctggaatc agtttcccca agagtccatt tggtgctcta   133620
cacccactgt ggcagaacca gtacccaagc tgcaagacaa agtcctcttt actcttcctt   133680
ctcctttaca gagactctcc ctatagccac cacagctggg aatatgctgg gtcactcttg   133740
aagcaagaac agctctgagt ctcactcaaa actcctggca agtactgcct ggctatcaca   133800
ctgattattc agggcccaag ggctctttag tcagcaggag atgaatcctg ccagtactga   133860
ttccttccct tcaaggcagc cggtttcttt ctggcccagt gtgtatctag aaatatcatt   133920
tgggagctag ggcctggcat ggtgacctca ggactctgcc tggtgccctg ttctactgtg   133980
gctgatgtag tatccaaatt gcaagaccaa gtcctcttta ctctccctc tcctgtcttc    134040
aagcagaagg aatgagtccg ccctggagtt gggagctgca ttgcctggga ttggaggagg   134100
```

```
ggtggcacaa gcactctctt ggtcacccca gctggtgtct tactaggtcg catgttcccc   134160
aagtccactg gctctgaggc tagcacacca ggatttgacc aagaattgca attcttgtgt   134220
cttacactgc cttcaagtt tatttgagat cccagagcac tttagcccac agtgacaggg   134280
cttgccagaa tttagtttct gactgctgag atggacaatt tgcgtctgat tagggctggt   134340
ctaagtgctc cttctgtggg cactggctga gttctgctcc atgttgcttt ctgctgtgac   134400
agggcaacat tgagtttcaa tgcaagtccc acagtcactg caatcttcct ctcccaagcc   134460
tgctctgaac accatgtggt tgctgctggg ggctggggga gggatgttgt aggcaattca   134520
agaatgtctt tcctaccctt ttcggtgctt ctttccttgg tatgatatta aaaccagtta   134580
ctgtgattgc tcacctgatt tttggttctt atgaaggtgc ttttttgtgt ggatcactgt   134640
tcaatttgtg cctgcaagcg gggatggggg acaattgctg gaggcttctc tttggccatc   134700
ttgctccacc tctaccctag tattagcaat ttcaaagcag ttgggatgga ggtagaagga   134760
aagggcgctt ggaatcagaa aatccatgtc ttagctttga gccttagaaa attcatttga   134820
cccttgtaag cctcagttgc ttcatctgta aaagagaaat aatataatgg ctgaaaagat   134880
caaaggtgat aatgcttttg aaaacactat agaaaatgac aaaatatcac atgagtatta   134940
ttttctagtt tctaggagtc tccttaccat tgtacaggac aaccatgtct attttttaaat 135000
aaattattat ttgcctctga gcaaccctgc aaagagttgc ctgtaggaga aacagcttta   135060
cttgcaaatc actccactgt tttctttgtg cacagcttat taatacataa ggcacatgtc   135120
ctccagcctg cagtaacatt ggaatcatta cctctttgga gtacctacca gagcttctca   135180
aagtgaattt tgtttatcac cacaaaaaat agtctgttgc agagataacc tccaaattca   135240
atgcacaatat ttccaatcac tttttgcatga tgcagaaata gacaaatata taattttgct   135300
tatagagaca attattgtct cccaacaagt gatcagtagt cagaaaatgg ccaagaaata   135360
ccatggggtg tgccttccca taacagctta tctttgtgtt ttagttgcaa ggttactaaa   135420
agcctgtgca gggtttatgg caaaagtaaa acttgctcca ggagcaagcc cttgtttcat   135480
tgtctaatgt tcttaatccc cagcagacag gatttggatc tggcatttgg taacagggca   135540
gtttccaaag ttgctgtacg caacttgagg aagagaggtg atattatcgg aatgaatttc   135600
tttgttgtaa gttataaaatg tatgggcttt tccaatccca tcacccttaa aactttattt   135660
gttttctgca gtgagggtgt ctccgttgtc tttaatatgc ttgctttgag ttcatggatg   135720
aacattcctg cctggctgac atgtggactc tctgaaattg ttataaggtc ttttttcttg   135780
ttttttctt gatgcccaag ctgccaaggg tagtactggc agtggtgggc agacaaggag   135840
gtgatagcaa actttgtcct ctggcctccc ttgacccatt ccattcatta tctaagggac   135900
tccaagccag cattccacag agtgccctca ccaaactcac taagactgaa ggcgaaccag   135960
gattccaaac agccattatg aaaggaaaga gagagagact tagggtttgc aaaataagat   136020
accctgttga ttcttttttat tccatacaga tactactatt ctttaggaaa acgttaaaat   136080
cacatgatct tccaggacct gggctgcttc tttaagaagc atgttacaga aagctttatt   136140
ggccaacaac atattgaaag atagattaat caatcattca ttcaaataag gtatattcag   136200
aattgaggta tattgtagcc agacagtgag actacaaaaa aagaatgcac cgtacccta   136260
tctcttgcac aatctaacga gggagataac cactctttca atttatagtg acctataaca   136320
tttcgtacac tgctgaatat cttttacatgg taataacaca atggaaagct tgcaaaatag   136380
acagaggcta gggggaagaag gattgagtgt gaatatagcc tcttataaat cgagaggaat   136440
```

```
ggtctgtgtc ttctgatcat acagagataa taaatatgga aatgatttca aactaacaaa   136500
gcaaatgtgc agaaaatact gagaatatag tgggcaggat acctgagttt tggttccatc   136560
tctgttattg actcattgtg taatctgagt caggtctgtt ctgctctctg gatctcaccc   136620
tttcctatct gtaaaatgag attgttggat tagatgatct ccatagaggt tctcacctat   136680
tctgacattc aaaaggactc ctaattttc ttatataata ataatatata tgatctgtag   136740
agtgctttac actttatatg atattttgc atctgttatc tcatgtgaga aaagcactgg    136800
actgctggac tggcaatgag gacacctgga ttcttgtctc tgttttgaca ctgattcatg   136860
gtgtgatctt caagcaaatt ctctgagttt cagtttctca atctgtaaaa tagggggta    136920 tgaagattgg actaaatcag taggtctcta aaatgttcca caaagccctg gggtgggggg   136980
ctcctacaga gtttcgctaa ggcaaaccac aacgctaagc ctgcatggaa gaggagaaaa   137040
agagtggcct gacaagagaa gttcccagtt tcctatgcca accccaggca gattacattt   137100 aatttatct gatttatata gagagtttct atgtaatgtt ttattcttaa aaatagttta    137160
ctataaaaaa ctcaactggt ttgattttta aagattgcac atataagtga gatcatgcag   137220
tcagtatttg tctttctatg cctggcttat ttcacttagc ataatgtctt ccagcatcat   137280
ctatgttgct gcaaatgaca gacttttctt ttcattaaag gctatatagt attccatcgt   137340
gtatgtacac cacatttttct cttttgtaac tttcatttta ggttcagggg ttcatgtgca   137400
tgtttgatat ataggtaaac tgcatgtcag agaggtttct tgtacagatt atttcatcac   137460
ccaggtaata agcatagtat ctaatcaatt tttttctgat cctctcccctt ctcccaccct   137520 acaacctcaa gtaggccctg gtgtctattg ttccctctt tgtgtccatt acaccacatt    137580
ttctttatcc acttatccat ccatggacac ttagtttgct tccatatgtt ggctattgtg   137640
aataatgctg aaaaaagtca aactcataga agcagagagt agaatggtgg ttaccaggga   137700
ctgggaggca gttgactgag ctaggaaaag agagataata aaagggtaca atgtgtcagt   137760
tatatagaag gaataagtta tattgaacta ttgcacagca tggtgaccat agttaataat   137820
aatgtattat atgtctcagt attgctaaaa gagtaaattt aaatattcta accacaaaaa   137880
attattagta ggcaaggtga tggatatgtt aatttgcttg atttaatctt tctagaatgc   137940
atacatatat caaaacatcc cactgtaccc cataaatata tacaattatt atttgtcaat   138000
ttagaaattt aaaaacttga tttagatgag ctctaaggcc ttaagtatta aagtattaag   138060
tattaaagtg atatgtaacc aagtatattg tttggtaact tcatttttgt tattattta    138120 acaaaccaat atattgtgaa tatacttcca agtgaaaaga aaaaagacat tgcagtcatc   138180
actaataact gcaaaacatt cctttgcaag aatatggaat aattcattta atcattcccc   138240
taatgttaga cattcaaatg tttccaactt tttctattta ataatgcta caataaactt    138300 ctattttgtg cttattgtat tattttctta caacacatcc ctagaagtgg aattcctaga   138360
agtttataca catttccaat ttttttccaa atatatggca aaattctct ctaaagtatt    138420 tttattccta ccagaaatac ctcttcacca acacgtagta tttaatctgt accaatctgg   138480
cttaagacaa tgatatttaa tttgtatttc tgtgatttct agctaaatta aataatcttc   138540
atatgcttat tggtcatttg tacttctaac tgctttctcc tgtctgttgc ccattttcct   138600
attgtgctgt ttattttat atatcgaata tattgaccat tggttttaca tacttgatgc    138660
taataattat tcttagttta tggtttgtct ttgagtttta taatggtgtt tatttcacat   138720
aagaaattat aaatgttttc taatgaaatt tatcaagtct gtcttcactt atgttttctt   138780
cattgtcaat aacttaaaat gaccttttct acctttaaaa attttgaaat tttcctctgt   138840
```

```
attgtctaat agtacttaca tgatttcctc ttttaaattg acatatttaa tccatttgga  138900
atttattttg attttaacta gtaatttaac tttatttttct tctccaaatg attcactagt  138960
tgttctgaca ttatttagtg aataattcat cctttcttca ctgaattgga atggcatatt  139020
ccatatactg tgtctggttt tggcttttct gatctcttcc actgatcaac ctaagctgga  139080
gccagtatca aactgttgta atcattatgc ctttagatac tttaaatgta cagcagggaa  139140
tgtcttatta ctcttatttt tcacaaatat cttggcattg tctcatgttt tattccttca  139200
gataaatttt gggattattt tgtcaagatt ttgtttgagt tgttttaaat ttttagattt  139260
cattgggaaa gaactgaaat ccttgaaata ttgcttcttc ttagccagga atatggtaca  139320
actttgcatt taattcagtt cttttccttaa ataccaccat gaagttttt gttttgttca  139380 tataggtcct gcattaacac catatatata aagtgtgaga aatactacat tcttcaggat  139440
tctctgtagg ttaacaatga agatgatgac tcaacccttt ctttgtttgc ataatgtgat  139500
gccactaata gtgggtaact tctctgcctt acctcctctg ttccaaacag gattttcag   139560 aatgaacaaa ttaaaagaat cataatcaga cactaacccc aagccatact gcatggcagc  139620
accaatggga ctgacagaaa acaacagaaa taggaagaaa tcctacagag aaacaaactt  139680
gaaagctgtc tcatggcctt tgaatcatac ttaagtttta tgatggaagg atacgactat  139740
gaagaaagac acagagcaac atcagacagt caagaatttc agagccagct ggcatgcagt  139800
ggacctcatg ccagcccatt ttatgactat ttaggtagtc aagggtttaa gattttcta   139860 ataagacagt tattatgcat ttcaatgagt gatttctttg cagctctaga gtgtggcctt  139920
acctacttca acatgagaag attttttgtat tttgtcagtc atttcacaat gacttttagt  139980
gagcccttca ttatagactg tggatacaac tttgctgttg gaaattaaca gtgtcaaaca  140040
actgggtata atgtttgtaa tatctgagga gggggagctg cctaggaagt tgtattccct  140100
gtgttaattt ttcagtctct taggttatag aggaccttct agaaccacct tacagcagga  140160
ttacatccca tttacacagt tctctgtcac ttgaatacag agaagggatc cacaaggcca  140220
tatgcttcct agacaaagag aaaagatttc tgccacactc agaacgcttt gtcttcagac  140280
tataatcacc cacaccatat ttcctttgga tccacttttcc agatttttgt gctggcacta  140340
acaccaactt gctgtggctt ggggcatgta atttcaatac tttgtgccca ttttcataag  140400
tgaagtgtca ggcatcacat tggacatttt aagattcttt acagcccaat gattctgtgt  140460
ttctaattag gcccaatggg ttagagctaa aaggaaacag tgagtttcct ggaaggaaag  140520
gacatataac acagtccaga ggtaaaatgg gctgtattca agaaaagata ggacaatact  140580
ttgcagggat gctgcagaga ggattcaagc cttgtatgga ggaatggatg tgatacaacc  140640
aaaaagtctt taaaaattct ttccaactaa tctgagattt gtaaccttat ggactgtgat  140700
ttgcagcaaa ccaaggatgt gataaagact agtattgttt ctagaatgca aggatggttc  140760
aacatatgca aatcaatagt attaacagaa tgaaggacaa aaactatatg atcatctcaa  140820
tagatgcaga aaaataattt gacaaaattc aacatcattt tatgataaaa tctttcaaga  140880
aattgggtat tagaaggaat gtttctcaac acaataaagg ccatatcaga caagcccaca  140940
gctaacatta tattcaatga ccaggaatga gataaggatg ctcactctca ccacttctgt  141000
ttaacatagt actggaagtc ctagccaatt tcatattaat gagcctcatt ttcttcatca  141060
tagaatgaag tatataataa tccctgttat acttactttg cacagattat tattattatt  141120
taattattat tttgagacag ggtctcactc tgtcacccag gctggagtgc agtaccacaa  141180
```

```
tcacagctta cttcagccac gacctcccag gcataaagga tcctagcccc tcagcctcct   141240
gagtagctgg gagtacaggt gcacaccacc acacctagct aatttttttt tttcattttt   141300
ttatagagac ggagtctcac tatgctgccc aggctggtct caaactcctg tgctcaagca   141360
atctttccac cttggccttc caaagtgctg ggattacagg agtgagccac tgcacctggc   141420
cttgcagatt attattaaac tttgtaaact aatcaaatga gagtgattat tgttactgtt   141480
aagaactctg atagcctcat ccatatattt ggagaaattg aataaataat aggaaagaaa   141540
taatagcatc ccaatgattt taccttggct ctaccatcat ttggggaagt gataattcag   141600
ataggagaag tgacttggaa gcagtcttga gagattgcct gttccatccc ctatctttgt   141660
ccttaaacca aattgtacag ataaataagg tcttattttt aggacttaca gaaaaaagat   141720
tcctttcata tccatctttg caatcctcaa cccacttctgt cactattatg tgtcatttca   141780
aacattaaat tcctcattct gctttgaagg aacacatgtg tcatgtgtac ccatttgtat   141840
gttttggtgt gttttatgct ttatgtgatc acccacatat gcacagataa ttccaaaatc   141900
cagtgtgtgg gtgttgtatt ccctgtgtta attattcagt cacactcaaa cacctatgca   141960
ctcacacata catgaataca cacatgtaca ttagcatgtt tatgcttatg ttgcatgtga   142020
ctggcaacat cagtgccttt ctaaggcaat gttaactacc ttgagttttg ggagagcttt   142080
agagaacaaa gacaagagac taaatgattc tagatgtaag agacaatgtt gcaataagtt   142140
actatcctaa aaagacagaa tacagggaca agagactatt attttggata gtttcttgct   142200
taccagtaat acttaagtcc tttacattaa aaaaaaaaa ctctgtaaat atattgcaga   142260
agaaatccag acatccttca agattcttag agctggaaaa gattttaatg actttccagt   142320
ccaatctatc tcatgtaatc aatggggccc agagaggcaa aaggtcttgt ccaaggtcat   142380
atagtgagtt agtgataagg ctgaacaagg attcagatgt tggggcttcc agcccactgc   142440
tctttctctc atctgggatt tgtgtatttt tgttcattag agattttcct ctgtaaccte   142500
aatatccaat gcagggcctt gcacataata gattatcagt aaatgttaaa ttaatatgtc   142560
atggctttgg ttgtactggg cttttgcact tactcctgag taaattgtaa agaatatcta   142620
cgttttaggt tgccttgttt tagaccaaga ggtacccaga gaaaaggtgt gaactatgct   142680
aaggaaatta tccgagttcc aaattgaaaa aaaaaaaaaa tcatgctttt ccgctataac   142740
ctctctcatt cacagagtga ttctctttca gaagggcaat ctagaactat tatgggagcc   142800
atattccatt ggtggtgcaa ccatttcttg acaaactagg gtccaagaaa gtattttcct   142860
ggggaagatg agatttctca aagaaggcac gcactttcta acctaagctt atttcagtaa   142920
tcaatgtaac aagctggtct tgatgattgc agcagtacca atactgtggg agtgtaccag   142980
ttctagaaca gctacaacat tggaattgaa cgcactagaa ttggatacag gacctgtttt   143040
tgaggagcta acacccaaag gctgaacagc actcgtagca ccgtcctttc tgtgcacata   143100
tggtagtcct cagtttgcaa cagaaataaa gctgttagca aattatgtgt tctatttatg   143160
caaataaaat cttgtggtat gctagaaaga gcactggcct ggagacctta gttttctcat   143220
atgttaaaaa cccctaacac aggcctggtt catagtaggc acccaataaa tagtagtttt   143280
cttcctttgg gggcctccga ttcagtgtgc ttcttcaggt aagtcacttc cctggaactc   143340
ctccttggaa tgagagttgt actgttgtga tttttaacag ttccttcaag ccaagcattt   143400
tggaatcctt tcataaaggg agaaggaag gaaagaagaa aggaaaatta aaggaaaaag   143460
aacaaataaa acgttaaaaa ggaggaaagg aaaaaggatc ctttactaca ataaaactaa   143520
tcttatgttc ttgcaagtag cactttaagt aaaagaagtt cttttgctgac ctggttacta   143580
```

```
ctgaacctac tacataaaat agcctactat aatagatgca tttatgtgcc taatcttcac   143640 ttttttaggct tagtaaaggg agaggaaagc tgatgtatag ttaaatttat gttttttagtt  143700 gttttttttt ctactctcaa atatcaatca ctctttagtt tctctttctt tttccgacca   143760
caagcattct tcctctgctt aaagaagctt ccctaaaatc ccagtctatc cagtaagcca   143820
aagcacagca ataaatttga ggaaaaaata ccagggactt agagacagaa aggagtgagg   143880
ggatgcagaa gctgaagctg gagcacggtt gcaagcatga gaagttctgc gtgtttcaga   143940
gcagccaagg atgtattttt gcctattcct gctggtgact ctgtgtgtct atgcatccat   144000
ctgctatatt tacatgttta gtcagtcaat ccacgtttgc tgagagcctg ctgtgtgcca   144060
ggattgtgct agcgtaaagg agcaaagtat tgagcaaaat atgtttgagc agctgtaatt   144120
ctgaggatct ctaggtctga gcatgtgtat gtgtgtgcgc ttctatgtat ctgtgacaac   144180
tccaggtgtt catgacagtg atctttgtta ctctgttggc ttcatcgaac ttccttttac   144240
ttgctgtgat tcactacata gagtgggctt tatctctgat ttttataacc tgcaagactg   144300
ggggtatgat caccagcaat ctaaaaacag ttagaaatcc catggagtta tcttttgtag   144360
aaattttcct ctactaatat tatgaaaaat aagcatctta ttagctcgag tgtaattcta   144420
tgcatgatta caggtatcaa taggaagaaa cattgactga gttcaaatct cttctacgcc   144480
atgctaaagg ggtgacaagt tccacaatgg atcattttct catgggcatt tctgactttt   144540
ggtaaaagta gagcacctta ttttaaaaac cattgagtag tcctaatagt ggagatatca   144600
tcaggatctg aattgttcat ccctaaaaaa aacaccaatg gaaatcaaac aatatagtgc   144660
caaattaaac tgtttgaata tttaggttct gtatgatcaa attgtttggt gccatactct   144720
gtccactttt ttcatgtggt aggatataat ttcatatctt ttctgttcta gaaatacccg   144780
aagaaagaga ctctggaaac tcattatcag gtctatcaac tcttgtattt gttctcccag   144840
ggaaacagaa gtacctgtgc gccagcagaa atgattgcac tattgataaa ttccgaagga   144900
aaaattgtcc atcttgtcgt cttcggaaat gttatgaagc agggatgact ctgggaggta   144960
agatactttt cttctctctc ctcctccttc ctctctcccc cttctccctc attttctagt   145020
ctctctttag accagatttt cttctttgat gcttccaagg ggaccagcca tgctctagac   145080
acaggctgac cctttcatag gcaacgtggc catcagccag ctggtgcctt ttttttaatc   145140
cttatctata ccaatcccca ttccggggct cagcattaga gcaggcggtg tgaagcaggg   145200
atcaggagcc aacagaaggt gagtgaggat gcatctgact gggcagggcc cccaggggac   145260
ttaatgatac tggcctgatg ttgttcagtg gtagctagga tgagagaact aagaaatcca   145320
gaacagtcag aggtgcagga tgacccaggc ataggcgcag gatgacccag gcacaggctg   145380
atcctgaaca cctgggaata tcccttagct aactgctgcc tatgttgtag ggccagccac   145440
ctcgaatgag aagctacttc tctttggagc ctgtgactag gctgccacac agagccaatt   145500
tcctatccta tctctcccaa agatgagcag gtgttttaat aatttccttt tctttgcaaa   145560
gctattgacc atttccaaaa gcattttttt tcagtagcac agtaacgtga tagatggaag   145620
atacagctct ttcaagggcg ttcctctatc ataaggctct ctgtcccaca aacctgtcta   145680
ccatgagtgt tgtcaccatt ccagaaaggc ttgacatcag ttgattgaga cttatatttt   145740
ccctctccaa actcccccat ctcttcatgt ttacatctgc ccaatgccag ggtcctcgct   145800
gctgcctgct acttccaaaa agatgtgtct ttcatgagaa aaacaagatc attaatccac   145860
ttcgatttgg aaatggaatt tgaagaaagg caagcctatt tctgagtgcc tgcaactgta   145920
```

```
gcctcatacc caattattca ttattagcct ggaaaaccca agtgcctaga atccaaccct   145980
ctcccctctc ctcttaagtc taatttagac cagttgtcta tctctggctt tctgtgaggt   146040
gttcaatacc ttgtctgcct atgtgcacat ttatagacaa caactagttc tcttatcctg   146100
gagcagggcc atgtgtggat cttcatatag ataactatat cctccccatc ctcacagggc   146160
agtagtatta tttaaacaga acaaagtacc tcacatgaat tgacccaggc tggatgagag   146220
acaatttcaa aagaatcatc tcaagtagcg tccagtactc ccaaacatca caggtagatg   146280
ttctgtgagt ggctttccaa gcatccacat caaatgagac tcagatatct gagaaaactc   146340
aaccttgttt tggtttgctt ggtgcacccc aaagaaatcc aacaattgag gtctacagtg   146400
gagaagaagt aggactgggg tcagggagta cagaggcaaa ggcaggaagg gtgacaaagt   146460
gattgacaag aaaaaatgtt ctccatatga atgttgcagc cccatgttga gggttcttat   146520
acactcaact gtcaattatt tagccttctg tgaattatgt atagtataaa agatagggac   146580
tctcaagtag ggaaccctct tggcttgccat ctggcaatat gaattgcaag tccactttga   146640
tgcaggtaaa gtttaatggt aacaaaagtc ctcataacat ttggatgcaa atcttaacat   146700
taattccatg tctcagccaa cattctccat tattaagcag cctgtgatgt gattacagtg   146760
aaccactttt gaaaaggagc ctgtgtataa cagatagttt cactatacta tataaccgtc   146820
agatgcaggc ttgtaaatta atttgttggt gacaatgttt cagtacattt tcaaattgat   146880
tcattggtat agtactcaaa tttgagtggg cttggtgaac acaatgaaga caagctgaga   146940
agtgctgtga ctggccttca tttcagttgc aggcccatga tattttgagt gtcttccatg   147000
tacaaggcac catgctaggc attagagctt gaggctggca aacttcagga agtgttcaca   147060
agataccagg attcttgatg ttgtgtaaat ggccttgcct ttagagtcag gcagatctag   147120
tttaaaggct cagctccttt atttactgtg tgccctctg agcctcaatt tcctcatctc   147180
tgatttagaa ataccatcct catagagtta taatgagtat cagatgacat gatgaatgtg   147240
aacatccttg ataaatagca aaatgctaga caaatatggg ggcttaatat gacattgagg   147300
tcactagtaa tttagctgga aagtctgtaa cacagcactt cccgatggct tttaccctaa   147360
gtaacttggt atgccatata atatgtaaca gcaccaacag gcagagaatc gccagaaaac   147420
actcttgatt acctcaaacg aaaaagtacc accaggatcc tgttcagaag ctaattttag   147480
taattaaggg aatcatatgc tatgttcaaa taccatgcca gtaaaaaccc aattgtttac   147540
cttcttaaat cactgcttga agagcaaatc tttccatttt gctgaatgaa cttatctcca   147600
cgttccctgc cctactgaca caaccccctc ccaagtttat tgttaactta cacattcaat   147660
gcacagcaca cctttactca aacaatggaa aagaaagaaa gtgtcaattc aaagtggccc   147720
ttgtctattc cttaaggagt agacttccat tttcatcaga tttggattta gcatagacat   147780
attgattacc ttgaagaaga attcatataa ttttatcttc tgattcccat cactcaaatc   147840
aaaattacat aatatattcc aaaatggcaa ctaggaatgt ggccttgggc aagtcccttc   147900
tctcctctga tgcttggttt tcccatcata gaactggaat tgtggcttca ccgaggacct   147960
ttctggtgct aacattttgt gattctatgt aaaaagccac acagaaagga ttgttttttca   148020 gccctttctt agattgtctg ttccctgctc ccagaagtat agatagtgag acttgagtgc   148080
tttgatacat cgtaattgta tctacctcca ttcacaccta cttaagatat ctgtctaaaa   148140
gtagactaga cagattattc agagagtgga gggcagaagg gctgtctctg tatcttaaag   148200
aagctggcac tcttcagctg atggctgctt ggtcttgagg cctcaagatc tttaatctgg   148260 cttttctctat agtgtttcat tcactgtttg gtgatggaat ctcttcagtt cagagatact   148320
```

```
taatagatat agcttttct ttcctgcttc caggcctacc tacctgtttc ttgctttttt 148380
ttctagcagc tgttgttgtt tctgaaagaa tcttgagggt gtttggagtc tcagaatggc 148440
ttccttaaag actaccttca gactctcagc tgctcatcca caacagagat cagcctttct 148500
ttgtagatga ttcattcctg gctgcatttg aaaaccacat attgttaatt gcttgacgaa 148560
tttaaatccc ttgactactt ttcatttcag aaaacactta caaaaaaagt ccaaatgagg 148620
accttccctc cagtgaatta gctgtggctt tctcacagtc catagttagg ataaatgtaa 148680
agccatttct cattttctc cgcactttcc aagggtacac tccttgtttc caagatggaa 148740
tgagaaataa agaagtgccc ttcctgccat cttctcccct gacccttcc tccttcccac 148800
tttcctccta ttcctcccca aacatgattt atttctgcgt tttgcaactc ttgagttctc 148860
agcatttagt aaatggtgtt ggtccctgtt gattccttcc tctcctggac catgaaggt 148920
agtaggcctt tcagaaattt caggtagcag ccaaacccca gaagaagaga aggaacacag 148980
agacctagac catgtgagaa cctgaggtgt gcagcattta cttcacagat tcgtctagca 149040
tatttgagag gtgtctttcc tactaggaga ctgaactctg catctgagaa taaaaactta 149100
acatatctac aggttttgac aacctctgtg aattatctag ttgagaggat ggctcaagga 149160
gcctattgcc atggtctgat gtcgttatgg acgctatgaa catccttgca gtttccattg 149220
ttgaagacag ccctgatgcc agctgtctca tcattcccca tgttcaagag catcccagca 149280
ttgctacctc aggatcccat gtcctgaatg caacagagtg atttcgctgc tgaattacta 149340
ttcatggcat ggctcttcac agcatttatt catccatgta tctatccatt catccttcca 149400
gccagccaag aagttcacgc tttcatcttt tcatccattt actcacctat ttattcattt 149460
agcaaatatt tattgagtac caactatgtg ccagacactc tgctaggcat tttgggaag 149520
cagaactgaa taagatacta ttcctttcct caaaaatttg agcaagagga gaaggaagt 149580
aatgaggaat attccttagc cataaaggaa aaataagaaa tcacttggaa gaagttaggt 149640
gagatggaag gaaaaggaca tctaaggtaa agcgtacagt ttgaataaag gcacagagac 149700
atgaacaaaa tgcattgagg gtttgaggaa cagcaattgg tttaacatgg ccagagctgg 149760
ggaaatggta agggcaagct gaaaccacat tgaaagcaaa cttggttatt atactaggta 149820
gtttagactt caagcagttg aaaatctttg agcatgggat aggcatgatg acattgtgtt 149880
tatttgcatg tttcttaaa gaaaactggc agcagcacaa atgttttgtt gatgagggt 149940
taaattgtag aaagtgagac aattttagga aggccagcta gagagaaatt tctagcatca 150000
aattttgcta aacacctagg atttgtagtt acctccattt gggttgttac ctgcaagtac 150060
tgaccacgta tatgaagaag tactggttta gaccaaggca attggcttgt ataagaggcc 150120
tacctcata ccaaaagcca gtttccttgg tctaggccag tgtttactgg tatgtgtcct 150180
gagaaaacta gttccatgac atgttccatg aaaaatatga tttctattgt caaataagtg 150240
agggaaactt gcatatcatg gtcctgctca ggaagattta caatcctat tagcatatca 150300
caggtcctgg tgaatactgc ggtaaagtaa ccgaggagct ttgtaactca ggattcccga 150360
agttgattca accacaggac ctcatttatt cacataacac ctgttatcct acaaaaccac 150420
tgttctctgg aatacacttt cgaaaacatg ggtatagaca aaaactctat cctataggca 150480
gagaatacct atacctctag ctcaggtcat cattttgcag atgtgtgtgt cattaagaat 150540
cagtcaataa tgcattaatg atcaaaagca gaccatcctt accacatggt gcataagatt 150600
atgctattat gctattagct actaatgcca ctaaagttaa ttatgttggg tctgcaacgt 150660
```

```
tgtcatacac aaaggatagg atgcaaaact gtcctaggcc aaagcatggt tattgcccaa  150720
gttatctaat gtctgcaggt acatattcct ggcctaagga ttgtgctaaa gaagttattt  150780
ctaagaaata tagtgacttc cagcatcatg cagaatgacc atttaatatt ttgaatatct  150840
agacattctg ctgtagaatt taatagtcct tttatacact gtctgaccaa cattttgaca  150900
tttactcaga accccatcac agtgctacca cataacctca ttgctaaagt gggaggccta  150960
gaaatcacag atttgtagaa accatccaat gattgaatcc cctctacttc ctgttcagca  151020
ggcagcagag tgtcataaag aattaacaac gtggaactca gttactggga tttcttccat  151080
tctcctttga ttctctagac tagaattcca aagaccctca ggctggtgat gcaagtggga  151140
agtctcattt ctgagaagtg ctgcttccta cccacaattc tttgatagct gagtgcttta  151200
gctgatctgc ataactgagg tgtgcaccaa ggagcagaat tactctataa attttggcat  151260
caacatgtgc aacttgtgac tcagcacttt gaaactctgg ggattttttt gtttggttgg  151320
tttttgtttt aagatgtcct gtggtatagt ggaaatagta caatagactc agatacagag  151380
aggccttgtt tctagtcttg gttctgtcac ttactatctt gatgtccttg cacaaatcac  151440
cagacctctc tgagcctcag tttctccaac cacactgtgg gaataataaa atcttttta  151500 cggcattgtt gtaagtatgt agagaaactg gtacacagta ggcacacaat caatgtcacc  151560
gtacccttca gcccttcttt tgtggatgaa aaatggtctt tgtgctccca gtcaccactg  151620
gggtctgttc tctctctctc tgctgttaca gtgtggcttt tggttcttgt ttctttgttc  151680
tttggtctgt aaattaccct tgaaacaacc cttgaaattt ccactccatg acctaaatcg  151740
tcatccctaa attggttaca tacatatttg gtgacacttt ggaggggaaa agctttatgt  151800
ctctctaact gtagttctta agggaatttg catatggaaa aaacagagac tgcgtctctt  151860
aattcctcca aaccaaatta tctgggatag cacatatatg ttgtactctg tctctgagca  151920
tttgctctta gagaactatg gttagagcga agtaaatttt tctaatcata aaaattaatg  151980
ataccgcata tctgatactt gaatgagtac ctccttgtaa aatttatact taaatccttg  152040
agttttaaaa gtgtaatagc aatagaaaga tttttattgtt gtttacttttt actgtgagtg  152100 ctccaaaatc cctcagttgc tcttgaaaga gcaagatgat gccataggca atattttcca  152160
aaggtagtag gcagaaaact gagtacacag cacacaatag gccatatata caaaagcaag  152220
tattttgcaa ataataataa ttcaggaaaa aagcttcact ttcgttggta acctgtttgt  152280 ttaaaccat tttattattt attatttaaa aagagtgtca cttgttacag attgtgggat  152340
gtgttcctta agatcacaaa aatgtaaaat atttttcttt tatactgaac acatgcatag  152400
acaacttacc tgagcaagct gcttttttgga gacatttgca catcttttgg gatcacgttg  152460
ttaagaagta gaactaaggg aaaaacacgc agccacccag aaatcggtag agccttcagc  152520
tcatctgtta ttaatatttc tgtgacaaca gatatctagg aagtaaacag gaaattgcat  152580
cgctatcctg catcacctt tttggaatca ggttccattc ttctcagtcc agttcaacct  152640
tgtgatactt tttagatctc aaccaaggca tagaaatata ttttcccttg cttaataccc  152700
catggaacca atgcccctgt ggttgaagta aaaattgatt gttgagggac atttcagccc  152760
tctagcagtc aacaattaaa aacatgtaag caccgagcac ctgcagaaaa cttggactgg  152820
catttggatc taagaagaaa atctgcatct tgaccaagat gaaaagtcac cagcccaagc  152880
ttgtgcagtg aagtgtcatg ttggccacaa tgaaactgaa agagactgat gactctcctc  152940
agggtggaaa atgaggcatg gaagctttga ttagtgagct gttaggcaca cagacattaa  153000
tttcaaagca ttctcatctc cagtctgagt aataatgctt atagtattat gcaattgttt  153060
```

```
ggctgctgca agaaattcag cagactccaa caagtagtct ttcttggtct ctgagtgact    153120
gtaacttaaa ttctacctcc cttctcttct cctacatctt ctcactcccc accccacccc    153180
cacatacaca caattcttgt ccactatgtt cagagagatg cacgcacaca tatatatgta    153240
tatatatagt atatttgtca ataaagcaga aagaagaaa aaactccaag taaacaattt     153300
tccatttccc catctcactt ctgtcttaca agtggatagg aaaagaaaaa cccccagtaa    153360
aaaatggcaa ccgcccacct ccccaacttt acatgctgct tcctatgtta gaggatctgt    153420
cttaggcatc tgattatgga gcctgctaga tacaagcccg tatttagact gctacagtca    153480
acaatgtctc tctttcatac tagaaaaatt ccgggttggc aattgcaagc atctcaaaat    153540
gaccagaccc tgaagaaagg ctgacttgcc tcattcaaaa tgagggctct agagggctct    153600
agtggatagt ctggagaaac ctggcgtctg aggcttagga gcttaggttt ttgctcctca    153660
acacagactt tgacgttggg gttggggct actctcttga ttgctgactc cctccagcgg     153720
gaccaatagt gttttcctac ctcacaggga tgttgtgagg acgggctgta gaagtaatag    153780
tggttaccat tcatgtagtt gtgagtatca tgattattgt ttcctgtaat gtggcttggc    153840
attggcaaag tgcttttga ttgttcttga tcacatatga tgggggccag gcactgactc     153900
aggcggatgc agtgaagctc tggctcagtc gcttgctttt cgtggtgtgc tgccaggaag    153960
aaactttgct gatgggactc aaggtgtcac cttggacaag aagcaactgt gtctgtctga    154020
ggttcctgtg gccatcttta tttgtgtatt aggcaattcg tatttccccc ttaggttcta    154080
gccttctgga tcccagccag tgacctagat cttagcctca ggccctgtca ctgagctgaa    154140
ggtagtagct gatccacaga agttcagtaa acaaggacca gatttctgct tctccaggag    154200
aagaagccag ccaacccctc tcttcaaaca cactgagaga ctacagtccg actttccctc    154260
ttacatctag ccttactgta gccacactcc ttgattgctc tctcacatca catgcttctc    154320
ttcatcagtt gtaagcctct cattcttctc ccaagccaga ctcaaatatt gtattgatgt    154380
caaagaagaa tcacttagag tttggaatat cttgttctct ctctgctcca tagcttccat    154440
attgacacca gtttctttct agtggagaag tggagtctgt gaagccaggg aaacacacat    154500
gtgagagtca gaaggactct ccctgacttg cctggggcct gtctttccca ccttctccag    154560
tctgtctaaa cacacacaca cacacacaca cacacacaca cacgctctct ctctctctcc    154620
ccccccaaca cacacact ctctctctct ctcacacaca cacacataca cacacacttc      154680
tttctctttc ccctgactca gcaacattct ggagaaaagc caaggaagga cttcaggagg    154740
ggagtttccc ccttctcagg gcagaatttt aatctccaga ccaacaagaa gttccctaat    154800
gtggattgaa aggctaatga ggtttatttt taactacttt ctatttgttt gaatgttgca    154860
tatttctact agtgaaattt tcccttaata aagccattaa tacaccaatc gtatttctt     154920 atttacaaca gactgagaga attaatgctg ttaacattgg atcttttttc tttttttttt    154980
ttcctttttt ttctctctcg tttgctttcc aggtcatgct gacctgttca gcttggactg    155040
tttcacattt gttttaatg tcagtttaaa tgtaattgta aaagcatgta tgctctaaaa      155100
tcatgtagtt actttttca gtggaaaagc ctggtattcg aaagcatttc caggctctgc     155160
aatttcatat gagcaggttt ttggtaaaat cttttgtccc tcactcaggg tggtatctgg    155220
acagtgagcc cctttcttct ggctcagtag tcagagagag gagacttgga gacagtttct    155280
gctggatcct gtgctttggc aaggatgtgc agcattgcat atcattctat cattaattat    155340
gtttactcct ccatgaacta aaaaccatta gactaaatag tccaacataa accttgaaag    155400
```

```
ataaaatttg atattctttt gcctggccat ttctctgacc cagaattggg gctgggaggg    155460
gattggagac ttgggggaaa gaatcaagga gccttcttgc ctgggggaat ttggcatgca    155520
cttattaatc ccatttggtt gcactcccta ctaatccctc actccatacc tgccaaggat    155580
tggctctgct ccctgcttct catccctgtc ctagttcttc ctcacctatc tccatttccc    155640
actactgatc cttctctcca gtaagatgct attcaacccg atgaaatata aagagtagca    155700
ccaccctgga agtcaggata ccttagtttt agctcctgct ctaccattat ctagctgtgt    155760
gacctggggc atgacttaac ctttgctctt cagtctgaac agtctttaag aattggtttg    155820
gaggaggaag gaagggatag acaagatcca aggcctttga actcttttt ggaaatgggt    155880 ccttttcttc aaacaaaatt tgatgcagag tcccaaattt acctacagaa taaaatactg    155940
ctgttcttgt ttgaaaggaa gtggggtgct tggagccaca tgctcaggcc cactttgccc    156000
cctctcagga accctcgaaa aaacttatag gacttatagg actgttgggg atctgccaag    156060
tctctcttat gttacatttc agtccttgtg aaactctata tgtttcatca gttcactttt    156120
tcagaaagtt caccttgcttg gggtaaaggt catgaagtgg agaatgtggg gctcagtaac    156180
tagcaatagt aaaaaacatc attgattggc ttgcagaatt tactctgttc taagcatctt    156240
acacacatac tcatccgaaa actcacaaca accttgtgag gtagatctgt tattatctta    156300
agattctgaa acctgccagc atgactctca atctttgact tgagaccagt tgcccaacat    156360
ggaaggttat acttttcaca gtttaccacc ataagcagtc tttcagagtg atttctagct    156420
agagatccat tcttagaaaa agtcagaacc tgcccattag catacactgt cacatggtgc    156480
agagtacctt cactgggttc atctcatttc ctcctaaaaa tagtcctatg cagtagtcca    156540
gtcatatcat caccattata tagatgagaa aaactgaggt gtaggagaaa tcaagagatc    156600
tgttcaaggt cacacattcc ataagactct gaataccacc atcaagaata ataaaccttt    156660
tatgtgaaaa gcattttaga acttcagtgt cattattgca ttctgcctcc tggagttcag    156720 tgcactttt caccatgctt taatcttgga gtcctggtgg tacagaatct gccttctact    156780
ctcagacaac accacagtgt ctttatccct cataacaaac ttatgaatta agtaatgata    156840
ttatccccat tttacaaatt agttaactga gataccaaga ggctaagtct tgcccaaagt    156900
cacacagcta gtcagtgata gagccggagt tacaaatgag gcatcctgac tccagaatat    156960
ttgctcttaa ctactactct ttatacatat gtaaggaaac taaaagcaaa agagggaaag    157020
atgtccctga ggccccacag tgagctcccc tgactcacaa tccagtattc ctctgacctt    157080
ctaatcctaa agttatacag taaggtccct tgactctaat cctagtagat ggaaagatgg    157140
ctggcatgat ttaagccaga ggccacaaac tggcttcccc agagccagaa ttcacctgca    157200
gaattctgtt tgtccagcac agtgtttgtt tagaaaattg acgtagactg ccccctaggca   157260 gggcatcaat cactgtcatt gtccccagcc ctccttattt atgtttgcca ggcttttta    157320 ctcatttatg tgtctgcctg acttgtgaag gtatttgagt ttatgacttt tagatttaag    157380
cattgcaata tataagcact gcacacatgc attcacaaaa gtatagccta gtctagcttc    157440
acaaagaatt tgtagcccta caccaaacac acctttatgt ttacttagtg tttagaatta    157500
gatttaagat cagaatttag tttcacaggc attcatgtgt ggaagaacct cagttattgt    157560
tttttgtttc atactgtctc acccttgctt tccctgctgt gtctggaccc ctgtcaatcc    157620
tgctttctgc cattcttcat gcctgagtta gggcccctgc aagccattca ctggttaatc    157680
tttaggaatg aatggagagt gaaaaccagt ttggagggtt cactgtgtcc caagcatcct    157740
ctcatttagt tctcataagt gtcctaagag acaggtagca gcacattcgt tttataaatg    157800
```

```
aggaaactaa atctcagaga agctgaacaa agacctcaaa gtcattaagg tagtaattaa   157860
cggagccggg atttgaacgc aagactgttg gactccagag cctattcttt tgccctacac   157920
cacagttcct tacaaggaag atgtattcat tttctattac tgcataacac attgccacaa   157980
atttagcagc ttcaaacatt tatcagctca ctgttttgta agtcagaagt ctggcacagc   158040
atggctagat tctcagttca gggtctctga aggatgaaac tgatgtgttt accaggatgc   158100
attctaatct gaagctcagg gttctcttcc aagctcatgt aattattgca ggattcagtt   158160
atttgtggtt gtaggactaa ggctccctct tcctttctgg ctaccagcca agggccattc   158220
tcagctcttg gaggctgccc tctttcctta tcatgtggac cccaacgcct tcaaagccaa   158280
caacagagac tcttccttgt gttgaatgtt tctcactcta cggatgtctt tcctggagga   158340
tcccagtccc gtaagggctc acctgatgag gtcaggtaca tcaagaatag ccacccttca   158400
aattcaactg aattagcacc ttcattacat ctacctagcc tttttacaac agcatctagg   158460
ttagtgcttg actgaatgac tggaaactaa ggtctcagaa tctcggggac cgtcttagaa   158520
gtcagcctac tacagatgtt gattcttttc atgtgtcaaa tttcatagtg agatagggag   158580
aacagaaaca tcacatcctt gaccttaggt aaagggattc aaacttccta agactttgga   158640
aacttcacgc cactttcacc ttttccttaa tcatggttga gaaggcctat atcttggagt   158700
ggccaggagt gagactggaa cagtacctaa aggttaagga cgctaaagaa gttacagatt   158760
ggttacatct gctcctccct aggaatgatc catggaacct gatttgaaat tttttctct   158820 ggtgctatag atagctccca cagggtctca atgcccagg gctgaaaagt tagttcccca   158880
taggatccat ccaggcatga tatcaggcca ggtgttacaa tctcctaaag aggaggtatg   158940
gactggaaag cccccttgcca atggcccttt cttgtcactg ctctgaccca agactaacag   159000
ggcagagata gtgaactcac atactattaa aactatccac ttatacttcc ccctttctct   159060
ttgctttatc actccattta agtaaaccaa tgagtctctg ccttgacaca gtggcaagct   159120
gacctgtatc ttatatgaaa gaattagatt tgactctggg gctcaggtgc agagggcagg   159180 agggcataa ggatggcctt catggaagaa aagaagtcct tggatactga gtaacagctg   159240
agactagcaa gcctcattgt ccaggattcc aagtcgtcta gcaacatcct ggtctctgct   159300
gcagacagaa cagaggatcc cccggcagaa tgaatggagt ctgatttcaa ttacgttcag   159360
tatagtcact ctcttttaggc agagaagcca gaacacctgg tgcagctagg gccactgtgg   159420
tcacagggac aagcacacta cctgggtcct ggaggcaagt gggaatgcag ttttcttcc   159480 ttaagcagat gccatatagg cctggggagg aggatgtgag aataccagcc aagttctcat   159540
tggcactata cagagaaagg ggaattattt catcttgatg gattctcccc acagtctctg   159600
cacatattga tcttacttgt aatgagtttg cttaggttca cgagtcatca tcccaggag   159660 atctgagtca ttggtgggaa agtcgaggcg acagattata tctcactgat ctcactgtca   159720
ccaattgctc tgtgtgtccc tccacctttt gaaaaagtcc atggattcat ttgtgtgtaa   159780
ttcatttgga tttatttctt ctttatcaat agctttagtg gggtattgca aatgggaaag   159840
ttgccccaga gaacagtgta cattcacagc attattcagt agaactttct gagatgatga   159900
aaatcttcta tatcttatgt tgtacaatat aatacagcca ctaactacat gtagcttttg   159960
aacactggaa atgtggcagg tgagactgag ggattatatt tttaattttt taatgttgta   160020
attaatttaa ttttttaaaa ttttttgcttt ctattttata gttaataat taaactaaac   160080 ttacgtagcc cacatgtggc tagttggcta ctatactgga cagtacaagt ctagaaggat   160140
```

```
ctcagagaga cacatgctga gatacagcag gaataagtca aaaagagagc caatgtaaca   160200
tagggaattc tggattggga attagagccc tggctctaat ctcagctctg ccactaggtg   160260
accttgccct ctctggcttc agcctcccca tctttgactt gaaaggttaa actaactaac   160320
gtcgaaagtc ccaaaatggt ggctatggac tgaattcaat tttgggatac acaagtttca   160380
ggattttttt aaaaatctat taatgccttc taggtgtgtg tatgcacgct tgcagacatg   160440
tgcccatgca caagcatggg aaggcagtaa ggcattcatt tcaattcacc agtgtactaa   160500
ccattcacac acacacacac acacacacac acacacacac atgcacacac accctactgt   160560
attgcctatg tagagcctga agatcttttta atctgtcacc attggataag ataatttcta   160620
aggacccttc ctgttttgtc atgctgaaaa tctttaagcc actatagtgt cccaaatcta   160680
ttccagtttg gcagatgac tggagtattc catagcctc ctgtctattc ccttctggat   160740
ttgatactag ttatgaagtt tggagtcaag ggtgaagaag ggaggcaggg atgatataac   160800
cccagcccca ctcctcaact ctgcttttga gttagaagta gggttcaggg cttcagattc   160860
cttggggagg cagtagagag aatatgggct ttataatcag aagatgaggt tcagatgatt   160920
gggttctcac cttttttata gctgtgttac ctcagtttat tcatttgtaa aatagggata   160980
agaaatatct ttaacctcct aagatcatgt ggaattaagt gatgtaatgt gatgaagcga   161040
ggcacgcaga aggccctgaa aaaattagta gttaccctta aggggactaa atggtctggc   161100
aactcccgag ctcaaagcta gaaaggtcca gtaatgggga agatgggtc tttctgtagg   161160 aactgtagca ggggagcaga tcctgtaggc caccagtctg tggagctgtg tccaagaact   161220
catgtttgca ataagcccac caaatgacaa gttattgtgg ggttcaggcc tctaactcaa   161280
gaagatggtc ttggcccaga tcataccttg cagcctgtgc ctttggtggg atgtgggtgt   161340
tggcagtggc tatgcatatc tccttattac tggctgtgcc aaagcccgc agaaatgatt   161400 gttggacaaa gtcatcttgc actcagggct ggttttccag gcttccttgt tattttcccc   161460
tgagttcttc tgtgttcctc ttgcaacacc aaccccacta ttttcctctt ccctacccta   161520
gttgttggtc caaacatgta atccattctt gcagtgattt attgggtgac accatgactg   161580
gagtttgcat tgaaggactt ctttttctaa ttagaactaa aagtcagttc caggctgggt   161640
gtggtggctc acgcctataa tcccagcact ttgggaggcc gagatgggag gattgcttaa   161700
ggccaggagt ttgagtccag cctggacaac atagtgagat cccatctcta caaaaaatgt   161760
taaccaggag tggtagtgta caactctggt cccagctact gggagactg aggagggaga   161820 attgcttgag cccaggaagt tgaggctaca gtgagctttg atcgtgccac tgctctccag   161880
ctgggtgaca gaggaagatc ctccttcaaa aaataaataa aaactaaaaa aaagtcagt   161940 tccaggttgt atcttttttc acaggggcca gacacagatg agagcaggtt ttgttgtatt   162000 tatccatttta aattgagcaa taaaattctc tctttggttt ctaccttct tatttattat   162060 tattatgtta aagggattaa agtggttcat ggtctttctc agtgcaactg cttatgctag   162120
acctcagaat tatgaccttt tcaattattt atatttctgt ctatataaat actgaaaaa   162180 atagtacaaa gtaagcatcg gaatgcctaa ggacctctaa attgtgtgtg tgagcacatg   162240
gggaagatgg ttcttaaggt ttgagttttg gattattgtg gttgtcttaa ataatgttat   162300
ttctatcatt ctttccaatg actgtctcct agcatagttc ccattttaca gactgatggc   162360
agaggcagaa agattctctc acttctttga tactattgag gacttcagcc tttcaccgct   162420 cttctccct ttgctaaaaa agaaaaaaat caatatgtat gttacagtgc attttttaa   162480 atattttta ttatacttta agttctaggg tacgtgtgca caacttgcag gtttgttaca   162540
```

```
tatgtataca tgtgccaagt tggtgtgctg cacccattaa ctccttattt acattaagta   162600
tatctcctaa tgctatccct ccaccctttcc ccaaccccac aacaggcccc agtgtgtgat   162660
gttccccttc ctgtgtccag gtgttctcat tgttcaattc ccacctgtga gtgagaacat   162720
gcagtgtttg gcttttttgtc cttgagatag tttgctgaga atgatggttt ccagcttcat   162780
ccatgtccct acaaaggaca tgaactcatc attttttatg gctgcatagt attccatggt   162840
gtatatatgc cacattttct taatccagtc tatcattgat ggacatttgg gttggttcca   162900
aggctttgct attgtgaata gtgccacaat aaacatatgt gtgcatgtac ctttagagca   162960
gcatgacata taatcctttg ggtatatacc caataatggg atggctgggt gcaatggtat   163020
ttctagttct agatccctga ggaatcacca cactgacttc cacaatggtt gaactagttt   163080
acagtcccac caacagtgta aaagtgttcc tatttctcca catcctttcc agcacctgtt   163140
gtttcctgac ttttttaatga tcgccattct aactggtgtg agatggtatc tcattgtggt   163200
tttgatttgc atttctctga tggccagtga tgatgagcat ttttttcatgt gtctgttggc   163260 tgcataaatg tctttttttg agaagtatct gttaatatcc tctgcccact ttttgatggg   163320
gttgtttgtt ttttttcttgt aaatttgttt gagttctttg tagattctgg gtatttgccc   163380
tttgtcagat gagtagatgg aaaaaatttt ctcccattct gtaggttgcc tgttcactct   163440
gatggtagtt tcttttgctg tgtagaagct ctttagttta attagatccc atttgtcaat   163500
tttggctttt gttgccattg cttttggtgt tttagacatg aagtccttgc cggtgcctat   163560
gtcatgaatg gtattgccta ggttttcttc tagggtttta tggttttagg tctaacattt   163620
aagtcttgaa tccatcttga attaattttt ctataaggtg taaggaaggg atccagtttc   163680 agcttttctac atatggctaa ccagttttca cagcaccatt tgttaaatag ggaatctttt   163740 cccaattct tgttttttgtc aggttgtca aagatcagat ggttgtagat acgcagcatt   163800
atttctgagg gctctgttct gttccattga tctatatctc tgttttggta ccagtatcat   163860
gctgttttgg ttactgtagc cttgtagtat agtttgaagt caggtagcgt gatacctcca   163920
gctttgttct tttggcttag gattgtcttg gcaatgcagg ctcttttttg gttccatatg   163980
aactttaaag tagtttttctc caattctgtg gagaaagtca ttgatagctt gatggggatg   164040
gcattgaatc tatgaattac cttgggcagt atggccattt tcacgatatt gattcttcct   164100
acccatgagc atggaatgtt cttccatttc tttgtatcct cttttatttc attgagcagt   164160
ggtttgtagt tctccttgaa gaggtccttc acgtcccttg taagttggat tcctaggtat   164220
tttattctct tagaagcagt tgtgaatggg agttcactca tgatttggct tctgtttgtg   164280
tgttattggt gtataagaat gcttgtgatt tttgcacatt gattttgtat cctgagactt   164340
tgctgaagtt gcttatcagc ttaaggagat tttgggctga gacaatgggg ttttctagat   164400
atacaatcat gtcatcggca aacagggaca atttgacttc ctcttttcct aattgaatac   164460
cctttatttc tttctgctgc ctgattgtcc tagccagaac ttccaacact atgttgaata   164520
ggaatggtga gagagggcat ccctgtcttg tgccagtttt caaagggagt gcttccagtt   164580 tttgccctatt cagtatgata ttggctgtgg gtttgtcata aatagctctt attattttga   164640
gatacgtccc atcaatacct aatttattga gagttttttag catgaaggc tgttgaattt   164700 tgtcaaaggc cttttctgca tctattgaga taatcatgtg gttttttgtct ttggttctgt   164760 ttgtatgctc aattacatttt attgatttgc atatgtggaa ccagtcttgc atcccaggga   164820
tgaagcccac ttgatcatgg tggataagct tttttgatgtg ctgctggatt cagtttgcca   164880
```

```
gtattgtatt gaggtttttt gcatcgatat tcatcaggga tattggtgta aaattctctt  164940
tttttgttgt gtctctgcca ggctttggta tcaggatgat gctggcctca taaaatgagt  165000
tagggaggat tccctctttt tctagtgatt ggaatggttt cagaaggaat ggtaccagct  165060
cctccttgta cctctggtag aattcagctg tgaaatccat ctagtcctgg acttttttg   165120
gctggtaagc tattaattat tgcctcaatt tcagaacctg ttattggtct attaagagat  165180
tcaacttcct cctagtttag tcttgggagg gtgtatgtgt cgaggaattt atccatttct  165240
tctagatttt ctagtttatt tgcatagagg tatttatagt attctctgat ggtagtttgt  165300
atttctgtgg gatcggtggt gatctcccct ttatcatttt ttattgcatc tatttgattt  165360
ttctctcttt tcttctttat tagtcttgcc agcagtctat caattttgtt gatcttttca  165420
aaaaaccagc tcctggattc attgattttt tgaagggttt cccatgtctc tatctccttc  165480
agttcttctc tgatcttggt tatttcttgc cttctgctag cttttgaatg tgtttgctct  165540
tccttctcta gttcttttaa ttgtgatgtt agggtgtcaa ttttagatct ttcctgcttt  165600
ctcttgtggg aatttggtgc tataaatttc cctctacaca ctactttaaa tgtgtcccag  165660
agattctggt atgttgtgtc tttgttctca ttggtttcaa ggaacatctt tatttctgcc  165720
ttcatttcat tatgtaccca gtagtcattc aggagcaggt tgttcagttt ccatgtagta  165780
gagtggtttt gagtgagttt cttaatcctg agttccagtt tgattgcact gtggtctgag  165840
agacagtttg ttataatttc tgttcttta catttgctga ggagtgtttt acttccaact   165900
cagtggtcaa ttttggaata ggtgtggtgt ggtgctgaga agaatgtata ttctgttgat  165960
ttggggtgga gagttctgta taagtctatt aggtccactt ggtacagagc tgagttcaat  166020
tcctggatat cctttgtgtc ttgttgatct gtctaatgtt gacagtgggg tgttaaagtc  166080
tcccttgatt attgtgtggg agtctaagtc tctttgtagg tctctaagta atcactttat  166140
gaatctggtt gttcctgtat tggtgcatat atatttagga tagttagttc ttcttgttga  166200
actgatccct ttaccattat gtaatggcct tcttgtctc ttttgatctt tgttggttta   166260
aagtctgttt tatcagagac tagcattgca atccctgcct cttttggttt tccatttgct  166320
tggtagatct tcctccatcc ctttgttttg agcctatatg tgtctctgca catgagatgg  166380
gtttcctgaa tacagcacac tgatgggtct tgactctta tccaatttgc cagtctgtgt   166440
cttttaattg gagcatttag gttaatattt acgtttaagg ttaatattgt tatatgtgaa  166500
tttgatcctg tcattgtgat gttagctggt tcttttgctc gttggttgat gcagtttctt  166560
cctagcctcg atggtcttta caatttggca tgttttgca gtggctggta ccggttgttc    166620
cttccatgt ttagtgcttc cttcaggagc tcctgtagtg caggcctggt ggtgacaaaa    166680
tctctcagca tttgcttgtt tttaaagtat tttattctc cttcacttat gaagcttagt    166740
ttggctggat atgaaattct gggttgaaaa ttcttttctt taagaatgat gaatattggc   166800
ccccactctc ttctggcttg tagagtttct gccaagaaat ccactgttag tctgatggct   166860
tcccttgtg ggtaacccga cctttctctc tggctgccct taacattgta tccttcattt    166920
caactttggc gaatctgata attatgtgtc ttggagttgc tcttctcgag gagtatcttt   166980
gtggcgttct ctgtatttcc tgaatgtgaa tgttggcctg tcttgctagg ttgggtaagt  167040
tctcctgggg aatatcctgc agagtgtttt ccaacttggt tccattctcc ctgtcacttt   167100
caggtacacc aatcagatgt agatttggtc ttttcacata gtcccatatt tcttggaggc   167160
tttgttcgtt tcttttact cttttttct ctaaacttct cttctcgctt catttcattc     167220
atttgatctt caatcactga tacccttttt tccagttgat cgaatcagct actgaagctt   167280
```

```
gtgcattcgt catatagttc tcgtgccatg gttttcagct ccatcaggtc atttaaggcc  167340
gtctctacat tgattattct agttagccat tcgtctaatc ttttttcaag gttttttaact 167400
tctttgcgat gggttcaaac ttcctccttt agcttggaga aatttggtca tctgaagcct  167460
tctctcaact catcaaagtc attctccgtc caggtttgtt ctgttgctgg tgaggagctg  167520
tgttcctttg gaggagaaga ggggctctga ttttttagaat gtttcagttt ttctgctctg  167580
ttttttcccc atctttgtgg ttttatctac ctttggtctt tgatgatggt gacatacaga  167640
tgggattttg gtgtggatgt cctttctgtt tgttagtttt ccttctaaca gtcaggaccc  167700
tcagctgcag gtctgttgga gtttgctgga ggtccactct agaccctgtt tgcctgggtg  167760
tcggcagcag aggctcagaa cagcgaatat tgctgaacag caaatgttgc tgcctactca  167820
ttcttctgga agtttcgtct cagagggta cctagccatg tgaggtatca gtctgcccct  167880
actggtgggt gtctcccagt taggctactc gggggtcagg gagccacttg aggaggcagt  167940
ctgtccgttc tcagatctcc agctgtgtgc tgggagaacc actactctct tcaaagctgt  168000
cagacaggga catttaagtc tgcagaggtt tctgctgcct tttgttcggc tatgccctgc  168060
ccccagaggt ggagtctaca gaggcatgca ggcctccttg agttgcggta ggctccaccc  168120
agttcgagct tcccagctgc tttgtttacc tactcaagcc tcagcaatgg cgggtgcccc  168180
tcccccagcc tcactgctgc cttgcagttc gatttcagac tgctctgcta gcagtgagcg  168240
atgctccatg ggcgtgggac cctccgagcc aggtgtggga tataatctcc tggtgtgccg  168300
tttgctaaga ccattggaaa agtgcagtat tagggtggga gtgacccaat tttccaggtg  168360
ccatctgtca cagctttgct tggctaggaa agggaatttc ctgaccctt gcacttccg  168420
ggtgaggcga tgcctctccc tgctttggct cacacttggt gcactgcacc cactgtcctg  168480
tacccactgt ccaacaagcc ccagtgagat gaacccggta cctcagtcgg aaatgcagaa  168540
atcactcatc ttctgcgtca ctcacgctgg gagctgtaga ctggagctgt tcctattcgg  168600
ccatcttatg aatcatgcat gttcaactat gagcaactat gtgtattcaa tgggaaatgg  168660
aataccataa aattgtcata tgttgagccc aaaatgatag gatagaattt gatagtctga  168720
ggatggaaag gaccttcaag gccactttta aaaacccccat tcccatatga tgcttgaatt  168780
cttaaccact gtgtgtctag tattttctca tttccagtga tatgtgtgcc tgccaacctt  168840
tccgtctcca agagctttaa ctatcaaaat gtatgtgtgt gtgtttttgt gtgtgcatgt  168900
gtgtgtgagt gtgcgtgtgt gtgtgtgtgt gtttagagag agagagagag acagaaagag  168960
aaggagagac taaaatccaa ttcactgttc tttctgggac ccaaagaaca agtctagtca  169020
ttctccattt ctagtctctt tccctagcaa tcggctagac atgctagaca tagacacatg  169080
tacatcactc ctttgaatta caacattcag tatttgtcta tcacttatat gataaaatac  169140
aaacttagct tttattttta ttttttttaga gacagtgttt tactatgtca cccaggctag  169200
agcatcagtg gcacaatcat agcccactgc agcctggaac ccctgggctc aaggaatcct  169260
tccacctctg cctcctgagt agcagagact acagatgtgc accaccagac ccagctaatt  169320
tggttttta ctattttttg tggagatggt gtattgtctt gtggtgttgc tcaggctgat  169380
cttgagctcc tggcctcaag cactcctccc atctcagcct cccaaaatgc tgggattaca  169440
ggcatgaacc accttaccca gccaaatttc ttaatatgat atacatgctc ctttaaaatc  169500
aagcaccatc tttgctttca acctcattat taaccacttt cccatatatg caacatatgt  169560
ttcagccata ctagtgtcta gttttcccct gaacactcct tggtgctttt gtttatgccc  169620
```

```
tttctgccca cctttgcctg gtgaaatcct catcaatctt caaattctat caaatactat    169680
cttccatata aagcatttc  taaacccacc tatgtaaaaa gattagtgtt ttcctatttt    169740
gttgatgcct ccattgcagc attttccagt ccaacgtttt ctagaattga ttgtggccag    169800
gctaccagac tgggccaggg cctgtgtctt ttctgtcacc cagaagcaaa ggtctaacaa    169860
tggatatctg ctgaatgaat gaacgaaaat gaatcattaa tatattagta aatacgttaa    169920
ttaaagttcc aggtatgaat actgaaggct gcattcaggc agagctggat ccaaggatat    169980
gctaggttgg tctagcacaa gaatcagagt tttcctctgc aagctatgaa aaatttgggt    170040
ttagcaggta tttgggatga tgaattatac atttaaccag tgttgaatga gcacttgtcc    170100
ttaaggagtt tagagtctgt gaccagggag aatggtgatt ttcttagcta gggcagtttt    170160
tctaaaaagg tagttgcatt gtgtgttttt gaccactgat gataaattca agtctctctt    170220
ccttcccaat agcccggaag ctgaagaaac ttggtaatct gaaactacag gaggaaggag    170280
aggcttccag caccaccagc cccactgagg agacaaccca gaagctgaca gtgtcacaca    170340
ttgaaggcta tgaatgtcag cccatctttc tgaatgtcct ggaagccatt gagccaggtg    170400
tagtgtgtgc tggacacgac aacaaccagc ccgactcctt tgcagccttg ctctctagcc    170460
tcaatgaact gggagagaga cagcttgtac acgtggtcaa gtgggccaag gccttgcctg    170520
gtaaggaaaa gggaagtggg agcatgagat aaggggatc  atatttagtg aacgctccta    170580
tggaccagcc accatgtctg gtgcttttct gcccattaac tcaggcagtc ttcatcataa    170640
ccctgtggga gagggattgt tacaagtctc aatttaaaca tacagggatc gaaactcaga    170700
aagcaaagag aaagatagta ttatcgggtg tcttatgtgg cccacattga tgcacagcag    170760
tcatgctttc atattcaact cacaaaaatg gtcagcaaat tttccattaa tcacaaatca    170820
catagacata cccatatatg ccttaggatg ctcttctata tttgcacaca caggctcacc    170880
ccaaagataa tctctagttt gactgacatt ctgtcttcaa tgtcatcttt aggagctata    170940
tcatgggaac tctcataata tggtatggtg gaaagaacat gaggttggga atcagaacac    171000
ttcgggtctg ctcttagctc tgctagtaac ttattgtgtg atcccttccc cttctgggtc    171060
tcaatttctc tatctgtata atgtataaag cgtggtttgt atcaaattga tggtttccag    171120
tttttgaaaa aaggaacgct ttttgcacct taaactacct aaggaatcat aatgagagga    171180
aagattaggt aatagtgaaa gaattaccaa gtgttggtct aacagaagtt ggataacaga    171240
agttcctcag tgatggggaa ctcacttctt tcttatgtca tctgttgttt aaacaagtct    171300
ggttattaaa atattacagc ttaaggaatt cttagagatc ctctatccaa tgattcacaa    171360
actttccttt agcagccaag tgctttattt ctcaaaagaa ttgtacacag atacaagtgg    171420
agctagttta tttaaagcca gagcctgtag cttgggcctc accagttcag cctctttctc    171480
tctatcccag ggaagcccta ggtcactctt gcaaaatctt agggctccaa ggaacacagt    171540
ttgaaaacca gtgaagtata tgccctttaa aggttctcct aatcctgcaa ttatgattca    171600
aagattcttt tgaaataaca acaaccaaac cttctcttgt ggagtcaaag attaacctgc    171660
ctttcaataa taactgccat tcaggtagaa atttatagtg aacagagcaa ttttgtatgt    171720
attacctgaa ttgattctta taggaatcct ataacatgag attctttctc ttattttaca    171780
gaccaaatag ggaagctgtg agaatgatgt gattggccta tagttacata gtcagaaaat    171840
agcaggacca gaacttgagc ccaggttctc tcctgattcc aaattctctc tattccactc    171900
cacctgtagg ctgtagcacc actgcagttc tgtagctctg ggcttacag  tgaggggcca    171960
aggcttcatt gaaggccact tgggtcatag tatgggcttg ttgcatttga agacatttca    172020
```

```
tgttggctgt caagtcttag atttgtattt ccaactcaca gggcctggtc acagccctaa  172080
ccatctctta taccttctca gcttgggaag ctgaggtcga ctagccaata agaacactgg  172140
gaaggaaacc caaggactct gactggatat gctctgtgcc aaaacagagg gttcactcag  172200
agaggaaaaa tataaaaaag aaaaaggaga aggttgcttt aattcttatc acttttcat   172260
ctggatattt tgatatcatg tgtttgacag agattcaaag tttaatcttc ccaagcagtt  172320
tccaaacact tatctcattt tataggctac agagcttttt catatatatg atcccactta  172380
atctttacaa caattctatg aatcatagag actattattt ccatttcaca tgccaaggct  172440
caaagaggtt aactaacttg ctccatttgg tcacttaaca catggaacca gaacttgacc  172500
tagaccttcg ggtttctaaa ttggttatct tgacaataac ctagtgcaaa acactatagc  172560
agaatttgta tgacttggga tcactggggc tttccttggc ccaaccacca agatggaaag  172620
cccccctcccc ttacattaac aaatctgcaa gccaatatca gttcaccatc tagcttgcca 172680
gactaaatga tttctgaccc caagtctttt aaaagaatag cttcaaaaga aagccaatta  172740
ccacattcac aagaactgtt cttcatatta tctataatta cctacaagta caagtaattt  172800
gctaattcaa tagattgagt tcttgacctg taagatgaac tgtgctaggc ccctaataag  172860
ataaattttg ttttaagttt tctgtgacag taaagatgta tgaaaattgc ctagtagagt  172920
acctggcaca ttaataaatg ataactgtta atttggagtg ggtgagtaga ctgggtgtgc  172980
acagtatatt tagaatcaaa tttatctggt ttggaatcct agctatggac tagttctgtg  173040
accttgagca aatcacatgt cttctctgtg cttctgtgtc ctcatttgta agatgataga  173100
ataatcacta cctttcaaat tgttgtcaac aaaaagatta tgtataaaga gcacctagta  173160
acgtagcctg aaacatagtc aatgctctgt aaatggtggt ttattattat gagacttgaa  173220
tgctaagcca ctgctttcac gaaactcaat tttagctacc acttgccttg cctagaagct  173280
catgcatgga ccccaaggtg aaattgtgtt ctctgaagac ctcggctggc agatgtacta  173340
cagcagcaaa gatttccaaa ctggcctttc tttgagccca ttctcccaga ctagacagga  173400
gactacaagt ttctgctgca catgaaaaaa atatgatgtc aatcggattc tagtgagaaa  173460
acagagtctc aaagaaactg cttctgctcc ctagcgtgtt taatgtgttt cagaacctga  173520
gaatgactcc tctctgtttc tccagaacag cctaacacag tggcaaatgg gtgttgagtg  173580
aatgcatact taaggaaatc tgtagggttg cagctactct ttcctcaagt aatcccttga  173640
tagtcatgta ggctacttca gagattgggc attagagaac agagtcaggt attataatca  173700
gattagactc tagggaggtt agccagccat attgctgata tgtgcacagt tactgggttt  173760
gagtgctaag cagctctcat taaggacggt taattaatat tatggccaaa ttaagctttc  173820
cctttctctc cctctttgtt agttcggtgg cattttaggg agaaaaaaat aagcatcagt  173880
atggacaatt tgcttgatac ctgtacaatt taattctcat ccttccatgt gccttcacat  173940
tcacacattc caccagaaga ccaaggttca ccagccaaaa gcttttcttg ctccccactg  174000
cctcctaccc aagatattca gggtcaacct cccaggcctc ttctctaaga gatccttggt  174060
tgctacatgc ttagaccctg cttcttattt cctgctgaga agggtcagtc caaggcattc  174120
tgtgctacag aagggttcca agcaggaact actctggat ctgaggctcc agccggtctg  174180
tcagcgtgtc attacagtga aggtgggaag cacaggcctg ggagctaaga ctgctaagat  174240
gagggactct agaatccctg atacctggaa ggcctaggat ctaaagaaa agaacaggga  174300
aatggggcta tatgagtgga cagggaccaa ccaagcagaa caatgtgtct ggataatgta  174360
```

```
gacttcagac ctgatcctat ggctgacaaa agctggtgac cttggtagtt cctgagctgt    174420
aaccttcatt agtggagtag aaaaaacact ggagaagaga atcagaacac ctgggttcta    174480
gtattagttc agccacatat aaaccatatg accttgggta agtcagttta tttctctggc    174540
cctcatgttc cttgttggta aaataagtgc cacatcacct aacctctggg attattgtga    174600
gagttaaatt aggtcatcaa caggaaagtg agaagtttga tctaaatttg gggaagcatt    174660
cctaatgagg tatgatgaca aaatttcaga taattctgga tttgttggtg agaagagaga    174720
gtgttggtag ggacgagctc tgaggtgatg cctttataac tttaagcatc caactgtttc    174780
aaaaactcca ggagaacatg gccatgtctg ttctacctgt gtattattgt agacgtagct    174840
tctgggagcc tctgctctct gagcttaagg gaggtaattt ggagatcatt taattctcat    174900
tttacaaaag gaaaaaaaat tgagggtctt taggccattt gtttaggtaa tatttcttaa    174960
gtgcccactc aaatacgtgg actgtactaa gtactaggga ggtaaagata aataagaaga    175020
tatggtccct gtcttcaaga agctccaagt cttgtggggg agacagacat gtatatacat    175080
agacttcaat gctgtgtaat gactgctata attgggtgag gctacacaag gtgcaatgag    175140
aatgtaaaag aagaatcttt aagccttctt cttggatgag ttgggaaagc cttcacagaa    175200
gaggtagcct ttgagtgaag acttgaaaga tgagtagtgt ttaccggatg aaaggcctga    175260
gaaggaggaa tgcattctag gcaaaagtaa ctgcctgtgc agagataaca gagatataga    175320
ggcatgtgag agcgcaagtg gcaagagatc agtctaggta ggcaggtcat aaagggccta    175380
ttcatgtata atgatggcag taagatgagg atggcagtag ggtgggaaat tagtagggcc    175440
agggtaccta ttgagtagaa aagaatggag aggaaatgcc aggcagaaag aggatggacg    175500
caagagaggg aacatgaaag tggtgaacag gtggcagtgg ctgtcaagac atctctccat    175560
accctgtaca ctgtatgtaa tatccatctc ccagggttgt tagaagggtc aaaccagatc    175620
gtagctggaa aacagctttg tgaagtgaaa actgctgttt atgtggggga aatgattgtt    175680
aaactgcatc tttggaaagg tgaagtgatc aagagcacag accttggaat ctgactgctt    175740
tgctttgtaa cttggtctgc caattactag ctgtatgatc ttggacaagt tccttaacct    175800
ctctctgact cacttgtact ggttcacaga atggagataa taatagtact taccttactc    175860
attgttgtga atgttaaatg agataatata agtaaagtgc ttagaaaaga gttaaatgta    175920
ccccataaat acatcaaact atcatgtacc caaaattatt tttaatttttt ttaaaaaga    175980 gcaatccaat agcaaaagaa aaaagagtt cactcatata agcagtcaat aagtgttaga    176040 ttattttct cttacaactg acaatgccct ttttgtctcc atcatcatct catttgagca    176100
gctcagggaa gtagggagga taaggaatat tatcctcacc atatagtttg tgcttttccc    176160
caccacccct taatggccag cctggatggt ccctggggat ccttagggga tgcccgaata    176220
ccagagcatc tctgcccaac agggactcag acttagctca acccgtcagt acccagactg    176280
accactgcct ctgcctcttc ttctccaggc ttccgcaact tacacgtgga cgaccagatg    176340
gctgtcattc agtactcctg gatggggctc atggtgtttg ccatgggctg gcgatccttc    176400
accaatgtca actccaggat gctctacttc gcccctgatc tggttttcaa tgagtaagtg    176460
ctcctggggc ccagacctca ctaaaataca gcagcttggc cagacctggt tggtggtgat    176520
ggtgatgggg tgacagtgaa gcttagctca tttgatctgc agttgtcgca gcggatgccc    176580
cagccagcca atccagtatg aggcggcttt gccctggctt tcagccaact ggcaggagcc    176640
caggaggatg gtgctgagac caccccttc acacccaaga accaatccta gtcatatttc    176700
tggtctgctt tgcagcttat ctcaaaacca catggaaaga ttcctcccct tcacatataa    176760
```

```
aagaggcaga aagactctgg ctttaagggc tggagtttct tgggttcttt tgctaccacc   176820
aaaggctact tctagtcacc atttgctgag caactagttt gtgccaagac tatgctagat   176880
actttctaaa tcctagctca ttgagtcctc atggtgacct gacctcacct ttttatagat   176940
aacactattt ttttatggat ggggaaaatc aggctcagca aaataaagtg actcacccaa   177000
agtcacagag ctagtgcctg ttggagacaa gattcaaacg tatgtccctg tcgatctcag   177060
ctcttctgcg tcatggtggt aactgatggg aaggagtacc tctaccgctc tctggctgtg   177120
tgaccttggt actgccattt tccttcccct aaacagcttt aattaatacc tgccctgcca   177180
ccagctccat ataacatcat gaatttggcc agtggctcag attttggaat tacattttc   177240
tccactaaaa tctcagttct actattttct tagtcagcat ctttgggaaa gacctttaac   177300
ttttccgacc ctcaatttct tcatccatta atgataacag aaccttcata agtaatttct   177360
tatgataact aaatgggaat tgacagatgt ggaatgtctg gcccatagta ggcaagaagg   177420
aaaaaaaaag tcccttttctg attcacccctt tccctaatag tgatacattt tttttcccg   177480
agatggggtt ttgctctgcc acccaggctg gagggcagtg gcgcaatgat ctcagcccag   177540
tgcaacctcc acctccctgg ttcaagcaat tctcctgcct cagcttcccg agtagctggg   177600
attatagatg cccgccaccg tgtccatcta attttgtat tttggtaga gacgggattt   177660
caccatgtta gccaggctgg tctcaaactc ctgacctcat gatctgcccg cctcagccgg   177720
gcatgataat cttttctatg tctgctgtat gaggtccctc gatggcattg tgaatggagc   177780
tggccagaga aatcttccca aggaccttga gctagtctca ccacagagaa tccttccagt   177840
caggacagga attgaccttc cccctcttc agccctctaa cccagaagag tcttaaaata   177900
aaatctacag gccaatggtt ccttccagta cagcactgca atgcgaggga gagtgagcgt   177960
ccccagctgc cctctcccaa ccctgccagc ctggtagcca aaagctaaga ataaccacta   178020
ggcttttggc acaaactgct ttgtggtttt cagatctccg caaagttgcc tatgatgcca   178080
tcttctgggg caggccttga aaagcccct aactgttcat ctcccatcct taaaccctg   178140
ctgcccttaa gcagttgaat caactccatg agcacctgct ctaccttccc cagagccctg   178200
agacctttgg agctttgaaa agtgataatt ggttgttctc taaatcctca tttccttctc   178260
tgcctctaag taagcatgtg gcatcccacc tcggcttcct ggtccagtct tgttcatctt   178320
ataaaaggc ctccctacgg ggtcagaggc ctagacccat caaacccagg gctcctgaaa   178380
caataggacc cctattcctc ctgtaggaag ccactgtgtt agagctctca gggtgtctac   178440
aaacatctag ataagtgttt ctcaacatgg attctgttga catattggga aaataattt   178500
tgtcattatg tagaatatgg ttaacatacc tggcaccagc ctactctata ccaaatagga   178560
ttccagtcat tctgacagcc caaactgctc ccacacattt ctgacaccca ctgaagaggc   178620
agtactctcc agttgagtgc aactaatccc tgccagcctt cctaaggtgc taatggggag   178680
cctcagaccc aaagagagag agaagaactt gtccaatgta ggtcaaccca tttgctgatc   178740
tcttcaacac caagctctat tatcagccct gttttttct ttctttctct ctttgtagag   178800
atcacatgtt gtgaggataa tgagcttgaa ccttagctgt gtgaccttgg gcaaattact   178860
gaacttctat gtgccgcaaa ttttatctgg agactgctga agagtattat aatagccct   178920
ttctatatgt catttattga acacctgcta tgtgtcaggc actgtgctca gtgttttcca   178980
atcttcattt ctcctcttat tttctctctt gcactccac caaccttgtt ctcttcctaa   179040
attccattcc tgcctcattt ttctaccctc cattctcctc tctcttcctt cctttaactg   179100
```

```
tctccctagt attttcccc ttttccccct ttcttttccc cttccccat gaatttcttc   179160
tctttccttt ccccttctct ttcctccatt ccccactttt tctgcccctg aggcctgcag   179220
caatgttaaa ggaatcctca ttccagcatt gtgatttcaa tggtaaaaag attgcagcat   179280
tgtcatcaac agaggtggga aagtacattg gagactggag cagagccaga cctcagggtc   179340
agccaatctt actaaaaaat tctctacagt gaaagagctt ggagcaacac tgttctgctc   179400
aattgatttg tgataccatc taaacacttc ctctttctag ttgggcttca gcctgagttg   179460
aataattcta caccatctgc cctcttctct ctttctccag acagccaag atctctctga    179520
gataggatgc tgagcttcca cccagacaat accaggcctg ctcatcctat ggagtaggct   179580
agtggcttgg aaaccaaaat gtcaaaccat agcctttagg ctccatctgg gaggtctttg   179640
tcctcaccac ttaagtgggt gtcaaatttc cttcccttc tgcacacgct gcacaatcaa    179700
tttctgtctt acacacacac acacacacac acacacacac gattttgaa gtgctgaaaa    179760
ctggaaggcc tactagcatg aggatgctgt gtcttctctt agaggtatgc catggtcagc   179820
catgaaccg agaggttgct cttccttgaa aagctggcca agcattggcc acttcccat     179880
ataatttata ggtgataatg tggtgatctg ttcagaagtg actataataa atgcaactca   179940
catatgtcta cagtttccaa actgtggtaa ggagcagcca gcatatgagg gaatgggctc   180000
cccttcagca ggggacattt aaactagaca ttcaaaaaca ctccctggca gatttaacat   180060
tggaactcgt tttgaaagaa caatgtgaa tctccttcac tgggagtttt tgaataagta    180120
tgaaatttct agtattccag ccagaggca aggggtcaa caggatgacc aaacacttcg     180180
ggtcatttgc aaatcttgat gtcctgatgt taagagctga ctactgggc ttctcctaaa    180240
aatccttcat gttgagctgc ctggaaggca ggttctcatt ctggctgtag ctgagatgtt   180300
agaactgtag tcagggagac catgtgcctc cccattgtg ttcatttggt taggcttcc     180360
tgtccctgac tcagaaaaca gaaggggcac agagacctgg aaattccatg tgctaaccca   180420
tatcctggcc agagaagatg agtagttatc agggtgtcag gattttggaa aacagagaga   180480
gaaaaaaac aaacaaacag acaaacaaac aaaaaaacct tttcctggtc cctggagcac    180540
cagcaggaga acagcaagc tcttcttgga aaacctggcg agggatggca atcagagaca    180600
ttccctctgg gcttattgta aacttcccct cattccttt tcctctgtgt atctccttcc    180660
caggtaccgc atgcacaagt cccggatgta cagccagtgt gtccgaatga ggcacctctc   180720
tcaagagttt ggatggctcc aaatcacccc ccaggaattc ctgtgcatga aagcactgct   180780
actcttcagc attagtaagt gcctagaagt gcagggaatg ccccctgagg gcacagagat   180840
tcagagagga ccacttttgc cattaaaaca ttattaggga aaagccagct cctggacatt   180900
tcccttcttc attccccctc cccatcccca ctctactctc tctcagcatc attttcctaa   180960
caagaaacaa tttcatgact agaagccaat ttatttgcta gaagtcaacc tccatcagat   181020
tccccaccta tccccagtct gtctttggga caaggccttt ttgactggtt acagcaggtc   181080
tctgaatttt tccatagctt ctgctataga aacagacatg gccaccttg tattctttgc    181140
agggcagtag agcaggaggc atttcctcct ggaaagattt cctcttctgc caacaggagg   181200
agatctatgt aagcaactca gataggattt gtatggcagc caaggaactt ttctttaata   181260
tcttttctaa gagccctctc ttagccccta cggagggaga agggcaaaat ttgatattca   181320
aagctatgtg ttttggttat ctaaatcagg gttttactgt gaatgacata aaagcttagg   181380
tcctaaaaaa tgagtatctg agaagagtag aaaaagaaaa ggttcaggaa atttgattta   181440
cttgactcct ttcagatcgg atccagctat cctttccct gagatctccc tgacagactg    181500
```

```
aaggcccaa gcacacagac ttcaactaac aggaagccaa gtagatggtt ccctgtgggg    181560
gtggggtca agtctgtggt cagaaaactt ggtgctttgt ctaatgctcc ttcgtgggca    181620
tgcttcccct ccccattctg tcttcatccc acatcagttc cagtggatgg gctgaaaaat   181680
caaaaattct ttgatgaact tcgaatgaac tacatcaagg aactcgatcg tatcattgca   181740
tgcaaaagaa aaaatcccac atcctgctca agacgcttct accagctcac caagctcctg   181800
gactccgtgc agcctgtaag caaacgatgg agggtgcttt atcagggaga acagcctgat   181860
agagccaatg ataatatgct tctctagagt ctggcaccac ctgttgggag gtgcttccat    181920
tccctctgg ctttgagtgt ggtccaggaa gaaaatgtgg tgaagaaaag aacacgggtc     181980
acagtgtccc agctggatat tgtgaagggg gtggaggagt tgagaacaga gcagttggga    182040
ctcagggaag ggacttgcag cagatgaatt ctctaggcag acaaaacaga cctggatgtt    182100
tttccctct tctttgagtc atgttcatgt gagtttgtct gtctgtgtgt gtgtgtgtgt      182160
gtgtgtgtgt gtgtgtgtgt gtgtcagaga gagagagaga gagagagaga tggagtgcgg    182220
aggcttgggt gagagcacaa gctggagaag tcttgagtca gagagcttac aatggtataa    182280
gacatctctt gggagccctc agtgactcca tggagaccat ttctttctct ctctctcgct    182340
gtctctctct aacacacaca cacacacaca cgacctcatg ggggaggacc aaggaagtac    182400
ggggaagggg gaggaaacaa aaggctgaaa gaccaaaaat cagaggttgg ggaagaggct    182460
agcagaggcc acctccttgt caaccctgtt tttctccctc ttattgttcc ctacagattg    182520
cgagagagct gcatcagttc acttttgacc tgctaatcaa gtcacacatg gtgagcgtgg    182580
actttccgga aatgatggca gagatcatct ctgtgcaagt gcccaagatc ctttctggga    182640
aagtcaagcc catctatttc cacacccagt gaagcattgg aaaccctatt tccccacccc    182700
agctcatgcc ccctttcaga tgtcttctgc ctgttataac tctgcactac tcctctgcag    182760
tgccttgggg aatttcctct attgatgtac agtctgtcat gaacatgttc ctgaattcta    182820
tttgctgggc ttttttttc tctttctctc ctttctttt cttcttccct ccctatctaa      182880
ccctcccatg gcaccttcag actttgcttc ccattgtggc tcctatctgt gttttgaatg    182940
gtgttgtatg cctttaaatc tgtgatgatc ctcatatggc ccagtgtcaa gttgtgcttg    183000
tttacagcac tactctgtgc cagccacaca aacgtttact tatcttatgc cacgggaagt    183060
ttagagagct aagattatct ggggaaatca aaacaaaaac aagcaaacaa aaaaaaaag     183120
caaaacaaa acaaaaaata agccaaaaaa ccttgctagt gttttttcct caaaaataaa    183180
taaataaata aataaatacg tacatacata cacacataca tacaaacata tagaaatccc   183240
caaagaggcc aatagtgacg agaaggtgaa aattgcaggc ccatggggag ttactgattt    183300
tttcatctcc tccctccacg ggagacttta ttttctgcca atggctattg ccattagagg    183360
gcagagtgac cccagagctg agttgggcag ggggtggac agagaggaga ggacaaggag     183420
ggcaatggag catcagtacc tgcccacagc cttggtccct gggggctaga ctgctcaact    183480
gtggagcaat tcattatact gaaaatgtgc ttgttgttga aaatttgtct gcatgttaat    183540
gcctcacccc caaacccttt tctctctcac tctctgcctc caacttcaga ttgactttca    183600
atagtttttc taagaccttt gaactgaatg ttctcttcag ccaaaacttg gcgacttcca    183660
cagaaaagtc tgaccactga gaagaaggag agcagagatt taacccttg taaggcccca     183720
tttggatcca ggtctgcttt ctcatgtgtg agtcagggag gagctggagc cagaggaaa     183780
gaaaatgata gcttggctgt tctcctgctt aggacactga ctgaatagtt aaactctcac    183840
```

```
tgccactacc ttttccccac ctttaaaaga cctgaatgaa gttttctgcc aaactccgtg 183900
aagccacaag caccttatgt cctcccttca gtgttttgtg ggcctgaatt tcatcacact 183960
gcatttcagc catggtcatc aagcctgttt gcttcttttg ggcatgttca cagattctct 184020
gttaagagcc cccaccacca agaaggttag caggccaaca gctctgacat ctatctgtag 184080
atgccagtag tcacaaagat ttcttaccaa ctctcagatc gctggagccc ttagacaaac 184140
tggaaagaag gcatcaaagg gatcaggcaa gctgggcgtc ttgcccttgt cccccagaga 184200
tgatacccct ccagcaagtg gagaagttct cacttccttc tttagagcag ctaaaggggc 184260
tacccagatc agggttgaag agaaaactca attaccaggg tgggaagaat gaaggcacta 184320
gaaccagaaa ccctgcaaat gctcttcttg tcacccagca tatccacctg cagaagtcat 184380
gagaagagag aaggaacaaa gaggagactc tgactactga attaaaatct tcagcggcaa 184440
agcctaaagc cagatggaca ccatctggtg agtttactca tcatcctcct ctgctgctga 184500
ttctgggctc tgacattgcc catactcact cagattcccc acctttgttg ctgcctctta 184560
gtcagaggga ggccaaacca ttgagacttt ctacagaacc atggcttctt tcggaaaggt 184620
ctggttggtg tggctccaat actttgccac ccatgaactc agggtgtgcc ctgggacact 184680
ggttttatat agtcttttgg cacacctgtg ttctgttgac ttcgttcttc aagcccaagt 184740
gcaagggaaa atgtccacct actttctcat cttggcctct gcctccttac ttagctctta 184800
atctcatctg ttgaactcaa gaaatcaagg gccagtcatc aagctgccca ttttaattga 184860
ttcactctgt ttgttgagag atagttttct gagtgacatg atatgatcca caagggtttc 184920
cttccctgat ttctgcattg atattaatag ccaaacgaac ttcaaaacag ctttaaataa 184980
caagggagag gggaaccctaa gatgagtaat atgccaatcc aagactgctg gagaaaacta 185040
aagctgacag gttcccttt tggggtggga tagacatgtt ctggttttct ttattattac 185100
acaatctggc tcatgtacag gatcactttt agctgtttta aacagaaaaa aatatccacc 185160
actcttttca gttacactag gttacatttt aataggtcct ttacatctgt tttgaaatga 185220
ttttcatctt ttgtgataca cagattgaat tatatcattt tcatatctct ccttgtaaat 185280
actagaagct ctcctttaca tttctctatc aaattttttca tctttatggg tttcccaatt 185340
gtgactcttg tcttcatgaa tatatgtttt tcatttgcaa aagccaaaaa tcagtgaaac 185400
agcagtgtaa ttaaaagcaa caactggatt actccaaatt tccaaatgac aaaactaggg 185460
aaaaatagcc tacacaagcc tttaggccta ctctttctgt gcttgggttt gagtgaacaa 185520
aggagatttt agcttggctc tgttctccca tggatgaaag gaggaggatt ttttttttct 185580
tttggccatt gatgttctag ccaatgtaat tgacagaagt ctcattttgc atgcgctctg 185640
ctctacaaac agagttggta tggttggtat actgtactca cctgtgaggg actggccact 185700
cagacccact tagctggtga gctagaagat gaggatcact cactggaaaa gtcacaagga 185760
ccatctccaa acaagttggc agtgctcgat gtggacgaag agtgaggaag agaaaaagaa 185820
ggagcaccag ggagaaggct ccgtctgtgc tgggcagcag acagctgcca ggatcacgaa 185880
ctctgtagtc aaagaaaaga gtcgtgtggc agtttcagct ctcgttcatt gggcagctcg 185940
cctaggccca gcctctgagc tgacatggga gttgttggat tctttgtttc atagcttttt 186000
ctatgccata ggcaatattg ttgttcttgg aaagtttatt attttttttaa ctcccttact 186060
ctgagaaagg gatattttga aggactgtca tatatctttg aaaaagaaa atctgtaata 186120
catatatttt tatgtatgtt cactggcact aaaaaatata gagagcttca ttctgtcctt 186180
tgggtagttg ctgaggtaat tgtccaggtt gaaaaataat gtgctgatgc tagagtccct 186240
```

```
ctctgtccat actctacttc taaatacata taggcataca tagcaagttt tatttgactt 186300
gtactttaag agaaaatatg tccaccatcc acatgatgca caaatgagct aacattgagc 186360
ttcaagtagc ttctaagtgt ttgtttcatt aggcacagca cagatgtggc ctttccccc  186420 ttctctccct tgatatctgg cagggcataa aggcccaggc cacttcctct gccccttccc 186480
agccctgcac caaagctgca tttcaggaga ctctctccag acagcccagt aactacccga 186540
gcatggcccc tgcatagccc tggaaaaata agaggctgac tgtctacgaa ttatcttgtg 186600
ccagttgccc aggtgagagg gcactgggcc aagggagtgg ttttcatgtt tgacccacta 186660
caaggggtca tgggaatcag gaatgccaaa gcaccagatc aaatccaaaa cttaaagtca 186720
aaataagcca ttcagcatgt tcagtttctt ggaaaaggaa gtttctaccc ctgatgcctt 186780
tgtaggcaga tctgttctca ccattaatct ttttgaaaat cttttaaagc agttttaaa  186840 aagagagatg aaagcatcac attatataac caaagattac attgtacctg ctaagatacc 186900
aaaattcata agggcagggg gggagcaagc attagtgcct cttttgataag ctgtccaaag 186960 acagactaaa ggactctgct ggtgactgac ttataagagc tttgtgggtt ttttttttcc 187020
taataatata catgtttaga agaattgaaa ataatttcgg gaaatggga  ttatgggtcc 187080 ttcactaagt gattttataa gcagaactgg ctttccttt  ctctagtagt tgctgagcaa 187140
attgttgaag ctccatcatt gcatggttgg aaatggagct gttcttagcc actgtgtttg 187200
ctagtgccca tgttagctta tctgaagatg tgaaaccctt gctgataagg gagcatttaa 187260
agtactagat tttgcactag agggacagca ggcagaaatc cttatttctg cccactttgg 187320
atggcacaaa aagttatctg cagttgaagg cagaaagttg aaatacattg taaatgaata 187380
tttgtatcca tgtttcaaaa ttgaaatata tatatatata tatatatata tatatatata 187440
tatatagtgt gtgtgtgtgt tctgatagct ttaactttct ctgcatcttt atatttggtt 187500
ccagatcaca cctgatgcca tgtacttgtg agagaggatg cagttttgtt ttggaagctc 187560
tctcagaaca aacaagacac ctggattgat cagttaacta aaagttttct cccctattgg 187620
gtttgaccca caggtcctgt gaaggagcag agggataaaa agagtagagg acatgataca 187680
ttgtacttta ctagttcaag acagatgaat gtggaaagca taaaaactca atggaactga 187740
ctgagattta ccacagggaa ggcccaaact tggggccaaa agcctaccca agtgattgac 187800
cagtggcccc ctaatgggac ctgagctgtt ggaagaagaa aactgttcct tggtcttcac 187860
catccttgtg agagaagggc agtttcctgc attggaacct ggagcaagcg ctctatcttt 187920
cacacaaatt ccctcacctg agattgaggt gctcttgtta ctgggtgtct gtgtgctgta 187980
attctggttt tggatatgtt ctgtaaagat tttgacaaat gaaatgtgt  ttttctctgt 188040 taaaacttgt cagagtacta gaagttgtat ctctgtaggt gcaggtccat ttctgcccac 188100
aggtagggtg ttttctttg attaagagat tgacacttct gttgcctagg acctcccaac 188160
tcaaccattt ctaggtgaag gcagaaaaat ccacattagt tactcctctt cagacatttc 188220
agctgagata acaaatcttt tggaatttt  tcacccatag aaagagtggt agatatttga 188280
atttagcagg tggagtttca tagtaaaaac agcttttgac tcagctttga tttatcctca 188340
tttgatttgg ccagaaagta ggtaatatgc attgattggc ttctgattcc aattcagtat 188400
agcaaggtgc taggtttttt cctttcccca cctgtctctt agcctgggga attaaatgag 188460
aagccttaga atgggtggcc cttgtgacct gaaacacttc ccacataagc tacttaacaa 188520
gattgtcatg gagctgcaga ttccattgcc caccaaagac tagaacacac acatatccat 188580
```

```
acaccaaagg aaagacaatt ctgaaatgct gtttctctgg tggttccctc tctggctgct  188640
gcctcacagt atgggaacct gtactctgca gaggtgacag gccagatttg cattatctca  188700
caaccttagc ccttggtgct aactgtccta cagtgaagtg cctgggggt tgtcctatcc    188760
cataagccac ttgatgctg acagcagcca ccatcagaat gacccacgca aaaaaaagaa    188820
aaaaaaatt aaaagtccc ctcacaaccc agtgacacct ttctgctttc ctctagactg     188880
gaacattgat tagggagtgc ctcagacatg acattcttgt gctgtccttg gaattaatct   188940
ggcagcagga gggagcagac tatgtaaaca gagataaaaa ttaattttca atattgaagg   189000
aaaaaagaaa taagaagaga gagagaaaga aagcatcaca caaagatttt cttaaaagaa   189060
acaattttgc ttgaaatctc tttagatggg gctcatttct cacggtggca cttggcctcc   189120
actgggcagc aggaccagct ccaagcgcta gtgttctgtt ctcttttgt aatcttggaa    189180
tcttttgttg ctctaaatac aattaaaaat ggcagaaact tgtttgttgg actacatgtg   189240
tgactttggg tctgtctctg cctctgcttt cagaaatgtc atccattgtg taaatattg    189300
gcttactggt ctgccagcta aaacttggcc acatccctg ttatggctgc aggatcgagt    189360
tattgttaac aaagagaccc aagaaaagct gctaatgtcc tcttatcatt gttgttaatt   189420
tgttaaaaca taaagaaatc taaaatttca gatgaatgtc atcagagttc ttttaattag   189480
ctctttttat tggctgtttt tattgaagtc aagagttggt atcatgcccg gttgcgtttt   189540
atgctatttt gattttcata tattttaaa agtctttgca caagggttac aaatttgccc    189600
tgtggtggcc ttagcataag ctgacctggg accaccaaaa taacaaggaa tttgggctag   189660
aaagcacaga tggacactgg tgacccatca caacttctct tgaaaaccc caaacttgtc    189720
agctggggaa aagccacaca aagcccagct gcccaccttc acatccttat ccttgtagga   189780
gcataaaatg gtgtcatcac tgcccagttc taaccaagct tcagttaaag aatgggtacc   189840
ttcacatctt cactattttt caggggcctt accgtccttg accacccaag taaaatctaa   189900
atcagccttc ttttgggttc ttcagttcaa gcaaggcctc ttcttgtggc ctctcagtat   189960
taatatttat gaggttgcag attgaatttt tgggcctgag atacaagcca tcaatgaggt   190020
gtgacaaagc atgtcaatga ataataagaa aattatctat tcttccatat cctcccctgt   190080
aataagggtt gtcagaatgc cttctttctg ggctgggttg aggattcagt gagaacatat   190140
gtgacacagc tggtgggcta ttaagctctg gctttgctcc ctgttaaaat gccagaaccc   190200
ttgagaggga tcccacattg agccatgttt atcactgacc accttagaat ggatggattt   190260
ctcagatttt tcctgagatc aatgcttgat ggagaggaga ggagaacaat agattcttgg   190320
gatgtgtgtt atgcatgtgt ttaagtaaga gacagagagt atgtttattt gcaggttgtg   190380
tgtgtaaagt cagagcctgc ctccagagga tcttctctaa ccaccattgc ttaggtcctg   190440
ttcgtttgca tctacagcga atgaccttac agccatctga cttggcttca ctcaccactc   190500
agctcctgcc taaacagacg aggtggttag catccaccat aagttttcca aggagtagca   190560
aagcacaaag gacacctatt gggttgaaaa gagcctagag gcatgagtcc tgtgtgtgac   190620
ttgttcatag tcatgcagct agtgtatagc taggattctc ccctgctgat ttactatgtg   190680
acactaggca gcaatctgcc cttgctggac ctcggttttc taatctgtaa aatgtgtgga   190740
gtaaaactac atgagatggg aagtccccttc tagtgcagat gccatggtta ttgaaaactg   190800
cagcaacatc tttcttaatc gtaaggggaa agaaaaagac catttactac tcctagaaca   190860
gttttggagc tagaatattc acatttgcac tcaataatta tttacaaaac aactagtgtg   190920
gagagggtca aaacaacagc tgagtcctgt gtaatagata ttgtcaaccc cttgatggat   190980
```

```
gaggaagggg ctcaaaggga a                                              191001

<210> SEQ ID NO 2
<211> LENGTH: 10661
<212> TYPE: DNA
<213> ORGANISM: Homo sapiens
<220> FEATURE:
<221> NAME/KEY: CDS
<222> LOCATION: (1116)...(3878)

<400> SEQUENCE: 2
cgagatcccg gggagccagc ttgctgggag agcgggacgg tccggagcaa gcccagaggc     60
agaggaggcg acagagggaa aaagggccga gctagccgct ccagtgctgt acaggagccg    120
aagggacgca ccacgccagc cccagcccgg ctccagcgac agccaacgcc tcttgcagcg    180
cggcggcttc gaagccgccg cccggagctg ccctttcctc ttcggtgaag tttttaaaag    240
ctgctaaaga ctcggaggaa gcaaggaaag tgcctggtag gactgacggc tgcctttgtc    300
ctcctcctct ccaccccgcc tcccccacc  ctgccttccc ccctccccc  gtcttctctc    360 ccgcagctgc ctcagtcggc tactctcagc caacccccct caccacccctt ctccccaccc    420 gccccccgc  ccccgtcggc ccagcgctgc cagcccgagt ttgcagagag gtaactccct    480
ttggctgcga gcgggcgagc tagctgcaca ttgcaaagaa ggctcttagg agccaggcga    540
ctggggagcg gcttcagcac tgcagccacg acccgcctgg ttaggctgca cgcggagaga    600
accctctgtt ttcccccact ctctctccac ctcctcctgc cttccccacc ccgagtgcgg    660
agccagagat caaagatga  aaaggcagtc aggtcttcag tagccaaaaa acaaaacaaa    720
caaaaacaaa aaagccgaaa taaagaaaa  agataataac tcagttctta tttgcaccta    780
cttcagtgga cactgaattt ggaaggtgga ggattttgtt ttttttcttt aagatctggg    840
catcttttga atctaccctt caagtattaa gagacagact gtgagcctag cagggcagat    900
cttgtccacc gtgtgtcttc ttctgcacga gactttgagg ctgtcagagc gcttttttgcg    960 tggttgctcc cgcaagtttc cttctctgga gcttcccgca ggtgggcagc tagctgcagc   1020
gactaccgca tcatcacagc ctgttgaact cttctgagca agagaagggg aggcggggta   1080
agggaagtag gtggaagatt cagccaagct caagg atg gaa gtg cag tta ggg      1133
                                        Met Glu Val Gln Leu Gly
                                         1               5 ctg gga agg gtc tac cct cgg ccg ccg tcc aag acc tac cga gga gct     1181
Leu Gly Arg Val Tyr Pro Arg Pro Pro Ser Lys Thr Tyr Arg Gly Ala
         10                  15                  20 ttc cag aat ctg ttc cag agc gtg cgc gaa gtg atc cag aac ccg ggc     1229
Phe Gln Asn Leu Phe Gln Ser Val Arg Glu Val Ile Gln Asn Pro Gly
     25                  30                  35 ccc agg cac cca gag gcc gcg agc gca gca cct ccc ggc gcc agt ttg     1277
Pro Arg His Pro Glu Ala Ala Ser Ala Ala Pro Pro Gly Ala Ser Leu
 40                  45                  50 ctg ctg ctg cag cag cag cag cag cag cag cag cag cag cag cag cag     1325
Leu Leu Leu Gln Gln Gln Gln Gln Gln Gln Gln Gln Gln Gln Gln Gln
 55                  60                  65                  70 cag cag cag cag cag cag cag cag cag caa gag act agc ccc agg cag     1373
Gln Gln Gln Gln Gln Gln Gln Gln Gln Glu Thr Ser Pro Arg Gln
             75                  80                  85 cag cag cag cag cag ggt gag gat ggt tct ccc caa gcc cat cgt aga     1421
Gln Gln Gln Gln Gln Gly Glu Asp Gly Ser Pro Gln Ala His Arg Arg
         90                  95                 100 ggc ccc aca ggc tac ctg gtc ctg gat gag gaa cag caa cct tca cag     1469
```

```
                                                            -continued

Gly Pro Thr Gly Tyr Leu Val Leu Asp Glu Glu Gln Pro Ser Gln
        105                 110                 115 ccg cag tcg gcc ctg gag tgc cac ccc gag aga ggt tgc gtc cca gag      1517
Pro Gln Ser Ala Leu Glu Cys His Pro Glu Arg Gly Cys Val Pro Glu
    120                 125                 130 cct gga gcc gcc gtg gcc gcc agc aag ggg ctg ccg cag cag ctg cca      1565
Pro Gly Ala Ala Val Ala Ala Ser Lys Gly Leu Pro Gln Gln Leu Pro
135                 140                 145                 150 gca cct ccg gac gag gat gac tca gct gcc cca tcc acg ttg tcc ctg      1613
Ala Pro Pro Asp Glu Asp Asp Ser Ala Ala Pro Ser Thr Leu Ser Leu
                155                 160                 165 ctg ggc ccc act ttc ccc ggc tta agc agc tgc tcc gct gac ctt aaa      1661
Leu Gly Pro Thr Phe Pro Gly Leu Ser Ser Cys Ser Ala Asp Leu Lys
            170                 175                 180 gac atc ctg agc gag gcc agc acc atg caa ctc ctt cag caa cag cag      1709
Asp Ile Leu Ser Glu Ala Ser Thr Met Gln Leu Leu Gln Gln Gln Gln
        185                 190                 195 cag gaa gca gta tcc gaa ggc agc agc agc ggg aga gcg agg gag gcc      1757
Gln Glu Ala Val Ser Glu Gly Ser Ser Ser Gly Arg Ala Arg Glu Ala
    200                 205                 210 tcg ggg gct ccc act tcc tcc aag gac aat tac tta ggg ggc act tcg      1805
Ser Gly Ala Pro Thr Ser Ser Lys Asp Asn Tyr Leu Gly Gly Thr Ser
215                 220                 225                 230 acc att tct gac aac gcc aag gag ttg tgt aag gca gtg tcg gtg tcc      1853
Thr Ile Ser Asp Asn Ala Lys Glu Leu Cys Lys Ala Val Ser Val Ser
                235                 240                 245 atg ggc ctg ggt gtg gag gcg ttg gag cat ctg agt cca ggg gaa cag      1901
Met Gly Leu Gly Val Glu Ala Leu Glu His Leu Ser Pro Gly Glu Gln
            250                 255                 260 ctt cgg ggg gat tgc atg tac gcc cca ctt ttg gga gtt cca ccc gct      1949
Leu Arg Gly Asp Cys Met Tyr Ala Pro Leu Leu Gly Val Pro Pro Ala
        265                 270                 275 gtg cgt ccc act cct tgt gcc cca ttg gcc gaa tgc aaa ggt tct ctg      1997
Val Arg Pro Thr Pro Cys Ala Pro Leu Ala Glu Cys Lys Gly Ser Leu
    280                 285                 290 cta gac gac agc gca ggc aag agc act gaa gat act gct gag tat tcc      2045
Leu Asp Asp Ser Ala Gly Lys Ser Thr Glu Asp Thr Ala Glu Tyr Ser
295                 300                 305                 310 cct ttc aag gga ggt tac acc aaa ggg cta gaa ggc gag agc cta ggc      2093
Pro Phe Lys Gly Gly Tyr Thr Lys Gly Leu Glu Gly Glu Ser Leu Gly
                315                 320                 325 tgc tct ggc agc gct gca gca ggg agc tcc ggg aca ctt gaa ctg ccg      2141
Cys Ser Gly Ser Ala Ala Ala Gly Ser Ser Gly Thr Leu Glu Leu Pro
            330                 335                 340 tct acc ctg tct ctc tac aag tcc gga gca ctg gac gag gca gct gcg      2189
Ser Thr Leu Ser Leu Tyr Lys Ser Gly Ala Leu Asp Glu Ala Ala Ala
        345                 350                 355 tac cag agt cgc gac tac tac aac ttt cca ctg gct ctg gcc gga ccg      2237
Tyr Gln Ser Arg Asp Tyr Tyr Asn Phe Pro Leu Ala Leu Ala Gly Pro
    360                 365                 370 ccg ccc cct ccg ccg cct ccc cat ccc cac gct cgc atc aag ctg gag      2285
Pro Pro Pro Pro Pro Pro Pro His Pro His Ala Arg Ile Lys Leu Glu
375                 380                 385                 390 aac ccg ctg gac tac ggc agc gcc tgg gcg gct gcg gcg cag tgc          2333
Asn Pro Leu Asp Tyr Gly Ser Ala Trp Ala Ala Ala Ala Gln Cys
                395                 400                 405 cgc tat ggg gac ctg gcg agc ctg cat ggc gcg ggt gca gcg gga ccc      2381
Arg Tyr Gly Asp Leu Ala Ser Leu His Gly Ala Gly Ala Ala Gly Pro
            410                 415                 420
```

```
ggt tct ggg tca ccc tca gcc gcc gct tcc tca tcc tgg cac act ctc    2429
Gly Ser Gly Ser Pro Ser Ala Ala Ala Ser Ser Ser Trp His Thr Leu
        425             430             435 ttc aca gcc gaa gaa ggc cag ttg tat gga ccg tgt ggt ggt ggg        2477
Phe Thr Ala Glu Glu Gly Gln Leu Tyr Gly Pro Cys Gly Gly Gly
    440             445             450 ggt ggt ggc ggc ggc ggc ggc ggc ggc ggc ggc ggc ggc ggc ggc        2525
Gly Gly Gly Gly Gly Gly Gly Gly Gly Gly Gly Gly Gly Gly Gly
455             460             465             470 ggc ggc ggc gag gcg gga gct gta gcc ccc tac ggc tac act cgg ccc    2573
Gly Gly Gly Glu Ala Gly Ala Val Ala Pro Tyr Gly Tyr Thr Arg Pro
        475             480             485 cct cag ggg ctg gcg ggc cag gaa agc gac ttc acc gca cct gat gtg    2621
Pro Gln Gly Leu Ala Gly Gln Glu Ser Asp Phe Thr Ala Pro Asp Val
    490             495             500 tgg tac cct ggc ggc atg gtg agc aga gtg ccc tat ccc agt ccc act    2669
Trp Tyr Pro Gly Gly Met Val Ser Arg Val Pro Tyr Pro Ser Pro Thr
        505             510             515 tgt gtc aaa agc gaa atg ggc ccc tgg atg gat agc tac tcc gga cct    2717
Cys Val Lys Ser Glu Met Gly Pro Trp Met Asp Ser Tyr Ser Gly Pro
    520             525             530 tac ggg gac atg cgt ttg gag act gcc agg gac cat gtt ttg ccc att    2765
Tyr Gly Asp Met Arg Leu Glu Thr Ala Arg Asp His Val Leu Pro Ile
535             540             545             550 gac tat tac ttt cca ccc cag aag acc tgc ctg atc tgt gga gat gaa    2813
Asp Tyr Tyr Phe Pro Pro Gln Lys Thr Cys Leu Ile Cys Gly Asp Glu
        555             560             565 gct tct ggg tgt cac tat gga gct ctc aca tgt gga agc tgc aag gtc    2861
Ala Ser Gly Cys His Tyr Gly Ala Leu Thr Cys Gly Ser Cys Lys Val
        570             575             580 ttc ttc aaa aga gcc gct gaa ggg aaa cag aag tac ctg tgc gcc agc    2909
Phe Phe Lys Arg Ala Ala Glu Gly Lys Gln Lys Tyr Leu Cys Ala Ser
        585             590             595 aga aat gat tgc act att gat aaa ttc cga agg aaa aat tgt cca tct    2957
Arg Asn Asp Cys Thr Ile Asp Lys Phe Arg Arg Lys Asn Cys Pro Ser
600             605             610 tgt cgt ctt cgg aaa tgt tat gaa gca ggg atg act ctg gga gcc cgg    3005
Cys Arg Leu Arg Lys Cys Tyr Glu Ala Gly Met Thr Leu Gly Ala Arg
615             620             625             630 aag ctg aag aaa ctt ggt aat ctg aaa cta cag gag gaa gga gag gct    3053
Lys Leu Lys Lys Leu Gly Asn Leu Lys Leu Gln Glu Glu Gly Glu Ala
        635             640             645 tcc agc acc acc agc ccc act gag gag aca acc cag aag ctg aca gtg    3101
Ser Ser Thr Thr Ser Pro Thr Glu Glu Thr Thr Gln Lys Leu Thr Val
        650             655             660 tca cac att gaa ggc tat gaa tgt cag ccc atc ttt ctg aat gtc ctg    3149
Ser His Ile Glu Gly Tyr Glu Cys Gln Pro Ile Phe Leu Asn Val Leu
        665             670             675 gaa gcc att gag cca ggt gta gtg tgt gct gga cac gac aac aac cag    3197
Glu Ala Ile Glu Pro Gly Val Val Cys Ala Gly His Asp Asn Asn Gln
680             685             690 ccc gac tcc ttt gca gcc ttg ctc tct agc ctc aat gaa ctg gga gag    3245
Pro Asp Ser Phe Ala Ala Leu Leu Ser Ser Leu Asn Glu Leu Gly Glu
695             700             705             710 aga cag ctt gta cac gtg gtc aag tgg gcc aag gcc ttg cct ggc ttc    3293
Arg Gln Leu Val His Val Val Lys Trp Ala Lys Ala Leu Pro Gly Phe
        715             720             725 cgc aac tta cac gtg gac gac cag atg gct gtc att cag tac tcc tgg    3341
Arg Asn Leu His Val Asp Asp Gln Met Ala Val Ile Gln Tyr Ser Trp
        730             735             740
```

```
atg ggg ctc atg gtg ttt gcc atg ggc tgg cga tcc ttc acc aat gtc    3389
Met Gly Leu Met Val Phe Ala Met Gly Trp Arg Ser Phe Thr Asn Val
        745                 750                 755 aac tcc agg atg ctc tac ttc gcc cct gat ctg gtt ttc aat gag tac    3437
Asn Ser Arg Met Leu Tyr Phe Ala Pro Asp Leu Val Phe Asn Glu Tyr
    760                 765                 770 cgc atg cac aag tcc cgg atg tac agc cag tgt gtc cga atg agg cac    3485
Arg Met His Lys Ser Arg Met Tyr Ser Gln Cys Val Arg Met Arg His
775                 780                 785                 790 ctc tct caa gag ttt gga tgg ctc caa atc acc ccc cag gaa ttc ctg    3533
Leu Ser Gln Glu Phe Gly Trp Leu Gln Ile Thr Pro Gln Glu Phe Leu
            795                 800                 805 tgc atg aaa gca ctg cta ctc ttc agc att att cca gtg gat ggg ctg    3581
Cys Met Lys Ala Leu Leu Leu Phe Ser Ile Ile Pro Val Asp Gly Leu
        810                 815                 820 aaa aat caa aaa ttc ttt gat gaa ctt cga atg aac tac atc aag gaa    3629
Lys Asn Gln Lys Phe Phe Asp Glu Leu Arg Met Asn Tyr Ile Lys Glu
    825                 830                 835 ctc gat cgt atc att gca tgc aaa aga aaa aat ccc aca tcc tgc tca    3677
Leu Asp Arg Ile Ile Ala Cys Lys Arg Lys Asn Pro Thr Ser Cys Ser
840                 845                 850 aga cgc ttc tac cag ctc acc aag ctc ctg gac tcc gtg cag cct att    3725
Arg Arg Phe Tyr Gln Leu Thr Lys Leu Leu Asp Ser Val Gln Pro Ile
855                 860                 865                 870 gcg aga gag ctg cat cag ttc act ttt gac ctg cta atc aag tca cac    3773
Ala Arg Glu Leu His Gln Phe Thr Phe Asp Leu Leu Ile Lys Ser His
            875                 880                 885 atg gtg agc gtg gac ttt ccg gaa atg atg gca gag atc atc tct gtg    3821
Met Val Ser Val Asp Phe Pro Glu Met Met Ala Glu Ile Ile Ser Val
        890                 895                 900 caa gtg ccc aag atc ctt tct ggg aaa gtc aag ccc atc tat ttc cac    3869
Gln Val Pro Lys Ile Leu Ser Gly Lys Val Lys Pro Ile Tyr Phe His
    905                 910                 915 acc cag tga agcattggaa accctatttc cccaccccag ctcatgcccc             3918
Thr Gln
    920 ctttcagatg tcttctgcct gttataactc tgcactactc ctctgcagtg ccttggggaa   3978 tttcctctat tgatgtacag tctgtcatga acatgttcct gaattctatt tgctgggctt   4038 ttttttctc tttctctcct ttcttttctt cttccctcc ctatctaacc ctcccatggc     4098 accttcagac tttgcttccc attgtggctc ctatctgtgt tttgaatggt gttgtatgcc   4158 tttaaatctg tgatgatcct catatggccc agtgtcaagt tgtgcttgtt tacagcacta   4218 ctctgtgcca gccacacaaa cgtttactta tcttatgcca cgggaagttt agagagctaa   4278 gattatctgg ggaaatcaaa acaaaaacaa gcaaacaaaa aaaaaagca aaacaaaac     4338 aaaaaataag ccaaaaaacc ttgctagtgt ttttttcctca aaaataaata aataaataaa  4398 taaatacgta catacataca cacatacata caaacatata gaaatcccca agaggccaa    4458 tagtgacgag aaggtgaaaa ttgcaggccc atggggagtt actgattttt tcatctcctc   4518 cctccacggg agactttatt ttctgccaat ggctattgcc attagagggc agagtgaccc   4578 cagagctgag ttgggcaggg gggtggacag agaggagagg acaaggaggg caatggagca   4638 tcagtacctg cccacagcct tggtccctgg gggctagact gctcaactgt ggagcaattc   4698 attatactga aaatgtgctt gttgttgaaa atttgtctgc atgttaatgc ctcaccccca   4758 aacccttttc tctctcactc tctgcctcca acttcagatt gactttcaat agttttttcta 4818
```

```
agacctttga actgaatgtt ctcttcagcc aaaacttggc gacttccaca gaaaagtctg   4878
accactgaga agaaggagag cagagattta acccttttgta aggccccatt tggatccagg   4938
tctgctttct catgtgtgag tcagggagga gctggagcca gaggagaaga aaatgatagc   4998
ttggctgttc tcctgcttag gacactgact gaatagttaa actctcactg ccactacctt   5058
ttccccacct ttaaaagacc tgaatgaagt tttctgccaa actccgtgaa gccacaagca   5118
ccttatgtcc tcccttcagt gttttgtggg cctgaatttc atcacactgc atttcagcca   5178
tggtcatcaa gcctgtttgc ttcttttggg catgttcaca gattctctgt taagagcccc   5238
caccaccaag aaggttagca ggccaacagc tctgacatct atctgtagat gccagtagtc   5298
acaaagattt cttaccaact ctcagatcgc tggagccctt agacaaactg gaagaaggc    5358 atcaaaggga tcaggcaagc tgggcgtctt gcccttgtcc cccagagatg ataccctccc   5418
agcaagtgga gaagttctca cttccttctt tagagcagct aaaggggcta cccagatcag   5478
ggttgaagag aaaactcaat taccagggtg ggaagaatga aggcactaga accagaaacc   5538
ctgcaaatgc tcttcttgtc acccagcata tccacctgca gaagtcatga gaagagagaa   5598
ggaacaaaga ggagactctg actactgaat taaaatcttc agcggcaaag cctaaagcca   5658
gatggacacc atctggtgag tttactcatc atcctcctct gctgctgatt ctgggctctg   5718
acattgccca tactcactca gattccccac ctttgttgct gcctcttagt cagagggagg   5778
ccaaaccatt gagactttct acagaaccat ggcttcttc ggaaaggtct ggttggtgtg    5838
gctccaatac tttgccaccc atgaactcag ggtgtgccct gggacactgg ttttatatag   5898
tcttttggca cacctgtgtt ctgttgactt cgttcttcaa gcccaagtgc aagggaaaat   5958
gtccacctac tttctcatct tggcctctgc ctccttactt agctcttaat ctcatctgtt   6018
gaactcaaga aatcaagggc cagtcatcaa gctgcccatt ttaattgatt cactctgttt   6078
gttgagagga tagtttctga gtgacatgat atgatccaca agggtttcct tccctgattt   6138
ctgcattgat attaatagcc aaacgaactt caaaacagct ttaaataaca agggagaggg   6198
gaacctaaga tgagtaatat gccaatccaa gactgctgga gaaaactaaa gctgacaggt   6258
tccctttttg gggtgggata gacatgttct ggttttcttt attattacac aatctggctc   6318
atgtacagga tcactttag ctgttttaaa cagaaaaaaa tatccaccac tcttttcagt    6378
tacactaggt tacatttaa taggtccttt acatctgttt tggaatgatt ttcatctttt    6438
gtgatacaca gattgaatta tcattttc atatctctcc ttgtaaatac tagaagctct     6498
cctttacatt tctctatcaa attttcatc tttatgggtt tcccaattgt gactcttgtc    6558
ttcatgaata tatgtttttc atttgcaaaa gccaaaaatc agtgaaacag cagtgtaatt   6618
aaaagcaaca actggattac tccaaatttc caaatgacaa aactagggaa aaatagccta   6678
cacaagcctt taggcctact ctttctgtgc ttgggtttga gtgaacaaag gagattttag   6738
cttggctctg ttctcccatg gatgaaagga ggaggatttt tttttctttt tggccattga   6798
tgttctagcc aatgtaattg acagaagtct cattttgcat gcgctctgct ctacaaacag   6858
agttggtatg gttggtatac tgtactcacc tgtgagggac tggccactca gacccactta   6918
gctggtgagc tagaagatga ggatcactca ctggaaaagt cacaaggacc atctccaaac   6978
aagttggcag tgctcgatgt ggacgaagag tgaggaagag aaaaagaagg agcaccaggg   7038
agaaggctcc gtctgtgctg ggcagcagac agctgccagg atcacgaact ctgtagtcaa   7098
agaaaagagt cgtgtggcag tttcagctct cgttcattgg gcagctcgcc taggcccagc   7158
ctctgagctg acatgggagt tgttggattc tttgtttcat agcttttttct atgccatagg   7218
```

```
caatattgtt gttcttggaa agtttattat tttttaact cccttactct gagaaaggga   7278
tattttgaag gactgtcata tatctttgaa aaagaaaat ctgtaataca tatattttta   7338
tgtatgttca ctggcactaa aaatataga gagcttcatt ctgtcctttg ggtagttgct   7398
gaggtaattg tccaggttga aaaataatgt gctgatgcta gagtccctct ctgtccatac   7458
tctacttcta aatacatata ggcatacata gcaagtttta tttgacttgt actttaagag   7518
aaaatatgtc caccatccac atgatgcaca aatgagctaa cattgagctt caagtagctt   7578
ctaagtgttt gtttcattag gcacagcaca gatgtggcct ttcccccctt ctctcccttg   7638
atatctggca gggcataaag gcccaggcca cttcctctgc cccttcccag ccctgcacca   7698
aagctgcatt tcaggagact ctctccagac agcccagtaa ctacccgagc atggcccctg   7758
catagccctg gaaaaataag aggctgactg tctacgaatt atcttgtgcc agttgcccag   7818
gtgagagggc actgggccaa gggagtggtt ttcatgtttg acccactaca aggggtcatg   7878
ggaatcagga atgccaaagc accagatcaa atccaaaact taaagtcaaa ataagccatt   7938
cagcatgttc agtttcttgg aaaaggaagt ttctacccct gatgcctttg taggcagatc   7998
tgttctcacc attaatcttt ttgaaaatct tttaaagcag ttttttaaaaa gagagatgaa   8058
agcatcacat tatataacca aagattacat tgtacctgct aagataccaa aattcataag   8118
ggcaggggg gagcaagcat tagtgcctct ttgataagct gtccaaagac agactaaagg   8178
actctgctgg tgactgactt ataagagctt tgtgggtttt ttttttcccta ataatataca   8238
tgtttagaag aattgaaaat aatttcggga aaatgggatt atgggtcctt cactaagtga   8298
ttttataagc agaactggct ttccttttct ctagtagttg ctgagcaaat tgttgaagct   8358
ccatcattgc atggttggaa atggagctgt tcttagccac tgtgtttgct agtgcccatg   8418
ttagcttatc tgaagatgtg aaacccttgc tgataaggga gcatttaaag tactagattt   8478
tgcactagag ggacagcagg cagaaatcct tatttctgcc cactttggat ggcacaaaaa   8538
gttatctgca gttgaaggca gaaagttgaa atacattgta aatgaatatt tgtatccatg   8598
tttcaaaatt gaaatatata tatatatata tatatatata tatatatata tatagtgtgt   8658
gtgtgtgttc tgatagcttt aactttctct gcatctttat atttggttcc agatcacacc   8718
tgatgccatg tacttgtgag agaggatgca gttttgtttt ggaagctctc tcagaacaaa   8778
caagacacct ggattgatca gttaactaaa agttttctcc cctattgggt ttgacccaca   8838
ggtcctgtga aggagcagag ggataaaaag agtagaggac atgatacatt gtactttact   8898
agttcaagac agatgaatgt ggaaagcata aaaactcaat ggaactgact gagatttacc   8958
acagggaagg cccaaacttg gggccaaaag cctacccaag tgattgacca gtggccccct   9018
aatgggacct gagctgttgg aagaagagaa ctgttccttg gtcttcacca tccttgtgag   9078
agaagggcag tttcctgcat tggaacctgg agcaagcgct ctatctttca cacaaattcc   9138
ctcacctgag attgaggtgc tcttgttact gggtgtctgt gtgctgtaat ctggttttg   9198
gatatgttct gtaaagattt tgacaaatga aaatgtgttt ttctctgtta aaacttgtca   9258
gagtactaga agttgtatct ctgtaggtgc aggtccattt ctgcccacag gtagggtgtt   9318
tttcttttgat taagagattg acacttctgt tgcctaggac ctcccaactc aaccatttct   9378
aggtgaaggc agaaaaatcc acattagtta ctcctcttca gacatttcag ctgagataac   9438
aaatcttttg gaattttttc acccatagaa agagtggtag atatttgaat ttagcaggtg   9498
gagtttcata gtaaaaacag cttttgactc agctttgatt tatcctcatt tgatttggcc   9558
```

-continued

```
agaaagtagg taatatgcat tgattggctt ctgattccaa ttcagtatag caaggtgcta    9618
ggttttttcc tttccccacc tgtctcttag cctggggaat taaatgagaa gccttagaat    9678
gggtggccct tgtgacctga aacacttccc acataagcta cttaacaaga ttgtcatgga    9738
gctgcagatt ccattgccca ccaaagacta gaacacacac atatccatac accaaaggaa    9798
agacaattct gaaatgctgt ttctctggtg gttccctctc tggctgctgc ctcacagtat    9858
gggaacctgt actctgcaga ggtgacaggc cagatttgca ttatctcaca acctttagccc   9918
ttggtgctaa ctgtcctaca gtgaagtgcc tgggggttg tcctatccca taagccactt    9978
ggatgctgac agcagccacc atcagaatga cccacgcaaa aaaagaaaa aaaaattaa     10038
aaagtcccct cacaacccag tgacaccttt ctgctttcct ctagactgga acattgatta   10098
gggagtgcct cagacatgac attcttgtgc tgtccttgga attaatctgg cagcaggagg   10158
gagcagacta tgtaaacaga gataaaaatt aattttcaat attgaaggaa aaaagaaata   10218
agaagagaga gagaaagaaa gcatcacaca aagattttct taaaagaaac aattttgctt   10278
gaaatctctt tagatggggc tcatttctca cggtggcact tggcctccac tgggcagcag   10338
gaccagctcc aagcgctagt gttctgttct cttttttgtaa tcttggaatc ttttgttgct  10398
ctaaatacaa ttaaaaatgg cagaaacttg tttgttggac tacatgtgtg actttgggtc  10458
tgtctctgcc tctgctttca gaaatgtcat ccattgtgta aaatattggc ttactggtct   10518
gccagctaaa acttggccac atcccctgtt atggctgcag gatcgagtta ttgttaacaa   10578
agagacccaa gaaaagctgc taatgtcctc ttatcattgt tgttaatttg ttaaaacata   10638
aagaaatcta aaatttcaaa aaa                                           10661
```

<210> SEQ ID NO 3
<211> LENGTH: 8112
<212> TYPE: DNA
<213> ORGANISM: Homo sapiens
<220> FEATURE:
<221> NAME/KEY: CDS
<222> LOCATION: (163)...(1329)

<400> SEQUENCE: 3

```
gctgcgagca gagagggatt cctcggaggt catctgttcc atcttcttgc ctatgcaaat     60
gcctgcctga agctgctgga ggctggcttt gtaccggact ttgtacaggg aaccagggaa    120
acgaatgcag agtgctcctg acattgcctg tcactttttc cc atg ata ctc tgg       174
                                                Met Ile Leu Trp
                                                  1 ctt cac agt ttg gag act gcc agg gac cat gtt ttg ccc att gac tat      222
Leu His Ser Leu Glu Thr Ala Arg Asp His Val Leu Pro Ile Asp Tyr
 5               10                  15                  20 tac ttt cca ccc cag aag acc tgc ctg atc tgt gga gat gaa gct tct      270
Tyr Phe Pro Pro Gln Lys Thr Cys Leu Ile Cys Gly Asp Glu Ala Ser
                 25                  30                  35 ggg tgt cac tat gga gct ctc aca tgt gga agc tgc aag gtc ttc ttc      318
Gly Cys His Tyr Gly Ala Leu Thr Cys Gly Ser Cys Lys Val Phe Phe
             40                  45                  50 aaa aga gcc gct gaa ggg aaa cag aag tac ctg tgc gcc agc aga aat      366
Lys Arg Ala Ala Glu Gly Lys Gln Lys Tyr Leu Cys Ala Ser Arg Asn
         55                  60                  65 gat tgc act att gat aaa ttc cga agg aaa aat tgt cca tct tgt cgt      414
Asp Cys Thr Ile Asp Lys Phe Arg Arg Lys Asn Cys Pro Ser Cys Arg
     70                  75                  80 ctt cgg aaa tgt tat gaa gca ggg atg act ctg gga gcc cgg aag ctg      462
Leu Arg Lys Cys Tyr Glu Ala Gly Met Thr Leu Gly Ala Arg Lys Leu
```

```
                        85                    90                    95                   100
aag aaa ctt ggt aat ctg aaa cta cag gag gaa gga gag gct tcc agc                          510
Lys Lys Leu Gly Asn Leu Lys Leu Gln Glu Glu Gly Glu Ala Ser Ser
                    105                   110                   115 acc acc agc ccc act gag gag aca acc cag aag ctg aca gtg tca cac                          558
Thr Thr Ser Pro Thr Glu Glu Thr Thr Gln Lys Leu Thr Val Ser His
                120                   125                   130 att gaa ggc tat gaa tgt cag ccc atc ttt ctg aat gtc ctg gaa gcc                          606
Ile Glu Gly Tyr Glu Cys Gln Pro Ile Phe Leu Asn Val Leu Glu Ala
            135                   140                   145 att gag cca ggt gta gtg tgt gct gga cac gac aac aac cag ccc gac                          654
Ile Glu Pro Gly Val Val Cys Ala Gly His Asp Asn Asn Gln Pro Asp
        150                   155                   160 tcc ttt gca gcc ttg ctc tct agc ctc aat gaa ctg gga gag aga cag                          702
Ser Phe Ala Ala Leu Leu Ser Ser Leu Asn Glu Leu Gly Glu Arg Gln
165                   170                   175                   180 ctt gta cac gtg gtc aag tgg gcc aag gcc ttg cct ggc ttc cgc aac                          750
Leu Val His Val Val Lys Trp Ala Lys Ala Leu Pro Gly Phe Arg Asn
                    185                   190                   195 tta cac gtg gac gac cag atg gct gtc att cag tac tcc tgg atg ggg                          798
Leu His Val Asp Asp Gln Met Ala Val Ile Gln Tyr Ser Trp Met Gly
                200                   205                   210 ctc atg gtg ttt gcc atg ggc tgg cga tcc ttc acc aat gtc aac tcc                          846
Leu Met Val Phe Ala Met Gly Trp Arg Ser Phe Thr Asn Val Asn Ser
            215                   220                   225 agg atg ctc tac ttc gcc cct gat ctg gtt ttc aat gag tac cgc atg                          894
Arg Met Leu Tyr Phe Ala Pro Asp Leu Val Phe Asn Glu Tyr Arg Met
        230                   235                   240 cac aag tcc cgg atg tac agc cag tgt gtc cga atg agg cac ctc tct                          942
His Lys Ser Arg Met Tyr Ser Gln Cys Val Arg Met Arg His Leu Ser
245                   250                   255                   260 caa gag ttt gga tgg ctc caa atc acc ccc cag gaa ttc ctg tgc atg                          990
Gln Glu Phe Gly Trp Leu Gln Ile Thr Pro Gln Glu Phe Leu Cys Met
                    265                   270                   275 aaa gca ctg cta ctc ttc agc att att cca gtg gat ggg ctg aaa aat                          1038
Lys Ala Leu Leu Leu Phe Ser Ile Ile Pro Val Asp Gly Leu Lys Asn
                280                   285                   290 caa aaa ttc ttt gat gaa ctt cga atg aac tac atc aag gaa ctc gat                          1086
Gln Lys Phe Phe Asp Glu Leu Arg Met Asn Tyr Ile Lys Glu Leu Asp
            295                   300                   305 cgt atc att gca tgc aaa aga aaa aat ccc aca tcc tgc tca aga cgc                          1134
Arg Ile Ile Ala Cys Lys Arg Lys Asn Pro Thr Ser Cys Ser Arg Arg
        310                   315                   320 ttc tac cag ctc acc aag ctc ctg gac tcc gtg cag cct att gcg aga                          1182
Phe Tyr Gln Leu Thr Lys Leu Leu Asp Ser Val Gln Pro Ile Ala Arg
325                   330                   335                   340 gag ctg cat cag ttc act ttt gac ctg cta atc aag tca cac atg gtg                          1230
Glu Leu His Gln Phe Thr Phe Asp Leu Leu Ile Lys Ser His Met Val
                    345                   350                   355 agc gtg gac ttt ccg gaa atg atg gca gag atc atc tct gtg caa gtg                          1278
Ser Val Asp Phe Pro Glu Met Met Ala Glu Ile Ile Ser Val Gln Val
                360                   365                   370 ccc aag atc ctt tct ggg aaa gtc aag ccc atc tat ttc cac acc cag                          1326
Pro Lys Ile Leu Ser Gly Lys Val Lys Pro Ile Tyr Phe His Thr Gln
            375                   380                   385 tga agcattggaa accctatttc cccaccccag ctcatgcccc ctttcagatg                               1379
tcttctgcct gttataactc tgcactactc ctctgcagtg ccttggggaa tttcctctat                        1439
tgatgtacag tctgtcatga acatgttcct gaattctatt tgctgggctt tttttttctc                        1499
```

```
tttctctcct ttcttttttct tcttccctcc ctatctaacc ctcccatggc accttcagac    1559
tttgcttccc attgtggctc ctatctgtgt tttgaatggt gttgtatgcc tttaaatctg    1619
tgatgatcct catatggccc agtgtcaagt tgtgcttgtt tacagcacta ctctgtgcca    1679
gccacacaaa cgtttactta tcttatgcca cgggaagttt agagagctaa gattatctgg    1739
ggaaatcaaa acaaaaacaa gcaaacaaaa aaaaaaagca aaacaaaac aaaaaataag    1799 ccaaaaaacc ttgctagtgt ttttttcctca aaaataaata aataaataaa taaatacgta    1859
catacataca cacatacata caaacatata gaaatcccca agaggccaa tagtgacgag    1919 aaggtgaaaa ttgcaggccc atggggagtt actgatttttt tcatctcctc cctccacggg    1979
agactttatt ttctgccaat ggctattgcc attagagggc agagtgaccc cagagctgag    2039
ttgggcaggg gggtggacag agaggagagg acaaggaggg caatgagca tcagtacctg    2099 cccacagcct tggtccctgg gggctagact gctcaactgt ggagcaattc attatactga    2159
aaatgtgctt gttgttgaaa atttgtctgc atgttaatgc ctcaccccca aacccttttc    2219
tctctcactc tctgcctcca acttcagatt gactttcaat agttttttcta agacctttga    2279 actgaatgtt ctcttcagcc aaaacttggc gacttccaca gaaagtctg accactgaga    2339 agaaggagag cagagattta acccttttgta aggccccatt tggatccagg tctgcttttct    2399 catgtgtgag tcaggagga gctggagcca gaggagaaga aaatgatagc ttggctgttc    2459
tcctgcttag gacactgact gaatagttaa actctcactg ccactacctt ttccccacct    2519
ttaaaagacc tgaatgaagt tttctgccaa actccgtgaa gccacaagca ccttatgtcc    2579
tcccttcagt gttttgtggg cctgaatttc atcacactgc atttcagcca tggtcatcaa    2639
gcctgtttgc ttcttttggg catgttcaca gattctctgt taagagcccc caccaccaag    2699
aaggttagca ggccaacagc tctgacatct atctgtagat gccagtagtc acaaagattt    2759
cttaccaact ctcagatcgc tggagcccctt agacaaactg gaaagaaggc atcaaaggga    2819
tcaggcaagc tgggcgtctt gcccttgtcc cccagagatg ataccctccc agcaagtgga    2879
gaagttctca cttccttctt tagagcagct aaaggggcta cccagatcag ggttgaagag    2939
aaaactcaat taccagggtg ggaagaatga aggcactaga accagaaacc ctgcaaatgc    2999
tcttcttgtc acccagcata tccacctgca gaagtcatga gaagagagaa ggaacaaaga    3059
ggagactctg actactgaat taaaatcttc agcggcaaag cctaaagcca gatggacacc    3119
atctggtgag tttactcatc atcctcctct gctgctgatt ctgggctctg acattgccca    3179
tactcactca gattccccac ctttgttgct gcctcttagt cagagggagg ccaaaccatt    3239
gagactttct acagaaccat ggcttctttc ggaaaggtct ggttggtgtg gctccaatac    3299
tttgccaccc atgaactcag ggtgtgccct gggacactgg ttttatatag tcttttggca    3359
cacctgtgtt ctgttgactt cgttcttcaa gcccaagtgc aagggaaaat gtccacctac    3419
tttctcatct tggcctctgc ctccttactt agctcttaat ctcatctgtt gaactcaaga    3479
aatcaagggc cagtcatcaa gctgcccatt ttaattgatt cactctgttt gttgagagga    3539
tagtttctga gtgacatgat atgatccaca agggtttcct tccctgattt ctgcattgat    3599
attaatagcc aaacgaactt caaaacagct ttaaataaca agggagaggg gaacctaaga    3659
tgagtaatat gccaatccaa gactgctgga gaaaactaaa gctgacaggt tccctttttg    3719
gggtgggata gacatgttct ggttttcttt attattacac aatctggctc atgtacagga    3779
tcacttttag ctgtttttaaa cagaaaaaaa tatccaccac tcttttcagt tacactaggt    3839
```

-continued

```
tacattttaa taggtccttt acatctgttt tggaatgatt ttcatctttt gtgatacaca      3899
gattgaatta tatcattttc atatctctcc ttgtaaatac tagaagctct cctttacatt      3959
tctctatcaa attttcatc tttatgggtt tcccaattgt gactcttgtc ttcatgaata       4019 tatgttttc atttgcaaaa gccaaaaatc agtgaaacag cagtgtaatt aaaagcaaca       4079
actggattac tccaaatttc caaatgacaa aactagggaa aaatagccta cacaagcctt      4139
taggcctact ctttctgtgc ttgggtttga gtgaacaaag gagattttag cttggctctg      4199
ttctcccatg gatgaaagga ggaggatttt ttttttcttt tggccattga tgttctagcc      4259
aatgtaattg acagaagtct cattttgcat gcgctctgct ctacaaacag agttggtatg      4319
gttggtatac tgtactcacc tgtgagggac tggccactca gacccactta gctggtgagc      4379
tagaagatga ggatcactca ctggaaaagt cacaaggacc atctccaaac aagttggcag      4439
tgctcgatgt ggacgaagag tgaggaagag aaaagaagg agcaccaggg agaaggctcc       4499
gtctgtgctg ggcagcagac agctgccagg atcacgaact ctgtagtcaa agaaaagagt      4559
cgtgtggcag tttcagctct cgttcattgg gcagctcgcc taggcccagc ctctgagctg      4619
acatgggagt tgttggattc tttgtttcat agcttttct atgccatagg caatattgtt        4679
gttcttggaa agtttattat tttttaact cccttactct gagaagga tattttgaag          4739 gactgtcata tatctttgaa aaagaaaat ctgtaataca tatatttta tgtatgttca         4799 ctggcactaa aaaatataga gagcttcatt ctgtcctttg ggtagttgct gaggtaattg      4859
tccaggttga aaaataatgt gctgatgcta gagtccctct ctgtccatac tctacttcta      4919
aatacatata ggcatacata gcaagtttta tttgacttgt actttaagag aaaatatgtc     4979
caccatccac atgatgcaca aatgagctaa cattgagctt caagtagctt ctaagtgttt      5039
gtttcattag gcacagcaca gatgtggcct ttccccctt ctctcccttg atatctggca       5099
gggcataaag gcccaggcca cttcctctgc cccttccag ccctgcacca aagctgcatt       5159
tcaggagact ctctccagac agcccagtaa ctacccgagc atggcccctg catagccctg      5219
gaaaaataag aggctgactg tctacgaatt atcttgtgcc agttgcccag gtgagagggc      5279
actgggccaa gggagtggtt ttcatgtttg acccactaca aggggtcatg ggaatcagga      5339
atgccaaagc accagatcaa atccaaaact taaagtcaaa ataagccatt cagcatgttc      5399
agtttcttgg aaaaggaagt ttctacccct gatgcctttg taggcagatc tgttctcacc     5459
attaatcttt ttgaaaatct tttaaagcag tttttaaaaa gagagatgaa agcatcacat    5519
tatataacca aagattacat tgtacctgct aagataccaa aattcataag gcaggggg       5579 gagcaagcat tagtgcctct ttgataagct gtccaaagac agactaaagg actctgctgg     5639
tgactgactt ataagagctt tgtgggtttt ttttcccta ataatataca tgtttagaag      5699
aattgaaaat aatttcggga aaatgggatt atgggtcctt cactaagtga ttttataagc     5759
agaactggct ttccttttct ctagtagttg ctgagcaaat tgttgaagct ccatcattgc     5819
atggttggaa atggagctgt tcttagccac tgtgtttgct agtgcccatg ttagcttatc     5879
tgaagatgtg aaacccttgc tgataaggga gcatttaaag tactagattt tgcactagag     5939
ggacagcagg cagaaatcct tatttctgcc cactttggat ggcacaaaaa gttatctgca     5999
gttgaaggca gaaagttgaa atacattgta aatgaatatt tgtatccatg tttcaaaatt    6059
gaaatatata tatatatata tatatatata tatatatata tatagtgtgt gtgtgtgttc   6119
tgatagcttt aactttctct gcatctttat atttggttcc agatcacacc tgatgccatg     6179
tacttgtgag agaggatgca gttttgtttt ggaagctctc tcagaacaaa caagacacct    6239
```

```
ggattgatca gttaactaaa agttttctcc cctattgggt ttgacccaca ggtcctgtga      6299
aggagcagag ggataaaaag agtagaggac atgatacatt gtactttact agttcaagac      6359
agatgaatgt ggaaagcata aaaactcaat ggaactgact gagatttacc acagggaagg      6419
cccaaacttg gggccaaaag cctacccaag tgattgacca gtggcccect aatgggacct      6479 gagctgttgg aagaagagaa ctgttccttg gtcttcacca tccttgtgag agaagggcag      6539
tttcctgcat tggaacctgg agcaagcgct ctatctttca cacaaattcc ctcacctgag      6599
attgaggtgc tcttgttact gggtgtctgt gtgctgtaat tctggttttg gatatgttct      6659
gtaaagattt tgacaaatga aaatgtgttt ttctctgtta aaacttgtca gagtactaga      6719
agttgtatct ctgtaggtgc aggtccattt ctgcccacag tagggtgtt tttctttgat       6779 taagagattg acacttctgt tgcctaggac ctcccaactc aaccatttct aggtgaaggc      6839
agaaaaatcc acattagtta ctcctcttca gacatttcag ctgagataac aaatcttttg     6899
gaattttttc acccatagaa agagtggtag atatttgaat ttagcaggtg gagtttcata     6959
gtaaaaacag cttttgactc agctttgatt tatcctcatt tgatttggcc agaaagtagg     7019
taatatgcat tgattggctt ctgattccaa ttcagtatag caaggtgcta ggtttttcc      7079 tttccccacc tgtctcttag cctggggaat taaatgagaa gccttagaat gggtggccct     7139
tgtgacctga acacttccc acataagcta cttaacaaga ttgtcatgga gctgcagatt      7199
ccattgccca ccaaagacta gaacacacac atatccatac accaaggaa agacaattct      7259 gaaatgctgt ttctctggtg gttccctctc tggctgctgc ctcacagtat gggaaccctgt    7319 actctgcaga ggtgacaggc cagatttgca ttatctcaca accttagccc ttggtgctaa     7379
ctgtcctaca gtgaagtgcc tgggggttg tcctatccca taagccactt ggatgctgac      7439
agcagccacc atcagaatga cccacgcaaa aaaagaaaa aaaaattaa aaagtcccct       7499 cacaacccag tgacaccttt ctgctttcct ctagactgga acattgatta gggagtgcct     7559
cagacatgac attcttgtgc tgtccttgga attaatctgg cagcaggagg gagcagacta     7619
tgtaaacaga gataaaaatt aattttcaat attgaaggaa aaaagaaata agaagagaga    7679
gagaaagaaa gcatcacaca aagattttct taaaagaaac aattttgctt gaaatctctt     7739
tagatggggc tcatttctca cggtggcact tggcctccac tgggcagcag gaccagctcc    7799
aagcgctagt gttctgttct cttttttgtaa tcttggaatc ttttgttgct ctaaatacaa    7859
ttaaaaatgg cagaaacttg tttgttggac tacatgtgtg actttgggtc tgtctctgcc    7919
tctgctttca gaaatgtcat ccattgtgta aaatattggc ttactggtct gccagctaaa     7979
acttggccac atcccctgtt atggctgcag gatcgagtta ttgttaacaa agagacccaa     8039
gaaaagctgc taatgtcctc ttatcattgt tgttaatttg ttaaaacata agaaatcta     8099 aaatttcaaa aaa                                                         8112
```

<210> SEQ ID NO 4
<211> LENGTH: 3641
<212> TYPE: DNA
<213> ORGANISM: Homo sapiens
<220> FEATURE:
<221> NAME/KEY: CDS
<222> LOCATION: (328)...(2265)

<400> SEQUENCE: 4

```
gacactgaat ttggaaggtg gaggattttg ttttttctt ttaagatctg ggcatctttt      60
gaatctaccc ttcaagtatt aagagacaga ctgtgagcct agcagggcag atcttgtcca    120
```

```
ccgtgtgtct tcttctgcac gagactttga ggctgtcaga gcgcttttg cgtggttgct        180 cccgcaagtt tccttctctg gagcttcccg caggtgggca gctagctgca gcgactaccg        240
catcatcaca gcctgttgaa ctcttctgag caagagaagg ggaggcgggg taagggaagt        300
aggtggaaga ttcagccaag ctcaagg atg gaa gtg cag tta ggg ctg gga agg        354
                                Met Glu Val Gln Leu Gly Leu Gly Arg
                                  1               5 gtc tac cct cgg ccg ccg tcc aag acc tac cga gga gct ttc cag aat        402
Val Tyr Pro Arg Pro Pro Ser Lys Thr Tyr Arg Gly Ala Phe Gln Asn
 10              15                  20                  25 ctg ttc cag agc gtg cgc gaa gtg atc cag aac ccg ggc ccc agg cac        450
Leu Phe Gln Ser Val Arg Glu Val Ile Gln Asn Pro Gly Pro Arg His
                 30                  35                  40 cca gag gcc gcg agc gca gca cct ccc ggc gcc agt ttg ctg ctg cag        498
Pro Glu Ala Ala Ser Ala Ala Pro Pro Gly Ala Ser Leu Leu Leu Gln
             45                  50                  55 cag cag cag cag cag cag cag cag cag cag cag cag cag cag cag cag        546
Gln Gln Gln Gln Gln Gln Gln Gln Gln Gln Gln Gln Gln Gln Gln Gln
         60                  65                  70 cag cag cag cag cag cag cag cag cag cag cag caa gag act agc ccc        594
Gln Gln Gln Gln Gln Gln Gln Gln Gln Gln Gln Glu Thr Ser Pro
 75                  80                  85 agg cag cag cag cag cag cag ggt gag gat ggt tct ccc caa gcc cat        642
Arg Gln Gln Gln Gln Gln Gln Gly Glu Asp Gly Ser Pro Gln Ala His
 90                  95                 100                 105 cgt aga ggc ccc aca ggc tac ctg gtc ctg gat gag gaa cag caa cct        690
Arg Arg Gly Pro Thr Gly Tyr Leu Val Leu Asp Glu Glu Gln Gln Pro
                110                 115                 120 tca cag ccg cag tcg gcc ctg gag tgc cac ccc gag aga ggt tgc gtc        738
Ser Gln Pro Gln Ser Ala Leu Glu Cys His Pro Glu Arg Gly Cys Val
            125                 130                 135 cca gag cct gga gcc gcc gtg gcc gcc agc aag ggg ctg ccg cag cag        786
Pro Glu Pro Gly Ala Ala Val Ala Ala Ser Lys Gly Leu Pro Gln Gln
        140                 145                 150 ctg cca gca cct ccg gac gag gat gac tca gct gcc cca tcc acg ttg        834
Leu Pro Ala Pro Pro Asp Glu Asp Asp Ser Ala Ala Pro Ser Thr Leu
        155                 160                 165 tcc ctg ctg ggc ccc act ttc ccc ggc tta agc agc tgc tcc gct gac        882
Ser Leu Leu Gly Pro Thr Phe Pro Gly Leu Ser Ser Cys Ser Ala Asp
170                 175                 180                 185 ctt aaa gac atc ctg agc gag gcc agc acc atg caa ctc ctt cag caa        930
Leu Lys Asp Ile Leu Ser Glu Ala Ser Thr Met Gln Leu Leu Gln Gln
                190                 195                 200 cag cag cag gaa gca gta tcc gaa ggc agc agc agc ggg aga gcg agg        978
Gln Gln Gln Glu Ala Val Ser Glu Gly Ser Ser Ser Gly Arg Ala Arg
            205                 210                 215 gag gcc tcg ggg gct ccc act tcc tcc aag gac aat tac tta ggg ggc       1026
Glu Ala Ser Gly Ala Pro Thr Ser Ser Lys Asp Asn Tyr Leu Gly Gly
        220                 225                 230 act tcg acc att tct gac aac gcc aag gag ttg tgt aag gca gtg tcg       1074
Thr Ser Thr Ile Ser Asp Asn Ala Lys Glu Leu Cys Lys Ala Val Ser
        235                 240                 245 gtg tcc atg ggc ctg ggt gtg gag gcg ttg gag cat ctg agt cca ggg       1122
Val Ser Met Gly Leu Gly Val Glu Ala Leu Glu His Leu Ser Pro Gly
250                 255                 260                 265 gaa cag ctt cgg ggg gat tgc atg tac gcc cca ctt ttg gga gtt cca       1170
Glu Gln Leu Arg Gly Asp Cys Met Tyr Ala Pro Leu Leu Gly Val Pro
                270                 275                 280
```

| | |
|---|---|
| ccc gct gtg cgt ccc act cct tgt gcc cca ttg gcc gaa tgc aaa ggt<br>Pro Ala Val Arg Pro Thr Pro Cys Ala Pro Leu Ala Glu Cys Lys Gly<br>285 290 295 | 1218 |
| tct ctg cta gac gac agc gca ggc aag agc act gaa gat act gct gag<br>Ser Leu Leu Asp Asp Ser Ala Gly Lys Ser Thr Glu Asp Thr Ala Glu<br>300 305 310 | 1266 |
| tat tcc cct ttc aag gga ggt tac acc aaa ggg cta gaa ggc gag agc<br>Tyr Ser Pro Phe Lys Gly Gly Tyr Thr Lys Gly Leu Glu Gly Glu Ser<br>315 320 325 | 1314 |
| cta ggc tgc tct ggc agc gct gca gca ggg agc tcc ggg aca ctt gaa<br>Leu Gly Cys Ser Gly Ser Ala Ala Ala Gly Ser Ser Gly Thr Leu Glu<br>330 335 340 345 | 1362 |
| ctg ccg tct acc ctg tct ctc tac aag tcc gga gca ctg gac gag gca<br>Leu Pro Ser Thr Leu Ser Leu Tyr Lys Ser Gly Ala Leu Asp Glu Ala<br>350 355 360 | 1410 |
| gct gcg tac cag agt cgc gac tac tac aac ttt cca ctg gct ctg gcc<br>Ala Ala Tyr Gln Ser Arg Asp Tyr Tyr Asn Phe Pro Leu Ala Leu Ala<br>365 370 375 | 1458 |
| gga ccg ccg ccc cct ccg ccg cct ccc cat ccc cac gct cgc atc aag<br>Gly Pro Pro Pro Pro Pro Pro Pro Pro His Pro His Ala Arg Ile Lys<br>380 385 390 | 1506 |
| ctg gag aac ccg ctg gac tac ggc agc gcc tgg gcg gct gcg gcg gcg<br>Leu Glu Asn Pro Leu Asp Tyr Gly Ser Ala Trp Ala Ala Ala Ala Ala<br>395 400 405 | 1554 |
| cag tgc cgc tat ggg gac ctg gcg agc ctg cat ggc gcg ggt gca gcg<br>Gln Cys Arg Tyr Gly Asp Leu Ala Ser Leu His Gly Ala Gly Ala Ala<br>410 415 420 425 | 1602 |
| gga ccc ggt tct ggg tca ccc tca gcc gcc gct tcc tca tcc tgg cac<br>Gly Pro Gly Ser Gly Ser Pro Ser Ala Ala Ala Ser Ser Ser Trp His<br>430 435 440 | 1650 |
| act ctc ttc aca gcc gaa gaa ggc cag ttg tat gga ccg tgt ggt ggt<br>Thr Leu Phe Thr Ala Glu Glu Gly Gln Leu Tyr Gly Pro Cys Gly Gly<br>445 450 455 | 1698 |
| ggt ggg ggt ggt ggc ggc ggc ggc ggc ggc ggc ggc ggc ggc<br>Gly Gly Gly Gly Gly Gly Gly Gly Gly Gly Gly Gly Gly Gly<br>460 465 470 | 1746 |
| ggc gag gcg gga gct gta gcc ccc tac ggc tac act cgg ccc cct cag<br>Gly Glu Ala Gly Ala Val Ala Pro Tyr Gly Tyr Thr Arg Pro Pro Gln<br>475 480 485 | 1794 |
| ggg ctg gcg ggc cag gaa agc gac ttc acc gca cct gat gtg tgg tac<br>Gly Leu Ala Gly Gln Glu Ser Asp Phe Thr Ala Pro Asp Val Trp Tyr<br>490 495 500 505 | 1842 |
| cct ggc ggc atg gtg agc aga gtg ccc tat ccc agt ccc act tgt gtc<br>Pro Gly Gly Met Val Ser Arg Val Pro Tyr Pro Ser Pro Thr Cys Val<br>510 515 520 | 1890 |
| aaa agc gaa atg ggc ccc tgg atg gat agc tac tcc gga cct tac ggg<br>Lys Ser Glu Met Gly Pro Trp Met Asp Ser Tyr Ser Gly Pro Tyr Gly<br>525 530 535 | 1938 |
| gac atg cgt ttg gag act gcc agg gac cat gtt ttg ccc att gac tat<br>Asp Met Arg Leu Glu Thr Ala Arg Asp His Val Leu Pro Ile Asp Tyr<br>540 545 550 | 1986 |
| tac ttt cca ccc cag aag acc tgc ctg atc tgt gga gat gaa gct tct<br>Tyr Phe Pro Pro Gln Lys Thr Cys Leu Ile Cys Gly Asp Glu Ala Ser<br>555 560 565 | 2034 |
| ggg tgt cac tat gga gct ctc aca tgt gga agc tgc aag gtc ttc ttc<br>Gly Cys His Tyr Gly Ala Leu Thr Cys Gly Ser Cys Lys Val Phe Phe<br>570 575 580 585 | 2082 |
| aaa aga gcc gct gaa ggg aaa cag aag tac ctg tgc gcc agc aga aat<br>Lys Arg Ala Ala Glu Gly Lys Gln Lys Tyr Leu Cys Ala Ser Arg Asn<br>590 595 600 | 2130 |

```
gat tgc act att gat aaa ttc cga agg aaa aat tgt cca tct tgt cgt    2178
Asp Cys Thr Ile Asp Lys Phe Arg Arg Lys Asn Cys Pro Ser Cys Arg
            605                 610                 615 ctt cgg aaa tgt tat gaa gca ggg atg act ctg gga gaa aaa ttc cgg    2226
Leu Arg Lys Cys Tyr Glu Ala Gly Met Thr Leu Gly Glu Lys Phe Arg
            620                 625                 630 gtt ggc aat tgc aag cat ctc aaa atg acc aga ccc tga agaaaggctg     2275
Val Gly Asn Cys Lys His Leu Lys Met Thr Arg Pro
            635                 640                 645 acttgcctca ttcaaaatga gggctctaga gggctctagt ggatagtctg gagaaacctg   2335
gcgtctgagg cttaggagct taggttttg ctcctcaaca cagactttga cgttggggtt    2395
gggggctact ctcttgattg ctgactccct ccagcgggac caatagtgtt ttcctacctc   2455
acagggatgt tgtgaggacg ggctgtagaa gtaatagtgg ttaccactca tgtagttgtg   2515
agtatcatga ttattgtttc ctgtaatgtg gcttggcatt ggcaaagtgc ttttgattg    2575 ttcttgatca catatgatgg gggccaggca ctgactcagg cggatgcagt gaagctctgg   2635
ctcagtcgct tgcttttcgt ggtgtgctgc caggaagaaa ctttgctgat gggactcaag   2695
gtgtcacctt ggacaagaag caactgtgtc tgtctgaggt tcctgtggcc atctttattt   2755
gtgtattagg caattcgtat ttccccctta ggttctagcc ttctggatcc cagccagtga   2815
cctagatctt agcctcaggc cctgtcactg agctgaaggt agtagctgat ccacagaagt   2875
tcagtaaaca aggaccagat ttctgcttct ccaggagaag aagccagcca cccctctct    2935 tcaaacacac tgagagacta cagtccgact ttccctctta catctagcct tactgtagcc   2995
acactccttg attgctctct cacatcacat gcttctcttc atcagttgta agcctctcat   3055
tcttctccca agccagactc aaatattgta ttgatgtcaa agaagaatca cttagagttt   3115
ggaatatctt gttctctctc tgctccatag cttccatatt gacaccagtt tctttctagt   3175
ggagaagtgg agtctgtgaa gccagggaaa cacacatgtg agagtcagaa ggactctccc   3235
tgacttgcct ggggcctgtc tttcccacct tctccagtct gtctaaacac acacacacac   3295
acacacacac acacacacac acacacacac gctctctctc tctctccccc cccaacacac   3355
acacactctc tctctcacac acacacacat acacacacac ttctttctct ttcccctgac   3415
tcagcaacat tctggagaaa agccaaggaa ggacttcagg aggggagttt ccccttctc    3475 agggcagaat tttaatctcc agaccaacaa gaagttccct aatgtggatt gaaaggctaa   3535
tgaggtttat ttttaactac tttctatttg tttgaatgtt gcatatttct actagtgaaa   3595 ttttcccta ataaagccat taatacaccc aaaaaaaaaa aaaaaa                   3641

<210> SEQ ID NO 5
<211> LENGTH: 2430
<212> TYPE: DNA
<213> ORGANISM: Homo sapiens
<220> FEATURE:
<221> NAME/KEY: CDS
<222> LOCATION: (328)...(2274)

<400> SEQUENCE: 5
gacactgaat ttggaaggtg gaggattttg ttttttctt ttaagatctg ggcatctttt     60
gaatctaccc ttcaagtatt aagagacaga ctgtgagcct agcagggcag atcttgtcca   120
ccgtgtgtct tcttctgcac gagactttga ggctgtcaga gcgcttttg cgtggttgct    180 cccgcaagtt tccttctctg gagcttcccg caggtgggca gctagctgca gcgactaccg   240
catcatcaca gcctgttgaa ctcttctgag caagagaagg ggaggcgggg taagggaagt   300
```

-continued

```
aggtggaaga ttcagccaag ctcaagg atg gaa gtg cag tta ggg ctg gga agg        354
                             Met Glu Val Gln Leu Gly Leu Gly Arg
                              1               5 gtc tac cct cgg ccg ccg tcc aag acc tac cga gga gct ttc cag aat          402
Val Tyr Pro Arg Pro Pro Ser Lys Thr Tyr Arg Gly Ala Phe Gln Asn
 10              15                  20                  25 ctg ttc cag agc gtg cgc gaa gtg atc cag aac ccg ggc ccc agg cac          450
Leu Phe Gln Ser Val Arg Glu Val Ile Gln Asn Pro Gly Pro Arg His
             30                  35                  40 cca gag gcc gcg agc gca gca cct ccc ggc gcc agt ttg ctg ctg cag          498
Pro Glu Ala Ala Ser Ala Ala Pro Pro Gly Ala Ser Leu Leu Leu Gln
                 45                  50                  55 cag cag cag cag cag cag cag cag cag cag cag cag cag cag                  546
Gln Gln Gln Gln Gln Gln Gln Gln Gln Gln Gln Gln Gln Gln
                 60                  65                  70 cag cag cag cag cag cag cag cag cag caa gag act agc ccc agg              594
Gln Gln Gln Gln Gln Gln Gln Gln Gln Gln Glu Thr Ser Pro Arg
         75                  80                  85 cag cag cag cag cag cag ggt gag gat ggt tct ccc caa gcc cat cgt          642
Gln Gln Gln Gln Gln Gln Gly Glu Asp Gly Ser Pro Gln Ala His Arg
 90                  95                 100                 105 aga ggc ccc aca ggc tac ctg gtc ctg gat gag gaa cag caa cct tca          690
Arg Gly Pro Thr Gly Tyr Leu Val Leu Asp Glu Glu Gln Gln Pro Ser
             110                 115                 120 cag ccg cag tcg gcc ctg gag tgc cac ccc gag aga ggt tgc gtc cca          738
Gln Pro Gln Ser Ala Leu Glu Cys His Pro Glu Arg Gly Cys Val Pro
                 125                 130                 135 gag cct gga gcc gcc gtg gcc gcc agc aag ggg ctg ccg cag cag ctg          786
Glu Pro Gly Ala Ala Val Ala Ala Ser Lys Gly Leu Pro Gln Gln Leu
             140                 145                 150 cca gca cct ccg gac gag gat gac tca gct gcc cca tcc acg ttg tcc          834
Pro Ala Pro Pro Asp Glu Asp Asp Ser Ala Ala Pro Ser Thr Leu Ser
         155                 160                 165 ctg ctg ggc ccc act ttc ccc ggc tta agc agc tgc tcc gct gac ctt          882
Leu Leu Gly Pro Thr Phe Pro Gly Leu Ser Ser Cys Ser Ala Asp Leu
170                 175                 180                 185 aaa gac atc ctg agc gag gcc agc acc atg caa ctc ctt cag caa cag          930
Lys Asp Ile Leu Ser Glu Ala Ser Thr Met Gln Leu Leu Gln Gln Gln
                 190                 195                 200 cag cag gaa gca gta tcc gaa ggc agc agc agc ggg aga gcg agg gag          978
Gln Gln Glu Ala Val Ser Glu Gly Ser Ser Ser Gly Arg Ala Arg Glu
             205                 210                 215 gcc tcg ggg gct ccc act tcc tcc aag gac aat tac tta ggg ggc act         1026
Ala Ser Gly Ala Pro Thr Ser Ser Lys Asp Asn Tyr Leu Gly Gly Thr
                 220                 225                 230 tcg acc att tct gac aac gcc aag gag ttg tgt aag gca gtg tcg gtg         1074
Ser Thr Ile Ser Asp Asn Ala Lys Glu Leu Cys Lys Ala Val Ser Val
         235                 240                 245 tcc atg ggc ctg ggt gtg gag gcg ttg gag cat ctg agt cca ggg gaa         1122
Ser Met Gly Leu Gly Val Glu Ala Leu Glu His Leu Ser Pro Gly Glu
250                 255                 260                 265 cag ctt cgg ggg gat tgc atg tac gcc cca ctt ttg gga gtt cca ccc         1170
Gln Leu Arg Gly Asp Cys Met Tyr Ala Pro Leu Leu Gly Val Pro Pro
                 270                 275                 280 gct gtg cgt ccc act cct tgt gcc cca ttg gcc gaa tgc aaa ggt tct         1218
Ala Val Arg Pro Thr Pro Cys Ala Pro Leu Ala Glu Cys Lys Gly Ser
             285                 290                 295 ctg cta gac gac agc gca ggc aag agc act gaa gat act gct gag tat         1266
Leu Leu Asp Asp Ser Ala Gly Lys Ser Thr Glu Asp Thr Ala Glu Tyr
```

|  |  |
|---|---|
| tcc cct ttc aag gga ggt tac acc aaa ggg cta gaa ggc gag agc cta<br>Ser Pro Phe Lys Gly Gly Tyr Thr Lys Gly Leu Glu Gly Glu Ser Leu<br>315                 320                  325 | 1314 |
| ggc tgc tct ggc agc gct gca gca ggg agc tcc ggg aca ctt gaa ctg<br>Gly Cys Ser Gly Ser Ala Ala Ala Gly Ser Ser Gly Thr Leu Glu Leu<br>330                 335                  340                  345 | 1362 |
| ccg tct acc ctg tct ctc tac aag tcc gga gca ctg gac gag gca gct<br>Pro Ser Thr Leu Ser Leu Tyr Lys Ser Gly Ala Leu Asp Glu Ala Ala<br>                350                  355                  360 | 1410 |
| gcg tac cag agt cgc gac tac tac aac ttt cca ctg gct ctg gcc gga<br>Ala Tyr Gln Ser Arg Asp Tyr Tyr Asn Phe Pro Leu Ala Leu Ala Gly<br>             365                  370                  375 | 1458 |
| ccg ccg ccc cct ccg ccg cct ccc cat ccc cac gct cgc atc aag ctg<br>Pro Pro Pro Pro Pro Pro Pro Pro His Pro His Ala Arg Ile Lys Leu<br>380                 385                  390 | 1506 |
| gag aac ccg ctg gac tac ggc agc gcc tgg gcg gct gcg gcg gcg cag<br>Glu Asn Pro Leu Asp Tyr Gly Ser Ala Trp Ala Ala Ala Ala Ala Gln<br>             395                  400                  405 | 1554 |
| tgc cgc tat ggg gac ctg gcg agc ctg cat ggc gcg ggt gca gcg gga<br>Cys Arg Tyr Gly Asp Leu Ala Ser Leu His Gly Ala Gly Ala Ala Gly<br>410                 415                  420                  425 | 1602 |
| ccc ggt tct ggg tca ccc tca gcc gcc gct tcc tca tcc tgg cac act<br>Pro Gly Ser Gly Ser Pro Ser Ala Ala Ala Ser Ser Ser Trp His Thr<br>                430                  435                  440 | 1650 |
| ctc ttc aca gcc gaa gaa ggc cag ttg tat gga ccg tgt ggt ggt ggt<br>Leu Phe Thr Ala Glu Glu Gly Gln Leu Tyr Gly Pro Cys Gly Gly Gly<br>                   445                  450                  455 | 1698 |
| ggg ggt ggt ggc ggc ggc ggc ggc ggc ggc ggc ggc ggc ggc ggc ggc<br>Gly Gly Gly Gly Gly Gly Gly Gly Gly Gly Gly Gly Gly Gly Gly Gly<br>460                 465                  470 | 1746 |
| gag gcg gga gct gta gcc ccc tac ggc tac act cgg ccc cct cag ggg<br>Glu Ala Gly Ala Val Ala Pro Tyr Gly Tyr Thr Arg Pro Pro Gln Gly<br>             475                  480                  485 | 1794 |
| ctg gcg ggc cag gaa agc gac ttc acc gca cct gat gtg tgg tac cct<br>Leu Ala Gly Gln Glu Ser Asp Phe Thr Ala Pro Asp Val Trp Tyr Pro<br>490                 495                  500                  505 | 1842 |
| ggc ggc atg gtg agc aga gtg ccc tat ccc agt ccc act tgt gtc aaa<br>Gly Gly Met Val Ser Arg Val Pro Tyr Pro Ser Pro Thr Cys Val Lys<br>                510                  515                  520 | 1890 |
| agc gaa atg ggc ccc tgg atg gat agc tac tcc gga cct tac ggg gac<br>Ser Glu Met Gly Pro Trp Met Asp Ser Tyr Ser Gly Pro Tyr Gly Asp<br>                   525                  530                  535 | 1938 |
| atg cgt ttg gag act gcc agg gac cat gtt ttg ccc att gac tat tac<br>Met Arg Leu Glu Thr Ala Arg Asp His Val Leu Pro Ile Asp Tyr Tyr<br>540                 545                  550 | 1986 |
| ttt cca ccc cag aag acc tgc ctg atc tgt gga gat gaa gct tct ggg<br>Phe Pro Pro Gln Lys Thr Cys Leu Ile Cys Gly Asp Glu Ala Ser Gly<br>             555                  560                  565 | 2034 |
| tgt cac tat gga gct ctc aca tgt gga agc tgc aag gtc ttc ttc aaa<br>Cys His Tyr Gly Ala Leu Thr Cys Gly Ser Cys Lys Val Phe Phe Lys<br>570                 575                  580                  585 | 2082 |
| aga gcc gct gaa ggg aaa cag aag tac ctg tgc gcc agc aga aat gat<br>Arg Ala Ala Glu Gly Lys Gln Lys Tyr Leu Cys Ala Ser Arg Asn Asp<br>                   590                  595                  600 | 2130 |
| tgc act att gat aaa ttc cga agg aaa aat tgt cca tct tgt cgt ctt<br>Cys Thr Ile Asp Lys Phe Arg Arg Lys Asn Cys Pro Ser Cys Arg Leu<br>             605                  610                  615 | 2178 |
| cgg aaa tgt tat gaa gca ggg atg act ctg gga gca gct gtt gtt gtt | 2226 |

```
                                                      -continued

Arg Lys Cys Tyr Glu Ala Gly Met Thr Leu Gly Ala Ala Val Val Val
        620                 625                 630 tct gaa aga atc ttg agg gtg ttt gga gtc tca gaa tgg ctt cct taa      2274
Ser Glu Arg Ile Leu Arg Val Phe Gly Val Ser Glu Trp Leu Pro
    635                 640                 645 agactacctt cagactctca gctgctcatc cacaacagag atcagccctt ctttgtagat    2334
gattcattcc tggctgcatt tgaaaaccac atattgttaa ttgcttgacg aatttaaatc    2394
ccttgactac ttttcatttc aaaaaaaaaa aaaaaa                              2430

<210> SEQ ID NO 6
<211> LENGTH: 2427
<212> TYPE: DNA
<213> ORGANISM: Homo sapiens
<220> FEATURE:
<221> NAME/KEY: CDS
<222> LOCATION: (328)...(2271)

<400> SEQUENCE: 6
gacactgaat ttggaaggtg gaggattttg ttttttttctt ttaagatctg ggcatctttt     60
gaatctaccc ttcaagtatt aagagacaga ctgtgagcct agcagggcag atcttgtcca    120
ccgtgtgtct tcttctgcac gagactttga ggctgtcaga gcgcttttg cgtggttgct     180 cccgcaagtt tccttctctg gagcttcccg caggtgggca gctagctgca gcgactaccg    240
catcatcaca gcctgttgaa ctcttctgag caagagaagg ggaggcgggg taagggaagt    300
aggtggaaga ttcagccaag ctcaagg atg gaa gtg cag tta ggg ctg gga agg    354
                                Met Glu Val Gln Leu Gly Leu Gly Arg
                                1               5 gtc tac cct cgg ccg ccg tcc aag acc tac cga gga gct ttc cag aat      402
Val Tyr Pro Arg Pro Pro Ser Lys Thr Tyr Arg Gly Ala Phe Gln Asn
 10              15                  20                  25 ctg ttc cag agc gtg cgc gaa gtg atc cag aac ccg ggc ccc agg cac      450
Leu Phe Gln Ser Val Arg Glu Val Ile Gln Asn Pro Gly Pro Arg His
             30                  35                  40 cca gag gcc gcg agc gca gca cct ccc ggc gcc agt ttg ctg ctg cag      498
Pro Glu Ala Ala Ser Ala Ala Pro Pro Gly Ala Ser Leu Leu Leu Gln
         45                  50                  55 cag cag cag cag cag cag cag cag cag cag cag cag cag cag cag cag      546
Gln Gln Gln Gln Gln Gln Gln Gln Gln Gln Gln Gln Gln Gln Gln Gln
     60                  65                  70 cag cag cag cag cag cag cag cag cag cag caa gag act agc ccc agg      594
Gln Gln Gln Gln Gln Gln Gln Gln Gln Gln Gln Glu Thr Ser Pro Arg
 75                  80                  85 cag cag cag cag cag cag ggt gag gat ggt tct ccc caa gcc cat cgt      642
Gln Gln Gln Gln Gln Gln Gly Glu Asp Gly Ser Pro Gln Ala His Arg
 90                  95                 100                 105 aga ggc ccc aca ggc tac ctg gtc ctg gat gag gaa cag caa cct tca      690
Arg Gly Pro Thr Gly Tyr Leu Val Leu Asp Glu Glu Gln Gln Pro Ser
             110                 115                 120 cag ccg cag tcg gcc ctg gag tgc cac ccc gag aga ggt tgc gtc cca      738
Gln Pro Gln Ser Ala Leu Glu Cys His Pro Glu Arg Gly Cys Val Pro
         125                 130                 135 gag cct gga gcc gcc gtg gcc gcc agc aag ggg ctg ccg cag cag ctg      786
Glu Pro Gly Ala Ala Val Ala Ala Ser Lys Gly Leu Pro Gln Gln Leu
     140                 145                 150 cca gca cct ccg gac gag gat gac tca gct gcc cca tcc acg ttg tcc      834
Pro Ala Pro Pro Asp Glu Asp Asp Ser Ala Ala Pro Ser Thr Leu Ser
 155                 160                 165 ctg ctg ggc ccc act ttc ccc ggc tta agc agc tgc tcc gct gac ctt      882
```

```
Leu Leu Gly Pro Thr Phe Pro Gly Leu Ser Ser Cys Ser Ala Asp Leu
170             175                 180                 185 aaa gac atc ctg agc gag gcc agc acc atg caa ctc ctt cag caa cag      930
Lys Asp Ile Leu Ser Glu Ala Ser Thr Met Gln Leu Leu Gln Gln Gln
                190                 195                 200 cag cag gaa gca gta tcc gaa ggc agc agc agc ggg aga gcg agg gag      978
Gln Gln Glu Ala Val Ser Glu Gly Ser Ser Ser Gly Arg Ala Arg Glu
                205                 210                 215 gcc tcg ggg gct ccc act tcc tcc aag gac aat tac tta ggg ggc act     1026
Ala Ser Gly Ala Pro Thr Ser Ser Lys Asp Asn Tyr Leu Gly Gly Thr
                220                 225                 230 tcg acc att tct gac aac gcc aag gag ttg tgt aag gca gtg tcg gtg     1074
Ser Thr Ile Ser Asp Asn Ala Lys Glu Leu Cys Lys Ala Val Ser Val
235                 240                 245 tcc atg ggc ctg ggt gtg gag gcg ttg gag cat ctg agt cca ggg gaa     1122
Ser Met Gly Leu Gly Val Glu Ala Leu Glu His Leu Ser Pro Gly Glu
250                 255                 260                 265 cag ctt cgg ggg gat tgc atg tac gcc cca ctt ttg gga gtt cca ccc     1170
Gln Leu Arg Gly Asp Cys Met Tyr Ala Pro Leu Leu Gly Val Pro Pro
                270                 275                 280 gct gtg cgt ccc act cct tgt gcc cca ttg gcc gaa tgc aaa ggt tct     1218
Ala Val Arg Pro Thr Pro Cys Ala Pro Leu Ala Glu Cys Lys Gly Ser
                285                 290                 295 ctg cta gac gac agc gca ggc aag agc act gaa gat act gct gag tat     1266
Leu Leu Asp Asp Ser Ala Gly Lys Ser Thr Glu Asp Thr Ala Glu Tyr
                300                 305                 310 tcc cct ttc aag gga ggt tac acc aaa ggg cta gaa ggc gag agc cta     1314
Ser Pro Phe Lys Gly Gly Tyr Thr Lys Gly Leu Glu Gly Glu Ser Leu
315                 320                 325 ggc tgc tct ggc agc gct gca gca ggg agc tcc ggg aca ctt gaa ctg     1362
Gly Cys Ser Gly Ser Ala Ala Ala Gly Ser Ser Gly Thr Leu Glu Leu
330                 335                 340                 345 ccg tct acc ctg tct ctc tac aag tcc gga gca ctg gac gag gca gct     1410
Pro Ser Thr Leu Ser Leu Tyr Lys Ser Gly Ala Leu Asp Glu Ala Ala
                350                 355                 360 gcg tac cag agt cgc gac tac tac aac ttt cca ctg gct ctg gcc gga     1458
Ala Tyr Gln Ser Arg Asp Tyr Tyr Asn Phe Pro Leu Ala Leu Ala Gly
                365                 370                 375 ccg ccg ccc cct ccg ccg cct ccc cat ccc cac gct cgc atc aag ctg     1506
Pro Pro Pro Pro Pro Pro Pro Pro His Pro His Ala Arg Ile Lys Leu
                380                 385                 390 gag aac ccg ctg gac tac ggc agc gcc tgg gcg gct gcg gcg gcg cag     1554
Glu Asn Pro Leu Asp Tyr Gly Ser Ala Trp Ala Ala Ala Ala Ala Gln
395                 400                 405 tgc cgc tat ggg gac ctg gcg agc ctg cat ggc gcg ggt gca gcg gga     1602
Cys Arg Tyr Gly Asp Leu Ala Ser Leu His Gly Ala Gly Ala Ala Gly
410                 415                 420                 425 ccc ggt tct ggg tca ccc tca gcc gcc gct tcc tca tcc tgg cac act     1650
Pro Gly Ser Gly Ser Pro Ser Ala Ala Ala Ser Ser Ser Trp His Thr
                430                 435                 440 ctc ttc aca gcc gaa gaa ggc cag ttg tat gga ccg tgt ggt ggt ggt     1698
Leu Phe Thr Ala Glu Glu Gly Gln Leu Tyr Gly Pro Cys Gly Gly Gly
                445                 450                 455 ggg ggt ggt ggc ggc ggc ggc ggc ggc ggc ggc ggc ggc ggc ggc ggc     1746
Gly Gly Gly Gly Gly Gly Gly Gly Gly Gly Gly Gly Gly Gly Gly Gly
                460                 465                 470 gag gcg gga gct gta gcc ccc tac ggc tac act cgg ccc cct cag ggg     1794
Glu Ala Gly Ala Val Ala Pro Tyr Gly Tyr Thr Arg Pro Pro Gln Gly
475                 480                 485
```

```
ctg gcg ggc cag gaa agc gac ttc acc gca cct gat gtg tgg tac cct    1842
Leu Ala Gly Gln Glu Ser Asp Phe Thr Ala Pro Asp Val Trp Tyr Pro
490                 495                 500                 505 ggc ggc atg gtg agc aga gtg ccc tat ccc agt ccc act tgt gtc aaa    1890
Gly Gly Met Val Ser Arg Val Pro Tyr Pro Ser Pro Thr Cys Val Lys
                510                 515                 520 agc gaa atg ggc ccc tgg atg gat agc tac tcc gga cct tac ggg gac    1938
Ser Glu Met Gly Pro Trp Met Asp Ser Tyr Ser Gly Pro Tyr Gly Asp
            525                 530                 535 atg cgt ttg gag act gcc agg gac cat gtt ttg ccc att gac tat tac    1986
Met Arg Leu Glu Thr Ala Arg Asp His Val Leu Pro Ile Asp Tyr Tyr
        540                 545                 550 ttt cca ccc cag aag acc tgc ctg atc tgt gga gat gaa gct tct ggg    2034
Phe Pro Pro Gln Lys Thr Cys Leu Ile Cys Gly Asp Glu Ala Ser Gly
    555                 560                 565 tgt cac tat gga gct ctc aca tgt gga agc tgc aag gtc ttc ttc aaa    2082
Cys His Tyr Gly Ala Leu Thr Cys Gly Ser Cys Lys Val Phe Phe Lys
570                 575                 580                 585 aga gcc gct gaa ggg aaa cag aag tac ctg tgc gcc agc aga aat gat    2130
Arg Ala Ala Glu Gly Lys Gln Lys Tyr Leu Cys Ala Ser Arg Asn Asp
                590                 595                 600 tgc act att gat aaa ttc cga agg aaa aat tgt cca tct tgt cgt ctt    2178
Cys Thr Ile Asp Lys Phe Arg Arg Lys Asn Cys Pro Ser Cys Arg Leu
            605                 610                 615 cgg aaa tgt tat gaa gca ggg att ctg gga gca gct gtt gtt gtt tct    2226
Arg Lys Cys Tyr Glu Ala Gly Ile Leu Gly Ala Ala Val Val Val Ser
        620                 625                 630 gaa aga atc ttg agg gtg ttt gga gtc tca gaa tgg ctt cct taa        2271
Glu Arg Ile Leu Arg Val Phe Gly Val Ser Glu Trp Leu Pro
    635                 640                 645 agactacctt cagactctca gctgctcatc cacaacagag atcagccctt ctttgtagat    2331
gattcattcc tggctgcatt tgaaaaccac atattgttaa ttgcttgacg aatttaaatc    2391
ccttgactac ttttcatttc aaaaaaaaaa aaaaaa                              2427

<210> SEQ ID NO 7
<211> LENGTH: 4039
<212> TYPE: DNA
<213> ORGANISM: Homo sapiens
<220> FEATURE:
<221> NAME/KEY: CDS
<222> LOCATION: (328)...(2376)

<400> SEQUENCE: 7
gacactgaat ttggaaggtg gaggattttg ttttttttctt ttaagatctg ggcatctttt     60
gaatctaccc ttcaagtatt aagagacaga ctgtgagcct agcagggcag atcttgtcca    120
ccgtgtgtct tcttctgcac gagactttga ggctgtcaga gcgcttttg cgtggttgct     180 cccgcaagtt tccttctctg gagcttcccg caggtgggca gctagctgca gcgactaccg    240
catcatcaca gcctgttgaa ctcttctgag caagagaagg ggaggcgggg taagggaagt    300
aggtggaaga ttcagccaag ctcaagg atg gaa gtg cag tta ggg ctg gga agg    354
                                Met Glu Val Gln Leu Gly Leu Gly Arg
                                  1               5 gtc tac cct cgg ccg ccg tcc aag acc tac cga gga gct ttc cag aat     402
Val Tyr Pro Arg Pro Pro Ser Lys Thr Tyr Arg Gly Ala Phe Gln Asn
 10                  15                  20                  25 ctg ttc cag agc gtg cgc gaa gtg atc cag aac ccg ggc ccc agg cac    450
Leu Phe Gln Ser Val Arg Glu Val Ile Gln Asn Pro Gly Pro Arg His
             30                  35                  40
```

| | |
|---|---|
| cca gag gcc gcg agc gca gca cct ccc ggc gcc agt ttg ctg ctg cag<br>Pro Glu Ala Ala Ser Ala Ala Pro Pro Gly Ala Ser Leu Leu Leu Gln<br>                45                        50                  55 | 498 |
| cag cag cag cag cag cag cag cag cag cag cag cag cag cag cag cag<br>Gln Gln Gln Gln Gln Gln Gln Gln Gln Gln Gln Gln Gln Gln Gln Gln<br>      60                      65                        70 | 546 |
| cag cag cag cag cag cag cag cag cag cag caa gag act agc ccc<br>Gln Gln Gln Gln Gln Gln Gln Gln Gln Gln Gln Glu Thr Ser Pro<br>     75                     80                      85 | 594 |
| agg cag cag cag cag cag cag ggt gag gat ggt tct ccc caa gcc cat<br>Arg Gln Gln Gln Gln Gln Gln Gly Glu Asp Gly Ser Pro Gln Ala His<br>90                       95                      100                105 | 642 |
| cgt aga ggc ccc aca ggc tac ctg gtc ctg gat gag gaa cag caa cct<br>Arg Arg Gly Pro Thr Gly Tyr Leu Val Leu Asp Glu Glu Gln Gln Pro<br>                110                      115                      120 | 690 |
| tca cag ccg cag tcg gcc ctg gag tgc cac ccc gag aga ggt tgc gtc<br>Ser Gln Pro Gln Ser Ala Leu Glu Cys His Pro Glu Arg Gly Cys Val<br>              125                      130                      135 | 738 |
| cca gag cct gga gcc gcc gtg gcc gcc agc aag ggg ctg ccg cag cag<br>Pro Glu Pro Gly Ala Ala Val Ala Ala Ser Lys Gly Leu Pro Gln Gln<br>            140                      145                      150 | 786 |
| ctg cca gca cct ccg gac gag gat gac tca gct gcc cca tcc acg ttg<br>Leu Pro Ala Pro Pro Asp Glu Asp Asp Ser Ala Ala Pro Ser Thr Leu<br>     155                     160                      165 | 834 |
| tcc ctg ctg ggc ccc act ttc ccc ggc tta agc agc tgc tcc gct gac<br>Ser Leu Leu Gly Pro Thr Phe Pro Gly Leu Ser Ser Cys Ser Ala Asp<br>170                      175                      180                  185 | 882 |
| ctt aaa gac atc ctg agc gag gcc agc acc atg caa ctc ctt cag caa<br>Leu Lys Asp Ile Leu Ser Glu Ala Ser Thr Met Gln Leu Leu Gln Gln<br>              190                      195                      200 | 930 |
| cag cag cag gaa gca gta tcc gaa ggc agc agc agc ggg aga gcg agg<br>Gln Gln Gln Glu Ala Val Ser Glu Gly Ser Ser Ser Gly Arg Ala Arg<br>            205                      210                      215 | 978 |
| gag gcc tcg ggg gct ccc act tcc tcc aag gac aat tac tta ggg ggc<br>Glu Ala Ser Gly Ala Pro Thr Ser Ser Lys Asp Asn Tyr Leu Gly Gly<br>     220                     225                      230 | 1026 |
| act tcg acc att tct gac aac gcc aag gag ttg tgt aag gca gtg tcg<br>Thr Ser Thr Ile Ser Asp Asn Ala Lys Glu Leu Cys Lys Ala Val Ser<br>            235                      240                      245 | 1074 |
| gtg tcc atg ggc ctg ggt gtg gag gcg ttg gag cat ctg agt cca ggg<br>Val Ser Met Gly Leu Gly Val Glu Ala Leu Glu His Leu Ser Pro Gly<br>250                      255                      260                  265 | 1122 |
| gaa cag ctt cgg ggg gat tgc atg tac gcc cca ctt ttg gga gtt cca<br>Glu Gln Leu Arg Gly Asp Cys Met Tyr Ala Pro Leu Leu Gly Val Pro<br>              270                      275                      280 | 1170 |
| ccc gct gtg cgt ccc act cct tgt gcc cca ttg gcc gaa tgc aaa ggt<br>Pro Ala Val Arg Pro Thr Pro Cys Ala Pro Leu Ala Glu Cys Lys Gly<br>            285                      290                      295 | 1218 |
| tct ctg cta gac gac agc gca ggc aag agc act gaa gat act gct gag<br>Ser Leu Leu Asp Asp Ser Ala Gly Lys Ser Thr Glu Asp Thr Ala Glu<br>     300                     305                      310 | 1266 |
| tat tcc cct ttc aag gga ggt tac acc aaa ggg cta gaa ggc gag agc<br>Tyr Ser Pro Phe Lys Gly Gly Tyr Thr Lys Gly Leu Glu Gly Glu Ser<br>            315                      320                      325 | 1314 |
| cta ggc tgc tct ggc agc gct gca gca ggg agc tcc ggg aca ctt gaa<br>Leu Gly Cys Ser Gly Ser Ala Ala Ala Gly Ser Ser Gly Thr Leu Glu<br>330                      335                      340                  345 | 1362 |
| ctg ccg tct acc ctg tct ctc tac aag tcc gga gca ctg gac gag gca<br>Leu Pro Ser Thr Leu Ser Leu Tyr Lys Ser Gly Ala Leu Asp Glu Ala<br>              350                      355                      360 | 1410 |

```
gct gcg tac cag agt cgc gac tac tac aac ttt cca ctg gct ctg gcc    1458
Ala Ala Tyr Gln Ser Arg Asp Tyr Tyr Asn Phe Pro Leu Ala Leu Ala
            365                 370                 375 gga ccg ccg ccc cct ccg ccg cct ccc cat ccc cac gct cgc atc aag    1506
Gly Pro Pro Pro Pro Pro Pro Pro Pro His Pro His Ala Arg Ile Lys
        380                 385                 390 ctg gag aac ccg ctg gac tac ggc agc gcc tgg gcg gct gcg gcg gcg    1554
Leu Glu Asn Pro Leu Asp Tyr Gly Ser Ala Trp Ala Ala Ala Ala Ala
395                 400                 405 cag tgc cgc tat ggg gac ctg gcg agc ctg cat ggc gcg ggt gca gcg    1602
Gln Cys Arg Tyr Gly Asp Leu Ala Ser Leu His Gly Ala Gly Ala Ala
410                 415                 420                 425 gga ccc ggt tct ggg tca ccc tca gcc gcc gct tcc tca tcc tgg cac    1650
Gly Pro Gly Ser Gly Ser Pro Ser Ala Ala Ala Ser Ser Ser Trp His
            430                 435                 440 act ctc ttc aca gcc gaa gaa ggc cag ttg tat gga ccg tgt ggt ggt    1698
Thr Leu Phe Thr Ala Glu Glu Gly Gln Leu Tyr Gly Pro Cys Gly Gly
        445                 450                 455 ggt ggg ggt ggt ggc ggc ggc ggc ggc ggc ggc ggc ggc ggc ggc ggc    1746
Gly Gly Gly Gly Gly Gly Gly Gly Gly Gly Gly Gly Gly Gly Gly Gly
460                 465                 470 ggc gag gcg gga gct gta gcc ccc tac ggc tac act cgg ccc cct cag    1794
Gly Glu Ala Gly Ala Val Ala Pro Tyr Gly Tyr Thr Arg Pro Pro Gln
475                 480                 485 ggg ctg gcg ggc cag gaa agc gac ttc acc gca cct gat gtg tgg tac    1842
Gly Leu Ala Gly Gln Glu Ser Asp Phe Thr Ala Pro Asp Val Trp Tyr
490                 495                 500                 505 cct ggc ggc atg gtg agc aga gtg ccc tat ccc agt ccc act tgt gtc    1890
Pro Gly Gly Met Val Ser Arg Val Pro Tyr Pro Ser Pro Thr Cys Val
            510                 515                 520 aaa agc gaa atg ggc ccc tgg atg gat agc tac tcc gga cct tac ggg    1938
Lys Ser Glu Met Gly Pro Trp Met Asp Ser Tyr Ser Gly Pro Tyr Gly
        525                 530                 535 gac atg cgt ttg gag act gcc agg gac cat gtt ttg ccc att gac tat    1986
Asp Met Arg Leu Glu Thr Ala Arg Asp His Val Leu Pro Ile Asp Tyr
540                 545                 550 tac ttt cca ccc cag aag acc tgc ctg atc tgt gga gat gaa gct tct    2034
Tyr Phe Pro Pro Gln Lys Thr Cys Leu Ile Cys Gly Asp Glu Ala Ser
555                 560                 565 ggg tgt cac tat gga gct ctc aca tgt gga agc tgc aag gtc ttc ttc    2082
Gly Cys His Tyr Gly Ala Leu Thr Cys Gly Ser Cys Lys Val Phe Phe
570                 575                 580                 585 aaa aga gcc gct gaa ggg aaa cag aag tac ctg tgc gcc agc aga aat    2130
Lys Arg Ala Ala Glu Gly Lys Gln Lys Tyr Leu Cys Ala Ser Arg Asn
            590                 595                 600 gat tgc act att gat aaa ttc cga agg aaa aat tgt cca tct tgt cgt    2178
Asp Cys Thr Ile Asp Lys Phe Arg Arg Lys Asn Cys Pro Ser Cys Arg
        605                 610                 615 ctt cgg aaa tgt tat gaa gca ggg atg act ctg gga gga ttt ttc aga    2226
Leu Arg Lys Cys Tyr Glu Ala Gly Met Thr Leu Gly Gly Phe Phe Arg
620                 625                 630 atg aac aaa tta aaa gaa tca tca gac act aac ccc aag cca tac tgc    2274
Met Asn Lys Leu Lys Glu Ser Ser Asp Thr Asn Pro Lys Pro Tyr Cys
635                 640                 645 atg gca gca cca atg gga ctg aca gaa aac aac aga aat agg aag aaa    2322
Met Ala Ala Pro Met Gly Leu Thr Glu Asn Asn Arg Asn Arg Lys Lys
650                 655                 660                 665 tcc tac aga gaa aca aac ttg aaa gct gtc tca tgg cct ttg aat cat    2370
Ser Tyr Arg Glu Thr Asn Leu Lys Ala Val Ser Trp Pro Leu Asn His
```

|  | 670 |  | 675 |  | 680 |  |  |
|---|---|---|---|---|---|---|---| act taa gttttatgat ggaaggatac gactatgaag aaagacacag agcaacatca     2426
Thr gacagtcaag aatttcagag ccagctggca tgcagtggac ctcatgccag cccatttat      2486 gactatttag ggaaacagaa gtacctgtgc gccagcagaa atgattgcac tattgataaa    2546
ttccgaagga aaaattgtcc atcttgtcgt cttcggaaat gttatgaagc agggatgact    2606
ctgggagaaa aattccgggt tggcaattgc aagcatctca aaatgaccag accctgaaga    2666
aaggctgact tgcctcattc aaaatgaggg ctctagaggg ctctagtgga tagtctggag    2726
aaacctggcg tctgaggctt aggagcttag gttttttgctc ctcaacacag actttgacgt   2786
tggggttggg ggctactctc ttgattgctg actccctcca gcgggaccaa tagtgttttc     2846
ctacctcaca gggatgttgt gaggacgggc tgtagaagta atagtggtta ccactcatgt    2906
agttgtgagt atcatgatta ttgtttcctg taatgtggct tggcattggc aaagtgcttt     2966
ttgattgttc ttgatcacat atgatggggg ccaggcactg actcaggcgg atgcagtgaa    3026
gctctggctc agtcgcttgc ttttcgtggt gtgctgccag gaagaaactt tgctgatggg    3086
actcaaggtg tcaccttgga caagaagcaa ctgtgtctgt ctgaggttcc tgtggccatc    3146
tttatttgtg tattaggcaa ttcgtatttc cccccttaggt tctagccttc tggatcccag    3206
ccagtgacct agatcttagc ctcaggccct gtcactgagc tgaaggtagt agctgatcca    3266
cagaagttca gtaaacaagg accagatttc tgcttctcca ggagaagaag ccagccaacc    3326
cctctcttca aacacactga gagactacag tccgactttc cctcttacat ctagccttac    3386
tgtagccaca ctccttgatt gctctctcac atcacatgct tctcttcatc agttgtaagc    3446
ctctcattct tctcccaagc cagactcaaa tattgtattg atgtcaaaga gaatcactt     3506 agagtttgga atatcttgtt ctctctctgc tccatagctt ccatattgac accagtttct    3566
ttctagtgga gaagtggagt ctgtgaagcc agggaaacac acatgtgaga gtcagaagga    3626
ctctccctga cttgcctggg gcctgtcttt cccaccttct ccagtctgtc taaacacaca    3686
cacacacaca cacacacaca cacacacaca cacacacgct ctctctctct ctcccccccc    3746
aacacacaca cactctctct ctcacacaca cacacataca cacacacttc tttctctttc    3806
ccctgactca gcaacattct ggagaaaagc caaggaagga cttcaggagg ggagtttccc    3866
ccttctcagg gcagaatttt aatctccaga ccaacaagaa gttccctaat gtggattgaa    3926
aggctaatga ggtttatttt taactacttt ctatttgttt gaatgttgca tatttctact    3986
agtgaaattt tcccttaata aagccattaa tacacccaaa aaaaaaaaaa aaa           4039

<210> SEQ ID NO 8
<211> LENGTH: 3922
<212> TYPE: DNA
<213> ORGANISM: Homo sapiens
<220> FEATURE:
<221> NAME/KEY: CDS
<222> LOCATION: (328)...(2259)

<400> SEQUENCE: 8
gacactgaat ttggaaggtg gaggattttg ttttttttctt ttaagatctg ggcatctttt       60
gaatctaccc ttcaagtatt aagagacaga ctgtgagcct agcagggcag atcttgtcca     120
ccgtgtgtct tcttctgcac gagactttga ggctgtcaga gcgctttttg cgtggttgct     180
cccgcaagtt tccttctctg gagcttcccg caggtgggca gctagctgca gcgactaccg    240
catcatcaca gcctgttgaa ctcttctgag caagagaagg ggaggcgggg taagggaagt    300

```
                                                                             -continued aggtggaaga ttcagccaag ctcaagg atg gaa gtg cag tta ggg ctg gga agg              354
                             Met Glu Val Gln Leu Gly Leu Gly Arg
                              1               5 gtc tac cct cgg ccg ccg tcc aag acc tac cga gga gct ttc cag aat                402
Val Tyr Pro Arg Pro Pro Ser Lys Thr Tyr Arg Gly Ala Phe Gln Asn
 10              15                  20                  25 ctg ttc cag agc gtg cgc gaa gtg atc cag aac ccg ggc ccc agg cac                450
Leu Phe Gln Ser Val Arg Glu Val Ile Gln Asn Pro Gly Pro Arg His
                 30                  35                  40 cca gag gcc gcg agc gca gca cct ccc ggc gcc agt ttg ctg ctg cag                498
Pro Glu Ala Ala Ser Ala Ala Pro Pro Gly Ala Ser Leu Leu Leu Gln
                     45                  50                  55 cag cag cag cag cag cag cag cag cag cag cag cag cag cag cag cag                546
Gln Gln Gln Gln Gln Gln Gln Gln Gln Gln Gln Gln Gln Gln Gln Gln
                         60                  65                  70 cag cag cag cag cag cag cag cag cag cag caa gag act agc ccc                    594
Gln Gln Gln Gln Gln Gln Gln Gln Gln Gln Gln Glu Thr Ser Pro
             75                  80                  85 agg cag cag cag cag cag cag ggt gag gat ggt tct ccc caa gcc cat                642
Arg Gln Gln Gln Gln Gln Gln Gly Glu Asp Gly Ser Pro Gln Ala His
 90                  95                 100                 105 cgt aga ggc ccc aca ggc tac ctg gtc ctg gat gag gaa cag caa cct                690
Arg Arg Gly Pro Thr Gly Tyr Leu Val Leu Asp Glu Glu Gln Gln Pro
                110                 115                 120 tca cag ccg cag tcg gcc ctg gag tgc cac ccc gag aga ggt tgc gtc                738
Ser Gln Pro Gln Ser Ala Leu Glu Cys His Pro Glu Arg Gly Cys Val
                    125                 130                 135 cca gag cct gga gcc gcc gtg gcc gcc agc aag ggg ctg ccg cag cag                786
Pro Glu Pro Gly Ala Ala Val Ala Ala Ser Lys Gly Leu Pro Gln Gln
                        140                 145                 150 ctg cca gca cct ccg gac gag gat gac tca gct gcc cca tcc acg ttg                834
Leu Pro Ala Pro Pro Asp Glu Asp Asp Ser Ala Ala Pro Ser Thr Leu
            155                 160                 165 tcc ctg ctg ggc ccc act ttc ccc ggc tta agc agc tgc tcc gct gac                882
Ser Leu Leu Gly Pro Thr Phe Pro Gly Leu Ser Ser Cys Ser Ala Asp
170                 175                 180                 185 ctt aaa gac atc ctg agc gag gcc agc acc atg caa ctc ctt cag caa                930
Leu Lys Asp Ile Leu Ser Glu Ala Ser Thr Met Gln Leu Leu Gln Gln
                    190                 195                 200 cag cag cag gaa gca gta tcc gaa ggc agc agc agc ggg aga gcg agg                978
Gln Gln Gln Glu Ala Val Ser Glu Gly Ser Ser Ser Gly Arg Ala Arg
                        205                 210                 215 gag gcc tcg ggg gct ccc act tcc tcc aag gac aat tac tta ggg ggc               1026
Glu Ala Ser Gly Ala Pro Thr Ser Ser Lys Asp Asn Tyr Leu Gly Gly
            220                 225                 230 act tcg acc att tct gac aac gcc aag gag ttg tgt aag gca gtg tcg               1074
Thr Ser Thr Ile Ser Asp Asn Ala Lys Glu Leu Cys Lys Ala Val Ser
235                 240                 245 gtg tcc atg ggc ctg ggt gtg gag gcg ttg gag cat ctg agt cca ggg               1122
Val Ser Met Gly Leu Gly Val Glu Ala Leu Glu His Leu Ser Pro Gly
250                 255                 260                 265 gaa cag ctt cgg ggg gat tgc atg tac gcc cca ctt ttg gga gtt cca               1170
Glu Gln Leu Arg Gly Asp Cys Met Tyr Ala Pro Leu Leu Gly Val Pro
                    270                 275                 280 ccc gct gtg cgt ccc act cct tgt gcc cca ttg gcc gaa tgc aaa ggt               1218
Pro Ala Val Arg Pro Thr Pro Cys Ala Pro Leu Ala Glu Cys Lys Gly
                285                 290                 295 tct ctg cta gac gac agc gca ggc aag agc act gaa gat act gct gag               1266
Ser Leu Leu Asp Asp Ser Ala Gly Lys Ser Thr Glu Asp Thr Ala Glu
```

```
                        300                 305                 310
tat tcc cct ttc aag gga ggt tac acc aaa ggg cta gaa ggc gag agc        1314
Tyr Ser Pro Phe Lys Gly Gly Tyr Thr Lys Gly Leu Glu Gly Glu Ser
    315                 320                 325 cta ggc tgc tct ggc agc gct gca gca ggg agc tcc ggg aca ctt gaa        1362
Leu Gly Cys Ser Gly Ser Ala Ala Ala Gly Ser Ser Gly Thr Leu Glu
330                 335                 340                 345 ctg ccg tct acc ctg tct ctc tac aag tcc gga gca ctg gac gag gca        1410
Leu Pro Ser Thr Leu Ser Leu Tyr Lys Ser Gly Ala Leu Asp Glu Ala
                350                 355                 360 gct gcg tac cag agt cgc gac tac tac aac ttt cca ctg gct ctg gcc        1458
Ala Ala Tyr Gln Ser Arg Asp Tyr Tyr Asn Phe Pro Leu Ala Leu Ala
            365                 370                 375 gga ccg ccg ccc cct ccg ccg cct ccc cat ccc cac gct cgc atc aag        1506
Gly Pro Pro Pro Pro Pro Pro Pro Pro His Pro His Ala Arg Ile Lys
        380                 385                 390 ctg gag aac ccg ctg gac tac ggc agc gcc tgg gcg gct gcg gcg gcg        1554
Leu Glu Asn Pro Leu Asp Tyr Gly Ser Ala Trp Ala Ala Ala Ala Ala
    395                 400                 405 cag tgc cgc tat ggg gac ctg gcg agc ctg cat ggc gcg ggt gca gcg        1602
Gln Cys Arg Tyr Gly Asp Leu Ala Ser Leu His Gly Ala Gly Ala Ala
410                 415                 420                 425 gga ccc ggt tct ggg tca ccc tca gcc gcc gct tca tca tcc tgg cac        1650
Gly Pro Gly Ser Gly Ser Pro Ser Ala Ala Ala Ser Ser Ser Trp His
                430                 435                 440 act ctc ttc aca gcc gaa gaa ggc cag ttg tat gga ccg tgt ggt ggt        1698
Thr Leu Phe Thr Ala Glu Glu Gly Gln Leu Tyr Gly Pro Cys Gly Gly
            445                 450                 455 ggt ggg ggt ggt ggc ggc ggc ggc ggc ggc ggc ggc ggc ggc ggc            1746
Gly Gly Gly Gly Gly Gly Gly Gly Gly Gly Gly Gly Gly Gly Gly
        460                 465                 470 ggc gag gcg gga gct gta gcc ccc tac ggc tac act cgg ccc cct cag        1794
Gly Glu Ala Gly Ala Val Ala Pro Tyr Gly Tyr Thr Arg Pro Pro Gln
    475                 480                 485 ggg ctg gcg ggc cag gaa agc gac ttc acc gca cct gat gtg tgg tac        1842
Gly Leu Ala Gly Gln Glu Ser Asp Phe Thr Ala Pro Asp Val Trp Tyr
490                 495                 500                 505 cct ggc ggc atg gtg agc aga gtg ccc tat ccc agt ccc act tgt gtc        1890
Pro Gly Gly Met Val Ser Arg Val Pro Tyr Pro Ser Pro Thr Cys Val
                510                 515                 520 aaa agc gaa atg ggc ccc tgg atg gat agc tac tcc gga cct tac ggg        1938
Lys Ser Glu Met Gly Pro Trp Met Asp Ser Tyr Ser Gly Pro Tyr Gly
            525                 530                 535 gac atg cgt ttg gag act gcc agg gac cat gtt ttg ccc att gac tat        1986
Asp Met Arg Leu Glu Thr Ala Arg Asp His Val Leu Pro Ile Asp Tyr
        540                 545                 550 tac ttt cca ccc cag aag acc tgc ctg atc tgt gga gac gaa gct tct        2034
Tyr Phe Pro Pro Gln Lys Thr Cys Leu Ile Cys Gly Asp Glu Ala Ser
    555                 560                 565 ggg tgt cac tat gga gct ctc aca tgt gga agc tgc aag gtc ttc ttc        2082
Gly Cys His Tyr Gly Ala Leu Thr Cys Gly Ser Cys Lys Val Phe Phe
570                 575                 580                 585 aaa aga gcc gct gaa gga ttt ttc aga atg aac aaa tta aaa gaa tca        2130
Lys Arg Ala Ala Glu Gly Phe Phe Arg Met Asn Lys Leu Lys Glu Ser
                590                 595                 600 tca gac act aac ccc aag cca tac tgc atg gca gca cca atg gga ctg        2178
Ser Asp Thr Asn Pro Lys Pro Tyr Cys Met Ala Ala Pro Met Gly Leu
            605                 610                 615 aca gaa aac aac aga aat agg aag aaa tcc tac aga gaa aca aac ttg        2226
```

```
Thr Glu Asn Asn Arg Asn Arg Lys Lys Ser Tyr Arg Glu Thr Asn Leu
            620                 625                 630 aaa gct gtc tca tgg cct ttg aat cat act taa gttttatgat ggaaggatac    2279
Lys Ala Val Ser Trp Pro Leu Asn His Thr
    635                 640 gactatgaag aaagacacag agcaacatca gacagtcaag aatttcagag ccagctggca    2339
tgcagtggac ctcatgccag cccatttat gactatttag ggagacagaa gtacctgtgc     2399
gccagcagaa atgattgcac tattgataaa ttccgaagga aaaattgtcc atcttgtcgt    2459
cttcggaaat gttatgaagc aggggtgact ctgggagaaa aattccgggt tggcaattgc    2519
aagcatctca aaatgaccag accctgaaga aaggctgact tgcctcattc aaaatgaggg    2579
ctctagaggg ctctagtgga tagtctggag aaacctggcg tctgaggctt aggagcttag    2639 gttttgctc ctcaacacag actttgacgt tggggttggg ggctactctc ttgattgctg     2699
actccctcca gcgggaccaa tagtgttttc ctacctcaca gggatgttgt gaggacgggc    2759
tgtagaagta atagtggtta ccactcatgt agttgtgagt atcatgatta ttgtttcctg    2819
taatgtggct tggcattggc aaagtgcttt ttgattgttc ttgatcacat atgatggggg    2879
ccaggcactg actcaggcgg atgcagtgaa gctctggctc agtcgcttgc ttttcgtggt    2939
gtgctgccag gaagaaactt tgctgatggg actcaaggtg tcaccttgga caagaagcaa    2999
ctgtgtctgt ctgaggttcc tgtggccatc tttatttgtg tattaggcaa ttcgtatttc    3059 cccccttaggt tctagccttc tggatcccag ccagtgacct agatcttagc ctcaggccct   3119
gtcactgagc tgaaggtagt agctgatcca cagaagttca gtaaacaagg accagatttc    3179
tgcttctcca ggagaagaag ccagccaacc cctctcttca aacacactga gagactacag    3239
tccgactttc cctcttacat ctagccttac tgtagccaca ctccttgatt gctctctcac    3299
atcacatgct tctcttcatc agttgtaagc ctctcattct tctcccaagc cagactcaaa    3359
tattgtattg atgtcaaaga agaatcactt agagtttgga atatcttgtt ctctctctgc    3419
tccatagctt ccatattgac accagtttct ttctagtgga gaagtggagt ctgtgaagcc    3479
agggaaacac acatgtgaga gtcagaagga ctctccctga cttgctggg gcctgtcttt     3539 cccaccttct ccagtctgtc taaacacaca cacacacaca cacacacaca cacacacaca    3599
cacacacgct ctctctctct ctcccccccc aacacacaca cactctctct ctcacacaca    3659
cacacataca cacacacttc tttctctttc ccctgactca gcaacattct ggagaaaagc    3719
caaggaagga cttcaggagg ggagtttccc ccttctcagg gcagaatttt aatctccaga    3779
ccaacaagaa gttccctaat gtggattgaa aggctaatga ggtttatttt taactacttt    3839
ctatttgttt gaatgttgca tatttctact agtgaaattt tcccttaata aagccattaa    3899
tacacccaaa aaaaaaaaaa aaa                                             3922

<210> SEQ ID NO 9
<211> LENGTH: 21
<212> TYPE: DNA
<213> ORGANISM: Artificial Sequence
<220> FEATURE:
<223> OTHER INFORMATION: Primer

<400> SEQUENCE: 9
tccttcacca atgtcaactc c                                                 21

<210> SEQ ID NO 10
<211> LENGTH: 21
<212> TYPE: DNA
```

```
<213> ORGANISM: Artificial Sequence
<220> FEATURE:
<223> OTHER INFORMATION: Primer

<400> SEQUENCE: 10
gagccatcca aactcttgag a                                              21

<210> SEQ ID NO 11
<211> LENGTH: 22
<212> TYPE: DNA
<213> ORGANISM: Artificial Sequence
<220> FEATURE:
<223> OTHER INFORMATION: Probe

<400> SEQUENCE: 11
agtaccgcat gcacaagtcc cg                                             22

<210> SEQ ID NO 12
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 12
gcgctctgac agcctc                                                    16

<210> SEQ ID NO 13
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 13
cacctgcggg aagctc                                                    16

<210> SEQ ID NO 14
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 14
ggctgtgatg atgcgg                                                    16

<210> SEQ ID NO 15
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 15
cttcgcgcac gctctg                                                    16

<210> SEQ ID NO 16
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 16
atggtgctgg cctcgc                                                    16
```

```
<210> SEQ ID NO 17
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 17
ggtcgaagtg cccect                                                   16

<210> SEQ ID NO 18
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 18
gacaccgaca ctgcct                                                   16

<210> SEQ ID NO 19
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 19
cccgaagctg ttcccc                                                   16

<210> SEQ ID NO 20
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 20
cttgcctgcg ctgtcg                                                   16

<210> SEQ ID NO 21
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 21
gttgtagtag tcgcga                                                   16

<210> SEQ ID NO 22
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 22
aagttgtagt agtcgc                                                   16

<210> SEQ ID NO 23
<211> LENGTH: 16
<212> TYPE: DNA
<213> ORGANISM: Artificial Sequence
<220> FEATURE:
```

<223> OTHER INFORMATION: Synthetic Oligonucleotide

<400> SEQUENCE: 23
gcgctgccgt agtcca                     16

<210> SEQ ID NO 24
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 24
aggatgagga agcggc                     16

<210> SEQ ID NO 25
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 25
gctcccgcct cgccgc                     16

<210> SEQ ID NO 26
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 26
cgctttcctg gcccgc                     16

<210> SEQ ID NO 27
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 27
gccgccaggg taccac                     16

<210> SEQ ID NO 28
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 28
ccaaacgcat gtcccc                     16

<210> SEQ ID NO 29
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 29
agcttcatct ccacag                     16

-continued

```
<210> SEQ ID NO 30
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 30
tcccttcagc ggctct                                                       16

<210> SEQ ID NO 31
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 31
tttctgctgg cgcaca                                                       16

<210> SEQ ID NO 32
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 32
gttcattcga agttca                                                       16

<210> SEQ ID NO 33
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 33
gaggatcatc acagat                                                       16

<210> SEQ ID NO 34
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 34
ctaaacttcc cgtggc                                                       16

<210> SEQ ID NO 35
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 35
ttgatttaat ggttgc                                                       16

<210> SEQ ID NO 36
<211> LENGTH: 16
<212> TYPE: DNA
<213> ORGANISM: Artificial Sequence
<220> FEATURE:
<223> OTHER INFORMATION: Synthetic Oligonucleotide
```

```
<400> SEQUENCE: 36
gttgatttaa tggttg                                               16

<210> SEQ ID NO 37
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 37
atggttgatt taatgg                                               16

<210> SEQ ID NO 38
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 38
tggttgattt aatggttgca                                           20

<210> SEQ ID NO 39
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 39
tgatttaatg gttgca                                               16

<210> SEQ ID NO 40
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 40
ggttgattta atggtt                                               16

<210> SEQ ID NO 41
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 41
tggttgattt aatggt                                               16

<210> SEQ ID NO 42
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 42
agttgtagta gtcgcg                                               16

<210> SEQ ID NO 43
<211> LENGTH: 16
```

```
<212> TYPE: DNA
<213> ORGANISM: Artificial Sequence
<220> FEATURE:
<223> OTHER INFORMATION: Synthetic Oligonucleotide

<400> SEQUENCE: 43
gatttaatgg ttgcaa                                                      16

<210> SEQ ID NO 44
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 44
acagcactgg agcggc                                                      16

<210> SEQ ID NO 45
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 45
aacttcaccg aagagg                                                      16

<210> SEQ ID NO 46
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 46
agtctttagc agcttt                                                      16

<210> SEQ ID NO 47
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 47
gcttcctccg agtctt                                                      16

<210> SEQ ID NO 48
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 48
ccttgcttcc tccgag                                                      16

<210> SEQ ID NO 49
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 49
```

```
gcactttcct tgcttc                                                      16

<210> SEQ ID NO 50
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 50
tcagtcctac caggca                                                      16

<210> SEQ ID NO 51
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 51
gactgaggca gctgcg                                                      16

<210> SEQ ID NO 52
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 52
ccgactgagg cagctg                                                      16

<210> SEQ ID NO 53
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 53
gctagctcgc ccgctc                                                      16

<210> SEQ ID NO 54
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 54
cagctagctc gcccgc                                                      16

<210> SEQ ID NO 55
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 55
gcaatgtgca gctagc                                                      16

<210> SEQ ID NO 56
<211> LENGTH: 16
<212> TYPE: DNA
<213> ORGANISM: Artificial Sequence
```

```
<220> FEATURE:
<223> OTHER INFORMATION: Synthetic Oligonucleotide

<400> SEQUENCE: 56
gtcgcctggc tcctaa                                                    16

<210> SEQ ID NO 57
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 57
ctggctccgc actcgg                                                    16

<210> SEQ ID NO 58
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 58
atctctggct ccgcac                                                    16

<210> SEQ ID NO 59
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 59
tgatctctgg ctccgc                                                    16

<210> SEQ ID NO 60
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 60
agtgtccact gaagta                                                    16

<210> SEQ ID NO 61
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 61
aggctcacag tctgtc                                                    16

<210> SEQ ID NO 62
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 62
gacacacggt ggacaa                                                    16
```

<210> SEQ ID NO 63
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 63
agaagacaca cggtgg                                                  16

<210> SEQ ID NO 64
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 64
cgctctgaca gcctca                                                  16

<210> SEQ ID NO 65
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 65
gtcgctgcag ctagct                                                  16

<210> SEQ ID NO 66
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 66
ggtagtcgct gcagct                                                  16

<210> SEQ ID NO 67
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 67
gcggtagtcg ctgcag                                                  16

<210> SEQ ID NO 68
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 68
atgcggtagt cgctgc                                                  16

<210> SEQ ID NO 69
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 69
gtgatgatgc ggtagt                                                    16

<210> SEQ ID NO 70
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 70
ctgtgatgat gcggta                                                    16

<210> SEQ ID NO 71
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 71
gaagagttca acaggc                                                    16

<210> SEQ ID NO 72
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 72
gcttggctga atcttc                                                    16

<210> SEQ ID NO 73
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 73
ccttgagctt ggctga                                                    16

<210> SEQ ID NO 74
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 74
atccttgagc ttggct                                                    16

<210> SEQ ID NO 75
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 75
tccatccttg agcttg                                                    16

<210> SEQ ID NO 76

```
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 76
gtaggtcttg gacggc                                                    16

<210> SEQ ID NO 77
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 77
gattctggaa agctcc                                                    16

<210> SEQ ID NO 78
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 78
gctctggaac agattc                                                    16

<210> SEQ ID NO 79
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 79
cgcgcacgct ctggaa                                                    16

<210> SEQ ID NO 80
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 80
tcacttcgcg cacgct                                                    16

<210> SEQ ID NO 81
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 81
tggatcactt cgcgca                                                    16

<210> SEQ ID NO 82
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 82
```
gttctggatc acttcg 16

<210> SEQ ID NO 83
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 83
cgctcgcggc ctctgg 16

<210> SEQ ID NO 84
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 84
tgcgctcgcg gcctct 16

<210> SEQ ID NO 85
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 85
gctgcgctcg cggcct 16

<210> SEQ ID NO 86
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 86
aggtgctgcg ctcgcg 16

<210> SEQ ID NO 87
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 87
gctgttcctc atccag 16

<210> SEQ ID NO 88
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 88
tgctgcggca gcccct 16

<210> SEQ ID NO 89
<211> LENGTH: 16
<212> TYPE: DNA

```
<213> ORGANISM: Artificial Sequence
<220> FEATURE:
<223> OTHER INFORMATION: Synthetic Oligonucleotide

<400> SEQUENCE: 89
ggtgctggcc tcgctc                                                      16

<210> SEQ ID NO 90
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 90
tgcatggtgc tggcct                                                      16

<210> SEQ ID NO 91
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 91
gttgcatggt gctggc                                                      16

<210> SEQ ID NO 92
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 92
tgctgttgct gaagga                                                      16

<210> SEQ ID NO 93
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 93
ggatactgct tcctgc                                                      16

<210> SEQ ID NO 94
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 94
tcggatactg cttcct                                                      16

<210> SEQ ID NO 95
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 95
tgccttcgga tactgc                                                      16
```

<210> SEQ ID NO 96
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 96
ctcgctctcc cgctgc                                                     16

<210> SEQ ID NO 97
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 97
tgtccttgga ggaagt                                                     16

<210> SEQ ID NO 98
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 98
tggtcgaagt gccccc                                                     16

<210> SEQ ID NO 99
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 99
cagaaatggt cgaagt                                                     16

<210> SEQ ID NO 100
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 100
tgttcccctg gactca                                                     16

<210> SEQ ID NO 101
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 101
agctgttccc ctggac                                                     16

<210> SEQ ID NO 102
<211> LENGTH: 16
<212> TYPE: DNA
<213> ORGANISM: Artificial Sequence
<220> FEATURE:

<223> OTHER INFORMATION: Synthetic Oligonucleotide

<400> SEQUENCE: 102
gaagctgttc ccctgg                                                        16

<210> SEQ ID NO 103
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 103
ccgaagctgt tcccct                                                        16

<210> SEQ ID NO 104
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 104
gtacatgcaa tccccc                                                        16

<210> SEQ ID NO 105
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 105
acagcgggtg gaactc                                                        16

<210> SEQ ID NO 106
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 106
ggacgcacag cgggtg                                                        16

<210> SEQ ID NO 107
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 107
gtgggacgca cagcgg                                                        16

<210> SEQ ID NO 108
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 108
tgcattcggc caatgg                                                        16

```
<210> SEQ ID NO 109
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 109
cctttgcatt cggcca                                                    16

<210> SEQ ID NO 110
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 110
aacctttgca ttcggc                                                    16

<210> SEQ ID NO 111
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 111
gctcttgcct gcgctg                                                    16

<210> SEQ ID NO 112
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 112
cagtgctctt gcctgc                                                    16

<210> SEQ ID NO 113
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 113
ttcagtgctc ttgcct                                                    16

<210> SEQ ID NO 114
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 114
tcttcagtgc tcttgc                                                    16

<210> SEQ ID NO 115
<211> LENGTH: 16
<212> TYPE: DNA
<213> ORGANISM: Artificial Sequence
<220> FEATURE:
<223> OTHER INFORMATION: Synthetic Oligonucleotide
```

```
<400> SEQUENCE: 115
actcagcagt atcttc                                                16

<210> SEQ ID NO 116
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 116
atactcagca gtatct                                                16

<210> SEQ ID NO 117
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 117
tttggtgtaa cctccc                                                16

<210> SEQ ID NO 118
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 118
cctttggtgt aacctc                                                16

<210> SEQ ID NO 119
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 119
ctaggctctc gccttc                                                16

<210> SEQ ID NO 120
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 120
cagcctaggc tctcgc                                                16

<210> SEQ ID NO 121
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 121
agcagcctag gctctc                                                16

<210> SEQ ID NO 122
<211> LENGTH: 16
```

```
<212> TYPE: DNA
<213> ORGANISM: Artificial Sequence
<220> FEATURE:
<223> OTHER INFORMATION: Synthetic Oligonucleotide

<400> SEQUENCE: 122
ctgccagagc agccta                                                         16

<210> SEQ ID NO 123
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 123
tcgcgactct ggtacg                                                         16

<210> SEQ ID NO 124
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 124
agtcgcgact ctggta                                                         16

<210> SEQ ID NO 125
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 125
gtagtcgcga ctctgg                                                         16

<210> SEQ ID NO 126
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 126
tagtagtcgc gactct                                                         16

<210> SEQ ID NO 127
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 127
tctccagctt gatgcg                                                         16

<210> SEQ ID NO 128
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 128
```

```
cagcgggttc tccagc                                                     16
```

<210> SEQ ID NO 129
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 129

```
ccttcttcgg ctgtga                                                     16
```

<210> SEQ ID NO 130
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 130

```
ggtccataca actggc                                                     16
```

<210> SEQ ID NO 131
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 131

```
acacatcagg tgcggt                                                     16
```

<210> SEQ ID NO 132
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 132

```
cgccagggta ccacac                                                     16
```

<210> SEQ ID NO 133
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 133

```
catgccgcca gggtac                                                     16
```

<210> SEQ ID NO 134
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 134

```
accatgccgc cagggt                                                     16
```

<210> SEQ ID NO 135
<211> LENGTH: 16
<212> TYPE: DNA
<213> ORGANISM: Artificial Sequence

```
<220> FEATURE:
<223> OTHER INFORMATION: Synthetic Oligonucleotide

<400> SEQUENCE: 135
ctgctcacca tgccgc                                                   16

<210> SEQ ID NO 136
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 136
acacaagtgg gactgg                                                   16

<210> SEQ ID NO 137
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 137
cccttcagcg gctctt                                                   16

<210> SEQ ID NO 138
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 138
cagagtcatc cctgct                                                   16

<210> SEQ ID NO 139
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 139
caccctcaag attctt                                                   16

<210> SEQ ID NO 140
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 140
aaggtagtct ttaagg                                                   16

<210> SEQ ID NO 141
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 141
gttttcaaat gcagcc                                                   16
```

<210> SEQ ID NO 142
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 142
gccatgagac agcttt            16

<210> SEQ ID NO 143
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 143
attcttgact gtctga            16

<210> SEQ ID NO 144
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 144
gcatgccagc tggctc            16

<210> SEQ ID NO 145
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 145
cgcgcaggta ggagcc            16

<210> SEQ ID NO 146
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 146
tctaaacatg acggtt            16

<210> SEQ ID NO 147
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 147
atgcaattgc ctgcca            16

<210> SEQ ID NO 148
<211> LENGTH: 16
<212> TYPE: DNA
<213> ORGANISM: Artificial Sequence
<220> FEATURE:
<223> OTHER INFORMATION: Synthetic Oligonucleotide

```
<400> SEQUENCE: 148
atgggagtaa cttttg                                                       16

<210> SEQ ID NO 149
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 149
catattattg tgctgc                                                       16

<210> SEQ ID NO 150
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 150
gtcaatatca aagcac                                                       16

<210> SEQ ID NO 151
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 151
gagttgtgat ttcagg                                                       16

<210> SEQ ID NO 152
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 152
ttgatggaat gctgat                                                       16

<210> SEQ ID NO 153
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 153
ggttaacttt ctctga                                                       16

<210> SEQ ID NO 154
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 154
tggattgtaa attacg                                                       16

<210> SEQ ID NO 155
```

```
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 155
gaacattatt aggcta                                                        16

<210> SEQ ID NO 156
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 156
tcaatctaga taccat                                                        16

<210> SEQ ID NO 157
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 157
cacatcagaa ggagta                                                        16

<210> SEQ ID NO 158
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 158
gagtgttaat gaagac                                                        16

<210> SEQ ID NO 159
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 159
ctgattagct atgacc                                                        16

<210> SEQ ID NO 160
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 160
atgagtcctc agaatc                                                        16

<210> SEQ ID NO 161
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 161
```
gtagattcta gctttg                                                    16

<210> SEQ ID NO 162
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 162
acaggctctg actagg                                                    16

<210> SEQ ID NO 163
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 163
tgtgtgaccc ttggac                                                    16

<210> SEQ ID NO 164
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 164
aagtatgagc atggtt                                                    16

<210> SEQ ID NO 165
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 165
ggattctcta cacaca                                                    16

<210> SEQ ID NO 166
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 166
ccatttgtgc caaacc                                                    16

<210> SEQ ID NO 167
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 167
aggttaggga gtaggc                                                    16

<210> SEQ ID NO 168
<211> LENGTH: 16
<212> TYPE: DNA

```
<213> ORGANISM: Artificial Sequence
<220> FEATURE:
<223> OTHER INFORMATION: Synthetic Oligonucleotide

<400> SEQUENCE: 168
tagggtttgg tcagaa                                                      16

<210> SEQ ID NO 169
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 169
ccttatggat gctgct                                                      16

<210> SEQ ID NO 170
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 170
gttatcttac tctccc                                                      16

<210> SEQ ID NO 171
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 171
gattgtgtat agctgc                                                      16

<210> SEQ ID NO 172
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 172
ggttatggtt ctgtct                                                      16

<210> SEQ ID NO 173
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 173
cttcattgca ggtctg                                                      16

<210> SEQ ID NO 174
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 174
tagccaactt tcttta                                                      16
```

<210> SEQ ID NO 175
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 175
cattgtacta tgccag                                              16

<210> SEQ ID NO 176
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 176
tttggtaaca ttaggc                                              16

<210> SEQ ID NO 177
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 177
atggttgtcc tgtaca                                              16

<210> SEQ ID NO 178
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 178
accaagtttc ttcagc                                              16

<210> SEQ ID NO 179
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 179
tcttatgttt ccgaaccgtt                                          20

<210> SEQ ID NO 180
<211> LENGTH: 21
<212> TYPE: DNA
<213> ORGANISM: Artificial Sequence
<220> FEATURE:
<223> OTHER INFORMATION: Primer

<400> SEQUENCE: 180
gccactggat ggatagctac t                                        21

<210> SEQ ID NO 181
<211> LENGTH: 21
<212> TYPE: DNA
<213> ORGANISM: Artificial Sequence
<220> FEATURE:

<223> OTHER INFORMATION: Primer

<400> SEQUENCE: 181
ccacagatca ggcaggtctt c                                            21

<210> SEQ ID NO 182
<211> LENGTH: 24
<212> TYPE: DNA
<213> ORGANISM: Artificial Sequence
<220> FEATURE:
<223> OTHER INFORMATION: Probe

<400> SEQUENCE: 182
actgccaggg accatgtttt gccc                                         24

<210> SEQ ID NO 183
<211> LENGTH: 18
<212> TYPE: DNA
<213> ORGANISM: Artificial Sequence
<220> FEATURE:
<223> OTHER INFORMATION: Primer

<400> SEQUENCE: 183
cttgcgcccc aggagtct                                                18

<210> SEQ ID NO 184
<211> LENGTH: 27
<212> TYPE: DNA
<213> ORGANISM: Artificial Sequence
<220> FEATURE:
<223> OTHER INFORMATION: Primer

<400> SEQUENCE: 184
ctcagagtaa gctctagcac acatgtc                                      27

<210> SEQ ID NO 185
<211> LENGTH: 28
<212> TYPE: DNA
<213> ORGANISM: Artificial Sequence
<220> FEATURE:
<223> OTHER INFORMATION: Probe

<400> SEQUENCE: 185
agtgtgtgag cctccatctc ctgtccaa                                     28

<210> SEQ ID NO 186
<211> LENGTH: 19
<212> TYPE: DNA
<213> ORGANISM: Artificial Sequence
<220> FEATURE:
<223> OTHER INFORMATION: Primer

<400> SEQUENCE: 186
gccaaggagg gagggtctt                                               19

<210> SEQ ID NO 187
<211> LENGTH: 21
<212> TYPE: DNA
<213> ORGANISM: Artificial Sequence
<220> FEATURE:
<223> OTHER INFORMATION: Primer

<400> SEQUENCE: 187 cccccccatag tgaatcagct t                                           21

-continued

```
<210> SEQ ID NO 188
<211> LENGTH: 28
<212> TYPE: DNA
<213> ORGANISM: Artificial Sequence
<220> FEATURE:
<223> OTHER INFORMATION: Probe

<400> SEQUENCE: 188
atgaagtaag gagagggact ggacccccc                                          28

<210> SEQ ID NO 189
<211> LENGTH: 174000
<212> TYPE: DNA
<213> ORGANISM: Macaca mulatta
<220> FEATURE:
<221> NAME/KEY: misc_feature
<222> LOCATION: (1)...(174000)
<223> OTHER INFORMATION: n = A,T,C or G

<400> SEQUENCE: 189
aagttgtggt gggattaaat gttgcaatga gtattcaaat aaggttgaag tatctatgca        60
ttctacttac atatggttga ggtatattca aggaagcctg tagccattaa aatctcaggg       120 aacaatttttt cacctcctca ggtgaaaggg tcttcaggcc tttgtgttct ggaaggttca      180
tttatagcca tttcccaaat aacattgaga cggatgagtc tagagtctag ctcaaatggc      240
aatgggctgg aagactagtt tagttttttac taatgtggaa catagaacaa aattatgtcc    300
ttgtttcagc ctgctcatct gtgaagtaga gcctatcata tccagtctcc cttgccttta     360
ggtttgagtt accttctttg gtcaaggtaa gtaaatgcct atgatgtttt gctgtgcaca     420
agataaagct acaacaaagc tacaacctgt cttttctctg tagaagacgg caaaaagcaa     480
aagagaccca ggcaaaaatc tcggaatgac ttttgaaaca gacagcctcc ctagaatcag     540
aagtcaaagg aatttaaaac atagggaggc ccagggtctc tactgacata aagaaagct     600 gttttcgtta taggtttact tttacatttt ctctctcttt ccattcccac ctgcctctcc    660
acctttacac agggcttatg ggacctcctc cacaaaagag cagttgcaat aacccacatc    720
atcctccacg cctggctgtc catcaagagg cgaaaagcag ccctatatag gttctatcct    780
tggatagttc cggttggaaa gtttaaaata tgcaaagca acttggaaaa gcaagcggct     840
gcatacaaca caaacctttg caaagctctg cacaaaattg agggcctatg cgtacatggc    900
aagtgttttt agtgtttgcg tgtttacctg cttgtctggg tggttttgcc tttgcaagtc    960
tggatgagaa atgcatggtt aaaggcaatt ccagacagga agaaaggcag agaagagggt   1020
agaaatgacc tctgattctt ggggctgagg gttcctagag caaatggcac aatgccagga   1080
ggcccgatct atccctatga cggaatctaa ggtttcagct agtatctgct ggcttggtca   1140
tggcttgctc ctcagtttgt aggagactct cccgtctgca cgctcttatc agtcctgaaa   1200 agaaccctg gcagccatta ggagcaggta ctcctatcgt ccttttcctc cctcctcctc    1260 tacacccgt tggtttttta gattgggctt tggaaccaaa tttggtgagt gctggcctcc    1320
aggaaatctg gatctctggc gcttaaagct tggtttagca aagcaggagc tattcaggaa    1380 gcagggtcc tccagggcta cagctagcct ctcctgccct cgcccacgct gcgccagcac    1440
ttgtttctcc aaagccacta ggcaggcgtt agcgcgcgat gaggggaggg gagaaaaga    1500 aaggggaggg gagggaaaag gaggtgggaa ggcaaggagg ccggcccggc ggggggcggga  1560 cccgactcgc aaactgttgc atttgctctc cacctcccag cgccccctcc gagatcccgg   1620
ggagccagct tgctgggaga gcgggacggt ccggagcaag cccagaggca gaggaggcga   1680
```

```
cagagggaaa aacggccgag ctagccgctc cagtgctgta caggagccga agggacgcac    1740
cacgacagcc ccagcccggc tccagcgaca gccaacgcct tttgcagcgc ggcgacttcg    1800
aagccgccgc cccggagctg ccctttcctc ttcggtgaag ttttaaaaag ctgctaaaga    1860
ctcggaggaa gcaaggaaag tgcctggtag gactgacggc tgcctttgtc ctcctcctct    1920 ccacccccgcc tccccccacc ctgctccccc ccccgccccg cgtcttctct cccgcagctg    1980
cctcagtcgg ctactctccg ccaacccccc ttactgcccc tctccccacc ctccctcccc    2040
cgtcggccca gcgctgccag cccgagtttg cagagaggta actcccttg gctgcgagcg    2100 ggcgagctag ctgcacattg caaagaaggc tcttaggagc caggcgactg gggagcggct    2160
tcagcactgc agccacgacc tgcctggtta ggctgcacgc ggagagaacc ctccgtttcc    2220
ccccactctc tctctacttc ctcctgcttt ccccacccg agtgcggagc cagagatcaa    2280
aagatgaaaa gacagtcagg gcttcagtag ccaaaaaata aacaaacaa aacaaaaca    2340 aaacaaaaaa acgaaataaa agaaaaagat aataactcag ttcttatttg cacctacttc    2400
agtggacact gaatttggaa ggtggaggat tttgtttttt cttttaagat tcgggcatct    2460
tttgaatcta cccttcaagt gttaagagac agactgtgag cctagcaggg cagatcttgt    2520
ccaccgtgtg tcttcttctg caggagactt tgaggctgtc agagcgcttt ttgcgtggtt    2580
gctcccgcaa gtttccttct ctggagcttc ccgcaggtgg gcagctagct gcagcgacta    2640
ccgcatcatc acagcctgtt gaactcttct gagcaagaga aggggaggcg gggtaaggga    2700
agtaggtgga agattcagcc aagctcaagg atggaggtgc agttagggct ggggagggtc    2760 tacccctcggc cgccgtccaa gacctaccga ggagcttttcc agaatctgtt ccagagcgtg    2820
cgcgaagtga tccagaaccc gggccccagg cacccagagg ccgcgagcgc agcacctccc    2880
ggcgccagtt tgcagcagca gcagcagcag cagcaagaaa ctagccccg gcaacagcag    2940 cagcagcagc agggtgagga tggttctccc caagcccatc gtagaggccc cacaggctac    3000
ctggtcctgg atgaggaaca gcagccttca cagcctcagt cagcccccgga gtgccacccc    3060 gagagaggtt gcgtcccaga gcctggagcc gccgtggccg ccggcaaggg gctgccgcag    3120
cagctgccag cacctccgga cgaggatgac tcagctgccc catccacgtt gtctctgctg    3180
ggccccactt tccccggctt aagcagctgc tccgccgacc ttaaagacat cctgagcgag    3240
gccagcacca tgcaactcct tcagcaacag cagcaggaag cagtatccga aggcagcagc    3300
agcgggagag cgagggaggc ctcggggct cccacttcct ccaaggacaa ttacttaggg    3360
ggcacttcga ccatttctga cagcgccaag gagctgtgta aggcagtgtc ggtgtccatg    3420
ggcttgggtg tggaggcgtt ggagcatctg agtccagggg aacagcttcg gggggattgc    3480
atgtacgccc cagttttggg agttccaccc gctgtgcgtc ccactccgtg tgccccattg    3540
gccgaatgca aaggttctct gctagacgac agcgcaggca agagcactga agatactgct    3600
gagtattccc ctttcaaggg aggttacacc aaagggctag aaggcgagag cctaggctgc    3660
tctggcagcg ctgcagcagg gagctccggg acacttgaac tgccgtccac cctgtctctc    3720
tacaagtccg gagcactgga cgaggcagct gcgtaccaga gtcgcgacta ctacaacttt    3780
ccactggctc tggccgggcc gccgccccct ccaccgcctc ccatcccca cgctcgcatc    3840 aagctggaga acccgctgga ctatggcagc gcctgggcgg ctgcggcggc gcagtgccgc    3900 tatgggacc tggcgagcct gcatggcgcg ggtgcagcgg gacccggctc tgggtcaccc    3960
tcagcggccg cttcctcatc ctggcacact ctcttcacag ccgaagaagg ccagttgtat    4020
ggaccgtgtg gtggtggggg cggcggcggt ggcggcggcg gcggcggcgc aggcgaggcg    4080
```

```
ggagctgtag cccctacgg ctacactcgg ccacctcagg ggctggcggg ccaggaaggc    4140
gacttcaccg cacctgatgt gtggtaccct ggcggcatgg tgagcagagt gccctatccc    4200
agtcccactt gtgtcaaaag cgagatgggc ccctggatgg atagctactc cggaccttac    4260
ggggacatgc ggtaagtttc tccttccaga aatgtcgcct ttcggcccag ggcacagagt    4320
cgctctgcat tctggggtgt ctagtggctc ctacctgcgc gaacactcag actgcccctg    4380
ggagagctca gcagggtaaa cctagagctc tccccgtgga ctcccggcct gccagaggtt    4440
taacctgagc tctcctaatt tctgctgcgt gtcctgggtg ctgattcctg ccctcccaga    4500
ttcttcaact cccccaacgg ccccaaattc tcgctacctc ctggtacccg agtcccaaac    4560
ttaaatccta ttgtacgggc caccttcaga gacaaagctc ataagccctc cactcttcct    4620
tttctcctgt cctcgaagtc tgagaacctc aatcagaaat ttgggcaatt tcttctcttc    4680
gggtctgtta ggacttccct ttcagcctgt gcagattaga gtcaaaaaga ctggcccaag    4740
agcttctcag cggatctcct ccaaagaggt aaaatgaaat tctcggttag ggaaagaaag    4800
tggtctctgg gtgctgaggt ctgctatgtg aaggagtgaa cttcttccc ggaagcaact    4860 ggggacttgc tccagggctg gaggtcagta gagataatct gaaccgtcat gtttagagta    4920
ggcagagggg caacttctt ggtaaagact ccacaggatt tgcattcaca gtttctcaac    4980
gttggttgac tatgttgaaa gtagttgctt gggtcggttt tctcttataa agtgtttatt    5040
ttctctgtgg attttaacag atccacaacc ccctacttca ggtttgcatc agatctataa    5100
agaggagaat attcttttaa tgtacaattt aattaggctt cagtctgact tacaaaagtg    5160
ttggaaaaca tatttttgtg aaacatttcc tgctatttca gtgtgcccca aaatctccac    5220
tggggaggga ggagtgaggt ttttcttatt atattccttc attttttagga catgttggca    5280 ttttagaata catgctgtta gctctaacaa attgagtaag aactcttagt gacctatgag    5340
ccataatctt accccagagt tttaattagc atatgagaaa agtggcaggc aattgcatcg    5400
tgcttattaa aaattattcc tcaccgcaat tgttgagctt cttggagacc atgctgaaga    5460
ttttctcccc cagcaaatta agatattagt ttatctagtg agggaggaca tactgaattg    5520
gggaattcac tcctcaggta gaccaggtgc tgatgtccct gtggacttat gtcttattct    5580
ttgtttctat ggctgttttc ttttatctgt gacttctccg aaatttcttt gttagcctta    5640
acatcttcgt ttggggactt aaatccagca atttgccttc tttcactgat gctttccttg    5700
ttacaaggta gagatagcac gctattagtg aagaaagaaa gaggagggta ggatttcata    5760
ttattttgtg ggctgttgaa gaaacagctt cttaccaggc tttacattcc attaggtttt    5820
taatgtttgg cttacaagat tttgaaaggg ttcatttgat atcgtcaaag tatttttccag   5880 ttaatttaga ctctttattt ttgtaatggg tttatcctat gggacaaaaa aagtattctt    5940
cattttataa gaataaattt tcttggcagg gttaattttt tttctaagcc tgtcactaga    6000
cggtggagcc cttcttctac tgtaaacttt cttgtgggaa aaatgtctaa ggtgcatttt    6060
gacctgccat gatactaaac ccagactctg gaaccttcca tcttctgcat gcctccccca    6120
caacttactt acttagcagg gaaaaaactg atggttccac atatttctta aaaaatgtgt    6180
gccttcaaag gcaaaaccaa aattttagg gaataactat agagagcaaa agttactccc    6240
atcaggtaga caatgagctt ggtgattta tttcaggtct taatgaaaaa agcttcttta    6300
tgaggaagat tatcatatct tggtgcctcc ttgacagtct gcttaaatta atgacataaa    6360
ctaatgagaa tttagcagtt cctgcagaaa gtacaagatt ttttttttctg gttttttgatt  6420
```

```
gctgcactga ttatgaggag tctagttaaa aggaaaactg gtgttcctgt ctcgtaagtt    6480
gacgaagact ttccatttct aggatagaga aaatccttaa gtcagtttat tgaaaattaa    6540
tcaatttaat cagaatgcaa tcaattccaa tccaaaagtt gatattttct tactttctct    6600 tttttcccc tcactttgta ggggtgcaat ttggtgaaag gcaagagatt tcttaagcca    6660
aatcaagagt gtcttccctt tctgtattgc atgcattatg tgccattttt tagctaaaaa    6720
tctcaaaatt gtgcaggctt ccagtgacct gttgggttcc tctcttttcc attcatgtgt    6780
gtgtttatgc acattagtta attttgtgaa gggattttt taaaccttag taacatctgc    6840
actcactctg tgttcttaca catttacaat gtttctgctg agaggatggg agatgcaaag    6900
gtggtctctt ttacttaatt tagcatgtga tttaaacaga aggaaaaata aaaagtgatg    6960
ggacttgtgt gcaaccctga tgatattttg tggagttgtc tgtcttctct ctgagatcaa    7020
acaggactac aactttgtta attgaccact ggctcccttg gcagaggtag ggcttcttag    7080
attccagcag gcagcacaat aatatgacaa aaatttattc ttgggagttg ggttctaaga    7140
gagtctgcat gccagaatta gagtttgggg tttagagaaa ttatccagat gcaaaaagaa    7200
cattttaatt tttctcttgg taatttgttc tggtctccat agtaggtagt actttagcag    7260
tgctttgata ttgacaagtc ttgttccctt tttctattag attttacaaa ataaggcatt    7320
ttattaattc ctctttcctt ctcctctctc ctctcagtta ccaagcattt ttatgactat    7380
cttacaaggg acagtttgtc ttgtaaagca gaattttcct ttgaaaccaa gacagactat    7440
ttctccccat aggcttcaag aaccaatatt ttggcaagaa gcatctttc cttgtggtca    7500 gcaaataggt agtgagttct gtctggattc caacaatcaa cacctgagga ccaaatagcc    7560
acactgggtg gcaccccatc tggaagtata cacaggatgt agccctcttt cttgtccaca    7620
gctcaagtca gccaaagatt aacactggtg agagatattt tcgaagaagt ttgcaggctt    7680
ccaattgcag ggtcgttttg gggtgctttc ttgcctgtgc taattttatc tcatcaggct    7740
tccattcttt gagctgtaaa ctttgaaata atatattaga ttcgctggta cgtttaatttt    7800 tctttgtcaa gtgtttttca ttccaatagt aattttttcat ctggtgtaca tatatgcatt    7860
taaaacaaaa aattctttgg tctcctttcg cgtacatgca ctgtggcttg tacgtgtgca    7920
agccacttgg tgggattatg tgaattgggg ttagaaatgt ggacaatttt attatgatta    7980
tttttaatgg tgatatcaag atcaccagtt tcattcagaa ccttgcataa gcagggagca    8040
gaatgtggac tgggtgtggc aaagcaaggg cttattttat agccaaacct gaaatcacaa    8100
ctctgaaata taaaaaaaaa agcaaacaaa aaaatcaagt tttgtgagct tggtcagaga    8160
aggaaaagaa aatctctccc caccccccac ctccaccatt ttctctttgt ctgcagcttc    8220
ctcaagtgct gcctgtcccc gattttcttt tattccactc ctttcatgtt tttgacattg    8280
aaatacagac tcttctttcc acttctcagg gcatttttct cattcaccct gtggcatgct    8340
cctaaataat ttcttaaaaa aaaaaaatct gtaaagtagc cgattagatc aaccccagca    8400 tctctcccctt aagacctaga tgacatgagg ggattgcaaa atgaatagct gggtttttt    8460 taccttgagg ttaaagcctg gttcaacagt tgctgaggga gttaactaga tggcttgagg    8520
acttggcaat ttcataaagt attttgtctt atgctgtcgc tgtctctgtc tctgtcttga    8580
tctctgtctc tctctgtgta ctgtaatgtt ggccaccttc tctcagaacc tgagagagag    8640
ctctgagacc cttcccaggt cggttcggtt cagacctcgg tagcctggtc acaagcagta    8700
cctaatatgc atatgtgggt gcatgctgta agtgtcctgc tgggctaatc tgcttaagct    8760
acataaaaat taatcatatg aaaacaaaga aagatattaa agaaattatt ctacctccga    8820
```

```
cttctcatat cagcattcca tcaagttctg ggatgttaaa ttcagagaaa gttaacctca   8880
tcttaaacac aaagttgact tttaaacaaa attgcttata aagttccgta cagttaccag   8940
cattggttgc cctttgtcat acggaagaga attatgaaat ctcatattta catagcattc   9000
ttaaaaaaaa aaaaaagaca cagtgttttc cagtttattc actgcattca tgttagtttg   9060
agtaggccag gaggggtgct tagtgattac ccttttgcta ggtaaagaag tagaaagata   9120
gattttctat gatgtttgtt taccatgtag gggaatctct ttagagcaac actcccaggc   9180
ttttcttct tgaaatttcc cacctgacaa atactttaga ttgttactcc taaggacttc   9240
tctcagtagc tgctacatag agacgatagt ctatgaatta ttgcttgcac actcatgggt   9300
gatgccacac gctctctctc ctggcagttc ttgctgccaa cctgcaggcc acaccaggac   9360
tgaaggcagc tcatctagat aagtttatag cattaaagtg ctgggtcact tgagaatgtt   9420
gtcaatttag gttacttagt acctaagtgt tattttttaa ataatagctt tattgagacg   9480
taatttacaa tccatacaat tcactcttct aaagtgtaca gttccatgct tttcagtata   9540
ttcagagttg tgcaaccatt attgcaatca attttagaac attttaatca cccccaaagg   9600
aaacgctatg caccttttg ttcaatgcct tatgttccct cagtccttag caaccaataa   9660
tctacttcta tctatggatg tgcttattct aatattttgt atgaatgaaa tcatgtaata   9720
tgtggtcttt tgtgactagc ttcttcaca cagaatatgt tttcaaggtc atccatgctg   9780
aagcacgtat cagtacttcg ctatttttta tagcctaata atgttccact gtatgactat   9840
acaacatttt atctatccgt ttatcaggag atgagcatta gggttgtttc cacctttga   9900
ctattatgaa taatactgct gtgaacattc atgtacaagt ttattgtgga catattcagt   9960
ccacatattg tggacatttt caattctttt ggatacatac ataggattga aatctctgag  10020
tcatatggta cctctatgtt tatcctttga agaactgtca aactgttttc gaaagtgtct  10080
gcactgtttt acaatcccat cagcaacgta tgaggggtcc atttcttcca catccttgca  10140
aacacttgta attctctttt ttattacagc tatattagtg ggtgtgaagt ggtacctcat  10200
tgtggttttt atttctattt ccctaataac gaataatgtt cagtatctat tcatgttctt  10260
attggccatt tgtatatctt ctttttttgag aaatatctat ttggattctt tgcccatttt  10320
ttagttgggt tttttattat tgagttttaa gagttttaaa aaatatattc tggatgcatg  10380
tcctttaata gattgtgatt tgtggatatt ttttcacatt ctgtgggttg tctttttttac  10440
tttcctttt tttcttttg tgttcttaat ggtatctaga ttgaagcaca aaaaagttt  10500
ttaagtttga tgaagtccaa ttcatctgtt ttttttttc tgttttggcg tatgattttg  10560
gcatcatatc taagaaggct ttgcctaatc caagattaca aagatttaca catatgtttc  10620
cttctaagag ttttatagtt ttcgctgttt acacttaggg cttttcatcag ttttgatgta  10680
atgtttatat atgattgagg taggggtccg acttcattct tttacacata gatactcatt  10740
tcttacaata ttcttgttga attttttcctc acttaactgt cttggcaccc tttgtgtaaa  10800
atcagttgac tgtaaatgtg agggtttatt tgtggactct caactgtatt cagttgatct  10860
atatgtttat tcctatgcca gtaccacatt atcttgatta ttgtaggttt ttagtgagtt  10920
ttgaaattag gaattttgtg ctctttgact ttggtcttgt ttttcaaggt tgttttggct  10980
cttgtgggtc ccttgagttt tcatatgaat tgggataagt ttgtcaattt ctacaaagaa  11040
gtcagctggg attctcacag gaactatatt acatctgtaa atcaatttgg ggagcattgc  11100
catctcaaca acgttaagtt ttttcatcca taaatatgag atgtcttccc atttatttag  11160
```

```
atcttccttt tgtcaacaat ttttattgt tttcagatga taagttttgc agttcttttt    11220
aaaatttagt cttaagtgat ttattttttg atactattat aaattgaact gttttgttga    11280
ttttcttttc agattattca ctgccaatgt atgaaaacat aattgttttg tgtattgatc    11340
ttgcatcctg caaccttgct gaaaatacct gagttttgaa tacttctggg acttatgggg    11400
aagagggctt ctgctgtttc actgaacgtt aaagcttatt tcatttcatc ctgtatgaag    11460
gctgcataca agccttctgt atgaagggga cactgttgtc attttactc agctataaat     11520
ttgaactggt aatcccatcc cctttcagga tgaataggag agtgttttta aatgttcatc    11580
tctttagaga acagcgggaa agaagcctaa taaggtttgg gtcgtttata atccctttt     11640
cagaatttgg atttgggaac tattagcaag ggagtgagta ataataataa tttctacata    11700
gaaaactaac atgtagaggt gacaaatgaa atcactagct atatttggct tatgtttagg    11760
tttttataag cagctaaaat cataattttg tgtttttatc tcttgtcctt tggacagagt    11820
aaattccaat actccttctg atgtgcattt ctagatgggg aaggattcc tttactctca     11880
tataatttaa gcttcttttt agagatgtac tccatagcca tgaagcaaag ataaaattca    11940
tctatgtaga gattgaactt tgtcttcatt aacactctag ctaaaggtc atagctaatc     12000
agctacaact gtcatgtcct gataattgtg agttaactgc aggccaccca gcaaaaggtt    12060
tagttataat ctgatagctg tctgtagaga ttaccctaat aaagggaatt ttttaaaaaa    12120
gaatctggca ggggatagta gctcactcct gtaatcccag cactttggga ggccgaggtg    12180
ggcggatcat ctgaggtcag gagttcaaga ccagcctggc caacatggtg aaaccccatg    12240
tctactaaaa atacaaaaat tatccaggcg ttttggtggg cacccataat cccagctact    12300
tgggaggctg aggcaggagg atcacttgag cctaggaggc agatgttgca gcgagccgag    12360
atcatgccac tgcactccag gatccgtcaa aaaaaaaaa aaaaaaaaaa aaaaaaaaa     12420
aaaagactct atcaatcaac cacttttcat taagcacctg ctatgtgtcc agcatgtact    12480
aggaagagat aagataaaag gggacacaat tcagacagaa tcttcttgag gtaattgctt    12540
acaaggagct tatagccact gaaaacaaaa acaaacaaaa acaaataacc aaaacccaaa    12600
cagaaatgca gcaccatcat gccataatgc ctgtatgaga tcctggattg tacggtgtgg    12660
atcttttaa atgtagatat ttaaaaaaaa aaaaaagag agagagagag agagaaatga     12720
atcaatagag gctgaagtgg tcaacaatgt tacctgtggc tgcttttaat cctttgtggc    12780
agtaagtagg agcatgtcta aactcaagca atagattaaa gatcctgatg tatatttaa     12840
ataacagaag ttggtacctc tggaaagaat taactgagg catgggttga aatctatttc     12900
tgcttattaa atagtgcacc ccagtcaagt tagttgccaa ttttttttca gtttctttgg    12960
ctatatcatc gcacttgttg ggtacatgtt tttgatgtat ttatctgaac aagtccgcaa    13020
taatatgagt aataaattag aatagaaggt gattaatagc tctgaatttg atataagatg    13080
cccagtgtgg tggtcagatc aagagttgtt tttcggccgg gcgcggtggc tcaagcctgt    13140
aatcccagca ctttgggagg ccgaggcggg tggatcacga ggtcaggaga tcgagaccat    13200
cctggctaac atggtgaaac cccgtctcta ctaaaaatac aaaaaactag ccgggcgtgg    13260
tggcgggcgc ctgtagtccc agctactcgg aggctgaggc gggagaatgg cgtgaacccg    13320
ggaggcggag cttgcagtga gccgagatcg cgccactgca ctccagcctg ggcgacacag    13380
cgagactccg tctcaaaaaa aaaaaaaaaa gagttgtttt tctgccttct aagtttccat    13440
tgatcctgat ggattgcaca aatagaacaa ttcggggagt atgggggcac atgacgatct    13500
tataagagct ttgctgtaat agacaacgta acattctgaa acggcctacc acctaacatg    13560
```

```
ggctctggtt ctctgcaggt tgagtgagtt ccttgcttgt ggaactgtag tcccgctatc   13620
tggccgctag ggggactgca agtgccccgt ggcaggattt ccctgggaat ggtgagcctc   13680
cattgacggt ttcaacacac agccaaggcc ctatcgcagg ataacttcaa ccagaactgc   13740
ttagcaccag acaataaata agctactatg gtacttactg tttcatttgg gatgttcttt   13800
ctcgaagtgt caagcatttt aaagtaatat tttgactttt taatacctct ctttgcatat   13860
ggagcaggac acagcaaata tattcaagta gcactgtcca gtttatagag aagtttcata   13920
ttccattatt gcatttcatt cttgtttcta ccctgtacaa gtaactagag tttggagtat   13980
tataatagta ttcatactat tacaatactt ttattcccat tataaaaatt atgctaagag   14040
tggttaagtt acatgtttac aatcaaacag catcaaagtg acagatctgg gatttcagtc   14100
tcattctttc ttctccagat catgtgttcc ctgcttttat ctcacagctc ttttttacctt   14160 atagatagga aacatgagag tcagagaggc aaaagaacca caagtggtgt caatactaga   14220
aatttatgaa gttcttaagg cttctaggtt tgttacccat ccaccagact gatggatttg   14280
gttgtgtgag agttctgggt gtcaataacc ttgccattct actttacaga ctgcatacat   14340
tcaataaatg cctattaagc atctactatg tgccaaattc tgtactaggc accaatgatg   14400
tagcagcgaa cagaacacac aaaaatatct gaatggagct gacagtttaa tgagaggaga   14460
catgtagtat acatctgagc atgaatagtg tcatgcagaa taacttcaga gtataggta    14520 tagagattca tggtgagagg gaatatttta tatctgctgg ccagggaaaa ccttactgga   14580 aagtaaatt ttgagcagtg acctgaagga aattaggaaa tgagctgcta tttggacatc    14640
tggagttaga atattccagg cccagggaac cacaggcaca aagggcctga ggcaggagag   14700
catgcttgct ttgatggagg acaaaaaggc tcatatggct ggtttaaata agtgaaggat   14760
ggtagacaat gagatcagag ttaatgaggt tgcatggtag gtcttcttta agactttgga   14820
ttttactcct aagcagggtg tattggaagg ttttgagcaa agtaacatga cctgacttac   14880
actttaacag gctccctcct cttcataaca tctgtcactc tgatatatta tacgtttgtt   14940
tgtttactta ctgtatgtgt ggagaagaga ctgtgggagc aaggagggaa gcagggagac   15000
aaggccactg cagtgatctg ggtgagaggt aaccatgtct cagactaagg tagtattggt   15060
ggagaagata ggaagtggct gaattctaga tgagttttga tggtagagcc aacagcattt   15120
actgacaggt tggatattca ctgtgaaaaa aatagaggag atgaggatga ttgccaaatt   15180
tttggtctga gtaactggaa aaatgagatt gccatttact aaaattgtga agactgtatg   15240
tagagcaggt gcatgggcag gatagaaatc aagagtttga tttttttactt ataaagtttg   15300 agttatctga tgagcatcct gatggcttct cagttttcat tcagtgccct cagctttgct   15360
gttcttcaag aagattaaaa aggacccttag agatcaccta ggctgtaggt accctctccc   15420
ttctttcctt ttactttata gaggtctata aagggtagg gacttatcca aggtaaaaca    15480
gtgagctggt gacagaacta gggcacaaac ccagttctct tcgattctga ttcagtagat   15540
ttttgtgtgt gtgtgtgtga ttctgaggac tcatttgggc aagagtgagt tttttgtttg   15600
tttgtttgtt tgcgcaaacc taaaaccagg tgattaaact aaatagtgac taaaactgga   15660
aaactataca aattggttgc tctccccaat caaactgaaa tattattatt aggttttac    15720 tgaactacat accaaaatat ttttttcctg taaaaacaca gtaagtgggc ttttaaaggc   15780
aattgagctt ttatcaaagc tagaatctac agggcacctg acaaaaatg gcctaaaatc    15840 ctaagaaatt agagttcatg gaacctggaa gaccatcttg tccagctagc tcattttatt   15900
```

```
ggtagagtgc ctgaggcacc gagatggaaa gggacttggc taagctcata cagcaagcta   15960
gtgcctgacc tagtcagagc ctgttctaag tattagttgt atgttgtttt cttgaaaaaa   16020
gtctatattg gaaaaatgaa aattctttgt tccatactga gaacaaagaa ttatatataa   16080
tcatatataa taataatgat agcacttact gaatgtttgc tgtgtaaact tccgcacctt   16140
gcatgaactg attcatttaa ttctcatgtc aactttagga agcaggccta gagacgttaa   16200
ataacttgtc caagggtcac acagctagga agtagcagaa cttgtgtgca ctcccaggaa   16260
gtctggcttc taaccacaag gttctaacta ctgtgcaata tcagcagctt ctcagattac   16320
tcttcacctt caccatccca aaagactggc gacataggtg acttcattat gcactgcccc   16380
tattatagtc cactgatcct caccaaatag ctgggtggcc tagaggttaa agtaggggca   16440
cagtgatgga aaggggtggt tagaagaggt tgataactta tgatagggat tggaaaacag   16500
aactctagga attattgaaa agggcctaga gatcccaagg aggttgatct cagactgcta   16560
caaaccaggg caattcgatg cctgcttaaa taggagagtt aagataagaa aaataaaatt   16620
gccagttttt acagtcaggc attgttttat ttcttttaca tgtattaatt cgtttaatcc   16680
tcaaaataat ccatgaggta gctacaatta tcatttctat gttatagatg aagaaacagg   16740
cacagagcaa ttaagtaacc tgcccaagat tagagaacaa gtaagtgaaa gtgccaatat   16800
tagaatctag gtgattcagc tccacaactt atgttatttt ccaatacatt tatggaacga   16860
ggtaattttc atataacaga aagtgtttaa agtgcaaaaa cattgtgcct gaacttcaaa   16920
cattgaacaa ctcatatcct taatatacac cagctgcttt taaggactct tagaagtaag   16980
gatacttacc taaagtcata tgttgaacaa gtagcagaac cggaacttga atttgagact   17040
ccagactgcc agacctcttt ccactctatc acttgggctc ccttctaacg ttgatttgtc   17100
tctctccatt cttcctccgt attgctctgc ccttcacctt ttaattacct gtctccatca   17160
acaagattgg acagagaatt gggggagtga gcagagtcca tttccttcca gagactggac   17220
aaaaggaaca aaatgttggg aaaaaagtca gcatgtggat tttgtgggat ttacactaaa   17280
taagaacgga cacttgccag gactgacaag atgctacctc aatccctcta ggccccaatg   17340
tgttatgcag gatcccataa gaagtcatga atgtagttgt cagataatct ttttgttact   17400
gtggaaatgg aagcaggata ctgcaaaaat ctgtctctcc aggttttctt ttaaagaagg   17460
tacagtcttg ctaaatgata actgtttgga catttatttg aaaatgggca gtgcaggaga   17520
gaaagaattt ttccaagctt gtcacattgg gccatctctc tgaagcattg tccaacctct   17580
aattagatga ggagactgca ttaaccaaga gttgagagta aagatggaaa cacttgatgt   17640
ttggtgtttg ggtgcagaaa ggattccaaa acatgttctg agtttcttta ctctgcccat   17700
ccctccttcc ctttcatctt tgtttaaaaa ccatggttag caaatgtgtg tagtctgttt   17760
gcaattgttc atctgaaaaa tttgtttgat cagcctttg aaaaaagat caaaatagac   17820
tgagatattt tagtcaccaa ctatctaata atagaccaaa aatttaaacc atgctcatac   17880
tttcatatgg tatgtggttt gttttagacg ctttctgggc ttcgctgagg tgctagattg   17940
actcaaagta tggcaggtca gatgtggaat tgagtagggt ggactcttct ctatgcctcc   18000
agattcagaa ttccccatca gagatgatct catagtgttt ggaaaaacca agctgaaggc   18060
tttgggaatt agggtggtga agggatatgt tgtttcccaa agccttctca gtcattcctt   18120
ctcccccaat tcagattctt aacacctctt gccgggatta gtgcagtgat cccacatcct   18180
ttctctctag ctctctctgc tactctctaa ttcctattgt atttgtgcca ccagatcttt   18240
ccaaagttta gctccaaccg tttctgtata ctgctttaaa tgtctattag tctttaagct   18300
```

```
ccataagggc aggagtcctg tcttattttt tccctattct tcatgcttaa tacaaaggaa   18360
gctttgtatg attaaaattt cagcttctcg ccattggctt atgggtaagt ccaaattatt   18420
taaatctggt gttcaagtcc ttttatgatc tgcttatttt tccagcctga attcctggag   18480
ttcccttaca aaactcttaa aacccagcca aatggatcta gtcaccgtca ctttaaacca   18540
tcctcactct cttgtttttt gaacatgtta cttttattat tatccctttg accttgaagg   18600
ctatcccaat ttcaatacta tccattcttc tataacagtc ccctacaaaa tgaatattat   18660 caaccccca  acccaaggag aagtgatcta tatgacacaa catggttgaa agaatgttgg   18720
tttcactact ttatctgtaa accagggggct agaaatctct agtttataag attttgtgga   18780
gaggggatca catgtgatta tggatgttag gctcgagtca agagtgcata agacttttttg   18840 gatttatccc tttcttcttt ctccatcaat atggtactta gtcccttaag tactcgtggt   18900
acttgtgtta atgactgata gcatccttct aaatatactt ctaaacatct gtctctttttt  18960 agggcaaagg ttggatatat ctgcaaagat tctctttgga tataagatat ccacagcaca   19020
taacttaaca gtgttgtaca tagtagatat tccataagta tttctttatt aaatgattca   19080 gagtcaaatag tagtaagtga ctgccgaaga caactgatag attgtaagtt ccattaacag   19140
aaatacagtt agccctccac atccataggt tccatatcca cagatttaag caacagcaga   19200
tggaaaatat atttttagaga cacagtaaaa ataacaattc aacagtaaaa aaaaaagtta   19260
tgtaaaacaa ctatttacat aacacattgt attggctatt acaagtaatc tagatataaa   19320
tgaaatatat gggggatgtg tataggttaa atacaaatgt gacaccatt  tatatgtttt   19380 aggtaaggaa catgaatatt tttggatttt ggtattcctg ggagtgggg  aatggaacca   19440 agccccttca ataccaagg  gactattata tgggatacag aataaaggaa ttgattgtct   19500
tgctctgtta aattctggtc agacacattt gcaatgtgtt gttcagcccc aatattcatg   19560
gagcatctcc ttttgtaaag catggaggag ctatgagaga gacatggagc agtgaacata   19620
actattgttt caatgaacct gaaggattat catggaataa agaagttaga tgttttctg   19680 tagcaccca  aagggcaaac gcaatgagga cagattacaa ttcagtaaaa gaaagagttt   19740 ttttttttt  gtttggtttg ttttgttttt gggttttttt gggttttttt tgtttgtttg   19800 tttgttttttg ttttttttt  tttagatgga gtcttcactc ttgttgccca ggctggagtg   19860
caatggcgca atcttggctt actgcaacct ctgcctccct ggttcaagtg attcctgc    19920 ctcaccctct ggagtagctg ggattacagg tgcacaccac caatcctggg caatttttttt  19980 ttttttttt  tttagtaga gatggggatt tcaccatgtt ggccaagctg gtctcaaact   20040
cctgactgca ggtgatccgc ctgcctcggc ctcccaaagt gttgggatta caggcgtgaa   20100
tcaacgagac cagcctgaaa gatattttct tagaagggct tctttcatcc ttcatcagaa   20160
gttgttaaca tggaccatat gagttttgtt tggtctatat ggggtgtgtg tgtgtgtttg   20220
tgtgtgtgtg tgtgtgtgtg tgtgtgtgtg tgtattgaat tacttgctaa cattttactt   20280
caaaattcag atttccaccg tagggaatga agatctgaca atacagaact ttcattctta   20340
catggtaatg accagctgca ggtgaaaagc agctgatcct ctggatgggc catgcacttt   20400
gcagtttgcc caggcaccag tgacccactt tattcattta agttacctgc ttgactcttc   20460
tagtcattcg agtatgtcat ccctgtcaga tcagagacct aagcaaatct tgagtccctt   20520
gcttactcca agggctttca ctcctcgtat aggaggggct aaagaaatgt acaagcagca   20580
ccacaatagg atcagacctg actttcaatt ctagcacagc catgtaacat agttggatga   20640
```

```
cctcaggtca gtaatataac ccctctgagc ctctagatct tcattatctg tagaacactc   20700
tccttacaga gttattgtaa gaatgaaata aaacaactag gataaagggc attacactta   20760
gtaggtgctg aaatattggt tcccttcttc ttattcatca caccatttct gtctgtctat   20820
tggctgaatt acataaatag taaattcaca ttcactgaag acatttaaga agagtctgga   20880
ccctttggga accatgtata ggacaaagat ttggactcat agattatttt tacagtcact   20940
ttctaacaat ttaaaagcct atggatgact ccaaaatgcc catttggatg atttgaggca   21000
tactttgtgt agttaaggat tttaaataca taacagagag actgaagggc ctttgggaaa   21060
caagctgggg taagagtcaa aatgtaatat gttgactgat gttcaggaat aggctttggc   21120
atctgataga ttttgttttc agtactgccc ctgggtctta ctagcttcca gttctgggcc   21180
acttcacctc tcttgagttt tagtttcttt atttctaaaa tgaagatact aatgcttcct   21240
ttgttgggtt tttgtgaaga taagtgagat aataaatgta aaacatgtag cccagggcct   21300
ggtgcatagt aaaagcttca taaattgtac ctattattat tagtagtagt agtagtccag   21360
acaaacagag cttgggaaaa tgctagactc tggctgacat acatggactt ttccccaggc   21420
cactgctgcc tggcttcccc ttccacaaag ctttgagtct ccaaaatgct ttggctggaa   21480
tgtaagcgtg aggtcattgc agataacagg ggagcatgat ttgcttcggt aatgcaagtt   21540
attaagttac ttccctcagc ccagctaaaa tctcttattg gttgatgttt gcttcaaagt   21600
gtgagactga gctagtttga ggagagaggg agagtaagaa gattcctctt cttggccaga   21660
ggtcatggtc ttccacaagg aacagaatga ctcaacgcaa attatgggac ctctttgagt   21720
ttggggcccc tacattttaaa ccagtcactc cattgcacaa attggtaccc ttcccccaac   21780
aaaattactg ggcaggaatt ttcttgactc cttccatggc ctggaatgat ctcccttctc   21840
atccttgtga tccacacagc tggcaaatgg caggcagcag aacaaaaaca agcctcttag   21900
catagagaga gagagaaaga gtcacagcag tactgaattt gcttgggaac ctaatgttaa   21960
caaaggatct tcctctcaac accccaaaca gattaaaaca tttttttta acagcaagtt   22020 gtgtctcaga gcagctcttt gcttgggtat atttaaagat ctgctgagtc atttaagagc   22080
aggctggcag atcgtaagag gcaaggacta tacccccagtc tatggggggag taagttgaga   22140 ggtgaaatct gttttggcttt ctcccatgtg aaacaaacaa ggtgatccac ttccatctcc   22200
cacaactctg gagagcatct actaaggctt cttattctat caactttgaa ctcctcagag   22260
tataatagag taagggtgag agggaaggag cagttgtacc agtgtgtctg ctgtctgaaa   22320
ttgtaatgcc cctgcattgg tagctgagag tagcatggaa gtgtcaggtt gatgggttca   22380
tttcattctt ttcttttcag tttctggtca catgcattgt taccatggca tatgacagtt   22440
gctagaaagt gaaataattt tttctacttt attcttaatt gcacttctaa atttattaaa   22500
ggagaaatta gcagttagca actgttaact ataggtacac attggggttt ccttagagcc   22560
aattttcccc ctagttttca acttgtaaat ctgatagatt ttgtcctaaa agttggcaaa   22620
acctggagct tctctttggt cctggccttt ttgaaccctg ttccacagag cccaatcttc   22680
tttcttgttt gagacaacta tccttctctt tgcccactgc catttttcctt catctacttt   22740 tcccatctct agcacctcag actgtcttcc cacagtggca cagactccca ctccactttc   22800
actgtgccat cttcttgcta tcaaaaccat cctcacagac ccttactttg ctgaaaccac   22860
ttctaggaag ggaaatcaca gtggatccat gaaggatgct ttctggatga ctttaaaaga   22920
ttggtattaa gatattttat tagtggtggc aacactgact tactcaggca gccatgccca   22980
ggatctataa gaaatcagat aagctaaaag ttgcttgagc tggcaggaga cctagttctc   23040
```

```
tgttttccttt tccctcatgc attttgttta tcaatggttt tcagagggct tagaggctgg    23100
ctttgttata gttagttggt aagagaaatg gtggaggact ggaaaatggg agtggaacca    23160
ttgagcatgt tattacaatt cctaggatgt ataaatcgct tgaaagtcta ccaagtactt    23220
tcagacacat tatcttttt actcttcaaa atcaacttgg aggtaggcac aacagggatc     23280
aaatccttag ttcacagatg agtaaaacga gactggagga aattaaagga cattccaagg    23340
taactcagac aataagcaac agaactagga tttgattagt tttttggggg gtggggagga    23400
cagagtctca ctcaggctgg agtgcagtgg caaggtctcg tctcactgca acctctgcct    23460
cctgagttca agtgattctc atgcctcagc ctcctgagta gctgggatta cagacatacg    23520
ccacaatgcc tggcaaattt ttgtctttt agtagagatg gggttttgtc atgttgccca     23580
ggctggtcct gaattcttgg tctcaagtga tccaccccca ttggccttcc aaagtgcgtg    23640
gaaccactgc tcccggcccc ggaccattaa ttttgatgg taggtccacg ttttttcaag     23700
ttcacagctc ggatttgcta tataatgaat gaatgagtat atatgtcatt tgggaacatt    23760
attccaactt tcggttgaag atttgtttta tcagttgtgg aactttttt catttttagc     23820 attatcagtt tagttaaatg aacatttcgt tcatgaattc actaattaat tattttattc    23880
atcaatacat ttcctgagta ccaaactttc tatcaaatgc tgtgctggat tctgaggcta    23940
caaaaagaaa tacgcacacca tctcatgact ctaaaatatc acagactggg gactgacatc   24000
tcagtagtaa acatatgaat agcaacttat gaaatgccat tagaaaaatc tcaagttata    24060
ttcctcagtg agtatggcca tcctaaaaat gagaagtctt ttatttgg tacatgaaaa      24120 tgaagcgttg tgagaaattg catttaatc taatcttgtc ttactaagaa cagaagtgaa     24180
atgtttcagc ctctgtgtgt gtatttgtgt gagtgaaggt tgagtgtgtg atgatggatg    24240
gggctgcgag attgctaagt aggatctatg gggggcctta gatggtcctg gtgagtccca    24300
actttctggt tatgtatttg ggtgcagtat gggagtgaca aagattgttg tttaagagtt    24360
gattttagat tttttccaag taaatagtca gcagacttgg agcatcatca ttccacttgc    24420
tttgaaaacc taccacttaa ggctccttct tgtcataggt taactctttc tggtcaagta    24480
ttactctttt tgagcatttg cctgtcagtg acaggtgcaa tgttagatgt tgtctctctg    24540
ttttcttgtt taatctttac tttgatccta ggtagctctt attagttcca ctttataggt    24600
aagaaactga atttcagaga ctttaatgac ttgttcaaga tcacatagta agtaacttgg    24660
tagtttggga cttgaatttt gattgttcaa ttttttttcg tttcctggcc tcactgctgt    24720
tttcactatt ccacaccact tcagctttat ttttcacaga ggccgttaaa tgtaccctcc    24780
atcagccaaa gcctcttgcc tcccttcaac gtaactcttc tctagcgtgt tcctaataat    24840
cttctgaaaa ggtttacag cctttctggg tactgggacc cagagtctta atccaggctc     24900
ttaagtgcct tagttaactg taatatggat aatcaaagtc acagctaatt caggaaaaat    24960
gagtttggga tgtgaatttc ctgggcaaca tgtcatctct tttttactcc cttagcttca    25020
taaacttacc cacaatgttc cctgaggact aacagtaatg gagggtgatg aggaaaggct    25080
ttcctccctt cctggtttcc aagagtcctt tagccaaatg ccacacctcc tcctgttcc     25140 ctagtctctg tgcagagatg gaggtgggag atagacatgg gttcttttca gccctgagtt    25200
catgccagag tttttttttt ccctctagct ggagtgaagt aggaagagag gttcaatgtc    25260
caccaagaag accatgagtg aagaagacta aagtacttga aagaacatca gacctatgcg    25320
taaaatacca gggtttgtgt ccagactttg tgggttacta tctgtataat tttgggcaag    25380
```

```
tcaacagttc tgagtcagag tttccttatc agcagattgg aagataaatt ctaattatat    25440
ggatgaaaca ttaagtctag aagtattttg taaattcaga aagggcttat agatttaaag    25500
tgtagctgtt ttatcacata ctaaatccta tacttcaggg ataaaacctt ctcctgtttt    25560
ttctaaaagc ctgtgcatgt gtggtgtaag ggatgggttt tgcccctgta ccagccactt    25620
agcaattgta gtaactgggg gctgagggca gtggcctgct tctgcactga gcaagtgtga    25680
aaagagggta atgcattcag gggtcagcag atgacaggca gagtagcccc tccaaatctc    25740
cctcccatac cgcaaagccc cttatttatt caaacttaac attggaaact catttcaagt    25800
aggtacgtct gtgtctgggc gtctattttc tttctttgta tatagcaggc atttgtcaac    25860
ttggtgaaaa gcattaccct tctttccatt tctgaggact aattgtgctt attcgctaga    25920
catgagttca aaacagtggg ttgaaagagg gcaagtttat gccaaagaat cagaagtagt    25980
cataatttag agagaattct agaggtcagt tcccttccgt gtggattggg caactgaaac    26040
ccagatagaa aagcggatta gaccaagttc acaagcacaa acacgttact ggcacattca    26100
gattggaagt tgagggcttc tgctcccagg tcagaactaa atgcccttc cagctagggc    26160 gttctttgat ctcagtgatt tggactcttt ctactacact ctggggacag tgggttctga    26220
gataccaact ccaattaaag taggaatatg taccagctcc tccccttggt ttttttctag    26280
aggcctggca ttcagaggca gtgtgatctc tatatgtaat attttcacac tattgttctt    26340
atttaaatca catttgaatt ttggcaatta acaaggcagt aattggcatc aggaaggtat    26400
gttagtttgc ttatctgccc catccccct cttcccgacc cactgtgcat tgcagaatgt    26460
tttatcagct ctgatttgcc aagttgctct cttctccagt aggtgctgca agcagagagg    26520
gattcctcgg aggtcatctg ctccatcttc ttgcctatgc aaatgcctgc ctgaagctgc    26580
tggaggctgg ctttgtacca gactttgtac agggaaccag ggaaatgaat gcagagtgct    26640
cctgacattg cctatcactt tttcccatga tactctggct tcacacgtgg gaggttcttc    26700
agctgaaaac ttagaactca tttttctaggg tagtgagtgt tgtaaggttt ggactgtgac    26760
ctaatattat gcagccatga cattatctat taggcatcta gaccagcttg cttgaatatc    26820
ttagcatgtt gactaatttg gggcagacta cagtgtgggt ggaggattgt gtgtgtgtgt    26880
gtgtgtgtgt gtgtgtgtgt gtgtatgggg ttgagcaatt cattattatt aatatgcaaa    26940
aagcacttat ttcgctatga caaggttgcc ttttcatgc atattggcct acctgcaaga    27000
cccctagaga cagtaagcaa catacatggt gtcttccagt tttcagcctt tgtgcaagga    27060
acaactgtgg gttttttgcat gtgtgttgtg gtttgatgtt tgtgtgtgat tgtgtaccag    27120
ggtatgtgtg tctgttactg tgagttcact tctgagcagt tgtgacacac agagatccag    27180
aaacagtgtc ttactctgtg tgctctgcta gtgggaacgt gtcttctctt ttgtgctcgt    27240
atctctgtgt aatcaagtgt cttgctaagt cagtgtgcct ctgtctcttt ttaccagttc    27300
ttccgtcttt gtgtctctat gccttcttgc gtttctttcc cctgagtttg cacatgtctc    27360
tgtctatgtg gatatctctc actccaggcc actgtgtcac tgtgtctgta tttacagctg    27420
tttctttctg tcggtgtgtg gattctttct gtcggtgtgt ggatttctat gtctgttttc    27480
atcttaattt gtgtgtctaa gcaagaagac tgttttgggg tcactatttc cgtttatgtc    27540
atagccccga ttgtccccat ctccatgtct ctctgtgtgt atatgttcta atgtatctgc    27600
ctacttatct ttattcgtat ttctctgggc atatatccct ctcttgcagt tcttggcctt    27660
tgcagttttt ggcttatgtt tttgtatata tcgactagaa ttggcctcct tatgtttttt    27720
gtgcatgttt tagttttttg tatatatcca ctagaattga cctccttatc attttgtgc    27780
```

```
atgtatgagt gagcatatcc aactctgtct ttgagaagca gaactgtcta tgtttgcagt   27840
caattgtgtt ggctgtccct gtgtttgtcc ctgtgtgtgc atttcattgt atgtgcaccc   27900
attcatgtat ctttctgctt ctgtatgacc atatacttct gtgtagctgt ctatgtatat   27960
tggcttctat ctgtgtctgt gttgttggct acatgtctgt gcatatgcac ccactgagtt   28020
cataaaagc tcacctgctc tctaaggaat ctaccagatt gttttgtgaa ataactcaca    28080
tctcgttttt tacttgctta gttatcttct ggcttgccag atgctttggt acttaaaagt   28140
gtgttggtac gtaggggtgc ataatttatt catgtaggat gtcaaaagag tcagttaaaa   28200
attatacaca gtgtgtcttt attaacagga cagttgtgtg tagagaatcc ttgagaaatg   28260
agcggttaga tgataaatct tttcatatta atttcatgat ttgagtgaag taaatttgaa   28320
aggtacaggc tgcataagag ctatgtgctt tttaaaactc attgtattga tggtggagaa   28380
agcatttatt tgtactgcaa agtcttattt gtgatgttca ttactgggtt agaaggtgtt   28440
acttttctga ttttgtttgg cttttttgaag agttactaca aatgcatctt tagagacaaa  28500
gagctctgaa ggtgacttag aacacatgga gtacagacaa aaaggagaat ggaaaataac   28560
agagagatgg gcatattcct catttgaatg gagtcagcca ggggctcagg atggggtgca   28620
caggaaatgg agaggtgacg gtcatagaga gaagcttagc aggaccagat cttttccttgt 28680
cctgggctgc tgtgaccata taaggaaggc agtaaggga ggggtaggga tgaggaagag    28740
accagctctc cctttctttc tgatggaagg ttaccacctc tatttaaaac ttctgttctt   28800
ttggttctct ttcttttgttt gattatatta ttttctggtc ttgttctgcc atagcaagaa  28860
ggaaattcca catgtggctc actcatttat tatacttgtt tctttgcatg atattataga   28920
gagcttgtta agtgtcactg cgaacatcac acacactgat ccactgatat gggcagggtg   28980
gtctttatgc cagctctgct cccttcccag tgtatctgtg gtgcttaatg gggacaacca   29040
tgattttcct gatgtcagtc tgtgatgtca gttgtccagt gtgtatgcag actgcttaaa   29100
agtacataca gttccttttgt aattatggta gtccctgaga aggaagtgct cactaataaa  29160
agactaggtt cagtagaaac atgtaagttg tctaggtgtt ggaaattaat atagtactct   29220
gctaagggaa tatatatcta gaagttaact ggattatgct caataaaaag attacaaaag   29280
tttcataaat atttttaact aattctataa gattaggaga gggatatttc agatattcaa   29340
ataattttt taattgacaa acaccttaga catattattt acatacaatt gacataataa    29400
ttaaatcatt atgtctgttt tatgataaaa caggatcttt tggcttagtt tgaattattg   29460
aatgtaaaat aatgaaaatt taaaaaaaac agaggaggaa tctatcctat tttataattc   29520
agaccgttga attgaatttt tcttttgttg tattgatttc aatgtagaga agtctgtggt   29580
gctggattcc agtcaaaaga taaacatttg tatgtgggct ctacattgca gccaatcttg   29640
ataatttcaa accttgattt tctcatctgt ataatggtaa taataaagac tgtctcagct   29700
accaaatgat tgcatatgac aaacctctca cttatgtaag ggaaaaaaga aaaagaagga   29760
caatggggtg gattttttcgt atagtaaaat ttattcagtt agggtaatat tctgagcttg   29820
tcttctgaag caaaccctgc aaactctggc cattctgttt tgtttaggaa agagttaatc   29880
agttctgatt ctgcgttttc tggggaagga ggctgagtat ggattgaaga ggagtcacta   29940
cttttctgag atgatatatc tgtgctaaaa attagtaatg ctttgcacat gcaacataca   30000
gtgttcaatt ttgttagtca acagatattt aagtggcagc tgttatgacc tcaggggtgt   30060
agtgacttcc ttatataatg tcctttaatt attgaaaaag aaatctacat cagaatatca   30120
```

```
ggtaaaatct tattacatca aatattataa caaagatact ttttatattc tctaaaaaaa   30180
gtggagatct cagatgttgg ttcatttatc aatataatat tggatttgaa aattccagta   30240
tacaaaggga aaaagacagc ttcttaaagt ttatagtgat tttctatgaa ctttcaattc   30300
aggattttt  ctgttttact ggtatgatag agctaaattt cgaattgtaa gtagtagatc   30360
attagactgc agggtaagcc ttgagattgc ttcttttcag gtaggaaact ctactgtgta   30420
tttggctagt tcaacatatc atgggtagtc aaaaatagtt acatatccaa gtcagcattt   30480
tttaagttgt tcagttgtgc ttaaagattg gtcctttcca ggaccaatcc agctttatca   30540
aaaagttatt atgtacatct aaagtgttct gacattttaa tgctcacagt agccgaatga   30600
tgtgagtagg aatctttgtc ttcattttat agatgaagag acacagagaa ataaactaac   30660
tgggccaggg tcctaccact agaatgtgac agatgacaat ttgagcccag catatagttg   30720
tttccctata atattcgttt tatgattgta tagatatctg ctgaccaacc ttaatctctg   30780
ctccctgaga ttaaccgttc tacaaagcag aaactggagg tcgttcaaat gaaaactcta   30840
cacttttaga gggccattaa caatgctcaa gttaaagaaa agcaatcaaa gacaactgaa   30900
atactggtac cttcagacag tacatatgga ttttttttt ttttttttgta ttatactttta  30960
agttctaggg tacatgtgca caacatgcag gtttgttaca tatgccatgt tggtgtgctg   31020
cacccattaa ctcgtcattt acaataggta tgtctcctaa tgctatccct ccccctcc   31080
cctgccccaa acaggccct  ggtgtgtcat gtttcccttc ctgtgtccaa gtgttctcat    31140
tgttcaattc ccacctgtga gtgagaacag gcggtgtttg gttttttgt ccttgcgata    31200
ttttgctgag aatgatggtt ccagctgca  tccatgtccc tacaaaggac atgaactcag   31260
cctttttat  ggctgcatag tattccatgg tgtatatgtg ccacattttc ttaatccagt   31320
ctatcattga tgtacatttg ggttggttcc aagtcttggc tattgtgaat actgccgcag   31380
taaacatacg tgtgcatgtg tctttatagc agcatgattt ataatccttt gggtatatac   31440
ccagtaatgg gatggctggg tcaaacggga tttctagttc tagatccttg aggaattgcc   31500
acactatctt ccacaatggt tgaactagtt tacactctga ccaacagtgt aaaagtgttc   31560
ctatttctcc acatcctctc cagcacctgt tgtttcctga cttttaatg attgccattc    31620
taactggtgt gagatggtat tcattgtgg  tttgatttg cattctctg atggccagtg     31680
atgatgagca tgttttcatg tatctgttgg ctgcataaat gtcttatttt gagaagtgtc   31740
tgttcatatc ctttgcccat ttttgatgg ggttgtttgt tttttcttg taaatttgtt     31800
tgagttcttt gtagattctt gatattagcc ctttgtcaga tgagcagatt gcaaaaattt   31860
tctcccattc tgtaggttgc ctgttcactc tgatggtagt ttcttttgct atacagaagc   31920
tctttagttt aattagatcc catttgccag ttttggcttt tgttaccatt gcttttggtg   31980
ttttagacat gaagtccttg cccatgccta tgtcctgaat ggtattgcct aggttttctt   32040
ctcgggtttt tatggtttta ggtcttacat ttaagtctct aatccatctt gaattaattt   32100
ttgtataagg tgtaaggaag ggatccagtt tcagctttct acatatggct agccagtttt   32160
cccagcacca tttattaaat aggaaatcct ttcccaattt cttgtttttg tcaggtttgt   32220
caaagatcgg atggttgtag atatgtggta ctgtttctga gggctctgtt ctgttccatt   32280
ggtctatatc tctgttttgg taccagtacc atgctgtttt ggttactgta gccttgtagt   32340
atagtttgaa gtcaggtagc acgatgcctc cagctttgtt cttttggctt aggattgtct   32400
tggcaatgcg ggctcttgtt tggttccata tgaactttaa agcaattttt tccaattctg   32460
tgaagaaact cattggtagc ttgatgggga tggcattgaa tctataaatt accttgggca   32520
```

-continued

```
gtatggccgt tctcattata ttgatacttc ctatccatga gcatggaatg ttcttgtttg   32580
tttgtgtcct cttttatttt gttgagcagt ggtttgtagt tctccttgaa gaggtccttc   32640
acatccattg taggttggat tcctaggtat tttattctct ttgaagcaat tgtgaatggg   32700
cgttcactca tgatttggct ctctgttgt ctcttactgg tgtataagaa tgcttgtggg    32760
ttttgcacat tcattttgta tcctgagact ttgctgaagt ttcttatcag cttaaggaga   32820
ttttgggctg agacaatggg gttttctaaa tatacaatca tgtcatctgc aaacagggac   32880
aatttgactt catctttcc taactgaata ccctttaatg aattatttaa ccttagataa    32940
tttggctttg agctagaaag gtagagaaag atggaggaac caattcttcc ctgggttggt   33000
acttatttat cttgctcttt tgaagtctag gtcaatcgtc ctatttgttc tgaatggccc   33060
attcatgttt atccatttag ggacagcagg tttggcacaa atggattggt tttctgaggt   33120
ctcatgtaga gggctgcact gactgacttc tgaaagtccc ctctaaccct tcaaatctcg   33180
ggatcatttg atctcaagcc ttcattcatg catacatttc tatttccttt ttgagtacca   33240
gcacaacact gcaggctgac ccactggatg gatagaatgg ggctcttgcc ctaccaccct   33300
ttggcaaaca atttgagggt ggcattgtca ctatctcatt gatataggggt ctcttgaggc   33360 ccagaatgac aaagtaattt tcccactctc acacagctag ttattgtcag agtaaatagc   33420
aattttgaat ttgtagaaca cgtggtttta cctctatcat ttctgtttat tatgaaaatt   33480
ttagaagtaa taattaatta gaagtagaaa tgatgattaa aataaatgcg taactactaa   33540
aaagtagttc attgcagcac cacctaaatt catctcacca ttctaccagt agtcacacatt  33600 tcgccattgg gttaacattg ttttggatct tatagctgtt gaagaagaca aaattctttc   33660
cattctctag attatatttt ccccatttgt aaaacataat ggaagtgtat ggaaaatagg   33720
agttgataat ttttaaggcc cctgtcagca tattggcaca taggattctt gtaagtggtg   33780
gtttacttca cttcagctat ggaaggccta tgcgacacca cccatagagg atagtttgaa   33840
agaaactgct agtgactgcg tgtgtttcct tcctgacata tttgctagaa ggtgatgagt   33900
tccagctttt tttcagactt ggatctggct ttcattcccc ttctcctccc accctcttaa   33960
acaacagagg cagcaaccat ttatacactt tccagaagta agtaagactc tattccagaa   34020 acacccctatt tcaaaatgga aatatactca gtgccccaat gacccattgg gcgagtttga   34080
acgtgtgcat tctctgtgct ccccgttta gcttaggcct actccctaac ctgtcatatg     34140
tcacccagcg atggagccta gggcaatgag tgccatcata tctgactttg tggcctctca   34200
gctttcaatg actagctttg tagcagaagt ttagcctctc atcccagac ctttggaagt    34260 agtgttgaga taaagagagg ttgaattgaa ggttgtgttt tctagatttc tttcaattgc   34320
tccttaggct ttagaagaca aattctccta aaagacaggt gctacaatta atccaagcaa   34380
agggaaagat gtcaatagag ctgccccttt tcgtagaggt gtggcaactg ctgggaagga   34440
agaaattagc tggaggccgt gtgatcacta ataaaactca aagcggtgtt tttttacttc   34500
tcaatatgag gttgaaacta aagcttaaa ttgctgactt tctggcagca ccaaacagta    34560
aggaaaccac aaagataaac ccaaataata gagccaattt tctttttttg tggggtggg    34620 ggatgacttc taactggtga tatgaggaag gataagaaaa tgtttatttt aatctaaaaa   34680
aaatggatag cacatatgat ctttgctaag tgcactgaat gtatgtagag gagacaagtc   34740
tgctaaaggt atgagaattg ggccgagatt taacacattt tcaaagctcc atgaagaaac   34800
ctactgaaca gtgggagtgg agcaggttgg ggatagtgaa gtatttgtaa tttattttta   34860
```

```
aaaaggagag ggagagagag aaaaggaaaa actgggccac ccatcctttg aaaagaaacc    34920
ttgaaagagg tccaaatatc cttagaaatc cttgacttct taaaagtgat aagagtttgt    34980
tttttccccc tgacaattat agaggtcaga gagttttctt ttctattgca aaacattgag    35040
agtgtgtaga aataattgta ggtagcttag ccttggctgt agtcagaact tttgtactgt    35100
gactttagga tctgtataga attgtatgat atgaggatac accaaaaact ctatgggcta    35160
tcaaaatggg atagcattaa aagaaatagt gcttttgttt agaagaagaa atgaaatgct    35220
tgtgtccagg tgcttaaagg aaggcagtgc agactttcag aaactagact ttaagagcta    35280
tactcagata ctgagaaggt ctgatggctg aaggaggaac aatttaaaag aatagccatc    35340
tctcccttcc ctgtaaatta gacataaaag aatatcccat tcatctcaga aatgtaatac    35400
aacattttag cttgctagta actttacatg ctatttcctt tacctcttat atttgaggtg    35460
tctatttgga gtgggctgtg tttctagcta ttctgtttat ctggtttgtt tttgtttgca    35520
taggaaactg gtgtacattt tatttgggta aatatcacct caattttcaa ataaagcttt    35580
atttaagttt cacatgaaaa agacaaatga gacaaagaag agaataattg cattgtcaga    35640
attataagaa aaaaatcaaa taaacatatt tgaaatgtcc agaaaaccta gagttttatg    35700
tatattatac aggagagata ttctgtcatc tggttgccaa actatggagg gtgggagact    35760
tagaattttt gtccaaaagt attgcttcat tagaaagata catgggtgtg cttccacatc    35820
agcaacatga ctgcagaccg ggaagtcctc acggagagct ggaatatggg tattttggac    35880
tctctggtaa gatgcggctt ttacttcact tcctcagtgg tactactgta aattttcatt    35940
ttcctatgga atacctatt tggttccatt gtatatagtt gacaactaga attcgttcgc    36000
tgttgcttga actcaactgt aacttcttgg cactatacat atcttctgat gcgcctgtgg    36060
aagagctacc ataatgactg tgtacatgga caaaaaaaaa aaaagagag agagagagag    36120 aattaaatca tgagtttgtg ccttgggagc tacagtttaa acatttgctg gttttctcaa    36180
ttaatgaaaa atttatttga aaataacagc acagaaagga agaaagacag gccggcaagc    36240
atcctcctcc taatatactt atccactttt ggataccttg atctcagtct cagaggtcat    36300
atttttagta aaatggccac cagaagtaaa ggatttattt ttccagactt tggtgtttgg    36360
agctggtgtg ctgagagctg gtagagaaag cgctactcag gtagatgtac caaaggagga    36420
tggttgctgg tggatatggc agagtacctt ttatgtggtt atctcttcct tgtaactctt    36480
ggctgcataa ctcttatttt cttttctatt tttgttctct ctcttggaaa aaatttggtg    36540
gtaaattttc atatgagcca tattgtcttt ttaaatagtt ttattaatat aaaatgtaca    36600
taccataaag catacccatt taaactgtaa aattcaatgg gtctctctct ctctctctct    36660
ctcttttttt tttgtatact cagagttgtg caacaattat caaatcaat tttgaaacat    36720 tttcattgcc ccaaaaggaa accctctgcc cattagcagt tactccccat ttcccccacc    36780
cccagtcccc ttcaacccta ggcaaccaca aatctacttt ctgtctctat agatttagct    36840
gttctggaca tttcatgtaa acggaatcat gcagcatgtc acccttttgta tctgcttct    36900 ttcacttagc atgatgtttc caaggttcag ccgcattgta gcatctgcca atacttcatt    36960
ccttatttat gactgaataa tattccattg tattaatgta tcatatttgt ttttccaat    37020 catcagttga tggacacttg ggttgttttc atcctttgtt tttttcttgg ctattttaaa    37080
taatgctgct atgaatgttc atgtacaaat tttttaatga acatctgttt ttatttctcc    37140
ttggtataca cctaggagtg gaattgctgg gtaaatatggt agcttaacat ttaacctttt    37200
gaggaactgc cagatttttc caaagcagca caatcatttt acatttgac cagaagtata    37260
```

```
tgggagtttt agtttctcca catcctcaac aacactcatt attgtcattg tccttttcag   37320
ctcttttgat aatagtaatc tcaatgggtg tgaattggga ccccattatg gtttttaattt  37380 gcatttcctt gaagactaag gatattgatc atcttttcat gtgcttattg gccgtttgta   37440
tattttttga tcttttgctc atttccaaat tgtgttgtct tttcattatt gagttgtaag   37500
attttaaaat atattttgga tatgtttgtc attttaggga tgatacttca cagttacatg   37560
atgttttcta gcaagcattt gtgttgttct actggtgtta catatcttag ctgcattagc   37620
cacttcgttg ggtatgaatg ccagcagaat ctaaatgacc ttggcttcac tgctgagaat   37680
gcaacccaag aacagaaatt tgtcagaaat ttaacactta agccccccac ttcccaaact   37740
catctgggac aaggagaatc tacatttaaa gttctatatt ttgtgttgct gtggttttt    37800 ttttttttt  ttttactttt agcttggttg ggtttaggat cttttctttt tgttttgcct   37860
taggcatacc taagcagagg caagggagga aagggatatg aaactgatag aaaagtgagt   37920
aagctttatt cagatcagca tattcatctt aatatggttc aattggctga agaaatatct   37980
caactaaaac tctggaatac tttgaagtac caataaaatg tacctaatgt acattttatt   38040
tatgtttggt ctctatgtac ttgtgtgtga acaatgagc  acaaataatt ccctcctttt   38100
ttttaagcaa tttatattgg tgatttaaaa ataaaataaa tgcaagtggg aagtcatgaa   38160 acccatgta  aaacgaataa gagcatatat taaaatccca cagactttag tttcaaatag   38220
tggttttgct gtttcttagc tgtgtgtcac tgtgcaagtt actttgcttc tctgagtctt   38280 tatttctttta ttggtgatgt atgtaaaaac ccaccttctc gaattattgt gaggacaaaa  38340
tgaattaatt aacataaagt tcctggtgta taataagtgg tcatattttg tatttgagca   38400
cagggcaact gagttttga  aactgcacat taatgttgca gtcaaatccg gcatgaaatt   38460
agagagtgca tagacagagt gggctgggaa aatgaaagga ctttgaacat ttatattctg   38520
ctttatttag gcatcagtgc ttaataatta ttgatagttt cttctggtta tctgacattt   38580
tgaagagact attcctagc  agaaatttct tgtaataata atctcttaca cttatatagt   38640
gttttgtgcc tttagaagta cttaatgctc tttatttcac tatccataaa tattctctga   38700
agcaagcata cagtcagtat caattccatt tttcagatga gactgcaaga catagagtta   38760
cttgtttcaa ttcacatagt aaagtgacag tttgaaccag agcccaggtc ttctctctga   38820
acatagctct ttttctcctt cattatatca ggcatagcgg caatgtatta ttttactagc   38880
tttttatctt gaatatcctt ttagtgacct gcctttggtg ttagtgtgcc tataacattg   38940
tcgttgaata tcttaataca tttagtggtc ttagcaagca gttttgtctt cagaaggaca   39000
ctgaaatctg tggaaaggac tgcagaagat tgggtgggca gatacctatc actttctggg   39060
ctggtagact ttctgttgaa gctatttgca aggctagttt gtattatcga aaagcactac   39120
ttcagaagag ggttgtgatg tcaaagtagg cactttgagt gaagaaaggg ctgtaagcat   39180
gggtggaaaa tgtggtagat gattgtcttg agttattttc tttaatgtca agcaggcagt   39240
ccttggaatg ctatttcaaa aagtgttgta taatgttgaa gacacagtta cagatttcca   39300
acacgaagct cataaatctg caattccctg tcctcctagg cacatgaagg aaaatttatg   39360
agcttcaggt ttctatgcag ctattaaagc atatttaatc tgctttgagc tcaagctccc   39420
tctcatttgc tctcttcgtt tgttcctctt acatgagcaa actgcctttc ttttcttta    39480 aaagtagtaa gtagatttgt tttcctccag gtgtcatgaa tgcaaacatt gtaataacctc  39540 atctgttagt tcagtctttt gcaaaacaaa atggcagcac ccaggaggtt gaaagagtta   39600
```

```
aattgtttcc ttctctgagt ggtaccataa gttgttagtc tgctactctt tctcccagtt   39660
ggcacatgac gctaacatcc aatcgctagt gatgtggcca ttttttgcct tattttggcc   39720
tttcctcagc caccagtcat cagttttcat gcatatttgt cagaccctgc ttcctcaact   39780
ccacagttct tagttcatct taagcaaatc gctgtctttt ctctaaagat cctcaaggaa   39840
aataaaaagc atctccaggg ggaatttact gcctcatagc cctgacagag atttctgacc   39900
aaaccctaac caaaaatttt cttccctcca tttgtctttt attgttttta caggggagat   39960
atgtaacata ataacaatta tattgtacat aataattact tttacaaata ataatatctg   40020
tcatcaaaaa tatacagagc tttggatttc cttagtatgg cacttcatta agttgtggtt   40080
taagaatagc tatgattatt acttttgtga taattacgtt ccataatatg gaaacttata   40140
aaattacctt taaatgttta ctcttattct ggccacagga tggaaagatg ttcgctagtt   40200
actcatttat aacctgaatg tacttttttac tgaatctaaa ggtatcatct ttgcttggca   40260
attcccatga cttgtctttc tgactcttca gatctcagct taaaagctca ctcttcaaag   40320
aagccttccc ctgaccactc tggttttgtc ttcttnnnnn nnnnnnnnnn nnnnnnnnnn   40380
nnnnnnnnnn nnnnnnnnnn nnnnnnnnnn nnnnnnnnnn nnnnnnnnnn nnnnnnnnnn   40440
nnnnnnnnnn nnnnnnnnnn nnnnnnnnnn nnnnngagtt tatattttaa ctcttagttg   40500
aataatctaa gccaagaatt atcaaccttg ggttgcacat gagaatcacc aatgaagctt   40560
taaaacagtg acaaggctat cccaatctat tcattaatta tctccaggtc taaactttag   40620
catgtatata catttttaaa agctcataag tgattcttat gtatagccag tgctatctgt   40680
ctcttctcct gttctttccc ctcctctcct tactccttc tcatagttt  aagataagca   40740 tggccccaca acaagccttt aattcgcatg gcagtttcta gggtttatca tggaaaatga   40800
gccaaattgc cttcaagaag ttttttacgta cctcttatat agagtgtgac attttatatg   40860
tacctcttat aaaatgtgag cttttaagag tcatatctta ttgcaagaaa tttcaatgtc   40920
gaaaaaagta ttgaatattt ataaagtcac aaatacaaac ttttatatga ttctcaaacc   40980
tgtgaagtta tgtcatgttc aggccttctt taaagcatgt ggctctcagc cctggtactg   41040
tccttaacca taaacctcat cttttgccctc tatagggaga ggattgtgat tataattact   41100
cattttaaat aatgtatatt agtaatgtac cttattcata tatttgttga gcacctccta   41160
tgtgccaacc actatgctag aaattttta atattcttca aaatcttcaa gatattaaca   41220
tatccccatt ttacaaatga ggaaactgct ctcaaagagc ttagtttaca cagccagtaa   41280
gctgctaagc ctagattgga tggagggtgt gtgagaaaaa aagcagcatc cataaggttt   41340
tcattctcct accctgtatg atagaggtac tagaaattat taaagaaaca atagaatttt   41400
acaagacttt aggaagggag aatgtgaagg gtacagttcc cagttgctgg aatgagtact   41460
ggagtaccaa tacatggctt gccatggggt ttggactacc tatcttaact cctttgctcc   41520
tcccaatctt gatctcattt gtttgaaaga tcatctgccc aacataaaaa tgcatttcta   41580
attctgtaat ttaagtcagt ggcaagatca gattcagtta aagtttactt tcctgacaac   41640
tatttaggat gatatctatt ttgcaaaact ctagtgataa atgtatgcac acttacacat   41700
catacagcgt ctcttctgat tctgactaag atgtgatgga gctgtgcaga tgtgatgggc   41760
tctttggaag aaaggtttga tatactacta atctaaggac tgaattttct ctctcatctt   41820 tgttttgtgtc cctttgaat gatgatgaga gcagcagcac ataacattct tttgtgctaa   41880
cagtatctct gcatcacatt gatcaggaga attggccctg gaatggtatc ttctcagttg   41940
attttcagga aagattaggt gattattttc tccataggaa gaggatgttt gatgtgtctt   42000
```

```
ggctttggca aaaggaagct tgtcgactca actgtaagta gatagaattg cctttgactt    42060
catctgtttc agtcgttgtt catactcagg tcctccagaa ggcctttaag catttttatt    42120
gactttgtgg tctattacac aaaactaaag atactgattc tcagtcgtga gtctgcttca    42180
aaattgccta gagaatcaaa ataattgta ccagttcctg ttcctggaca ttgtgattca     42240
tttggtctgg tatgaaggcc aggaatctgt attttaaaa ttcactcaag taattttgt      42300 atatagctat agttatgaaa ttataacaat aatgaaataa taataatgaa taatgaaata    42360
ataatgaaaa tctgtggctg aacttgtcca ctcccctatc ccctgcaata cttccccaag    42420
gtggcattta agatgggcct agaaggttat ataagatttg aatattaaaa catggattga    42480
cagtgaggac ttttgagag gtgacaatgt gctagcagcc ctggcttgct cttggcacct     42540
cctcgacctt ggcgtccact ctggccacac ttgaggagcc cttcagccta ccgctgcact    42600
gtgggagccc ctctctgggc tggctgaggc cagagccagc tccctctgct tgcagggagg    42660
tgtggaggga gaggcatgcg tgggaaccgg ggcacgggc tcatgggcca gctcgagttc     42720
ctggtgggca caggctccac cggccctgca ctcggagcag ctgactggcg ccgtgggccc    42780
tgggcagtga ggggcttagc acccggggca ataactgcgg agggtgcacc aggtccccca    42840
gcagtgctgg cacaccaatg ccacgcttga attcttgcag ggcctcagct gccttcccgc    42900
ggggcagggc tcaggacctg cagcccgcta tgcccaagcc atcccctgt gggatcctgt     42960 gtgtgccaag cctccccaac gggcaccatc ccctgctcca cagtgcctgg tcccatctac    43020
tgcccaaggg ctgaggagtg tgggcacgta gtgcgggact ggtgggcagc tccacccaca    43080
gccgcagtgc cagatccact aggtgaagcc agctgagctc ctgagtaggg tggggacttg    43140
gagaactttt atgtctagct ggaggattgt aaatgtacca atcagcactc tgtgtctagc    43200
tccgggttcg tggatgcacc aatcagcact ctgtatctag ctaatctggt ggggacttgg    43260 agaacttta tgtctagctg gagaattgta aatgcaccaa tcagcacttt gtgtctagct     43320
caagtttgta aatgcaccaa taagcactct gtgtctagct caaggtttgt aaatgcacca    43380
atcagtgctc tgtgtctagc taatctatgg gaacttggag aacttttgtg tctagctaaa    43440
ggattgtaaa tgcaccaatc agcactctgt gtctggctca aggtttgtaa atgcaccaat    43500
cagcaccctg tcaaaacaga ccaatcagtt ctctgtaaaa tggaccaatc agcaggatgt    43560
gggcagggtc agataaggta ataaaagcag gctgcctgag ccagcagctg caaccactct    43620
ggtccacttc cacacagtgg aaggtctgtt cttgggctct ttgcagtaaa tcttgctgcc    43680
gctcactctt tgggtccaca atgccttcat gagctgtaac actcaccgtg aagatctgca    43740
acctcactcc tgaaatcagt gagaccacga acccactggg agggatgaac aactccaaac    43800
gcgccacctt aagagctgta acactcactg caaaggtctg cagcttccct cctgaagcca    43860
gtgagaccac aaactcacca gaaggaagaa actctggaca tgtatgaaca tctgaaggaa    43920
caaactctgg agataccatc gttaagaact gtaacaccta ccacaagcgt ctgcagcttt    43980
attcttgaag tcagtgagac caagaaccca ccaattccgg acacgttttc acatggagat    44040
aatttggaag aaaaacttgt aaaaatgtga gaacattgag aactttatt ttccaaggaa     44100 agaagtggca gcttcatttt tggtcattgc aaacagcagt gccatacatg aaaggaaagt    44160
ggtggtgctc atcaacttag aacacttgag actctttct gcttataaag aaaaagtgtc     44220
aactgtaaag ttgatttatt tatgaaccat aggctactat gaaatctctg ttcacagcta    44280
gaggcctggg agagtaagat aactacttgt ttattccatg aagccactta ctgtttcttt    44340
```

```
tctattgcac atacctcaaa tgaagcattt caatagaaga accacattct attcacttgc   44400
ttcattttat tctgatttct gtaaaaactc aaaaattcct caagcagtgt ttctttgcaa   44460
ggcaacaatc ttcagttctg ttgcaaaggt caggagtgat agaatgaaaa tggtactaga   44520
ttcaacagaa ctttggtatt tgcatggcta aacattgcc atggggctgc aagacttgtg    44580
agagcttgat attttgcttg ttgatgaatg agtctgtgtt ggtgctggtg gagtgatttg   44640
agaggtagtt ttccactgtc aatcaagagg ttggttttga aagctgattg ccagtagtca   44700
ttctgctaac cactctggtt ctcctttaga tagagaccta ctcagattca agtctcatgt   44760
actttgtggc ataaacattg tacacaccag atgtattgaa caaccacaaa gaaaactatt   44820
aggactcaag tagtatgtca gagagtagtc actgatgatg tataattctc cacttccaag   44880
aagatgtaag cgcactgttg agtggctaca tcctacatat gttggccaga atttaggaat   44940
acacatgtgc tctatacatt ttgaggtact gcctgacccc tagagaatcc tggtgaagtt   45000
tttctggtgt cagtttggtc ttaatgttta ggaaatgccc acagacgact cctgctttct   45060
gcttactcat gtagtaaaca caaagcacag gactagtttg tcttctggat caaggagaaa   45120
tgagttagca gatataaaac aaatcagaaa ggaagtagtt ctcacatatt taaccataaa   45180
tagttgctgg atgttcatta actctatagc aatatttact acttattggg gatcctggaa   45240
agaaaatata ctgtccatgt ccactgttca ctgagggccc cccgccaccg agaaactccc   45300
tgtcttcatc actcactctc cacattcatt gacctagagg aacagttcat ggatgagtga   45360
gagcttgagc tatatcttaa aggatggagt tggatttcaa ggcaagaggt ataagagaaa   45420
attcagagac aatattgacc atggtctttg cgaagaaaag tactttggga gataaggttg   45480
aggaaaagta cgtttgaatc ttcatccaga ggtagcccct aaatatgttg actctgttga   45540
aagagtactt gacttggatt cagacagatc tgcatttgac tcctgttttg ccatttataa   45600
gaacttgagt aattattgtt tctgaataag agtttattta gccaagcact cagtaaatgc   45660
ttgaatgtga aaatttactg ccctgttttt ctattgtcag atggtcccct tccttggata   45720
actttgtaat cgttgataac ctttttctcag gaatcagaag gtagaaggat tgggaaaata   45780
taagaaacaa aaaggcatat tcttattttt attttcatat tgtcttccaa ctctccaagg   45840
catcttcgtt tgcaaggctg acttatctaa tacttgttgg gtagagcagg tctttctttg   45900
gttttcccct gtttggggtt aaactctgag taacgttatt ttctaggtct cagccaactt   45960
tgaagcgcat gaactcacag tagcctcacg agggtcactt cagcagtgag aagttacctt   46020
tcccatataa aagtgtaaga gtcgatggcg gccaggcgca atggctcatg cctgtaatcc   46080 cagcattta ggaggccgag acgggtggat catctgaggt caggagttca agaccagcct    46140
gaccaacatg gtgaaactct gtgtctacta aaaatactaa aattagttgg gcgtggtggc   46200
acacacctgt aatcccagct actcagaagg ctgagacagg agaattgctt gaacccggaa   46260
ggcagaagtt ggaggttgca gtgagccgag actgcaccac tgcactccag cctgggtgac   46320
agaatgagac tctgtcaaaa aataataata ataataagag ttgatagcaa ataactatc    46380 tgtagcgtaa acctcagtat tctttatcat tcagtatcaa cattattacc aaaaaaacga   46440
taagcaatag ggactgagtt tctgtggggt ggaaatgtga agtggatctt ggcatgatat   46500
aacttgtgat ttggcttcct ttataaacat tatcaactac ctcagctcta tcaatcactt   46560
ggcagtccat agtgaacatt ataactcaaa tgactagtcg agtctgttca ttgtccatgt   46620
aaaggcgtat acctgaagtg agaagtctga ggtaacttag caataagttt gcagtacagt   46680
gtttagtgaa gtctgaaaat tcaaggcttc gagtcatgcc agattgctcc ataaccatag   46740
```

```
cctatctctg tcacaagtaa gaaggtttaa aaatcacata ccattattgg tcacaatgtt   46800
tggagatggg gaagagtttg tggatggatc atggcagtgc atggacagtg attagcccac   46860
agcacagcca gtgagcactg ttgtacccaa agcacgtaaa tcaccacata tactatcaat   46920
atatttatgg atgacaacag acactatagt tttatgtcag tgctttctgc tgctgaaaac   46980
aaagttagtt aagggtacct tttgtatatt tgcaacatat ctccacacct gttcctttgt   47040
ctccttcttg caagttcttt ctttcagctg actatccgct gttcctacta tggctcccag   47100
tggcttttca agagggtgat tgttttttaa gagaagatcc ttgaaggaca gagaaagcct   47160
gaatcgttca aaataatgaa ttactcagga tgaaatttca ataatttgca agtttgtgga   47220
gacagatatt ttggggaagc ataattttct atgtaccoct caaatcatgg ctggagatga   47280
cagcctcttc cacctccata taagaccatt tcatttcttt ctacttttt ctccctcctt   47340 cccccaaaa cacaaacata cacatatcct gtgcttcagc cacccagaac ttcttactat   47400
gtcttttcaa ttctctgtgg ctttgcatgt tctgctcctt ctgcctagaa tgctcctttc   47460
cttttcttac ctggaaacac cccaattcaa atgtcacctt ccttatttat accaactttg   47520
tccataactc ctttatcaca cttcttcttg tgattagtct attcacttgt ctgctgttac   47580
acctgtatga gagatgaaaa ttccttcttc atctctggaa ctcacgccct tagcatatag   47640
tagacaatct gtaaatgttt gaaggttgag tgaattaatg aatgaccttc aacctttcag   47700
gcttccaatt ttctctctga aaaggacagc taaatgaaaa ctcataattt tagaagatga   47760
ggttagacgg ttggtaggtg catgcagaga ccaattatta tttaggcatt atagaagtgt   47820
atagttcttg tatgttgagt gcagtgtaag agtggcccca aatatagtta atgcccactc   47880
cagacccagt tattatagag ttggcccag ctgtattgct tctatttaag actgagataa   47940
gaaatgacac tttcctattt ttttaccta ttgaaagggt aggggctggc tgttatcaat   48000
ctcagttcac ttgttgattg cattggcttg ccaagtgaga atattagcac ccctgcacat   48060
ttctatagtt ctgccactta tgagatcctt ccttcccatt gtcatattta ataatcagga   48120
tagccctata aaatatgcat tcttatttcc cagatgagga tactaaggct caagtaggag   48180
aacttacttg tttagtaaga tcgtacaact aggaagtggg agaggcaaga gttgaaccca   48240
gatcttccta gctcccggta catcgctctg tctactgagt cacactggag cagccaggag   48300
gcaggaaaat catctgggga atgtggtgcc aacgtgtgat gtttgcctaa atgtgtgcat   48360
ccttgctgga agccagccat gattccatgc tgcataagta ttcattaatg ttcatttcat   48420
ttatttggct atccatatgc tttccagggc gaaggcaagc taggacaagg gcagacaagc   48480
agccttaaag tttgggtgct ttccttcaaa gctgggctgc ctgtttgaaa atcaaacatt   48540
tttggtgata gaagatggtt ccagtacaga ttttattcat tactgcatct acatggacag   48600
acattttcca aagcatagct gaaaatatgt gtaagtccca gaatatttcc tgatttagac   48660
acagactttg agcatgataa ccacatttag catgttagga aattctgtca gaatgcttct   48720
ggaaaggcta ccttttccaga atgaaatgaa aaaaaaaaaa aaaaaagga tggactttga   48780 aactgattag atttgggtta tactccctca cagtgtgacc ctggcaaatg atttaactta   48840
tccgagtttc acttttctta ttctttgaag tgaattttta aaatgtcatc ttgcctgatt   48900
tttgtgagaa tgaaaatgag atcccacacc aggaatttag aagctactca gtaaatattg   48960
cttctctcct ttccccttcc cgagtcctgt cccccaagtc attcattagt tattcagagg   49020
catgcattct gaaatctgcc tactgctcca cgttgaaatg cactgctctt gcaaagactg   49080
```

```
attatctatt tttttgtctt ccaaggcccc ctgtgttcca ctccaccctc ccaattctgg   49140
gggcttccaa agtgggcagg tacagaatgt tctgtggagc atcggaggct gttactcaat   49200
atcctggcca gcactctcaa ctgctctttg cacatactcc atatgaaggc aaactccaga   49260
acttggagtc catgtttgtg tcatgcattg cactgcttct tttacccaaa tccatctcaa   49320
gggtgagtag accaagctca gacttgtctt tggagcagat ttctcaagct gcccatgtcc   49380
ccacactgct tgattaaaag gaggtgcttc aaactctttg gctttatata gactagaagc   49440
agaatgattg gtggtgcctc tgttctcaag gtatcccaaa gcactttgta aggaaatatg   49500
acaagcgctg aggccacgca ggctagtaca acagccgcca cccagcactt cacaattagt   49560
catgcccagc ctgggatcat caagcctgtt tttgttggaa gagcaagaga gggagggaat   49620
gctagctggc aatttccccc ggtacccttt atgaaagtgc ccttggctct tccaatttca   49680
cctgaataac cagctcaggc aaattttcct ctatcaaaaa gcagaacgtt atagtgacaa   49740
gctgatgcct ggctgatgcc ccaggacatt gaccaaatag gcttggcctc acaattggtt   49800
tttattcccc atatcctttc ttcccttttg ttctttttct atgtttcttt ccccatcgc   49860
catctgcaga gtgtcctcag tcagaagtca gctgtggggt ggacagtttg tcatttaaaa   49920
tcatccctat tctgtctacc cttcttatcc ctcacataat tgcttttaga gcaaggacaa   49980
ttctggaagt gaaactacaa taacaccctg ggctcctttc cctctagtag tactcagcac   50040
acttgcaatt acatgttcaa atttgtcttt cttattctg tttaggttca tgaaggcaag   50100
ggacatgcct gtgttgctta ctttctcttg gcaggcacat atagcaagtc ttcaaaaaat   50160
gcttgttaac tataaattaa gtgtttaaga agcccatcgt tagtatcttt gcccctgcct   50220
tatttgtaaa caaccggccc cttctatttg taagttacct tgttttgatt tccatatccc   50280
ccaaagcaaa cttagctca tggccttaca gagtgtgtat attagtatgt taaaatgaaa   50340
tcaactctcc tccccaagc cttctaattg acatgaattt gggagttgac ttgcattggc   50400
ctttgtcctg acagccaaca gagtcctctt ctggtgtatt cactgttggc ttccatgaag   50460
atgctatgga gaaagtttgc cattgacata cattttgagg gcagactcaa cctgagtaga   50520
ccggattgag ctttccccat ctgcctgcca gagatcacta cctgtgtgtt gctaaaaaga   50580
gaattatagg agtcctctca aggcagaaag acctaaaatt agacatggca gccatgcctt   50640
tggtgtgtat gggggtggga tacaggcagc cagtttcccc tctgtttct cccttgctta   50700
cacagccaag gagtggagcc aagcctcaaa gggaagagct gtatactgga gcatgccagt   50760
atacaggttc ctggccctgg ctgagttact atttttatata ttccaataga gaagcataga   50820
agacttctag gttgccactg tcatttgaaa ttgggtattt ttaaaagaga aacttgaaga   50880
ctcaaagaaa gctttctttt gcctcccctt acagttgatt tttgagcttc ataaagctac   50940
ctagtccaaa gtacccacac tcttattatt tttgtctttc ctaccggttt ttttttttt    51000
ttttttttttc atcttcccag gtgtttgatg atcactaaga gcttcaacat tgctcacctt   51060
gaccaggtat gaaaccaaga gttttgttta aggcataaaa gaatgtagga actcaaggat   51120
taggttgaga tggggaaggg ggatgaaggc ttctttttc ttgggttaaa cagaaatgac    51180
ttagatctca gagtgaaagc cttgaattgt cacatatatc actggcaaag actagttctt   51240
tgctatgata agaattgttc atcatctcgc ccctgaggat ttagggtcaa ggcctggcta   51300
cacctttga tgatctcagt catatgactt aacctcttta aagttaacct ttggtgagca   51360
ctgtgccccc tgcaacccca gtaaggccca acagggctct ccaaggaggc aaaattctga   51420
tgatacattt ctgtttagtg aaaatgggta gggaaaatta tgtcttagaa tcaattaacc   51480
```

```
aaacataaaa tcctccaagg ggcttggtag gatgcctagg gaagagcaac gagataaaaa   51540
ctccaggctg gaagggcatt gttgcagcac tgtcattctc cagtttctct tggagttgtc   51600
actaccctct cctttgttct cactgctgac atcatttgta aaataatttc ttcccataaa   51660
taaacaaaac gtacaatcct ctaaatgact aagaacagt tatctagaag aacagtggaa    51720
agtattttct tcacctaagg gatgattctc tttacagagg tggagtaaag gatgtgcgag   51780
gaggcataat caagctaaga gatgcatgct gacttaaaag gcatgacatg tgtgaaacta   51840
agataatgtg ttcaagagtg atgctttgtt gatgcagaac ccactgaatt ccttactgtt   51900
atgtttgact gactatcagc ttattaataa agaaattgtg gtttgagtgt tcattgaaat   51960
tagccatgtt aggtttatgt ggggatgtga ggatctatgt ctaccaattg cagcttctga   52020
tgcagattgg aggcagaaat ctggcctgaa caataagtaa gagtgtcagc tctacagata   52080
tctcacatgc taagcaagca caatatagg caatccaggt ttacacaaag gattaatttg    52140
ggaacaatta tcctcatttt cactttctta aacgattttg aataaggtct tttaagtaag   52200
aagctccctg aatgcattta aaatatggtt tgattatgta catttaagat ttttctacct   52260
ttgtaggagt atctctgttg tataaaaaca caaaattccg gaacttttga aaggaagatg   52320
tgcctctctt catacatttg tcattcttga aagattgtaa aatgaagtga ctgcatatca   52380
tgtcgtgttc cctattgatt tctttttctca ttttaggaat attcccagaa taaaaaaaa   52440 tttttttaa tctactaagc atgctaggta agactgaaga tgaatctatt taagttatgt    52500
caatatctat ttataaagat ttttgtgata ttctttttac tgtagaactt gaagcatatc   52560
ctaaagggaa tggttagcta tgtctgcaaa ctgtggcaat gacttactga gtaattgcta   52620
gcaactgatt tttggtgctt cttgttttga tagtatagca gtgcgagtag gttttagaaa   52680
agcaaaacta agaaaatcca gggaaatgcc atttgagaat ttctaacttt aaaaaacaaa   52740
taaaatagtg tcaagaaaaa atattatcca actaacccca aagtctacaa tgtaactctt   52800
ttattttgat aatgctgttc taactctatc tacttcagtc cattgccatc cagctggttt   52860
aggaatcaaa ttcccaatgt ttcatcactg ttaacattac tgttttactc ttcagtttag   52920
ttcttaaatg gcatagtgtc ttaaattccc tcagcctctt tcacgtttga tttctttgga   52980 aacttttac cttttcattg aagcccatat gatcttttct gaaacagacc cttatcttta    53040
ccttcttctt tggagtcttt ctcctacttg aattctgaa cttcttaaaa tggccgcttt    53100
ggattggtgt aataaatttt cttttctttc tttctttcct tttttttttt tttttttttt   53160
tttttttgag aaggagtctt gctttgtcac caggctgcag cctgtagtgc tgtggagcaa   53220
tcttggctca ctgcaacctc cacttcccag gttcaagcga ttctcctgcc tcagcctccc   53280
aagtagctgg tactacagga gtgcagcacc atgcccagct aatgtttgta tttttagtag   53340
agttggggtt ttaccatgtt ggccaggatg gtctcgatct cttgacctca tgatctgcca   53400
ggctcgcccc tcccaaagtgc tgggattaca ggcgcgtgcc actatgcctg gccagtaata   53460
agttttctta agtgctttct taatgttctg atattttaaa aaagatctgg actattttgt   53520
catacaggca acagaatgtt aaaccatttc ataaagcaat gacaaatata catgattttt   53580
catcagttat aaatgctttt cctttataac attgaacatg tttttgcaac tgaaataagt   53640
gtgattttca tttttagaag gtacatgata aagttaaggc agtggttaat taatttttc    53700 agattaattt ttcagaaaag tgactgtttc tgtctgttca cttaaccca ggcatcaaac    53760 gactttaatc agaaagaact gaagagtaat ttggttattt tagtgccctt ttttgaggca   53820
```

```
aagtcttatt ctgtcaccca ggctggattg cagtagtgtg ctcatggttc actatagcct    53880
cgatctcctg ggttcaagtg atcctccaac ttcagtttcc cagataactg ggaccacagg    53940
tgggccccac actctctgct atttttttt  ttttaatttt tcatagaaat ggggtctcac    54000
tatgttgcct tggctggtct caaaatccta ggttcaagca atccttccac ctcagcctcc    54060
taaattgctg tgattacagg cgtaagccac tacacttgcc ctattttaga gatttgtcaa    54120
gctttggaaa gagaaccatt tacaatataa taggtaaatt atggatattt gaggcagttt    54180
ttatcatagt atttgtagta aactacagcc cccctttat  aatatttgta tttaataaaa    54240
atgaaaatat tacttttatc ttgaacaaca aacataagtt ttaacaaagc aagcatattt    54300
agattagcac taataaccaa acgaaaacct ttataatgat agctgttttt aacatgatta    54360
caaaaaattc gctacacaaa tttttatcct aatcagtgtg aaaaacggaa atattagct    54420 tatagggcca acttagtctt cagagtcctc ttcctaccta ctactgctaa taagccaatg    54480
aaaaactccc tgatgtgtgt ggtggctcag gcctgtaatc ccagcacttt gggaggccaa    54540
ggtgggtgga ttgcttgcac tcaggagttt aagaccaacc tgggcaacat ggtgaaactt    54600
tgtctctact aaaaatacaa aaaattagct aggtgttgtg gttcacacct gtagtctcag    54660
ctactcagga ggttgaggtg gggggatcgt ttgagcccag gtggtcgagg ttgcagtgag    54720
ccgagatcac aggactgcac tccagcctaa gctacaaagt gaaaccttgt caaaagaaa    54780 gaaagagaga gagaaaaaga gagagagaaa gagagagagg caggcttctc cgcttttttca    54840 gttcctgaat aattttccaa tctagaatgc aaaagattct gaaggaagac agttaccatt    54900
tcagattggc agaagttgtg actttaatct ggacttgaat atgttttaca tcaaagggtt    54960
gcctcaacag tgctcaaacc tgcctctctg aaaacatgct gagcgcaaag gttacttgaa    55020
gtcttagctt gagtacttaa gagaatgcta tggagggatt gttgaagaga gctgtgtcac    55080
agctaattct tctttagtaa ttaaaggttt agaaaactct tacactgcat attgacaaat    55140
ttagcaacaa aatgagcttg agaaaaaaat caaggcctgc tgtggaatct tttttttttt    55200
tctctaaaac aaacaaacaa acaaacgaaa ccttttttaga aagattatgc aactgtatta    55260
tctgtaacta ctgcaatagt gtaaattctg atagtataat ttgcttttta aagctatctt    55320
tacttcagtg caacttagat taaatttatt ttaaatttaa acgatatttt tctctttgtt    55380
tattatttta tagtaagttt cccatagaat tcacaaaatt cattagaaag attttctttt    55440
ttttacttcc ttaggtcatt aagtttctga tttgtcagtg gatttcacag aaaccctgtc    55500
tttccaaaaa tatacaaaaa aaaaaaaaa  aaaaaaagcc aggtgtgatg gtgtgtgcct    55560
gtagtcccag ctactcagaa agccgagttg ggaggactgc ttgagcccag aagttgtggc    55620
tgcagtgagc tatggtcaca ccacttcact ccagcctggg caacaaagcg acccccatc    55680 tccaataaat aaataaacaa ataagtaaaa agttttttcac cttgaaaagc ttataaacat    55740
atgaaacacc attagggtct ctgatatagt ttggatgtgt gtccccgccc aaatttggtt    55800
ttgaattgta atcccagtg  ttggaggtgg ggcctgcggg gaagtaattg gatcatgagg    55860
gcagtttttt catgaatggt ttagcaccat ccccttggta ctgttgtcgt gatagtgagt    55920
aagttctcat gagatctggt tgtatagcac ctctccctt  gctctcttgt tcctgctttc    55980
accatgtgac atgcctgctc cccttcacc  ttctgccata attttaagtt gcctgaggcc    56040
tccccagaag ccgagcagat gccagcacca tgctttttgt acagcttgca taaccatgag    56100
ccaattaaac ctcattttta atataaatta cacagtctca ggtattcttt atagcaaggc    56160
aagaatggac ttacacagtc tcttttgtat cagggagaag gtctcctggg tgactccact    56220
```

```
tcttttcttg tttatgtatc cttccagatg atgtatttat ttcctttgtt tttcaattga    56280
tatttactct taaattaaac taatttatta ataaaaagca ttttaaagtc tcatttaga     56340 ttattttgac tatctgattt tttaaatgga gtaaaaaaaa tctaccttgg cctccatatg    56400
caatcaagca agaaacacat tttaagcata ttatttgcct tgtggattct gccttcctcg    56460
atgtgttcag tctgtatata ttcatttctc ccacactgta agaagctagt cagatgtata    56520
attggattat catgctacat gatcttagca cactcatttt aagcttacat agactagtga    56580
gcaccactca ttacatgtca tttctctaga gaaactagtt gggccgtggc tgcaggactc    56640
tcacttgaag agacacatgt ggtgatgttt tctcaggcag ttaagcaata aagtgtaccc    56700
tgatttgcac tgaaaataaa gattccttta aagggagcag ttctagttat ctctctcttt    56760
agataccata tgctaaacgt ttttctatgc actaaaacaa taactaggtt ttatactctg    56820
ccttacagcc tacttcacac ccatttcaca gggagaggaa cagagaggta agtgatttgc    56880
cccaacttac ataactagga agttatttac tcagtgtgga aacttgttca gacggtcatt    56940
tcattgaaat gtaggaagag tttctggcac ttctcttgag caggagtcaa aaacttcttt    57000
tttgcactag cccagatagt aaatatttta ggctttctgg gccatatggt ctctgtcaaa    57060
actcctctac tttgttgttg tagtgcataa gcagctatac acaatcctga aatgaatggg    57120
tgtggccgtg ttccagtaca accttacaga aaaggcaata ggctggattt ggctctgaga    57180
ctgtagtttg ctgacctcag ctcttgaact gagctcttta actgacctca gctctcgaac    57240
tatggtccaa gatcccgtgg tcctgtttgg tacctccatt tgccctcctt ttcactctct    57300
gggagcatag ctaagttcaa aattgaatta ggtacttgta gtaagagtac acttataatc    57360
ctgggatctt catgttgcca gatattaacc tcttgaagtt tatcaccaca gcctgggcac    57420
ttttctgatt tgctcacttc tagccccacg tttgggcccc ttcacaagca acatgcaga    57480 ttttccagag agctgtatgc tactgaatgt agaaaatttg gctcatactg gcctatggac    57540
tatctgctca ctgccctgat aactatttc caagggagtg ggtgccctac ctttcctaca    57600
cagagttttt ttgctagtct cgccctaaaa attctaggta tcccttgctt ttaggataaa    57660
tatgtttcac taggaccagc cgaaaaatga aaaatagagt tatccaacta ccactttaaa    57720
actggacaag gattttttgtt gctgttgttg gaggggggtgg taaacatcat tttggcagac    57780
caaatatact tttggtgtaa ggcagccttt tgcaaagaca gaacacttgg acaagatttt    57840
gaagtcctgg ttgcctttac tactgattta actacagtat ttgtggactt gggcaagtca    57900
cttcccttct gtgagcctca ggttattcat ctttgaaatg agtataatac ctgtgattat    57960
aattacttct ctggattctg cagagaactg aaggagataa tggatgtaaa agtactttag    58020
tgcccagcac tgctccttat gaaaatgagg aaataattga gatgagtgag ccattgagac    58080
aaccgtacaa aaagtgctga aaactcactg cttaaataag cacctcttac tgcttttgtg    58140
gcactttgta gcaatgtgtt tttattctga ttagaaagta atgttggtt ttgtttggct      58200 ctttgctcag taaacccata ataaggatac ctatttgccc ttggaccatc agttcaaata    58260
ttattttact aatatggaat tatttggctc cagaagccac agttttctta gctgctcccc    58320
atccccactc tcacctcaaa tttttttttc actttatttt tttttcttc tcagggaaag    58380 gtttgaggca aaaaaatgcc ttcttatgat ccaaaaccaa gcatggtggt gatttattca    58440
ccaagcgatt cctgagtacc tgtgtgatgg acatggtaga atctttgtcc tgatccatgc    58500
cttctgatat gcagccagta gccacttgtg gtaatggagc aacagaaaca tcactagttc    58560
```

```
aagtggaaat gtgagatgag aagtaggagg tggagagaac taaccagaag agggtaccca    58620
aataaaccag aaataggtat ttgttagaga aggggcctat tgagtgggtg gcagtggtat    58680
gtgtggcatt acttgctcct gtattctctg cttttttactt agttgtggct ttggtggtat   58740
agtctcagat ctctaagtta tgcaggtaat attgttatgt atcatgtttt ggcaatgtag    58800
actgaatact tgctcataag agtacaggac aatgaagata gtttggtttt atttactgca    58860
tggaaagtac aggatgttta gtaaacagat ccatggcata gtgagttcac cactaaaatc    58920
agactctgag aatgggtttg atttagatgg ctagtttaga atactggatt caggccactt    58980
gattaagaaa ggccattttg gctaattata agccaccaac attgtgtttt caatgttaaa    59040
gcttatattt gtcttccagt taccagaatg taagcttctt gaggaagaaa agaggagttt    59100
tcttaatctc tgaacctata cctgtctttc ttctgtgtct agcccagtgc ctggcaccaa    59160
acaggtgctc aatcaatgtt gattctatgc taccaacaaa aatgagttca tgatgtttac    59220
tattcgataa atgaatgcaa ttttagagtc aattttttact acttacacta catgtagatt    59280
ttcttttttag agatttcaca atgctgattt ttttcaaaat aagcttgaag ctaagtgaca    59340
aagctgaatg atgatttgtt ttttattttt aattctaaac ttacaatttt ccatgtcatt    59400
gccagaaaaa tcattaaata aattatgata tactcatatg gaatactttg caaccattaa    59460
atcaaccatt aaatactatg caaccattaa atcagccatt aacgtattta atggctgatt    59520
taatggttgc atagtattta atggttgatt tgcacatttg catataccaa catattatt    59580
agttgagtga gaaagttag tttcaaatga ctatgttaat atcccctgac tcttgcaaaa    59640
agaaaaccat acatttgaat gtacgtatac gcgtatgttt atacgtgcat agaaaaagct    59700
atgggggat ataccctcaag ttgctaaaag tggctccacc tggagaggga catggaaagg    59760
agctggctaa aaactgaggt ttgttacgtt atacacccct gcacagtttg atttcttaaa    59820
agcgatgatt ataaattcct tttgttattt ataaaaatat tatttaaaac tttggtacta    59880
aaaacagagc tccatcaaca gatcaatgga taaagaaat gtggtacgta tatacagtgg    59940
agtactattc ggccataaaa aatgagatcc tgtcattttt acaacaaaat ggatggaact    60000
ggaaattatt atattaagtg aaataaggca ggcacagaaa ggcagacatt gcatgttctc    60060
atttaatctg tggaatctaa aaatcaaaac aattgaactc atggatatag agagtagaat    60120
gatggtaacc aaaggctagg aaggatagtt ggtggggcag gggagggtga ggtgaggatg    60180
ttaaatgggc acaaaaaaat agaaagaatg ccattctaac tggtgtgaga tcaggaaaca    60240
acaggtgctg gagagaatgt ggagaaatag gaacactgtt tacactgttg gagggattgt    60300
aaactagttc aaccattatg gaaaacagta tggcaattcc tcaacgattt agaactagat    60360
gtaccatatg acccagccat cccattattg gggatatacc caaaggatta taagtcatgc    60420
tgctataaag acacatgcac acatatgttt attgtggcac tattcataat agcaaagact    60480
tggaatcaag ccaaatgtcc atcagtgaca gactggatta agaaaatgtg gcacatatac    60540
accatggaat actatgcagc cataaaaaag gatgagtttg tgtcctttgt agggacatgg    60600
atgcagctgg aaaccatcat tctcagcaaa ctatcactag aacagaaaac caaacaccgc    60660
atgttctcac tcataggtgg gaactgaaca atgagatcac ttggactcgg aaggggaac    60720
atcatacact ggggcctatc acggggagag gggagagggg agggattgca ttgggagtta    60780
tacctgatgt aaatgacgag ttgatgggtg ctgacgagtt gatgggtgca gcacgccaac    60840
atgacacaag tatacatatg taacaaacct gcacgttatc cacatgtacc ctagaactta    60900
aagtataata ataaaaaaaa attaaaaaaa tagaaagaat gaataagacc tactatgtga    60960
```

```
taacacaata aggtgactat agttataatg atttaattgt acattttaaa ataactaaag   61020
gggtacaata ggattgattg taacacaaag aataaatgct tgagggatgt atacctcatt   61080
ctctataatg tgattagtac acattgcatg cttctatcaa acatttcat atacccata    61140 aatatataca cctattgtgt actcacaaaa atttaaaaaa aaactgtaca ttaaagaaaa   61200
acaaaaataa aaactgtagt tcaagttata aacaaaataa aagtaatttg gaggaaaact   61260
atcttcagtt atattggata tttgggggac atttttgtat gttagttagc aaaaatcact   61320
tgaaaaaaag gattcttcct tccatgattc aaaggagcat agcaaaaaat aaatgaaata   61380
aaataaaata ataaaaagag aaaaagaaaa ttattccata aattctactt acttatttct   61440
ggcaaacttg ttgacagcac atgtgacctt tttggtaaaa agacatattt ttatatttt    61500 agttaagttt caaatataaa ttgtttgtgt ttttaaaata aattaaatgg atgacttcag   61560
ccaggtcatc atgaaaacac atgagatatt gggttatgca atgactaaca gtgtgtacgt   61620
tttcttggta tttattcata aactgggaa taaaaatact ttttggctca tttactcccc    61680
aaataatttt atgtctccca aggagaattg taagttgttt gatagtaaat gctatgtatt   61740
ttgtatctta gtgtatgtat gggatttcag cgttagaaga gctcttaaat gccgtcttca   61800
tagtccaacc tgtcttctga tgcttgaaag ccccttgcaa taggaaatgc aaagtagaga   61860
gtagatactc aataatgtgg ttattgaatt atttagaaag aggcattttg agcccataat   61920
gtacaatagg tacttctaga tttattgttt tattctttgc agagctgcag aaaactaaga   61980
aaaaagttta tttcagattc atgtgtttat ttgattaatc tcttcataag tttcattttt   62040
cagctcctgt cagaaaatac agattcttat aaggttcacc tttacccata agaataatag   62100
tataaagggg ttaatgtgaa atacaatcac ttcacagact gtttcaatta aataagagct   62160
cgtagataat tcagtccacc ccaccccatt ttacagatgt tgaaattgaa gcccccacca   62220
aaagtaaaag acttgctcaa agtcacacag caagtcagtg gtgagcctaa ttaggccccc   62280
tgccttccat tttggtgaga ttcctgtgct gatagtcata cccgtgtcaa atcctcttcg   62340
gcagttatgg cttgcccaca gtaatgtgtc ctgaaaaata tgacaataaa ttaagttgga   62400
gacagaacca taacctcttt ataaaaatgt tctggaaagt ttacatgaca gtacgtaata   62460
tataattaga aaggataatt cttatttcat atttatcttt ttgtttcaga ataataaact   62520
aagctatctc tactcagtcc attttaatac aaaaatattt ttaaccagat tgagtttta    62580 tgcttttag gaacttttg tctacctcac ttaattaaaa tactagctgc actaatcact     62640
tactgtggta ggcagaattc tagaatgacc ctgattacct tgtccttgta tgattccttc   62700
ctctttaagt aaggatagaa actgtgaata tgatatcact cccatgatta agctttgtta   62760
catggcgcag ttaactttaa gaaaggacca gtcacacaag ccatttgaaa gcagagagtt   62820
tgggattttt ttaactggtg acagaaagcc acgcagagat ttgaacattg agggtaattt   62880
gaatttgata tgccagtact aacttgaaga tagaggaggc tgcacagaaa gtggccttta   62940
ggaatgatcc ctggctgaca gccatctaga aaatgagggc ctcagaccta cggccataaa   63000
gaattctgtc aacgaacttg aacttggaag tggattcttt ctccagaact tccatataag   63060
agtccagcct gattgacact gtgattttgg ccttgtgcga ccctgagtag agaatccagt   63120
tgacttctga cttaaaaaaa aagtaagata ataaatgagt attgttttaa actgctaatt   63180
ttgtgataat ttgttacgca gcaataaaaa ctaatatatt taccatacaa gtcaaggcat   63240
ttatcctttc atgattcagt ttcttttac ctgacataat ggaattaatt tatactgttg    63300
```

```
tgaaattgta gttgagaaac acgacttcca aagtaataaa atacatgtat tattaatttt   63360
aatagtatta atagtaatga tactgattct ccgaggccta tacaaatcct ttgatacaca   63420
aatgaatagt aaaggaacat aagttgtctc taggtaggct ttcccacaat gcaattttac   63480
gatacagaag tcatatgcct attattctac tatggcagag aaaataagga gcctggaaaa   63540
ctgttcattt gcatcacata catcttaaga gctcactctg aacctggtac cttaataagc   63600
tctgtagaca gtataaagaa gaaaggaatc agacatggtg tctgacctca ggtgtctcat   63660
aatggagtag aagaggtaaa atatgggtca cactaactct actgctaaat aggaagtgct   63720
cgttgccttg agattgacaa aatttgataa gagttcagag gacattttct gtgaactggg   63780
ccttgaaaaa taggatatga gtaggagaag atgaagaagg aaggcattcc agctagagag   63840
aagagcacaa gcaaaagaat agataacctt gaaagtcatc atatgggata attcaagagt   63900
tcagtataat ggaagtataa gatgcataaa ataagtgta gtaggaaacg agtttgaaag   63960
tacagattgg ggtttgtcat agaaggcctt gaatttcagg ctgaggagtt ttaatattaa   64020
catttgtttt tgaacaaagg ggttaactga tcacatctgt gatttagaaa gaaaattcta   64080
gcaatagtgt agataagggt tgatggtaaa gtttggaggg tggtgaggca gagactggag   64140
acagggaggg catttaggat agaaagatga tgaagagatg atttagaaga gttgttttgg   64200
aaaaggagga gagagaaaat gttttagatg tgtcacagag ataaaatggg catggcatgg   64260
tgcaaggagg taaagcccaa tagctttgta aggtgctgag atagattgaa atcacagagt   64320
taagaagttt tagaatcagg attagtacca agacagcttg gctctagatc tcatacttaa   64380
ccattatggt ataatcctga gagggtgggt aacagcaata gtcagaggaa agaacccttt   64440
tatacatgat ggtacaggaa cagcactgtc ttccaacccc acagctgctc tttaacagaa   64500
ggtcagaaac tggggagaaa ttgtgtgtgt gtgtgtgtgt gtgtgtgtgt ctgtgtgtgt   64560
gtgtgtgtgc catttctgga actaaggatg ggaagtagat tagatgaggc cactgcagtg   64620
gagtctgcaa gttactagca ctcacccgtt ccaagaggcc ttaagggtgt tgacctgttc   64680
cctgggcatc accacattct acaaatttat gttcctctga gagaataggg tgattcaatt   64740
tcactgtgct tgaaggttac ttttgggggtt catgtttgtt tgttctaact ctatgctaat   64800
gatctgccaa ctgtttgtca ctttctctaa cccttaggat gtctaaactg atctgttggg   64860
aaatgtgtag catttacagg atggtaggat ttgtaacatg cgatcacagg gctgtctata   64920
tagagtcctt gggaagggga gagaagagta tttctgttac aaatgcagat tcctagggcc   64980
ctcctcaaac ttactgaggt tcaaggattg atatttataa taagcacata tccattttca   65040
ataagcatga aagtttcata ccctcttta atgtttgaaa tcctcaaata aattagtcat   65100
tgatgccaga gtattacata attatggtac agaatgtgtt tctctgaatg acactttctc   65160
ccagagattc tgatatatat tcctctgcac tcaccctgtt tgataattac cagtatatgg   65220
accatttacc tgaagaataa gagtagggtt ttctactatt gttgaaaatg ttctcgactc   65280
ttaacaactt gtgtgtgact gtaacaagat cacacagggt aaacagtatt agcttattca   65340
accactggct gaagaaattt aggaaagtga acacattttt ctttacattt ctctttgttc   65400
tgtgagcctt ttatgctgga atagttttca ctgcaggctg ttattgtctg ccccccagagg  65460 agggagttga cctagcgatg gtaactggag agtgtttttt gaaacctctt tcctaggttg   65520
gttgccaatg gcatctttgg aacagtgtcc ttcactttag tccctcaggg accagtgtga   65580
gaatgggaac tttatgatct ggagctggtt aagtgaagtc caaaaataat taggaaagtg   65640
tttccttccc tgggaatgag ttcagtagga atctcaatat attgtagagc acgaaggact   65700
```

```
cagcatcagg catttgcaaa ggattcttcc agttgcctgt gttacagagg acacagttgg   65760
aatttccttt tagtgttgag gggagatgtg tacatgattg tgagatgact caccctttt    65820
gcttagatgg ttccactttc attgtggaca gactctttgg agggccagtt tggcatgcac   65880
gtgtgtgttc attccatcct ggagcattct ttatgagaaa gccatttgtt gagtggtttg   65940
ccattttgtt ttacagccac tctgtgggct atgaaatggt catctggccg ctttatttgt   66000
ccctaaaaaa gcagtttttt cctttcttat cttcaaggct gccaagcagc agaaagagta   66060
actcagggaa gccatgtgat agccttttat ctgtctgttc agaaactgat gatgtatcgg   66120
atttgataat tcatgaaatg tgaggtttac tggtttgcat ttgcctcaaa atgggcatgc   66180
aatattttgt caggtaacat aatagataat tggcattgct ttattgaagt gaattaattc   66240
aataagccta taagtgcctg acatgtgcca ggcactgtgc taggcattct gttaatagat   66300
gagacaaatc tctgtctttt aggtgttttt agtcaaccag gggagacaaa acacctttaa   66360
aaagacaaaa acacttttta aattgctatt ttaaaaaaaa ttcatagtgt acgtaatat    66420
aaggtgctga atatgtgatt gattctgagg gaaaagagtg ataagggaaa attctcagag   66480
aaactcaagc tgagggaaga aaaggacccc agacagaggg actaggctag agctatgcta   66540
ctacattgca ttaaggggaa tggcacatac ttcactgttg cttcagcaga gagcaggcct   66600
gtgttaggtt acaaagggcc ttggatgaca tcctgtgggg tttttaaaatt ttatttaatt   66660
tttaattgac aaaatataat tatatatttc agtggggtac aatgtgatgt tatgatgtag   66720
gtatgcaatg tagaatgatt aaatcaagct aatttgcata tttatcactt cacatactta   66780
tggtttggtt acaacattta aaatttattc ttaacaattt tgaaatagac aacacattat   66840
tatcaactat agtcaccatg ttgtgcagat ttcaaaaact tctaacaaaa acttttgcc    66900
cttcgaagat attgaacttt gtcttatgaa catagtctta gaaggattta aaaaataatt   66960
tgctattcac tgagtacttc ttatgtcacac tgtgcatgaa atgagtatta cttttctaa    67020
tattagtttt cttgattgag gcttggcaat tattagtttg tatgcctgta gaaggattat   67080
aaacagaggt gtatcccagt aggatttgca ttttagaatg atgactgcga gtaaaataca   67140
gagaagtaaa accaaagata gtgggatcat tcaggagtct gtttcctaca ctgaacagta   67200
gttgagcaaa aaaaggatgg gcagaatgtg ttgcttctgg gtactgcaaa ttcatggcac   67260
ttgaatgaac aagtttaagc cttttattgg ctctttgtgc atatcttcaa catgtatgac   67320
tacaaagaga ccacacggtt ttgttgttgt tgttgttgtt gttgttgttg ttgttttatc   67380
tgaggtggag tttcactctt cttgcccagg ctggagtgca atggctcgaa tttggctcac   67440
tgcaacctcc gcctcctggg ttcaagcgat tctcctgcct aagcctcccg agtagctgga   67500
attagaatca tgtgccacca ctcccagcta attttgtatt tttagtagag acagggtttc   67560
catgttggtc gggctggtct tgaactccca acttcaggtg atcctcccgc ctcagcctcc   67620
caaagtactg ggattacagg tatgagccac cacggccggc ccacacgta tttttgaaag    67680
aacagtgagc ttggaattag aacactagtg tctgggccct ggtgctactg cataagtaat   67740
tatgaatcca tagccatctt gttgctcttc ttctctaagc cttggtttct ttagctataa   67800
aatggaaagt tgaaactttc tagctacttc tttgagttat gagtaacaag ttaggtaata   67860
cacttgaagg agaatgtgct atacaaatac tggttcttaa gacagctgtt gttaatgtac   67920
tgagtattat gcttacctca cagggttgtt gtgagcatca aatgggataa tggatttgaa   67980
agcattttgt ttaaagtgtg attcaaatgt taagaattag taaaaatagt aaaagagaac   68040
```

```
aattcattct ccatccagat gttccgtccc cacttatgtg ctcattcaga gttgtacaga    68100
aaaacctcca cgtaattttc acagactgga gttccacatg taacagaatc atatgggacc    68160
aaaaaagctc tctattgact tctttcctgc catattttgg ctctgggacc aacaagacac    68220 ctattttttca tgagctgcct gccaccaact ttgggctcac atctagttct gttgcccatg    68280
tgcatgctga atttgggccc atgtccccag atctaacatg aaactcaagt ttccttctgt    68340
tcaaactgtc caggcataat agtcttgaag tgtgatgccc aggagagctg tagattttc    68400 actgtccaaa aatcaacatg aaccagatg tatctgtaaa tctagtttca tgccactttg    68460
tagtcaatgg aaatacacta gcaggcagac aagaccagag tttactattt ccagcggaat    68520
taatagccac atggaaactt tgcctttggt atctgtgaga tggaagataa aggtgagaaa    68580
tcaaagcagt tcccacctca tcctctaaat tccaacataa agaggccttg aatatccttc    68640
tatcttattg tatatttcat taacagaagt atgttcctaa ttacttagtc attctatctc    68700
cattctcctt tgttttaact tcagtggtgc caggttaaga tgctctggct ttcagctttc    68760
atggagcatg gcatgttttt aaacttattt ttaaggacag gtatgttggg aagatcctag    68820
ttcctcatct ctttgctcct ggcaaggaaa tttagaattg cctaaagaaa agctgtattg    68880
gccaacataa taataaatca gtattagtga atctaaagcg tattggagaa ctttgtaaca    68940
tgagttgaaa ttcagacctg caatgaagtt tttttaaaag atttaaaatt gaataataa    69000 aaaaaaagtt aaaaacaagt aaaacatatc agtagttaat cattctacca aaatttggtt    69060
ttacgtttgc atatttaacc attttttattt tctgtatttg tccatgaaca tgtgtttttg    69120
tatattgttt atattaaaca tggttttaat catggcttat ttcttttatg ttttacttct    69180
tttcctttga cataaaatat tgtatttta aaattttaac tgcttcttgg tataccattc    69240
caatataggt ggctacatag attgaagtta aaactaatta caatcagaga aaattaacaa    69300
ttcatccctt cagtctcatt agtcacaagt taaatactca atagccacat gtatctagtt    69360
gctaccgttt tgaatagaac agatataaga cattttcatc aacacagaaa attcagttgg    69420
aaagtattgc cctggagtaa atgtgccata ctgtactaaa tcattttttct cttgttggac    69480 atctaagtta tttcttattt ttttaatatt ttatataact tgacggtgaa tatacatacg    69540
tacatagcta tttgctttgc tgaattattt cttagaatca atttcaaaag tggagttatc    69600
aggtcaaaga gcctgagaag attttttgga acctgtagtg tattgccata gtcctttcac    69660
aaaagtttat gtcaacttaa agtacttcta gcagcaaatg attgtactaa tttcgctgca    69720
atctcaacaa cactggacat tataagttttt tattctaccc tattttccat taaaagataa    69780
cttatgcttg attgactttg catttttattt tattattaat aatgttgtgg tttccttttt    69840
ctgattttat ttttagttaa ggtatccttt aattttaacc tgatattttt ctctaaaaat    69900
tattctaaga aaagacaaag gtgatgtcaa atatatcctg agtttttcatt ttttcttgca    69960 tggaatttgt atatttgcac ctttgcccat ttatatttatg atttcttagt gtcttcccta    70020
tcaattttaa tgaagatttc atatatatca atttttccac aaatataatc ttttttaaaaa    70080 tatattttt ccacgatata attctaatgt attctccgaa atgttggaaa aacttaagta    70140
gtcatcaaag catttgaaga ttttttaaag gttgttttta taccagtctt aaatgttaat    70200
ttaagggtcg taaaagagg tgaaaattaa atcattttttc agtaagggt aagaccattt    70260 aactcttgga aaatacagga aacatgtaga tttctagagg ccaagaagga ggtagggatt    70320
aattattttg taactgcccc caaccttcta acctataatg aaagaaccac tgaaggccct    70380
taaatatttt taggcttaat tggctgtcct tgtacttagg gcacatctaa aaatcctgag    70440
```

```
gcaaccactt aagagaacat gcttttgtta attcacaggg agctgtccta agagtgtcca   70500
gaatcctctg tagtcttggg cctggtgctt gagagaccca aaggaaaggt caatggaatt   70560
gcagcttagt gttagagttt tcatggatca cactaattag ttaatgtcat aaaggtctct   70620
ctcctgttat gggaaaaagc agcaaatagg aacttctggt agggtgctta aagttggttt   70680
gatatttttc ttagtaattt taactaataa aagtaataca tgcttatggt agaatgataa   70740
acctgaacga aaaggtatga aaatgtagaa gttctcctac ttatgacctc accccttctt   70800
tgcactccca gtttcactcc tcagagggta accatagtga ctagtttctt gtgtttggtt   70860
cctgagattt tctgtgcata tatattgtta gatatatgca tattatattt tcaaaattcc   70920
tatcacatga caactactgt tctgtaactt aatttcttca cttaattaat agaccttata   70980
tatgcttttc catatcaata tatatagatc tatataagtt ttcctaaagg ttgcacaatt   71040
ttcaactgta tggctgtctt gtaatttact ttttgtttcg cctactaatg gatatttcat   71100
gttttcataa ctcttttgat attaaaagta gtgctgcaat taacatcctt gagaggcagt   71160
atatatggtg tttaaggtga atggctctgg agccagacta ctttggactg aatattgatg   71220
ccactaattc cttgctgtat gaccttaggc aagttgctta atttctttgc ctcagtgtcc   71280
ttgtgtgaaa aaatggaggc aataatggtc actatccagt agagttttta tgaggattta   71340
ataagttaat aatgcacatt aagaacttag ttattttttag attaagtagt gaaggactat   71400
ataattgtta gtataattgt atacctttat tagcatactt ttgcatgtat agcaataaga   71460
caaattctta gatgtttaac agttggacat aaggagtgta cacattttca gtactggtag   71520
atgttacctt ttccctgcca aaaattgcaa atatttgata ttaactttta aaatcttagt   71580
aaatctgata agtataaata acaatttatg atcattttaa gttgcctttc ttaattttgt   71640
gtgaaaatga gtatcttttc acatgttttt tggccattta tgtttctttc catgtgaact   71700
aactgttctt ggccgttgcc tattttttgt tcctgttact atatggcttt tcatctgttt   71760
ctcgttgggt tatggagctc tttgtatata aaaggattta gcctcttgtt atatgtgtga   71820
caaatacttt ttccaattta tatttcaact ttgcttatgt tttcctattc atcagtctaa   71880
aattatgtag ttaaattcat cattgttttt tcttacggct ttggagtttg gagatcatgc   71940
ttcaaaggtc tttctaggtg gggttgattt aaatcaagta ctggaagtat ttttgccaaa   72000
aagactcatg aattatagat gttagagcta aaagggacct tagagatttg ctagttcaac   72060
ctccttttct tcatacccttt ttaatttttc tctgcagatg aaaagaagtt tagtcccaaa   72120
gaaagaaagg actctaaagg ttctccagta agctaatggc aaaaatgtag actgaaactt   72180
ctagctcctg atgggtattt cagtgatcat tcaatttaac cagatggttt cacaaaagga   72240
gctttctact aaaaaataaa atacatattt aagcaactca gataaatatt ttttatttat   72300
cagattaatt tttacttaga gattcatcag catatgtact atatatgtac aaatcaccta   72360
tgtgttttgg atatttagtt gaacaaatgt gcaaatattt taaccaaagg agcatatcta   72420
ttttcatttt actttcttaa tggttttagt tatgaatgtg aaatgtgtac ttaccttaac   72480
agaaattaag tagattttttg gtctgacata tatgagaact gaaaagcatt ggcttggctg   72540
ctaactgcat tctcatcttt cttccctgc tttggcaaag tctgggatta aatctaatac   72600
cttttaaact gtttgggact tcagccagag tgacctgtct tgaattcaga actgtgcaga   72660
tcattcccca ttctaaggtc ctctcatggc tcctcattgc ctgtaggatg agatccaagt   72720
accttagcat agcttacgca ctgcagtcac ttgacctcta gcacctatgc agtcttccag   72780
```

```
tcttatttcc acattcctttt gcacatgctg tttccccatg tggggcaact ttttcttgc    72840
ctgtctgcct gcctaagcca acttaaataa acatgatttc tgtaacttct gtgaagcctt    72900
ttccaatctc tccattccaa gacgaaggtg tttctatagg catgacttct ggaatggcag    72960
atcaaggatc tggtggaccc tctactcagt gaaacaacca tttaactggt aaaaatgatt    73020
taactggtaa aaatgatcaa tcaaccattt aaaatcttca gaaaatatcc taagggcaca    73080
tagcaaaaag agaaatgttt attcaagaaa agctattaag cctcagtaaa acagcaagaa   73140
gtctatggca tttgagtcat gacctgttcc tattccttcc cttagctcca ttctacaggc   73200
aagtgcaacc aagaagacgt aggcttcctc tctttcaaaa tcttactcca tagttataat   73260
ttcaccctac aatggggcag gccacaagca tctctttccc cccccacccc agccctatat   73320
tacagaagca ctgttctagg aaggcatagc tgagaggatt ggagattcct tcctcaccca   73380
cttctacat atgagggctt tgccccaggg atggtaaacc aagaatacag gggtcctgct    73440
tgtgcctgcc tcagctcatc tataaggtaa aacttccaca ctaggaaagg ctaattaaga   73500
ggactaggga acataccatt atccccaggg tccacttgta gaacagggga gttattctgg   73560
gagaagcagg tcactgcccc acttgtggaa caggggagtc actctgggag aagcagatca   73620
ccgtccctgc tcccaattct attgcagtga cagaagttct gtcccaggga aaggcattag   73680
gatggagaac tctatagttc tccctgaggt gactgacttt atttggaaca gagcatgaag   73740
aagcttatgc ctaagggcac tgtcaaaaat aatgcagatc ttggtggtaa gcaattaaga   73800
gtggattggt agctccatga taactagtag caacaagcaa acagcagac caacatggag    73860
gataccagag aaccagacaa aggaatcact aagaagcgcc cttgtggaac tacactcact   73920
gctgggtgtg tggaaagtta tgcatgtgtg ctttactgta ccctctcaaa agcaacctaa   73980
acaggatgtg gcgtaggctc taagcattc ctcaagccac acatggatcc atcagtaaaa    74040
tatggagggc ttaaggttaa aaaggcttaa gtacaatgtc tggccctaca ttttctacat   74100
gttatgccac cctgaccaag gggcaactcc tacaaagcca ggcataataa taaaatcata   74160
tttgtctctt ttggaatgga tgactgtgcc taaaactgtg cccttttgaaa agcaactaga  74220
gagataattt ctgaagtgtt tgtccctacc tgaatgcggg caaaattcta aactccctga   74280
agtgtgaaag tgttttccaa gtcacatgca catccagtag tggtaaaggg taaaaatcta   74340
actgactaag agggcttcac agcaacatta accaaaaagt ggtttatgta atctttgcct   74400
acctcataat tccctaggca ttctatgcta ttctgtactc agaaggctta aaagtcaggt   74460
tagggaaagg aggcctttga ggttactgtg cagaggcagt gctgggaaag gaatgaagtt   74520
caataaattt aggccatcat ggtttaaaga atggattatg tagataggaa ggataaagga   74580
aacccagagt caagaaaagt aaagcttttc attggtgcta tgccaaccca tatctgagcc   74640
tgaggcaaaa ggaaaaatgt gctccccaat atacatttat acaaaatatc aactaatttt   74700
atttgttgaa ctgaatttaa aaagtcaaca aaaattaaaa ataaaaaaat cgtgactata   74760
ttcttaataa gtggtttatg taaacccaga gttgaccaat gggatgccag tctcaaccat   74820
aaaaacaaac aaataatgtg agtagcaaca ccagaagttt caagtgtca gggaaaccag    74880
tttcacagaa gtggttcagc caagtcacta acaaagaaa tgactaagca aaaaacaaaa    74940
tgagtctcag agagggtcag gtcaatatcc agagttgtta caatatagta actaaaatat   75000
tgttttgaac taaaaatttt gaggcatgca aagaatgagg aaagtgtaac tcatacatgg   75060
tattatatga aaaaatcaac aaaaaactat ccatgaggaa acaaggatgt tgaacttaac   75120
taggcaaaaa ctttaaaaat cagctattta aacatattca aagaactgaa ggaactatgt   75180
```

```
ctaaaatact aaaataaagc gtaataacaa tttctcatca agtagagaat gctaataaag    75240
agatagaagt tatagaaaaa gaagaaaatg gaaaatctgg agttgaaaag tataactgaa    75300
atgaaaaata cactagaaaa ggtcacaaga agatataact tggcagaaga aacaatcagc    75360
aatttagaac atagatcaat atagattatt cattttaaaa gatagaagga aaaaagaat     75420 gaaccaaact gaagattccc aaagaaatgt aggacatctt aaaggcacat cattaggaga    75480
agaaaagaag aaaaagaaaa gagcagaaag aatatttttt aaaaatggat aaaatcttcc    75540
caaatttaat gaaaaacatc aatctacaca tcaaagaaga ttttttttta atttcaagga    75600
ggaaaatgta aagatattga tacttagata catcatagtc aaaatattgg agccaaatat    75660
aaagagaaaa ttttgaaatt agcaagagaa aaatgaaacg gaaccacaat aagattaaca    75720
actgattctc atcagaaata gcagagagca gaaggcagtg caatgccata ttctaaacat    75780
tgaaagaatg aaaaaactgt cagccaagaa tcatatattc aacaaaagta tctttaaagg    75840
taaaaatgaa atgaagacat tcctaggtaa acaaaggctg agaaaatttt ttgttagctg    75900
acatgccttg aaagaaatac taaaagcttc ctagacagta gcttgaatct gcatgaaaaa    75960
agcaattcca ataagggaa atttgtaaat aataaaaagg tatcattata tattattttc     76020
cacttaactt acttaaaatc aatttcttaa agcactatct gtaaaaatgt attgttattt    76080
gataataaaa tgtaaaagag gggagtggga attaagctaa attggagtaa ggaaatggta    76140
tcatatggta aattgaattt acagaaagaa atgaaaaaaa ttaagtggca aatatgaaga    76200
ttaacaaaaa cttctataaa ttaattgtgt tctctttccc ttagcttctg taaaagacat    76260
aagactattc aaaatgacaa tagcttaaac gcattgtttt attggtaaca aatatagaca    76320
aattatgtac aacaattatt attatacaag gagagagaat ggagctatag aggattaaag    76380
tttttataac ctattggaac taagtcagta taaatctgat gtggattctg ttaatttaag    76440
atatatgtta gaagccccaa agtaatcact gagaaaatga tgcaaaaata cagtttaaa    76500 aagttaaaaa catagtttag cttatgtatg cctagtattc cattatttt ttttttatac     76560 tttaagttct ggggtacatg tgcagaacgt gcaggtttgt tacataagta tacaagtgcc    76620
atggtagttt gcagatccca tcaacacgtc atctacatta ggtatttctc ctaatgctat    76680
ccctcccaca gtcccccacc cccctcgaca ggccctagtg tgtgatattc ccctccctgt    76740
gtccatgtgt tctcattgtt caactccac ttacgagtga gaacatgcgg tattccgttt     76800
tctgttctgt gttagtttgc tgagaatgat ggtttccagc ttcatccatg tccctgcaga    76860
ggacatgaac tcatcctttt ttatggctgc atagtattcc atggtgtata tgtgccacat    76920
tttctttctg cttgttccta ggagaaagtg gctgaagctt ccagagagaa gctgagagta    76980
gtttaattct ttttgccata aacacggcaa cccagttttc tgcaagctgt gttagtttgc    77040
tctctccttg gttcatccat tcatttattc atagcttcca taaatgttta acaaacatta    77100 attagggggcc aagccatgtg ctaggcgcag gggataaaac tgtggacaaa acaagccca    77160 gctactctta aggaactgat agacaaatgg accagcaaac aggctggtcc tgtttttgaag   77220 gcaaagtgcc tggtgctcct gatctcatga gcacaaagca tttagcctaa atctcatcct    77280
cctaaggcct cagaaacaag gccttatttt aataactgca agtcagtcat ttgaagacta    77340
aatcatagaa tcctagaaaa ctagtactgg gagcaaaaca aaagaatggg atgagcatga    77400
aacatatatt cagaagttgt ggtgtgtagg tgtataagcc aagctctttt cttcacttgc    77460
ttgctaagtc acttagcttt tctgcctttt tctttgctct gtctggaaat tgagttaatg    77520
```

| | |
|---|---|
| aaatatatct acatgataga gatattgaga tgattaaata agatgctgct gtcacccagt | 77580 |
| atgcccttac ctgctgtact tagaagtatc tgtaattcat tttctaaact ttttgtatga | 77640 |
| gtgcttcatg catgcccacc accatggaag ctaccttaag acagtgaggg cctttgttta | 77700 |
| acttgtttgt actgtatcct cagtctaatg gtgtctggct tatagtaggc accgaataca | 77760 |
| attttattga cagaatggat tataatgaat gtgaaggcat ttttaaattt atgaagtgtt | 77820 |
| gtgcatattg ttgttaattt taagctgttc agttaaagaa cccctaatcc aactctcttg | 77880 |
| agttttatag atatcataga agatatatct tcccttgaca cagaagcttt ccttgaagct | 77940 |
| tcccttgact catctatttg cctcacagag tgattgtgca gatcccacaa gataaattta | 78000 |
| tgtgaatgtg ctttatgtgt ttgaagcgct ccacaaatac gggttttata agttgagaaa | 78060 |
| atagagtcag ggagaaaggt gactgatcca aggtcatgca gcgagttagt atcagaattt | 78120 |
| atgatggaat ttcaggctcc caatttccag tccagtatac taaggcagat tccagagaag | 78180 |
| aaacagtgga gagcaggcac tgacgaggga cgaagaaaag caggctccgt ctggctgcaa | 78240 |
| cttgtctctt catggcaaag agaaactagg acagtactat gccagagacc acatgataac | 78300 |
| tttgcagaat ggaaagagct tgtttaccaa attgaacact ttatctgtgt ttatctaaca | 78360 |
| atgacagttc caccagctcc ttaccagctc tcttttgcct agtttaacaa tataccaact | 78420 |
| atgcacatt ttccttctca gtttttattc tagattacat tttgttcaac ttcatcttaa | 78480 |
| tgtgtagtat agaaagagta aggtaagagt ataacaagtg gttattttcc atttctactg | 78540 |
| aggacagaga aataatctaa gggatttgta ttagatatga agaagttcat ggccgggaca | 78600 |
| tgagagatac tgtgatagaa tggatattgt taagtctttg gtagttttg aggggaaaaa | 78660 |
| agagaaattt tttatttgtc tgataatagt ttagcaatgt cttaatttag gattcaaaag | 78720 |
| ttgttcaggg tccatcttgg ccttcaaatt aagatgcctg ttgagagata acgttgttgt | 78780 |
| tttcaaactc cattctgtga cttaagaatg agagaaggag gaagaaaaga ggagaaaatt | 78840 |
| ggagggaaaa gtgcccaggc agtgtcaagg ctagacactg gaaatttatc aatgaaagcc | 78900 |
| acatggtgga tgggaatcag atatgtgcat caattatttg tgttctaatc catagagaag | 78960 |
| taccgtataa tgcaccaaga tatgagatgc tttgaaagaa gaccatataa gtggagatgt | 79020 |
| gttcctattc tatctaggga tagagtcaga aagggcttca ttgaataagt ggcagcctct | 79080 |
| tgggctgaga cctgagttat gagatgatgt ggcaaaggag acagatgatt gggggcaagg | 79140 |
| tggggtcatt gaagttggag gcagtgacaa tataagcaaa gctacagggg catgaaacag | 79200 |
| caaggttaga ttagggaatt gcaacagggt ggtactgctg gaaggtcaca tggaaaagat | 79260 |
| tatgagagta ttgagataag aagctagaaa taagctttga atgccatcct agtgctttga | 79320 |
| atttgtatcc tgcaagccaa gtggttttca cttggtcatt taataaaatt gcagattctc | 79380 |
| aggtctcacc tgtaacttca gattcagaag agtctgtgct aactgaaggt ggaatcagtt | 79440 |
| tccatattgc taattagctc ctcagaggat tctaatatat cagtgagtta caaccactgc | 79500 |
| tgtaagccat aggtagttat tgaaagctgc tagggagagg agccacagaa gcagatgttt | 79560 |
| tagataggat ccctctgggg ttctgtgtaa tttatggact ggactggaga ggatcagaca | 79620 |
| ggaaacagaa agacttgaat aaggcagttg cagttagttt ggaggcaaag attctctctc | 79680 |
| tctctctctc tctctctctc tctctctctc tctctgtgtg tgtgtgtgtg tgtgtgtgtg | 79740 |
| tgtgtgtaat tgtaggaact atttaggcag taaaattaac agatattagt cactgattga | 79800 |
| ctgattggat ggcagtgata ggtggggtgc attgagggaa ttgtattaca ttaagtccag | 79860 |
| gatgactcat ggttttctaa gttgagtcat tggggattgc cagccaatgt gagaaactat | 79920 |

```
atcgtctaat agttgatctt ggagttagac ttgaattaaa atcttgaagc catcaattgc   79980
tgtatgtggt cttgggcaga acacttaagg tttctagacc tcagctcttt cttctataaa   80040
ataaggataa taatgcatac ctcatgcatt tgttgtaaag actaaatgag gttaaattat   80100
gtagagtgta gtatagtaac tagcacatac agtgggccag taaacgtcag ctgttattat   80160
tgtgctatat gttgtgatgt gtactggagt gagatggggt aggggatttt ttagtctctg   80220
acaatgactc ctctccccat gatcaaaatc agaaaatcag tctcttatgt gctgagaaga   80280
gagacacttc tcccaagtgt ttaaggctaa taccttgcct tgttttgcct tgggccagac   80340
ctcactacac atctgtttaa gagataaggg taagctctgt tcttggtgag tatctcagtg   80400
gggctgtttt tctagttctt gtagtttctt tgggccaaca tgaaatgtct aaccttggct   80460
tcttggttgt ggattctcgt caacatttca ctgctaccca agttgtgtct gctcacatga   80520
tgctatcttc cttcttttgg gtttccgaag ccctcagaca cttggctgaa cacttttttc   80580
acatttctta agctatatca tctgtgtttt ccctgccaca gacaaagtca caaaaggact   80640
ttaagatagg gtctttttcc ccccagggtt tttatacatt ttgagtaagg gcaagtggta   80700
aatgctgctt ttctgcctta accagtagtg tctgacagag gaggcagcat gatgattgca   80760
gagctcactg aactgaaagt cagatgcctt acccacctgg actctagtac caaggggaag   80820
atggagtggg atgggaaaa tgggataaa ttatcattta ttttgagtgt gccaggccct   80880
ttcccatgta ttgtctgatg catttgtcac aattctcttt gggtttgaaa tgtgattttc   80940
ttcattttat agataaggaa acttatggga agggagatta ggttcatctc gtgcccaact   81000
ttacatggct agtgatcaat aatagtgaga ttcaaactca ggtttctctg ttccaaaacc   81060
tttgcttttt catcttttga cactgtaact tattagaaga tgtctttgac tctgagtctc   81120
atttgcctca actgtaaaat ggagctctgt aacccttgct ctgtatgaca gtaaatctcc   81180
tgagaccaga tttatgatag gggacaagga tatttgtatc tttgggcccc taatgtattg   81240
aaagtgcctc tcagtgcctg gcacagagaa gggcactcaa taaatattta ctaatcattt   81300
tccagaaaga gggtagctcc ataatgagcg agattcattt tgatggctgc tgtagtgttt   81360
aatgttttta ccacctgtta aaatgatttt ggagtataga tggataactg atgatggttg   81420
ttatatagat ttttcatag gttgcctgtt ccaaattcta tgccctggaa gaagctaaat   81480
atccagaatt tgacaggaaa tattattcta caacagatcc ctggcataag aacagtaaca   81540
cctctgttct attctcagac ttgcctctga ataactgttt ctcctggtca attctctgtc   81600
tctatctggg attgaaactt ccccctggac aatgagggag ttgaactagt ttagtggggt   81660
tcagccttga gtggccatta caattatttg gggattgttg aaaaaaattg gatgcccaga   81720
tttttgtcgt tgttgttgtt gtttgttttt taattatact ttaagttctg ggatacatat   81780
gcagaatgtg caggttggct acataggtat acacgtgcca tggtggtttg ctgcacccat   81840
caacccgtca tctatattag gtatttctcc tgatgctatc cctccctagc ccctagccc   81900 cagacaggcc atagtgtgtg atgttcccct ccctgagtct atctgttctc attgttcaac   81960
tcccacttat gagtgagaac atgtggtgtt tggttttctg ttcctgtgtt agtttgctga   82020
gaatgatggt ttccagcttc atctgtgttc ctgcaaagga catgaactca tccttttata   82080
tggttgccta atatttcatg gtgtattgaa ctgcttaccc cagttcaatc aaataagaat   82140
acagaatgtt gagaggagca tcagtatttt aagaaggcca cctagtgagt tcaatgtgca   82200
accaaggatg agaaacactg aactagatga ttggtaaggg ccatccaact ttgatagtcg   82260
```

```
acaagagaca atgctataga gtatggtgga cagagcatgg gctttagagt tagccaggca   82320
tgcattcaga ccctggctct gttacttact agttgtgtga tcttgaagaa atcaaaatgg   82380
agatacactt tgtccctggc agtaatagtt gtggggatta agcacctttg ccagtgctta   82440
ggacataata aaccccagt aaatagcttc tttagtatca gaagttcaga tggaagatgt    82500
gagaaaaata ttggttcagt aagatttaac atgtagatta aaatcaagta tttaaaaaaa   82560
ttttcctgtt tctttagcaa tggattccag aaacataatg tggaaatagc tctgagtcct   82620
aagatttgat gacattgcag aaagaaatct ggctagttgt cccatggctg attggctatg   82680
atggctaaga agccattgga aaaaaaaatt ggctcacaga agacagcaga tgtggcttgg   82740
gaaatgcaag gacatgactc taataaggat ttgtcccatt tatgagagtg attccaggag   82800
aaaaggacag atttgtattg tcagtgggat atgctgttaa aaaacacttt tgctaccacc   82860
actccagctg tcttggcatg tttgttggtg atgtaagcta cagaaaatgg aaatcaccaa   82920
aagggctata gcagcctgat gcatagtgac aagtaattgt tctattcatg gttatgtgtt   82980
gtacagagca cttgctgcat gtcaggtttg aggtttgagt atgcattagg gccatggata   83040
cccccatctt ctctctaagt agatttcaaa gtaaatattt gatgagtatg taaaatattt   83100
agtttggtca gtcataggac tgagaacgtg gtggggtta cctcctagta tctgcaggca    83160
aaaaaacttt tttcttccta tagcaattgc catctcagcc ccttttgcag cgtttctctt   83220
gctcactttt gcattaacca tctgtgcact tgtcttagcc tcaaacaggc catgaaagct   83280
ccttgaggat aggggctatg tcttttcat ctttatatat gcatcattta gcagagctgc    83340
tcctttataa tgtactaatt actgaatgaa gggatccata gatgaataaa tgaatgcaaa   83400
gtaggagtga cctctcttct gtctttcttc atgatgggga ttagtgtgtg tgtataaggg   83460
aataatcgtg tcacataaaa tataaccctta cttagaaggc aagacttcca gaatggtgga   83520
atgagaacca accccgccc ccataaattc accctttcat gaaagcaatg aaaacactag    83580
gaaacgttgt gaaattaac ttttccagaa ctctgggaag gaaacaaagg tttccaacaa    83640
tctgagaaga atgtattcaa gaaaaacttc ggtaagttct ctgatcacag tggaaataat   83700
aaacaattag taatagaagg atatttggga aattcaccat tgtagaaca taaacagtgg    83760 atcaaagaag aaatcataag gggaatgaga aaatactttg agattaatga aatgaaaat    83820 acattatacc gaaacttaca ggatacagcc aagctaaagc agtacttaaa gggtaattta   83880
taactgtgaa tgcctacatc aacaaagaca aatgatctca aatcaagaac ctaactttcc   83940
accttaggaa actaggaaag gaacagcaaa ctacaaagaa agaaggaaga aagattaata   84000
aagactagaa gggaaataaa tgaaatatag aatagaaaaa cactagaatc aatgaaatta   84060
aaaattgttt ctttgaagag atcaacaaaa ttgaaaaaac tttagtcaga ttgaataaga   84120 aaaaaagag agaagattca aattatcaaa atgagcagtg aaactggggc catcactacg    84180
taccttaaaa agaattctca aaggattaaa aggaaatacc attgcattag tttattctca   84240
tacagctata aaaacaacta cctgagactg ggtgtttatg aagaaaagcg ctttaattga   84300
ctcatagttc cacaggctgt acaggaggca tggatggtga agcctcaaga aacttacaat   84360
caggtggaag gctaagggc atgaaagaca tgtcttcaca caatggcagg agagagagag    84420
agagcaaagg gggaagtgcc acaaactttt aaaccatcag atcttatgac aactcactca   84480
ctacaatgag aacagcaagg agaaaatctg cccacgtgat ccagttacct cctacgaggt   84540
cccttcccca acactggaaa ttacaattca acgtgagatt tgggtgggga cacagagcaa   84600
aaccatatca accatactgt atgccaaaaa cttagatgat ctagatgaaa tggacaaata   84660
```

```
ctcagagaaa cacaaactat ctgaagtgtc tgaagtgacc agtgaagaaa cagaaaatct   84720
gagtagtcct gtaacaagtc ttgtaacaaa actggattaa taattaagaa acttcccaca   84780
aataaaaacc caggttcaga tgtcttcact ggtgaatatt atcaaatatt taaggaaaat   84840
ttaatccttc acaaattctt tcaaaaattg gaagaggctg gaaccccttcc cttcccaact   84900 aattctgcac agtcagcatt accctgatgc caaaaccaaa gatatgacac aaaaataaaa   84960
ctgcaggcta atatcacatt tgaatataga taactttcta aaaatcttaa caaatgcta    85020 gcaaactgaa ttcaacaaca aataaaaagg tttataaagg gtgaccaggt aggatttatc   85080
tctgcaatgt aaattaatat tcaaaaagct aagaatagga ggaaactttc ttaactttgt   85140
aatggacatc tctgaaaaac acacagctaa catcatactt agtagtgaaa gactgaaatt   85200
tttccttgta agatcaggaa caagacaagg atgactgctg tcaccatttc aatttaccat   85260
tgtattgtag gtttattgta ggctcaagtc aagcaaaaaa aaaaaaaaaa gtaaaagaca   85320
cccatattgg aaaggaagag gtgaaattat ctatattcac agatgacatg atcttataca   85380
aagaaaaccc ctaaagaatc catgacaaac tattaaaatg agtaaacgag ttcagcaagg   85440
tttcagaata caagattaat gtgcaaaaat caattgtatt tctgtgcact agcaatgaac   85500
aatctgaaaa tgaaattaag agaacagttc actcacaata tcatcaaaat accagaatac   85560
ttaaaaataa atttaacaaa agaagtgtaa gacttgtatg ctacaaaccg taaaacactg   85620
tggaaagtaa ttaaaaatct aaataaatag aaaaacattc cttgttcatg tgccagagga   85680
ctcaatattg tcaagatgga aatactcccc aaaggttgaa ggaaatccct gtcaaaatcc   85740
tggctgtttt cttagcagaa aatgaaaatc tgaccctaaa attaatattt aaatacatag   85800
aatctaggat agccaaaata atattgagaa agaaaaacaa agtcagtgta cccacgcttc   85860
ctgattccaa accttactac aaagcagtgg taatcaagag cgtatggtat tggcatacgt   85920
acaaacagat caataaatgg aatactattg agaatccaaa aattaactct tacatttaag   85980
ggcaattgat cttcaaaagt gttgttaaga caatttaatg aggaaagaat agtcttttca   86040
ataaattgta ctggaaaaat tggatatcca catgaaaata aaagatgttg gaccacttca   86100
aacctgcaaa aaaaaaaaaa aatgatctaa tggtgtatca tggatctaaa tgctatagag   86160
ctaagatgat aaatctcaga agaaaatatc agagtaaatc tttatgacct tgaagtaggc   86220
aatgtttttt tggctgtaac accagaagca caagtagtaa gagaaaaaaa aaatggactt   86280
catcagattt gaaattttg tgctgcaaat gatgccatca agaaagtgaa aatctcaccc    86340
acagaatgag agaaagtatt tgcaaatcat atatctgata agggtattga atttagaata   86400
tataaagaac tcttgcaact caatataaaa agacaaccca atttaaaat gggcaaagta    86460 tttgaatata aatttcttga tagaagatat acaaatttaa aactgctcaa cttcattagt   86520
cattagggaa atgcagatca aaaccaaatt gagataccgg tttacaccta ttaggatggc   86580
tatagtgaaa aagaacaaat aacaagtatt ggctttaatg tggaggaacc ttatacattg   86640
gtggtaaaat gtaaagtcgt gcagcccttt ggaaaacagt ctgaaagtct ttaaaaattt   86700
actatttgtt atttggtttt tcttcacttt taatttaggt tcagaggtac atatgcaggt   86760
ttgctatata gctaaattat gtgtcacagg ggtttagtgt acacattatt tcatcaccca   86820
ggtaataagc atggtaccca ataggtagtt tttggatctt caccctcctc ctaacctcca   86880
ccatcaagta ggccctggtg cctcttgctc tcttctttgt gttcatatgt actcaatatt   86940
tagcttccac ttatcagtga gaatatgcgg tatttggttt tctgttcctg ctttagtttg   87000
```

```
cttaggatat tggcctccag attcatccac gttgctgcaa aggacatgat ctcattcttt    87060
ttgcatagtg tactatggtg tacatgtatc aaaaatgtta ctgtttgacc tagtaattct    87120
attccaatat aactactcaa gagaaatgaa acatgtcca  cacaaaaact tgtacacaaa    87180
tgttcattgc agcattattt ataatagcca aagagtggaa gacaaatgtc ttccaaatgt    87240
gggctccaaa tgtccaccaa ctgataaatg gaaaacaaa  atgtggtata tccacgccat    87300
ggtttatctg tcaataataa gaaatgaagt aatgatacat gctacaatga accttgaaaa    87360
tattatgcta ggtgagagaa gcaactcaca aaagaccaca ctgtatgatt ttatttatat    87420
taaatgtcca taaaagaaaa atatttagag atagaaagga aattagtgtt tccagggtct    87480
gggaggagat ggtataagca atggctgcta atgggtacag gatttctttt tggggtgata    87540
taattgctct aaaattagtt tgaggtaata gatgtgaata tgctaaaatg ggtgaatttt    87600
ataatatgtg aaatataact cagtaagccc attaaaaaca acctaattaa attaaaagca    87660
agctataaca gaaatattat atagccttgg cagtttagaa tagtgggaaa atatggagtt    87720
ggggcaggga aatagtcgca agtataattc tggttttgtc actactagtg tatggacttg    87780
gatgagtcat ttcctttctc taagtctcag tttgcatata tgcaaaatag aggtaatgat    87840
acctacctca gtggtagctt ttcaaaacct tgttctccct catctctcct ctacaacttt    87900
ctcgtaagat tattacagta ataaccattt attaagcact gtgtcagcaa tggtgtggga    87960
ccacaacttc actgaatcct cattgcaatc ttgtggggtc tgtatttctt tgcctgtttt    88020
acatgtaaag aaattgacgt caaaagagtt gttcaaggtc attctgttag caagtggcag    88080
agatggacat gaaaactaga tgttctacct atatgtcttt ccacttcaac taagaatttt    88140
attaaagaga attaaaaagc tatgaactac ttttaatagt aaacattgct gtcctcgtga    88200
atgaacacac actaaatttc aaatctcacg atggcaggga ataagatgc  tacctgtctt    88260 aagccattac ttcaccaact tctccaccaa aatattcctt gtaaccacaa ataagtaagt    88320
acaatagatc tataaggaga gaataattga gaactctctg attttatctt aaaagtcatg    88380
tagggatgtc atgttccaca atgtaattaa taaaatatat tttgttacta aacataagga    88440 aaaatttat  gttcaacata aagatgtttg gtggttgcct caacctcttt tagttttgaaa   88500 agtaggtatg tatgagaaag atacgtgttt acatgtctac ccttgccctc tctgtctctt    88560 ccctctctc  tctctctctc cctccctccc caccccctct gccctacacc cccaacccc     88620 cacatgtatt tacctttctc taaaagctct gcataaccaa gaaaaatggt cttttttatt    88680
tttaggatgt tagatatttc attttcttat ggtaagacaa aagattaagg caaccaagac    88740
ttacaatgta tctaccgtgt ggcaggcacg gaggcaaggg cttttacatg tgttatttaa    88800
tgtaattgta attctcacaa aagccgtcta gagttgaaaa tatttccagc tctaattgag    88860
gcaaatggag cacagagagc cttaattatt tcacccaaag ttcagtggta gaggcaggat    88920
tccaacccag gtctggtggg ctccaaagcc ttgttggttt gccattcctc tcgctaacaa    88980
atgaaactgg tctgtgactt ttgcatttca ccccacttcc acagtcactg gtgggactta    89040
tttaaattaa tcagatcctt caaagtatcc ccaagtcctc cttaaaaag  aaagttaggg    89100 ggcagggga  ggagcagagg agaggagata aaaggaaag  gagtcagaga gagagagaga    89160
gagagagaga gagagagaga gagagagaga cctggtggtc tcagctgggt gccaaggttt    89220
cctaagccca agttccccat ggttgagcct gcattagcag gccgacagct tctagtaatt    89280
cacttttatt taattaatag tgaaactgtt gaagaattgc aagtggtgtt ctagttcaga    89340
aaccttccat tctatggggc attgcttttg cctcagactc ataaaaccaa atgccctgcc    89400
```

```
tcaggataat aagtgaacat gtaacccacg agaggtaaga aaaaacacaa tgtcacgtgc   89460
aaattctgca cttgttctca aagcaaacct ctcctgtgtt tgcaattagg atgttatcta   89520
ggagcatatt caaaactttt gaggttttta ttttagtttt tcttttatta tgtgctgttt   89580
tagtaatatc aaagaataca tgtaatatat gttatatggc ataacaataa aattaatgtt   89640
tatgagccct gattaaagaa tcaacaacat taacatcatc attgcaacaa ccctattaga   89700
atggaagctc tgtgaaggca aggattttt tctgttttgt tcactgctat atccccagga    89760
cctagaggag tgtcagccac ataataggag cttagtcaat attttttaaa taagagcata   89820
aatctactta tatcctcttt cctcttatca tcactcccag cctcccctca gaggtagcca   89880
ctatcctatt ttagggtttt aatattccct tgcattttgt taacttttca catgtgtatt   89940
cccaaataat atattgtttg cttttgcttc tttttgaact ttatataatg gaatcatatt   90000
gtatgtatcc aattgtgagt tatgactttt acgcaacatt agtatttgag attcaactat   90060
gtgtagctcg attccattcc ttttcattgc tgaattgtat tttattggat atgtgtgcca   90120
taaattattt ttctcctgtc agttgatgtt tatcttttat gcttttataa acaaaacggc   90180
tatgactgtt cctgcatgtg cctcctggta catatgtgcc caactttctc taggatataa   90240
gcctcagagg gggactgcac ttggaatttt catttccaga gcccaaagtt tagctcatga   90300
gtcagagctg caatgtgccc tttgtccaca ctaggtcagg atcagtggga gtgctaccca   90360
aaatattttc ctagtggggg aatcagggag aggcagagac tgacctagtg aggccaggag   90420
ttactatctc aggtctctag tcaaaatggg ttgcaattag taaaagttca gattctgaat   90480
ccccttcatt atttatcttc ttcttcctcc tttacagtta tttttgttca aggtgcactt   90540
tattaaactc atacctaaca aacaaaactc taatgaatat tttgtctttc attgattgta   90600
aattcaatta gattctttga aaaaatttta actgtatttt cactttagca tggatgaaaa   90660
tttcgatttc tttaaaaaac atttttaata ataacacaat aaggtctacc ctcataacaa   90720
aatttaaggg cacaacacca tattgttaac taggcaca atgttgtaca gcagatgtct    90780
agaatttttt tcttcatgct taactgaaac tttatagcca ttgaacggca acagtccatt   90840
tctatttctt aaaagtcctt tacaaaatga gctttctaca tgtttccatt ttgtttatct   90900
gataattttt tttcgttttt tattatactt taagttctgg gatacatgtg cagaatgtgc   90960
aggtttgtta cataggtata cacgtgccag ggtggcttgc cacacccatc aacccgtcat   91020
ctacattaga tattactcct aaagctattc cctccgcttg cccctcaccc atcactggcc   91080
ccagtgtgtg atgttccctg tcctgtgtcc aagtgttctc attgttcaac tcccacttat   91140
gagtgagaac atgtagtgtt tggttttctt ttcttgtgtc agtttgctga gaatgatggt   91200
ttccagcttc atccatgccc ctgcaaagga catgaactca tcttttata tggctgcata    91260 gtattccatg gtgtatatgt gccacatttt ctttatccag tctatcattg atgggcattt   91320
gggttggttc caagtctttg ctattgtgaa tagtgcctct gtaaacatac gtgtgcatgt   91380
gtctttatag caccatgatt tataatcctt tgggtatata cccagtattg ggatggctag   91440
gtcaaatggt atttctagtt ctagatcctt gaggaattgc cacactgtct tccacaatgg   91500
ttgaactaag ttacaacccc accaacaatg taaaagcatt cctatttctc cacatcctct   91560
ccagcatctg ttgtattctg acttttaat gatcatgatt ctaactggca tgtgatagtc    91620
tctcattatg gttttgattt gcatttctct aatgaccagt gttgatgacc ttttttttat   91680
atgtttgttg gttgcataaa tgtcttcttt tgagaagtgc ctgttaattt ccttcaccca   91740
```

```
cttttttgatg gggttgtttt tttcttgtaa atttgtttaa gttccttgta cattctggat    91800
attagccttt tgtcagatgg atacattgca aaaattttct ctcattctgt aggttttctg    91860
ttcactctga tgataattta ttttgccgtg cagaagctct ttagtttaat tagattccat    91920
ttgtcaattt tggcttttgt tgccgttgct tttggtgttt tagtcatgaa gtctttgacc    91980
atacttatgt cttgaatagt attacctagg ttttcttcta gggatttaat ggttttaggt    92040
cttacgttta agactcatct tgatttaatt tttgtataag gtgtaaggaa ggggtccagg    92100
ttcagttttc tgcatatggc tagccagttt tcccaacacc atttattaaa gagggaatcc    92160
tttccccatt gcttgctttt gtcaggtttg tcaaagatca gatggttgta gatgtgtggt    92220
gttatttatg agacctctgt tctgttccat tggtctgtat atctgttttg gtaccagtat    92280
catgctgttt tggttactgt agccttgtag tatagtttga agtcaggtag cgtgatgcct    92340
ccagttttgc tcttttttgct tagaattgtc ttggctatgg gggctcttta ttggttccat    92400
atgaaattta aagtagttttt ttctaattct gtgaggaaag tcattggtag cttgatggga    92460
ttagcattga atctgtaaat tactttgggc agtatggcca ttttcatgat aatgattctt    92520
cctagccttc agcatggaat ggttttccag ttatttttgt cctctcttat ttacttgagc    92580
agtggtttgc aattctccat gaagaggtcc ttcacatccc ttgtaagttg tattcctaca    92640
tattttattc tgtttgtagc aattgtgaat gggagttcac tcatgatttg gttctctgtt    92700
tgtctgttat tggtgtatag gaatgcttgt gattttcaca cactgatttt gtatcctgag    92760
actttgctga agttgctgat aagcttaagg tgattttgga ctgagacgat ggggttttct    92820
gaatatacag tcatgtcatc tgcaaacaga gacaatttga cttcctgttt tcctatttga    92880
atacccttta ttgatttctc ttgcctgatt gccctggctg gaacttccaa tgctatgttg    92940
aataggagtg gtgagagacg gcatccttgt cttgtgctgg ttttcaaagg gaatgcttcc    93000 agttttgcc cattcagtat gatattgggt ctgagtttgt cataaatagc tcttattttg    93060
agatatattt cattaatacc tagttttattg agagttttag catgaagggg tgttgaattt    93120
tgtcaaaggc cttttctgca tctattgaga taatcatatg gttttttgtca ttggttctgt    93180 tgatgtgatg gattatgttt actgatttgc gtatgttgaa ccagccttgc attccaggga    93240
tgaaacccac ttgatcatgg tggataagct ttttgatgtg ctgctggatt cggtttgcca    93300
gtatttattt gaggattttc gcattgatgt tcatcagggt tattgtcctg acattttctt    93360 ttttttgttgt gtctctgcca ggttttggtg tcaggatgat gctggcccat aaaatgagtt    93420
agggaggatt ccttcttttt ctattgattg gaatagtttc agaaggaata gtaccagctc    93480
ctctttgtac ctctggtaga attcggctgt gaatccatct ggtcctggac attttctggt    93540
tggtaggcta ttaattactg cctcaatttc agaacttgtt attggtctat tcagggattt    93600
ggaggtctat ttaggcttgg gagggtatat gtgttcagga attttctat ttcttctaga    93660 ttttctattt tatgtgcccc agaggtgttt atagtattct ctgatggtaa tttatatttc    93720
tatgggatga gtggtgatat actctttatc atttttttatt gcatctatga ttcttctctc    93780
tcttcttttt tattagtctg gctagtggtc tatctacaaa atagatagac tgtttatctg    93840
atatttattt tgtaattatc taataataat catcattatc atcagcatca tcattgtcat    93900
ctcctttacc catacataca tttgtgtctt tcaaataata atcccatctt tgaagtacat    93960
cctcatctgt agcagtcttc actctgcttt cttatatcat ttactatctt attttataat    94020
tatttacttc ccgtctttct tctctaacag atagtatttt tttagggcca aggaaaatatc    94080 tcgatcacca ctatatcccc agcatctacc cctgtgcctg gtccataggg ctagatgcta    94140
```

```
agagttgagt tgaaccaatc tacctaatct taaccttcag tagcacaaca tggtttgtca    94200
gtggttaaga atctacactt tggagtcaga ctcacccagg atggaatcct ggcattacca    94260
cttattatta atagatacat gaccttgaac aagttcactt aattgttctt agcatcagtt    94320
tcctcttctg tgatataggg atgatacaga gctacctggt aggttgttgg aataattaaa    94380
tgagatgata tgtatgaaat ggcctggcac atagagtgcc taaatacacg ttgttctgat    94440
tttatttgga ctgtttgtgt tagtaacaga aatcaaaaag gtggagaaag gagaaaggta    94500
cttgggaaaa ttttctattt cttctccatg tttcattcaa gactgaggaa gggggcacag    94560
tttttaccca aggaaacgac attttttagcc aaaggaatta tgatcttagc atttagctga    94620
attgtatatt ggaagtaagc tccttccttg tggaacttat ggccttgcta gccttggttt    94680
gttggaagtg ctcttgctgg ctttctagtt agggtaggga aaggaaggct tgtggggagt    94740
gaagataggc catgatatca agccactgag tgtgcaaatc agtagaactt ttcgattgct    94800
ttctgttgta cttgggactt gaataaaggc tgatatttgt gtcttgctgg taaagtgctt    94860
gtaaagtgag tgaaagtttt ctttgttctt gtcctgccag agctgttcac ttggggctga    94920
ggggaggata acctttcatg ttttttatttt tttttattct gatgactgtg ctgagcattt    94980
gaacgaaatg gccattggtg gaaagtaaag gtgaatggtg agaagacaat aggataatgg    95040
aaactgtgat ggacttggag tcaaattctt ctgaacttct cctctccaag tcttacttct    95100
ttcatctgta caatgaatat taaatgaga aataagctt gtcttcacag agttattgtt      95160
aggtgttgaa atcacccgac acagcaaaca ggctcccatt agggctcatt ttccttcatt    95220
ccttagtaag gaagaagtac ttataaaata cagcagttgt gctcttgtga atgatagcat    95280
gggcagttgt catctctctg aggcagatta acccagaatg ccacttgagt tttgttaat     95340 gcttaggcat aagacatagg aaagacaaaa gttgaccttt gggtagtaag aacaatgttc    95400
cattttgttc aaacttgaat ttttttacta taggagactg agaattaacc ttccatgaag    95460
gttttaggat ttgctttctg actcttctct ttcatatcca cctgaaagag cttgggcaca    95520
gatgttcttg gagaaaggta gttaaacaag gtgacttctg aagctccatc cttgcccaaa    95580
gaacttatga gtcccttagt ggccaagtat tttgatggta gtagcctaaa agatgtccag    95640
gatcaccgtg catcattttt tcaacagaag cctcaggcat agggattatg cttggtactt    95700
tatgttgtgg aatggaatcc ggcagatgtc catgtgatct agagaaacac ctaaggaaag    95760
tgaagaaatg ggggaaaaaa taacaagact tgtatgataa tactaatcac tatccttgtg    95820
tatttattcc aaggacattt tctccattat ctgatttata ttaccactca cagcagcagc    95880
tcaataggat gggagatatt atccctatttt tatagatgag atttgaggct cgaggagcta    95940
aaacaagaaa catcaaattc ctttgatatt tggtctgatt ttgttatagt tctccctttg    96000
gatgaggtaa agtcacaaaa ctgggttcat atcatttaat tagtctgaaa atgttgcctg    96060
aacaccacct taagttagat atcttaacct caggtttcct actttcattg ctgcctctta    96120
tagacataga ctatgagatt ggctaatccc agagaacttc cctaatccct tggcaagatc    96180
caaaaaggct cagtcacacc ctactaccac catctttagg agaagtctca gaaaattcag    96240
cttcacacta actcacttga gcatcaaata atagtagttc atgcatgcag gttaatcctg    96300
aagacctcag acttcacttg cctatttctg ccattctatg acatgtgttg cattggtttt    96360
ttgtgtcttt ccagtttgga gactgccagg gaccatgttt tgccaattga ctattacttt    96420
ccaccccaga agacctgcct gatctgtgga gatgaagctt ctgggtgtca ctatggagct    96480
```

```
ctcacatgtg gaagctgcaa ggtcttcttc aaaagagccg ctgaaggtaa agggacatgc   96540
acatgcactt ctgtttccct ttctccttta ccttccagag agagacacta acctttcagg   96600
gcccaggatt ttatcatctc agaaacagag tcattggcaa ggcccatca aataacttag    96660 gagcctaagg aagcaaattt ttgcacttgc tagttccctg gtttcagcag ccttgtttgt   96720
acaggcaatg taggcagtga aggtggtccc agctgggct tggggctcag tgggtcctag    96780
aaatgaagga aaaattaatg atttgaaaag atttaatttc ctcccttctt gttttctact   96840
ctgctggcta gtaaaggaaa aatttgtcct tattagagag gttagaagtg gagaaacccc   96900
aactgagtcc ccagcctgtt ccttgggatg aaatatgagac tgtttcttag caaaggcttc  96960
ctggcctcgg ccccagaaag agagtgttct cactcttcag cagactatca gtctctgcac   97020
ctgctccctc ctgttgctgc ctccttggga cctgtctttg cgttaatagt tcctaggtag   97080
gtaagaactc agagtgaaga aacacattta ttctcctctc cagagacctg acctcaaagc   97140
ctgtccatta gtccctaacc ttaatctaag gtagcatctt atatctggct aaattggttc   97200
aagccctagc tccttagttt tatttagctt agaacaactc atgtctgctc aacccctaaa   97260
ggtgctcagc ctacattctg cagtagaaac tcccattttc aggcctctta tatatgataa   97320
tgtctcttcc tctaaccacc cagggcttaa gcttcctgct tatccacttc actctccacc   97380
ctgtatcgag ggctttcttc tcaaaaggac attgatgagg agcccctaga gagagatttt   97440
gtgctctggg accagacccg ttgttaaacg ccagtattca cctctgcccc gactttcccc   97500
aaagaggtac ttcccgccaa ggcctttctc tttcctctca ctggctggaa gtgttgagtt   97560
ccatgtcaga accagaatag agaaccttc cttctataag ggctataaac cttgagaaca    97620
gtcttaaaga taggtatgta ggccacacca ttcaccacaa atgtactgat actcatcaga   97680
ggatggaaga agcaccagag agtttgaagc atctagagaa aaggtagaaa gagaatgccc   97740
tttaactgac ctcctcgatg atagtcaatc acaatgatga gtgttgattc atcattttgg   97800
ctgggtggca gaaatatcta taaaacagaa gctgccgtgt tgtttacttc cagtcctcgg   97860
ggcccacaag aaggcagcta tcatttggta ttactaaaaa catgccccat gttcagctca   97920 taccccaaa tgacccactg ctactgttta tgctgggcta gcatgaagcc cagggcccta   97980
gtgtctaggt ctggtcagtg aggcctagag cagagcctaa agagcctgag agcagtgcct   98040
tcctttcttc agagtactca tgaaaggatg gctgtcagaa aaggaagtga ggaggggctc   98100
cagagacttc agaccacccc aacttcccca atgagaccct ggcacttccc cataacctct   98160
cactcagcgg gccctgtcta tagagcagaa aatgaaacag agcagtcatc tagaggtagt   98220
gtatcagcaa gcccaggcac cacagtaata gcaaccatat cagatgggaa aggagttcaa   98280
gtgaacaaac aagcaaattc aatagtcaga taggttagat tatacttgat gctgtttctg   98340
ggttttacaa atctgggtta ccaaattgtt attttcagaa aacagaggaa atgctctatc   98400
acattgtgaa agggaagatt ttactgtcgt atcatatatc ctacatggga gctttctgca   98460
gaagttagag ctgaaggagg gagacaggca gaagggcagc tggcagggct gcctgggagg   98520
agctctgcta taaggtggat cctgtgccat ttgagaacag ggaagaaagc aatgaagttg   98580
tggggaggga atcactcaac tcacagaaca tacagaaatc cagcaaggtt tcaaaatgct   98640
ctacacccta gagtctctta agttagggaa actctctgag ctcatggggc caaatgctct   98700
tgcctgcttg aaatatgaaa aatcaacaat ggattccttg caaaaccagg aaaagggaac   98760
cttctgagcc ccttggttat tttgaaatac ggaccataaa tttcagtcct gagcccttt    98820 aaggtaggag aaggtggttt agaaaacaca gacacagaca catacacaca cacccccaa    98880
```

```
aataaagcaa aaaaaaaaat actggtgttt tctttctccc cacatctgta aagttgttgg   98940
attgatttta ctgccatcgt tatccctatt tgaaggcagg gggctgtctt attacccaaa   99000
gaggacattt attgatttga ttatcttttt ccattttac agtgcatcat cttttcacc    99060
catatggcct ttctggaggt ggttctcaat ctggcttgtt gaagcatcaa attacacctg   99120
tcttagagag agtagaaaca caaatctttc tcttcctcat ttacttgttg tagtcagtta   99180
actcagactg tgtattcaga ctcttgatta tcacttaatt catagtttca gaaatctctg   99240
gaatgggcac aagtacagga cttaaaagcc tggaatctca gacagaaata tatttctagc   99300
tttgatggtt tataacacat gggacttta ggctgtcatt gatgcagggc tcagcacaga    99360
gtcagttgta atctggccag gttttgttgt tgaggaagag tgggaagggg gagtcctaca   99420
ttttctcctt gtcagtaata ttggagaatt ggggtgagag tgaagctggg cagggaaagg   99480
tctgcataga aaaagggtc tggcgagaaa aaatcatgct actaagccat gagggtaaaa    99540
tgaccaagtt atggttgaca gaaacttggt catagtgtgt gggggaggg tagggggtga    99600
gggcagagag aaagttggtc taagtctgtg ttggggaca gtgcttggtg ggatgaactc    99660
tgggttagaa acaggcatgt agggaaatag ttggtttatg gtgtgggtag gatgaatggg   99720
gcggtgaaag ggaaggcatt ttgaatgcta agagaccagg aagtcaaagc aaagcaatac   99780
ccataaacag aggtaagggc tcagagaggt tttagttgta tagtcttggg taagaaattt   99840
ccccttttga acctcagttt tccttgactg taaaacaacg gacttgaact agatatttca   99900
aaatgtgctt ccaacttaga cattttgtga tcgttctaca aattacaaac ataatcatca   99960
tcatttcagc aaactcacgt gtatttatac ctgcatatgt ttttggtctt gctttcctag  100020
aagatgacta atccaagatc ctaatcaatt aaagaagcaa tcttcagatg gggatagagc  100080
cagctgagag agtgtactat gtatggagtg ggttaaaact caggactctg agattttac  100140
cttgtgatca ttgctgggta acttcctttc ttttctattt ctcatctgga aaatcaggat  100200
atgaatcccc atctctacct cattatgttt caaagagggt taattaatcc atcatgtgca  100260
ttatgtgctc aagaatttac tatttttcag atattttcta gtaaaacgtt ggagattata  100320
tgtccatttg ttttgtacac atggagtgct gtttggtaca catcataaaa ttgaaactgt  100380
agtttacatt ctgaactcaa agaattacac catcctcact gatgtttaca ataggtccca  100440
atttagtttc tttggcaaat tttatgtaag tatggctttg attctctctc tcaccccagg  100500
tttttgttag ggaagaaatg caagtgaacc ctcattgaac tctttctgtc ctttaaatcc  100560
attctttccc acctcaactc atgtggaatt gaatgttacc tctagtttgg agtctagcag  100620
agagttttg gtgcatatca gtgtccccct cactccctga cttttgagt aacatttccc    100680
agaggcaaat taactctgct aagaggatct gcttgcagct tcaacagagc cttcatcagg  100740
tatctttggc caaggagttg actgatcctg actttgcgag tcctagagat cttttcacaa  100800
aactcctctc atgtttctgt ctctggtttt cttaaaagtc gcagacagac tttagattta  100860
ggggttggtt aacttttgt aaagggccat gtagtaaata ttttaggctt tgtagatcat   100920
atggtctctg tgtcaactac tcagctctgc ctttgcagga tgaaagcagc catggataat  100980
acttgaacta atgggagtag ctgtgttcca ataaactttt atgggcactg aaatttgaat  101040
ttcacttaat tttcacatat catttaatat tattttctt tttaaccatt taaaaattta   101100
gaaatcattc ttatctcgtt gggcctcaca aaaacagatg gtagagtaga tttggtttat  101160
gggctgcagt ttgttgacct ctgctttaga taatcacttc tgtacttata aatctgcaaa  101220
```

```
ggttttatgt tttcccatct cttggtattt tagtagctct ctagattatc taatttaaaa 101280
atttttctc  agtaggccaa agtttgcaca tcttgttagc acagaatgcc tggcctagtg 101340
gcttcttggc cctgagcctt ttactaaaca ggagaaaaac taaatgtcta gaaatgctag 101400
aagaggatac tattttgttt taatgatcta gtagatcact cctccttgca atacccagag 101460
gagaaactga aaatatttca agcattttct agacttctgt gttgtaaatg tgtggataac 101520
tatgaactat acatgaaagc acttttctgg atgacacata tattccagat ggcaaaaagg 101580
aagcactttg gggactctct ggtaccaagt atcatggaaa aattgtgtgt ctcatagaaa 101640
gtagatccca ggaagccagc tgagttgtgg atctgccata tattacctca tgattctgtc 101700
ttcgcacact cactggctta attctgggcc tccccataac acgactagac cacaggcttg 101760
cagaagaaat aatttagctc tgtaactcat tgcagttggt gcccacccaa gtctctgtca 101820
gtgcccaatt cgggagccat gccaagaatt tgccattgct gcttcgtagt ggccctgtgc 101880
ctgcttattt atagcctgtg cattttatga aacagagatt aataagaagt tgccatagta 101940
cttgcaccat tatgtaaata tctgcaatgc ttacatagcc tttgtcactt gcaagatctt 102000
ttgagtccac tgccttctgc taccatgcct taccaatttc ctagtccctt attattattt 102060
tttaatttat tatatttaac ttttgtgata catgttcaga atgtgcaggt ttcttatata 102120
ggtatacacg tgctgtggtg gtgtgctgaa accaacaacc cgtcatctgc attagttatt 102180
tattctaatg ctatccctcc cctagcccag tgtgtgatgt tcccctccct gtgtccatgt 102240
tttctcattg ttcaactccc acttatgagt gagaacatgc agtgtttggt tttctgttcc 102300
tgtgtttgtt ttctgagaat gatggttttcc agcttcatct atgtccctgg aaaggacatg 102360
aactcatcct ttttgatggc tgtatagtat tccatggtgt atatgtgcca cattttcttt 102420
atccagtcta tcattgatgg gcatttcggt tgattccaag tctgtgctat tgtgaatagt 102480
gctgcaataa acatacgtat gcatgtatct ttatagaaga atgatttata atcctttggg 102540
tgtatacccca gtaatgggat tgctgggtca aatgatattt caggttctag atccttaagg 102600
aatctccaca ctgtctttca taatggttga actaatttac accccccacca ccaatgtaaa 102660
agcattccta ttttcttcaca tcctctccat catctgttgt ttcctgactt cttaatgatc 102720
accattctaa ctggcatgac atggtatctc attgtggttt tgatttgcat ttctctaatg 102780
accagtgatg atgagctttt tttcatatgt ttgctggccg cataaatgtc ttcttttgag 102840
aagtgcctgt tcatatcctt cacccatttt ctgatgtggt tgttttttttc ttgtaaatat 102900
gtttaagttc cttgtagatt ctggatatta gccctttgtc agatggatgg attgcaaaaa 102960
tttctctcat tctgtagctt ggttgttcac tctgatgcta gtttcttttg ctatgtagaa 103020
gctctttagt ttaattagat ttcatttgtc attttggct tttgttgcca ttactttttgg 103080
tattttagtc atgaagactt tgcccattca ctattgctac aaagagaaca aaatacctag 103140
gaatacaact tacaagggat gtgaaggacc tcttcgagga gaactacaaa ccactgctca 103200
aggcaataag agaggacaca aacaaatgga aaaacattcc atgctcatgg ataggaagaa 103260
tcaatatcgt gacaattgcc atactgccca agtaaattta tagattcggt gctatcccca 103320
ttaagctacc attgactttc ttcacagaat tagaaaatac tactttaagt ttcatatgga 103380
accaaaaaga gcccatatac cctagacaat tctaagcaaa aagaataaag ctagaggtat 103440
caagttacct gacttcaaac tacagtacaa ggctacagta acccttatca attttgtatt 103500
gcctgtccat tttctgcagc cagaagcttc ttcagtcctt taagggaatt tctgggtgac 103560
tatcaaactc tggtagttca ttttttgcagt tgactgctat tgtgaggata agtgtcagac 103620
```

```
tcactctctc ttcagagata gaaattatgt attaattatc tggattctag acccacagca   103680
aggagcaaac tgctcctcaa aataactgaa ttcttcgaga agtcatcatt gtaaaacaat   103740
atcttcagtt atagtagcca tgtgtgcatg cttctggaaa ctgttttca gattttcatc    103800 ttccttccct gtctcttcat agcaaggcag ctgctttcag ccttgtacag atgctagtga   103860
gctttgtacc tacaaacctg agaaaattga actgagattt ggaggtgaat gactcttgat   103920
aaagggaaca aggtttagaa ttatcagtcc ctttgctccc aggctgtgtt gtgactactt   103980
aggcactcca gtgaaatcac tattcctcct atctagacta atgcctgtcc ctgcagagca   104040
cctcatgaga acaggcctgg tagtaatatc ctcatgcatt cagtcagtaa atatttacgg   104100
agtgcttact acatgtagga tattgggctg acatactcaa ggtacagggc ttgcttccag   104160
gaggttatag tttattaatc ataaaagtgg cattttttt gagacggagt cttgctctgc    104220
ctgtcgccca gactggagtg cagtggcatg atctcggctc actgcaagct ccgcctccca   104280
ggttcatgcg attctcctgc ctcaccctcc cgaacagctg gactacagg ggtgcaccac    104340 cacacctagc tatttttct tttatatata tatatatata tatatatata tatatatata   104400 tatattttt tttttttttt tttttcagta gagacagagt ttcaccatat aggccaggct    104460
ggtctcgaac tcttgacttc gtgatccacc cacctcagcg tcccaaagtg ctgagattac   104520
aggtgtgaaa atgtgacaat cttaaagct cttcagtgga tgaaaggcca ccctatctac    104580
tgtccatttg aactttgcaa ctatcttggt acagagtgag aagttattct cttggttttc   104640
catatgagta aactgaggct ttgccagttc atcagcaggt aataaataat gtatctgaaa   104700
tttgaaccca ggtcttctgg ggtcaaaggc agcattcact ctgttccatc acagcagctc   104760
ctcaaataag ccaacataga aaccaagtac tatgcctagg caacaagaaa ggcagcaatg   104820
aagagcaaca gcagagtgaa atatgagaga aggaagttaa gaaagatgtt aagtactgtg   104880
gggagtaacc aagaaaccac caagtatcgc taacatcaca gggagcttgt cttcctaaga   104940
aaactccaag cacttaaaac agctggtagt tcatcagcaa ctctctttat tagatgtatg   105000
agggacatgt gggccatagt ccttctacca acttatatgc ttcaggggga agttctgatt   105060
ctgatgagac ccagcatggt cgcttttaat tcactgttgt cacacaacta tagaacagga   105120
agcacaactt aacacctgtg ctcatgagaa ttttgctcct tatgaccaag ctaaagaaag   105180
agcttagaca ggatgtgagg atataaatgt agattcatgg ttccttggct ctttggtttg   105240
agccttctca gcagagcatg ccacagagtg ttttccatgg ggccagtagc aagagaaatc   105300
catttccctc ctcctcgatg tcagaaaaca gagaatattg tctttcagga tagaattaaa   105360
aagtcataga ggcagcaact tgttttccta tattagggtt ttaaaattct gttttcctt    105420 cctctcctga gtcacatcat tgtgtggatg gaccttgatt tcactgtggt atctggatgt   105480
gggccctgaa ggccatggac ttctaacagt tccttaagtt acagaagcac attcctatag   105540
gtcacaagct catttactta caggatggtt gattcagtca caggttattt catgaaaata   105600
cttaaaagat ttgcagtgtt caaaactgca ggatctttaa acactaaaac ttgaaggaag   105660
ggaatttgga aatcaaaaaa tctggtcaaa ccgtttcatg gaaaagtaaa gtgaggctca   105720
gagagaggaa attactttcc tgggtttcta tagcatataa atggcagaag tgagagcctc   105780
cctgccattt atagttttct gcctgagaga ccctcctgct tcacagctaa ttagcagagt   105840
tacagaggtc attccttgc aattctcaag aattatgtga ggcagtatag taagcattta    105900
tggcccttgg ttcccagaag gagcttagtc cctgatagtc ctctctgcct ttgctgccat   105960
```

```
tgtgtgagac catcttctgt aactgtatgt cttcccccct agtaagttaa tgagtaataa    106020
aggtattccg tagtgagagg actctgtaag agaattcttg gtgtaaggat tgttgcaagg    106080
ttgttttgtg tgtatgtgca tgtataaact ttttagggga gtgtattcat agcttttaca    106140
tggatctcag aggctctgta acagaaaatt acagaatact ggtcttgtct ttggtaagga    106200
ttttatagac ccataaggga gtattctgac tacagtgata tccaacatgg ctatttaatg    106260
cctggcattt tccccacata acatacgttt attcaacagt cagtgcctac tgtgtacatg    106320
agacctatac caggcactgg gataagagac atgaaataac agctaaaact gtttattgag    106380
cagtcaatat gcattagatg ctttgtaggc attttcttat tcaatctgta taccctcaat    106440
ttacaaatga gggaaccgag acacaaaaga gttgagtgat ttgcccaaag tcatacaaat    106500
agtcagtggc tatgtggtga atagttacca acatgaaaga gtgagattac tgctgtacta    106560
aaagtaggca cataattccc tgagcagata gtatgagaga atgatttatt ttacctggaa    106620
agtttaggaa ggcttcacag aggagttaag ggttgatctg gatcttgagg gatggataag    106680
aatttgccag atacaaaaag gtagaaagag aacttcagga ggagggaaca ggttgagcaa    106740
agacaaggtg atatgaaagc gggaggcttg tttggggagc attatggaat ctcgaagtca    106800
ttgtggggaa tctcatcaga tgcagcaagc tgcttgacag gccttcaatt ggctctttgt    106860
accttgctcc ctccccatgc tgagctgtcc atagctgcct taggctggtg tctgggattt    106920
tcggaaggtt actatccagg tagtgtaaca agatgcagtg taagagcacc agatcggggc    106980
tctggctctg ctactgactt aacacctggc attaagcatg tctagttccc tctttgtaca    107040
ttaaaatctc cattggagca gtaacatggt tgtattaaat gatcttgaag attttaaaaa    107100
taaatatata acaatataaa tcgttaacaa taattttagt agtaaatctc taaaatttta    107160
cagataatcc agattcatcc attggccaat ggttcacttt gtatgcataa ttttttggga    107220
aacaggcaga ccgaatttca atccttagtt gtaagactta atacatatgt gacctcaagc    107280
aaattatatt gaatgcctct ataaggataa taatatctta cagaactatt gtaagaacta    107340
aatgatgtgt aataaagctc ctggtactca gtcagttttg gatcctttc ctagagtgag    107400 tcttggtcat aggcacgcat atacttgcag gggtccctga gtaggcagaa agaacaaatg    107460
agagatggta tctgtggtat tccccaggta aaggaggcct tgggttggtg taagatttca    107520
cttcacttta gagttactta attagggacc agaaaggcca tcgcatctgt atgagaatat    107580
aacaaaggtc aatttcttcc tctttacttt ttacgctgtg agtaacattc cccagccagc    107640
ccagccggca cgtgttcttt gcctctcctg acttccagac tttggtcttg aaggtgtcag    107700
agctctctgt gtatctttgc ccccaacagg ataagtctga cctccccagc aaattcaact    107760
cctaagccac tgtccaggag aagagctagc aaggtcataa attattctcc atattttcca    107820
gccattggtt tcccttgtcc agccagaggt gtgtcttaaa gtatgctgag gctagattca    107880
atagaaacct gagccagcac ctgtgtaact aattttttaaa actcccttc ctgaagctgg    107940 atgaatattt tttaaaacta agctggatta tcttttatct agcatgccgt ttcctacatt    108000
cctagtgcta tggacctctt ggaggaatgt agtttggtta tagtggtatt gtcttgcttg    108060
tctgttgtgg gggaggagga catttctttc aaaaacaagg taatacttcg gtctggacta    108120
tgactatttt gtttaaaatg aaactatggc actgtactgg tactcattct gcttcctata    108180
ggttagcttt acatccctct gtcttcaccc actctacagt tctgatcctt ttaaaaagca    108240
gccaaccaaa accagcaagt acatactgct tatctctgac ttctacctga atcaacttca    108300
gatcttgtcc aaagctccat ctgaagagag ggggataaca ccctgccaag agccctcagg    108360
```

```
gcccatcagt aagtagacat cctgtccttg aggtctctta actctgctca gcttcagaat    108420
acagaagggg ttggttcttc atttgtgttg tttataacta aaagcctcct acttcccgct    108480
ttttttgcat agcttcttct gccatcccac ctgtgtagcc tcttcaactc ccctaaaact    108540
cctctgtagc ccgtgtcact tggaaagagt tttctttgtc tcttttgcaa cttgacaatg    108600
actagccagc aagtttaagt tcaaattatt gttccatggg aacagagata gatataggaa    108660
acaaaaaaag ggatatggag gtatggagta atttcccacc tacctagtga gcactactga    108720
gatattcaaa tgctctctac tcaagaattc tattgatata aacgtaaaaa acttgatctt    108780
aggtctaata tccattagta gtgtgacctt gggaaaacga taccactccc aaaggcttag    108840 ttttttaac tataaaatag gaataatgat gaccaccccc agaggattca taaggataac    108900
atgagataag gcaacttgaa atttcctagc atggcgatag acttttgaaa ataaaatgaa    108960
ccaaacactg ataacagtac ttcctagtgc acaaatgaga aatcagtccc tcatcaaatt    109020
acagcacatt tccaatgctc cgattatgtc actgtagaaa tgctaatgtg gattaaataa    109080
tttgtctgtt gctatttata tggataattt gatagtaatt attttttggac atggatagtt    109140 ttgaagcctt acagatgagt ccatccccaa gtacccaaaa ttaaagaaag ttggctagag    109200
tgatggcaag gtggcagcac agagctccct gggttctggg ccctgtcccc tagctaggga    109260
gaactccagg ctataagcat ttgtattctc atagtccaat ggcagggaaa agggttgaag    109320
gtgagtactt ttcactcatt tattttttca acaagcatgt atggtgtcag gccttgtatg    109380
catccacaga caaatgtgag ctagccctga cctcaaggag atttcagttg cagctttagc    109440
actgcaaaga gtatctacct gcggcagata caatgtgatg ggacatggcg gagaaaaaat    109500
ctataaacag agcctcccca tccccaggca tggaaacaat cctaacccag gctggcatag    109560
tacaatgggc ctgtctctat cagcaggttt ggaagcttta acaacaacaa aaaaaacaat    109620
aataatgatg atgataatca tagtgcctaa tgttaccaaa cattttccgt gtgttaagta    109680
ctatactaag tgcatactta atcctcacag caactctata aggtagtaga tactcttact    109740
actaccctga ttttacaaat atggaaactg aggcacagaa gactgagaga acaggaatac    109800
acctaattca cctcagttca acaaacacca agcatctgtt ttatgtcagg cctcgtgctg    109860
ggtgccaggg agagagaaat gagtaaagca tagtttcagt ccagtgggag caaatgacag    109920
cacacagtgg acacatatat tgcagcccct ctgctttatg ctaagaactc attgtcagtg    109980
atgaatcaaa cacagtcctt ctctcaaaga tcttcaagct tagtaggaga tatctgtgtg    110040
aaaacaaaaa ttaagactg ctgtgataag tgtcataaga gataagtgga aaatgagaga    110100
gagatcactg tagcagttga ttggtttaaa tcaaagcccc ccaaaaaaca gtgttattga    110160
gaattataga acaactaatt gatttaaatc aaagcccaaa cagaacagtg tttgctaatt    110220
ttatttcagg ttggttgata gattttcatt ttttattcca tcccgacaat ggaagattag    110280
tgcttgtttc ccacccaagg ataccaggat atttcaggga ctgtattaca atatagtaa    110340 attattcctt tatctcaaag cacacccaca ctttctccta tcctttcctt tactcaggct    110400
atctcttctg cctcaggtgc ttttctcca catttccata ttcttaagtc ctaccttcct    110460
tcaaggcctc actcgaatgc ctcctcctcc atgaagcatc caccccatcg aaaggtacct    110520
cgccatctcc tgtactccca catcacttca tgggtgtctc tctgtggttc ttaccacttc    110580
ctgctttatc tttcagtaat gcacttacag ttctctttcc tccactagac agagctcttc    110640
agacaaagat tcacttggct gaaaccatga ttttacttta aacacattga aaacctctac    110700
```

```
cggaatgcat tgtgtctggt gggcttcaac cttaattctt aagtatgtga aaatacatta  110760
cctatctgga ggtttacact ttctgctaat gactttattt ttaagtccac caccctaaca  110820
caacaaatgc ttaaaacatg tcttcatttc ctttaggtct ggccctcatg catgcatata  110880
atttatagag tcactgtttt gctcggttgt cctcatgcct ctatattatt ggaggtttag  110940
attgtttcca cacacttagg ttgtattcat gtacatttttt ttttctttttt aaatttccct  111000
agcatccatt cccaccattg gaaattcagg gtcaaaacag gggttgggaa ttggagcatg  111060
tgtatcacag ataaccaatc atgtgttatg acttaagaat ttatgaaagg gccctctacc  111120
tgaagatatc ttgctactga tgctgtctca cagtgtctga aactcccatc atatgtggaa  111180
ttgttttgga agattttgcc tcctggggca cattcagcca taatcaggaa atagtattga  111240
gcattagact gtcagtatgt ccattagcaa gactgtggaa gaatggaatc accaatatta  111300
tattttatag gggatacaga attcaagaga agttctgaag agaaaatgct tatctagaat  111360
aggaaggctt agatacagca tgaaagctgc aggctttgag gagccagagg tcaaatgaaa  111420
gcactgagta tttgtttata tgaaagaaca gaaagggaaa agagaagcag aggaagggat  111480
agtagagaga aatgaataag ttttatccat ttaacttgga attgtgtttg gctatgggca  111540
caacagaagc agtgagatca ctttatttta ttttattctt catagacagg gtcttgctat  111600
gttgcgcagg ctggagtgtg cagctcttca caggtgtgat catagtgtac tacaccctcg  111660
aactcctgaa ctcaagcaat cctccaacct cagcctcctg agtagctggg acaagtgcac  111720
accaccacac ccaatgagat cacttaaaaa ctagggagag atgtgtgagt tctgggcaac  111780
cagtagttag aaaaccagga gggggtttgga aatcagaaaa ccagcagagg caggaaaact  111840
cagggcagca tggcagattt agtatataca agtaggttca caccagtcat cagacagaat  111900
tgtaactgct gatgtggagt agaggctagc tttgtctgct gtgtgatacc caaacccttta  111960
agaatagtag gtgtatacgg ggaattggag ggagataggt ggctgtattt actaattggt  112020
tgatttcact gagatggttt gggtattgtg gcttccagat gctcatattt tcttttttgg  112080
gtagagactc caacatcatt acagaactat aaattacata tggaaaagaa aggcctccta  112140
tgttagaata gaaaatagaa tgctgtgggg ttgagggaca gagggtctgt ctaggaagtc  112200
agatagcatt ttcccgttct gtccctcaga gttccttgtc cccattgaga ctcaatttct  112260
cttactttgg tttctagtgt taccacccac tgttcttttc catctcaacc ctgagtataa  112320
gtacagatca cattccttgg gttcttagaa cataatagaa atgaactctc attcatcaaa  112380
atgcccatta gtaaatactg agggagaaca aactagaaat ccagtataga agtaaaaat  112440
aggattatat tccttgcaat ctcagaaaaa acaatgaaga gctttcttcg ggcattagac  112500
accttcccat aaggtggctg actctctttt agtcatgtca acttgaccaa atcttcactt  112560
ggtagcactt ctttcttgtt cattaaccca tctgctatgc tcctatgggg tcctagagaa  112620
atgccgctca tgtacacgca tatccaataa cacaaagatc actctcgact ggcaagccct  112680
tttatgatgc tgtgagcatt tgatacccctt gttgctagta atatcagtga gtgacctgac  112740
ccatatttgg aacagaatat gatcagtata ttgcctcaaa gaggccctca ctgttctaaa  112800
aaatataatt ccagagtttg ctgactcaca ccgtggaata tgtgcaaaaa tgaatcctgc  112860
agataagcct ttctctgact agtttcagaa ttttttttctg ggtaatttta aaattatttt  112920
tttattttttg taggtacaaa gtaggtgcat atatgtatga ggtacctgag gcattttgat  112980
acaagtatac agtgtgtaat aatcaccagc gtcaatgggg tatcccttac cacaagtatt  113040
tatcctttct ttgtgataca aacaatccaa ttatattctt ttagttattt taagatggac  113100
```

```
aatgttattg ttgactgcag tcaccttgtt gagctatcaa atactagatc tcattcattc 113160
taactatatt tttgtaccca gtagccatcc cacttcctcc cctcccacta ccctttccag 113220
cctctgataa ccatcattcc actctctatg tctatgagct caattgtttt aagttttagc 113280
tcccacaaat atgtgagaaa atgccaagtt tgtcttctg tgcctggctt atttcacgta 113340
atataatgtc ttctagtgcc atccatgtta ttgcaaatga caggatctct ttcttttta 113400 tggctgaata gtactttatt gtacgtatgt accacatttt cttcatccat ttgcctgttg 113460
atggacaaga gttgcttcca aatattggct attgtgaata gtgctgcaat aaatgtggga 113520
atgcagatat ctcttcaata tgctgatttt cttctttag ggtgtatacc cagcagtggg 113580
attgctgggt catatgatag ctctattttt agtattttgt ggaacctcaa atctattctc 113640
cataatggtt ttactgactt acatatccac caacagtgta tgaggatact cttttctcca 113700
catcctcacc agcattcatt acttcctgtt ctttggatga aagccatttt aaccgtggtg 113760
aaatgagatc ccattgttgt tttgatgtgc acttctctga tgatcagtga ggttgaggac 113820
cttgtcatat atctgtttgt catttgtatg ttttattttg agagatatct acccagatct 113880
tttgcccatt ttgtaatcag attgttatat atttttttcc tatagagtta cttgagctcc 113940
ttatataccc tagttattaa tacttggtca gatgggtagt ttgcaaatag tttctctcat 114000
tctgtgcatt gtctcttcac tttgttgact gaatcctttg ctgtgcagaa gctttttaac 114060
ttgatgtgac ctcatttgtc cattttttagt tgcctgtgct ggtatggtat tatccaagaa 114120 attttttggcc agattaatgt tttggagagt ttccccaatg ttttcttgaa gtcgtttcat 114180
ggattgatgt cttagattta agtctttaat atgttttgat tattatattt gtatttgctg 114240
agagataggg ctctagtttc cttctgcata tggatatcca gtttttccag caccatcttt 114300
tgaagagact atccattctt taatatacat ccttggtacc tttgttgaaa ataagttcac 114360
tgtagatgta tggacttgtt tctgggttct ctgttctgtt tcattcgtct atgtgtttgc 114420
tttcatatga ataccatgtt gttttggtta caatagctct gtattataat ttgaagtcag 114480
ataatgtgat tcttccagtt ttgcttggtt cttttttcctc aagatagctt tgcctatcct 114540
gggtctcttg tggttctata tacattttag gattattttt tctatttatg tgaagaatgt 114600
cattgatatt ttgatataaa ttgcattgaa tctgtagata gcttcaggta gtgtggacat 114660
tttaacaata tcaattcttg aaattcacga gcatggaata tcattctatt atttggatgt 114720
cttcaatttc ttatatatgt attatatata tattagtttt cattgtagag atatttaatt 114780
tatttaacta aatttattgc taggtatttt attttatttt tacctattgt caatgggatt 114840
gttgtcttga tttctttttt agattgttca ctgttggcat acagaaaagc tactgatttt 114900
tatatgttga ttttgtatcc tgcaacttta ctgaatttgt ttatcagttc taataggctt 114960
ttggtgcagt ctttaggttt ttccaaatat aagatcatat cgtctgcaaa caagaataat 115020
ttgacttctt tcttttcaat ttggatgccc ttcattcttt tctcttgtct gattgctcta 115080
gctaggactt ccagtactct gttgaataac agtggggaaa gttaacatcc ttgttttgtt 115140
tcagatctta tagccaatgc cttcagtttt tccaaattta gtatgatgct agctatgggt 115200
ctgtcatata tggcttttgt tatgctgaag tatgctccct agttttttga aagttttttgt 115260 cttttaagga agataaaaat tgaatgttat caaatgcttt tcatgtaaca attgaaatga 115320
tcaagtgctt tttgtccttc attctgttga tatgatatat cacattgatt gacttagatg 115380
tattttgagc catccttgca gcccttggta aatcccactt agtcatggtg aatgaacttt 115440
```

```
ttaatgtgtt gttgaattca gtttgctagt attttcttga ggattttttgc atcaatgttt    115500 atcagggata ttggcctata gttttccttt ttgtgtgtgt atattttgga ttttgttatc    115560
aggttaatac tggccttgta gattgagttt ggaatgattc tctcctctat tttttgaaat    115620
actttgaata ggattgatgt tacttttttct taaaatgttt ggtaaaattc tgcactgaag    115680
ccactgggtc ctggactttt tactgctgag aagacttttt gttacagctt caatcttatt    115740
atttgttatt ggtctgttca agttttagat ttttttcgtg gttcaatctt cccaagttgt    115800
ctgtttctcg aaatttatca atttattcta ggttttccaa tgtattgtca tatagttgct    115860
catagtagcc tctaatgatc ccttgaattt ttgcagtaac cattgtaata tttcctttt    115920 ttaaatctct gatttttattt gagcattctc tttttttctt agtctagcta aatatttgtc    115980
aatgttgttt cttcatccac aaaaccaact tttcgtttca ctgatgtttt ttgtattttt    116040
tccttttaat tttatttatt tctactctga tctttatcat ttcatttatt ccagttattt    116100
gagtttggtt tgctcttgct tttctagttc tttaatatgc attgttaggt tatttatttg    116160 aacttttttga tgtaggtgca tattgctata aactttcgtt ataatattgc ttttgctgga    116220
tcccataggt tttagtatgc tgtttagtat gttttcaatt tggtacattt caataaattt    116280
ttaaattttc ttcttttattt attgacatag tcattccaga gtatactgtt taatttccat    116340
gtggttggta tagtttccaa aattcctcgt gtttttgatt tctagtttta ttctattgtg    116400
gtcagagaat aagcttgata tgattgcaat ttttaatact ttttttaaaaa cttgttttgt    116460 ggcctaagat atgatctgtc attgagaatg atctatatgc tgaggaaaga atgtatattc    116520
tgcagccatt ggataaaatg gtctttaaat atctattatg tccatttaag acataatgca    116580
ggccaggcgc ggtggctcaa gcctgtaatc ccagcacttt gggaggccga cgggcgga     116640 tcacgaggtc aagagatcga gaccatcctg gccgacacgg tgaaacccccg tctctactaa    116700 aaaatacaga aaactagccg ggcgaggtgg cgggcgcctg tagtcccagc tactcgggag    116760
gctgaggcag gagaatggcg taaacccggg aggcggagct tgcagtgagc cgagatccgg    116820
ccactgcact ccagcctggg cgacagagcg agactccgtc tcaaaaaaaa aaaaaaaag    116880 acataatgcg gattaaggcc aatgtttcat tgttcatttt tctgtctgga taatcttttc    116940
aatgctgaaa gtggggtgtt aaaatctcca aatgttattg tattgggatc tttctcttct    117000
ttcaactctg ataatatttg ctttagatat ctgggtgctc cagtgttggg tgcatatata    117060
cttaaaattg ttgtatcctc ctgatgaatt gacccctttta tcattatata atgaccttct    117120
ttttctcttt gtgtagtgtt ggtcttgaaa tctatttttgt ctgatattag tatagctgct    117180
aatttttttg gtttccattt gcatgaaata tcttttttcat tcctttattt tcaatcaatg    117240 tgtttctttta tatttaatag gtgaaatatg tttcttgtaa ataaaaatta ttatttttaac    117300 atatttttaaa aataatactt tttaaataat aacagttatt attattttt aaattttcat    117360 tagtttggg agcccaggtg gattttgatt acatgagtga gttctttagt agtggatttt    117420
gagattttag tggagcagtc acctgagaag tgtacattac ccaacatgta gttgtatgta    117480
tattatatat acagtatata tataaagcat atatacacac tatatatagt atatatgtac    117540
atatagtata aatatatata gtatatatgc tttatatata gtgtatatat gctttataat    117600
tgtatatata tgctttatat atgttgtgta tatctagtat atattgtata tatagtatat    117660
ataatatata atgctttatg tattgtattt atatattgta taatatataa agcatatata    117720
gtatatatac tatatataaa gcatatattt tgtatatata ttatatatgt tgtgtatata    117780
tattatatat ataattaaat tctgggatac atgtgcagaa cttgcagttt tcttacatag    117840
```

-continued

```
gtatacatgt gccatggtgg tttgctgcac ccatcaacct gccatataca ttaggtattt   117900
ctcctaatgc tatccctccc ctagccccac cctactccct gacaggcccc agtgtgtgat   117960
gtcccctcc  ctgtgtccat gtgatctcat tgttcaactg ccacttatga gtgagaatat   118020
gcggtgtttg gttttctgtt cttgtgttca ctgagaatga tggtttccag cttcatccat   118080
gtccctgcaa aggacatgaa ctcatccttt tttatggcta catagtattc catggtgtat   118140
aggtgccaca ttttctatat ccagtctatc actgatgggc atttcggttg gttccaagtc   118200
catgctattg tgaatagtgc tgcaataaac atatgcgtgc atttgtcttt atagaagaat   118260
ggtttataat cctttgggta tacccagt   aatgggattg ctgagtcaaa tggtatttct   118320
ggttctagat ccttaaggaa ttgccacact gtcttccaca atggttgaac taatttatgc   118380
tcccaccaac aatgtaaaaa cgttcctatt tcttcaaatc ctcactaaca tctgttattt   118440
cctgactttt taatgatcac cattctaact ggcatgagat ggtatgtcat tgtggttttg   118500
ctttgcattt ctctaatgac cagtgatgat gagctttttt tcatgtgtgt tggcagcata   118560
aatgtcaaga agtgtctgtt catattcttc acccactttt ggatggggtt gtttggtttt   118620
tttttcttg  taaatttgtt taagttcctt gtagattctg gatattaccc ctttgtcaga   118680
tggatagatt gcaaaaattt tctcccattc tgtaggttgc ctcttcattc tgctgatagt   118740
ttcttctgct gtgcagaagc tttttagttt aattagatcc catttgtcaa ttttggcttt   118800
tgttgccatt gcttttggtg ttttagtcat gaagtctttg cccatgccca tgtcctgaat   118860
ggtattgcct tggttttctt ctatggtttt tatggtttta ggtcttgcat ttaagtcttt   118920
aatccatctt gagttaattt ttgtataaca tgtaaggaag gggtccagtt tcagttctct   118980
gcgtgaggtt agccagtttt cccaacacca tttattaaat agagaatcct ttccccattg   119040
cttgttttg  tcaagtttgt caaagatcag gtggttgtag atgtgtggtg ttatttctga   119100
ggcctctcct gtgttccact tgtctatata tctgtttttgg taccagtacc atgtggtttt   119160
gggtaatgta cccttgtagt atggtttgaa gtcaggtagc gtgatgcctt cggctttggt   119220
cttttgttt  aggattgtct tgactatatg agctcttttt tggttccata tgaaatttga   119280
aaagtaaaca gtacaataag atgtaaatag aaacaacaaa gtgataacaa gcagagagat   119340
gaattagaaa aaaatatttt ttttctaatt ctgtgaagaa agtcaatgat agcttattgg   119400
ggatagcatt gaatctataa gttgctttgg gcagtgtggc cattttcatg ataatgattc   119460
ttcctatcca tgagtatgga atgttttttcc atttgtttgt gtcctctctt atttccttga   119520
gcaatggttt gtagttctcc ttaaagaggt atttcacatc cttgtgaatt gtattcctag   119580
gtattttatt ctctttgtag caattgtgaa tggcggttca ttcatgattt gattctctgt   119640
ctgttattgc tgtataggaa tgcttgtgat ttttgcaaat tgattttgta tactgagatt   119700
ttgataaagt tgcttatcag ctttaaggat attttttgggt gaggtgatgg ggttttctaa   119760
atatatggtc atgtcatctg caaacggaga caatttgact tcctctcttc ctatttgaat   119820
acctttattt ctttctcttg cttgattgcc ctcactgtaa ctttcaatac tatgttgaat   119880
aggattggtg aaagagagct tccttgtctt gcactggttt tcaaagggaa tgcttcagct   119940
tttgcccatt cagtatgacc aatatgtagt ctttttattcc tcaccttctc tcaaccccta   120000
ccccaacgga gtcctcaagt cctttacatc actgtgtgtt attgcatcct catagcttag   120060
ctcccactta taaatgagaa aatgcagtat ttggttttct attctttgct tacttaatta   120120
gaataatggc ctccagctcc atccaggtgt cttgtttttc attcattcag ccagtctaca   120180
```

-continued

```
tgttttgctt ggagagtttc gtccatttag attcagtgtt atgactgata actaaggact   120240
tactcctgcc atttggttgt tttctggttg ttctgtggtc ttctcttcct tttttccttc   120300
cttcctgtct gcctttagt gaaagtgatt ttctctggtg gtgtatttta ttttattttc    120360
ttccttttta tttttatttt ttgtgtgtgt atttgttgta cgttattgat ttgaggttac   120420
cgtgaggctt gcgcataata ttttctaact cattatttta aactgatgac aacttaacac   120480
tctattgtgt aaaaaatcat ggaaagagaa aactaataaa aactgtacat tttaacttta   120540
tcgctctgct tgttatcact tgtcatttc tatttacatc ttactgtact gtttatgtct    120600
tgaaaagtag tttcagttat tatttttat tggtccatct catagtcttt ctactcaaga    120660
tatgagtagt tcacatacca caattacagt gttacaatat tctgtgtttt tctctgtact   120720
tttaattacc agtgagtttt gtattttcag ataatttgtt attgctcact aacattctat   120780
tctttcagat taaagaggtc cctttagcat tacttatagg aaaagtctgg tgttaatgaa   120840
ttccttcagc ttttgtttgt ctgtgaaagt ctttattttt ccttcatgtt tcataggtat   120900
tttcactgga tattctattc tattctaagg taaaaggttt ttttgtttgt ttgtttgttt   120960
gttttcttca gccctttagg tatgtcatgc cactctctcc tgacctataa ggctaccact   121020
gaaaagtctg ctgccagaca tatatgagct ccatttatg ttacttgttt cttttctctt    121080
gttacttta ggatcctttc tttatccttg gacctttggg agtttgatta ttaaatgcct    121140
tgaggtggtc tttttggat taaatcttct tggtgttctg taactttctt gtacttggat    121200
gttaatatct ttctctaggt ttgggaagtt ctctgttatt atccctttga ataaactttc   121260
taccaagatg tctctctctc tctctccctc tctctctcat tcttaaggcc aataactctt   121320
agatttgccc ttttgaggct attttctaga tctcgtaggt gtgcttcatt gtttgttatt   121380
cttttttgtc tcttctgact acattttcaa atagcctgtt ttaaaactca ctaattcttt   121440
cttctgcctg atcaattatg ttgttaagag actctgaggc attcttcagt gtgtcagttg   121500
cattttcag caccagaatg tctgcttatt tttcttaatt atttccatct ctttgtttaaa  121560
tatatctgac agaattttga attctttctg tgttatcttt aatttccttg aatttcctca   121620
acacatctat tttgaattat ctgtctgaaa ggtcacatat ctctatttt ccaggatggt    121680
tatctggtgc tttatttagt tcattttgtg aggtcatgtt ttcctggatg gtgttaatgc   121740
cagatgtttt tcagtgtctg agcattcaaa agttaggtgt ttattgtagt cttcacagtc   121800
tgggcttgtt catacctgcc cttcttggga gactttccaa gtattccaag ggatttggat   121860
tctgtgatct tagtctttgg tcactacagc catatctgct ttatggagca tcccatgctc   121920
agtaatgctg tggctctttc agactcatag agttactgcc tgcatgctct tgggtaagag   121980
ccaggaaaat tccctggatt accaagcaga gactcttgtt ctcttccctt acttccccc    122040
aaacagagta tctgtcgcat tctctttttc tctctttctc tctctctctc tctctctctc   122100
gctcattctc tgccgacctg cctggatctg gggtagggat gacataatca catttgtagt   122160
caccaccaat gggactgtgc taggtcagac ccaaagccag cacagcactg agtctcgccc   122220
aaagcccaca gagaccactc cctgggtact gtccgtgctt gctcaaggcc caagggctgt   122280
acaagctggt gaggccagcc tgtcttatgt ccttcccttc agggtgatga gttcttcaag   122340
caggtcaagg gatggtgtcc aggagccaag gcctcgagct gtgactgagc tggcacccaa   122400
tccataagac aacgattttt tccacacttt ccttcctttt tctcaagcaa aggagtctct   122460
ccctgtggcc accaccaccc ccatgttcat ggcaagtatt gtctggctac caccaatctt   122520
cactcaaggc ccaagcgttc tttagtcaac ttaaggtgaa tgctaccagg gctgggtctc   122580
```

```
taccttcagg gaagtgggct cctctctggc ccagggcagg tccagaaata ccatccaaga  122640
gccaaggcct gaaatcaggt tccccaagag cccatttggt gctctacccc cactgtggca  122700
gaaccagtac ccaagctgca agacaaagtc ctctttactc ttccttctcc tttacagaga  122760
ctctccctat agccaccaca gctaggaata tgctgggtca ctcttgaagc aagaacagct  122820
ctgagtctca ctcaaaactc ctggcaagtg ctgcctggct accacactga ttattcaggg  122880
cccaagggct ctttagtcag caggagttgc atcctgccag tactggttcc ttcccttcaa  122940
ggcagccgat taccttctgg cccagtgtgt atctagaaat atcgtttggg agctagggcc  123000
tggcatggtg acctcaggac tctgcctggt gccctttttct actgtggctg atgtagtgtc  123060
caaattgtaa gacaaagtcc tctgtactct cccctctccc atctttaagc agaaggaaag  123120
agtccaccct ggagttggga catgcattgc ctgagattgg aggaggggtg gcacaagcac  123180
tctcttggtc acctcagctg gtgtttcact aggtcacatg ttccccaagt ccactggctc  123240
tgagcccagc acaacaccag gagttgacca agaattgcaa ttcttgtggt ttagactgcc  123300
tttcaagttt atttgggact gcagaccact ttagcccaca gtgacagggc ttgccagaat  123360
ttagtttctg actgctgaga tgggcaattt gcctctgatt aggacggatc taagtgctcc  123420
ttctgtgggc actggctgag ttctgctcca tgttgctttc tgctgtgaca gggcaacatt  123480
gagtgccaat gcaagtccca caatcactgt aatcttcctc tcccaagcct actctgaaca  123540
ccatgtggtt gctgctggga gattggcgag ggatgttgta ggcaattcaa gaatgtcttt  123600
cctacccttt tcagtgcttc tttccttagt atgatgttaa aaccagttac tgtgattgct  123660
catctgattt ttggttctta ggaaggtgct ttttgtgtgg atcactgttc aatttgttgt  123720
gcctgcaggc aggggtgggg gacaattgct ggaggcttct cttagccat cttgctccac  123780
ctcttcccta gtattagaaa tttcaaagca gttaggatga gggtagaagg aaagggtgct  123840
tggaatcaga aaatccatgt cttagctttg agccttagga aattcatttg acccttgtaa  123900
gcctctgttg cttcatctgt aaaagagaaa taatatagtg actgaaaata tcaaggtga   123960
taatgctgtt gaaagcacta tagaaaatga tgaaatatca catgagtatt attttctagt  124020
ttctaggagt ctccttacca ttgtacagga caaccatgtc tattttttaaa taaattatta  124080
tttgcctctg agcaccccctg caaagagttg cctataggag aaacagctta acttgcaaat  124140
cactccactg ttttctttgt gtacagttta ttaatacata aggcacatgt cctccagtct  124200
gtagtaacat tggaatgatt acctctttgg agtacctacc agagcttctc aaagtgaatt  124260
ttgtatatca ccaccaaaaa tagtctgttg cagagataac ctccaaattc aatgacaata  124320
tttccaatca cttttgcatg atacagaaat agacaaatat ataattttgg ttatacagat  124380
aattattgtc tcccaacaag tgattagtag tcagaaaatg gccaagaaat accatgggt   124440
gtgccttccc ataacaactt atctttgggt tttagttgca aggttactaa aagcctgtgt  124500
agggttcatg gcaaaagtaa aacttgctcc aagagcaagc ccttgtttca ttgtctaatg  124560
ttcttaatcc ccagcagaca tgatttggat ctggcatttg gcaacaggac agtttccaaa  124620
gttgctgtat gcaacttgag gaagagaggt gatattattg gaatgaattt atttgttgta  124680
agttataaat atatgggctt ttccaatccc atcacccttaa aaattttttc tgcagtaagg  124740
gtgtctctct tgtctttaat atgcttgctt tgagttcatg gatgaacatt cttgcttggc  124800
tgacatgtgg actctctgaa attgttctaa ggtcttttttc tttgtttttt tcttgattcc  124860
caagctgcca agggtagtac tggtagtggt gggcagacaa ggaggtgata gcaagctgaa  124920
```

```
ctttgtcctc tggcttccct tgacccattg cattcattat ctaagggact ccaagtcagc    124980
attccacaga atggccttac caaactcact gagactgaaa gagaaccaag attccaaaca    125040
gccaatatga aggaaagag  agagagactt agggtttgca gaatgggata ctctgttgat    125100
tatttttatt ccatacagat actaatattc tttaggaaaa cattaaaatc acatgatctt    125160
ccaggacctg ggctgcttct ttaagaagca tgttacagag agctctcttg gccaacaaca    125220
tattgaaaga taaattaatc aatcattcat tcaaataagg tatattcaga attgaggtat    125280
attgtagcca gacagtgaga ctataaaaat gaatgcacct tacccttgtc tcttgcacaa    125340
tctaatgagg gagataacca ctcttccaat ttatagtgac ctataacatt tcatacgctg    125400
ctgaatatct ttacatgata atgacacaat agaaagattg caaaatagac agaggctggg    125460
ggaagaagga ttgagtgtga atatagcctc tcataaatcg aggggaatg  gtctgcatct    125520
cctgatcatg cagaggtaat aaatacagaa atgatttcaa actaacaaac caaatgtgca    125580
gaaaatactg agaatatagt gggcaggata cctgagtttt agttctatct ctgttattga    125640
ctcattgtgt aatctgggtc aggtctgttc tgctctctgg atctcaccct ttcctatctg    125700
taaaatgaga ttattgaatt agacgatatc tatagaggtt ctcgcctatt ctgacattca    125760
aggagttttt ctttaagtaa taatatatgt gatctgtata gtgctttaca cttgacatga    125820
tatttttgca tctattatct catgtgagaa aatcactgga ctgctggact gggaatgagg    125880
acacctggat tcttgtccct atttttgacac tgattcatgg tgtgaccttt aagcaaattc    125940
tctgagtttc agtttctcaa tctgtaaaat agggaggtat gaggattgga ctaaatcagt    126000
aggtctctaa aatgttccac aaagccctgg ggttggggac tcctacagag tttcactaag    126060
gcaaaccaca aggctaggcc tgcatagaag aggagaaaaa gagtgacctg gcaagagaag    126120
ttccaagttt cctatgccaa ccccaggcag attaggttta attttatctg ttttataaac    126180
agagcttcta tgtaatgttt tattggtaaa aagactttac tataaaaaac tcaactagtt    126240
tgattttta aaattgcaca tttaagtgag atcatacagt cagtatttgt ctttctgtgg    126300
ctggcttatt tcacttagca taatgtcctc cagcatcatc tatgttgctg caaatgacac    126360
actcttcttt tcattaaagg cgatatagca ttccattgtg tatgcacacc acattttctg    126420
ttttgtaact ttcatttag  gttcagggg  tcatgagcat gtttgataca taggtaaact    126480
gcatgtcaga gaggtttctt gtacagatta tttcatcacc caggtaataa gcatggtagc    126540
atagtaccta atggattttt tttttctgat cctctcccctt ctcccaccct ccaacctcag    126600
gtaagccctg gtgtctgttg ttccctctt  tgtgtccatt acaccagatt ttctttatcc    126660
acttatccat ccatggacac ttagtttgct tccatatgtt ggctattgtg aataatgacg    126720
aaaaaagtca aactcataga agcagagagt agaatggtgg ttaccaggga ctgggaggca    126780
gttcagtgag ctaggaaaag agagctaata aaagggtaca atgtgtgagt tatatagaag    126840
gaataagtta tattgatcta ttgcccagca tcgtgaccat agttaaaaat aatgtattat    126900
atgtcttagt attgctaaaa gagtagattt taaatattct aaccacaaaa aattataagt    126960
aggtgaggtg atggatatgt taatttactt gatttaatct ttctacaatg catacatata    127020
tcaaatatc  ccactgtatc ccataaatat atactattat tatttgtcaa ttaaaaaatt    127080
taaaaacttg atttagatga gctctaaggc cttaagtatt aaaatattat taagtgata     127140
tgtaaccaag tatattgctt ggtaacttca tttttgttgt tgttttaaca aaccaatata    127200
ttgtgaatat acttccaagt gaaagaaaa  aaagacatta cagtcatcat taattactgc    127260
aaaatattcc tttgcatgaa tatggaataa ttcatttaat cattccctta atgttagaca    127320
```

```
ttcaaatgtt tccaactttt tctgtttaaa taatgctaca ataaacttct attttgtgct 127380
tattgtatta ttttcttata acacatccct agaagtggaa tttctagaag tttatagaca 127440
tttccaattt ttttccaaat atgtgggaaa atttctctct aaagtattta tgttcctacc 127500
agaaatacct ctttaccaac acacagtgtt taatctgtac caatctggct tgagaaaatg 127560
atatttactt tgtatttctg tgatttctag ctaaattaaa taatcttcac atgcttattg 127620
gtcatttttta tttctttgaa ttgcctcttc ctgtctgttg cccattttc tattgtgctg 127680
tttatttttta tatatcaaat atattgacca ttgatttac atacttgatg ctaataatta 127740
gtnnnnnnnn nnnnnnnnnn nnnnnnnnnn nnnnnnnnnn nnnnnnnnnn nnnnnnnnnn 127800
nnnnnnnnnn nnnnnnnnnn nnnnnnnnnn nnnnnnnnnn nnnnnnnnnn nnnnnnnnnn 127860
nnnnnnnnnn nnnnnnnnnn nnnnnnnnnn nnnnnntttt gattttaact agtaatttaa 127920
ctttattttc ttctccaaat gattcactag ttgttctgac attatttagt gaataattca 127980
tcctttttc actgaattgg aatggcatat tccatatact gtgtctggtt ttggcttttc 128040
tgttctcttc cactgatcaa cctaagctgg agccagtatc aaactgttat aatcattatg 128100
gctttagata ctttaaatgt acagcaggga atgtcttatt actcttattt ttcacaaata 128160
tcttgacact gtctcatgtt ttattccttc gataaatttt gggattcatt tgtgatgatt 128220
ttgtctgagt tgttttaaat ttttagattt cactggggaa gaactgaaat ccttgaaata 128280
ctgcttctta ttagccagga atatggtaca actttgcatt taattcaggt cttccttaa 128340
ataccacaat gaagttttt gttttgttca tataggtcct gcattaacac tgtttatata 128400
aagtgtaaga aagactatag tcctcaggct tctctatagg ttaacaatga agatgatgac 128460
tcaacctttt ctttatttgc ataatgtgat gccactaata gtgggcaact tccctgtctt 128520
acctcctctg ttccaaacag gattttttgg aatgaacaag ttaaagaat cgtaatcaga 128580
cactaaccc aagccatact gcatggcagc accaacggga ctgacagaaa acaacagaaa 128640
taggaaggaa gcctgcagaa aaacaaactt gaaagctgtc tcatggcctt tgttcctgct 128700
ggagctttga gtcatactta agttttatga tggaagaata ggagtgtgaa gaaagataca 128760
gagcaccatc agacagtcaa gaatttcaga gccagctggc atgcagtgga cctcatgcca 128820
gcccattttg ttactattta ggtagtcaag gatttaagat tcttctaata agacagtttt 128880
tatgcattta aatgagtgac ttcttttgcag ctctagcgtg tggccttacc tacttcaaca 128940
tgagaagatt tttgtatttt gtcactcatt tcacaatgac ttatagtgag cccttcatta 129000
tacactgtgg atacaacttt gctgttggaa attaacagtg tcaaaaaact gggtataatg 129060
tttgtagtat ctgaggaggg agagctgcct aggaagttgt attccctgtg ttaattttc 129120
agtctcttag gttatagaag accttctaga accaccttac agcaggccta gatctcattt 129180
acacacttct tctgtcactt gaatacagag aagggatcca caaggtcata tacttcctag 129240
acaaagagca aagatttcta ccacactcag aagactttgt cttcagactg taatcaccca 129300
caccatattt cctttggatc cagtttccag attttttgtgc tggcactaac accaacttgc 129360
tgtggcttgg ggcatgtaat ttcaatattt tgtgcccatt ttcttaactg aagagtcagg 129420
catcacactg ggcattttaa gattctttac agcccaatga ttctgtgttt ctaattaggc 129480
ccaatgggtt agagctataa ggaaacagtg agtttcctgg aaggaaagga cacataacac 129540
agtccagaga taaaacgggc tgcattcaag aaaagattgg gcaatacttt gcagggatgc 129600
tacagagaca attcaagcct tgtatggagg aatggatgtg atacaaccaa aaagtctttta 129660
```

```
aaaattctttt ccaactaatc tgggattcat aaccttatgg actgtgattt gcagcaaacc 129720
aaggatgtga tgccaggcag aacaatatct ctgatcaaca tcaatgcaag gttcctcaac 129780
aaaagactag tattgtttct ggaatgcaag gatggttcaa catatgcaaa tcaataatat 129840
taacagaatg aaggacaaaa actatatgat catctcaata gatgcagaaa ataaatttga 129900
caaaattcaa catcatttta tgatgaaatc tttcaagaaa ttgggtatta gaaggaatgt 129960
ttctcaacac aataaaggcc atatcagaca agcccacagc taacattata ttcaatgacc 130020
aggaatgaga taaggatgct cactctcatc acttctattt aacatagtac tggaagtcct 130080
agccaatttc atattaatga gtctcatttt cttcatcata gaatgaagta tgtaataatc 130140
cctattatac ttactttgca caattattat tattttatta ttattttgag acagggtctc 130200
actctgtcac ccaggctgga gtgcagtacc acaatcacag cttacttaaa ccacgacctc 130260
ccaggcacaa aggatccagc ccctcagcct cctgagtagc tgggacttca ggtgcacacc 130320
accatgccta actaattttc tttttttcat tttttatag agacggagtc tcactatgtt 130380
acccaggctg gtctcaaact cctgtgctca agcaatcttt ccaccttggt ctcccaaagt 130440
gctggtatta caggagtgag ccactgcacc tggccttgca gattattatt aaactttgta 130500
aactaatcaa atgagagtga ttattgttac tgttaagaac tctaatagcc tcattcatat 130560
atttggagaa attgaataaa taggaaagaa ataatagcag accaatgatt ttaccttggc 130620
tctatcatca tttggggaag tgataattca gataggagaa gtgacttgta agcagtcttg 130680
agagattacc tgttccatcc cctatatttg tccttaaacc aaattgtaca gataaataag 130740
gtcttatttt taggacttac agaaaaaaag attcctttca tatccatctt tggaatcctc 130800
agccacttct gtcactatta aatgtcattt taaacgttaa attcatcatt ctgctttgaa 130860
ggaacacatg tgtcatgtgt acctatttgt atgttttggt gtgttttatg ctttatatga 130920
tcacccacat atgcacagat aattagtgtg caggtgttgt attccctgtg ttaattattc 130980
agtcacacac tctcacacac ctatgcactc acacatacat gaatacacac atgttcatta 131040
gaatgtttat gcttatgttg catgtgactg gcaacatcag tgcctttcta aggcaatatt 131100
aaccactttg agttttggga gagctttaga aaacaaagac aagagactaa atgattctag 131160
atgtaagaga caatgttgca ataagttact atcctaaaaa gacagaatac aaggacaaga 131220
gattattatt ttggataatt tcttgcttac cagtaatact taagtccttt acattaaaaa 131280
aaaaaaaaca actctaaata tattacagaa gacatccaga tgtccttcaa gattcttaga 131340
gttggaaaag attttaatga ctttccagtc caatctattt catgtaatca gtgggatcag 131400
agaggcaaaa ggacttgtcc aaggtcatat agtgagttag tgataaggct gaacaaggat 131460
tcagatgttg gggcttccag cccactgatc tgtctctcat ctgggacttg tatattttg 131520 ttcattagag attttcctct gtaacctcaa tatccaatgc agggccttgc acataataga 131580
ttaccagtaa atgttaaatt aatatgtcat ggctttggtt ttactgggct ttgcacttac 131640
tcctgagtaa attgtaaata atatctatgt tttaggtctc cttgttttag accaagatgt 131700
acccagagaa aaggtatgaa ctatgctaag aaaattatct gagtcccaaa ttgaaaaaaa 131760
aaaaaaaaaa tcatgctttt ccactatgac ctctctcatt cacagagtga ttctctttca 131820
aaagggcaat gtagaaccat tctggcattc tgggagccat attccattgg ctgtgcaatc 131880
atttattggc aaactggggt ccaggaaagt attttcctgg ggaagatgag atttctcaaa 131940
gaagtcatgc actttctaac ctaagcttat ttcagtaatc agtgtagcaa actggtcttg 132000
aggattgcag cagtaccaat actgtgggag tgtaccagtt ctagaacagc tacagcattg 132060
```

```
gaattgaacg cactagaatt ggatacagga cctgttttttg aggagctaac acccaaaggc  132120
tgaaagcact cgtagcactg tcctttctgt gcacatatcg tagtcctcag tttgcagcag  132180
aaaaaaaagc tgttagcaaa ttatgtgctc tgtttatgca aataaaatcc tgtggtatac  132240
tagaaagagc accggcctag aggccttagt tttctcatat gttaaaaaac cctaacacag  132300
gcctggttca tagtaggcac ccaataaata ctagagtttt tcctttgggg gcctctgatt  132360
cagtgtgctt cttcaggtaa ttcacttccc tggaactcct ccttgtaatg agagttgttc  132420
tgttgtgatt tttaacagtt ccttcaagcc aagcattttg gaatcctttc ataaagggag  132480
aaaggaagga aaggagaaag gaaaattaaa ggaaaaaaaa ggaaataaaa agttaaaaag  132540
gaggaaagga aaaagaatcc tttactacaa taaatctaat ctcatgctct tgcaagtagc  132600
actttaagta aaagaagttc tttgctgacc tggttactac tgaacctact acataaaata  132660
gcctactgta acacatgcat ttctgtgcct aatcttcacc ttttagcctt agtaaatgta  132720
gaggaatgct gatgtatagt taaatttatg tttttagttg cttttttttt ctactctcaa  132780
atgtcaatca ctctttagtt tctctttctt tttccgaccg caagtattct tcctctgcct  132840
aaagaagctt ccctaaaatc ccagtctatc cagtaaatca aagcacagca ataaatttga  132900
ggaaacaata ccagagacaa aaaggagtga ggggatgcag aagctcaagc tggagcagga  132960
ttgtaagcat gagaagttct gcgtgcttca gagcagcgaa ggatgtattt ttgcttattc  133020
ctgctggtga ctcttttgtct atgcatccat ctgctgcaat tgcatgttta gtcagtcaat  133080
ccacgtttgt tgagagactg ctgtgtgcca ggattgtgct agcataaagg agcgaagtat  133140
tgagcaaaat atgtttgagc agctgtaatt ctgaggatct ctaggtctga gcatgtgtat  133200
gtgtatgcac ttctgtgtat ctgtgacaac tccaggtgtg catgacagtg atctttgtta  133260
ctctgttggc ttcatcaaac ttcctttttag ttgctgtgat tcactacata gagtgggctt  133320
tatctctgat ttttataacc tgcatgacta ggggtatgat caccagaaat ctaaaaacag  133380
ttagaaatcc catggagtta tcttttatag aagttttcct gtactaatat tatgaaaaat  133440
aagcatcttg ttaacttgag tgtaattcta tgcatgatta caggtgtcaa taggaagaaa  133500
cattgactga gttcagatct cttctacgcc atgctaaagg ggtgacaagt tccacaatgg  133560
atcattttct catgggcatt tctggctttt ggtaaaagta gggcatctta ttttaaaaac  133620
cagtgagtag tcctaataat ggagatatca tcaggatctg aattgttcat ccctaaaaaa  133680
aaacaaaaaa aacaaaaaaa caaaacaaa acaaaaaaaa aaaaaccaat ggaaatcaaa  133740
taatatagtg ccaaattaaa ctgctttaat atttaggttc tgtaggatca aattgtttgg  133800
tgccatactc tgtccacttt tctgtccact tttctcatgt gataggatat aatttttatat  133860 cttttctgtt ctagaaatac ccaaagaaag agactctgga aactcattaa caggtctgtc  133920
cactcttgta tttgttatcc cagggaaaca gaagtacctg tgtgccagca gaaatgattg  133980
cactattgat aaaattccgaa ggaaaaattg tccatcttgc cgtcttcgga aatgttatga  134040
agcagggatg actctgggag gtaagatact tttctttctc ttcttcctcc tccttcctgt  134100
ctcccctttt cctccctcat tttctagtct ctctttaaac cagattttct tctttgatgc  134160
ttccaagggg accagccatg ctccagacac aggcggaccc tttcatagcc aacgtggcca  134220
tcagccagct ggtgcctttt tttttttaat ccttaactat accaatcccc attctgggc   134280 tcagcattag agcaggaggt gtgaagcagg gataaggagc caacagaggg tgagtgagga  134340
tgcatgtgac tgggcagggt ccccagggga cttaatggta ctgacctgat gttgttcaat  134400
```

```
ggtagctagg atgagagaac taagaaatcc agaacagtca caggtgcagg atgacccagg   134460
cataggtaca ggatgaccca ggcacagtct gaccctgaac acctgggaat atccctcagc   134520
taactgctgc ctatgttgta gggccagcca cctggaatga aagctgctt ctctttggag    134580 cctgtgacta ggctgacaaa cagtgccaat ttcctatcct atctctccca aagatgaaca   134640
ggtgttttaa tcatttcctt ttctttgcaa agctattgat catttccaaa agcattttt    134700 tttcagtagg acagtaacat tacagaagga agatacagct ctttcaaggg tgttcctcta   134760
tcataaggct ctctgtccca tgaacctgtc tgccatgagt gttgtcatca ttccagaaag   134820
gcttgacatc agttgattga catttatatt ttccctctcc aaactccccc atctctccat   134880
gtttacatct gcccaatgcc agggtcatca ctgcagcctg ctgcttccaa aaatatgtgt   134940 cttccttag  aaaaacaaga tcattaatct acttcaattt ggaaatggaa tttgaagaaa    135000
ggcaagccta tttctgagtg cctgcaactg tagcctcata tccgattatt cattattagc   135060
ctggaaaacc caagtgccta gaatccaacc cttcccccta tcctcttaag gctaatttag    135120
accagttgtc tatcactggc tttctgtgag ttgttcaata ccttgtctgc ctatgtgcac   135180
atctatagac aacaactagt gctcttatcc tggaacaggg ccatgtgtga atctatatgt    135240
agataactat atccttccca tcctcacagg gcagtggtat tatttaaaca gaacaaagta   135300
cctcaaatga attgacccag gctggatgag agacaatttc aaaagaatca tctcaagtag   135360
catccagtac tcccaaacat cacaggtaga tattctgtga gtggctttcc aagcatccct   135420
atcaaatgag aatcagatat ctgagaaaac tcaaccttgt tttggtttgc ttagtgtacc   135480
ccaaagaaat ccaacaattg aggtctacag tggagaagaa gtaggactgg ggtcagggag   135540
tacagaggca aaggcaggaa gggtgacaaa gtgattgaca agagaaaatg ttctccatat   135600
gaatgttgca gccccatgtt gagggttctt atacactcag ctttcaatta tttagccttc   135660
tgcgaattat gtatagtata agagatagag actctcaggt agggaacctc ttggctggtc   135720
atctggcaat atgaattgca agtccacttt gatgcaggta agtttaatg gtaacaaaag    135780 tcctcataat atttggatac aaatcttaac attaattcca tgtctcagcc aacattctcc   135840
attataaatc aggctgtgat atgattacag tgacccactt ttgaaaagga gcctgtgtat   135900
aacagataat ttcactatac tatatagtac tcagatgcag gtttgtaaat taatttattg   135960
gtgagaatgg ttcagtacat tttcaaattg atttattagt agagtactca aatttgagtg   136020
ggcttggtga acacaatgaa gacaagctga gaagtgttgt gactggcctt catttcagtt   136080
gcaggcccat gatattttga gcatcttcca tgtacaaggc accatgctag tcattagagc   136140
ttgaggctgg caaacttcag gaaatgttca caagatacca gcattcttga tgttgtgtaa   136200
atggccttgc ctttagagtc aggcagatct agtttaaagg ctcagctcct ttatttaatg   136260
tgtgcccctc tgagcttcaa gatcttcgtc tgtgatttag aaataccatc ctcatagaat   136320
tataatgaag atcagatgac atgatgaatg tgaacatcct tgataaatag caaaatgcta   136380
gacaaatgtg ggggcttaat atgtcattga ggtcactagt aatttagctg gaaaggctgt   136440
aacacagcac ttcccgatgg cttttaccct aagtaacttg gtatgccata taatatgtaa   136500
cagatccaac aggcagagca tcgccagaaa acagtcttga ttacctcaaa ccaaaaagtt   136560
ccaccaggat cctgttcaga agctaatttt agtaattaag ggaatcatat gctatgttca   136620
agtaccatgc cagtaaaaac ccaattgtgt accttcttaa atcactgctt gaagagcaaa   136680
tctttccact ttggtgaatg aacttatctc cacattccct gccctactga cacaactccc   136740
tcccacgttt attgttaact tacacattca atgcacagca cacctttact caaacaacgg   136800
```

```
aaaagaaagt gtcaatacaa agtggccctt gtctattcct taaggagtag acttccattt 136860
tcatgagatg tggatttagc atagacatat tgattacctt gaagaagaat tcatataatt 136920
ttatcttctg attctcatca ctcaaatcaa aattatataa tatatcccaa aatgacaact 136980
agaaatgtgg ccttgggcaa gtcccttctc ttctctgatg cttggttttc ccatcataga 137040
attggaattg tgggcttcac caaggacctt tctggtgcta acattttgtg attctgtgta 137100
aaaagccacg cagaaaggat tgttttcag cccttctta gattgtctgt tccctgctcc 137160
cagaagtata gataatgaga cttgagtgct ttgatacatc gtaattgtat ctacctccat 137220
tcatacctac ttaagatatc tgtctaaaag tagactagac agattattga gagagtggag 137280
ggcagaaggg ctgtctctgt atcttaaaga agctggcact tttcagctga tggctgcttg 137340
gtcttgaggc ctcaagatct ctaatctggc tttctctata gtgtttcatt cactgtttgg 137400
tgatggaatc tcttcagctc agagatactt aatagatata gctttttatt tcctgcttcc 137460
aggcctacct acctgttcct tgcttttttt tttttttttt tttttttat actagttgct 137520 gttgtttctg aaagaatctt gagggtggtt ggagtctcag aatggcttcc ttaaagacta 137580
ccttcaggct ctcagctgct catccacaac aaagataagc ctttatttgt agatgattca 137640
ttcctggctg catttgaaaa ccacatattg ctaattgctt gaagaattta aatcccttga 137700
ctacttttca tttcagaaaa cccttacaaa aaagtccaa atgaggacct tccctccagt 137760
gaattagctg tggctttctc acagtccata gttaggatta atgtaaagcc atctctcatt 137820
tttctggaca cttcccaagg atacactcct tgtttccaaa atggaatgag aaagaaagaa 137880
gtgcccttcc tgccatcttc tcccatgacc cttttctcct tcccacttc cctcctattc 137940 ctcctcaaac atgatttatt tctgtgtttt gcaactcttg agttctcatc atttagtaaa 138000
tggtgttggc ccctattgat tccttcctgt cctggaccat ggagagtagt aggcctttca 138060
gaaatttcag gtagcagcca aaccctggaa gaagagaagg aacacggagt cctagaccat 138120
gtgagaacct gaggtgtgca gcatttcctt cacagattcg tctagcatat ttgagaagta 138180
tctttcccac taggagactg aactctgcat ctgagaaaaa aaaaaactta acatatctac 138240
aggttttgac aacctctatg aattacctag ttgagaggat ggctcaagga gcctatggcc 138300
atggtctgat gtcattatgg acactatgaa catccttgag gtttccattg ttgaagacag 138360
ccctgatgcc agctgtctca tcattcccca tgttcaagag catcccagca tcgctacctc 138420
aggatcccat gtcctgaatg caacagagtg atttcgctgc tgaattacta ttcatggcac 138480
ggctcttcac agcattttatt catccatgtc catccgtcct tccagccagc caagaagctc 138540
atgctttcat cttttcatcc tgagtaccaa ctatgtgcca gacactctgc taggcatttt 138600
ggggaagcag aactgaataa gatatcattc ctttcctgaa aaatttaagc aagaggagaa 138660
aggtagtgat aaggaatata ccttagccat aaaggaaaaa taataaatca cttagaagaa 138720
gttgagtgag atgaaggaa aaggacatcc aaagcaaagg gtacagttg aataaaggca 138780 gagagacatg aacaaaatgc attgagggtt tgaggaacag caattggttt aacatggcca 138840
gagctgggga aatggtaaag gcaagctgaa agcacattga aagcaaactt cgttactata 138900
ctaggtagtt tagacttcaa agagttgaaa atctatgacc atgggacagg tatgatgaca 138960
tattattttg tttattttct tttttttttt tttttttttt tgagacggag tctcgctctg 139020
tcgcccaggc tggagtgcag tggccggatc tcagctcact gcaagctctg cctcccgggt 139080
ttacgccatt ctcttgcctc agcctcccga gtagctggga ctacaggcgc ctgccacctc 139140
```

```
gcccggctaa ttttttttt  tgtattttt  agtagagacg gggtttcact gtgttagcca 139200
ggatggtctc aatctcccga cctcgtgatc cgcccgtctc ggcctcccaa agtgctggga 139260
ttacaggctt gagccaccgc gccgggcctt aatttgttt  attttcatgt ttctttaaag 139320
aaaactggca gcagcacaaa tgttttgttg atgagggctt aaattttaga aagtgagaca 139380
attttagaaa ggccagctag agagaaattt ttagcatcaa gttttgctaa acacctagaa 139440
tttattcctg gagctagtta cctccatttg ggttgttacc tgcaagtact gaccacgtat 139500
atgaagaaat actggtttag accaaggcaa ttggctgtat aagaggccta ccctcatacc 139560
aaaagccagt ttccttggtc taggccagtg tttaccagta tgtgttctga gaaaactagt 139620
tccatgacat gttccatgaa aaatacgatt tctattctca ataagtgag  agaaacttgc 139680
atattatggt cctgctcagg aagatttaca gtccttatta gcatatcgca ggtcctggtg 139740
aatactgcaa taaagtaacc tgaggagctt tgtaactcag gattcccaaa gttgattcaa 139800
ccacagaacc tcatttattc acataacacc tgttatccta caaaaccact gttctctaga 139860
atacactttc gaaaacttgg gtatagataa aaactctatc ctataggcag agaataccctc 139920
tagctcaggt catcattttg cagatgtgtg tgtcattaag aatcaatcca taatgcatta 139980
atgatcaaaa gcagaccatc cttaccacat ggtgcataag attatgctat tagctactaa 140040
agccactgaa gttaatcatg ttgggtctgt aatattgttg ttatgcacaa aggataggct 140100
gcaaaagtgt cctaggccaa agcatggcta ttgcccaagt tatctaatgt ctgcaggtac 140160
atattcctga cctaaggatt gtgctaaaga agttatttct aagaaatata gtgacttcca 140220
gcatcatgca gaatgatcat ttaatatttt gaatatctag acattttgct gtagaattta 140280
atagtccttt tatacactgt ctgaccaaca ttttgacatt tactcagaat cccatcacag 140340
tgctaccaca taacctcatt actaaagtag gaggcctaga aatcacagat ttgtagaaac 140400
catccaatga ttgaatcccc tctacctcct gttcagcagg cagcagagtg tcataaataa 140460
ttaacaatgt ggaactcagt tactgggatt tcttccattc tcctttggct ctctagacta 140520
gattctaaag accctcaggc tggtaatgca agtggtaagt ctcatttctg agaaatgctg 140580
cttcctacac acagttctct gatacctgag tgctttgact gatctgcata actgaggcat 140640
gcaccaagga gcagaattac tctataaatt ttggcatcaa tatgtacaac gtgtgactca 140700
gcactttgaa actctgggga ttttttttgtt cggttggttt ttgttttaag aggtcctgtg 140760
gtatagtgga aatcgtatgg tagactcaga tacagagagg ccttgtttct agtcttggtt 140820
ctgtcactta ctatcttgat gaccttgggc aaatgactag aactctctga gcctcagttt 140880
ctccaaccac actgtaggaa taataaaatc ttgtttacgg cattttgta  aatacgtaga 140940
gaaactggta cacagtaggc acacagtaaa tgtcaccata cccttcagtc cttcttttgt 141000
ggatgaaaaa tggtctttct ttgtgctccc agtaaccact ggggtctgtt ctctctctct 141060
gctggacagt gtggcttctg gttcttgttt ctttgttctt tggtctctaa attacccttg 141120
aaacaaccct tgaaatttcc actcgatgac ctaaattgtc atccctaagt tggttacatg 141180
catatttggt gacactttgg aggggaaaag ctttatgtct ctctaactgt agttcttaag 141240
ggaatttgca tatggaaaaa caagagactc catctcttaa ttcctccaaa ccaaattatc 141300
tgggatagta catatatgtt gtactctgtc tcttagcatt tgctcttaga gaaatatggt 141360
tagagagaag taattttttc taatcataaa aattaatgat actgcatatc tgatacttga 141420
atgagtacct ccttgtaaaa tttctactta aatccttgag ttttaaagt  gtaatagcaa 141480
tagaaagatt ttattattgt ttacttttgc tatgagtgct ccaaaatccc tcagtagctc 141540
```

```
ttgagagagc aagatgatgt cataggcaat attttccaaa ggtagtaggc agaaaactaa 141600
gtacacagca cacaataggc catatataca aaggcaagta ttttacaaat atagtaattc 141660
aagaaaaaag tttcattttc actggtaacc tgactgtttg tttaaaaaca ttttattatt 141720
tattatttaa aaagagtgtc acttgttaca gattgtggga tgtgttcctt aagatcacaa 141780
aaatgtaaaa tattttcttt ttatattgaa cacatacata gacaactaac ctgagcaagc 141840 tgcttttag agacatttgc acatcttttg ggatcacgtt gttaagaagt agaactaagg 141900
gaaaaagaca cagccaccca gaaaccggta gagctttcag ttcatctgtt attaatattt 141960
ccatgacaca gatatctagg aagtaaacag aaaatagcat cgctatcctg cgtcacctttt 142020 tttggaatca ggttccattc ttctcagtcc agttcatcct tctgatactt ttaagatctc 142080
aaccaagaca tagaaatatc atattttccc ttgcttaata ccccatggaa ccaatgcccc 142140
tgtggctgaa gtaaaaatta attgttgagg gacatttcag ccctctagca gtcaacaatt 142200
aaaaacatgt aagcaccgag cacctgcaga aaacttgcac tggcatttgg atctaagaag 142260
aaaatctgca tcttaaacaa catgaaaagt cgccagccca agcttgtgca gtgaagtgtc 142320
atgctggcca caatgaaacc gaaagagact gatgactctc ctcagggtgg aaaacgaggc 142380
atggaagctt tgattagtga gctgttaggc acacagacat taatttcaaa gcattctcat 142440
ctccagtctg agtaataatt cttgtagtat tatgcaattg tttggctgct gcaagaaatt 142500
cagcagactc caacaagtag tctttcttgg tctctgagtg actgtaactt aaattctacc 142560
tcccttctct tctcctacat cttcccactc cccacccgac ctcacccac acacacacac 142620 aattcttgta cactgtgttc agagagatgc acacacacat atatatgtat atatatagta 142680
tatttgtcaa taaagcagaa aagaagaaag aactccaatt aacaattttc catttccccca 142740 tctcacctct gtcttacaag tagataggaa aagagaaaac cccagtaaaa aatggcaacc 142800 accgcctcc ccaactttac atgctgcttc ctatgttaga ggacttggct taggcatctg 142860
attgtggagc ctgctagata caagcccata tttagactgc tacattcaac aatgtctctc 142920
tttcatatta gaaaaattcc gggttggcaa ttacaagcat ctcaaaatga ccagaacctg 142980
aagaaaggct gacttgcctc gttcaaaatg agggctctgc tctagtggat agtccggaga 143040
aacctggagt ctgaggctta ggagcttagg ttttgctcc tcaacacaga ctttgacgtt 143100
ggggttgggg gctactctct tggttgctga ctccttccaa cgggaccaat agtgttttcc 143160
tacctcacag ggatgttgtg aggacgggct atagaagtaa tagtggttac cattcatgta 143220
gttatgagta tcatgattat tgtttcctgt aatgcggctt ggcattggca aagtgctttt 143280
tgattgttct tgatcatata tgatggtggc caggcactga ctcaggcaga tgcagtgaag 143340
ctctggctca gtcacttgct tttcgtggta tgttgctggg aagaaacttt gctgatggga 143400
ctcaaggtgt caccttggac aagaaacaac tgtgtctgtc tgaggttcct gtggccatct 143460
ttttttgttt attaggcaat tcgtatttcc cccttcggtt ctagccttcc agatccctgc 143520
caaggaccta gatcttagcc tcaggcccca tcactgagct gaaggtagta gctgatccac 143580
agaagttcag taaacaagga ccagatttct gcttctcccg gagaagaagc cagccaaccc 143640
ctctcttcaa acacactggg atactagagt cagactttcc ctcttacatc tagccttact 143700
gtagccacac tccctgattg ctctttcaca tcacatgctt ctcttcgtca gttgtgaggc 143760
cctctcattc ttctccccaag ccagactcaa acattatatt gatgtcaaag aagaatcact 143820
tagagtttgg aataccttgt tctctctctg ctccatagct tccatattga aaccagtttc 143880
```

```
tttctcgtgg agaagtggag tctgtgaagc cagagacagg cacatacgag agtcagaagc  143940
actctccctg acttgcctgg ggcctgtctt tcccaccttc ttctccagtt tgtctaaact  144000
ctctctctct ctctctctct ctctctctct ctctctcttt ctctcccccc cctacacaca  144060
cacacacaca cacacacaca cacttttttc tctttcccct gactcagcaa cattctggag  144120
aaaagccaag gaaggacttc aggaggggag tttctccttt ctcagggcag aattttaatc  144180
tccagaccaa caagaaattc cctaatgtgg attgaaaggc taatgaggtt tattttttaac  144240
tgctttctat ttgtttgaat gttgcatatt tctgctagtg aaattttccc ttaataaagc  144300
cattaataca ccaatcgtat tttcttattt acaacagact gagagaatta atgctgttaa  144360
cattggacct ttttttcttt ttctgttttt cctttttttt tttttttcctt tttttctctc  144420
ttgtttgctt tccaggtcat gctgacctgt tcagcttgga ctgtttcaca tttgttttta  144480
atgtcagttt aaatgtaatt gtaaaagcat gtatgctcta aattcatgta gttactttt  144540
tcagtggaaa agcctggtat tcgaaagcat ttccaggctc cgcaatttca tatgagcagg  144600
ttttcggtaa aatcttttgt ccctcactca ggatggtatc tggacagtga gccccttct  144660
tctggctcag tagtcagaga gaggagactt ggagacagtt tctgccggat cctgtgcttt  144720
ggcaaggatg tgcagcattg catatcattc tatcattaat tacgtttact cctccatgaa  144780
ctaaaaacca ttagactaaa tagtccaaca taaaccttga aagataaaat ttgatattct  144840
ttcgcctggc catttctctg acccagaatt ggggctggga ggggaatgga gacttggggg  144900
agagaatcaa ggaggcttct tgcctggggg aatttggcat gcacttatta atcccatttg  144960
gttgtactcc ctactaatcc ctcactccat acctgccaag gattggcttt gctccctgct  145020
tctcatcccg gtcctagttc ttcctcaacc atctccattt cccaccactg atccttctct  145080
ccagtaagat gctattcaac ctgatgaaat ataagagta gcaccaccct ggaagtcagg  145140
ataccttagt tttagctcct gctctaccat tatctaactg tgtgaacttg ggtatgagtt  145200
aacctttgcc cttaatctg aacagtcttt aagaattggt ttataggaga aggaaggga  145260
tagacaagat ccaaggcctt tgaacccttt tttggaaatg aatccttttc ttcaaacaaa  145320
atttgactca gagtcccaaa tataggtaca gaataaaatg ctgctgttct tgtttgaaag  145380
gtggtggggt gcttggagcc acatgctcag gcccactttg ccacctctca ggaaccctcg  145440
aaaaaactta taggactctt ggggctctac cattgtacta gactgatgtc tggggagtct  145500
tctaactcca attttctctt ctgttacatt tcagtccttg tgaaaactct atatgtttca  145560
tcagttcact ttttcagaaa gttcacctgc ttggggtaaa gggcatgcag tggagaatgt  145620
ggggctcagt aactagcaat agtaaaaaac atcattggct ggcttacata atttactctg  145680
ttctaagcat cttaaacaca tactcatctg aaaaatcaca acaaccttgt gaggtagatc  145740
ctgttattat cttaggattc tgaaacctgc cagcttgact ctcaaccttt gacttgagac  145800
cagtcgccca agatggaaag ttatacttt cacagtttac caccgtaagc agttttcag   145860
agtgacttct agctagagat ccattcttag aaaaagtcag aacctgccca ttagcatgca  145920
ctatcaccgg gcgcagagta ccttcactgg gttcatccca tttcctccta aaaatagtcc  145980
tatgcagtag tcaagtcata tcatcaccat tatataggtg agaaagctga ggtgtaggag  146040
aaatcaagag atctgttcaa ggttacacat cccataagac tctgaatacc accatcaaga  146100
ataataagcc ttttatgtga aaagcatttt agaacttcag tgtcattatt gcattctgcc  146160
tcctggagtt cagtgcactt tttcaccatg ctttaatctt ggagtcctgg tggtacagaa  146220
tctgccttct actctcaggc aacaccatag tgtctttatc cctcataaca aacatatgat  146280
```

```
ttaagtaatg atattatccc cattttacaa attagttaac tgagataccg agaggctaag    146340
tcttgcccaa agtcacaaag ctagtcagcg atagagccgg agttacaaat gaggcagcct    146400
gactccagaa tatttgctct taactactac tctttataca tatgtaagga aactaaaagc    146460
caaagaggga aagacgtccc tgaggtccca cattgagttc cccgactcat ccagtattct    146520
tctgaccttc taatcctaaa gttatacagt aagatccctt gactctaatc ctcgtagatg    146580
gaaagatggc tggcatgatt taagctacag gccacaaact ggctttcccg gagccagaaa    146640
tcacctgcag aattctgttt gtccagcaca gtgtttgttt agaaaattga catagactgc    146700
ccctaggcag ggcatcaatc actgtcactg tccccagccc tccctattta tgtttgccaa    146760
gctttttttt ttttttctca tttatgtgtc tgcctgactt gtgaaggtat ttgagtttat    146820
gacttttaga tttaagcatt ggaatatata agcactgcac atacacacat actcacatgc    146880
attcacaaaa gtatagccta gtctagcttc acaaagaatt tgtagcccta caccaaacac    146940
acctttatgt ttacttaaca tttagaatta gatttaagat ctgaatttag tttcacaggc    147000
attcaagtgt ggaagaatct cggttattat tttttgtttc atactgtttc actcttgctt    147060
tccctgctgt gtctggaccc ctgtcagtcc tgctttctgc cattctccat gcctgagtta    147120
gggcccctgc aagccactca ctcattaatc tttaggaata gatggagagt ggaaaccagt    147180
ttggagggtt caccatgtgc caggcatcct ctcatttagt tctcataagt gtcctaagag    147240
acaggtggca gcacattcgt tttataaatg aggaaactaa atcttagaga agctcaacaa    147300
agacctcaaa gtcattaagg tactaattaa cggagctggg atttgaatgc aagattgtcg    147360
gactccagag cctattcttt tgccctatac cacagttcct tacaaggaag atgtattcgt    147420
tttctattac tgcataacac attgccacaa atttagcagc ttcaaacatt tatcagctca    147480
gttttgtaag tcagaagtct ggcacagcat ggctagattc tcagttcagg gtctctgaag    147540
gatgaaggtg tttaccagga tgcattctaa tctgaagctc agggttctct tccaaactca    147600
tgtaattatt gcaggattca gttatttgtg gttgtaggac taaggttccc acttcctttc    147660
tggctaccag ccaagggcca ttcttagctc ctggaggctg ccctctttcc ttttcatgtg    147720
gaccccaaca ccttcaaagc cagcaacaga gactcttcct tgtgttgaat gtttctcact    147780
ctacggatgt cttccagga gaatcccagt cctgtgaggg ctcacctgac gaggtcaggt    147840
acatcaagaa taaccacact tcaaattcaa ctgaattagc accttaatta catctgccta    147900
gttttttcaa cagcacctag gttagtgctt gactgaatga ctggaaggaa ggatgtgtat    147960
gctcaggcct cagaatcttg ggggccatct tagaagtcag cctaccacag acgttgattg    148020
ctttcatgtg tcaaatttca tagtgagaca gggagaacag aaatatcctt gaccttagat    148080
agagcgattc aaactttcta agactttgga aacttcacat cactttcacc tttcccttga    148140
tcatggttga gaaggcctat gtcttggagt ggcaaggagt gagactggaa cagtacctaa    148200
aggttaagga gactaaagaa gttacagatt ggtcacatct gctcctccct aggaatgagc    148260
catggaacct gatttgaatt tttttttttct ctggtgctat agagatagct cccacagggg    148320
tctaatgccc caaggctgaa aagttcgttc cccataggat ccaggcatga tatcagacca    148380
ggtgttacaa tctcctaaag aggaggtatg gacaggaaag ccccttgcca atgacccttt    148440
cttgtcactg ctctgactca agactaatag ggcagagata gtgagcaact cacatactac    148500
taaaactatc cacttatact gccccctttc tccttgcttt atcactccat ttaagtaagc    148560
cagtgagtct ctgccttgac acagtggcaa gctgatctgt atcttatatg gaagaattag    148620
```

```
atttgactct ggggctcagg tgcagagggc aggaggggca tagggtggc cctcatggaa   148680 gaaaacaagt ccttggatac tgagtaacag ctgagactag caagccttat tgtccaggat   148740
tccaagtcgt ctagcaacat ccttgcctct gctgcagaga gaacagagga tcccccggca   148800
gaatgaatgg agtctgattt caattacgtt cagtnnnnnn nnnnnnnnnn nnnnnnnnnn   148860
nnnnnnnnnn nnnnnnnnnn nnnnnnnnnn nnnnnnnnnn nnnnnnnnnn nnnnnnnnnn   148920
nnnnnnnnnn nnnnnnnnnn nnnnnnnnnn nnnnnnnnnn nnnnnnnnnn nnnnnnnnnn   148980
nnnnnnnnnn nnnnnnnnnn nnnnnnnnnn nnnnnnnnnn nnnnnnnnnn nnnnnnnnnn   149040
nnnnnnnnnn nnnnnnnnnn nnnnnnnnnn nnnnnnnnnn nnnnnnnnnn ngggtcctgg   149100
aggcaagtgg gaatgcagct tctcttcctt aagcagatgc catataggcc tggggaggag   149160
aatgtgagaa taccagccaa gttctcattg gcactatacg gagaaagggg aattatttca   149220
tcttgatgga ttctccccac agtctctgca catattgatc ttacttgtaa tgagtttgtt   149280
cagattcacg agtcatcatc ccagggagat ctgagtcatt ggtgggaaag tcgaggtgac   149340
agattatatc tcgctgatct cactgtcacc aattgctctg tgtgtccctc cacctttga    149400 aaaagcccat ggaatcattt gtgtataatt aatttggatt tatttcttat ttatcaatag   149460
ctttagtggg gtattgtaaa tgggaaagct accccagaga acagtgtaca ttcacagtat   149520
tattcaatag aactttctga gatgatgaaa atcttctata tcttatgttg tccagtataa   149580
tacagccgct aactacatgt agcttttgaa cactgaacat gtggctagtg agactgaggg   149640
attctatttt taattttta atgttgtaat taatttaatt ttttaaaagt tttgctttct    149700
attttatagc ttaataatta aactaaactt acatagccca catgtggcta gttggccact   149760
atactggaca gtacaagtct agaaagatct cagagagaca catgctgaga tacagcagga   149820
ataggttagt cagaaagaga gccaatgtaa catagggaat tctggattgg gaattagagc   149880
cctggctcta atctcagctc tgccactagg tgaccttgcc ctctctggct tcagtctccc   149940
catctttaac ttgaaaggtt aaactaacta acgtcaaaag tcccaaaatc gtggctatgg   150000
actgaattca atttgggata cataagtttc aggaattttt ttaaaaatct attaatgcct   150060
tctaggtgtg tgtatgcacg cttacaggca tgtacccatg cacaagcatg ggacggcagt   150120
aaggcattca ttccagttca ccagtgtact aaccattcac acatacacac acacacacac   150180
acacagacac atacacacac acgcatgcat acacaccccta ctgtattgcc tatgtagacc   150240
ctgaaggtct ttgaatctgt caccattgga taagataatt tctaacgacc cttcccgttt   150300
tgtcctgctg aaaatcttta agccactata gtgtccccaa tctatttcaa tttgggcaga   150360
tgactggagt attctcatag cttcctgtct cttcccctct gaatttgata ctagttatga   150420
agtttggcgt caaggatgaa gaagggaggc agggaggata taaccccagc cccactcctt   150480
aactccgctt ttggattaga agtagcgttc agggcttcag attccttggg gaggaagtag   150540
agataatatg ggctttgtaa tcagaagatg gggttcagat gattgggttc tcactttttc   150600
gatagctgtg ttacctcagt ttattcattt gtaaaatagg gataagaaat atctttaacc   150660
tcctaagatc atgtggaatt aagtgatgta acgtgatgaa gcgaggcatg cagaaggccc   150720
tgaaaaaata atagttaccc ttaagggaac taaatggtct ggcaacttgt gagctcaaag   150780
ctagaaaggc ccggtgatgg ggaagatggg gtctttctgc aggaactaca gcagggagc    150840 agaacctgta agccaccagt ctgtggagct gtgtccaaga actcatgttt gcaacaagtt   150900
caccaaatta caagatactg tggggtccag gcctctaact caagaagatg gtcttggccc   150960
agatcatacc ttgcagcctg tgcctttggt gggatgtgag tgttggcagt ggctatgcat   151020
```

```
atctccttat tactggctgt gcccaagccc tgcagaaatg attgttggac aaggtcatct    151080
tgcactcagg gttggttttc caggcttcct tgttatttc cccttagttc ttctgtgctc    151140
ctcttgcaac accaacccca ccatttccct cttccctacc ttagttgttg gtccaaacat    151200
gtaatccatt cttgcagtga tttattgagt gataccgtaa ctggagtttg cattgaagga    151260
cttattttc taattagaac taaaagtcag ttccaggctg ggtgtagtgg ctcacgcctg    151320
taatcccagc actttgggag gccgagatgg aaggattgct taaggccagg agtttgagtc    151380
cagcctgggc aacatagtga gatcccatct ctacaaaaaa acatgttagc caggagtggt    151440
agtgtacacc tctggtccca gctacttggg agactgagga gggagaattg cttgagccca    151500
ggaagttgag gctacagtga gctttatca tgccactgcc ctccagcttg ggtgacagag    151560
ggagatcctc cctcaaaaaa taaataaaaa ctacaaaaaa aaatgtcact tccaggttgt    151620
atctttttc acaggggcca gacacagatg aggagtaggt tttgttgtat ttatccattt    151680
aaattgagca atcagcttct ctctttggtt tataccttc ttatttatta ttattatttt    151740
aaaaggatta gagataaagt gctttatggt cttctcagt gcaactgctt atgctagacc    151800
tcagaattat gacctcttca attatttata tttccgtctt tataaatact ggaaaaaata    151860
gtacaaagta aacatcggga tgcctaagga cctctaaatt gtgtgtgagc acctggggaa    151920
gatggttctt aaggtttgag ttttggatta ttgtggttgt cttaaataat gttatttcta    151980
tcattccttc caatggctgt ctcctagcat ggttcccatt ttacagactg atggtagagg    152040
cagaaagatt ctctcacttc tttgatagta ttgaggattt cagcctttca ccgctcctct    152100
cccctttgct aaaaagaaa aaaatcaata tgtatgttat agtgtatgtt caactatgag    152160
caactatgtg tattcaatga gaaatggaat accataaaat taccatagtt gaaccaaaat    152220
gataggatag aattcgatag tctgaggatg gaagggaact tcaaggccac tttaaaaaac    152280
cccattccta tataatgctt gaattcttaa ccactgtgca tctagtattt gatcatttcc    152340
agtgatatgt gtgcctggca acttttccat ctcccagcgc tttaactatc aaaatgtatg    152400
tatgtgtgtg tgtgcatgta tgtgtgtgtg tttagagaca gagagagaca gaaagagaaa    152460
gagagattaa aatccaagtc actgttcttt ctgggaccca aaaaacaagt ctagtcattc    152520
tccatttcta gtctctttcc ctagcaatcg gctagacatg ctagacatag acacatgtac    152580
atcactcctt tgatttacag cattcagtat ttgtctatca cttataagat aaaacccata    152640
cttactttt attttatttt ttttagagac agtgttttac tatgtcaccc aggctagagc    152700
atcagtggca caatcatagc tcactgcagc ctagaactgc tgggctcaag caatccttcc    152760
acctctgcct cctgagtagc agagactaca gatgtgcacc accagacctg gctaatttag    152820
ttttttacta attttgtgga gatggtgtag tgtcttgcta tgttgctcag gctgatattg    152880
aggtcctggc ctcaagcact cctcccatct cagccttcca aaatgctggg attacaggta    152940
tgaaccacct tactcagcca gatttcttaa tatgatatac atgctccttt aaaatcaagc    153000
accatctttg ctttcaaccc cattattaac cactttccca tatacgcaac atatgcttca    153060
gtcatactag tctctggttg ttccccaaac actcctcagt gcttttgttt atgccctttc    153120
tgcccacctt tgcctggtga aatcctcatc aatcttcaaa ttctaggtca aatactatct    153180
ttcatataaa gcattttcta aacccacctg tgtaaaaaga ttagtggttt cctattttgt    153240
tgatgcctcc attgcagcat tttccagtct gacttttct agaattgact gtggcaaggc    153300
taccagcctg ggccagggcc tgtgtctttt ctgtcaccca gaagcaaagg tctaacaatg    153360
```

```
gatatctgct gaatgaatga atgaaaatga atcattaata tagtagtaaa tgagttaatt   153420
aaaggttcca ggtatgaata ctgaagcctg cattgaggca gagctgaatc caagactatg   153480
ttaggttggt ctggcacaag aatcagagtt ttcctctgca agctatgaaa aatttgggtt   153540
tagcacggat ttgggatgac gaattataca ttcaaccagt gttgaatgag cacttgtcct   153600
taaggagttt agagtctgtg accagggaga atgatgattt tcttagctcg ggcagttttt   153660
ctaacaaggt agttgcattg tgtgtttttg aacactgatg ataaattcaa gtttctcttc   153720
ctgccccata gcccggaagc tgaagaaact tggtaatctg aaactacagg aggaaggaga   153780
ggcttccagc accaccagcc ccactgagga gacagcccag aagctgacag tgtcacacat   153840
tgaaggctat gaatgtcagc ccatctttct gaatgtcctg gaggccattg agccaggtgt   153900
ggtgtgtgct ggacatgaca acaaccagcc cgactccttc gcagccttgc tctctagcct   153960
caatgaactg ggagagagac agcttgtaca tgtggtcaag tgggccaagg ccttgcctgg   154020
taaggaaaag ggaagtggga gcatgagata aggggggatca tatttagtga acgctccta   154080 gggccagcca ccacgtctgg tgcttttctg cccattaact caggtagtct tcgtcgtaac   154140
cctatgggag agggattgtt ataaatctca ctttaaacat acagggattg agactcagaa   154200
agcaaagaga aagataatat tataaggtgt cctatgtggc ccacattgat gcacagcagt   154260
catgctttca catttaactc acagaaatgg tcagcaaaat ttcccttaat cacaaaatca   154320
catagacata tccatatatg ccttaggata ctccttctata tttgcacaca caggctcacc   154380
ccaaagataa tctccagcct gactgacatt ctgtcttcag tgtcacctttt aggaactata   154440 tcatgggaac tctcataata tgatatggta gaaagaacat gaggttggga atcagaacac   154500
ttcagatcta ctttttagttc tgctagtaac ttattgtgtg attccttccc cttctgggtc   154560
tcagtttctc tatctgtata atgtataagg catggtttgt accaaattga tggttttcaa   154620
attttgcttc gagaaatgct ttgtgcactt taaactacct aaggaatcat aataggagga   154680
aagattaggt gatagtgaaa gaattatcaa ctgttggtct aacagaagtt ggataacaga   154740
agttccccag tgatggggaa ctcacttctt tcttatgtca tctgttgctt aaacaagtct   154800
ggttattaaa atattacagc ttaaggaatt cttagagatc ctctatccaa tgattcacaa   154860
actttcattt aacagccaag tgctttattt ctcaaaagaa ttgtacacag atatgagtgg   154920
agctagttta tttaaagcca gagtctgtgg cttgggcctc accagttcag cctctttctc   154980
tctatcccag ggaagccccc aggtcactct tgcaaaatct tagggctccg aggaacacag   155040
tttgaaaacc agtgaagtat atgctcttta aaggttctcc taatcttgca attatgattt   155100
aaagactctt ttggaataat aacaactaaa ccttctcttg tggagtcaaa gattaaccgg   155160
cctttcaata ataactgcca ttcaggtaga aatgtatagt gaacagagca atttttgtata   155220 tattacctga attgattctt ataggaatcc tataaaatga gattctttct cctgttttac   155280
agaccaaata gggaagctgt gagaataatg tgattgacct atagttacat agtcagaaaa   155340
tagcaggacc agaacttgag cccaggttct ctcctgattc caaatcctcc ctttattcca   155400
ctccacctgt aggctgcagc accactgcag ttctgtaact ctgggcttta cagtgagggg   155460
ccaaggcttc actgaaggcc acttgggtca tactgtgggc ttgctgcatt tgaagacatt   155520
gcatgttggc tgtcaagtct tagatttgta tttccaactc acaggttagg cctggtcaca   155580
gccctaacca tctcttgcac cttctcagct tgggaagctg aggttgacta ggcaataaga   155640
tcactgggaa ggaaacccaa ggactctgat tggatatgtt ctgtgccaaa gcagagggtt   155700
cacacagaga ggaaaaatat aaaaaagaaa aaggagaaag ctgctttaat tcttatcact   155760
```

```
ttttcatctg gatattttga tatcatgtgt ttgacaaaga ttcaaagttt aatcttccca  155820
agcagtttcc aaacacttat ctcattttat aagttacaga gcttttcat atatatgatc  155880 ccagttaatc ctcacaacaa ttctatgaat catagagact attatttcca tttcacatgc  155940
caaggctcaa agaggataac taacttgctc catttggtca cttaacacat ggaaccagaa  156000
cttgacctag accttcaggt ttctaaattg gttatcttga caataaccta gtgcaaaact  156060
ctatagcaga atttgtatga cttgggatca ctggggcttt ccttggccca gccaccagga  156120
tggaaagtcc cctcccctta cattaacaaa tctgcaaacc aatatcagtt caccatctag  156180
cttgccagac taagtgatct ctgactccga atcttttaaa agaatagctt caaaagaaag  156240
ccaattacca cattcataag aactgttctt catattatct ataattacct acaagttcaa  156300
gtaattcact aattcaatag attgagttct tgacctgtaa aatgaactgt gctaggcctc  156360
taataagata aattttgttg taagttttct acgacagtaa tgatgtatgg aaattgccta  156420
gtagagtacc tggcacatta ataaatgata actattaatt tagagtgggt gagtagactg  156480
ggtgtgcaca gtatatttag aatctaattt atctggtttg gaatcctagc tatggactat  156540
ttctgtgacc ttgagtaaat cacatgtctt ctctgtgctt ctgtgtcctc atttgtaaga  156600
tgatagaata atcgctacct ttcaaattgt cgtcaacaaa gagattatgt ataaagagca  156660
cctagtaagg tagcctgaaa catagtaaat gctctgtaaa tggtggttta ttattatgag  156720
acttgagtgc taagccactg ctttaatgaa actcaatttt agctaccact tgccttgcct  156780
gctcatgcat ggaccacaag gtgaaattgt cttctctgaa gaccttggca ggcagatgca  156840
ctacagcagc aaagatttcc aaactggcct ttctttgagc ctattctccc agaccagaca  156900
tgagactaca agtttctgct gcacatgaaa aaaatatgat gtcagttgga ttctagtgag  156960
aaaacagagt gtctaataaa ctgcttctgc tccctagcct gtttaatgtg tttcaaaacc  157020
tgagaatgac tcctctctgt ttctccagaa cagcctaaca caatggcaaa tgggcattga  157080
gtgaatgcat acttaaggaa atctgtaggg ctgcggctac tctttcctca agtaatccct  157140
tgatagtcat gcaggctact tcagagattg ggcattagag aacagagtca ggtattataa  157200
tcagattaga ctctagggag attagccagc catattgctg atatgtgcac agttactggg  157260
cttccgtgct aagcagctct cattaagcac agttaattaa tattatggcc aacttaagct  157320 ttccctttc tctcctgttt gttagttcgg cagcatttta gggagaaaaa aataagcatc  157380
agtatggaca atttgcttca tacctgtacg atttaattct catccttcca tgggccttca  157440
cattcacaca ctccactaga agaccaaggt tcaccagcca aagacttttc ttgctcccca  157500
ctgcctccta cccaagatat tcagggttca acctcccagg cctcttctct aagagatccc  157560
tggttgctac atgcctagac cctgcttctt atttcctact gagaagggtc agtccaaggc  157620
attctgtgct acagaagggt tccagacagg aactactctg ggatctgagg ctccagccag  157680
tctgtcagtg tgtcattacg gtgaaggtgg gaagcacagg cctgggagct aagactgcca  157740
agatgaggta ctctagaatc cctgatatct ggaaggctta ggatctaaag gaaaagaaca  157800
gtgaaatggg gctatatgag tggacaggga ccaaccaagc agaacaatgt atctggataa  157860
tgtagacttc agacctgatc ctatggctga caaaagttgg tgaccttggt ggttcctgag  157920
ctgtaacctt cagcagtgga gtagaaaaaa cactggagaa cagaatcaga acacctgggt  157980
tctagtatta gttcagccac atataaacca tatgaccttg gcaagtcaa tttatttctc  158040 tggccctcat gttccttgtt ggtaaaataa gtgtcacatc acctaacctc tgggattatt  158100
```

```
gtgagagtta aattaggtca tcaacaggaa agtgagaagt ttggtctaca tttggggaag 158160
cattcctaat gaggtatgat gacaaaattt cagataattc tggatttgtt agtgagaaga 158220
gagagtgttg gtagggatga gctctgaggt gatgccttta taactttaag catccaactg 158280
tttcagaacc tccaggagaa catggccatg tctgtactac ctgtgtgtta ttgtagaggt 158340
agcatctggg agcctctgct ctctgagctt aagggaggta atttggagat catttaattc 158400
tcattttata aaaggaaaac aaattgagga tctttaggcc atttgtttag gtttcttaag 158460
tgcccactca aatacgtgga ctgtactaag tactagggag gtaaacttga atatgaagat 158520
atggtccctg tcttcaagaa gctctaagtc ttgtggggga gacagacatg tatgtacata 158580
gatttcaatg ctgtgtaatg agtgctataa ctgtgtgagg ctacacaagg agcaatgaga 158640
atgtaaaata agaatcttta agccttcttc ttggatgagt tggaaaagcc ttcacagaag 158700
aggtagcctt tgagtgaaga cttgaaagat gagtaggtgt ttaaccggat gaaagacctg 158760
agaaggagga atgcattcta ggcaaaagca actgcctgtg cagagataac agagatatag 158820
aggcatgtga gagggcaagt ggcaacagat cagtctaggc agcaggtcat aaagggcctg 158880
ttcatatata atgatggcag taagatgggg atggcagtaa ggtgggaaac tagtagggcc 158940
aggctaccta ttgagtagaa aagaatggag aggaactgcc aggcagaaag tgggatggac 159000
gcaagaaagg gaacatgaaa gtggtcaaca ggaggcagtg gctgtcaaga catctctcca 159060
tacactgtac actgtatgta atatccgtct cccagggttg ttagaagggt caaaccagct 159120
catagctgga aaagagcttt gtgaagtgaa aactgtttat gtgggagaaa tgatgttatc 159180
ctgcatcttc ggaaaggtag agtgatcaag agcacagacc ttggaatctg actgctttgc 159240
tttggaactt ggtctaccaa ttactagctg tatgatcttg gacaagttcc ttaatctctc 159300
tctgactcac ttgtactggt tcacagaatg gagataataa tagtacctac tttactaatt 159360
gttgtgaata ttaaatgaga taatataagt aaagtgctta gaaaagagtt aaatgtgccc 159420
cataaataca tacaactatc atatacccaa aatatttttt aagttttttt aaaaaagcaa 159480
tccaatggaa atcaaaagaa aaaaagtttg ctcgtatatg cagtcaataa gtgttagatt 159540 attttttctct tacaactgac aatgcccttt ttttctccat catcatctca tttgagcagc 159600
tcagtgatgt agggaggaca acgaatatta tcctcaccat atagtttgtg cttttcccca 159660 ccaccctca gtggccagtc tggatggtcc ctggggatcc ttaggggatg tccaaatgcc 159720
agagcatctc tacccagcag gggctcagac ttagctcagc ccgtcagtac ccagattgac 159780
cactgcctct gcctcttctt ctccaggctt ccgcaactta cacgtggacg accagatggc 159840
tgtcattcag tactcctgga tggggctcat ggtgtttgcc atgggctggc gatccttcac 159900
caatgtcaac tccaggatgc tctactttgc ccctgatctg gttttcaatg agtaagtgct 159960
cctggggccc agacctcact aaaatacagc agcttggcca gacccagttg gtggtgatgg 160020
tgatggagtg acagtgaagc ttacctcatt tgacctgcag gtgtggcatt ggatgcccca 160080
gccagccaac tcggtatgag gcagctttgc cctggctttc agccaactgg taggagctga 160140
ggaggatggt gctgagacta ccccctttcac acccaagaac caatcctggt cgtgtttctg 160200 gtctcccttta cagcttatct cagaaccaca tggaaagatt cctccccttc actttgagca 160260
acatataaaa gaggcagaaa gactctggct ttaagggctg aagtttcttg ggttctgttg 160320
ctaccaccaa aggctactgc tagtcaccac ttgctgagca attagtttgt gccaagaata 160380
tgctagatac tttctaaatc ctatctcatt gagtcctcat ggtgacctga cctccccttt 160440
ttatagataa ctctattttt tttatggacg gggaaagtca ggctcagcaa agtaaagtga 160500
```

```
ctcacccaaa gtcacagagc tagtgcctgt tggagagaag attcaaatgt atttccgtgt 160560
gaatcccagc tcttctgcgt catggtggta actgatgggg aggagtacct ctaccactct 160620
ctgtctgtgt gaccttggta ctgccatttt cttctctta aacagcttta attaatacct 160680
gccctgccac tagctctata taacatcatg aatttggcca gtggctcaga ttttggaatt 160740
acatttttct ccactaaaat ctcagttcta ttattttctt aatcagcatc tttgggaaag 160800
acccttaact tttctgaccc ccaatttctt catcaattaa tgataataga accttcataa 160860
gtaatttctt atgataacta aatgggaact gacagatgtg gaatgtctgg cccatagtgg 160920
gcaagaagaa aaaaaaaaaa gtcccctttct gatccaccat tccctaagag tgatattttt 160980
ttccccccaa gatggagttt ggcgctgcca cccaggctgg agggtggtgg tgcaatgatc 161040
tcggcccact gcaacctcca cctctctggt tcaagcaatt ctcctgcctc agcttcccga 161100
gtagctgggc ttatagatgc cagccagcaa tgtccagcta attttgtat ttttggtaga 161160 gatgggattt caccatgtta gccaggctgg tcttgaactc ctgacctcat tatctgccca 161220
cctcagccag gcatgataat cttttctatg tctgctgtat gaggtccctc gatggcataa 161280
tgaatggagc tggccagaga aatcttccca aggaccttga gctagtctcc ccacagagaa 161340
tccttccagt caggacagga attgaccttc cccctcttc agccctctaa cccagaagag 161400
tcttaaaata aaatctacag gccagtggtt ccttccagta cagcactgca atgtgaggga 161460
gagtgagcgt cccccagctgc cctctcccaa ccctgccagc ctggtagcca gaagctaaga 161520
ataaccacta ggcttttggc acaaactgct ttgtggtttt cagacctcca aaaagttgcc 161580
tatgatgcca tcttctgggg caggccttga aaagccccct aactgttcat ctcccatcct 161640 caaaccctg ctgcccttaa gcaattgaat caactccatg agcacctgct ctaccttccc 161700
cagagctctg agacctttgg agctttgaaa agtgataatt ggctgttctc taaatcctca 161760
tttccttttc tacctctgag taagcatgtg gcatcccacc tcagcttcct ggtccagtct 161820
tgttcagctt ataaaaaggc ctcccccacag ggtcagaggc ctagacccat caaatcccag 161880
ggctcctgaa acaataggac ccctattcct cctgtaggaa gccactatgt tagaactctc 161940
agggtgtcta caaacatcta gataagtgtt tctcaacatg gattattttg acatattggg 162000
aaaaataatt ttgtcaatat gtagaatatg gttgacatac ctggcaccag cctactttat 162060
accaaagagg attccagtca ttctgacagc ccaaactgct cccacgcatt tctaacaccc 162120
actgaagaag cagtactctc cagttgagag tgactaattg ctgccagcct ccctaaggtg 162180
ctaatgggga gcctcagacc caagaggga gataagaact tgttcaaagt aggtcaaccc 162240
atttgctgat ctcttcaaca ccaaactcta ttatcagccc tgttttttcc tttccttctg 162300
tctttgtaga gatcacatgt tgtgaggata atgagcctga actttagctg tgtgaccttg 162360
ggcaaattac tgaacttcta tatgcctcaa attttatctg gagactgctg aagagtatta 162420
taatagcacc tttctacatg tcatttatgg aacacctgct atgtgtcagg cactgtgctt 162480
agtgttttcc aatcttcatt tctcatctta ttttctctct tgcactccca ccaaccctgc 162540
tctcctccta aattccattc ctgcctcatt tttataccct ccattctcct ctctcttcct 162600
tcctttaact gtctccctag tattttttcc cttttttccc ctttcttgtc cccttcccct 162660
atgaatttcc tccctttcct ttccccttct ctttcctcca ttccccactt tttctgcccc 162720
gaggcctgca gcaatgttaa aggaatcctc attccagcat tgtgatttca atggtaaaaa 162780
aagattgcag cactgtcatc aacagaggtg ggaaagtaca ttggagactg gagcagggcc 162840
```

```
agacctcagg gtcagccaat cttactaaaa aattctctat agtgaaagag cttggagcaa 162900
cactgttctg ctcaattgat ttgtgatacc atctaaacac ttcctctttc cagttgggct 162960
tcagcctgag ttgaataatt ctacaccatc tgccccttc tctctttctc caggacagcc 163020
aagatctctc tgagatagga tgctgagttt ccacccagac aataccaggc cttctcatcc 163080
tgtggagtag gctagtggct tggaaaccaa aatgtcaaac catagccttt aggctccatc 163140
tgggaggtct ttgtcctcac cacttaagtg ggtgtcagat ttccttccct ttctgcacat 163200
gctgcacaat caatttctgt cttacacaca cacacacaca cacacacaca cacacacaca 163260
caatttttga agtgctgaaa actagaaagc ctactagcat gaggatgctg tgtcttctct 163320
tagaggtatg ccatggtcag ccatggaacc aagagggtgc tcttccttga aaagttggcc 163380
aagcattggc cacctccccg tataatttat aggtgataat gtggtgatct gttcagaagt 163440
aactataata aatgcagctc acatatgtct acagtttcca aactgtggta aggagcagcc 163500
agcatatgag ggaatgggct ccccttcagc aggggacatt taaattagac attcaaaaac 163560
actccctggc agatttaaca ttgaaactca ttttgaaaga acaatgtgga atctccttca 163620
ctggaagttt ttgaagaaat attaaatttc tagtattcca ggccagaggc aaaggggtca 163680
acaggatgac caaacacttc gggtcacttg caaatcctgg tgtcctgatg ttaagagctg 163740
actactgggg cttctcctaa aaatccttca tgttgagctg cctgggaggc aggttcttgt 163800
tctggctgta gatgggatat tagaactgta gtcaggagaa ccatgtgcct gccccattgt 163860
gttcatttgg ttaggctttc ttgtccccga ctcagaaaac agaaggggca cagagacctg 163920
gaaattccat gtgctaaccc atatcctggc cagggaagat agtagtaatc aggatgtcag 163980
gattttggaa aagagagaga taaaaaaaaa acaaaaaaac aaaaaaaaaa acagaccaac 164040
aaacaaacaa aaacctcatc ctgatccctg aagcaccagc aggagaaaca gcaagctctt 164100
cttggagaac ctggggagga agggcaatca gagacattcc ctctgggctt attgcaagcc 164160
tcccctcatt cctttttcct ctatgtatct ccttcccagg taccgcatgc acaaatcccg 164220
gatgtacagc cagtgtgtcc gaatgaggca cctctctcaa gagtttggat ggctccaaat 164280
caccccccag gaattcctgt gcatgaaagc gctgctactc ttcagcatta gtaagtgcct 164340
agaggtgcag ggaatgcccc tgagggcaca gagactcaga gaggaccact tttgacatta 164400
aaacgttatt agggagaagc cagctccttg acatttccct tcttcatttc ccctccccat 164460
ccccactgta ctctccctca gtatcattct tctaacaaga aacaatttca tgactagaag 164520
ccaatgtatt tgctagaagt cagcttccat cagattcccc acctatccct agtctatctt 164580
tgggacaagg ccttttttgac tggttatagc aggtctgtga atttctccac agcttctgct 164640
atagaaacaa acatgggcca ccttgtattc cttgcagggc agtaaagcag gaggcatttc 164700
ctcctggaaa gatttcctct tctgccaaca ggaggaggtc tatgtaagca actcaggtag 164760
gatttatttg gcagccaagg aacttttctt taatatcttt tctaacaaga gcccttttctt 164820 agcctctgtt gagggagaaa ggcaaaattt gatattcaaa gctatgtgtt ttagttgtct 164880
aaatcagggt ttgactgtaa atgacataaa agcttaggtc ctaaaaaatg agtatatgag 164940
aagagtagaa aaagaaaaga ttcaggaaat ttgatttact tgactccctt cagattggat 165000
ccagctatcc tttccctga gatctccctg acagactgaa gtcccaagc ccacagactt 165060 caactaacag gaagccaagt agatggttcc ctgtgggggt gggggtcaag tttgtggtca 165120
gaaaacttgg tgctttgtct aatgttcctt cgtgggcatg cttccctcc ccattctgtc 165180 ttcatcccac atcagttcca gtggatgggc tgaaaaatca aaaattcttt gatgaacttc 165240
```

```
gaatgaacta catcaaggaa ctcgatcgta tcattgcatg caaaagaaaa aatcccacat  165300
cctgctcaag gcgtttctac cagctcacca agctcctgga ctccgtgcag cctgtaagca  165360
aacgatggag ggtgctttat cagggagaac agcctgatag agccaatgat aatatgcttc  165420
tctagggtct ggcaccacct gttgggaggt gcttccattc ccctctggct ttgagtgtgg  165480
tccaggaaga aaatgtggtg aagaaaggaa cacgggtcac agtgtcccag ctggatattg  165540
tgaaaggggt ggaggagttg agaacagagc agttgggact cagggaaggg acttacagca  165600
gatgaattct ctaggcagac aaaacagacc tggatgtttc tcccctcttc tttgagtcat  165660
gttcatgtga gtttgtgtgt gtgtgtgcgc gcgcgtgtgt gtgtgtgtgt gtgtgtgaca  165720
gagagagaga ggagagaggg agagagagag agagagagag agatggagtg cagaggctgg  165780
ggtgagagca caagctggag aagtcttgag tcagaaagct tacaatggta taagacatcg  165840
cttgggagcc ctcagtgact cnnnnnnnnn nnnnnnnnnn nctctctctc tctctctctc  165900
tctctctctc tcactcacac acacacacac acacacacac acacacacac acacacacac  165960
gacctcatgg gggaggacca aggaaggaca gggaagggggg aggaaacaaa agactgaaag  166020
accaaaaatc aaaggttagg gaagagtcta gcagagccca cctccttgtc aaccctgttt  166080
ttctctctct tattgttccc tacagattgc gagagagctg catcagttca cttttgacct  166140
gctaatcaag tcacacatgg tgagcgtgga ctttccggaa atgatggcag agatcatctc  166200
tgtgcaagtg cccaagatcc tttctgggaa agtcaagccc atctatttcc acacccagtg  166260
aagcattgga aatccctatt tcctcacccc agctcatgcc cccttttcaga tgtcttctgc  166320 ctgttataac tctgcactac tcctctgcag tgccttgggg aatttcctct attgatgtac  166380
agtctgtcat gaacatgttc ctgagttcta tttgctgggc ttttttttttc tctttctctc  166440 cttttcgtttt cttcttccct ccctatctaa tcctcccatg gcaacttcag actttgctcc  166500
ccattgtgac tcctatctgt gttttgaatg tgttgtatg cctttaaatc tgtgatgatc  166560
ctcatgtggc ccagtatcaa gttgtgcttg tttacagcac tactctctgc cagccacaca  166620
aacgtttact tatcttatgc cacgggaagt ttagagagct aagattatct ggggaaatca  166680
aaacaaaagc aagcaaaaaa aaaaaaaaag gcaaaaacaa aacgaaaaat aagccaaaaa  166740
accttgctag tgtttttcc tcaaaaataa ataaataaat aaataattac acacatacaa  166800
acaaatatat agaaatcccc aaagaggcca atagtgacta gaaggtgaaa attgcaggcc  166860
cctgggaagt tactgatttt ttcatctcct ccctccatgg gagactttat tttctgccaa  166920
tggctgttgc cattagaggg cagagtgacc ccagagctga gttgggcagg gggctggaca  166980
gagagagagg agaggacaag gagggcagat ggaacatcag tacctgccca cagccttggc  167040
ccctgggggc tagactgctc aactgtagag caattcatta tactgaaaat gtgcttgttg  167100
ttgaaaattt gtctgcatgt taatgcctca ccccccaaacc cttttctttc tcactctctg  167160
cctccaacct caaattgact ttcaatagtt tttctaagac ctttgaactg aatgttctct  167220
ttagccaaaa cttggtgact tccacagaaa agtcagacca ctgagaagaa ggggagcaga  167280
gatttaaccc tttgtaaggc cccatttgga tccaggtctg cttttctcatg tgtgagtcag  167340 agaggagctg gagccagagg agaagaaagt gatagcttga ctgttctcct gcttaggaca  167400
ctgactgaat agttaaactt tcactgccac tacatttttcc ccaccttttaa aagacctgaa  167460 tgaagttttc tgccaaactc cgtgaagcca caagcacctt atgtcctcca ttcagtgttt  167520
tgtaggcccg aacttcatca cactgcattt cagccatggt ggtcaagcct gtttgcttct  167580
```

```
tttgggcatg ttcacagatt ctctgctaag agctccccccc atcaagaagg ttagcaggcc 167640
aacagctctg acatctatct gtagatgcca gtagtcacaa agatttctta ccaactgtca 167700
gatcgctgga gcccttagac aaactggaaa gaaggcatca aagggatcag acaaactggg 167760
tgtcttgtcc ttgtccccca gagatgacac ccttccagca agtggagaag ttctcacttc 167820
cttctttaga gcagctaaag gggctgccca gatcagggtt gaagagaaaa ctcaattacc 167880
agggtgggaa gaatgaaggc actagaacca gaaaccctgc aaatgctctt cttgccaccc 167940
agcatatcca cctgcagaag tcatgagaag agagaaggaa caaagaggag actttgacta 168000
ctgaattaaa atcttcagcg gcaaagccta aagtcagatg aacaccatct ggtgagttca 168060
ctcatcatcc tcctctgctg ctgattctgg gctctgacat tgcccatact cactcagatt 168120
ccccacccttt gttgctgcct cttagtcaga gggaggccaa accattgaga ctttctatag 168180
aaccatggtt tcttccggaa aggtctggtt ggtgtggctc caatacattg ccacccatga 168240
actcaaggtg tgccctggga cactggtttc atctagtctt ttggcacgcc tgtgttctgt 168300
tgacttcatt ctccaacccc aagtgcaagg caaaatgtcc acctactttc tcatcttggc 168360
cactgcctcc ttacttagct cttaatctca tctgttgaac tcaagaaatc aagggccagt 168420
catcaagctg cccattttaa ttggttcact ctgtttgttg agaggatagt ttctgagtga 168480
catgatatga tccacaaggg tttccttccc tgatttctgc attgatatta atagccaaac 168540
gaacttgcaa aacagcttct ttaaataaca agggagaggg gaacctaaga tgagtaatat 168600
gccaatccaa gactgctgga caaaactaaa gctaacaggt tcccttttctg ggatgggata 168660
gacacattct ggttttcttt attactacac catctggctc atgtacagga tcactttttag 168720
ctgttttaaa cagaaaaaaa ttccaccact cttttcagtt acactaggtt acattttaat 168780
aggtccttta catctgtttt ggaatgattt tcatcttttg tgatacatgg attgaattat 168840
atcattctca tatctctcct tgtaaatact agaagctctc ctttacattt ctctatcaaa 168900
tgtttcatct ttatgggttt cccagttgtg actcttgtct ctatgaatat atgttttca 168960
tttgcaaaag ccaaaaatca gtgaaacagc agtgtaatta aaagcaacaa ctggattact 169020
ccaaatttcc aaatgacaag actagggaaa aatagcctac acaaggcttt aggccttctc 169080
tttctgtgct tggatttgag tgaacaaagg aggttttagc ttggctctgt tctcccatgg 169140
atgaaaggag gaggattatt ttttttttct tttggccatt gatgttctag ccaatgtaat 169200
tgacagaagt ctcatttttgc atgcactctg ctctacaaac agagttggta tggttggtat 169260
actgtactca cctgtgaagg actggccact cagacccact taactggcga gctagaagat 169320
gaggatcact caccggaaaa gtcacgagga ccatctccaa acaagttggc agtgcttgat 169380
gtggatgaag agtgaggaag agaaaaagaa ggagcaccag ggaaaagacc tcgtctgtgc 169440
caggcagcag actgctgcca ggatcacgaa ctctgtagtc aaagaaaaga gtcgtgtggc 169500
ggtttcagct ctcgttcatt gggcagctcg cctgggccca gcctctgtgt tgacatggga 169560
gttgttggat tctttgtttc atagcttttt ctatgccaca ggcaatgttg ttgttcttgg 169620
aaagtttatt attttttta attcccttac tctgagaaag ggatattttg aaggactgtc 169680
atatatcttt gaaaaagaa aatctgtaat acatatattt ttatgtatgt tcactggcac 169740
taaaaaaata tagagagctt cattctgtcc tttgggtagt tgctgaggta attgtccagg 169800
ttgaaaaaca atgtgctgat gctagagtcc ctctctgtcc atactctact tccaaatgga 169860
tataggcata cataataagt tttattcgac ttgtacttta agagaaaata tgtccaccat 169920
ccacatgata ctgacacaaa tgagctaaca ttgagcttca agtagcttct aagtgttcat 169980
```

```
ttcactaggc acagcacaga tgtggccttt ccccccttct ctcccttgat atctggcagg 170040
gcataaaggc ccaggccact tcctctgccc cttcccagcc ctgcaccaaa gctgcatttc 170100
aggagactct ctcgagacag tccagtaact accggagcat ggcccctgca tagccctgga 170160
aaaataagag gctggctgtc tacgaatcat cttgtgccag ttgcccaggt gagagggcac 170220
tgggccaagg gagtggtttt catgtttgac ccactacaag gggtcatggg aatcaggaat 170280
gccaaagtac cagatcaaat ccaaaactta aagtcaaaat aagccattca gcatgttcag 170340
tttcttggaa aaggaagttt ctacccctga tgcctttgta ggcagatctg ttctcaccat 170400
taatcttttt gaaaatcttt taaagcagtt tttaaaaaga aagatgaaag catcacatta 170460
tgtaaccaaa gattacattg tatctgctaa gataccaaaa ttcacaaggg cagggaggga 170520
gcaagcatta gtgcctcttt gataagctgt ccaaagacag actaaaggac tttgctggtg 170580
actgacttat aagagttttg tggggttttt tttccctaat aatatacatg tttggaagag 170640
ttgaaaataa ttttgggaaa atgggtttat gggtccttca ctaagtgatt ttataagtag 170700
aactggcttt ccttttcttt agtagttgct gagcaaattc ttgaagctcc atcattgcat 170760
ggttggaaat ggagctattc ttagccactg tgtttgctag tgcccatgtt agcttatctg 170820
aagatgtgaa acccttgctg ataaggaatc atttaaagta ctagattttg cactagaggg 170880
acagcaggca gaaatcctta tttctgccca ctttggatgg cacaagaagt tatctgcagt 170940
tgaaggcaga aagttgaaat atattgtaaa tgaatatttg tattcatgtt tcaaaattga 171000
aatatatata tatatatttt atatatatat atatacacac acacacatat atagtgtgtg 171060
tgtgtgtgtg tgcgcgcgcg cgcgcgtgtg tgtgttctga tagctttacc tttctctgga 171120
tctttatact tggttccaga tcacacctga tgccatgtac ttgtgagaga ggatgcagtt 171180
atgttatgga agctctctca gaacagacaa gacatgtaga ttaatcagat aactgaaagt 171240
tttctcccct attgggtctg acccacaggt cctgtgaagg agcagagggg taaaagagt 171300 agaggacatg atacattgta ctttactagt tcaagacaga tgaatgtgga aagtgtaaaa 171360
actcaatgga actgattgag atttaccaca gggaaggccc aaacttgggg ccaaaagcct 171420
actcaagtga ttgaccagtg gcgccctaat gggacctgag ctattgggag aagagaactg 171480
ttctttggtc ttcaccatcc ttgtgagaga aggacagttt cctgcattgg aacctggagc 171540
aagcgctcca tctttcacac aaattccctc acctgagatt gaggtgctcc tgttaatggg 171600
tgtctgtgtg ctgtaattct ggttttggat atgttctgta aagatttga caaatgaaaa 171660 tatgtttta tctgttaaaa cttgtcagag tactagaagt tgtatctctg taggtgcagg 171720
tccatttctg cccacgggta gggtgttttt ctttgactaa gagattgaca ccgggatctg 171780
ttgcccaggg cctcccaact caaccatttc taggtgaagg cagaaaaatc cacattagtc 171840
actcctcttc agacatttca gctgagataa caaatcattt ggaatttctt cacccataga 171900
aagagtggta gatatttgaa tttagtaggt ggagttttat agaaaaaaca gcttttgcct 171960
cagttttgat ttatcctcat ttgatttggc cagaacgtag gtaatatgca tcgattggct 172020
tctgattcca attcagtata gcagggtgct gggtttttc ttttccccac ccgtctctta 172080
gcctagggaa ttaaataaga agccttagaa tgggtggccc ttgtgacctg aaacacttcc 172140
tacataagct acttaacaag attgtcatgt agctgcagat tcctttgccc accaaagact 172200
agaacacacg catatccata aaccaaagga aagacaactc tgaaatgctg tttctctggt 172260
ggttccctct ctggctgttg cttcacagta tgggaacctg tactctgcat aggtgacagg 172320
```

```
ccagatttgc attctcttac aaccttagcc cttggtgtta actgtcctac agtgaagtgc  172380
ctgtggagtt gtcctatccc agaagccact tggatgctga gagcagccac catcagaacg  172440
acccacgcga aaaaaaaaaa attaaaaagt cccctcacaa cccagtgaca cctttctgct  172500
ttcctctaga ctggaacatt gattaggag tgcctcagac atgacattct tgtgctgtcc  172560
ttggaattaa tctgacagca ggagggcgca gactatgtaa acagagataa gaattaattt  172620
tcaaagttga aggggaaaaa aagaaagaaa aagaagaga gagagaaaga aagcatcgta  172680
caaagatttt cttaaaaaaa acaattttgc ttgaaatttc tttagatggg gctcagttgt  172740
cacagtggca cttggcctcc actgggcagc aggaccagct ccaagcgcta gtgttctgtt  172800
ctctttttgt aatcttggaa tcttttgttg ctctaaatac aattaaaaat ggtagaaact  172860
tgtttgttgg actaaatgtg tgactttggg tctgtctctg cctctgcttt cagaaatgtc  172920
atccattgtg taaatattg gcttgctggt ctgccagcta aaacttggcc acatcccctg  172980
ttgtggctgc aggatcgagt tattgttaac aaagagaccc aagaaaagct gctaatgtcc  173040
tcttatcatt gttgttaatt tgttaaaaca taaagaaatc taaaatttca gatgaatgtc  173100
atcagagttc ttttaattag ctctttttat tggctgtttt tattgaagtc aagagttggt  173160
atcatgccca gttgtgtttt atgctatttt gattttcata tattttaaa agtctttgca  173220
caaggcttac aaatttgccc tgtggtggcc ttagcataag ctgacctggg accaccaaaa  173280
taacaaggaa tttgggctag aaagcacaga tggacactgg cggcccatca caacttctct  173340
tgaaaaacac caaacttgtc agctggggaa aagccacaca aagcccagtt gcctactttc  173400
acaaccttat ccatgtggga gcataaaatg gtggcatcac tgcccagttc taaccaagct  173460
tcagttaaag aatgggtacc ttcacatcct cactatttt caggggcctt accatcctca  173520
accacccaag taaaatctaa atcagccttc ttttgggttc ttcagttcaa gtaaggcctc  173580
ttcttgtggc ctctcagtgt gaatacttac gaggttccag attgaatttt tgggcctgag  173640
atacaaggca tcaatgaggt gtgacaaaac atgtcaacga ataataagaa aattctctat  173700
tcttccatat cctcccctgt aataagggtt gtcagaatgc cttctttctc ggctgagttg  173760
aagattcagt gagaacatat gtgacacagc tggtgggcta ttaagctctg gctttgctcc  173820
ctgttaaaat gccagaaccc ttgagaggga tcccacattc agccatgttt atcattgacc  173880
acctagaat ggatggattt ctcagatttt tcctgagatc agtgcttgat ggagaggaga  173940
ggagaacaat agattcttgg gatgtgtgct ttgcatgtgt ttaagtaaga gacagagagt  174000
```

<210> SEQ ID NO 190
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 190
gcgtttgctc ttcttcttgc gttttt                                        27

<210> SEQ ID NO 191
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 191
tctggaacag attctg                                                   16

<210> SEQ ID NO 192
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 192
gcttcatctc cacaga                                                   16

<210> SEQ ID NO 193
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 193
ggctactacg ccgtca                                                   16

<210> SEQ ID NO 194
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 194
gagaaccatc ctcacc                                                   16

<210> SEQ ID NO 195
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 195
ggaccaggta gcctgt                                                   16

<210> SEQ ID NO 196
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 196
cccctggact cagatg                                                   16

<210> SEQ ID NO 197
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 197
gcacaaggag tgggac                                                   16

<210> SEQ ID NO 198
<211> LENGTH: 16
<212> TYPE: DNA
<213> ORGANISM: Artificial Sequence
<220> FEATURE:

<223> OTHER INFORMATION: Synthetic oligonucleotide

<400> SEQUENCE: 198
gctgtgaaga gagtgt                                                16

<210> SEQ ID NO 199
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 199
tttgacacaa gtggga                                                16

<210> SEQ ID NO 200
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 200
gtgacaccca gaagct                                                16

<210> SEQ ID NO 201
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 201
catccctgct tcataa                                                16

<210> SEQ ID NO 202
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 202
tggggagaac catcctcacc ctgc                                       24

<210> SEQ ID NO 203
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 203
tccaggacca ggtagcctgt gggg                                       24

<210> SEQ ID NO 204
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 204
tgttcccctg gactcagatg ctcc                                       24

```
<210> SEQ ID NO 205
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 205
tggggcacaa ggagtgggac gcac                                              24

<210> SEQ ID NO 206
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 206
ttcggctgtg aagagagtgt gcca                                              24

<210> SEQ ID NO 207
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 207
cgcttttgac acaagtggga ctgg                                              24

<210> SEQ ID NO 208
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 208
catagtgaca cccagaagct tcat                                              24

<210> SEQ ID NO 209
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 209
gagtcatccc tgcttcataa catt                                              24

<210> SEQ ID NO 210
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 210
ctgtgaagag agtg                                                         14

<210> SEQ ID NO 211
<211> LENGTH: 12
<212> TYPE: DNA
<213> ORGANISM: Artificial Sequence
<220> FEATURE:
<223> OTHER INFORMATION: Synthetic oligonucleotide
```

```
<400> SEQUENCE: 211
tgtgaagaga gt                                                          12

<210> SEQ ID NO 212
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 212
ttgacacaag tggg                                                        14

<210> SEQ ID NO 213
<211> LENGTH: 12
<212> TYPE: DNA
<213> ORGANISM: Artificial Sequence
<220> FEATURE:
<223> OTHER INFORMATION: Synthetic oligonucleotide

<400> SEQUENCE: 213
tgacacaagt gg                                                          12

<210> SEQ ID NO 214
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 214
tgacacccag aagc                                                        14

<210> SEQ ID NO 215
<211> LENGTH: 12
<212> TYPE: DNA
<213> ORGANISM: Artificial Sequence
<220> FEATURE:
<223> OTHER INFORMATION: Synthetic oligonucleotide

<400> SEQUENCE: 215
gacacccaga ag                                                          12
```